(12) United States Patent
Beyer et al.

(10) Patent No.: US 7,166,454 B1
(45) Date of Patent: Jan. 23, 2007

(54) CODON-OPTIMIZED β-SECRETASE AND METHODS OF REFOLDING AND PROCESSING

(75) Inventors: Brian M. Beyer, Lincroft, NJ (US); Bruce A. Malcolm, Westfield, NJ (US); Corey O. Strickland, Martinsville, NJ (US); Wenyan Wang, Edison, NJ (US); Eileen Wilson, Raritan, NJ (US)

(73) Assignee: Schering Corporation, Kenilworth, NJ (US)

( * ) Notice: Subject to any disclaimer, the term of this patent is extended or adjusted under 35 U.S.C. 154(b) by 511 days.

(21) Appl. No.: 10/443,949

(22) Filed: May 22, 2003

Related U.S. Application Data

(60) Provisional application No. 60/383,480, filed on May 24, 2002.

(51) Int. Cl.
*C12N 9/48* (2006.01)
*C12N 15/00* (2006.01)
*C12N 1/20* (2006.01)
*C12N 1/14* (2006.01)
*C12N 5/10* (2006.01)
*C12N 5/00* (2006.01)
*C07H 21/04* (2006.01)

(52) U.S. Cl. .................. 435/212; 536/23.2; 435/320.1; 435/252.3; 435/254.11; 435/419; 435/325; 435/252.33

(58) Field of Classification Search ..................... None
See application file for complete search history.

(56) References Cited

U.S. PATENT DOCUMENTS

| 2001/0016324 A1* | 8/2001 | Gurney et al. | 435/7.1 |
|---|---|---|---|
| 2001/0044521 A1* | 11/2001 | Lin | 530/350 |
| 2002/0055459 A1 | 5/2002 | Chopra et al. | 514/1 |
| 2004/0014194 A1 | 1/2004 | Beyer et al. | |

FOREIGN PATENT DOCUMENTS

| WO | WO 01/00663 A2 | 1/2001 |
|---|---|---|
| WO | WO 01/00665 A2 | 1/2001 |
| WO | WO 02/25276 A1 | 3/2002 |
| WO | WO 03/12089 A2 | 2/2003 |

OTHER PUBLICATIONS

Witkowski et al., Biochemistry, vol. 38, pp. 11643-11650, 1999.*
Lilie et al.,Curr. Opin. Biotech., vol. 9, pp. 497-501, 1998.*
Hong et al., Science, vol. 290, pp. 150-153 (2000).
Lin et al., Proceedings Nat. Acad. Sci., vol. 97, No. 4, pp. 1456-1460 (2000).
Mallender et al., Mol. Pharm., vol. 59, No. 3, pp. 619-626 (2001).
Bennett et al., J. Biol. Chem, vol. 275, No. 48, pp. 37712-37717 (2000).
Bruinzeel et al., Prot. Exp. and Pur., vol. 26, pp. 139-148 (2002).
Creemers et al., J. Biol. Chem., vol. 276, No. 6, pp. 4211-4217 (2001).
Kennedy et al., Measuring human beta-secretase (BACE1) activity using homogeneous time-resolved fluorescence. Anal Biochem. Aug. 1, 2003;319(1):49-55.
Wang et al., Crystallization of glycosylated human BACE protease domain expressed in Trichoplusia ni. Biochim Biophys Acta. May 6, 2004;1698(2):255-9.
Vassar et al., Beta-secretase cleavage of Alzheimer's amyloid precursor protein by the transmembrane aspartic protease BACE. Science. Oct. 22, 1999;286(5440):735-41.
Sinha et al., Purification and cloning of amyloid precursor protein beta-secretase from human brain. Nature. Dec. 2, 1999;402(6761):537-40.
Hussain et al., Identification of a novel aspartic protease (Asp 2) as beta-secretase. Mol Cell Neurosci. Dec. 1999;14(6):419-27.
Lin et al., Human aspartic protease memapsin 2 cleaves the beta-secretase site of beta-amyloid precursor protein. Proc Natl Acad Sci U S A. Feb. 15, 2000;97(4):1456-60.
Creemers et al., Processing of beta-secretase by furin and other members of the proprotein convertase family. J Biol Chem. Feb. 9, 2001;276(6):4211-7.
Bennett et al., A furin-like convertase mediates propeptide cleavage of BACE, the Alzheimer's beta-secretase. J Biol Chem. Dec. 1, 2000;275(48):37712-7.
Esch et al., Cleavage of amyloid beta peptide during constitutive processing of its precursor. Science. Jun. 1, 1990;248(4959):1122-4.

\* cited by examiner

*Primary Examiner*—Kathleen M. Kerr
*Assistant Examiner*—Alexander D. Kim

(57) ABSTRACT

The present application relates to methods for growing crystals of both the uncomplexed and complexed forms of β-secretase (BACE) polypeptide. Polypeptides used herein are derived from human BACE which is also known by the synonyms "mamapsin 2", "human β-site APP-cleaving enzyme, and Asp2". The present application also relates to crystalline forms of uncomplexed BACE and the three-dimensional structure of BACE, as determined from the crystals. In addition, the present application relates to the use of crystalline forms of BACE to identify ligands, preferably inhibitors (antagonists), which bind to, and preferably inhibit the enzymatic activity of, BACE. Furthermore, the present application relates to nucleic acid sequences encoding BACE polypeptide, and methods for making BACE in greater quantity than prior methods, resulting in more effective crystallization.

20 Claims, No Drawings

CODON-OPTIMIZED β-SECRETASE AND METHODS OF REFOLDING AND PROCESSING

This application claims priority under 35 U.S.C. § 119(e) to U.S. Provisional Application Ser. No. 60/383,480, filed May 24, 2002, which is incorporated herein by reference in its entirety.

All publications cited in the present application are incorporated in their entirety by reference.

BACKGROUND OF THE INVENTION

1. Field of the Invention

The present application relates to nucleic acids encoding β-secretase (BACE) polypeptides, methods for making BACE polypeptides, methods for growing crystals of BACE, crystalline BACE, the three-dimensional structure of BACE, and the use of the crystalline forms to identify ligands, such as antagonists, that bind to BACE.

2. Invention Background

Alzheimer's disease (AD) is a neurodegenerative disease characterized by neuronal loss due to the extracellular accumulation of amyloid plaques and intracellular accumulation of neurofibrillary tangles in the brain (reviewed by Selkoe, D. J. (1999) Nature 399: A23–31). Two major components of amyloid plaques are small peptide fragments Aβ40 and Aβ42, which are generated from cleavage of the membrane-anchored amyloid precursor protein (APP) by the proteolytic activity of β- and γ-secretases. APP is a type I integral membrane protein containing the Aβ segment, which begins at D672 in the longest isoform and spans the boundary of the exocytoplasmic region (28 amino acids) and the transmembrane domain (12–14 amino acids). The γ-secretase activity cleaves APP within the transmembrane domain to produce the carboxy-terminal end of Aβ polypeptide. The β-secretase activity (aspartic protease activity), identified in a protein that is known as "mamapsin 2", "human β-site APP-cleaving enzyme" or "BACE", and "Asp 2", cleaves APP on the extracellular side of the membrane to produce the amino-terminal end of Aβ. (Vassar, R. et al., (1999) Science 286,735, Sinha, S. et al., (1999) Nature 402,537, Yan, R. et al., (1999) Nature 402,522, Hussain, I. et al., (1999) Mol. Cell Neurosci. 14, 419 and Lin, X. (2000) et al., Proc. Natl. Acad. Sci. USA 97, 1456. Another enzyme, known as α-secretase, cleaves APP at a position within the Aβ sequence to produce a soluble APPα ((Esch et al., (1990) Science 248: 1122–1124).

During the course of AD, Aβ polypeptide accumulates extracellularly in the brain, and forms large, insoluble amyloid fibrils that elicit both cytotoxic and inflammatory responses. Thus, BACE and γ-secretase proteases are targets for potential inhibitor drugs (antagonists) against AD. Because it was discovered that BACE activity is the rate-limiting step in Aβ production in vivo (Sinha and Lieberburg, (1999) Proc. Natl. Acad. Sci. USA 96: 11049), BACE has become a prime target for the development of inhibitors (antagonists) to treat AD.

The BACE gene encodes a 501 residue polypeptide having, from N- to C-terminus, an N-terminal signal sequence of 21 amino acids; a pro-protein domain of 22 to 45 residues, which is proteolytically removed by furin to generate mature β-secretase (Creemers, J. W., et al. (2001) J. Biol. Chem. 276: 4211–4217; Bennet, B. D., et al. (2000) J. Biol. Chem. 275: 37712–37717); a protease (catalytic) domain; a connecting strand, an integral membrane (transmembrane) domain of about 17 amino acids; and a short cytosolic C-terminal tail of 24 amino acids (Vassar et al., supra). Sequence analyses indicate that BACE belongs to a subfamily of membrane-bound and soluble proteases, and contains a classic consensus active site motif found in aspartyl proteases (D T/S G T/S) at positions 93 to 96 and 289 to 292. The entire BACE sequence displays only mild homology with known aspartyl proteases, approximately 30% identity and 37% similarity with members of the mammalian pepsin family, with the highest homology found in the central portion of the extracellular domain.

Accurate information regarding the three-dimensional structure of β-secretase is helpful in the design and identification of ligands, particularly inhibitors (antagonists), of BACE, and in the enzymatic characterization of the enzyme. This information may be provided using crystals of the protein in X-ray crytallographic analysis.

Crystallization of a protein is a very time consuming and complex process. Crystallization of a protein requires a precise set of reagents and reaction conditions that promote the growth of crystallized protein. For example, specific amounts of protein, buffer, precipitating agent and salt, at a precise temperature, are required to produce X-ray diffraction quality crystals. There are an infinite number of combinations of the above reagents and reaction conditions. Therefore, the number of different combinations that can be tested is limited by the amount of protein that can be produced. Because the precise set of conditions that will produce crystals can not be predicted, one is more likely to discover crystals as more reagents and reaction conditions are tested. As a result, effective crystallization requires a large amount of refolded protein, typically milligram quantities. This is problematic because current methods for expressing BACE in E. coli provide low yields of unfolded protein. In addition, large amounts of unfolded protein are required to optimize the protein's refolding procedures. Thus, there is a need for nucleic acids encoding BACE that are optimized for E. coli expression, which utilize codons that are preferred by E. coli, to produce large quantities of BACE to both discover optimal refolding conditions and so that many different combinations of the above reagents and reaction conditions may be tested in order to optimize the crystallization conditions for BACE.

A crystal form of β-secretase complexed to an inhibitor is described in Hong et al., (2000) Science 290:150–153. In addition, several international applications published under the Patent Cooperation Treaty, international publication numbers WO 02/25276 A1, WO 01/00663 A2 and WO 01/00665 A2, provide crystal forms of BACE complexed to an inhibitor. Knowledge of the structure of a protein in both the uncomplexed and complexed forms allows one to determine how the three-dimensional structure of the protein changes upon binding to a ligand. This aids in structure based drug design because it provides more information regarding how a particular ligand may be altered to increase its binding to the protein. Thus, there is a need for crystals of β-secretase which have similar structure and activity to that of native BACE, and which can be produced in the uncomplexed form.

SUMMARY OF THE INVENTION

The present invention addresses the foregoing needs by providing nucleic acids encoding BACE polypeptides that are able to produce large quantities of BACE when expressed in E. coli cells. The present invention also addresses the foregoing needs by providing crystals of BACE in the uncomplexed form.

An embodiment of the invention provides an isolated or recombinant nucleic acid comprising the nucleotide sequence set forth in SEQ ID NO: 1. A further embodiment provides a nucleic acid comprising the nucleotide sequence set forth in SEQ ID NO: 17. An additional embodiment of the invention provides an expression vector comprising a nucleic acid comprising the nucleotide sequence set forth in SEQ ID NO: 17. A further embodiment of the invention provides a host cell comprising the above vector.

An embodiment of the invention also provides a method for making β-secretase polypeptide comprising transforming a host cell with an expression vector comprising an isolated or recombinant nucleic acid comprising the nucleotide sequence set forth in SEQ ID NO: 17 under conditions in which the polypeptide is expressed. Preferably, the host cell is a bacterial cell. More preferably, the bacterial cell is an $E.$ $coli$ cell. Most preferably, the $E.$ $coli$ cell is a BL21(DE3)Star cell. In addition, the vector is preferably pET 11a. Preferably, the method further comprises a refolding step wherein the polypeptide is refolded in the presence of about 0.5 mM reduced glutathione and about 0.5 mM oxidized glutathione.

In addition, the method for making β-secretase polypeptide further comprises a processing step wherein the polypeptide is exchanged into about 20 mM Hepes at about pH 7.5 and about 150 mM NaCl and then concentrated to about 5 mg/ml, and incubated at about 4° C. for about two weeks to form a processed polypeptide. Preferably, the processed polypeptide comprises the amino acid sequence set forth in either SEQ ID NO: 20 or SEQ ID NO: 22. Alternatively, the method for making β-secretase polypeptide further comprises a processing step wherein the polypeptide is exchanged into about 20 mM Hepes at about pH 7.5 and about 150 mM NaCl and then concentrated to about 15 mg/ml, and incubated at about room temperature for about 72 hours to form a processed polypeptide. Preferably, the processed polypeptide comprises the amino acid sequence set forth in either SEQ ID NO: 20 or SEQ ID NO: 22.

An embodiment of the invention provides a method for growing a crystal comprising adding about 16 mg/ml of a polypeptide comprising the amino acid sequence set forth in SEQ ID NO: 22 to a crystallization solution, the solution comprising about 13.75% to about 15.0% PEG3350 and about 0.6 M ammonium iodide, and crystallizing the solution at about 4° C. using a hanging drop method.

Another embodiment of the invention provides a method for growing a crystal comprising a polypeptide complexed to a ligand comprising adding about 16 mg/ml of a polypeptide comprising the amino acid sequence set forth in SEQ ID NO: 22 and about 0.5 mM to about 1.0 mM of the ligand to a crystallization solution, the solution comprising about 20% PEG3350 and about 0.2 M ammonium tartrate, and crystallizing the solution at about 4° C. using a hanging drop method. Preferably, the ligand is an antagonist.

An embodiment of the invention provides a crystal that is made by adding about 16 mg/ml of a polypeptide comprising the amino acid sequence set forth in SEQ ID NO: 22 to a crystallization solution, the solution comprising about 13.75% to about 15.0% PEG3350 and about 0.6 M ammonium iodide, and crystallizing the solution at about 4° C. using a hanging drop method. Preferably, the crystal has a space group of C2 with unit cell dimensions of a=236.0 Å, b=103.6 Å and c=65.0 Å. Alternatively, the crystal has a space group of C2 with unit cell dimensions wherein a ranges from about 231.3 Å to about 240.7 Å, b ranges from about 101.5 Å to about 105.7 Å, and c ranges from about 63.7 Å to about 66.3 Å. The crystal is preferably characterized by the structure coordinates set forth in Table 1. Preferably, the crystal effectively diffracts X-rays for determination of atomic coordinates of the polypeptide to a resolution of greater than about 5.0 Å.

Another embodiment of the invention provides a crystal of an uncomplexed β-secretase polypeptide wherein the β-secretase polypeptide is expressed in $E.$ $coli$ cells comprising a polypeptide comprising the amino acid sequence set forth in SEQ ID NO: 22, wherein the crystal effectively diffracts X-rays for determination of atomic coordinates of the polypeptide to a resolution of greater than about 5.0 Å. Preferably, the crystal has a space group of C2 with unit cell dimensions of a=236.0 Å, b=103.6 Å and c=65.0 Å. Alternatively, the crystal has a space group of C2 with unit cell dimensions wherein a ranges from about 231.3 Å to about 240.7 Å, b ranges from about 101.5 Å to about 105.7 Å, and c ranges from about 63.7 Å to about 66.3 Å.

An embodiment of the invention provides a crystal of an uncomplexed β-secretase polypeptide characterized by the structure coordinates set forth in Table 1. A further embodiment of the invention provides a crystal of an uncomplexed β-secretase polypeptide characterized by structure coordinates comprising a root mean square deviation of conserved residue backbone atoms of less than about 1.5 Å when superimposed on backbone atoms described by the structure coordinates set forth in Table 1. Preferably, the root mean square deviation is less than about 1.0 Å. More preferably, the root mean square deviation is less than about 0.5 Å. Most preferably, the root mean square deviation is less than about 0.1 Å. Preferably, the crystal effectively diffracts X-rays for determination of atomic coordinates of the polypeptide to a resolution of greater than about 5.0 Å. The crystal preferably has a space group of C2 with unit cell dimensions of a=236.0 Å, b=103.6 Å and c=65.0 Å. Alternatively, the crystal has a space group of C2 with unit cell dimensions wherein a ranges from about 231.3 Å to about 240.7 Å, b ranges from about 101.5 Å to about 105.7 Å, and c ranges from about 63.7 Å to about 66.3 Å.

An embodiment of the invention provides a magnetic data storage medium comprising the structure coordinates set forth in Table 1. Another embodiment of the invention provides a computer for producing a three-dimensional representation of β-secretase polypeptide which is defined by the structure coordinates set forth in Table 1, or a three-dimensional representation of a homologue of the β-secretase protein wherein the homologue has a root mean square deviation from the backbone atoms set forth in Table 1 of less than about 1.5 Å, wherein the computer comprises: (a) a machine-readable data storage medium comprising a data storage material encoded with machine-readable data, wherein the data comprises the structure coordinates set forth in Table 1; (b) a working memory for storing instructions for processing the machine-readable data; (c) a central-processing unit coupled to the working memory and to the machine-readable data storage medium for processing the machine readable data into the three-dimensional representation; and (d) a display coupled to the central-processing unit for displaying the three-dimensional representation. Preferably, the root mean square deviation is less than about 1 Å. More preferably, the root mean square deviation is less than about 0.5 Å. Most preferably, the root mean square deviation is less than about 0.1 Å.

An embodiment of the invention provides a method for identifying a ligand that binds to β-secretase comprising: (a) obtaining a set of atomic coordinates defining the three-dimensional structure of a crystal of an uncomplexed, processed β-secretase polypeptide expressed in *E. coli* cells that effectively diffracts X-rays for determination of the atomic coordinates of the β-secretase polypeptide to a resolution of greater than about 5.0 Å; (b) selecting a ligand by performing rational drug design with the set of atomic coordinates obtained in step (a), wherein the selecting is performed in conjunction with computer modeling; (c) contacting the ligand with the polypeptide; and (d) detecting binding of the ligand to the polypeptide. Preferably, the method provides a crystal having a space group of C2 with unit cell dimensions of a=236.0 Å, b=103.6 Å and c=65.0 Å. Alternatively, the method provides a crystal having a space group of C2 with unit cell dimensions wherein a ranges from about 231.3 Å to about 240.7 Å, b ranges from about 101.5 Å to about 105.7 Å, and c ranges from about 63.7 Å to about 66.3 Å.

An embodiment of the invention provides a method for identifying a ligand that binds to β-secretase comprising: (a) preparing a mixture of β-secretase with a potential ligand comprising adding about 1.5 to about 5 molar ratio of ligand to about 16 mg/ml of β-secretase comprising the amino acid sequence set forth in SEQ ID NO: 22; (b) crystallizing the mixture to form a crystal; and (c) performing X-ray diffraction analysis on the crystal.

Another embodiment of the invention provides a method for identifying a ligand that binds to β-secretase comprising: (a) soaking a crystal, which is made by adding about 16 mg/ml of a polypeptide comprising the amino acid sequence set forth in SEQ ID NO: 22 to a crystallization solution, the solution comprising about 13.75% to about 15% PEG3350 and about 0.6 M ammonium iodide, and crystallizing the solution at about 4° C. using a hanging drop method, in a solution comprising the ligand; and (b) performing X-ray diffraction on the crystal.

An additional embodiment of the invention provides a method for identifying a ligand that binds to β-secretase comprising: (a) preparing a mixture of β-secretase with a ligand comprising adding a first ligand to about 16 mg/ml of β-secretase comprising the amino acid sequence set forth in SEQ ID NO: 22; (b) crystallizing the mixture to form a crystal; (c) soaking the crystal in a solution comprising a potential ligand, wherein the potential ligand displaces the first ligand from the crystal; and (d) performing X-ray diffraction on the crystal.

An embodiment of the invention provides a method for identifying a β-secretase antagonist comprising the steps of: (a) selecting a potential antagonist by performing rational drug design using the three-dimensional structure of a crystal of an uncomplexed β-secretase wherein the β-secretase polypeptide is expressed in *E. coli* cells and comprises the amino acid sequence set forth in SEQ ID NO: 22, wherein the crystal effectively diffracts X-rays for determination of atomic coordinates of the polypeptide to a resolution of greater than about 5.0 Å, and wherein the selecting is performed in conjunction with computer modeling; (b) contacting the potential antagonist with β-secretase; and (c) detecting binding of the potential antagonist to the β-secretase, wherein an antagonist is identified on the basis of its ability to inhibit the catalytic activity of the β-secretase.

An embodiment of the invention provides a method for identifying an inhibitor of β-secretase comprising: (a) obtaining a set of atomic coordinates from a crystal defining the three-dimensional structure of an uncomplexed, processed β-secretase polypeptide expressed in *E. coli* cells; (b) selecting a potential inhibitor by performing rational drug design with the set of atomic coordinates obtained in step (a), wherein the selecting is performed in conjunction with computer modeling; (c) contacting the potential inhibitor with a β-secretase protein; and (d) measuring the activity of the protein, wherein the potential inhibitor is identified when there is a decrease in activity of the β-secretase in the presence of the inhibitor as compared to the activity of β-secretase in the absence of the potential inhibitor. Preferably, the method provides a crystal having a space group of C2 with unit cell dimensions of a=236.0 Å, b=103.6 Å and c=65.0 Å. Alternatively, the method provides a crystal having a space group of C2 with unit cell dimensions wherein a ranges from about 231.3 Å to about 240.7 Å, b ranges from about 101.5 Å to about 105.7 Å, and c ranges from about 63.7 Å to about 66.3 Å.

An embodiment of the invention provides a method for identifying a potential inhibitor of β-secretase comprising the steps of: (a) viewing a three-dimensional structure of the β-secretase as defined by the atomic coordinates of β-secretase set forth in Table 1; (b) employing the three-dimensional structure to design or select the potential inhibitor; (c) synthesizing the potential inhibitor; and (d) contacting the potential inhibitor with the β-secretase in the presence of a substrate to determine the ability of the potential inhibitor to inhibit the β-secretase.

DETAILED DESCRIPTION OF THE INVENTION

The present application relates to nucleic acids encoding β-secretase (BACE) polypeptides; methods for making, refolding and processing BACE polypeptides; methods for growing crystals of BACE in both the uncomplexed and complexed forms; crystalline BACE; the three-dimensional structure of BACE, and the use of the crystalline forms to identify ligands, such as antagonists, that bind to BACE.

Methods for Producing β-Secretase Nucleic Acids and/or Polypeptides

Embodiments of the invention provide methods for producing β-secretase (BACE) nucleic acids and/or polypeptides. A BACE nucleic acid or polypeptide can be produced by any conventional method, including, but not limited to, synthetic methods, such as solid phase, liquid phase, and combination solid/liquid phase polypeptide syntheses; recombinant DNA methods, including cDNA cloning, optionally combined with site-directed mutagenesis; and/or purification of the natural products, optionally combined with enzymatic or chemical cleavage methods to produce fragments of naturally-occurring BACE nucleic acids or polypeptides.

In addition, a BACE nucleic acid or polypeptide can be any form of BACE from any species. Preferably, the BACE nucleic acid or polypeptide is from an animal. More preferably, the BACE nucleic acid or polypeptide is from a mammal, including, but not limited to, mouse, rat, rabbit, dog, or human. Most preferably, the BACE nucleic acid or polypeptide is from a human.

Preferably, the BACE polypeptide is structurally and functionally similar to naturally-occurring human BACE. However, the BACE polypeptide need not be glycosylated or include any sort of post-translational modification.

Preferably, a BACE polypeptide is produced from a synthetic BACE gene that contains an optimized spelling of the native nucleotides of the first approximately one-third of the human BACE gene. The spelling of the nucleotide sequence is optimized by increasing or decreasing the GC content of the sequence to approximately 50% and by optimizing the codon usage for a particular expression system, yet keeping the resulting amino acid sequence unchanged from the native sequence. Decreasing the GC content of the nucleotide sequence reduces the potential for secondary structure formation of mRNA, which results in decreased levels of protein expression. The codon usage was optimized by using codons that are preferred in *E. coli*. Preferred codons are determined by sequencing genomic DNA of the host organism and applying statistical analysis to determine which codons are preferred in nature. Preferably, the synthetic optimized BACE gene used to produce the BACE polypeptide comprises the nucleotide sequence set forth in SEQ ID NO: 17. Most preferably, the synthetic optimized BACE gene used to produce the BACE polypeptide comprises the nucleotide sequence set forth in SEQ ID NO: 1. Alternatively, a BACE polypeptide can be produced comprising the amino acid sequence set forth in either SEQ ID NO: 2 or SEQ ID NO: 18.

A BACE gene comprising the nucleotide sequence set forth in either SEQ ID NO: 1 or SEQ ID NO: 17, or a BACE polypeptide comprising the amino acid sequence set forth in either SEQ ID NO: 2 or SEQ ID NO: 18 can be produced by any conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1996) (herein "Ausubel et al., 1996").

Most preferably, the nucleotide sequence set forth in SEQ ID NO: 1 is generated using polymerase chain reaction (PCR), as described in example 1 below. Briefly, and described in more detail in example 1, a three stage PCR strategy is adopted to construct a soluble synthetic BACE gene. In the first stage, primers are generated which are used to amplify two half fragments. In the second stage, the two half fragments are used to amplify the synthetic fragment of 1–420 bp of BACE (SEQ ID NO: 1). Finally, in the third stage, the synthetic soluble BACE comprising nucleotides 1–1362 (SEQ ID NO: 17) is amplified.

In addition to being derived from the above optimized nucleic acid, the BACE gene preferably includes an additional nucleotide sequence to drive protein expression, such as a T7 tag located on the amino terminus. The T7 tag preferably comprises a nucleotide sequence encoding the amino acid sequence MASMTGGQQMG (SEQ ID NO: 14). The BACE gene also preferably includes a C-terminal truncation that omits the transmembrane domain of the native BACE enzyme, which aids in purification of the protein. The C-terminal truncation preferably omits the nucleotide sequence encoding the final approximately 40–60 amino acid residues of the protein. More preferably, the C-terminal truncation omits the nucleotide sequence encoding the final 47 amino acid residues of the polypeptide so that the polypeptide is truncated after amino acid residue 454 of the native enzyme. However, the nucleotide or amino acid sequence need not include any N-terminal or C-terminal additions and/or truncations.

Finally, the synthetic BACE gene may be expressed. The terms "express" and "expression" mean allowing or causing the information in a gene or nucleotide sequence to become manifest, e.g., producing a protein by activating the cellular functions involved in transcription and, optionally, translation of a corresponding gene or nucleotide sequence. A nucleotide sequence can be expressed using a vector, such as pET 11a. Alternatively, a nucleotide sequence can be expressed using in vitro translation systems (e.g., rabbit reticulocyte lysate-based systems) or in or by a cell to form an "expression product" such as an mRNA or a protein. The expression product, e.g., the resulting protein, may also be referred to as "expressed". The BACE polypeptide may be expressed in any type of host cell. Preferably, the polypeptide is expressed in mammalian cells, insect cells or bacterial cells. More preferably, the polypeptide is expressed in *E. coli* cells. Most preferably, the polypeptide is expressed in BL21 (DE3)Star cells. Therefore, the resulting polypeptide is not post-translationally modified. However, the present invention contemplates crystals comprising BACE polypeptide which have been modified (e.g., post-translationally modified) in any manner, such as glycosylation, phosphorylation, sulfonation, or PEGylation. The optimized nucleotide sequences set forth in both SEQ ID NO: 1 and SEQ ID NO: 17 unexpectedly result in an increase in insoluble protein expression of approximately four fold when expressed in BL21 (DE3)Star cells.

An embodiment of the present invention provides polypeptides that differ from the BACE polypeptide comprising the amino acid sequence set forth in either SEQ ID NO: 2 or SEQ ID NO: 18 by having amino acid deletions, substitutions, and additions. Preferably, the BACE polypeptide used in the present invention contains catalytic (proteolytic) properties that are comparable to those that have been reported for synthetic peptides derived from the β-amyloid precursor protein (APP) peptide sequence. Examples of APP peptides which may be cleaved by BACE of the present invention are disclosed, for example, in Lin et al., (2000) *Proc. Nat. Acad. Sci.*, 97(4):1456–1460 and Turner et al., (2001) *Biochemistry*, 40(34):10,001–10,006. The bilobal protein, typically, is lightly glycosylated with glycan attachment, accounting for approximately 4 kD of the protein's molecular weight.

An embodiment of the present invention also provides various mutant forms, homologues and variants of BACE. The terms "mutant" and "mutation" mean any detectable change in genetic material, e.g., DNA, or any process, mechanism, or result of such a change. Therefore, embodiments of the invention provide nucleic acids which differ from the nucleotide sequence set forth in either SEQ ID NO: 1 or SEQ ID NO: 17. This includes gene mutations in which the structure (e.g., DNA sequence) of a gene is altered, any gene or DNA arising from any mutation process, and any expression product (e.g., protein) expressed by a modified gene or DNA sequence. The term "variant" may also be used to indicate a modified or altered gene, DNA sequence, polypeptide or enzyme, etc., i.e., any kind of mutant. Sequence- and function-conservative variants of BACE polypeptides are also contemplated for use in the present invention. "Sequence-conservative variants" of BACE are those in which a change of one or more nucleotides in a given codon position results in no alteration in the amino acid encoded at that position. "Function-conservative variants" of BACE are those in which a given amino acid residue in a BACE polypeptide has been changed without altering the overall conformation and function of the polypeptide, including, but not limited to, replacement of an amino acid with one having similar properties, such as, for example, polarity, hydrogen bonding potential, acidic, basic, hydrophobic, aromatic, and the like.

Protein or polypeptide homology, or sequence identity, is determined by optimizing residue matches, if necessary, by introducing gaps as required. See, e.g., Needleham, et al. *J. Mol. Biol.* 48:443–453 (1970); Sankoff et al., "Time Warps, String Edits, and Macromolecules: The Theory and Practice of Sequence Comparison", Ch. 1, Addison-Wesley, Reading, Mass. (1983); and software packages from IntelliGenetics, Mountain View, Calif. and the University of Wisconsin Genetics Computer Group (GCG), Madison, Wis. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural variations of the BACE amino acid sequence. Typical homologous BACE polypeptides used in this invention will have from 50–100% homology (if gaps can be introduced), to 60–100% homology (if conservative substitutions are included), e.g., with BACE comprising the amino acid sequence set forth in either SEQ ID NO: 2 or SEQ ID NO: 18. Homology measures are preferably at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length and number of BACE polypeptides compared.

It may also be desirable to add amino acids at the amino- or carboxy-terminus of a BACE polypeptide, e.g., to prepare a fusion protein. For example, the addition may be a polyhistidine tag of 5–20 amino acids, preferably 6 amino acids, in length. Alternatively, a histidine tag for aiding in purification of a BACE polypeptide may be located at the carboxy-terminus. Further, a myc tag may be added to the carboxy-terminus of BACE. The myc tag may be used for detection or immunopurification of BACE. The myc tag and the polyhistidine tag may both be located at the carboxy-terminus or amino-terminus in a doubly-tagged BACE.

Purification and Refolding of β-Secretase Polypeptide

After being expressed, BACE polypeptide may be purified from inclusion bodies within the host cells. Purification may be performed by any means known in the art, such as sucrose gradient centrifugation. However, BACE is preferably purified by the procedure described in example 2 below.

After purification, the BACE polypeptide may need to be refolded. Refolding may be performed by any means known in the art, such as dialysis. However, BACE is preferably refolded according to the procedure described in example 2 below.

Preferably, reshuffling compounds are added to improve the efficiency of refolding. The standard reshuffling solution includes about 1 mM reduced glutathione, about 0.1 mM oxidized glutathione and about 1 mM cysteine. However, the ratios of these compounds may be adjusted to further increase the efficiency of refolding by facilitating disulfide reshuffling. Most preferably, the reshuffling conditions include about 0.5 mM reduced glutathione, about 0.5 mM oxidized glutathione and about 0 mM cysteine.

The pH of the polypeptide solution also affects the efficiency of refolding. The BACE polypeptide appears to refold in the pH range of 4 to 8.7. Preferably, the pH is either maintained at 8.7 or reduced to 4.0 to facilitate refolding.

Once refolded, the BACE preparation may be subjected to anion exchange chromatography for further purification. It may also be desirable to subject the BACE preparation to standard size exclusion gel filtration. The protein preparation may be further concentrated using standard techniques. Finally, the preparation is preferably subjected to ultracentrifugation, which produces a monodisperse preparation of BACE. The BACE in the resulting supernatant is useful for crystallization purposes.

The terms "monodisperse" and "predominantly uniform molecular species", in reference to BACE, are used interchangeably to indicate that the mean radius of particles comprising BACE varies by less than about 30%, preferably less than about 15%, as determined by, e.g., conventional dynamic light scattering methods. A monodisperse BACE in solution preferably exists in a monomeric form, however, oligomers (e.g., dimers, trimers, tetramers, etc.) may also exist. Such mixtures of BACE have subunits of a molecular weight of about 45 kDa.

Processing of β-Secretase

The BACE polypeptide is processed to remove the propeptide before crystallization. The propeptide constitutes approximately the first 50 amino acids of the BACE polypeptide, and preferably constitutes amino acids 22–45 of the native BACE protein.

Processing may be performed by any means known in the art, such as by using the endoprotease furin. However, the polypeptide is preferably processed by the procedure in example 3 below, using trans cleavage processing. The term "trans-cleavage processing" refers to the ability of one BACE molecule to enzymatically remove the propeptide of another BACE molecule. Briefly, BACE polypeptide is exchanged into about 20 mM Hepes at about pH 7.5 and about 150 mM NaCl, and then concentrated to about 5 mg/ml and incubated at about 4° C. for about two weeks. This is the preferred processing method for producing crystals of BACE for X-ray crystallography. Alternatively, BACE polypeptide is exchanged into about 20 mM Hepes at about pH 7.5 and about 150 mM NaCl, and then concentrated to about 15 mg/ml and incubated at about room temperature for about 72 hours.

Both of the above trans processing procedures produce a ragged cut. This means that each trans processing procedure cuts the BACE polypeptide (SEQ ID NO: 18) in two separate locations to produce two separate processed polypeptides. Preferably, one of the processed polypeptides comprises the amino acid sequence set forth in SEQ ID NO: 20. Alternatively, the other processed polypeptide preferably comprises the amino acid sequence set forth in SEQ ID NO: 22.

Enzymatic Activity of Refolded β-Secretase

The enzymatic activity of the refolded and processed BACE polypeptide may be tested in order to assess the functionality of the expressed polypeptide. The term "enzymatically active" means a polypeptide is catalytically active and, preferably, can hydrolyze a peptide bond of a suitable substrate. Preferably, the term relates to the ability of BACE to cleave β-amyloid precursor protein or a fragment thereof. Enzymatic activity may be measured by any means known in the art, such as by quantitating the rates of peptide or protein hydrolysis. However, enzymatic activity is preferably measured by the procedure in example 4 below. Unexpectedly, the polypeptides comprising the nucleotide sequences set forth in either SEQ ID NO: 1 or SEQ ID NO: 17 exhibits enzymatic activity similar to BACE from other expression systems.

The term "active site", when referring to a BACE polypeptide, describes the area of the polypeptide responsible for peptide recognition and/or peptide bond hydrolysis. An active site in an "open configuration" means that the active site is accessible to interaction with a suitable substrate and/or inhibitor. Preferably, BACE polypeptide is made in a system which produces BACE with an active site in the open configuration.

Crystallization

Embodiments of the invention relate to methods for growing crystals of BACE. Proteins are crystallized in a crystallization solution. A crystallization solution preferably contains the protein of interest, a precipitant, a salt, a buffering agent and, optionally, a reducing agent, oxygen scavenger, protein stabilizing agent or detergent.

For crystallization of BACE, it is desirable to use a solution of processed BACE polypeptide having a concentration ranging from about 1 mg/ml to the upper limit of how high the protein can be concentrated in solution. Preferably, the concentration of BACE is about 10 mg/ml to about 20 mg/ml. More preferably, the BACE concentration is about 14 mg/ml to about 17 mg/ml. Most preferably, the BACE concentration is about 16 mg/ml. Preferably, the solution of processed BACE polypeptide comprises a mixture of two polypeptides comprising the amino acid sequences set forth in SEQ ID NO: 20 and SEQ ID NO: 22. Alternatively, the solution of processed BACE polypeptide comprises a polypeptide comprising the amino acid sequence set forth in either SEQ ID NO: 20 or SEQ ID NO: 22.

A "precipitant" is a compound that decreases the solubility of a polypeptide in a concentrated solution. Alternatively, the term "precipitant" can be used to refer to a change in physical or chemical parameters which decrease polypeptide solubility, including temperature, pH and salt concentration. Precipitarits induce crystallization by forming an energetically unfavorable precipitant-depleted layer around the polypeptide molecules. To minimize the relative amount of this depletion layer, the polypeptides form associations and, ultimately, crystals. This process is explained in more detail in Weber, *Advances in Protein Chemistry* 41:1–36 (1991). Various precipitants are known in the art and include, but are not limited to, ammonium sulfate, ethanol, 3-ethyl-2,4 pentanediol, and many of the polyglycols, such as polyethylene glycol.

Crystallization of BACE is preferably achieved in a precipitant solution containing polyethylene glycol 1000–20,000 (PEG; average molecular weight ranging from about 1000 to about 20,000 Da). Most preferably, the polyethylene glycol is PEG3350 (Hampton Research, Laguna Niguel, Calif.). Preferably, PEG3350 is present in a concentration ranging from about 13.75% to about 25% (w/v). More preferably, the concentration of PEG3350 ranges from about 13.75% to about 15% (w/v). The most preferable PEG3350 concentration is about 15% (w/v). It should be noted that PEG3350 seems to be the same as PEG4000. The name of the compound appears to depend upon the manufacturer.

The crystallization solution also contains a salt. Salts act as a co-precipitant because they are used to reduce the solubility of the polypeptide in solution. Examples of salts include, but are not limited to, sodium chloride, lithium chloride, sodium citrate, ammonium iodide, ammonium tartrate, $Na^+/K^+$ tartrate or any of the tartrate salts. A salt is preferably added to the crystallization solution in a concentration ranging from about 1 mM to about 1000 mM. Preferably, the salt is ammonium tartrate or $Na^+/K^+$ tartrate, in a concentration of about 0.2 M to about 0.4 M. Alternatively, a preferred salt is ammonium iodide, in a concentration ranging from about 0.1 M to about 1 M. More preferably, the concentration of ammonium iodide is 0.6 M or 0.8 M. Most preferably, the concentration of ammonium iodide is 0.6 M.

In addition, buffering agents or buffers are added to the crystallization solution to adjust the pH of the solution, and hence surface charge on the polypeptide. The pH of the buffering agent may range from about 4 to about 10, e.g., 5, 6, 7, 8 and 9, preferably between about pH 7 and about pH 8, e.g., 7.2, 7.4, 7.5, 7.6 and 7.8. Buffers are well known in the art and many are useful in the precipitant solution (Scopes, *Protein Purification: Principles and Practice*, Third ed., (1994) Springer-Verlag, New York). Examples of buffers include, but are not limited to, Hepes, Tris, MES and acetate.

Reducing agents may also be added to the crystallization solution. Examples of suitable reducing agents for crystallization include, but are not limited to, dithiothreitol (DTT), dithioerythritol (DET) and β-mercaptoethanol (BME). If desired, the reducing agent is present in the solution at a concentration of about 10 mM. Preferably, the BACE crystallization solution does not include a reducing agent.

In addition, oxygen scavengers may also be added to the crystallization solution. Oxygen scavengers are well known in the art and any may be used. Preferably, the BACE crystallization solution does not include an oxygen scavenger.

Protein stabilizers may also be added to the crystallization solution. Over time, proteins in solution have a natural tendency to become unfolded. Protein stabilizers prevent denaturation of the protein, and hence, precipitation of the protein in solution. Protein stabilizers are well known in the art. A preferred protein stabilizer is glycerol. If glycerol is chosen as the protein stabilizing agent, it is preferably provided at a concentration ranging from about 0.5% to about 20% (w/v). Preferably, the BACE crystallization solution does not include a protein stabilizer.

Detergents may also be added to the crystallization solution. Proteins in solution have a natural tendency to react with each other. Detergents prevent the protein from interacting with itself and with other protein molecules in solution. Detergents are well known in the art. Preferably, the BACE crystallization solution does not include a detergent.

Furthermore, other additives may be added to the crystallization solution. Examples of these other additives include, but are not limited to, ethanol and spermidine. A more complete list of additives can be found in the product catalog from Hamptom Research (Laguna Niguel, Calif.).

Crystallization may be accomplished by any of the known techniques in the art (Giegé, et al., (1994) *Acta Crystallogr.* D50: 339–350; McPherson, (1990) *Eur. J. Biochem.* 189: 1–23). Such techniques include, but are not limited to, microbatch, hanging drop vapor diffusion, seeding and dialysis. Preferably, hanging drop vapor diffusion (McPherson, (1976) *J. Biol. Chem.* 251: 6300–6303) or microbatch methods (Chayen (1997) *Structure* 5: 1269–1274) are used. Most preferably, crystallization is performed using hanging drop vapor diffusion. In each of these methods, it is important to promote continued crystal growth after nucleation by maintaining a supersaturated solution.

In hanging drop vapor diffusion, a protein of interest (in water) is solubilized in a drop of crystallization solution and placed on a substrate, such as a microscope slide. The substrate is then turned over so the drop hangs from the substrate. The surface tension in the drop keeps the drop from falling due to the forces of gravity. The substrate and drop are then placed over a pool of crystallization solution. The system is then sealed. Over time, the two solutions equilibrate by diffusion, causing the protein to crystallize. In the microbatch method, polypeptide is mixed with precipitants to achieve supersaturation, and the vessel is then sealed and set aside until crystals appear. In the dialysis method, polypeptide is retained in a sealed dialysis membrane which is placed into a solution containing precipitant. Equilibration across the membrane increases the precipitant concentration, thereby causing the polypeptide to reach supersaturation levels.

Crystals routinely grow in a wide range of temperatures. It is, however, preferred to grow crystals by the hanging drop method at temperatures between about 2° C. and about 26° C., more preferably between about 2° C. to about 8° C., and most preferably at about 4° C.

Crystals of BACE may be grown in either the uncrystallized or apo form, without a bound ligand, or, alternatively, complexed to a ligand, preferably an inhibitor. Each crystal form of BACE (uncomplexed form or complexed form) is useful because both crystal forms can be used to gather knowledge about the structure of BACE and potential ligands of BACE. BACE can be complexed with any ligand, such as OM-99-2 (SEQ ID NO: 15), to form a crystal.

In a preferred embodiment, uncomplexed, refolded processed BACE was crystallized. The crystallization procedures are described in more detail in example 6 below. Briefly, crystallization was carried out at about 4° C. using the hanging drop method. The optimal crystallization conditions included about 13.75% to about 15% PEG3350 and about 0.6 M ammonium iodide at about 4° C.

In another preferred embodiment, refolded processed BACE in the presence of OM-99-2 (SEQ ID NO: 15) was crystallized. The crystallization procedures are described in more detail in example 5 below. Briefly, crystallization was carried out at about 4° C. using the hanging drop method. The optimal crystallization conditions included about 20% PEG3350 and about 0.2 M ammonium tartrate at about 4° C.

Embodiments of the present invention also include crystals comprising BACE polypeptide as disclosed by Vassar et al., (1999) *Science*, 286: 735–741-Genbank Accession No. AF190725; Murphy et al., (2001) *Neuroreport*, 12(3):631–634; Capell et al., (2000) *J. Biol. Chem.*, 275 (40):30849–30854 and Haniu et al., (2000) *J. Biol. Chem.*, 275(28):21099–21106.

Crystallographic Analysis

The crystals of the present invention have a variety of uses. For example, high quality crystals are suitable for X-ray or neutron diffraction analysis, which can be used to determine the three-dimensional structure of BACE, and, in particular, to assist in the identification of the protein's active and effector sites. Knowledge of these sites and solvent accessible residues allow for structure-based design and construction of ligands, agonists and antagonists for BACE.

In addition, crystallization itself can be used as a purification method. In some instances, a polypeptide crystallizes from a heterogeneous mixture. Isolation of such crystals, by filtration and/or centrifugation, followed by redissolution of the polypeptide provides a purified solution suitable for use in growing high-quality crystals, which are preferred for diffraction analysis.

Once a crystal of a polypeptide or protein is grown, the crystal is frozen so that X-ray diffraction data of the crystal can be collected. A crystal of a protein may be frozen by any means in the art. In addition, the freezing process may occur in one step or in several steps. Preferably, the BACE crystal is frozen in two steps. In the first step, the crystal is frozen in a solution including about 20% PEG3350, about 0.48 M ammonium iodide, and about 15% glycerol. In the second step, the crystal is frozen in a solution including about 20% PEG3350, about 0.48 M ammonium iodide, and about 20% glycerol.

One method for determining the three-dimensional structure of a protein from X-ray diffraction data of a protein crystal includes the use of synchrotron radiation, under standard cryogenic conditions. However, alternative methods may also be used. For example, crystals may be characterized using X-rays produced by a conventional source, such as a sealed tube or a rotating anode. Methods of characterization include, but are not limited to, precession photography, oscillation photography and diffractometer data collection.

Preferably, the crystals or the soluble polypeptides which are used to form the crystals exhibit BACE catalytic activity (see above). Most preferably, the BACE crystals include a polypeptide comprising the amino acid sequence set forth in SEQ ID NO: 20 or SEQ ID NO: 22, which is derived from the nucleotide sequence set forth in SEQ ID NO: 1 and expressed in *E. coli* host cells.

An embodiment of the invention provides crystals of BACE polypeptide in the uncomplexed form. Preferably, the BACE polypeptide is derived from humans. Preferably, the BACE polypeptide comprises the amino acid sequence set forth in SEQ ID NO: 22. More preferably, the BACE polypeptide is derived from the nucleotide sequence set forth in SEQ ID NO: 1. Preferably, the BACE crystals effectively diffract X-rays for the determination of the atomic coordinates of BACE to a resolution greater than about 5.0 Å.

Still another embodiment of the invention provides a method for using a crystal of the present invention to obtain detailed three-dimensional structural data and coordinates for uncomplexed BACE, using X-ray crystallography. Preferably, the crystals of uncomplexed BACE are characterized by the structure coordinates set forth in Table 1. More preferably, the crystals of uncomplexed BACE have a space group of C2 with unit cell dimensions of a=236.0 Å, b=103.6 Å, and c=65.0 Å. However, the unit cell dimension values for a, b and c may vary by ±2%. Therefore, the crystals of uncomplexed BACE may have a space group of C2 with unit cell dimensions wherein the value for a may range from about 231.3 Å to about 240.7 Å, the value for b may range from about 101.5 Å to about 105.7 Å, or the value for c may range from about 63.7 Å to about 66.3 Å.

Another embodiment of the invention provides crystals of a protein-ligand complex comprising BACE and a ligand. Preferably, the BACE polypeptide is derived from humans. Preferably, the BACE polypeptide comprises the amino acid sequence set forth in SEQ ID NO: 22. More preferably, the BACE polypeptide is derived from the nucleotide sequence set forth in SEQ ID NO: 1. Preferably, the BACE crystals effectively diffract X-rays for the determination of the atomic coordinates of BACE to a resolution greater than about 5.0 Å.

Yet still another embodiment of the present invention provides a method for using a crystal of the present invention to obtain detailed three-dimensional structural data and coordinates for a protein-ligand complex comprising BACE and a ligand, using X-ray crystallography. Preferably, the crystals of complexed BACE are characterized by the structure coordinates set forth in Table 2. More preferably, the crystals of complexed BACE have a space group of $P2_12_12_1$ with unit cell dimensions of a=86.4 Å, b=89.1 Å, and c=131.3 Å. However, the unit cell dimension values for a, b and c may vary by ±2%. Therefore, the crystals of complexed BACE may have a space group of $P2_12_12$, with unit cell dimensions wherein the value for a may range from about 84.7 Å to about 88.1 Å, the value for b may range from about 87.3 Å to about 90.9 Å, or the value for c may range from about 128.7 Å to about 133.9 Å.

The crystallizable compositions of the present invention are preferably amenable to X-ray crystallography for providing the three-dimensional structure of a BACE polypeptide. Embodiments of the present invention include crystals which effectively diffract X-rays for a determination of the atomic coordinates of BACE to a resolution of greater than about 5.0 Ångströms, e.g., about 4.5 Å, about 4 Å, about 3 Å, about 2.5 Å, about 2 Å, about 1 Å, about 0.5 Å, about 0.1 Å, preferably greater than about 4.0 Ångströms, e.g., about 3 Å, about 2.5 Å, about 2 Å, about 1 Å, about 0.5 Å, about 0.1 Å, more preferably greater than about 2.8 Ångströms, e.g., about 2.5 Å, about 2.2 Å, about 2 Å, about 1 Å, about 0.5 Å, about 0.1 Å, and most preferably greater than about 2.0 Ångströms, e.g., about 1.7 Å, about 1.5 Å, about 1 Å, about 0.5 Å, about 0.1 Å.

As described above, embodiments of the present invention include BACE crystals whose three-dimensional structures are described by the structure coordinates set forth in either Table 1 or Table 2. Likewise, embodiments of the present invention also include crystals that possess structure coordinates which are structurally similar to those set forth in either Table 1 or Table 2. Structural similarity between crystals is discussed in detail below.

The term "structure coordinates" refers to Cartesian coordinates derived from mathematical equations related to the patterns obtained upon diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates for a polypeptide or a protein-ligand complex or a portion thereof is a relative set of points that define a shape in three dimensions. Thus, it is possible that an entirely different set of coordinates could define a similar or identical shape. Moreover, slight variations in the individual coordinates will have little effect on overall shape.

Embodiments of the present invention include crystals exhibiting structure coordinates which are structurally similar to those set forth in either Table 1 or Table 2, but for crystallographic permutations of the structure coordinates, fractionalization of the structure coordinates, additions, subtractions, rotations or translations to sets of the structure coordinates, or any combinations of the above.

Alternatively, modifications in the crystal structure due to mutations, additions, substitutions, and/or deletions of amino acids, or other changes in any of the components that make up the crystal may also account for variations in the structure coordinates. If such variations are within an acceptable standard error, as compared to the structure coordinates set forth in either Table 1 or Table 2, the resulting three-dimensional shape is considered to be the same and, accordingly, the modified crystal is considered to be within the scope of the present invention.

Various computational analyses may be necessary to determine whether a crystal is sufficiently similar to the crystals whose structure coordinates are set forth in either Table 1 or Table 2 as to be considered the same. Such analyses may be carried out in current software applications, such as the Molecular Similarity application of QUANTA (Accelyris, San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is divided into four steps: 1) input the structures to be compared; 2) define the atom equivalences in these structures; 3) perform a fitting operation; and 4) analyze the results.

Each structure is identified by a name. One structure is identified as the target, i.e., the fixed structure; all remaining structures are working structures, i.e., moving structures. Because atom equivalency within QUANTA is defined by user input, for the purpose of this application, we will define equivalent atoms as protein backbone atoms (N, Cα, C and O) for all conserved residues between the two structures being compared.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atoms is an absolute minimum. This number, given in Ångströms, is reported by QUANTA.

The term "root mean square deviation" (RMSD) is a common term in the art which, in general, means the square root of the arithmetic mean of the squares of the deviations from the mean distance of corresponding atoms. It is a way to express the deviation or variation from a trend or object. The term "least squares" refers to a method based on the principle that the best estimate of a value is that in which the sum of the squares of the deviations of observed values is a minimum.

For the purpose of this application, any set of structure coordinates of a molecule that has a RMSD of conserved residue backbone atoms (N, Cα, C, O) of less than about 1.5 Å when superimposed—using backbone atoms—on the relevant structure coordinates set forth in either Table 1 or Table 2 are considered identical and are within the scope of the present invention. Preferably, the root mean square deviation is less than about 1.0 Å. More preferably, the root mean square deviation is less than about 0.5 Å. Most preferably, the root mean square deviation is less than about 0.1 Å.

In a preferred embodiment of the invention, crystallographic analysis of uncomplexed, refolded, processed BACE comprising a polypeptide comprising the amino acid sequence set forth in SEQ ID NO: 22, which was derived from the nucleotide sequence set forth in SEQ ID NO: 1 and expressed in *E. coli* cells, was performed. The crystallographic analysis procedures are described in more detail in example 8 below. Briefly, the uncomplexed BACE crystals of example 6 were transferred to a solution containing about 20% PEG3350, about 0.6 M ammonium iodide and about 15% glycerol, and then frozen in liquid propane. Diffraction data were collected. Data reduction showed diffraction to about 2.2 Å resolution. The crystals had the space group of C2 with unit cell dimensions of a=236.0 Å, b=103.6 Å, and c=65.0 Å. The crystals may be characterized by the structure coordinates set forth in Table 1.

In another preferred embodiment of the invention, crystallographic analysis of refolded, processed BACE comprising a polypeptide comprising the amino acid sequence set forth in SEQ ID NO: 22, which was derived from the nucleotide sequence set forth in SEQ ID NO: 1 and expressed in *E. coli* cells, complexed to OM-99-2 (SEQ ID NO: 15) was performed. The crystallographic analysis procedures are described in more detail in example 7 below. Briefly, the BACE-inhibitor complex crystals of example 5 were transferred to a solution containing about 22% PEG3350, about 0.2 M ammonium tartrate and about 15% PEG400, and then frozen in liquid propane. Diffraction data were collected. Data reduction showed diffraction to about 1.7 Å resolution. The crystals had the space group of $P2_12_12$, with unit cell dimensions of a=86.4 Å, b=89.1 Å, and c=131.3 Å. The crystals may be characterized by the structure coordinates set forth in Table 2.

Uses of Crystals and/or Structure Coordinates

An embodiment of the invention provides a computer comprising the structure coordinates set forth in Table 1. Another embodiment of the invention provides a computer comprising the structure coordinates set forth in Table 2.

In accordance with an embodiment of the invention, the structure coordinates of BACE polypeptide and portions thereof may also be stored in a machine-readable data storage medium. Such data may be used for a variety of purposes, such as drug discovery and X-ray crystallographic analysis of a protein crystal, e.g., for producing a three-dimensional representation of BACE. Accordingly, embodiments of the invention provide machine-readable magnetic data storage media comprising a data storage material encoded with the structure coordinates set forth in either Table 1 or Table 2. The machine-readable magnetic data storage medium may also include any set of structure coordinates of a molecule that has a root mean square deviation of conserved residue backbone atoms (N, Cα, C, O) of less than about 1.5 Å, preferably, less than about 1.0 Å, more preferably less than about 0.5 Å, and most preferably less than about 0.1 Å when superimposed—using backbone atoms—on the relevant structure coordinates set forth in either Table 1 or Table 2.

A computer system, useful in reading the machine readable data storage medium, including a computer comprising a central processing unit (CPU) and a memory storage device, is also within the scope of the present invention. In general, the computer system may be any computer with an operating system, such as MS-DOS, PC-DOS, Windows, OS/2, Unix, Unix variant or MacOS. Particularly preferred computer systems are the Silicon Graphics Octane workstation or Compaq AlphaServer DS20. Other hardware systems and software packages are known to those skilled in the art.

Input hardware coupled to the computer system by input line, may be implemented in a variety of ways. Machine-readable data may be inputted via the use of a modem or modems connected by a telephone line or a dedicated data line. Alternatively, or additionally, the input hardware may comprise CD-ROM drives or disk drives. A keyboard may also be used as an input device.

Output hardware, coupled to the computer system by output lines, may similarly be implemented by conventional devices. By way of example, output hardware may include a display terminal, e.g., a cathode ray tube (CRT), for displaying a graphical representation of the three-dimensional structure of BACE or a portion thereof using a program such as INSIGHT (Accelyris, San Diego, Calif.) or QUANTA as described herein. Output hardware might also include a printer, so that hard copy output may be produced, or a disk drive, to store system output for later use. In preferred embodiments, the computer possesses a display which is displaying a three-dimensional representation of BACE or a fragment or homologue thereof.

In operation, the central processing unit (CPU) coordinates the use of the various input and output devices, coordinates data access from mass storage and access to and from working memory, and determines the sequence of data processing steps. A number of programs may be used to process the machine-readable data. Such programs are discussed in reference to the computational methods of drug discovery, as described herein. Specific references to components of the computer system are included, as appropriate, throughout the following description of the data storage medium.

A magnetic data storage medium can be encoded with machine-readable data by a computer system, as described above. The storage medium may be, for example, a conventional floppy diskette or hard disk, having a suitable substrate, which may be conventional, and a suitable coating, which may be conventional, on one or both sides, containing magnetic domains whose polarity or orientation can be altered magnetically. The magnetic domains of the coating of medium may be polarized or oriented so as to encode, in a manner which may be conventional, machine readable data, such as that described herein, for execution by a system as described herein. The storage medium may also have an opening for receiving the spindle of a disk drive or other data storage device. Alternatively, an optically-readable data storage medium can be encoded with such machine-readable data, or a set of instructions. The medium can be a conventional compact disk read only memory (CD-ROM), or a rewritable medium, such as a magneto-optical disk, which is optically readable and magneto-optically writable, or a CDRW.

In general, in the case of a CD-ROM, as is well known, the disk coating is reflective and is impressed with a plurality of pits to encode the machine-readable data. The arrangement of the pits is read by reflecting laser light off the surface of the coating. A protective coating, which preferably is substantially transparent, is provided on top of the coating.

In general, in the case of a magneto-optical disk, as is well known, the disk coating does not have pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data, as described above.

An embodiment of the present invention provides the use of structure-based drug design techniques to design, select, and synthesize chemical entities, including inhibitory compounds, that are capable of binding to BACE. Also, embodiments of the present invention provide de novo and iterative drug design methods that can be used to develop drugs from the structures of the BACE crystals of the present invention.

One particularly useful structure-based drug design technique enabled by the present invention is rational drug design. Rational drug design is a method for optimizing associations between a polypeptide and a ligand by determining and evaluating the three-dimensional structures of successive sets of protein/ligand complexes. The ligand can be any sort of compound, including, but not limited to a chemical, polypeptide, or modified polypeptide.

Those skilled in the art will appreciate that association of natural ligands or substrates with the binding pockets of their corresponding receptors or enzymes is the basis of many biological mechanisms of action. The term "binding pocket", as used herein, may refer to any region of a molecule or molecular complex, that, as a result of its shape, favorably associates with another chemical entity or compound. Similarly, drugs may exert their biological effects through association with the binding pockets of receptors and enzymes. Such association may occur with all or any part of the binding pockets.

An understanding of such associations will help lead to the design of drugs having more favorable associations with the target enzyme, and thus, improved biological effects. For example, associations between a polypeptide and ligand are optimized by filling the space in the binding pocket between the polypeptide and the ligand, yet not allowing the ligand to overlap the polypeptide. Therefore, information about where and how to alter a ligand to achieve increased binding, increased potentcy, etc., is obtained. Preferably, this analysis is performed in conjunction with computer modeling, i.e., the use of computers to visualize and aid in understanding the associations between a polypeptide and a ligand. Therefore, this information is valuable in designing potential enzyme ligands, such as inhibitors of BACE.

In iterative structure-based drug design, crystals of a series of protein/ligand complexes are obtained and then the three-dimensional structure of each complex is solved. Such an approach provides insight into the association between the proteins and ligands of each complex. This may be accomplished by selecting ligands that bind to the protein, obtaining crystals of a new complex, solving the three-dimensional structure of the complex, and comparing the associations between the new complex and previously solved complex. By observing how changes in the ligand affected the protein/ligand associations, these associations may be optimized. Preferably, this is performed in conjunction with computer modeling.

In some cases, iterative structure-based drug design is carried out by forming successive protein/ligand complexes and then crystallizing each new complex. This method can be time consuming because it takes approximately 7–21 days to grow a crystal. Alternatively, a pre-formed protein crystal may be soaked in the presence of a ligand, thereby forming a protein/ligand complex and obviating the need to crystallize each individual protein/ligand complex. This process usually only takes about 1 day to perform because the crystal is already formed. As used herein, the term "soaked" refers to a process in which the crystal is transferred to a solution containing the ligand of interest. Another method involves using a co-crystal, a crystal of a protein bound to a first ligand. The co-crystal is then soaked in the presence of a potential ligand. The potential ligand then displaces the first ligand from the crystal. Similarly, this process usually takes about 1 day to perform. Advantageously, BACE crystals provided by this invention may be soaked in the presence of a ligand, such as BACE inhibitors, substrates or other ligands to provide novel BACE/ligand crystal complexes.

For example, a preferred embodiment of the invention provides a method for identifying a ligand that binds to β-secretase. In this embodiment, about 16 mg/ml of β-secretase comprising the amino acid sequence set forth in SEQ ID NO: 22 is added to about 1.5 to about 5.0 molar ratio of a ligand to form a mixture. Preferably, the β-secretase is derived from human. More preferably, the β-secretase is expressed in E. coli cells and derived from the nucleotide sequence set forth in SEQ ID NO: 1. The mixture is then crystallized to form a crystal; and X-ray diffraction analysis is performed on the crystal.

Another preferred embodiment of the invention provides a method for identifying a ligand that binds to β-secretase comprising soaking a BACE crystal in a solution comprising a ligand and performing X-ray diffraction on the crystal. Preferably, the crystal is made by adding about 16 mg/ml of a polypeptide comprising the amino acid sequence set forth in SEQ ID NO: 22 to a crystallization solution, the solution comprising about 13.75% to about 15% PEG3350 and about 0.6 M ammonium iodide, and crystallizing the solution at about 4° C. using a hanging drop method. Preferably, the β-secretase is derived from human. More preferably, the β-secretase is expressed in E. coli cells and derived from the nucleotide sequence set forth in SEQ ID NO: 1.

Yet another preferred embodiment of the invention provides another method for identifying a ligand that binds to β-secretase. This embodiment involves preparing a mixture of β-secretase with a potential ligand comprising adding a first ligand to about 16 mg/ml of β-secretase comprising the amino acid sequence set forth in SEQ ID NO: 22; crystallizing the mixture to form a crystal; soaking the crystal in a solution comprising a potential ligand, wherein the potential ligand displaces the first ligand from the crystal; and performing X-ray diffraction on the crystal. Preferably, the β-secretase is derived from human. More preferably, the β-secretase is expressed in E. coli cells and derived from the nucleotide sequence set forth in SEQ ID NO: 1.

Another embodiment of the invention provides a method for identifying a ligand that binds to β-secretase by obtaining a set of atomic coordinates defining the three-dimensional structure of a crystal of an uncomplexed, processed β-secretase polypeptide expressed in E. coli that effectively diffracts X-rays for determination of the atomic coordinates of the β-secretase to a resolution of greater than about 5.0 Å; selecting a ligand by performing rational drug design with the set of atomic coordinates obtained above; contacting the ligand to the β-secretase; and detecting binding of the ligand to the β-secretase. Preferably, the selection is performed in conjunction with computer modeling.

The extent of binding may be determined by a standard binding assay. For example, a substrate of BACE, such as APP, may be attached to a solid support. Methods for attaching polypeptides to solid supports are known in the art. The substrate may then be labeled. The solid support may be washed to remove unreacted species. A solution containing BACE and/or potential inhibitor may then be contacted to the support. The solid support may then be washed again to remove any fragments of the substrate that were cleaved by BACE. The amount of labeled substrate remaining on the solid support may then be determined.

Alternative embodiments of the invention provide methods for identifying inhibitors, or antagonists, of β-secretase. An embodiment of the invention provides a method for identifying a β-secretase antagonist comprising the steps of: (a) selecting a potential antagonist by performing rational drug design using the three-dimensional structure of a crystal of a β-secretase polypeptide; (b) contacting the potential antagonist with β-secretase; and (c) detecting binding of the potential antagonist to the β-secretase, wherein an antagonist is identified on the basis of its ability to inhibit the catalytic activity of the β-secretase. Preferably, the β-secretase is expressed in E. coli cells. Preferably, the β-secretase comprises a polypeptide comprising the amino acid sequence set forth in SEQ ID NO: 22. It is also preferable that the crystal effectively diffracts X-rays for a determination of atomic coordinates of the polypeptide to a resolution of greater than about 5.0 Å.

Another embodiment of the invention provides a method for identifying an inhibitor of β-secretase comprising: (a) obtaining a set of atomic coordinates from a crystal defining the three-dimensional structure of a β-secretase polypeptide; (b) selecting a potential inhibitor by performing rational drug design with the set of atomic coordinates obtained above; (c) contacting the potential inhibitor with a β-secretase protein; and (d) measuring the activity of the protein, wherein the potential inhibitor is identified when there is a decrease in activity of the β-secretase in the presence of the inhibitor as compared to the activity of β-secretase in the absence of the potential inhibitor. Preferably, the β-secretase polypeptide is uncomplexed and expressed in E. coli cells. In addition, it is preferable that the β-secretase comprises a polypeptide comprising the amino acid sequence set forth in SEQ ID NO: 22. Furthermore, it is preferable to perform the selecting step in conjunction with computer modeling. Most preferably, the method provides a crystal having a space group of C2 with unit cell dimensions of a=236.0 Å, b=103.6 Å and c=65.0 Å. Alternatively, the method may provide a crystal having a space group of C2 with unit cell dimensions wherein a ranges from about 231.3 Å to about 240.7 Å, b ranges from about 101.5 Å to about 105.7 Å, and c ranges from about 63.7 Å to about 66.3 Å.

A further embodiment of the invention provides a method for identifying a potential inhibitor of β-secretase comprising the steps of: (a) viewing a three-dimensional structure of the β-secretase; (b) employing the three-dimensional structure to design or select the potential inhibitor; (c) synthesizing the potential inhibitor; and (d) contacting the potential inhibitor with the β-secretase in the presence of a substrate to determine the ability of the potential inhibitor to inhibit the β-secretase. Preferably, the β-secretase is defined by the atomic coordinates set forth in Table 1.

Another aspect of the invention is the use of the structure coordinates and atomic details of BACE or mutants or homologues or co-complexes thereof to design, evaluate computationally, synthesize and use inhibitors (antagonists) of BACE that prevent or treat the undesirable physical and pharmacological properties of Alzheimer's Disease. These inhibitors (antagonists) may be used in the treatment of Alzheimer's Disease.

In an embodiment of the invention, the structure coordinates set forth in either Table 1 or Table 2 may be used to aid in obtaining structural information about another crystallized molecule or molecular complex. This may be achieved by any of a number of well-known techniques, including molecular replacement.

In another embodiment of the invention, the structure coordinates set forth in either Table 1 or Table 2 may also be used for determining at least a portion of the three-dimensional structure of molecules or molecular complexes which contain at least some structurally similar features to BACE. In particular, structural information about another crystallized molecule or molecular complex may be obtained by well-known techniques, including molecular replacement.

Therefore, embodiments of the invention provide methods for utilizing molecular replacement to obtain structural information about a crystallized molecule or molecular complex, whose structure is unknown, comprising the steps of generating an X-ray diffraction pattern from the crystallized molecule or molecular complex and applying crystallographic phases derived from at least a portion of the structure coordinates set forth in either Table 1 or Table 2 to the X-ray diffraction pattern to generate a three-dimensional electron density map of the molecule or molecular complex whose structure is unknown.

Once the structure coordinates of a protein crystal have been determined, they are useful in solving the structures of other crystals. In addition, the structure of BACE homologues may be determined from the structure coordinates of the present invention. For example, polypeptides may be crystallized and their structure elucidated by, for example, difference Fourier techniques and molecular replacement.

By using molecular replacement, all or part of the structure coordinates of a BACE polypeptide provided by this invention, and set forth in either Table 1 or Table 2, can be used to determine the previously unknown structure of a crystallized molecule or molecular complex more quickly and efficiently than attempting to determine such information ab initio.

Molecular replacement provides an accurate estimation of the phases for an unknown structure. Phases are a factor in equations used to solve crystal structures that cannot be measured experimentally. Obtaining accurate values for the phases, by methods other than molecular replacement, is a time-consuming process. However, when the crystal structure of a protein containing a homologous portion has been solved, the phases from the known structure may provide a satisfactory estimate of the phases for the unknown structure.

Thus, this method involves generating a preliminary model of a molecule or molecular complex, whose structure coordinates are unknown, by orienting and positioning the relevant portion of the BACE crystal according to either Table 1 or Table 2 within the unit cell of the crystal of the unknown molecule or molecular complex so as to best account for the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions", in *Meth. Enzymol.*, 115: 55–77 (1985); Rossman, ed., "The Molecular Replacement Method", *Int. Sci. Rev. Ser., No.* 13, Gordon & Breach, New York (1972)).

Phase information from the structure coordinates of the present invention may be used to elucidate the structure of other crystals. For example, the structure of BACE in complex with other atoms or molecules may be elucidated. Such complexes include, for example, those containing atoms soaked into or co-crystallized within the crystal lattice. Other structures which can be elucidated using the phase information of the present invention include, for example, other proteases or homologues, or mutants thereof, having sufficient three-dimensional structure similarity to BACE complex as to be solved using molecular replacement. Examples of such proteins include, but are not limited to, cathepsin D, renin and pepsin. Also, these protein molecules in a complex with a small molecule substrate(s), inhibitor(s), transition state analog(s), product(s) or analog(s) of any of these may also be solved using the phase information of the present invention. Other complexes whose structure can be elucidated from the phase information of the present invention include BACE complexed with an inhibitor. Complexes containing a combination of the above molecules may also be solved using the phase information of the present invention.

The structure of any portion of any crystallized molecule or molecular complex that is sufficiently homologous to any portion of the BACE protein can be solved by this method. The difference Fourier method simply calculates an electron density map using phases calculated from the structure coordinates and observed diffraction amplitudes from a crystal of an unknown structure. This method is often used to solve structures of protein/ligand complexes where the ligand is small and does not affect the crystal form significantly.

In a preferred embodiment, the method of molecular replacement is utilized to obtain structural information about a molecule wherein the molecule comprises a BACE polypeptide complex. The structure coordinates of BACE provided by this invention are particularly useful in solving the structure of other crystal forms of BACE polypeptide complexes. This approach enables the determination of the optimal sites for interaction between chemical entities, including interaction of candidate inhibitors with BACE.

BACE crystals may be studied using well-known X-ray diffraction techniques and may be refined versus X-ray data to 3 Å resolution or better to an $R_{free}$ value of about 0.40 or less using computer software such as X-PLOR (Yale University, 1992, distributed by Molecular Simulations, Inc.; see e.g., Blundell & Johnson, supra; *Meth, Enzymol.*, vol. 114 & 115, H. W. Wyckoff et al., eds., Academic Press (1985)). This information may be used to optimize known BACE inhibitors and to design new BACE inhibitors.

EXAMPLES

The present invention may be better understood by reference to the following non-limiting examples, which are provided as exemplary of the invention. The following examples are presented in order to more fully illustrate embodiments of the invention, and should in no way be construed as limiting the broad scope of the invention.

Example 1

Cloning of β-Secretase

Rather than cloning an entire β-secretase gene from an organism, a synthetic optimized nucleic acid sequence of human brain β-secretase was generated. The human brain β-secretase gene was optimized by polymerase chain reaction (PCR) such that the first approximately one-third of the gene was modified.

Human brain β-secretase cDNA contains approximately 70% GC content at the N-terminus, approximately the first 1–420 bp (base pairs). This attribute may be responsible for DNA rearrangement observed during recombinant DNA manipulation and overall low expression levels of BACE. Therefore, the sequence analysis programs Oligo 6 (Molecular Biology Insights, Inc., Cascade, Colo.) and GCG 6 (Genetics Computer Group, version 6, Madison, Wis.) were used to redesign the DNA sequence to decrease the GC content to about 50%, to optimize the codon usage for *E. coli* expression, and to keep the resulting protein sequence unchanged from the native sequence. Decreasing the GC content of the nucleotide sequence reduces the potential for secondary structure formation of mRNA, which results in decreased levels of protein expression. The codon usage was optimized by using codons that are preferred in *E. coli*. Preferred codons are determined by sequencing genomic DNA of the host organism and applying statistical analysis to determine which codons are preferred in nature.

A total of 11 oligonucleotides were synthesized and purified by polyacrylamide gel electrophoresis (PAGE). The oligonucleotides are listed in the 5' to 3' direction.

1) Bwy1F (SEQ ID NO: 3) ATGGCTCMGCTTTGCCATG-GTTATTGTTGTGGATGGGTGCTGGTGTTTTACCTG CACATGGTACTCAGCACGGTATCCG

2) Bwy2F (SEQ ID NO: 4) TTTACCTTTACGTTCTGGTT-TAGGTGGTGCACCATTAGGTTTACGTTTACCTCGTG AGACTGACGAAGAGCCAGA

3) Bwy3F (SEQ ID NO: 5) CAGGTCGTCGTGGT-TCTTTTGTTGAGATGGTTGACMCT-TACGTGGTMGTCTGG TCAGGGTTACTACGT-TGAGATGACT

4) Bwy4F (SEQ ID NO: 6) GTTGGTTCTCCACCACA-GACTTTAMCATCTTAGTTGATACTGGT-TCTTCTAACTT TGCAGTTGGTGCAGCACCACACCC

5) Bwy5F (SEQ ID NO: 7) ATTCTTACATCGTTACTAC-CAGCGTCAGTTATCTTCTACTTACCGT-GACTTACGTA AGGGTGTTTATGTTCCAT

6) Bwy6R (SEQ ID NO: 8) ACCTMTGGTGCACCAC-CTAAACCAGMCGTAAAGGTAMCGGATAC-CGTGCTG AGTACCATGTGCAGGTMMCACCAGC

7) Bwy7R (SEQ ID NO: 9) AAGTTGTCAACCATCTCAA-CAAGAACCACGACGACCTGGCTCCTCTGGCTCTT CGTCAGTCTCACGAGGTAAACGTAA

8) Bwy8R (SEQ ID NO: 10) TATCAACTAAGATGTT-TAAAGTCTGTGGTGGAGAACCAACAGT-CATCTCAACGTA GTAACCCTGACCAGACTTAC-CACGT

9) Bwy9R (SEQ ID NO: 11) AGTAGAAGATAACT-GACGCTGGTAGTAACGATGTAA-GAATGGGTGTGGTGCTGC ACCAACTGCAAAGTTA-GAAGAACCAG

10) Bwy10R (SEQ ID NO: 12) CTCACCTTCCCACTTAC-CCTGAGTGTATGGAACATAAACACCCT-TACGTAAGTCA CGGA

11) Bs10R (SEQ ID NO: 13) ACGGATCCTTAGTGGTG-GTGGTGGTGGTGGCTCCCTGACTCATCT-GTCTGTGGA ATGTTGTA

A three-stage PCR strategy was adopted to construct the soluble synthetic β-secretase gene (SEQ ID NO: 17).

In stage 1, two separate half PCR reactions were assembled in two 0.5 ml PCR tubes. Reaction mix 1 contained the primers Bwy1F (SEQ ID NO: 3), Bwy2F (SEQ ID NO: 4), Bwy3F (SEQ ID NO: 5), Bwy6R (SEQ ID NO: 8), Bwy7R (SEQ ID NO: 9), and Bwy8R (SEQ ID NO: 10) at a final concentration of 2.5 µM. Reaction mix 2 contained the primers Bwy4F (SEQ ID NO: 6), Bwy5F (SEQ ID NO: 7), Bwy9R (SEQ ID NO: 11), and Bwy10R (SEQ ID NO: 12) at the final concentration of 2.5 µM.

Both reaction mixes were heated at 95° C. for 3 minutes, and then cooled to 4° C. at a ramp rate of −5° C./min. Then, using pfu DNA polymerase (Stratagene, La Jolla, Calif.), 25 thermal cycles of PCR were performed at 94° C. for one minute, 55° C. for 1 minute, and 72° C. for one minute. The reaction generated two half fragments, PM1 and PM2. The two PCR products were separated using agarose gel electrophoresis and subsequently purified using Gel Extraction Kit (Qiagen, Valencia, Calif.) according to the manufacturer's instructions.

In stage 2, the synthetic fragment of 1–420 bp of β-secretase (SEQ ID NO: 1) was amplified using the following PCR reaction mix: 50 ng of PM1, 50 ng of PM2, 0.2 µM Bwy1F (SEQ ID NO: 3), 0.2 µM Bwy10R (SEQ ID NO: 13), 0.5 mM dNTP, 5 µl of 10× reaction buffer, 1 U of pfu DNA polymerase (Stratagene, La Jolla, Calif.), and enough dH$_2$O to adjust the final reaction volume to 50 μl. As in stage 1, the mix was heated at 95° C. for 3 minutes, and then cooled to 4° C. at a ramp rate of −5° C./min. Then, using pfu DNA polymerase (Stratagene, La Jolla, Calif.), 25 thermal cycles of PCR were performed at 94° C. for one minute, 55° C. for 1 minute, and 72° C. for one minute. The amplified product of the PCR reaction, syn420 (SEQ ID NO: 1), was purified from the agarose gel using Gel Extraction Kit (Qiagen, Valencia, Calif.).

In stage 3, the synthetic soluble β-secretase, nucleotides 1–1362 bp (SEQ ID NO: 17), was amplified. The PCR reaction mix contained: 50 ng of syn420 (SEQ ID NO: 1), 50 ng of β-secretase cDNA (1–1362 bp), 0.2 μM Bwy1F (SEQ ID NO: 3), 0.2 μM Bs10R (SEQ ID NO: 13), 0.5 mM dNTP, 5 μl 10× reaction buffer, 1 U pfu DNA polymerase (Stratagene, La Jolla, Calif.), and enough dH$_2$O to adjust the final volume of the reaction mix to 50 μl. The PCR reaction was initiated with a hot start at 95° C. for 3 minutes, followed by a quick cooling to 4° C. Then, using pfu DNA polymerase (Stratagene, La Jolla, Calif.), 25 thermal cycles of PCR were performed at 94° C. for one minute, 55° C. for 1 minute, and 72° C. for 3.5 minutes. The pfu DNA polymerase was used because of its proofreading activity and its fidelity. The amplified DNA fragment of 1.3 kb (SEQ ID NO: 17) was separated using agarose gel electrophoresis and subsequently purified using Gel Extraction Kit (Qiagen, Valencia, Calif.) according to the manufacturer's instructions.

The resulting fragment, synthetic soluble β-secretase (1–1362 bp) (SEQ ID NO: 17) was inserted into the Topo TA cloning vector (Invitrogen, Carlsbad, Calif.) between the T overhangs. Using the DNA from the resulting construct, expression studies were accomplished by the subcloning of amino acid residues 14–454 (AGV . . . DEST) and 22–454 (TQH . . . DEST) into the BamH1 site of pET11a (Novagen, Madison, Wis.).

Example 2

Refolding and Purification of α-Secretase

Synthetic β-secretase (SEQ ID NO: 18) was overexpressed in BL21(DE3)Star cells (Invitrogen, Carlsbad, Calif.). The β-secretase polypeptides formed inclusion bodies in the cytoplasm of the cells. The cells were lysed and the inclusion bodies were purified by passing the cell lysate over a 27% sucrose cushion. The resulting inclusion bodies were solubilized at 2 mg/ml in 50 mM CAPS pH 10.7, 8 M urea and 50 mM β-Mercaptoethanol at room temperature. The solution was then rapidly diluted 100 fold into rapidly stirring water at room temperature. The pH of the solution was subsequently adjusted to 8.7 and then the solution was slowly stirred at room temperature for four hours.

Use of the optimized nucleic acid sequence (SEQ ID NO: 17) resulted in the expression of BACE polypeptide that is about 4× higher than the wild-type gene.

Subsequently, reshuffling agents were added to the solution. The standard condition contained 1 mM reduced glutathione, 0.1 mM oxidized glutathione, and 1 mM cysteine. However, adjustments in the above reshuffling ratios improved the efficiency of refolding. For example, the amount of cysteine was fixed while the amounts of reduced and oxidized glutatione was varied. Activity comparisons of refolds, a way of monitoring the efficiency of refolding, indicated that at day three post refold, 0.5 mM reduced glutathione: 0.5 oxidized glutathione resulted in an 18× increase in activity while 0.1 mM reduced glutathione: 1 mM oxidized glutathione resulted in an 11× increase over the control condition. Although these conditions resulted in faster folding, the final differences with respect to the control at two weeks was 6× and 4×, respectively.

After the reshuffling agents were added, the solution was further incubated at room temperature for four hours. The pH of the solution was then either maintained at 8.7 or reduced to 4.0 to facilitate refolding of the protease.

Activity plateaus were reached within three to five days. Upon obtaining maximal activity, the solution was concentrated one thousand fold and then subjected to a Superdex 200 gel filtration column (Highload, 26/60, Amersham Pharmacia, Piscataway, N.J.) that was equilibrated with 50 mM Tris pH 8.0 with 80 mM urea. The active fractions were pooled and then loaded onto a Resource Q column (Amersham Pharmacia, Piscataway, N.J.) that was equilibrated with 50 mM Tris pH 8.0 with 80 mM urea. Fractions were then eluted over 40 column volumes with a final gradient concentration of 50 mM Tris pH 8.0, 80 mM urea and 500 mM NaCl.

Example 3

Processing of β-Secretase

Processing occurred by one of two methods. First, purified β-secretase (SEQ ID NO: 18) was exchanged into 20 mM Hepes pH 7.5 and 150 mM NaCl, and then concentrated to 5 mg/ml and incubated at 4° C. for two weeks. This was the processing method used to generate BACE polypeptide for crystallization. Alternatively, purified β-secretase (SEQ ID NO: 18) was exchanged into 20 mM Hepes pH 7.5 and 150 mM NaCl, and then concentrated to 15 mg/ml and incubated at room temperature for 72 hours. The concentrations were proposed in order to drive intermolecular interactions, i.e., to promote a trans cleavage event. The times were determined by monitoring processing by SDS-PAGE.

Following trans-cleavage processing (determined by concentration dependence), which resulted in approximately amino acids 22–45 being removed, N-terminal sequencing (equal molar ratios of LRLPRE . . . :LPRE . . . ) and mass spectrometry were conducted to confirm completion of propeptide removal and to ensure that no C-terminal truncations took place. Trans cleavage processing means proteolysis occurring in an intermolecular fashion, one enzyme "chewing" on a neighboring enzyme rather than itself. In this example, it refers to the ability of one BACE molecule to proteolyze another with a suitable sequence for cleavage, e.g., removal of a propeptide. The equal molar ratios of LRLPRE . . . (SEQ ID NO: 20):LPRE . . . (SEQ ID NO: 22) showed where the propeptide is processed, and the ratios indicate the cut is a mixture of two species.

Upon completion of processing, the sample was applied to a Superdex 200 column (HighLoad, 26/60, Amersham Pharmacia) that was equilibrated in 20 mM Hepes pH 7.5 and 150 mM NaCl. The active fractions were then pooled and concentrated to 16 mg/ml for crystallization trials.

Example 4

Enzymatic Activity of Refolded β-Secretase

To assess the functionality of β-secretase refolded from *E. coli* overexpression, a high performance liquid chromatography (HPLC) was developed using a peptide substrate derived from the sequence of Swedish amyloid precursor protein. The substrate KSEVNLDAEFRK (SEQ ID NO: 16) was used with reverse phase chromatography and was determined to be a suitable substrate for β-secretase with a specificity constant ($K_{cat}/K_m$) of $1800\pm100$ $M^{-1}s^{-1}$. The substrate (SEQ ID NO: 16) is cleaved between amino acid residues L and D. The activity of this refolded β-secretase with this substrate sequence is consistent with β-secretase derived from other expression systems (Lin, Xinli et al., "Human aspartic protease mamapsin 2 cleaves the β-secretase site of β-amyloid precursor protein", Proceedings Nat. Acad. Sci., vol. 97, no. 4, pp. 1456–1460 (2000); Mallender, William M. et al., "Characterization of Recombinant, Soluble β-Secretase from an Insect Cell Expression System", Mol. Pharm., vol. 59, no. 3, pp. 619–626 (2001)) and confirms that this form of refolded β-secretase is enzymatically active.

Example 5

Crystallization of Refolded Processed β-Secretase in the Presence of Inhibitor

The refolded processed BACE was complexed with OM-99-2 (SEQ ID NO: 15), an inhibitor of BACE, at a 1:5 molar ratio. OM-99-2 (SEQ ID NO: 15) was purchased from Bachem Bioscience Inc. (King of Prussia, Pa.), catalog # H-5108, and is represented by the structure:

Example 6

Crystallization of Apo Refolded Processed β-Secretase

Apo BACE was screened for crystallization using standard screens purchased from Hampton Research and Emerald Biostructures, Bainbridge Island, Wash. Crystallization trials were carried out at 4° C. using the hanging drop method. The drops consisted of 1 μl of reservoir plus 1 μl of apo BACE. Crystals were obtained in condition #12 of the PEG/ION screen from Hampton Research, Laguna Niguel, Calif. PEG/ION screen condition #12 includes 0.2 M ammonium iodide and 20% PEG3350. The crystallization condition from #12 was optimized by varying the concentrations of salt and PEG. This yielded the optimal conditions of 15% PEG3350 and 0.6 M ammonium iodide at 4° C.

Example 7

Crystallographic Analysis of β-Secretase Crystallized in the Presence of Inhibitor The BACE inhibitor complex crystals of Example 5 above were transferred to a solution containing 20%

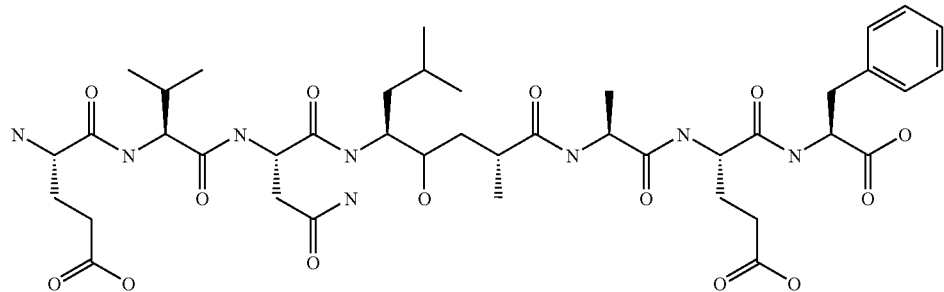

It should be noted that OM-99-2 (SEQ ID NO: 15) is a transition state mimetic that is also characterized by the structure EVN{(2R,4S,5S)-5-amino-4-hydroxy-2,7-dimethyl-octanoyl}AEF.

The complex is then incubated on ice for 5 minutes. The BACE-inhibitor complex was screened for crystallization using standard screens purchased from Hampton Research, Laguna Niguel, Calif., and Emerald Biostructures, Bainbridge Island, Wash. Crystallization trials were carried out at 4° C. using the hanging drop method. The drops consisted of 1 μl of reservoir plus 1 μl of the BACE-inhibitor complex. Crystals were obtained in conditions #12, #37 and #38 of the PEG/ION screen from Hampton Research, Laguna Niguel, Calif. PEG/ION screen condition #12 includes 0.2 M ammonium iodide and 20% PEG3350. PEG/ION screen condition #37 includes 0.2 M potassium sodium tartrate tetrahydrate and 20% PEG3350. PEG/ION screen condition #38 includes 0.2 M di-ammonium tartrate and 20% PEG3350. The crystallization condition from #38 was optimized by varying the concentrations of the salt and PEG. This yielded the optimal conditions of 20% PEG3350 and 0.2 M di-ammonium tartrate at 4° C.

PEG3350, 0.2 M ammonium tartrate and 15% PEG400, and then frozen in liquid propane. Diffraction data was collected on a Raxis IV detector, purchased from Rigaku/MSC, The Woodlands, Tex., equipped with osmic focusing mirrors. Two hundred fifteen (215) contiguous 0.5° oscillation images were collected with an exposure time of 6 minutes each. Data reduction with HKL2000 showed diffraction to 1.7 Å resolution and a 6.5% R-sym. The data were 93% complete with a 4.4 fold multiplicity. The crystals had the space group of $P2_12_12$, with a unit cell of dimensions of a=86.4 Å, b=89.1 Å, and c=131.3 Å. The structure was solved using molecular replacement, as implemented in CCP4 (Collaborative Computational Project, Number 4, 1994, "The CCP4 Suite: Programs for Protein Crystallography", Acta Cryst, D50, pp. 760–763) using 1FKN, a published BACE crystal structure from the PDB database, as the search model. There are two molecules in the asymmetric unit. There is clear density for the protein. Refinement was carried out with CNX (Accelrys, San Diego, Calif.) and yielded a final R of 0.18 and a $R_{free}$ of 0.21.

Example 8

Crystallographic Analysis of Uncomplexed β-Secretase

The uncomplexed BACE crystals of Example 6 above were transferred to a solution containing 20% PEG3350, 0.6 M ammonium iodide and 15% glycerol, and then frozen in liquid propane. Diffraction data were collected at the Industrial Macromolecular Crystallography Association, Argonne, Ill., beamline located at the Advanced Photon Source. Diffraction data was collected on a Q210 detector, purchased from ADSC, Poway, Calif. Four hundred (400) contiguous 0.5° oscillation images were collected with an exposure time of 2 seconds each. Data reduction with HKL2000, HKL Research, Inc., Charlottesville, Va., showed diffraction to 2.2 Å resolution and a 6.5% R-sym. The data were 99.8% complete with a 4.1 fold multiplicity. The crystals had the space group of C2 with a unit cell of dimensions of a=236.0 Å, b=103.6 Å, and c=65.0 Å. The structure was solved using molecular replacement, as implemented in CCP4 (Collaborative Computational Project, Number 4, 1994, "The CCP4 Suite: Programs for Protein Crystallography", Acta Cryst., D50, 760–763) using 1FKN, a published BACE crystal structure from the Protein Data Bank database as the search model. There are three molecules in the asymmetric unit. There is clear density for the protein. Refinement with CNX (Accelrys, San Diego, Calif.) yielded an R factor of 25.5% and an $R_{free}$ of 29.7%.

TABLE 1

Structure Coordinates for uncomplexed BACE

The structure coordinates for uncomplexed BACE (SEQ ID NO: 20 and 22 wherein disordered residues are not shown) are set forth below.
There are three molecules: A, B and C.
"Res" refers to the amino acid whose atomic coordinates have been determined.
"At" refers to the atom, of the corresponding residue, whose coordinates have been determined.
"C" refers to the chain identifier.
"#" refers to the amino acid number of the corresponding residue.
"X", "Y" and "Z" refer to the crystallographically determined atomic position determined for each atom (multiplied by a factor of 10).
"B" refers to the thermal factor that measures movement of the atom around its atomic center (multiplied by a factor of 10).
Notes: All occupancies are set to 1.0
A, B and C refer to protein molecules A and B and C
W refers to water
I refers to ordered iodine atoms

| Res | At  | C | #  | X   | Y    | Z   | B  |
|-----|-----|---|----|-----|------|-----|----|
| GLY | C   | A | 56 | 920 | −261 | 251 | 42 |
| GLY | O   | A | 56 | 932 | −259 | 248 | 43 |
| GLY | N   | A | 56 | 908 | −281 | 260 | 42 |
| GLY | CA  | A | 56 | 916 | −270 | 263 | 43 |
| ARG | N   | A | 57 | 910 | −256 | 245 | 41 |
| ARG | CA  | A | 57 | 912 | −248 | 233 | 41 |
| ARG | CE  | A | 57 | 898 | −243 | 227 | 42 |
| ARG | CG  | A | 57 | 899 | −238 | 213 | 43 |
| ARG | CD  | A | 57 | 897 | −249 | 203 | 44 |
| ARG | NE  | A | 57 | 887 | −246 | 193 | 45 |
| ARG | CZ  | A | 57 | 883 | −254 | 183 | 45 |
| ARG | NH1 | A | 57 | 888 | −266 | 182 | 45 |
| ARG | NH2 | A | 57 | 874 | −250 | 174 | 46 |
| ARG | C   | A | 57 | 920 | −236 | 235 | 40 |
| ARG | O   | A | 57 | 917 | −227 | 243 | 40 |
| GLY | N   | A | 58 | 932 | −235 | 229 | 38 |
| GLY | CA  | A | 58 | 941 | −224 | 230 | 36 |
| GLY | C   | A | 58 | 942 | −217 | 217 | 34 |
| GLY | O   | A | 58 | 948 | −206 | 216 | 33 |
| SER | N   | A | 59 | 937 | −223 | 206 | 32 |
| SER | CA  | A | 59 | 938 | −217 | 193 | 31 |

TABLE 1-continued

Structure Coordinates for uncomplexed BACE

| Res | At  | C | #  | X   | Y    | Z   | B  |
|-----|-----|---|----|-----|------|-----|----|
| SER | CE  | A | 59 | 947 | −226 | 184 | 30 |
| SER | CG  | A | 59 | 948 | −221 | 171 | 30 |
| SER | C   | A | 59 | 924 | −216 | 187 | 30 |
| SER | O   | A | 59 | 918 | −226 | 184 | 29 |
| PHE | N   | A | 60 | 920 | −204 | 184 | 29 |
| PHE | CA  | A | 60 | 907 | −202 | 178 | 29 |
| PHE | CB  | A | 60 | 898 | −193 | 186 | 28 |
| PHE | CG  | A | 60 | 896 | −198 | 200 | 28 |
| PHE | CD1 | A | 60 | 906 | −198 | 210 | 28 |
| PHE | CD2 | A | 60 | 883 | −203 | 204 | 27 |
| PHE | CE1 | A | 60 | 904 | −203 | 223 | 27 |
| PHE | CE2 | A | 60 | 881 | −208 | 217 | 27 |
| PHE | CZ  | A | 60 | 891 | −208 | 226 | 27 |
| PHE | C   | A | 60 | 909 | −196 | 164 | 29 |
| PHE | O   | A | 60 | 906 | −184 | 162 | 28 |
| VAL | N   | A | 61 | 914 | −204 | 155 | 29 |
| VAL | CA  | A | 61 | 917 | −200 | 141 | 30 |
| VAL | CB  | A | 61 | 923 | −212 | 132 | 30 |
| VAL | CG1 | A | 61 | 938 | −214 | 136 | 30 |
| VAL | CG2 | A | 61 | 915 | −224 | 135 | 30 |
| VAL | C   | A | 61 | 906 | −193 | 133 | 29 |
| VAL | O   | A | 61 | 909 | −184 | 126 | 29 |
| GLU | N   | A | 62 | 894 | −197 | 135 | 29 |
| GLU | CA  | A | 62 | 883 | −191 | 128 | 29 |
| GLU | CB  | A | 62 | 870 | −199 | 129 | 30 |
| GLU | CG  | A | 62 | 868 | −210 | 118 | 30 |
| GLU | CD  | A | 62 | 878 | −221 | 120 | 30 |
| GLU | OE1 | A | 62 | 887 | −223 | 111 | 30 |
| GLU | OE2 | A | 62 | 878 | −227 | 131 | 31 |
| GLU | C   | A | 62 | 880 | −176 | 133 | 29 |
| GLU | O   | A | 62 | 876 | −168 | 125 | 29 |
| MET | N   | A | 63 | 883 | −174 | 145 | 29 |
| MET | CA  | A | 63 | 880 | −160 | 151 | 29 |
| MET | CB  | A | 63 | 875 | −161 | 165 | 29 |
| MET | CG  | A | 63 | 861 | −167 | 167 | 31 |
| MET | SD  | A | 63 | 855 | −169 | 184 | 31 |
| MET | CE  | A | 63 | 853 | −187 | 185 | 32 |
| MET | C   | A | 63 | 891 | −150 | 149 | 28 |
| MET | O   | A | 63 | 889 | −138 | 149 | 27 |
| VAL | N   | A | 64 | 904 | −155 | 148 | 28 |
| VAL | CA  | A | 64 | 915 | −146 | 147 | 28 |
| VAL | CB  | A | 64 | 928 | −154 | 145 | 28 |
| VAL | CG1 | A | 64 | 940 | −145 | 143 | 29 |
| VAL | CG2 | A | 64 | 931 | −162 | 158 | 29 |
| VAL | C   | A | 64 | 913 | −137 | 135 | 28 |
| VAL | O   | A | 64 | 909 | −141 | 124 | 27 |
| ASP | N   | A | 65 | 916 | −124 | 137 | 29 |
| ASP | CA  | A | 65 | 915 | −113 | 127 | 30 |
| ASP | CB  | A | 65 | 923 | −117 | 114 | 32 |
| ASP | CG  | A | 65 | 927 | −105 | 106 | 34 |
| ASP | OD1 | A | 65 | 927 | −106 | 93  | 35 |
| ASP | OD2 | A | 65 | 929 | −94  | 112 | 34 |
| ASP | C   | A | 65 | 900 | −111 | 122 | 30 |
| ASP | O   | A | 65 | 898 | −106 | 111 | 29 |
| ASN | N   | A | 66 | 890 | −114 | 130 | 28 |
| ASN | CA  | A | 66 | 876 | −112 | 127 | 27 |
| ASN | CB  | A | 66 | 867 | −121 | 134 | 26 |
| ASN | CG  | A | 66 | 868 | −119 | 150 | 25 |
| ASN | OD1 | A | 66 | 875 | −110 | 155 | 24 |
| ASN | ND2 | A | 66 | 860 | −127 | 157 | 24 |
| ASN | C   | A | 66 | 872 | −97  | 128 | 27 |
| ASN | O   | A | 66 | 860 | −94  | 126 | 26 |
| LEU | N   | A | 67 | 881 | −88  | 132 | 27 |
| LEU | CA  | A | 67 | 877 | −74  | 133 | 29 |
| LEU | CB  | A | 67 | 880 | −69  | 148 | 27 |
| LEU | CG  | A | 67 | 873 | −77  | 159 | 26 |
| LEU | CD1 | A | 67 | 877 | −70  | 172 | 26 |
| LEU | CD2 | A | 67 | 858 | −78  | 158 | 26 |
| LEU | C   | A | 67 | 883 | −65  | 123 | 31 |
| LEU | O   | A | 67 | 895 | −67  | 119 | 31 |
| ARG | N   | A | 68 | 876 | −54  | 120 | 33 |
| ARG | CA  | A | 68 | 881 | −44  | 110 | 36 |
| ARG | CB  | A | 68 | 876 | −47  | 96  | 38 |
| ARG | CG  | A | 68 | 883 | −58  | 89  | 40 |
| ARG | CD  | A | 68 | 887 | −54  | 75  | 43 |
| ARG | NE  | A | 68 | 876 | −49  | 67  | 44 |
| ARG | CZ  | A | 68 | 877 | −43  | 56  | 45 |

TABLE 1-continued

Structure Coordinates for uncomplexed BACE

| | | | | | | | |
|---|---|---|---|---|---|---|---|
| ARG | NH1 | A | 68 | 889 | −41 | 50 | 45 |
| ARG | NH2 | A | 68 | 866 | −38 | 49 | 45 |
| ARG | C | A | 68 | 876 | −31 | 115 | 37 |
| ARG | O | A | 68 | 868 | −30 | 125 | 36 |
| GLY | N | A | 69 | 880 | −20 | 108 | 38 |
| GLY | CA | A | 69 | 875 | −7 | 111 | 40 |
| GLY | C | A | 69 | 884 | 4 | 105 | 42 |
| GLY | O | A | 69 | 895 | 2 | 100 | 42 |
| LYS | N | A | 70 | 879 | 16 | 106 | 43 |
| LYS | CA | A | 70 | 886 | 28 | 101 | 44 |
| LYS | CB | A | 70 | 877 | 36 | 92 | 44 |
| LYS | CG | A | 70 | 874 | 29 | 79 | 45 |
| LYS | CD | A | 70 | 865 | 38 | 70 | 46 |
| LYS | CE | A | 70 | 871 | 51 | 67 | 46 |
| LYS | NZ | A | 70 | 861 | 60 | 60 | 46 |
| LYS | C | A | 70 | 890 | 36 | 113 | 44 |
| LYS | O | A | 70 | 882 | 39 | 122 | 44 |
| SER | N | A | 71 | 903 | 39 | 114 | 44 |
| SER | CA | A | 71 | 909 | 47 | 125 | 44 |
| SER | CB | A | 71 | 921 | 54 | 121 | 45 |
| SER | OG | A | 71 | 929 | 46 | 112 | 46 |
| SER | C | A | 71 | 899 | 57 | 132 | 44 |
| SER | O | A | 71 | 893 | 65 | 125 | 44 |
| GLY | N | A | 72 | 898 | 56 | 145 | 43 |
| GLY | CA | A | 72 | 889 | 65 | 152 | 43 |
| GLY | C | A | 72 | 874 | 63 | 150 | 43 |
| GLY | O | A | 72 | 866 | 70 | 155 | 43 |
| GLN | N | A | 73 | 871 | 53 | 142 | 42 |
| GLN | CA | A | 73 | 857 | 50 | 139 | 42 |
| GLN | CB | A | 73 | 854 | 50 | 124 | 43 |
| GLN | CG | A | 73 | 861 | 62 | 117 | 44 |
| GLN | CD | A | 73 | 853 | 69 | 106 | 44 |
| GLN | OE1 | A | 73 | 849 | 62 | 97 | 44 |
| GLN | NE2 | A | 73 | 851 | 82 | 107 | 45 |
| GLN | C | A | 73 | 851 | 37 | 145 | 41 |
| GLN | O | A | 73 | 841 | 32 | 141 | 41 |
| GLY | N | A | 74 | 859 | 31 | 154 | 39 |
| GLY | CA | A | 74 | 855 | 19 | 160 | 37 |
| GLY | C | A | 74 | 858 | 6 | 153 | 36 |
| GLY | O | A | 74 | 858 | 6 | 140 | 35 |
| TYR | N | A | 75 | 859 | −5 | 160 | 34 |
| TYR | CA | A | 75 | 861 | −18 | 154 | 33 |
| TYR | CB | A | 75 | 870 | −27 | 164 | 33 |
| TYR | CG | A | 75 | 884 | −22 | 165 | 32 |
| TYR | CD1 | A | 75 | 888 | −11 | 173 | 32 |
| TYR | CE1 | A | 75 | 901 | −7 | 174 | 33 |
| TYR | CD2 | A | 75 | 895 | −28 | 158 | 33 |
| TYR | CE2 | A | 75 | 908 | −24 | 159 | 33 |
| TYR | CZ | A | 75 | 911 | −14 | 167 | 33 |
| TYR | OH | A | 75 | 924 | −10 | 168 | 33 |
| TYR | C | A | 75 | 848 | −25 | 153 | 32 |
| TYR | O | A | 75 | 839 | −24 | 161 | 33 |
| TYR | N | A | 76 | 846 | −33 | 142 | 31 |
| TYR | CA | A | 76 | 834 | −40 | 140 | 31 |
| TYR | CB | A | 76 | 825 | −32 | 129 | 31 |
| TYR | CG | A | 76 | 832 | −31 | 115 | 32 |
| TYR | CD1 | A | 76 | 833 | −42 | 107 | 32 |
| TYR | CE1 | A | 76 | 839 | −40 | 94 | 32 |
| TYR | CD2 | A | 76 | 837 | −18 | 111 | 32 |
| TYR | CE2 | A | 76 | 843 | −17 | 99 | 32 |
| TYR | CZ | A | 76 | 844 | −28 | 90 | 33 |
| TYR | OH | A | 76 | 850 | −27 | 78 | 34 |
| TYR | C | A | 76 | 836 | −54 | 135 | 30 |
| TYR | O | A | 76 | 847 | −58 | 130 | 29 |
| VAL | N | A | 77 | 826 | −62 | 137 | 28 |
| VAL | CA | A | 77 | 827 | −76 | 134 | 28 |
| VAL | CB | A | 77 | 826 | −85 | 147 | 28 |
| VAL | CG1 | A | 77 | 812 | −84 | 153 | 27 |
| VAL | CG2 | A | 77 | 829 | −100 | 144 | 27 |
| VAL | C | A | 77 | 815 | −79 | 125 | 28 |
| VAL | O | A | 77 | 804 | −72 | 126 | 28 |
| GLU | N | A | 78 | 816 | −89 | 116 | 28 |
| GLU | CA | A | 78 | 805 | −93 | 108 | 28 |
| GLU | CB | A | 78 | 811 | −100 | 95 | 29 |
| GLU | CG | A | 78 | 800 | −105 | 86 | 31 |
| GLU | CD | A | 78 | 806 | −113 | 74 | 33 |
| GLU | OE1 | A | 78 | 814 | −107 | 67 | 34 |

TABLE 1-continued

Structure Coordinates for uncomplexed BACE

| | | | | | | | |
|---|---|---|---|---|---|---|---|
| GLU | OE2 | A | 78 | 802 | −124 | 71 | 34 |
| GLU | C | A | 78 | 795 | −102 | 115 | 27 |
| GLU | O | A | 78 | 800 | −111 | 122 | 27 |
| MET | N | A | 79 | 783 | −99 | 113 | 26 |
| MET | CA | A | 79 | 772 | −107 | 120 | 27 |
| MET | CB | A | 79 | 766 | −99 | 132 | 26 |
| MET | CG | A | 79 | 777 | −97 | 143 | 26 |
| MET | SD | A | 79 | 769 | −89 | 158 | 26 |
| MET | CE | A | 79 | 761 | −103 | 165 | 26 |
| MET | C | A | 79 | 761 | −108 | 109 | 27 |
| MET | O | A | 79 | 761 | −102 | 99 | 27 |
| THR | N | A | 80 | 751 | −117 | 112 | 27 |
| THR | CA | A | 80 | 740 | −118 | 103 | 28 |
| THR | CB | A | 80 | 739 | −131 | 94 | 28 |
| THR | OG1 | A | 80 | 736 | −142 | 103 | 28 |
| THR | CG2 | A | 80 | 753 | −134 | 88 | 28 |
| THR | C | A | 80 | 727 | −119 | 112 | 28 |
| THR | O | A | 80 | 728 | −123 | 124 | 27 |
| VAL | N | A | 81 | 716 | −114 | 107 | 27 |
| VAL | CA | A | 81 | 704 | −114 | 114 | 28 |
| VAL | CB | A | 81 | 700 | −100 | 119 | 27 |
| VAL | CG1 | A | 81 | 711 | −95 | 129 | 27 |
| VAL | CG2 | A | 81 | 699 | −90 | 107 | 28 |
| VAL | C | A | 81 | 693 | −119 | 105 | 28 |
| VAL | O | A | 81 | 693 | −116 | 93 | 28 |
| GLY | N | A | 82 | 683 | −126 | 110 | 29 |
| GLY | CA | A | 82 | 672 | −131 | 102 | 30 |
| GLY | C | A | 82 | 673 | −144 | 95 | 30 |
| GLY | O | A | 82 | 684 | −150 | 94 | 30 |
| SER | N | A | 83 | 662 | −148 | 89 | 31 |
| SER | CA | A | 83 | 661 | −160 | 81 | 32 |
| SER | CB | A | 83 | 654 | −172 | 89 | 32 |
| SER | OG | A | 83 | 659 | −173 | 102 | 32 |
| SER | C | A | 83 | 653 | −157 | 69 | 32 |
| SER | O | A | 83 | 641 | −154 | 69 | 32 |
| PRO | N | A | 84 | 660 | −157 | 57 | 32 |
| PRO | CD | A | 84 | 653 | −154 | 44 | 32 |
| PRO | CA | A | 84 | 674 | −160 | 55 | 32 |
| PRO | CB | A | 84 | 675 | −160 | 39 | 32 |
| PRO | CG | A | 84 | 665 | −150 | 35 | 32 |
| PRO | C | A | 84 | 683 | −149 | 61 | 32 |
| PRO | O | A | 84 | 679 | −138 | 63 | 32 |
| PRO | N | A | 85 | 696 | −153 | 63 | 32 |
| PRO | CD | A | 85 | 701 | −166 | 60 | 32 |
| PRO | CA | A | 85 | 707 | −144 | 69 | 32 |
| PRO | CB | A | 85 | 719 | −154 | 69 | 31 |
| PRO | CG | A | 85 | 713 | −168 | 69 | 32 |
| PRO | C | A | 85 | 710 | −131 | 62 | 32 |
| PRO | O | A | 85 | 713 | −131 | 50 | 31 |
| GLN | N | A | 86 | 709 | −120 | 69 | 31 |
| GLN | CA | A | 86 | 712 | −107 | 64 | 31 |
| GLN | CB | A | 86 | 701 | −97 | 67 | 31 |
| GLN | CG | A | 86 | 688 | −100 | 60 | 31 |
| GLN | CD | A | 86 | 677 | −90 | 64 | 31 |
| GLN | OE1 | A | 86 | 679 | −78 | 64 | 32 |
| GLN | NE2 | A | 86 | 665 | −96 | 67 | 31 |
| GLN | C | A | 86 | 725 | −103 | 70 | 31 |
| GLN | O | A | 86 | 726 | −100 | 83 | 31 |
| THR | N | A | 87 | 735 | −101 | 62 | 31 |
| THR | CA | A | 87 | 749 | −97 | 67 | 31 |
| THR | CB | A | 87 | 759 | −100 | 56 | 31 |
| THR | OG1 | A | 87 | 758 | −114 | 53 | 30 |
| THR | CG2 | A | 87 | 773 | −98 | 62 | 30 |
| THR | C | A | 87 | 750 | −82 | 70 | 32 |
| THR | O | A | 87 | 745 | −73 | 63 | 32 |
| LEU | N | A | 88 | 756 | −79 | 81 | 31 |
| LEU | CA | A | 88 | 758 | −65 | 86 | 31 |
| LEU | CB | A | 88 | 747 | −61 | 95 | 31 |
| LEU | CG | A | 88 | 733 | −60 | 89 | 31 |
| LEU | CD1 | A | 88 | 723 | −56 | 100 | 30 |
| LEU | CD2 | A | 88 | 733 | −49 | 79 | 31 |
| LEU | C | A | 88 | 771 | −65 | 94 | 31 |
| LEU | O | A | 88 | 776 | −75 | 100 | 32 |
| ASN | N | A | 89 | 778 | −53 | 94 | 31 |
| ASN | CA | A | 89 | 790 | −51 | 102 | 31 |
| ASN | CB | A | 89 | 799 | −41 | 94 | 31 |
| ASN | CG | A | 89 | 806 | −48 | 83 | 32 |

TABLE 1-continued

Structure Coordinates for uncomplexed BACE

| | | | | | | | |
|---|---|---|---|---|---|---|---|
| ASN | OD1 | A | 89 | 809 | −60 | 84 | 32 |
| ASN | ND2 | A | 89 | 809 | −41 | 72 | 32 |
| ASN | C | A | 89 | 785 | −44 | 115 | 30 |
| ASN | O | A | 89 | 778 | −34 | 115 | 30 |
| ILE | N | A | 90 | 790 | −50 | 126 | 30 |
| ILE | CA | A | 90 | 785 | −45 | 139 | 29 |
| ILE | CB | A | 90 | 778 | −56 | 146 | 29 |
| ILE | CG2 | A | 90 | 772 | −50 | 159 | 29 |
| ILE | CG1 | A | 90 | 767 | −62 | 137 | 29 |
| ILE | CD1 | A | 90 | 756 | −52 | 133 | 29 |
| ILE | C | A | 90 | 797 | −40 | 148 | 28 |
| ILE | O | A | 90 | 806 | −48 | 150 | 27 |
| LEU | N | A | 91 | 796 | −28 | 152 | 27 |
| LEU | CA | A | 91 | 806 | −22 | 161 | 27 |
| LEU | CB | A | 91 | 802 | −7 | 163 | 28 |
| LEU | CG | A | 91 | 809 | 1 | 174 | 28 |
| LEU | CD1 | A | 91 | 824 | 3 | 170 | 28 |
| LEU | CD2 | A | 91 | 802 | 14 | 177 | 29 |
| LEU | C | A | 91 | 807 | −29 | 174 | 26 |
| LEU | O | A | 91 | 797 | −32 | 180 | 25 |
| VAL | N | A | 92 | 819 | −32 | 179 | 27 |
| VAL | CA | A | 92 | 821 | −39 | 191 | 27 |
| VAL | CB | A | 92 | 834 | −48 | 190 | 28 |
| VAL | CG1 | A | 92 | 835 | −56 | 203 | 28 |
| VAL | CG2 | A | 92 | 833 | −57 | 178 | 28 |
| VAL | C | A | 92 | 823 | −28 | 202 | 28 |
| VAL | O | A | 92 | 833 | −21 | 202 | 28 |
| ASP | N | A | 93 | 813 | −28 | 211 | 28 |
| ASP | CA | A | 93 | 814 | −18 | 222 | 27 |
| ASP | CB | A | 93 | 803 | −7 | 219 | 28 |
| ASP | CG | A | 93 | 803 | 4 | 230 | 29 |
| ASP | OD1 | A | 93 | 813 | 6 | 237 | 29 |
| ASP | OD2 | A | 93 | 793 | 11 | 231 | 29 |
| ASP | C | A | 93 | 812 | −24 | 236 | 27 |
| ASP | O | A | 93 | 801 | −28 | 239 | 26 |
| THR | N | A | 94 | 822 | −24 | 244 | 26 |
| THR | CA | A | 94 | 822 | −30 | 257 | 26 |
| THR | CB | A | 94 | 835 | −35 | 262 | 26 |
| THR | OG1 | A | 94 | 845 | −25 | 263 | 26 |
| THR | CG2 | A | 94 | 840 | −46 | 252 | 25 |
| THR | C | A | 94 | 817 | −19 | 267 | 26 |
| THR | O | A | 94 | 816 | −21 | 279 | 26 |
| GLY | N | A | 95 | 813 | −7 | 261 | 27 |
| GLY | CA | A | 95 | 809 | 4 | 268 | 27 |
| GLY | C | A | 95 | 794 | 5 | 268 | 27 |
| GLY | O | A | 95 | 788 | 14 | 275 | 27 |
| SER | N | A | 96 | 786 | −3 | 261 | 26 |
| SER | CA | A | 96 | 772 | −3 | 261 | 26 |
| SER | CB | A | 96 | 767 | 4 | 248 | 26 |
| SER | OG | A | 96 | 771 | −2 | 237 | 27 |
| SER | C | A | 96 | 766 | −17 | 262 | 26 |
| SER | O | A | 96 | 774 | −27 | 262 | 25 |
| SER | N | A | 97 | 753 | −19 | 263 | 25 |
| SER | CA | A | 97 | 747 | −32 | 265 | 25 |
| SER | CB | A | 97 | 743 | −34 | 280 | 25 |
| SER | OG | A | 97 | 754 | −31 | 288 | 26 |
| SER | C | A | 97 | 736 | −35 | 256 | 25 |
| SER | O | A | 97 | 729 | −45 | 258 | 25 |
| ASN | N | A | 98 | 733 | −27 | 246 | 25 |
| ASN | CA | A | 98 | 722 | −30 | 237 | 26 |
| ASN | CB | A | 98 | 714 | −17 | 234 | 27 |
| ASN | CG | A | 98 | 704 | −15 | 245 | 28 |
| ASN | OD1 | A | 98 | 707 | −10 | 256 | 28 |
| ASN | ND2 | A | 98 | 691 | −18 | 242 | 28 |
| ASN | C | A | 98 | 727 | −35 | 223 | 26 |
| ASN | O | A | 98 | 738 | −31 | 219 | 26 |
| PHE | N | A | 99 | 720 | −44 | 217 | 26 |
| PHE | CA | A | 99 | 724 | −49 | 204 | 25 |
| PHE | CB | A | 99 | 722 | −64 | 203 | 26 |
| PHE | CG | A | 99 | 724 | −69 | 189 | 27 |
| PHE | CD1 | A | 99 | 716 | −79 | 183 | 27 |
| PHE | CD2 | A | 99 | 735 | −65 | 181 | 27 |
| PHE | CE1 | A | 99 | 718 | −84 | 170 | 27 |
| PHE | CE2 | A | 99 | 738 | −70 | 168 | 27 |
| PHE | CZ | A | 99 | 729 | −79 | 163 | 27 |
| PHE | C | A | 99 | 713 | −42 | 195 | 25 |
| PHE | O | A | 99 | 701 | −44 | 197 | 24 |
| ALA | N | A | 100 | 718 | −33 | 186 | 25 |
| ALA | CA | A | 100 | 709 | −26 | 177 | 25 |
| ALA | CB | A | 100 | 707 | −12 | 183 | 25 |
| ALA | C | A | 100 | 715 | −24 | 164 | 26 |
| ALA | O | A | 100 | 727 | −23 | 162 | 26 |
| VAL | N | A | 101 | 706 | −25 | 153 | 26 |
| VAL | CA | A | 101 | 711 | −24 | 140 | 27 |
| VAL | CB | A | 101 | 711 | −38 | 133 | 27 |
| VAL | CG1 | A | 101 | 718 | −48 | 142 | 26 |
| VAL | CG2 | A | 101 | 697 | −43 | 130 | 27 |
| VAL | C | A | 101 | 702 | −15 | 131 | 27 |
| VAL | O | A | 101 | 690 | −13 | 134 | 27 |
| GLY | N | A | 102 | 708 | −8 | 122 | 29 |
| GLY | CA | A | 102 | 701 | 0 | 113 | 29 |
| GLY | C | A | 102 | 690 | −8 | 107 | 30 |
| GLY | O | A | 102 | 692 | −19 | 102 | 29 |
| ALA | N | A | 103 | 677 | −3 | 107 | 32 |
| ALA | CA | A | 103 | 666 | −10 | 102 | 33 |
| ALA | CB | A | 103 | 658 | −15 | 114 | 32 |
| ALA | C | A | 103 | 657 | −2 | 93 | 34 |
| ALA | O | A | 103 | 645 | −4 | 91 | 35 |
| ALA | N | A | 104 | 663 | 9 | 87 | 35 |
| ALA | CA | A | 104 | 656 | 18 | 78 | 35 |
| ALA | CB | A | 104 | 647 | 28 | 86 | 36 |
| ALA | C | A | 104 | 667 | 26 | 70 | 37 |
| ALA | O | A | 104 | 678 | 27 | 75 | 36 |
| PRO | N | A | 105 | 663 | 30 | 58 | 38 |
| PRO | CD | A | 105 | 650 | 30 | 51 | 39 |
| PRO | CA | A | 105 | 673 | 38 | 50 | 40 |
| PRO | CB | A | 105 | 666 | 41 | 37 | 39 |
| PRO | CG | A | 105 | 652 | 41 | 41 | 39 |
| PRO | C | A | 105 | 679 | 50 | 57 | 41 |
| PRO | O | A | 105 | 672 | 57 | 65 | 42 |
| HIS | N | A | 106 | 692 | 53 | 54 | 42 |
| HIS | CA | A | 106 | 699 | 64 | 60 | 44 |
| HIS | CB | A | 106 | 704 | 61 | 74 | 44 |
| HIS | CG | A | 106 | 711 | 72 | 81 | 44 |
| HIS | CD2 | A | 106 | 706 | 80 | 91 | 44 |
| HIS | ND1 | A | 106 | 724 | 76 | 79 | 45 |
| HIS | CE1 | A | 106 | 727 | 87 | 86 | 44 |
| HIS | NE2 | A | 106 | 716 | 89 | 94 | 45 |
| HIS | C | A | 106 | 710 | 67 | 50 | 45 |
| HIS | O | A | 106 | 715 | 58 | 44 | 45 |
| PRO | N | A | 107 | 714 | 80 | 49 | 46 |
| PRO | CD | A | 107 | 709 | 92 | 56 | 45 |
| PRO | CA | A | 107 | 725 | 84 | 40 | 46 |
| PRO | CB | A | 107 | 727 | 99 | 43 | 46 |
| PRO | CG | A | 107 | 713 | 103 | 47 | 46 |
| PRO | C | A | 107 | 738 | 76 | 42 | 46 |
| PRO | O | A | 107 | 745 | 72 | 32 | 46 |
| PHE | N | A | 108 | 742 | 74 | 54 | 46 |
| PHE | CA | A | 108 | 754 | 67 | 58 | 46 |
| PHE | CB | A | 108 | 759 | 72 | 71 | 46 |
| PHE | CG | A | 108 | 762 | 87 | 71 | 46 |
| PHE | CD1 | A | 108 | 764 | 94 | 83 | 46 |
| PHE | CD2 | A | 108 | 763 | 94 | 59 | 46 |
| PHE | CE1 | A | 108 | 766 | 108 | 84 | 46 |
| PHE | CE2 | A | 108 | 766 | 108 | 60 | 46 |
| PHE | CZ | A | 108 | 768 | 115 | 72 | 46 |
| PHE | C | A | 108 | 754 | 52 | 58 | 46 |
| PHE | O | A | 108 | 765 | 45 | 60 | 46 |
| LEU | N | A | 109 | 743 | 46 | 55 | 45 |
| LEU | CA | A | 109 | 742 | 31 | 55 | 45 |
| LEU | CB | A | 109 | 729 | 27 | 64 | 45 |
| LEU | CG | A | 109 | 730 | 30 | 78 | 45 |
| LEU | CD1 | A | 109 | 716 | 28 | 85 | 45 |
| LEU | CD2 | A | 109 | 741 | 22 | 85 | 45 |
| LEU | C | A | 109 | 741 | 25 | 41 | 45 |
| LEU | O | A | 109 | 732 | 29 | 33 | 45 |
| HIS | N | A | 110 | 749 | 15 | 39 | 45 |
| HIS | CA | A | 110 | 749 | 9 | 26 | 44 |
| HIS | CB | A | 110 | 763 | 3 | 22 | 46 |
| HIS | CG | A | 110 | 774 | 12 | 25 | 47 |
| HIS | CD2 | A | 110 | 786 | 10 | 32 | 48 |
| HIS | ND1 | A | 110 | 775 | 24 | 19 | 48 |
| HIS | CE1 | A | 110 | 786 | 30 | 23 | 48 |
| HIS | NE2 | A | 110 | 793 | 22 | 31 | 48 |

TABLE 1-continued

Structure Coordinates for uncomplexed BACE

| | | | | | | | |
|---|---|---|---|---|---|---|---|
| HIS | C | A | 110 | 739 | −3 | 25 | 43 |
| HIS | O | A | 110 | 735 | −8 | 15 | 43 |
| ARG | N | A | 111 | 735 | −7 | 37 | 41 |
| ARG | CA | A | 111 | 725 | −17 | 39 | 39 |
| ARG | CB | A | 111 | 732 | −31 | 37 | 38 |
| ARG | CG | A | 111 | 744 | −33 | 46 | 37 |
| ARG | CD | A | 111 | 752 | −45 | 43 | 36 |
| ARG | NE | A | 111 | 763 | −46 | 51 | 36 |
| ARG | CZ | A | 111 | 773 | −56 | 50 | 35 |
| ARG | NH1 | A | 111 | 771 | −66 | 41 | 35 |
| ARG | NH2 | A | 111 | 783 | −56 | 58 | 35 |
| ARG | C | A | 111 | 719 | −16 | 53 | 38 |
| ARG | O | A | 111 | 724 | −9 | 62 | 37 |
| TYR | N | A | 112 | 708 | −23 | 55 | 37 |
| TYR | CA | A | 112 | 701 | −22 | 68 | 36 |
| TYR | CB | A | 112 | 692 | −10 | 69 | 37 |
| TYR | CG | A | 112 | 682 | −8 | 58 | 38 |
| TYR | CD1 | A | 112 | 670 | −15 | 59 | 39 |
| TYR | CE1 | A | 112 | 661 | −13 | 48 | 40 |
| TYR | CD2 | A | 112 | 685 | 0 | 47 | 39 |
| TYR | CE2 | A | 112 | 676 | 2 | 37 | 40 |
| TYR | CZ | A | 112 | 664 | −5 | 38 | 40 |
| TYR | OH | A | 112 | 655 | −4 | 27 | 41 |
| TYR | C | A | 112 | 692 | −35 | 70 | 35 |
| TYR | O | A | 112 | 689 | −42 | 60 | 34 |
| TYR | N | A | 113 | 688 | −37 | 82 | 34 |
| TYR | CA | A | 113 | 680 | −49 | 86 | 33 |
| TYR | CB | A | 113 | 680 | −50 | 101 | 32 |
| TYR | CG | A | 113 | 672 | −61 | 107 | 30 |
| TYR | CD1 | A | 113 | 670 | −73 | 101 | 30 |
| TYR | CE1 | A | 113 | 663 | −83 | 107 | 30 |
| TYR | CD2 | A | 113 | 666 | −59 | 120 | 30 |
| TYR | CE2 | A | 113 | 659 | −69 | 126 | 30 |
| TYR | CZ | A | 113 | 657 | −81 | 120 | 30 |
| TYR | OH | A | 113 | 650 | −91 | 126 | 29 |
| TYR | C | A | 113 | 666 | −47 | 81 | 33 |
| TYR | O | A | 113 | 660 | −37 | 83 | 34 |
| GLN | N | A | 114 | 662 | −57 | 73 | 33 |
| GLN | CA | A | 114 | 648 | −56 | 67 | 34 |
| GLN | CB | A | 114 | 649 | −59 | 52 | 34 |
| GLN | CG | A | 114 | 655 | −47 | 44 | 34 |
| GLN | CD | A | 114 | 656 | −50 | 29 | 34 |
| GLN | OE1 | A | 114 | 664 | −58 | 25 | 36 |
| GLN | NE2 | A | 114 | 648 | −43 | 21 | 34 |
| GLN | C | A | 114 | 640 | −67 | 73 | 33 |
| GLN | O | A | 114 | 639 | −79 | 69 | 33 |
| ARG | N | A | 115 | 633 | −63 | 84 | 33 |
| ARG | CA | A | 115 | 625 | −72 | 92 | 33 |
| ARG | CB | A | 115 | 618 | −64 | 104 | 32 |
| ARG | CG | A | 115 | 629 | −60 | 114 | 32 |
| ARG | CD | A | 115 | 623 | −50 | 124 | 31 |
| ARG | NE | A | 115 | 621 | −37 | 117 | 30 |
| ARG | CZ | A | 115 | 614 | −27 | 122 | 30 |
| ARG | NH1 | A | 115 | 610 | −28 | 134 | 29 |
| ARG | NH2 | A | 115 | 613 | −16 | 115 | 29 |
| ARG | C | A | 115 | 614 | −80 | 84 | 33 |
| ARG | O | A | 115 | 611 | −91 | 87 | 33 |
| GLN | N | A | 116 | 608 | −73 | 74 | 33 |
| GLN | CA | A | 116 | 598 | −80 | 66 | 34 |
| GLN | CB | A | 116 | 591 | −69 | 57 | 35 |
| GLN | CG | A | 116 | 599 | −66 | 44 | 35 |
| GLN | CD | A | 116 | 609 | −54 | 46 | 36 |
| GLN | OE1 | A | 116 | 612 | −50 | 57 | 36 |
| GLN | NE2 | A | 116 | 613 | −49 | 35 | 36 |
| GLN | C | A | 116 | 603 | −92 | 58 | 33 |
| GLN | O | A | 116 | 595 | −100 | 53 | 34 |
| LEU | N | A | 117 | 616 | −92 | 56 | 33 |
| LEU | CA | A | 117 | 621 | −104 | 48 | 33 |
| LEU | CB | A | 117 | 632 | −99 | 39 | 33 |
| LEU | CG | A | 117 | 629 | −88 | 28 | 33 |
| LEU | CD1 | A | 117 | 641 | −85 | 20 | 33 |
| LEU | CD2 | A | 117 | 617 | −93 | 20 | 33 |
| LEU | C | A | 117 | 626 | −115 | 57 | 32 |
| LEU | O | A | 117 | 632 | −125 | 52 | 32 |
| SER | N | A | 118 | 624 | −114 | 70 | 31 |
| SER | CA | A | 118 | 628 | −125 | 79 | 31 |
| SER | CB | A | 118 | 636 | −119 | 91 | 30 |
| SER | OG | A | 118 | 641 | −129 | 99 | 30 |
| SER | C | A | 118 | 617 | −133 | 84 | 30 |
| SER | O | A | 118 | 607 | −127 | 90 | 30 |
| SER | N | A | 119 | 617 | −146 | 82 | 29 |
| SER | CA | A | 119 | 606 | −154 | 87 | 29 |
| SER | CB | A | 119 | 606 | −167 | 79 | 29 |
| SER | OG | A | 119 | 618 | −174 | 82 | 30 |
| SER | C | A | 119 | 607 | −157 | 102 | 28 |
| SER | O | A | 119 | 598 | −162 | 108 | 28 |
| THR | N | A | 120 | 618 | −154 | 108 | 27 |
| THR | CA | A | 120 | 620 | −157 | 122 | 27 |
| THR | CB | A | 120 | 634 | −164 | 125 | 27 |
| THR | OG1 | A | 120 | 644 | −159 | 117 | 26 |
| THR | CG2 | A | 120 | 632 | −179 | 121 | 27 |
| THR | C | A | 120 | 619 | −144 | 131 | 27 |
| THR | O | A | 120 | 621 | −145 | 143 | 26 |
| TYR | N | A | 121 | 616 | −133 | 124 | 27 |
| TYR | CA | A | 121 | 614 | −120 | 131 | 26 |
| TYR | CB | A | 121 | 613 | −109 | 121 | 26 |
| TYR | CG | A | 121 | 608 | −96 | 127 | 27 |
| TYR | CD1 | A | 121 | 616 | −88 | 136 | 27 |
| TYR | CE1 | A | 121 | 611 | −77 | 142 | 26 |
| TYR | CD2 | A | 121 | 594 | −92 | 125 | 27 |
| TYR | CE2 | A | 121 | 590 | −80 | 131 | 27 |
| TYR | CZ | A | 121 | 598 | −73 | 139 | 27 |
| TYR | OH | A | 121 | 593 | −61 | 145 | 28 |
| TYR | C | A | 121 | 602 | −120 | 140 | 26 |
| TYR | O | A | 121 | 591 | −125 | 136 | 25 |
| ARG | N | A | 122 | 603 | −115 | 152 | 26 |
| ARG | CA | A | 122 | 591 | −114 | 161 | 27 |
| ARG | CB | A | 122 | 592 | −125 | 173 | 27 |
| ARG | CG | A | 122 | 592 | −139 | 168 | 28 |
| ARG | CD | A | 122 | 591 | −149 | 180 | 28 |
| ARG | NE | A | 122 | 593 | −163 | 176 | 29 |
| ARG | CZ | A | 122 | 584 | −173 | 177 | 30 |
| ARG | NH1 | A | 122 | 572 | −170 | 183 | 31 |
| ARG | NH2 | A | 122 | 587 | −185 | 173 | 31 |
| ARG | C | A | 122 | 592 | −100 | 167 | 27 |
| ARG | O | A | 122 | 602 | −95 | 171 | 28 |
| ASP | N | A | 123 | 580 | −93 | 167 | 28 |
| ASP | CA | A | 123 | 579 | −79 | 171 | 28 |
| ASP | CB | A | 123 | 569 | −73 | 162 | 29 |
| ASP | CG | A | 123 | 568 | −58 | 164 | 29 |
| ASP | OD1 | A | 123 | 574 | −52 | 173 | 30 |
| ASP | OD2 | A | 123 | 560 | −51 | 156 | 29 |
| ASP | C | A | 123 | 575 | −78 | 186 | 27 |
| ASP | O | A | 123 | 565 | −83 | 190 | 28 |
| LEU | N | A | 124 | 584 | −71 | 194 | 26 |
| LEU | CA | A | 124 | 581 | −69 | 208 | 27 |
| LEU | CB | A | 124 | 594 | −67 | 215 | 26 |
| LEU | CG | A | 124 | 603 | −79 | 218 | 26 |
| LEU | CD1 | A | 124 | 617 | −75 | 223 | 26 |
| LEU | CD2 | A | 124 | 596 | −88 | 228 | 25 |
| LEU | C | A | 124 | 571 | −58 | 210 | 27 |
| LEU | O | A | 124 | 568 | −55 | 222 | 26 |
| ARG | N | A | 125 | 568 | −51 | 200 | 29 |
| ARG | CA | A | 125 | 558 | −40 | 201 | 31 |
| ARG | CB | A | 125 | 544 | −45 | 203 | 31 |
| ARG | CG | A | 125 | 540 | −55 | 191 | 32 |
| ARG | CD | A | 125 | 526 | −62 | 194 | 33 |
| ARG | NE | A | 125 | 527 | −70 | 207 | 34 |
| ARG | CZ | A | 125 | 518 | −68 | 217 | 35 |
| ARG | NH1 | A | 125 | 509 | −58 | 217 | 35 |
| ARG | NH2 | A | 125 | 519 | −76 | 228 | 34 |
| ARG | C | A | 125 | 562 | −30 | 212 | 31 |
| ARG | O | A | 125 | 553 | −26 | 220 | 31 |
| LYS | N | A | 126 | 574 | −26 | 212 | 33 |
| LYS | CA | A | 126 | 579 | −17 | 223 | 34 |
| LYS | CB | A | 126 | 585 | −25 | 234 | 35 |
| LYS | CG | A | 126 | 594 | −16 | 244 | 37 |
| LYS | CD | A | 126 | 587 | −12 | 256 | 38 |
| LYS | CE | A | 126 | 586 | −24 | 266 | 39 |
| LYS | NZ | A | 126 | 579 | −21 | 279 | 40 |
| LYS | C | A | 126 | 590 | −8 | 216 | 34 |
| LYS | O | A | 126 | 598 | −13 | 209 | 34 |
| GLY | N | A | 127 | 590 | 5 | 220 | 34 |
| GLY | CA | A | 127 | 601 | 13 | 215 | 35 |

TABLE 1-continued

Structure Coordinates for uncomplexed BACE

| | | | | | | | |
|---|---|---|---|---|---|---|---|
| GLY | C | A | 127 | 612 | 15 | 224 | 36 |
| GLY | O | A | 127 | 610 | 12 | 236 | 36 |
| VAL | N | A | 128 | 624 | 19 | 219 | 36 |
| VAL | CA | A | 128 | 635 | 21 | 228 | 37 |
| VAL | CB | A | 128 | 645 | 9 | 228 | 36 |
| VAL | CG1 | A | 128 | 651 | 7 | 214 | 36 |
| VAL | CG2 | A | 128 | 656 | 12 | 238 | 36 |
| VAL | C | A | 128 | 642 | 34 | 223 | 39 |
| VAL | O | A | 128 | 643 | 37 | 211 | 38 |
| TYR | N | A | 129 | 648 | 42 | 233 | 41 |
| TYR | CA | A | 129 | 655 | 54 | 230 | 43 |
| TYR | CB | A | 129 | 646 | 66 | 235 | 44 |
| TYR | CG | A | 129 | 651 | 80 | 234 | 46 |
| TYR | CD1 | A | 129 | 654 | 85 | 222 | 46 |
| TYR | CE1 | A | 129 | 658 | 99 | 221 | 47 |
| TYR | CD2 | A | 129 | 653 | 87 | 245 | 46 |
| TYR | CE2 | A | 129 | 658 | 100 | 245 | 47 |
| TYR | CZ | A | 129 | 660 | 106 | 232 | 47 |
| TYR | OH | A | 129 | 664 | 119 | 231 | 47 |
| TYR | C | A | 129 | 668 | 54 | 236 | 44 |
| TYR | O | A | 129 | 670 | 51 | 248 | 44 |
| VAL | N | A | 130 | 679 | 58 | 228 | 45 |
| VAL | CA | A | 130 | 692 | 58 | 234 | 47 |
| VAL | CB | A | 130 | 701 | 47 | 228 | 47 |
| VAL | CG1 | A | 130 | 715 | 48 | 235 | 47 |
| VAL | CG2 | A | 130 | 695 | 33 | 231 | 47 |
| VAL | C | A | 130 | 699 | 72 | 231 | 49 |
| VAL | O | A | 130 | 703 | 74 | 219 | 49 |
| PRO | N | A | 131 | 701 | 80 | 241 | 51 |
| PRO | CD | A | 131 | 694 | 80 | 254 | 52 |
| PRO | CA | A | 131 | 707 | 93 | 239 | 53 |
| PRO | CB | A | 131 | 701 | 102 | 250 | 52 |
| PRO | CG | A | 131 | 689 | 94 | 255 | 52 |
| PRO | C | A | 131 | 722 | 92 | 241 | 54 |
| PRO | O | A | 131 | 727 | 86 | 250 | 54 |
| TYR | N | A | 132 | 730 | 99 | 232 | 56 |
| TYR | CA | A | 132 | 744 | 100 | 233 | 58 |
| TYR | CB | A | 132 | 751 | 94 | 220 | 58 |
| TYR | CG | A | 132 | 750 | 79 | 219 | 59 |
| TYR | CD1 | A | 132 | 740 | 74 | 210 | 59 |
| TYR | CE1 | A | 132 | 739 | 60 | 208 | 60 |
| TYR | CD2 | A | 132 | 758 | 70 | 226 | 59 |
| TYR | CE2 | A | 132 | 756 | 57 | 225 | 60 |
| TYR | CZ | A | 132 | 747 | 51 | 216 | 60 |
| TYR | OH | A | 132 | 746 | 38 | 214 | 60 |
| TYR | C | A | 132 | 748 | 114 | 235 | 59 |
| TYR | O | A | 132 | 740 | 123 | 234 | 59 |
| THR | N | A | 133 | 761 | 116 | 236 | 60 |
| THR | CA | A | 133 | 767 | 130 | 238 | 60 |
| THR | CB | A | 133 | 782 | 130 | 239 | 60 |
| THR | OG1 | A | 133 | 786 | 124 | 252 | 61 |
| THR | CG2 | A | 133 | 788 | 144 | 238 | 61 |
| THR | C | A | 133 | 763 | 138 | 225 | 60 |
| THR | O | A | 133 | 755 | 148 | 227 | 60 |
| GLN | N | A | 134 | 767 | 134 | 214 | 60 |
| GLN | CA | A | 134 | 764 | 140 | 201 | 59 |
| GLN | CB | A | 134 | 771 | 133 | 190 | 60 |
| GLN | CG | A | 134 | 785 | 129 | 192 | 61 |
| GLN | CD | A | 134 | 790 | 117 | 182 | 61 |
| GLN | OE1 | A | 134 | 789 | 119 | 170 | 61 |
| GLN | NE2 | A | 134 | 794 | 106 | 188 | 61 |
| GLN | C | A | 134 | 749 | 141 | 198 | 58 |
| GLN | O | A | 134 | 744 | 152 | 198 | 59 |
| GLY | N | A | 135 | 743 | 129 | 196 | 57 |
| GLY | CA | A | 135 | 729 | 129 | 193 | 54 |
| GLY | C | A | 135 | 722 | 117 | 199 | 52 |
| GLY | O | A | 135 | 721 | 116 | 211 | 52 |
| LYS | N | A | 136 | 717 | 108 | 190 | 48 |
| LYS | CA | A | 136 | 709 | 96 | 195 | 45 |
| LYS | CB | A | 136 | 697 | 101 | 203 | 43 |
| LYS | CG | A | 136 | 686 | 108 | 194 | 40 |
| LYS | CD | A | 136 | 677 | 98 | 187 | 37 |
| LYS | CE | A | 136 | 666 | 104 | 179 | 34 |
| LYS | NZ | A | 136 | 667 | 103 | 164 | 32 |
| LYS | C | A | 136 | 704 | 87 | 184 | 44 |
| LYS | O | A | 136 | 707 | 89 | 172 | 43 |
| TRP | N | A | 137 | 696 | 77 | 188 | 42 |
| TRP | CA | A | 137 | 690 | 68 | 179 | 41 |
| TRP | CB | A | 137 | 699 | 57 | 173 | 41 |
| TRP | CG | A | 137 | 704 | 47 | 183 | 40 |
| TRP | CD2 | A | 137 | 698 | 36 | 189 | 40 |
| TRP | CE2 | A | 137 | 707 | 29 | 197 | 40 |
| TRP | CE3 | A | 137 | 684 | 31 | 189 | 40 |
| TRP | CD1 | A | 137 | 717 | 47 | 187 | 40 |
| TRP | NE1 | A | 137 | 719 | 36 | 196 | 40 |
| TRP | CZ2 | A | 137 | 704 | 18 | 204 | 40 |
| TRP | CZ3 | A | 137 | 681 | 20 | 196 | 40 |
| TRP | CH2 | A | 137 | 691 | 13 | 204 | 40 |
| TRP | C | A | 137 | 678 | 62 | 187 | 40 |
| TRP | O | A | 137 | 678 | 60 | 199 | 40 |
| GLU | N | A | 138 | 667 | 59 | 179 | 40 |
| GLU | CA | A | 138 | 655 | 53 | 185 | 40 |
| GLU | CB | A | 138 | 643 | 63 | 184 | 41 |
| GLU | CG | A | 138 | 646 | 77 | 188 | 42 |
| GLU | CD | A | 138 | 634 | 86 | 189 | 43 |
| GLU | OE1 | A | 138 | 635 | 98 | 186 | 43 |
| GLU | OE2 | A | 138 | 623 | 80 | 192 | 44 |
| GLU | C | A | 138 | 652 | 41 | 176 | 38 |
| GLU | O | A | 138 | 656 | 41 | 164 | 38 |
| GLY | N | A | 139 | 645 | 32 | 182 | 36 |
| GLY | CA | A | 139 | 642 | 20 | 174 | 35 |
| GLY | C | A | 139 | 631 | 12 | 180 | 34 |
| GLY | O | A | 139 | 625 | 15 | 190 | 33 |
| GLU | N | A | 140 | 628 | 1 | 173 | 33 |
| GLU | CA | A | 140 | 617 | −8 | 177 | 31 |
| GLU | CB | A | 140 | 608 | −10 | 165 | 32 |
| GLU | CG | A | 140 | 601 | 3 | 161 | 33 |
| GLU | CD | A | 140 | 594 | 3 | 148 | 34 |
| GLU | OE1 | A | 140 | 588 | 14 | 144 | 34 |
| GLU | OE2 | A | 140 | 595 | −7 | 141 | 34 |
| GLU | C | A | 140 | 623 | −22 | 181 | 30 |
| GLU | O | A | 140 | 631 | −28 | 174 | 29 |
| LEU | N | A | 141 | 619 | −26 | 193 | 29 |
| LEU | CA | A | 141 | 624 | −38 | 199 | 28 |
| LEU | CB | A | 141 | 621 | −39 | 214 | 28 |
| LEU | CG | A | 141 | 630 | −29 | 223 | 28 |
| LEU | CD1 | A | 141 | 624 | −28 | 237 | 28 |
| LEU | CD2 | A | 141 | 644 | −34 | 223 | 27 |
| LEU | C | A | 141 | 618 | −50 | 192 | 27 |
| LEU | O | A | 141 | 606 | −50 | 188 | 27 |
| GLY | N | A | 142 | 625 | −61 | 192 | 26 |
| GLY | CA | A | 142 | 621 | −74 | 186 | 25 |
| GLY | C | A | 142 | 632 | −84 | 188 | 25 |
| GLY | O | A | 142 | 642 | −81 | 195 | 24 |
| THR | N | A | 143 | 630 | −96 | 183 | 25 |
| THR | CA | A | 143 | 640 | −107 | 184 | 25 |
| THR | CB | A | 143 | 635 | −117 | 194 | 25 |
| THR | OG1 | A | 143 | 623 | −124 | 189 | 25 |
| THR | CG2 | A | 143 | 631 | −111 | 208 | 24 |
| THR | C | A | 143 | 641 | −113 | 171 | 25 |
| THR | O | A | 143 | 632 | −113 | 163 | 25 |
| ASP | N | A | 144 | 652 | −120 | 169 | 25 |
| ASP | CA | A | 144 | 654 | −127 | 156 | 25 |
| ASP | CB | A | 144 | 657 | −118 | 145 | 25 |
| ASP | CG | A | 144 | 652 | −124 | 131 | 25 |
| ASP | OD1 | A | 144 | 653 | −136 | 129 | 25 |
| ASP | OD2 | A | 144 | 648 | −116 | 123 | 26 |
| ASP | C | A | 144 | 666 | −136 | 159 | 25 |
| ASP | O | A | 144 | 673 | −135 | 169 | 26 |
| LEU | N | A | 145 | 669 | −145 | 149 | 25 |
| LEU | CA | A | 145 | 681 | −153 | 150 | 25 |
| LEU | CB | A | 145 | 679 | −166 | 141 | 24 |
| LEU | CG | A | 145 | 667 | −175 | 145 | 24 |
| LEU | CD1 | A | 145 | 666 | −187 | 135 | 24 |
| LEU | CD2 | A | 145 | 669 | −179 | 159 | 24 |
| LEU | C | A | 145 | 693 | −145 | 145 | 25 |
| LEU | O | A | 145 | 692 | −137 | 136 | 25 |
| VAL | N | A | 146 | 704 | −147 | 152 | 25 |
| VAL | CA | A | 146 | 716 | −140 | 149 | 25 |
| VAL | CB | A | 146 | 718 | −129 | 161 | 25 |
| VAL | CG1 | A | 146 | 731 | −121 | 158 | 24 |
| VAL | CG2 | A | 146 | 706 | −120 | 162 | 24 |
| VAL | C | A | 146 | 728 | −149 | 149 | 26 |
| VAL | O | A | 146 | 728 | −159 | 156 | 25 |

TABLE 1-continued

Structure Coordinates for uncomplexed BACE

| | | | | | | | |
|---|---|---|---|---|---|---|---|
| SER | N | A | 147 | 738 | −146 | 141 | 26 |
| SER | CA | A | 147 | 750 | −154 | 140 | 28 |
| SER | CB | A | 147 | 749 | −163 | 127 | 28 |
| SER | OG | A | 147 | 738 | −171 | 128 | 32 |
| SER | C | A | 147 | 762 | −145 | 138 | 28 |
| SER | O | A | 147 | 761 | −133 | 134 | 26 |
| ILE | N | A | 148 | 774 | −151 | 141 | 28 |
| ILE | CA | A | 148 | 787 | −144 | 139 | 29 |
| ILE | CB | A | 148 | 794 | −142 | 153 | 29 |
| ILE | CG2 | A | 148 | 806 | −133 | 151 | 29 |
| ILE | CG1 | A | 148 | 784 | −136 | 163 | 29 |
| ILE | CD1 | A | 148 | 790 | −134 | 177 | 29 |
| ILE | C | A | 148 | 795 | −153 | 130 | 29 |
| ILE | O | A | 148 | 802 | −163 | 135 | 28 |
| PRO | N | A | 149 | 794 | −151 | 117 | 30 |
| PRO | CD | A | 149 | 787 | −140 | 111 | 31 |
| PRO | CA | A | 149 | 801 | −159 | 107 | 31 |
| PRO | CB | A | 149 | 801 | −150 | 95 | 31 |
| PRO | CG | A | 149 | 788 | −144 | 96 | 31 |
| PRO | C | A | 149 | 816 | −163 | 111 | 32 |
| PRO | O | A | 149 | 819 | −175 | 111 | 32 |
| HIS | N | A | 150 | 824 | −154 | 115 | 33 |
| HIS | CA | A | 150 | 838 | −157 | 119 | 35 |
| HIS | CB | A | 150 | 847 | −146 | 114 | 35 |
| HIS | CG | A | 150 | 847 | −145 | 99 | 36 |
| HIS | CD2 | A | 150 | 841 | −136 | 91 | 36 |
| HIS | ND1 | A | 150 | 852 | −155 | 90 | 37 |
| HIS | CE1 | A | 150 | 849 | −151 | 78 | 37 |
| HIS | NE2 | A | 150 | 843 | −140 | 78 | 37 |
| HIS | C | A | 150 | 839 | −157 | 135 | 36 |
| HIS | O | A | 150 | 848 | −152 | 141 | 35 |
| GLY | N | A | 151 | 828 | −162 | 141 | 37 |
| GLY | CA | A | 151 | 828 | −163 | 155 | 39 |
| GLY | C | A | 151 | 824 | −178 | 158 | 40 |
| GLY | O | A | 151 | 827 | −187 | 151 | 41 |
| PRO | N | A | 152 | 816 | −180 | 169 | 41 |
| PRO | CD | A | 152 | 813 | −171 | 180 | 42 |
| PRO | CA | A | 152 | 812 | −194 | 172 | 42 |
| PRO | CB | A | 152 | 804 | −193 | 185 | 42 |
| PRO | CG | A | 152 | 810 | −181 | 191 | 41 |
| PRO | C | A | 152 | 804 | −199 | 160 | 43 |
| PRO | O | A | 152 | 797 | −191 | 153 | 44 |
| ASN | N | A | 153 | 804 | −212 | 158 | 45 |
| ASN | CA | A | 153 | 796 | −218 | 148 | 46 |
| ASN | CB | A | 153 | 802 | −231 | 142 | 47 |
| ASN | CG | A | 153 | 815 | −228 | 135 | 49 |
| ASN | OD1 | A | 153 | 815 | −223 | 123 | 49 |
| ASN | ND2 | A | 153 | 827 | −231 | 141 | 48 |
| ASN | C | A | 153 | 782 | −221 | 154 | 46 |
| ASN | O | A | 153 | 780 | −233 | 157 | 47 |
| VAL | N | A | 154 | 774 | −211 | 156 | 45 |
| VAL | CA | A | 154 | 761 | −213 | 162 | 44 |
| VAL | CB | A | 154 | 761 | −214 | 177 | 45 |
| VAL | CG1 | A | 154 | 768 | −227 | 181 | 45 |
| VAL | CG2 | A | 154 | 769 | −202 | 183 | 45 |
| VAL | C | A | 154 | 752 | −202 | 158 | 43 |
| VAL | O | A | 154 | 756 | −192 | 152 | 44 |
| THR | N | A | 155 | 739 | −203 | 161 | 41 |
| THR | CA | A | 155 | 729 | −193 | 159 | 39 |
| THR | CB | A | 155 | 720 | −197 | 146 | 40 |
| THR | OG1 | A | 155 | 728 | −195 | 134 | 39 |
| THR | CG2 | A | 155 | 707 | −189 | 146 | 39 |
| THR | C | A | 155 | 721 | −192 | 171 | 38 |
| THR | O | A | 155 | 716 | −202 | 176 | 38 |
| VAL | N | A | 156 | 718 | −180 | 176 | 36 |
| VAL | CA | A | 156 | 710 | −178 | 188 | 33 |
| VAL | CB | A | 156 | 719 | −173 | 200 | 33 |
| VAL | CG1 | A | 156 | 730 | −183 | 202 | 33 |
| VAL | CG2 | A | 156 | 724 | −159 | 197 | 32 |
| VAL | C | A | 156 | 699 | −168 | 186 | 32 |
| VAL | O | A | 156 | 700 | −161 | 176 | 32 |
| ARG | N | A | 157 | 689 | −169 | 194 | 31 |
| ARG | CA | A | 157 | 678 | −159 | 193 | 31 |
| ARG | CB | A | 157 | 665 | −165 | 197 | 32 |
| ARG | CG | A | 157 | 653 | −156 | 194 | 34 |
| ARG | CD | A | 157 | 640 | −163 | 197 | 35 |
| ARG | NE | A | 157 | 638 | −175 | 189 | 37 |
| ARG | CZ | A | 157 | 635 | −175 | 176 | 38 |
| ARG | NH1 | A | 157 | 632 | −163 | 170 | 38 |
| ARG | NH2 | A | 157 | 633 | −186 | 169 | 38 |
| ARG | C | A | 157 | 682 | −148 | 203 | 29 |
| ARG | O | A | 157 | 686 | −150 | 214 | 29 |
| ALA | N | A | 158 | 681 | −135 | 198 | 28 |
| ALA | CA | A | 158 | 685 | −124 | 207 | 26 |
| ALA | CB | A | 158 | 699 | −120 | 204 | 24 |
| ALA | C | A | 158 | 676 | −112 | 205 | 25 |
| ALA | O | A | 158 | 669 | −111 | 195 | 24 |
| ASN | N | A | 159 | 676 | −103 | 215 | 24 |
| ASN | CA | A | 159 | 668 | −91 | 214 | 22 |
| ASN | CB | A | 159 | 668 | −84 | 228 | 21 |
| ASN | CG | A | 159 | 659 | −90 | 237 | 21 |
| ASN | OD1 | A | 159 | 647 | −92 | 234 | 21 |
| ASN | ND2 | A | 159 | 664 | −94 | 249 | 21 |
| ASN | C | A | 159 | 675 | −82 | 204 | 22 |
| ASN | O | A | 159 | 688 | −82 | 203 | 22 |
| ILE | N | A | 160 | 668 | −75 | 196 | 23 |
| ILE | CA | A | 160 | 673 | −66 | 186 | 23 |
| ILE | CB | A | 160 | 673 | −73 | 172 | 23 |
| ILE | CG2 | A | 160 | 679 | −63 | 161 | 23 |
| ILE | CG1 | A | 160 | 681 | −86 | 172 | 23 |
| ILE | CD1 | A | 160 | 681 | −93 | 158 | 22 |
| ILE | C | A | 160 | 665 | −53 | 185 | 23 |
| ILE | O | A | 160 | 653 | −53 | 184 | 23 |
| ALA | N | A | 161 | 673 | −42 | 186 | 24 |
| ALA | CA | A | 161 | 666 | −29 | 185 | 24 |
| ALA | CB | A | 161 | 673 | −19 | 194 | 24 |
| ALA | C | A | 161 | 668 | −25 | 170 | 25 |
| ALA | O | A | 161 | 679 | −23 | 166 | 25 |
| ALA | N | A | 162 | 657 | −25 | 163 | 26 |
| ALA | CA | A | 162 | 657 | −21 | 149 | 28 |
| ALA | CB | A | 162 | 644 | −26 | 143 | 27 |
| ALA | C | A | 162 | 657 | −6 | 149 | 29 |
| ALA | O | A | 162 | 647 | 1 | 153 | 28 |
| ILE | N | A | 163 | 668 | 0 | 145 | 31 |
| ILE | CA | A | 163 | 670 | 14 | 145 | 32 |
| ILE | CB | A | 163 | 685 | 18 | 144 | 33 |
| ILE | CG2 | A | 163 | 686 | 34 | 143 | 32 |
| ILE | CG1 | A | 163 | 692 | 14 | 157 | 32 |
| ILE | CD1 | A | 163 | 706 | 17 | 158 | 32 |
| ILE | C | A | 163 | 663 | 20 | 133 | 34 |
| ILE | O | A | 163 | 665 | 17 | 122 | 35 |
| THR | N | A | 164 | 653 | 29 | 136 | 35 |
| THR | CA | A | 164 | 645 | 35 | 126 | 37 |
| THR | CB | A | 164 | 630 | 33 | 129 | 37 |
| THR | OG1 | A | 164 | 627 | 38 | 142 | 36 |
| THR | CG2 | A | 164 | 627 | 18 | 129 | 36 |
| THR | C | A | 164 | 647 | 50 | 125 | 39 |
| THR | O | A | 164 | 644 | 57 | 115 | 39 |
| GLU | N | A | 165 | 653 | 56 | 136 | 41 |
| GLU | CA | A | 165 | 656 | 70 | 136 | 44 |
| GLU | CB | A | 165 | 645 | 78 | 143 | 45 |
| GLU | CG | A | 165 | 632 | 80 | 135 | 48 |
| GLU | CD | A | 165 | 633 | 91 | 124 | 49 |
| GLU | OE1 | A | 165 | 640 | 101 | 126 | 49 |
| GLU | OE2 | A | 165 | 626 | 89 | 113 | 49 |
| GLU | C | A | 165 | 669 | 73 | 144 | 44 |
| GLU | O | A | 165 | 671 | 67 | 154 | 44 |
| SER | N | A | 166 | 677 | 82 | 139 | 44 |
| SER | CA | A | 166 | 690 | 85 | 145 | 45 |
| SER | CB | A | 166 | 700 | 75 | 141 | 45 |
| SER | OG | A | 166 | 702 | 74 | 127 | 44 |
| SER | C | A | 166 | 695 | 99 | 142 | 46 |
| SER | O | A | 166 | 692 | 104 | 131 | 47 |
| ASP | N | A | 167 | 703 | 104 | 151 | 47 |
| ASP | CA | A | 167 | 709 | 117 | 149 | 47 |
| ASP | CB | A | 167 | 702 | 128 | 157 | 48 |
| ASP | CG | A | 167 | 708 | 142 | 155 | 49 |
| ASP | OD1 | A | 167 | 716 | 146 | 164 | 50 |
| ASP | OD2 | A | 167 | 706 | 149 | 145 | 49 |
| ASP | C | A | 167 | 724 | 117 | 153 | 47 |
| ASP | O | A | 167 | 726 | 116 | 165 | 47 |
| LYS | N | A | 168 | 733 | 117 | 144 | 47 |
| LYS | CA | A | 168 | 747 | 117 | 146 | 47 |
| LYS | CB | A | 168 | 751 | 129 | 155 | 48 |

TABLE 1-continued

Structure Coordinates for uncomplexed BACE

| | | | | | | |
|---|---|---|---|---|---|---|
| LYS | CG | A | 168 | 748 | 143 | 149 | 49 |
| LYS | CD | A | 168 | 751 | 154 | 158 | 51 |
| LYS | CE | A | 168 | 746 | 168 | 154 | 51 |
| LYS | NZ | A | 168 | 748 | 178 | 164 | 52 |
| LYS | C | A | 168 | 752 | 104 | 153 | 47 |
| LYS | O | A | 168 | 760 | 105 | 163 | 47 |
| PHE | N | A | 169 | 747 | 93 | 149 | 46 |
| PHE | CA | A | 169 | 751 | 80 | 154 | 44 |
| PHE | CB | A | 169 | 738 | 71 | 157 | 44 |
| PHE | CG | A | 169 | 742 | 57 | 162 | 43 |
| PHE | CD1 | A | 169 | 748 | 55 | 174 | 43 |
| PHE | CD2 | A | 169 | 739 | 46 | 154 | 43 |
| PHE | CE1 | A | 169 | 751 | 43 | 179 | 43 |
| PHE | CE2 | A | 169 | 742 | 34 | 158 | 42 |
| PHE | CZ | A | 169 | 748 | 32 | 170 | 43 |
| PHE | C | A | 169 | 759 | 73 | 144 | 44 |
| PHE | O | A | 169 | 771 | 69 | 147 | 44 |
| PHE | N | A | 170 | 753 | 71 | 132 | 44 |
| PHE | CA | A | 170 | 760 | 64 | 121 | 45 |
| PHE | CB | A | 170 | 751 | 61 | 110 | 45 |
| PHE | CG | A | 170 | 740 | 51 | 114 | 45 |
| PHE | CD1 | A | 170 | 727 | 53 | 112 | 45 |
| PHE | CD2 | A | 170 | 744 | 39 | 120 | 45 |
| PHE | CE1 | A | 170 | 717 | 44 | 116 | 45 |
| PHE | CE2 | A | 170 | 734 | 29 | 123 | 45 |
| PHE | CZ | A | 170 | 721 | 32 | 121 | 45 |
| PHE | C | A | 170 | 772 | 73 | 116 | 46 |
| PHE | O | A | 170 | 770 | 86 | 116 | 47 |
| ILE | N | A | 171 | 783 | 68 | 112 | 47 |
| ILE | CA | A | 171 | 794 | 75 | 107 | 47 |
| ILE | CB | A | 171 | 807 | 71 | 115 | 47 |
| ILE | CG2 | A | 171 | 819 | 80 | 110 | 47 |
| ILE | CG1 | A | 171 | 805 | 74 | 130 | 47 |
| ILE | CD1 | A | 171 | 816 | 69 | 139 | 47 |
| ILE | C | A | 171 | 797 | 73 | 92 | 48 |
| ILE | O | A | 171 | 799 | 61 | 88 | 48 |
| ASN | N | A | 172 | 796 | 84 | 85 | 48 |
| ASN | CA | A | 172 | 799 | 83 | 70 | 48 |
| ASN | CB | A | 172 | 799 | 97 | 65 | 49 |
| ASN | CG | A | 172 | 801 | 97 | 50 | 49 |
| ASN | OD1 | A | 172 | 803 | 107 | 43 | 50 |
| ASN | ND2 | A | 172 | 800 | 85 | 44 | 49 |
| ASN | C | A | 172 | 812 | 76 | 68 | 47 |
| ASN | O | A | 172 | 822 | 81 | 72 | 48 |
| GLY | N | A | 173 | 811 | 65 | 60 | 47 |
| GLY | CA | A | 173 | 824 | 58 | 57 | 45 |
| GLY | C | A | 173 | 829 | 47 | 67 | 45 |
| GLY | O | A | 173 | 838 | 40 | 64 | 45 |
| SER | N | A | 174 | 823 | 47 | 79 | 44 |
| SER | CA | A | 174 | 827 | 37 | 89 | 42 |
| SER | CB | A | 174 | 819 | 39 | 102 | 42 |
| SER | OG | A | 174 | 806 | 34 | 99 | 42 |
| SER | C | A | 174 | 826 | 23 | 84 | 41 |
| SER | O | A | 174 | 835 | 14 | 88 | 42 |
| ASN | N | A | 175 | 816 | 20 | 76 | 39 |
| ASN | CA | A | 175 | 814 | 6 | 71 | 38 |
| ASN | CB | A | 175 | 826 | 0 | 66 | 38 |
| ASN | CG | A | 175 | 824 | −12 | 57 | 39 |
| ASN | OD1 | A | 175 | 814 | −12 | 50 | 39 |
| ASN | ND2 | A | 175 | 832 | −22 | 57 | 39 |
| ASN | C | A | 175 | 806 | −3 | 81 | 36 |
| ASN | O | A | 175 | 806 | −15 | 79 | 36 |
| TRP | N | A | 176 | 801 | 2 | 92 | 35 |
| TRP | CA | A | 176 | 793 | −6 | 101 | 33 |
| TRP | CB | A | 176 | 799 | −6 | 115 | 33 |
| TRP | CG | A | 176 | 803 | 7 | 122 | 32 |
| TRP | CD2 | A | 176 | 794 | 15 | 130 | 32 |
| TRP | CE2 | A | 176 | 802 | 25 | 136 | 32 |
| TRP | CE3 | A | 176 | 780 | 15 | 133 | 31 |
| TRP | CD1 | A | 176 | 815 | 12 | 123 | 32 |
| TRP | NE1 | A | 176 | 815 | 23 | 131 | 32 |
| TRP | CZ2 | A | 176 | 797 | 35 | 144 | 32 |
| TRP | CZ3 | A | 176 | 775 | 24 | 141 | 31 |
| TRP | CH2 | A | 176 | 783 | 35 | 147 | 32 |
| TRP | C | A | 176 | 779 | −1 | 101 | 33 |
| TRP | O | A | 176 | 776 | 11 | 99 | 32 |
| GLU | N | A | 177 | 770 | −10 | 104 | 31 |
| GLU | CA | A | 177 | 755 | −6 | 104 | 30 |
| GLU | CB | A | 177 | 748 | −14 | 92 | 31 |
| GLU | CG | A | 177 | 754 | −10 | 78 | 32 |
| GLU | CD | A | 177 | 765 | −19 | 74 | 32 |
| GLU | OE1 | A | 177 | 774 | −14 | 67 | 33 |
| GLU | OE2 | A | 177 | 766 | −31 | 77 | 33 |
| GLU | C | A | 177 | 748 | −9 | 117 | 30 |
| GLU | O | A | 177 | 736 | −7 | 117 | 30 |
| GLY | N | A | 178 | 755 | −13 | 127 | 29 |
| GLY | CA | A | 178 | 749 | −15 | 140 | 27 |
| GLY | C | A | 178 | 759 | −15 | 151 | 26 |
| GLY | O | A | 178 | 770 | −12 | 149 | 26 |
| ILE | N | A | 179 | 754 | −19 | 163 | 25 |
| ILE | CA | A | 179 | 763 | −19 | 175 | 24 |
| ILE | CB | A | 179 | 761 | −6 | 182 | 24 |
| ILE | CG2 | A | 179 | 747 | −4 | 186 | 24 |
| ILE | CG1 | A | 179 | 770 | −6 | 195 | 24 |
| ILE | CD1 | A | 179 | 770 | 8 | 202 | 24 |
| ILE | C | A | 179 | 760 | −31 | 184 | 24 |
| ILE | O | A | 179 | 748 | −35 | 186 | 23 |
| LEU | N | A | 180 | 770 | −37 | 189 | 24 |
| LEU | CA | A | 180 | 769 | −48 | 199 | 23 |
| LEU | CB | A | 180 | 778 | −60 | 193 | 22 |
| LEU | CG | A | 180 | 779 | −73 | 201 | 23 |
| LEU | CD1 | A | 180 | 765 | −79 | 203 | 22 |
| LEU | CD2 | A | 180 | 788 | −83 | 195 | 23 |
| LEU | C | A | 180 | 774 | −44 | 212 | 24 |
| LEU | O | A | 180 | 787 | −44 | 215 | 25 |
| GLY | N | A | 181 | 765 | −41 | 221 | 24 |
| GLY | CA | A | 181 | 769 | −37 | 235 | 24 |
| GLY | C | A | 181 | 772 | −50 | 243 | 24 |
| GLY | O | A | 181 | 763 | −58 | 245 | 24 |
| LEU | N | A | 182 | 785 | −51 | 247 | 23 |
| LEU | CA | A | 182 | 789 | −63 | 254 | 23 |
| LEU | CB | A | 182 | 803 | −68 | 249 | 22 |
| LEU | CG | A | 182 | 803 | −73 | 234 | 22 |
| LEU | CD1 | A | 182 | 818 | −74 | 230 | 21 |
| LEU | CD2 | A | 182 | 796 | −86 | 233 | 21 |
| LEU | C | A | 182 | 789 | −62 | 269 | 24 |
| LEU | O | A | 182 | 794 | −71 | 276 | 23 |
| ALA | N | A | 183 | 785 | −51 | 274 | 24 |
| ALA | CA | A | 183 | 785 | −48 | 289 | 25 |
| ALA | CB | A | 183 | 785 | −33 | 291 | 24 |
| ALA | C | A | 183 | 773 | −55 | 295 | 25 |
| ALA | O | A | 183 | 765 | −61 | 288 | 26 |
| TYR | N | A | 184 | 771 | −52 | 308 | 25 |
| TYR | CA | A | 184 | 760 | −59 | 315 | 26 |
| TYR | CB | A | 184 | 764 | −61 | 330 | 25 |
| TYR | CG | A | 184 | 777 | −68 | 332 | 25 |
| TYR | CD1 | A | 184 | 789 | −62 | 333 | 24 |
| TYR | CE1 | A | 184 | 801 | −69 | 335 | 24 |
| TYR | CD2 | A | 184 | 777 | −82 | 332 | 25 |
| TYR | CE2 | A | 184 | 788 | −89 | 334 | 24 |
| TYR | CZ | A | 184 | 800 | −83 | 336 | 24 |
| TYR | OH | A | 184 | 812 | −89 | 338 | 24 |
| TYR | C | A | 184 | 746 | −52 | 314 | 27 |
| TYR | O | A | 184 | 745 | −41 | 311 | 26 |
| ALA | N | A | 185 | 736 | −60 | 317 | 27 |
| ALA | CA | A | 185 | 722 | −56 | 316 | 29 |
| ALA | CB | A | 185 | 712 | −67 | 320 | 29 |
| ALA | C | A | 185 | 718 | −43 | 324 | 30 |
| ALA | O | A | 185 | 710 | −35 | 320 | 29 |
| GLU | N | A | 186 | 725 | −42 | 335 | 31 |
| GLU | CA | A | 186 | 723 | −30 | 344 | 33 |
| GLU | CB | A | 186 | 735 | −29 | 354 | 34 |
| GLU | CG | A | 186 | 734 | −17 | 362 | 37 |
| GLU | CD | A | 186 | 730 | −20 | 377 | 39 |
| GLU | OE1 | A | 186 | 739 | −24 | 385 | 40 |
| GLU | OE2 | A | 186 | 718 | −19 | 380 | 39 |
| GLU | C | A | 186 | 722 | −17 | 336 | 33 |
| GLU | O | A | 186 | 714 | −9 | 339 | 33 |
| ILE | N | A | 187 | 730 | −16 | 326 | 33 |
| ILE | CA | A | 187 | 730 | −4 | 317 | 33 |
| ILE | CB | A | 187 | 744 | 2 | 315 | 33 |
| ILE | CG2 | A | 187 | 750 | 7 | 328 | 33 |
| ILE | CG1 | A | 187 | 753 | −9 | 309 | 33 |
| ILE | CD1 | A | 187 | 767 | −5 | 306 | 34 |

TABLE 1-continued

Structure Coordinates for uncomplexed BACE

| | | | | | | | |
|---|---|---|---|---|---|---|---|
| ILE | C | A | 187 | 722 | −5 | 304 | 33 |
| ILE | O | A | 187 | 723 | 4 | 296 | 33 |
| ALA | N | A | 188 | 715 | −16 | 302 | 32 |
| ALA | CA | A | 188 | 707 | −18 | 290 | 33 |
| ALA | CB | A | 188 | 704 | −32 | 288 | 32 |
| ALA | C | A | 188 | 694 | −9 | 290 | 34 |
| ALA | O | A | 188 | 689 | −7 | 301 | 34 |
| ARG | N | A | 189 | 690 | −5 | 279 | 34 |
| ARG | CA | A | 189 | 678 | 3 | 277 | 35 |
| ARG | CB | A | 189 | 680 | 15 | 269 | 36 |
| ARG | CG | A | 189 | 692 | 23 | 272 | 38 |
| ARG | CD | A | 189 | 690 | 34 | 282 | 39 |
| ARG | NE | A | 189 | 680 | 44 | 277 | 41 |
| ARG | CZ | A | 189 | 676 | 55 | 283 | 42 |
| ARG | NH1 | A | 189 | 682 | 58 | 295 | 41 |
| ARG | NH2 | A | 189 | 667 | 63 | 277 | 42 |
| ARG | C | A | 189 | 667 | −6 | 271 | 35 |
| ARG | O | A | 189 | 671 | −15 | 262 | 34 |
| PRO | N | A | 190 | 654 | −5 | 274 | 35 |
| PRO | CD | A | 190 | 644 | −12 | 266 | 35 |
| PRO | CA | A | 190 | 648 | 5 | 283 | 35 |
| PRO | CB | A | 190 | 633 | 2 | 281 | 36 |
| PRO | CG | A | 190 | 632 | −3 | 267 | 36 |
| PRO | C | A | 190 | 653 | 3 | 298 | 36 |
| PRO | O | A | 190 | 653 | 13 | 305 | 36 |
| ASP | N | A | 191 | 656 | −9 | 301 | 35 |
| ASP | CA | A | 191 | 660 | −12 | 315 | 36 |
| ASP | CB | A | 191 | 649 | −12 | 325 | 37 |
| ASP | CG | A | 191 | 638 | −22 | 323 | 38 |
| ASP | OD1 | A | 191 | 629 | −22 | 331 | 40 |
| ASP | OD2 | A | 191 | 639 | −30 | 313 | 39 |
| ASP | C | A | 191 | 667 | −26 | 315 | 35 |
| ASP | O | A | 191 | 668 | −33 | 305 | 35 |
| ASP | N | A | 192 | 672 | −30 | 327 | 35 |
| ASP | CA | A | 192 | 680 | −42 | 328 | 34 |
| ASP | CB | A | 192 | 686 | −43 | 342 | 35 |
| ASP | CG | A | 192 | 676 | −46 | 353 | 35 |
| ASP | OD1 | A | 192 | 664 | −47 | 350 | 35 |
| ASP | OD2 | A | 192 | 680 | −46 | 365 | 36 |
| ASP | C | A | 192 | 672 | −55 | 325 | 34 |
| ASP | O | A | 192 | 678 | −66 | 326 | 34 |
| SER | N | A | 193 | 659 | −54 | 322 | 33 |
| SER | CA | A | 193 | 651 | −66 | 319 | 32 |
| SER | CB | A | 193 | 636 | −63 | 322 | 33 |
| SER | OG | A | 193 | 631 | −53 | 313 | 34 |
| SER | C | A | 193 | 653 | −71 | 305 | 31 |
| SER | O | A | 193 | 650 | −82 | 301 | 31 |
| LEU | N | A | 194 | 658 | −62 | 296 | 30 |
| LEU | CA | A | 194 | 661 | −65 | 282 | 29 |
| LEU | CB | A | 194 | 661 | −53 | 273 | 29 |
| LEU | CG | A | 194 | 661 | −56 | 258 | 29 |
| LEU | CD1 | A | 194 | 647 | −61 | 254 | 29 |
| LEU | CD2 | A | 194 | 666 | −44 | 250 | 29 |
| LEU | C | A | 194 | 675 | −72 | 282 | 28 |
| LEU | O | A | 194 | 685 | −65 | 283 | 28 |
| GLU | N | A | 195 | 675 | −85 | 280 | 27 |
| GLU | CA | A | 195 | 687 | −93 | 280 | 26 |
| GLU | CB | A | 195 | 684 | −108 | 279 | 26 |
| GLU | CG | A | 195 | 696 | −117 | 282 | 26 |
| GLU | CD | A | 195 | 692 | −131 | 283 | 27 |
| GLU | OE1 | A | 195 | 697 | −138 | 291 | 27 |
| GLU | OE2 | A | 195 | 684 | −136 | 275 | 26 |
| GLU | C | A | 195 | 697 | −89 | 269 | 25 |
| GLU | O | A | 195 | 693 | −89 | 257 | 26 |
| PRO | N | A | 196 | 709 | −86 | 272 | 25 |
| PRO | CD | A | 196 | 715 | −84 | 286 | 24 |
| PRO | CA | A | 196 | 720 | −83 | 262 | 24 |
| PRO | CB | A | 196 | 731 | −78 | 271 | 24 |
| PRO | CG | A | 196 | 725 | −74 | 284 | 24 |
| PRO | C | A | 196 | 724 | −95 | 254 | 24 |
| PRO | O | A | 196 | 722 | −107 | 259 | 24 |
| PHE | N | A | 197 | 729 | −93 | 243 | 24 |
| PHE | CA | A | 197 | 733 | −104 | 234 | 23 |
| PHE | CB | A | 197 | 741 | −98 | 222 | 22 |
| PHE | CG | A | 197 | 746 | −109 | 212 | 22 |
| PHE | CD1 | A | 197 | 736 | −114 | 203 | 22 |
| PHE | CD2 | A | 197 | 759 | −113 | 212 | 22 |
| PHE | CE1 | A | 197 | 740 | −124 | 194 | 22 |
| PHE | CE2 | A | 197 | 763 | −123 | 203 | 22 |
| PHE | CZ | A | 197 | 753 | −129 | 195 | 21 |
| PHE | C | A | 197 | 742 | −115 | 240 | 23 |
| PHE | O | A | 197 | 739 | −126 | 239 | 23 |
| PHE | N | A | 198 | 753 | −111 | 245 | 23 |
| PHE | CA | A | 198 | 763 | −121 | 251 | 23 |
| PHE | CB | A | 198 | 775 | −114 | 257 | 22 |
| PHE | CG | A | 198 | 787 | −122 | 257 | 22 |
| PHE | CD1 | A | 198 | 794 | −125 | 245 | 22 |
| PHE | CD2 | A | 198 | 791 | −129 | 269 | 22 |
| PHE | CE1 | A | 198 | 804 | −134 | 245 | 22 |
| PHE | CE2 | A | 198 | 802 | −138 | 269 | 22 |
| PHE | CZ | A | 198 | 808 | −140 | 257 | 22 |
| PHE | C | A | 198 | 756 | −130 | 261 | 24 |
| PHE | O | A | 198 | 758 | −142 | 262 | 24 |
| ASP | N | A | 199 | 747 | −124 | 270 | 25 |
| ASP | CA | A | 199 | 740 | −132 | 280 | 26 |
| ASP | CB | A | 199 | 731 | −123 | 288 | 28 |
| ASP | CG | A | 199 | 739 | −114 | 298 | 29 |
| ASP | OD1 | A | 199 | 739 | −118 | 310 | 30 |
| ASP | OD2 | A | 199 | 744 | −104 | 294 | 30 |
| ASP | C | A | 199 | 732 | −143 | 273 | 26 |
| ASP | O | A | 199 | 733 | −155 | 277 | 25 |
| SER | N | A | 200 | 724 | −139 | 263 | 25 |
| SER | CA | A | 200 | 716 | −148 | 255 | 25 |
| SER | CB | A | 200 | 708 | −141 | 244 | 25 |
| SER | OG | A | 200 | 698 | −133 | 250 | 26 |
| SER | C | A | 200 | 725 | −158 | 248 | 25 |
| SER | O | A | 200 | 722 | −170 | 248 | 25 |
| LEU | N | A | 201 | 737 | −154 | 243 | 25 |
| LEU | CA | A | 201 | 746 | −163 | 236 | 25 |
| LEU | CB | A | 201 | 758 | −155 | 230 | 25 |
| LEU | CG | A | 201 | 769 | −164 | 225 | 26 |
| LEU | CD1 | A | 201 | 764 | −170 | 212 | 26 |
| LEU | CD2 | A | 201 | 782 | −156 | 223 | 26 |
| LEU | C | A | 201 | 751 | −174 | 245 | 25 |
| LEU | O | A | 201 | 752 | −185 | 241 | 24 |
| VAL | N | A | 202 | 755 | −170 | 257 | 25 |
| VAL | CA | A | 202 | 760 | −180 | 267 | 25 |
| VAL | CB | A | 202 | 766 | −172 | 279 | 25 |
| VAL | CG1 | A | 202 | 770 | −183 | 290 | 24 |
| VAL | CG2 | A | 202 | 779 | −164 | 275 | 24 |
| VAL | C | A | 202 | 750 | −190 | 271 | 26 |
| VAL | O | A | 202 | 753 | −202 | 272 | 25 |
| LYS | N | A | 203 | 738 | −186 | 274 | 27 |
| LYS | CA | A | 203 | 728 | −195 | 279 | 28 |
| LYS | CB | A | 203 | 715 | −187 | 283 | 28 |
| LYS | CG | A | 203 | 717 | −179 | 296 | 29 |
| LYS | CD | A | 203 | 705 | −171 | 299 | 29 |
| LYS | CE | A | 203 | 706 | −163 | 311 | 30 |
| LYS | NZ | A | 203 | 693 | −156 | 315 | 32 |
| LYS | C | A | 203 | 723 | −205 | 268 | 30 |
| LYS | O | A | 203 | 721 | −217 | 271 | 30 |
| GLN | N | A | 204 | 722 | −200 | 255 | 31 |
| GLN | CA | A | 204 | 718 | −209 | 244 | 32 |
| GLN | CB | A | 204 | 712 | −200 | 233 | 31 |
| GLN | CG | A | 204 | 699 | −193 | 238 | 31 |
| GLN | CD | A | 204 | 694 | −183 | 228 | 31 |
| GLN | OE1 | A | 204 | 693 | −186 | 216 | 30 |
| GLN | NE2 | A | 204 | 690 | −171 | 233 | 30 |
| GLN | C | A | 204 | 728 | −218 | 239 | 33 |
| GLN | O | A | 204 | 725 | −228 | 232 | 34 |
| THR | N | A | 205 | 741 | −215 | 241 | 35 |
| THR | CA | A | 205 | 752 | −223 | 236 | 36 |
| THR | CB | A | 205 | 761 | −216 | 226 | 36 |
| THR | OG1 | A | 205 | 768 | −206 | 233 | 36 |
| THR | CG2 | A | 205 | 752 | −208 | 216 | 37 |
| THR | C | A | 205 | 761 | −228 | 247 | 37 |
| THR | O | A | 205 | 758 | −227 | 259 | 37 |
| HIS | N | A | 206 | 772 | −235 | 244 | 38 |
| HIS | CA | A | 206 | 781 | −240 | 254 | 40 |
| HIS | CB | A | 206 | 786 | −254 | 250 | 42 |
| HIS | CG | A | 206 | 775 | −265 | 253 | 43 |
| HIS | CD2 | A | 206 | 765 | −265 | 262 | 44 |
| HIS | ND1 | A | 206 | 775 | −277 | 247 | 44 |
| HIS | CE1 | A | 206 | 765 | −284 | 251 | 45 |

TABLE 1-continued

Structure Coordinates for uncomplexed BACE

| | | | | | | | |
|---|---|---|---|---|---|---|---|
| HIS | NE2 | A | 206 | 759 | −277 | 260 | 45 |
| HIS | C | A | 206 | 793 | −231 | 256 | 39 |
| HIS | O | A | 206 | 801 | −233 | 265 | 40 |
| VAL | N | A | 207 | 793 | −220 | 248 | 38 |
| VAL | CA | A | 207 | 804 | −210 | 248 | 37 |
| VAL | CB | A | 207 | 800 | −198 | 240 | 37 |
| VAL | CG1 | A | 207 | 811 | −188 | 240 | 36 |
| VAL | CG2 | A | 207 | 797 | −202 | 225 | 37 |
| VAL | C | A | 207 | 806 | −205 | 263 | 35 |
| VAL | O | A | 207 | 797 | −201 | 270 | 36 |
| PRO | N | A | 208 | 819 | −206 | 268 | 34 |
| PRO | CD | A | 208 | 830 | −214 | 262 | 33 |
| PRO | CA | A | 208 | 822 | −202 | 281 | 32 |
| PRO | CB | A | 208 | 837 | −204 | 282 | 32 |
| PRO | CG | A | 208 | 839 | −217 | 274 | 32 |
| PRO | C | A | 208 | 818 | −187 | 283 | 31 |
| PRO | O | A | 208 | 818 | −180 | 273 | 30 |
| ASN | N | A | 209 | 815 | −183 | 295 | 29 |
| ASN | CA | A | 209 | 811 | −169 | 297 | 28 |
| ASN | CB | A | 209 | 803 | −168 | 310 | 27 |
| ASN | CG | A | 209 | 797 | −155 | 313 | 27 |
| ASN | OD1 | A | 209 | 795 | −147 | 304 | 26 |
| ASN | ND2 | A | 209 | 793 | −152 | 325 | 28 |
| ASN | C | A | 209 | 823 | −160 | 298 | 27 |
| ASN | O | A | 209 | 827 | −155 | 309 | 26 |
| LEU | N | A | 210 | 829 | −158 | 286 | 26 |
| LEU | CA | A | 210 | 841 | −150 | 285 | 26 |
| LEU | CB | A | 210 | 853 | −158 | 291 | 26 |
| LEU | CG | A | 210 | 867 | −154 | 291 | 27 |
| LEU | CD1 | A | 210 | 876 | −162 | 301 | 27 |
| LEU | CD2 | A | 210 | 873 | −156 | 276 | 27 |
| LEU | C | A | 210 | 845 | −147 | 271 | 25 |
| LEU | O | A | 210 | 841 | −154 | 262 | 25 |
| PHE | N | A | 211 | 851 | −135 | 269 | 25 |
| PHE | CA | A | 211 | 855 | −131 | 255 | 24 |
| PHE | CB | A | 211 | 844 | −124 | 247 | 23 |
| PHE | CG | A | 211 | 841 | −110 | 253 | 23 |
| PHE | CD1 | A | 211 | 830 | −109 | 262 | 23 |
| PHE | CD2 | A | 211 | 847 | −99 | 248 | 23 |
| PHE | CE1 | A | 211 | 827 | −96 | 267 | 22 |
| PHE | CE2 | A | 211 | 844 | −86 | 253 | 23 |
| PHE | CZ | A | 211 | 834 | −85 | 262 | 22 |
| PHE | C | A | 211 | 868 | −123 | 257 | 24 |
| PHE | O | A | 211 | 870 | −117 | 268 | 24 |
| SER | N | A | 212 | 876 | −122 | 247 | 24 |
| SER | CA | A | 212 | 888 | −115 | 248 | 24 |
| SER | CB | A | 212 | 900 | −124 | 250 | 23 |
| SER | OG | A | 212 | 901 | −134 | 241 | 24 |
| SER | C | A | 212 | 890 | −106 | 235 | 24 |
| SER | O | A | 212 | 886 | −110 | 224 | 24 |
| LEU | N | A | 213 | 897 | −95 | 236 | 23 |
| LEU | CA | A | 213 | 899 | −86 | 225 | 23 |
| LEU | CB | A | 213 | 891 | −73 | 227 | 23 |
| LEU | CG | A | 213 | 876 | −74 | 227 | 23 |
| LEU | CD1 | A | 213 | 870 | −61 | 232 | 22 |
| LEU | CD2 | A | 213 | 872 | −77 | 212 | 23 |
| LEU | C | A | 213 | 914 | −82 | 223 | 23 |
| LEU | O | A | 213 | 921 | −78 | 233 | 23 |
| GLN | N | A | 214 | 918 | −83 | 211 | 24 |
| GLN | CA | A | 214 | 931 | −79 | 207 | 25 |
| GLN | CB | A | 214 | 939 | −90 | 201 | 25 |
| GLN | CG | A | 214 | 954 | −86 | 198 | 26 |
| GLN | CD | A | 214 | 961 | −96 | 188 | 26 |
| GLN | OE1 | A | 214 | 956 | −97 | 176 | 27 |
| GLN | NE2 | A | 214 | 972 | −102 | 192 | 25 |
| GLN | C | A | 214 | 929 | −68 | 196 | 27 |
| GLN | O | A | 214 | 927 | −72 | 184 | 27 |
| LEU | N | A | 215 | 929 | −55 | 199 | 27 |
| LEU | CA | A | 215 | 927 | −44 | 190 | 29 |
| LEU | CB | A | 215 | 920 | −33 | 196 | 28 |
| LEU | CG | A | 215 | 907 | −36 | 203 | 28 |
| LEU | CD1 | A | 215 | 900 | −23 | 208 | 26 |
| LEU | CD2 | A | 215 | 897 | −43 | 193 | 27 |
| LEU | C | A | 215 | 941 | −40 | 185 | 31 |
| LEU | O | A | 215 | 950 | −36 | 193 | 32 |
| CYS | N | A | 216 | 944 | −42 | 172 | 33 |
| CYS | CA | A | 216 | 957 | −39 | 167 | 36 |
| CYS | C | A | 216 | 960 | −25 | 161 | 38 |
| CYS | O | A | 216 | 971 | −22 | 157 | 39 |
| CYS | CB | A | 216 | 961 | −50 | 157 | 36 |
| CYS | SG | A | 216 | 961 | −66 | 164 | 37 |
| GLY | N | A | 217 | 949 | −17 | 159 | 40 |
| GLY | CA | A | 217 | 951 | −4 | 153 | 42 |
| GLY | C | A | 217 | 958 | −6 | 140 | 44 |
| GLY | O | A | 217 | 953 | −13 | 131 | 44 |
| ALA | N | A | 218 | 969 | 1 | 138 | 46 |
| ALA | CA | A | 218 | 977 | 0 | 126 | 48 |
| ALA | CB | A | 218 | 984 | −14 | 124 | 48 |
| ALA | C | A | 218 | 968 | 3 | 114 | 48 |
| ALA | O | A | 218 | 964 | 15 | 112 | 50 |
| ALA | N | A | 229 | 948 | 42 | 76 | 49 |
| ALA | CA | A | 229 | 935 | 46 | 82 | 49 |
| ALA | CB | A | 229 | 927 | 54 | 72 | 49 |
| ALA | C | A | 229 | 927 | 33 | 85 | 48 |
| ALA | O | A | 229 | 916 | 34 | 92 | 49 |
| SER | N | A | 230 | 932 | 22 | 82 | 48 |
| SER | CA | A | 230 | 925 | 9 | 84 | 47 |
| SER | CB | A | 230 | 927 | 0 | 72 | 48 |
| SER | OG | A | 230 | 924 | 6 | 60 | 49 |
| SER | C | A | 230 | 931 | 2 | 97 | 46 |
| SER | O | A | 230 | 943 | 1 | 98 | 46 |
| VAL | N | A | 231 | 922 | −3 | 105 | 44 |
| VAL | CA | A | 231 | 926 | −9 | 117 | 42 |
| VAL | CB | A | 231 | 920 | −3 | 130 | 42 |
| VAL | CG1 | A | 231 | 925 | 12 | 131 | 42 |
| VAL | CG2 | A | 231 | 905 | −3 | 130 | 42 |
| VAL | C | A | 231 | 921 | −24 | 117 | 40 |
| VAL | O | A | 231 | 912 | −27 | 110 | 40 |
| GLY | N | A | 232 | 928 | −33 | 125 | 38 |
| GLY | CA | A | 232 | 924 | −47 | 125 | 36 |
| GLY | C | A | 232 | 925 | −52 | 139 | 34 |
| GLY | O | A | 232 | 931 | −46 | 148 | 33 |
| GLY | N | A | 233 | 919 | −64 | 141 | 33 |
| GLY | CA | A | 233 | 919 | −70 | 154 | 31 |
| GLY | C | A | 233 | 912 | −84 | 155 | 30 |
| GLY | O | A | 233 | 908 | −89 | 145 | 30 |
| SER | N | A | 234 | 910 | −89 | 167 | 29 |
| SER | CA | A | 234 | 904 | −102 | 169 | 29 |
| SER | CB | A | 234 | 914 | −113 | 171 | 28 |
| SER | OG | A | 234 | 923 | −114 | 161 | 29 |
| SER | C | A | 234 | 895 | −102 | 181 | 28 |
| SER | O | A | 234 | 899 | −97 | 192 | 29 |
| MET | N | A | 235 | 883 | −107 | 180 | 27 |
| MET | CA | A | 235 | 874 | −108 | 191 | 26 |
| MET | CB | A | 235 | 860 | −102 | 189 | 27 |
| MET | CG | A | 235 | 850 | −105 | 199 | 28 |
| MET | SD | A | 235 | 834 | −95 | 200 | 30 |
| MET | CE | A | 235 | 826 | −102 | 186 | 28 |
| MET | C | A | 235 | 872 | −123 | 193 | 25 |
| MET | O | A | 235 | 865 | −130 | 185 | 26 |
| ILE | N | A | 236 | 878 | −129 | 203 | 25 |
| ILE | CA | A | 236 | 876 | −144 | 206 | 24 |
| ILE | CB | A | 236 | 889 | −149 | 212 | 23 |
| ILE | CG2 | A | 236 | 888 | −165 | 213 | 22 |
| ILE | CG1 | A | 236 | 901 | −145 | 204 | 23 |
| ILE | CD1 | A | 236 | 901 | −149 | 189 | 22 |
| ILE | C | A | 236 | 865 | −146 | 215 | 25 |
| ILE | O | A | 236 | 866 | −143 | 227 | 25 |
| ILE | N | A | 237 | 854 | −152 | 210 | 26 |
| ILE | CA | A | 237 | 842 | −155 | 218 | 27 |
| ILE | CB | A | 237 | 830 | −155 | 209 | 28 |
| ILE | CG2 | A | 237 | 818 | −159 | 218 | 28 |
| ILE | CG1 | A | 237 | 828 | −142 | 202 | 28 |
| ILE | CD1 | A | 237 | 825 | −131 | 211 | 28 |
| ILE | C | A | 237 | 844 | −168 | 225 | 28 |
| ILE | O | A | 237 | 845 | −178 | 219 | 28 |
| GLY | N | A | 238 | 843 | −167 | 239 | 27 |
| GLY | CA | A | 238 | 844 | −179 | 247 | 27 |
| GLY | C | A | 238 | 857 | −185 | 250 | 27 |
| GLY | O | A | 238 | 858 | −196 | 255 | 28 |
| GLY | N | A | 239 | 868 | −178 | 248 | 26 |
| GLY | CA | A | 239 | 881 | −183 | 252 | 26 |
| GLY | C | A | 239 | 892 | −174 | 251 | 26 |
| GLY | O | A | 239 | 891 | −162 | 248 | 26 |

TABLE 1-continued

Structure Coordinates for uncomplexed BACE

| | | | | | | | |
|---|---|---|---|---|---|---|---|
| ILE | N | A | 240 | 904 | −179 | 253 | 26 |
| ILE | CA | A | 240 | 917 | −171 | 253 | 26 |
| ILE | CB | A | 240 | 923 | −171 | 267 | 26 |
| ILE | CG2 | A | 240 | 936 | −163 | 266 | 26 |
| ILE | CG1 | A | 240 | 914 | −166 | 277 | 26 |
| ILE | CD1 | A | 240 | 919 | −167 | 292 | 26 |
| ILE | C | A | 240 | 926 | −178 | 243 | 26 |
| ILE | O | A | 240 | 929 | −189 | 244 | 25 |
| ASP | N | A | 241 | 930 | −170 | 233 | 26 |
| ASP | CA | A | 241 | 939 | −175 | 223 | 25 |
| ASP | CB | A | 241 | 936 | −169 | 209 | 25 |
| ASP | CG | A | 241 | 944 | −174 | 198 | 24 |
| ASP | OD1 | A | 241 | 938 | −178 | 188 | 24 |
| ASP | OD2 | A | 241 | 956 | −174 | 199 | 23 |
| ASP | C | A | 241 | 954 | −171 | 226 | 26 |
| ASP | O | A | 241 | 958 | −160 | 226 | 25 |
| HIS | N | A | 242 | 961 | −182 | 229 | 27 |
| HIS | CA | A | 242 | 975 | −181 | 233 | 28 |
| HIS | CB | A | 242 | 981 | −194 | 236 | 30 |
| HIS | CG | A | 242 | 989 | −195 | 249 | 31 |
| HIS | CD2 | A | 242 | 985 | −192 | 262 | 32 |
| HIS | ND1 | A | 242 | 1002 | −200 | 249 | 32 |
| HIS | CE1 | A | 242 | 1006 | −199 | 262 | 32 |
| HIS | NE2 | A | 242 | 996 | −194 | 270 | 32 |
| HIS | C | A | 242 | 984 | −174 | 223 | 28 |
| HIS | O | A | 242 | 995 | −169 | 227 | 28 |
| SER | N | A | 243 | 980 | −173 | 210 | 28 |
| SER | CA | A | 243 | 989 | −167 | 200 | 28 |
| SER | CB | A | 243 | 986 | −172 | 187 | 27 |
| SER | OG | A | 243 | 975 | −166 | 181 | 24 |
| SER | C | A | 243 | 987 | −152 | 200 | 28 |
| SER | O | A | 243 | 995 | −145 | 193 | 29 |
| LEU | N | A | 244 | 978 | −146 | 207 | 28 |
| LEU | CA | A | 244 | 975 | −132 | 207 | 27 |
| LEU | CB | A | 244 | 960 | −129 | 208 | 27 |
| LEU | CG | A | 244 | 952 | −136 | 197 | 27 |
| LEU | CD1 | A | 244 | 937 | −132 | 198 | 26 |
| LEU | CD2 | A | 244 | 957 | −132 | 183 | 26 |
| LEU | C | A | 244 | 983 | −124 | 217 | 27 |
| LEU | O | A | 244 | 982 | −112 | 217 | 27 |
| TYR | N | A | 245 | 990 | −131 | 226 | 27 |
| TYR | CA | A | 245 | 998 | −123 | 236 | 27 |
| TYR | CB | A | 245 | 990 | −122 | 249 | 26 |
| TYR | CG | A | 245 | 987 | −134 | 257 | 25 |
| TYR | CD1 | A | 245 | 977 | −143 | 253 | 25 |
| TYR | CE1 | A | 245 | 974 | −154 | 261 | 25 |
| TYR | CD2 | A | 245 | 995 | −137 | 268 | 26 |
| TYR | CE2 | A | 245 | 992 | −149 | 276 | 25 |
| TYR | CZ | A | 245 | 982 | −157 | 272 | 25 |
| TYR | OH | A | 245 | 979 | −168 | 280 | 26 |
| TYR | C | A | 245 | 1011 | −130 | 239 | 27 |
| TYR | O | A | 245 | 1014 | −141 | 234 | 26 |
| THR | N | A | 246 | 1019 | −124 | 247 | 28 |
| THR | CA | A | 246 | 1032 | −129 | 252 | 28 |
| THR | CB | A | 246 | 1044 | −122 | 245 | 28 |
| THR | OG1 | A | 246 | 1043 | −108 | 248 | 29 |
| THR | CG2 | A | 246 | 1044 | −124 | 230 | 29 |
| THR | C | A | 246 | 1032 | −126 | 266 | 28 |
| THR | O | A | 246 | 1024 | −118 | 271 | 27 |
| GLY | N | A | 247 | 1041 | −132 | 274 | 29 |
| GLY | CA | A | 247 | 1042 | −130 | 288 | 29 |
| GLY | C | A | 247 | 1030 | −135 | 296 | 29 |
| GLY | O | A | 247 | 1023 | −144 | 291 | 30 |
| SER | N | A | 248 | 1028 | −130 | 308 | 29 |
| SER | CA | A | 248 | 1017 | −135 | 316 | 29 |
| SER | CB | A | 248 | 1022 | −136 | 330 | 29 |
| SER | OG | A | 248 | 1034 | −143 | 331 | 31 |
| SER | C | A | 248 | 1005 | −126 | 315 | 28 |
| SER | O | A | 248 | 1006 | −114 | 312 | 28 |
| LEU | N | A | 249 | 994 | −131 | 319 | 27 |
| LEU | CA | A | 249 | 981 | −124 | 320 | 27 |
| LEU | CB | A | 249 | 970 | −133 | 315 | 29 |
| LEU | CG | A | 249 | 965 | −133 | 301 | 26 |
| LEU | CD1 | A | 249 | 957 | −146 | 298 | 26 |
| LEU | CD2 | A | 249 | 957 | −120 | 298 | 25 |
| LEU | C | A | 249 | 979 | −120 | 334 | 27 |
| LEU | O | A | 249 | 981 | −128 | 343 | 27 |
| TRP | N | A | 250 | 976 | −107 | 337 | 27 |
| TRP | CA | A | 250 | 974 | −103 | 350 | 27 |
| TRP | CB | A | 250 | 983 | −91 | 353 | 28 |
| TRP | CG | A | 250 | 997 | −95 | 356 | 29 |
| TRP | CD2 | A | 250 | 1003 | −98 | 369 | 30 |
| TRP | CE2 | A | 250 | 1016 | −102 | 368 | 30 |
| TRP | CE3 | A | 250 | 998 | −98 | 382 | 29 |
| TRP | CD1 | A | 250 | 1007 | −98 | 347 | 30 |
| TRP | NE1 | A | 250 | 1019 | −102 | 354 | 30 |
| TRP | CZ2 | A | 250 | 1025 | −106 | 378 | 30 |
| TRP | CZ3 | A | 250 | 1006 | −101 | 393 | 30 |
| TRP | CH2 | A | 250 | 1020 | −105 | 391 | 30 |
| TRP | C | A | 250 | 959 | −98 | 351 | 27 |
| TRP | O | A | 250 | 955 | −92 | 341 | 27 |
| TYR | N | A | 251 | 953 | −101 | 362 | 26 |
| TYR | CA | A | 251 | 938 | −98 | 363 | 26 |
| TYR | CB | A | 251 | 931 | −111 | 367 | 27 |
| TYR | CG | A | 251 | 930 | −121 | 355 | 27 |
| TYR | CD1 | A | 251 | 941 | −130 | 353 | 27 |
| TYR | CE1 | A | 251 | 940 | −139 | 343 | 28 |
| TYR | CD2 | A | 251 | 920 | −121 | 346 | 27 |
| TYR | CE2 | A | 251 | 919 | −130 | 336 | 28 |
| TYR | CZ | A | 251 | 929 | −139 | 334 | 28 |
| TYR | OH | A | 251 | 929 | −148 | 323 | 29 |
| TYR | C | A | 251 | 935 | −88 | 374 | 27 |
| TYR | O | A | 251 | 941 | −87 | 385 | 26 |
| THR | N | A | 252 | 925 | −80 | 371 | 27 |
| THR | CA | A | 252 | 920 | −69 | 380 | 27 |
| THR | CB | A | 252 | 922 | −55 | 374 | 27 |
| THR | OG1 | A | 252 | 921 | −46 | 384 | 28 |
| THR | CG2 | A | 252 | 913 | −52 | 363 | 28 |
| THR | C | A | 252 | 905 | −72 | 381 | 28 |
| THR | O | A | 252 | 898 | −76 | 372 | 28 |
| PRO | N | A | 253 | 900 | −71 | 394 | 28 |
| PRO | CD | A | 253 | 906 | −66 | 406 | 28 |
| PRO | CA | A | 253 | 886 | −74 | 396 | 28 |
| PRO | CB | A | 253 | 884 | −73 | 411 | 28 |
| PRO | CG | A | 253 | 898 | −74 | 417 | 29 |
| PRO | C | A | 253 | 876 | −64 | 389 | 28 |
| PRO | O | A | 253 | 879 | −53 | 386 | 27 |
| ILE | N | A | 254 | 864 | −70 | 385 | 28 |
| ILE | CA | A | 254 | 854 | −62 | 379 | 29 |
| ILE | CB | A | 254 | 844 | −70 | 370 | 28 |
| ILE | CG2 | A | 254 | 831 | −62 | 368 | 27 |
| ILE | CG1 | A | 254 | 851 | −74 | 357 | 28 |
| ILE | CD1 | A | 254 | 842 | −83 | 348 | 27 |
| ILE | C | A | 254 | 847 | −56 | 391 | 30 |
| ILE | O | A | 254 | 840 | −64 | 398 | 31 |
| ARG | N | A | 255 | 848 | −44 | 394 | 32 |
| ARG | CA | A | 255 | 842 | −38 | 406 | 33 |
| ARG | CB | A | 255 | 845 | −23 | 407 | 33 |
| ARG | CG | A | 255 | 843 | −17 | 421 | 35 |
| ARG | CD | A | 255 | 845 | −2 | 422 | 35 |
| ARG | NE | A | 255 | 843 | 3 | 435 | 36 |
| ARG | CZ | A | 255 | 838 | 14 | 438 | 36 |
| ARG | NH1 | A | 255 | 833 | 22 | 429 | 36 |
| ARG | NH2 | A | 255 | 837 | 19 | 451 | 36 |
| ARG | C | A | 255 | 827 | −40 | 407 | 34 |
| ARG | O | A | 255 | 822 | −46 | 417 | 34 |
| ARG | N | A | 256 | 819 | −37 | 397 | 34 |
| ARG | CA | A | 256 | 805 | −39 | 397 | 35 |
| ARG | CB | A | 256 | 797 | −26 | 401 | 36 |
| ARG | CG | A | 256 | 783 | −29 | 406 | 39 |
| ARG | CD | A | 256 | 772 | −20 | 399 | 40 |
| ARG | NE | A | 256 | 775 | −6 | 400 | 41 |
| ARG | CZ | A | 256 | 766 | 4 | 397 | 41 |
| ARG | NH1 | A | 256 | 754 | 0 | 391 | 42 |
| ARG | NH2 | A | 256 | 769 | 17 | 398 | 42 |
| ARG | C | A | 256 | 801 | −42 | 382 | 34 |
| ARG | O | A | 256 | 807 | −37 | 373 | 33 |
| GLU | N | A | 257 | 792 | −52 | 381 | 34 |
| GLU | CA | A | 257 | 788 | −56 | 368 | 34 |
| GLU | CB | A | 257 | 782 | −70 | 368 | 34 |
| GLU | CG | A | 257 | 793 | −80 | 372 | 35 |
| GLU | CD | A | 257 | 787 | −93 | 377 | 36 |
| GLU | OE1 | A | 257 | 779 | −93 | 387 | 37 |
| GLU | OE2 | A | 257 | 789 | −104 | 371 | 37 |

TABLE 1-continued

Structure Coordinates for uncomplexed BACE

| | | | | | | | |
|---|---|---|---|---|---|---|---|
| GLU | C | A | 257 | 777 | −47 | 361 | 33 |
| GLU | O | A | 257 | 765 | −49 | 361 | 33 |
| TRP | N | A | 258 | 782 | −36 | 355 | 32 |
| TRP | CA | A | 258 | 774 | −27 | 347 | 32 |
| TRP | CB | A | 258 | 769 | −15 | 355 | 32 |
| TRP | CG | A | 258 | 779 | −6 | 362 | 32 |
| TRP | CD2 | A | 258 | 777 | 8 | 365 | 32 |
| TRP | CE2 | A | 258 | 789 | 12 | 372 | 31 |
| TRP | CE3 | A | 258 | 767 | 17 | 363 | 32 |
| TRP | CD1 | A | 258 | 791 | −9 | 366 | 32 |
| TRP | NE1 | A | 258 | 797 | 1 | 372 | 31 |
| TRP | CZ2 | A | 258 | 791 | 25 | 376 | 32 |
| TRP | CZ3 | A | 258 | 769 | 30 | 367 | 32 |
| TRP | CH2 | A | 258 | 780 | 34 | 374 | 32 |
| TRP | C | A | 258 | 782 | −23 | 335 | 31 |
| TRP | O | A | 258 | 780 | −29 | 324 | 32 |
| TYR | N | A | 259 | 792 | −15 | 337 | 31 |
| TYR | CA | A | 259 | 801 | −12 | 326 | 30 |
| TYR | CB | A | 259 | 808 | 2 | 327 | 30 |
| TYR | CG | A | 259 | 799 | 14 | 323 | 31 |
| TYR | CD1 | A | 259 | 797 | 17 | 310 | 31 |
| TYR | CE1 | A | 259 | 789 | 28 | 306 | 32 |
| TYR | CD2 | A | 259 | 792 | 21 | 333 | 32 |
| TYR | CE2 | A | 259 | 783 | 32 | 329 | 32 |
| TYR | CZ | A | 259 | 782 | 35 | 316 | 33 |
| TYR | OH | A | 259 | 774 | 45 | 312 | 34 |
| TYR | C | A | 259 | 812 | −21 | 331 | 30 |
| TYR | O | A | 259 | 810 | −28 | 341 | 29 |
| TYR | N | A | 260 | 823 | −23 | 323 | 29 |
| TYR | CA | A | 260 | 834 | −32 | 328 | 29 |
| TYR | CB | A | 260 | 842 | −38 | 317 | 28 |
| TYR | CG | A | 260 | 834 | −49 | 310 | 26 |
| TYR | CD1 | A | 260 | 827 | −47 | 299 | 26 |
| TYR | CE1 | A | 260 | 819 | −57 | 293 | 25 |
| TYR | CD2 | A | 260 | 834 | −62 | 316 | 26 |
| TYR | CE2 | A | 260 | 826 | −72 | 311 | 25 |
| TYR | CZ | A | 260 | 819 | −70 | 299 | 25 |
| TYR | OH | A | 260 | 811 | −80 | 293 | 25 |
| TYR | C | A | 260 | 842 | −22 | 336 | 30 |
| TYR | O | A | 260 | 852 | −15 | 331 | 31 |
| GLU | N | A | 261 | 839 | −20 | 349 | 31 |
| GLU | CA | A | 261 | 845 | −11 | 358 | 31 |
| GLU | CB | A | 261 | 835 | −4 | 367 | 32 |
| GLU | CG | A | 261 | 841 | 2 | 380 | 33 |
| GLU | CD | A | 261 | 831 | 10 | 388 | 34 |
| GLU | OE1 | A | 261 | 820 | 4 | 391 | 35 |
| GLU | OE2 | A | 261 | 835 | 21 | 393 | 35 |
| GLU | C | A | 261 | 857 | −17 | 366 | 30 |
| GLU | O | A | 261 | 855 | −27 | 372 | 29 |
| VAL | N | A | 262 | 868 | −9 | 366 | 30 |
| VAL | CA | A | 262 | 879 | −13 | 374 | 31 |
| VAL | CB | A | 262 | 891 | −17 | 364 | 30 |
| VAL | CG1 | A | 262 | 887 | −30 | 356 | 30 |
| VAL | CG2 | A | 262 | 893 | −6 | 354 | 30 |
| VAL | C | A | 262 | 884 | −2 | 382 | 32 |
| VAL | O | A | 262 | 879 | 9 | 382 | 31 |
| ILE | N | A | 263 | 895 | −5 | 390 | 32 |
| ILE | CA | A | 263 | 900 | 5 | 399 | 33 |
| ILE | CB | A | 263 | 898 | 1 | 414 | 34 |
| ILE | CG2 | A | 263 | 906 | 10 | 423 | 34 |
| ILE | CG1 | A | 263 | 883 | 1 | 417 | 34 |
| ILE | CD1 | A | 263 | 880 | −5 | 431 | 35 |
| ILE | C | A | 263 | 915 | 8 | 397 | 34 |
| ILE | O | A | 263 | 923 | −1 | 399 | 34 |
| ILE | N | A | 264 | 918 | 20 | 394 | 33 |
| ILE | CA | A | 264 | 932 | 24 | 392 | 33 |
| ILE | CB | A | 264 | 933 | 36 | 381 | 33 |
| ILE | CG2 | A | 264 | 947 | 42 | 382 | 32 |
| ILE | CG1 | A | 264 | 930 | 30 | 368 | 32 |
| ILE | CD1 | A | 264 | 929 | 41 | 357 | 32 |
| ILE | C | A | 264 | 937 | 29 | 405 | 33 |
| ILE | O | A | 264 | 931 | 38 | 412 | 33 |
| VAL | N | A | 265 | 949 | 24 | 409 | 33 |
| VAL | CA | A | 265 | 955 | 28 | 422 | 34 |
| VAL | CB | A | 265 | 959 | 16 | 430 | 34 |
| VAL | CG1 | A | 265 | 947 | 7 | 434 | 34 |
| VAL | CG2 | A | 265 | 969 | 7 | 422 | 34 |
| VAL | C | A | 265 | 967 | 37 | 421 | 34 |
| VAL | O | A | 265 | 971 | 43 | 432 | 35 |
| ARG | N | A | 266 | 974 | 38 | 410 | 33 |
| ARG | CA | A | 266 | 985 | 46 | 408 | 32 |
| ARG | CB | A | 266 | 998 | 39 | 414 | 32 |
| ARG | CG | A | 266 | 1011 | 45 | 412 | 31 |
| ARG | CD | A | 266 | 1022 | 36 | 417 | 32 |
| ARG | NE | A | 266 | 1036 | 41 | 414 | 32 |
| ARG | CZ | A | 266 | 1043 | 50 | 421 | 33 |
| ARG | NH1 | A | 266 | 1038 | 54 | 433 | 33 |
| ARG | NH2 | A | 266 | 1055 | 53 | 417 | 34 |
| ARG | C | A | 266 | 988 | 50 | 393 | 32 |
| ARG | O | A | 266 | 984 | 41 | 385 | 31 |
| VAL | N | A | 267 | 993 | 61 | 391 | 31 |
| VAL | CA | A | 267 | 996 | 66 | 377 | 30 |
| VAL | CB | A | 267 | 986 | 76 | 372 | 30 |
| VAL | CG1 | A | 267 | 989 | 80 | 358 | 30 |
| VAL | CG2 | A | 267 | 972 | 71 | 374 | 30 |
| VAL | C | A | 267 | 1010 | 71 | 376 | 31 |
| VAL | O | A | 267 | 1015 | 79 | 384 | 31 |
| GLU | N | A | 268 | 1018 | 67 | 366 | 31 |
| GLU | CA | A | 268 | 1031 | 71 | 364 | 31 |
| GLU | CB | A | 268 | 1042 | 60 | 366 | 31 |
| GLU | CG | A | 268 | 1043 | 55 | 381 | 31 |
| GLU | CD | A | 268 | 1052 | 43 | 382 | 31 |
| GLU | OE1 | A | 268 | 1058 | 39 | 372 | 31 |
| GLU | OE2 | A | 268 | 1053 | 37 | 393 | 31 |
| GLU | C | A | 268 | 1034 | 76 | 350 | 31 |
| GLU | O | A | 268 | 1028 | 71 | 340 | 31 |
| ILE | N | A | 269 | 1042 | 86 | 349 | 30 |
| ILE | CA | A | 269 | 1046 | 92 | 336 | 31 |
| ILE | CB | A | 269 | 1043 | 107 | 335 | 31 |
| ILE | CG2 | A | 269 | 1046 | 112 | 321 | 31 |
| ILE | CG1 | A | 269 | 1028 | 110 | 338 | 31 |
| ILE | CD1 | A | 269 | 1018 | 103 | 329 | 31 |
| ILE | C | A | 269 | 1061 | 90 | 336 | 30 |
| ILE | O | A | 269 | 1068 | 97 | 343 | 29 |
| ASN | N | A | 270 | 1066 | 81 | 328 | 29 |
| ASN | CA | A | 270 | 1081 | 78 | 327 | 29 |
| ASN | CB | A | 270 | 1089 | 89 | 321 | 29 |
| ASN | CG | A | 270 | 1093 | 87 | 307 | 30 |
| ASN | OD1 | A | 270 | 1089 | 77 | 301 | 30 |
| ASN | ND2 | A | 270 | 1101 | 96 | 301 | 30 |
| ASN | C | A | 270 | 1086 | 74 | 341 | 28 |
| ASN | O | A | 270 | 1097 | 78 | 344 | 29 |
| GLY | N | A | 271 | 1078 | 67 | 349 | 28 |
| GLY | CA | A | 271 | 1082 | 63 | 362 | 29 |
| GLY | C | A | 271 | 1079 | 73 | 373 | 30 |
| GLY | O | A | 271 | 1078 | 69 | 385 | 29 |
| GLN | N | A | 272 | 1077 | 85 | 370 | 30 |
| GLN | CA | A | 272 | 1073 | 95 | 380 | 32 |
| GLN | CB | A | 272 | 1077 | 109 | 375 | 32 |
| GLN | CG | A | 272 | 1074 | 120 | 386 | 34 |
| GLN | CD | A | 272 | 1081 | 133 | 382 | 35 |
| GLN | OE1 | A | 272 | 1079 | 138 | 371 | 36 |
| GLN | NE2 | A | 272 | 1088 | 139 | 391 | 36 |
| GLN | C | A | 272 | 1059 | 95 | 385 | 32 |
| GLN | O | A | 272 | 1050 | 97 | 377 | 31 |
| ASP | N | A | 273 | 1057 | 92 | 397 | 33 |
| ASP | CA | A | 273 | 1043 | 92 | 403 | 35 |
| ASP | CB | A | 273 | 1044 | 89 | 418 | 34 |
| ASP | CG | A | 273 | 1030 | 87 | 424 | 35 |
| ASP | OD1 | A | 273 | 1021 | 85 | 416 | 35 |
| ASP | OD2 | A | 273 | 1029 | 87 | 436 | 35 |
| ASP | C | A | 273 | 1036 | 105 | 400 | 36 |
| ASP | O | A | 273 | 1042 | 116 | 400 | 36 |
| LEU | N | A | 274 | 1023 | 103 | 396 | 37 |
| LEU | CA | A | 274 | 1015 | 115 | 393 | 39 |
| LEU | CB | A | 274 | 1003 | 111 | 385 | 39 |
| LEU | CG | A | 274 | 996 | 122 | 376 | 40 |
| LEU | CD1 | A | 274 | 1007 | 128 | 367 | 40 |
| LEU | CD2 | A | 274 | 985 | 117 | 368 | 40 |
| LEU | C | A | 274 | 1012 | 122 | 406 | 40 |
| LEU | O | A | 274 | 1009 | 133 | 407 | 41 |
| LYS | N | A | 275 | 1012 | 113 | 416 | 41 |
| LYS | CA | A | 275 | 1010 | 118 | 430 | 42 |
| LYS | CB | A | 275 | 1021 | 128 | 434 | 42 |

TABLE 1-continued

Structure Coordinates for uncomplexed BACE

| | | | | | | | |
|---|---|---|---|---|---|---|---|
| LYS | CG | A | 275 | 1026 | 126 | 448 | 43 |
| LYS | CD | A | 275 | 1039 | 135 | 450 | 44 |
| LYS | CE | A | 275 | 1046 | 132 | 463 | 44 |
| LYS | NZ | A | 275 | 1059 | 140 | 463 | 45 |
| LYS | C | A | 275 | 996 | 124 | 433 | 43 |
| LYS | O | A | 275 | 996 | 135 | 439 | 43 |
| MET | N | A | 276 | 985 | 118 | 429 | 43 |
| MET | CA | A | 276 | 972 | 123 | 432 | 43 |
| MET | CB | A | 276 | 964 | 125 | 419 | 43 |
| MET | CG | A | 276 | 970 | 135 | 409 | 43 |
| MET | SD | A | 276 | 959 | 136 | 394 | 44 |
| MET | CE | A | 276 | 947 | 149 | 400 | 43 |
| MET | C | A | 276 | 965 | 114 | 441 | 44 |
| MET | O | A | 276 | 968 | 102 | 442 | 43 |
| ASP | N | A | 277 | 955 | 119 | 448 | 45 |
| ASP | CA | A | 277 | 947 | 110 | 457 | 46 |
| ASP | CB | A | 277 | 936 | 118 | 463 | 47 |
| ASP | CG | A | 277 | 926 | 110 | 471 | 47 |
| ASP | OD1 | A | 277 | 918 | 103 | 464 | 48 |
| ASP | OD2 | A | 277 | 925 | 110 | 483 | 48 |
| ASP | C | A | 277 | 941 | 100 | 447 | 47 |
| ASP | O | A | 277 | 934 | 104 | 438 | 47 |
| CYS | N | A | 278 | 944 | 87 | 449 | 47 |
| CYS | CA | A | 278 | 940 | 77 | 440 | 49 |
| CYS | C | A | 278 | 925 | 77 | 437 | 48 |
| CYS | O | A | 278 | 920 | 70 | 428 | 48 |
| CYS | CB | A | 278 | 945 | 63 | 444 | 50 |
| CYS | SG | A | 278 | 937 | 56 | 459 | 52 |
| LYS | N | A | 279 | 917 | 84 | 444 | 47 |
| LYS | CA | A | 279 | 902 | 85 | 442 | 47 |
| LYS | CB | A | 279 | 895 | 91 | 453 | 47 |
| LYS | CG | A | 279 | 887 | 81 | 462 | 47 |
| LYS | CD | A | 279 | 879 | 88 | 473 | 48 |
| LYS | CE | A | 279 | 870 | 79 | 481 | 48 |
| LYS | NZ | A | 279 | 878 | 69 | 489 | 48 |
| LYS | C | A | 279 | 900 | 93 | 429 | 46 |
| LYS | O | A | 279 | 890 | 91 | 422 | 46 |
| GLU | N | A | 280 | 908 | 103 | 427 | 45 |
| GLU | CA | A | 280 | 907 | 112 | 415 | 45 |
| GLU | CB | A | 280 | 918 | 123 | 415 | 46 |
| GLU | CG | A | 280 | 918 | 132 | 427 | 47 |
| GLU | CD | A | 280 | 905 | 140 | 428 | 47 |
| GLU | OE1 | A | 280 | 902 | 147 | 418 | 48 |
| GLU | OE2 | A | 280 | 898 | 140 | 439 | 48 |
| GLU | C | A | 280 | 908 | 104 | 402 | 44 |
| GLU | O | A | 280 | 902 | 107 | 392 | 43 |
| TYR | N | A | 281 | 916 | 93 | 403 | 42 |
| TYR | CA | A | 281 | 919 | 84 | 391 | 42 |
| TYR | CB | A | 281 | 929 | 74 | 394 | 40 |
| TYR | CG | A | 281 | 943 | 80 | 397 | 40 |
| TYR | CD1 | A | 281 | 951 | 74 | 407 | 39 |
| TYR | CE1 | A | 281 | 964 | 79 | 410 | 39 |
| TYR | CD2 | A | 281 | 948 | 91 | 390 | 39 |
| TYR | CE2 | A | 281 | 960 | 96 | 393 | 39 |
| TYR | CZ | A | 281 | 968 | 90 | 403 | 39 |
| TYR | OH | A | 281 | 980 | 96 | 406 | 40 |
| TYR | C | A | 281 | 906 | 77 | 387 | 42 |
| TYR | O | A | 281 | 904 | 74 | 375 | 42 |
| ASN | N | A | 282 | 897 | 75 | 397 | 42 |
| ASN | CA | A | 282 | 885 | 68 | 394 | 43 |
| ASN | CB | A | 282 | 884 | 55 | 402 | 43 |
| ASN | CG | A | 282 | 896 | 46 | 401 | 43 |
| ASN | OD1 | A | 282 | 898 | 40 | 390 | 42 |
| ASN | ND2 | A | 282 | 904 | 45 | 411 | 43 |
| ASN | C | A | 282 | 873 | 77 | 398 | 44 |
| ASN | O | A | 282 | 862 | 72 | 402 | 43 |
| TYR | N | A | 283 | 875 | 90 | 397 | 45 |
| TYR | CA | A | 283 | 864 | 99 | 401 | 46 |
| TYR | CB | A | 283 | 869 | 114 | 400 | 47 |
| TYR | CG | A | 283 | 857 | 123 | 402 | 47 |
| TYR | CD1 | A | 283 | 849 | 122 | 413 | 48 |
| TYR | CE1 | A | 283 | 837 | 130 | 414 | 48 |
| TYR | CD2 | A | 283 | 853 | 132 | 392 | 48 |
| TYR | CE2 | A | 283 | 842 | 140 | 393 | 48 |
| TYR | CZ | A | 283 | 834 | 139 | 404 | 48 |
| TYR | OH | A | 283 | 822 | 146 | 405 | 49 |
| TYR | C | A | 283 | 852 | 97 | 392 | 46 |
| TYR | O | A | 283 | 852 | 101 | 380 | 45 |
| ASP | N | A | 284 | 842 | 91 | 398 | 46 |
| ASP | CA | A | 284 | 830 | 87 | 392 | 45 |
| ASP | CB | A | 284 | 827 | 94 | 379 | 47 |
| ASP | CG | A | 284 | 813 | 92 | 374 | 47 |
| ASP | OD1 | A | 284 | 810 | 81 | 369 | 48 |
| ASP | OD2 | A | 284 | 805 | 101 | 375 | 48 |
| ASP | C | A | 284 | 832 | 72 | 390 | 43 |
| ASP | O | A | 284 | 826 | 63 | 397 | 44 |
| LYS | N | A | 285 | 841 | 68 | 380 | 41 |
| LYS | CA | A | 285 | 844 | 54 | 377 | 39 |
| LYS | CB | A | 285 | 831 | 47 | 372 | 39 |
| LYS | CG | A | 285 | 827 | 53 | 358 | 39 |
| LYS | CD | A | 285 | 814 | 46 | 353 | 39 |
| LYS | CE | A | 285 | 810 | 52 | 340 | 39 |
| LYS | NZ | A | 285 | 806 | 67 | 341 | 39 |
| LYS | C | A | 285 | 855 | 53 | 367 | 38 |
| LYS | O | A | 285 | 860 | 63 | 362 | 37 |
| SER | N | A | 286 | 859 | 41 | 364 | 35 |
| SER | CA | A | 286 | 870 | 38 | 354 | 34 |
| SER | CB | A | 286 | 883 | 35 | 361 | 34 |
| SER | OG | A | 286 | 889 | 47 | 367 | 35 |
| SER | C | A | 286 | 865 | 25 | 347 | 33 |
| SER | O | A | 286 | 862 | 15 | 353 | 32 |
| ILE | N | A | 287 | 865 | 26 | 334 | 32 |
| ILE | CA | A | 287 | 860 | 15 | 326 | 31 |
| ILE | CB | A | 287 | 846 | 17 | 320 | 31 |
| ILE | CG2 | A | 287 | 836 | 22 | 332 | 31 |
| ILE | CG1 | A | 287 | 846 | 29 | 310 | 31 |
| ILE | CD1 | A | 287 | 832 | 31 | 304 | 31 |
| ILE | C | A | 287 | 869 | 11 | 314 | 31 |
| ILE | O | A | 287 | 877 | 20 | 309 | 31 |
| VAL | N | A | 288 | 867 | −1 | 309 | 31 |
| VAL | CA | A | 288 | 875 | −6 | 298 | 31 |
| VAL | CB | A | 288 | 879 | −21 | 300 | 31 |
| VAL | CG1 | A | 288 | 890 | −24 | 290 | 30 |
| VAL | CG2 | A | 288 | 885 | −22 | 314 | 30 |
| VAL | C | A | 288 | 864 | −6 | 287 | 32 |
| VAL | O | A | 288 | 854 | −13 | 287 | 31 |
| ASP | N | A | 289 | 866 | 3 | 277 | 32 |
| ASP | CA | A | 289 | 856 | 5 | 267 | 32 |
| ASP | CB | A | 289 | 848 | 17 | 270 | 33 |
| ASP | CG | A | 289 | 839 | 21 | 258 | 34 |
| ASP | OD1 | A | 289 | 834 | 12 | 250 | 34 |
| ASP | OD2 | A | 289 | 836 | 33 | 257 | 34 |
| ASP | C | A | 289 | 861 | 5 | 252 | 32 |
| ASP | O | A | 289 | 867 | 15 | 248 | 32 |
| SER | N | A | 290 | 859 | −6 | 245 | 32 |
| SER | CA | A | 290 | 863 | −7 | 231 | 31 |
| SER | CB | A | 290 | 861 | −21 | 226 | 31 |
| SER | OG | A | 290 | 847 | −24 | 226 | 32 |
| SER | C | A | 290 | 856 | 3 | 222 | 31 |
| SER | O | A | 290 | 861 | 4 | 210 | 30 |
| GLY | N | A | 291 | 846 | 9 | 227 | 32 |
| GLY | CA | A | 291 | 839 | 19 | 218 | 32 |
| GLY | C | A | 291 | 844 | 33 | 219 | 33 |
| GLY | O | A | 291 | 840 | 42 | 212 | 34 |
| THR | N | A | 292 | 855 | 34 | 227 | 33 |
| THR | CA | A | 292 | 861 | 47 | 229 | 33 |
| THR | CB | A | 292 | 861 | 51 | 243 | 33 |
| THR | OG1 | A | 292 | 847 | 53 | 248 | 32 |
| THR | CG2 | A | 292 | 868 | 65 | 246 | 33 |
| THR | C | A | 292 | 875 | 48 | 223 | 33 |
| THR | O | A | 292 | 883 | 40 | 227 | 34 |
| THR | N | A | 293 | 877 | 57 | 214 | 34 |
| THR | CA | A | 293 | 890 | 58 | 208 | 34 |
| THR | CB | A | 293 | 890 | 69 | 197 | 34 |
| THR | OG1 | A | 293 | 881 | 64 | 186 | 34 |
| THR | CG2 | A | 293 | 904 | 72 | 191 | 34 |
| THR | C | A | 293 | 901 | 62 | 218 | 34 |
| THR | O | A | 293 | 911 | 55 | 218 | 34 |
| ASN | N | A | 294 | 899 | 73 | 225 | 34 |
| ASN | CA | A | 294 | 910 | 77 | 234 | 34 |
| ASN | CB | A | 294 | 909 | 92 | 236 | 34 |
| ASN | CG | A | 294 | 909 | 99 | 222 | 34 |
| ASN | OD1 | A | 294 | 913 | 94 | 212 | 34 |
| ASN | ND2 | A | 294 | 905 | 112 | 223 | 35 |

TABLE 1-continued

Structure Coordinates for uncomplexed BACE

| | | | | | | | |
|---|---|---|---|---|---|---|---|
| ASN | C | A | 294 | 910 | 72 | 249 | 35 |
| ASN | O | A | 294 | 902 | 64 | 253 | 35 |
| LEU | N | A | 295 | 902 | 76 | 256 | 35 |
| LEU | CA | A | 295 | 922 | 73 | 270 | 36 |
| LEU | CB | A | 295 | 937 | 72 | 273 | 35 |
| LEU | CG | A | 295 | 943 | 71 | 287 | 35 |
| LEU | CD1 | A | 295 | 944 | 85 | 293 | 35 |
| LEU | CD2 | A | 295 | 934 | 63 | 296 | 34 |
| LEU | C | A | 295 | 917 | 86 | 275 | 36 |
| LEU | O | A | 295 | 923 | 97 | 273 | 37 |
| ARG | N | A | 296 | 906 | 86 | 282 | 37 |
| ARG | CA | A | 296 | 900 | 97 | 288 | 37 |
| ARG | CB | A | 296 | 885 | 98 | 284 | 38 |
| ARG | CG | A | 296 | 882 | 97 | 269 | 39 |
| ARG | CD | A | 296 | 868 | 98 | 265 | 40 |
| ARG | NE | A | 296 | 862 | 111 | 268 | 41 |
| ARG | CZ | A | 296 | 850 | 113 | 274 | 42 |
| ARG | NH1 | A | 296 | 846 | 126 | 276 | 42 |
| ARG | NH2 | A | 296 | 843 | 103 | 279 | 42 |
| ARG | C | A | 296 | 902 | 97 | 303 | 38 |
| ARG | O | A | 296 | 901 | 87 | 309 | 37 |
| LEU | N | A | 297 | 905 | 109 | 308 | 37 |
| LEU | CA | A | 297 | 907 | 110 | 322 | 38 |
| LEU | CB | A | 297 | 922 | 113 | 325 | 37 |
| LEU | CG | A | 297 | 932 | 103 | 318 | 38 |
| LEU | CD1 | A | 297 | 946 | 110 | 318 | 37 |
| LEU | CD2 | A | 297 | 932 | 90 | 325 | 37 |
| LEU | C | A | 297 | 899 | 121 | 329 | 38 |
| LEU | O | A | 297 | 896 | 131 | 323 | 38 |
| PRO | N | A | 298 | 896 | 119 | 342 | 39 |
| PRO | CD | A | 298 | 898 | 107 | 350 | 39 |
| PRO | CA | A | 298 | 888 | 130 | 349 | 40 |
| PRO | CB | A | 298 | 888 | 124 | 363 | 39 |
| PRO | CG | A | 298 | 888 | 110 | 361 | 39 |
| PRO | C | A | 298 | 895 | 143 | 348 | 41 |
| PRO | O | A | 298 | 908 | 143 | 347 | 41 |
| LYS | N | A | 299 | 888 | 154 | 347 | 42 |
| LYS | CA | A | 299 | 894 | 167 | 346 | 44 |
| LYS | CB | A | 299 | 884 | 178 | 350 | 45 |
| LYS | CG | A | 299 | 890 | 192 | 349 | 47 |
| LYS | CD | A | 299 | 894 | 195 | 334 | 47 |
| LYS | CE | A | 299 | 900 | 209 | 333 | 48 |
| LYS | NZ | A | 299 | 903 | 213 | 319 | 48 |
| LYS | C | A | 299 | 908 | 169 | 353 | 44 |
| LYS | O | A | 299 | 918 | 172 | 346 | 44 |
| LYS | N | A | 300 | 908 | 168 | 366 | 45 |
| LYS | CA | A | 300 | 920 | 170 | 373 | 45 |
| LYS | CB | A | 300 | 918 | 168 | 388 | 46 |
| LYS | CG | A | 300 | 908 | 178 | 394 | 47 |
| LYS | CD | A | 300 | 907 | 176 | 409 | 48 |
| LYS | CE | A | 300 | 920 | 178 | 417 | 49 |
| LYS | NZ | A | 300 | 918 | 175 | 431 | 50 |
| LYS | C | A | 300 | 932 | 161 | 369 | 45 |
| LYS | O | A | 300 | 943 | 165 | 367 | 45 |
| VAL | N | A | 301 | 929 | 148 | 368 | 44 |
| VAL | CA | A | 301 | 939 | 138 | 365 | 43 |
| VAL | CB | A | 301 | 934 | 124 | 364 | 43 |
| VAL | CG1 | A | 301 | 945 | 114 | 361 | 43 |
| VAL | CG2 | A | 301 | 927 | 120 | 377 | 43 |
| VAL | C | A | 301 | 945 | 142 | 351 | 42 |
| VAL | O | A | 301 | 957 | 142 | 349 | 42 |
| PHE | N | A | 302 | 936 | 145 | 342 | 42 |
| PHE | CA | A | 302 | 940 | 149 | 328 | 42 |
| PHE | CB | A | 302 | 928 | 153 | 320 | 42 |
| PHE | CG | A | 302 | 932 | 158 | 306 | 42 |
| PHE | CD1 | A | 302 | 936 | 150 | 296 | 42 |
| PHE | CD2 | A | 302 | 931 | 172 | 304 | 42 |
| PHE | CE1 | A | 302 | 940 | 155 | 283 | 42 |
| PHE | CE2 | A | 302 | 934 | 177 | 291 | 42 |
| PHE | CZ | A | 302 | 939 | 169 | 281 | 42 |
| PHE | C | A | 302 | 950 | 161 | 328 | 42 |
| PHE | O | A | 302 | 960 | 161 | 321 | 41 |
| GLU | N | A | 303 | 947 | 171 | 336 | 42 |
| GLU | CA | A | 303 | 955 | 183 | 337 | 42 |
| GLU | CB | A | 303 | 948 | 193 | 346 | 43 |
| GLU | CG | A | 303 | 936 | 200 | 341 | 44 |
| GLU | CD | A | 303 | 939 | 207 | 328 | 45 |
| GLU | OE1 | A | 303 | 949 | 214 | 327 | 46 |
| GLU | OE2 | A | 303 | 931 | 206 | 318 | 46 |
| GLU | C | A | 303 | 969 | 180 | 342 | 41 |
| GLU | O | A | 303 | 979 | 183 | 336 | 41 |
| ALA | N | A | 304 | 969 | 172 | 353 | 41 |
| ALA | CA | A | 304 | 982 | 168 | 359 | 41 |
| ALA | CB | A | 304 | 979 | 160 | 372 | 40 |
| ALA | C | A | 304 | 990 | 160 | 350 | 41 |
| ALA | O | A | 304 | 1002 | 161 | 349 | 42 |
| ALA | N | A | 305 | 983 | 151 | 342 | 41 |
| ALA | CA | A | 305 | 990 | 142 | 332 | 41 |
| ALA | CB | A | 305 | 980 | 132 | 327 | 41 |
| ALA | C | A | 305 | 996 | 150 | 321 | 41 |
| ALA | O | A | 305 | 1008 | 148 | 318 | 41 |
| VAL | N | A | 306 | 988 | 158 | 314 | 41 |
| VAL | CA | A | 306 | 993 | 166 | 303 | 41 |
| VAL | CB | A | 306 | 983 | 176 | 298 | 42 |
| VAL | CG1 | A | 306 | 988 | 184 | 286 | 42 |
| VAL | CG2 | A | 306 | 970 | 168 | 294 | 42 |
| VAL | C | A | 306 | 1006 | 174 | 307 | 41 |
| VAL | O | A | 306 | 1015 | 176 | 299 | 42 |
| LYS | N | A | 307 | 1005 | 180 | 319 | 42 |
| LYS | CA | A | 307 | 1016 | 188 | 324 | 42 |
| LYS | CB | A | 307 | 1013 | 193 | 338 | 42 |
| LYS | CG | A | 307 | 1023 | 202 | 344 | 43 |
| LYS | CD | A | 307 | 1018 | 209 | 357 | 43 |
| LYS | CE | A | 307 | 1029 | 219 | 362 | 44 |
| LYS | NZ | A | 307 | 1024 | 226 | 374 | 44 |
| LYS | C | A | 307 | 1029 | 179 | 325 | 42 |
| LYS | O | A | 307 | 1039 | 183 | 320 | 41 |
| SER | N | A | 308 | 1028 | 168 | 331 | 42 |
| SER | CA | A | 308 | 1039 | 159 | 332 | 41 |
| SER | CB | A | 308 | 1036 | 146 | 341 | 41 |
| SER | OG | A | 308 | 1047 | 138 | 341 | 41 |
| SER | C | A | 308 | 1044 | 155 | 319 | 40 |
| SER | O | A | 308 | 1056 | 154 | 316 | 41 |
| ILE | N | A | 309 | 1035 | 151 | 310 | 40 |
| ILE | CA | A | 309 | 1039 | 147 | 296 | 40 |
| ILE | CB | A | 309 | 1026 | 142 | 289 | 40 |
| ILE | CG2 | A | 309 | 1030 | 137 | 275 | 39 |
| ILE | CG1 | A | 309 | 1020 | 130 | 296 | 39 |
| ILE | CD1 | A | 309 | 1006 | 126 | 292 | 39 |
| ILE | C | A | 309 | 1045 | 159 | 288 | 41 |
| ILE | O | A | 309 | 1053 | 156 | 280 | 40 |
| LYS | N | A | 310 | 1041 | 171 | 291 | 41 |
| LYS | CA | A | 310 | 1046 | 183 | 285 | 42 |
| LYS | CB | A | 310 | 1039 | 195 | 289 | 43 |
| LYS | CG | A | 310 | 1026 | 198 | 281 | 44 |
| LYS | CD | A | 310 | 1019 | 211 | 285 | 44 |
| LYS | CE | A | 310 | 1006 | 213 | 278 | 45 |
| LYS | NZ | A | 310 | 1000 | 227 | 281 | 45 |
| LYS | C | A | 310 | 1061 | 184 | 289 | 42 |
| LYS | O | A | 310 | 1070 | 185 | 280 | 41 |
| ALA | N | A | 311 | 1063 | 183 | 302 | 42 |
| ALA | CA | A | 311 | 1077 | 184 | 307 | 42 |
| ALA | CB | A | 311 | 1076 | 184 | 322 | 41 |
| ALA | C | A | 311 | 1086 | 173 | 302 | 42 |
| ALA | O | A | 311 | 1098 | 176 | 299 | 42 |
| ALA | N | A | 312 | 1081 | 161 | 301 | 43 |
| ALA | CA | A | 312 | 1089 | 150 | 296 | 43 |
| ALA | CB | A | 312 | 1081 | 137 | 299 | 43 |
| ALA | C | A | 312 | 1093 | 151 | 282 | 44 |
| ALA | O | A | 312 | 1103 | 146 | 278 | 44 |
| SER | N | A | 313 | 1084 | 157 | 274 | 45 |
| SER | CA | A | 313 | 1088 | 159 | 259 | 46 |
| SER | CB | A | 313 | 1075 | 155 | 251 | 46 |
| SER | OG | A | 313 | 1064 | 163 | 253 | 46 |
| SER | C | A | 313 | 1092 | 173 | 256 | 46 |
| SER | O | A | 313 | 1092 | 176 | 244 | 46 |
| SER | N | A | 314 | 1096 | 180 | 266 | 48 |
| SER | CA | A | 314 | 1101 | 194 | 264 | 50 |
| SER | CB | A | 314 | 1105 | 200 | 277 | 50 |
| SER | OG | A | 314 | 1116 | 193 | 283 | 51 |
| SER | C | A | 314 | 1111 | 197 | 253 | 52 |
| SER | O | A | 314 | 1112 | 208 | 248 | 52 |
| THR | N | A | 315 | 1119 | 187 | 249 | 54 |
| THR | CA | A | 315 | 1130 | 189 | 239 | 55 |

TABLE 1-continued

Structure Coordinates for uncomplexed BACE

| | | | | | | |
|---|---|---|---|---|---|---|
| THR | CB | A | 315 | 1138 | 176 | 236 | 55 |
| THR | OG1 | A | 315 | 1130 | 166 | 231 | 55 |
| THR | CG2 | A | 315 | 1145 | 172 | 249 | 55 |
| THR | C | A | 315 | 1123 | 194 | 226 | 56 |
| THR | O | A | 315 | 1130 | 201 | 219 | 57 |
| GLU | N | A | 316 | 1111 | 191 | 224 | 58 |
| GLU | CA | A | 316 | 1104 | 196 | 212 | 59 |
| GLU | CB | A | 316 | 1100 | 184 | 203 | 59 |
| GLU | CG | A | 316 | 1111 | 180 | 194 | 60 |
| GLU | CD | A | 316 | 1106 | 173 | 181 | 60 |
| GLU | OE1 | A | 316 | 1096 | 176 | 176 | 60 |
| GLU | OE2 | A | 316 | 1113 | 163 | 178 | 60 |
| GLU | C | A | 316 | 1091 | 204 | 217 | 60 |
| GLU | O | A | 316 | 1086 | 201 | 228 | 60 |
| LYS | N | A | 317 | 1086 | 213 | 209 | 61 |
| LYS | CA | A | 317 | 1075 | 221 | 212 | 62 |
| LYS | CB | A | 317 | 1079 | 236 | 212 | 63 |
| LYS | CG | A | 317 | 1088 | 239 | 224 | 63 |
| LYS | CD | A | 317 | 1083 | 235 | 237 | 64 |
| LYS | CE | A | 317 | 1092 | 238 | 248 | 64 |
| LYS | NZ | A | 317 | 1086 | 234 | 262 | 64 |
| LYS | C | A | 317 | 1063 | 219 | 203 | 62 |
| LYS | O | A | 317 | 1064 | 216 | 191 | 63 |
| PHE | N | A | 318 | 1051 | 220 | 209 | 63 |
| PHE | CA | A | 318 | 1038 | 219 | 202 | 63 |
| PHE | CB | A | 318 | 1032 | 205 | 205 | 63 |
| PHE | CG | A | 318 | 1042 | 194 | 206 | 64 |
| PHE | CD1 | A | 318 | 1049 | 192 | 218 | 64 |
| PHE | CD2 | A | 318 | 1045 | 185 | 196 | 64 |
| PHE | CE1 | A | 318 | 1059 | 182 | 219 | 64 |
| PHE | CE2 | A | 318 | 1055 | 175 | 197 | 64 |
| PHE | CZ | A | 318 | 1062 | 174 | 209 | 64 |
| PHE | C | A | 318 | 1029 | 229 | 206 | 63 |
| PHE | O | A | 318 | 1029 | 234 | 218 | 63 |
| PRO | N | A | 319 | 1020 | 234 | 197 | 64 |
| PRO | CD | A | 319 | 1018 | 230 | 183 | 64 |
| PRO | CA | A | 319 | 1010 | 244 | 201 | 64 |
| PRO | CB | A | 319 | 1003 | 247 | 187 | 64 |
| PRO | CG | A | 319 | 1004 | 234 | 180 | 64 |
| PRO | C | A | 319 | 1001 | 239 | 211 | 64 |
| PRO | O | A | 319 | 998 | 227 | 213 | 64 |
| ASP | N | A | 320 | 995 | 249 | 219 | 64 |
| ASP | CA | A | 320 | 986 | 245 | 230 | 64 |
| ASP | CB | A | 320 | 980 | 258 | 237 | 64 |
| ASP | CG | A | 320 | 990 | 264 | 246 | 65 |
| ASP | OD1 | A | 320 | 995 | 257 | 256 | 65 |
| ASP | OD2 | A | 320 | 993 | 276 | 244 | 65 |
| ASP | C | A | 320 | 974 | 236 | 225 | 63 |
| ASP | O | A | 320 | 969 | 228 | 233 | 62 |
| GLY | N | A | 321 | 970 | 238 | 213 | 62 |
| GLY | CA | A | 321 | 959 | 231 | 207 | 61 |
| GLY | C | A | 321 | 962 | 217 | 204 | 61 |
| GLY | O | A | 321 | 954 | 209 | 199 | 61 |
| PHE | N | A | 322 | 975 | 213 | 205 | 60 |
| PHE | CA | A | 322 | 979 | 199 | 202 | 60 |
| PHE | CB | A | 322 | 994 | 198 | 201 | 59 |
| PHE | CG | A | 322 | 1000 | 184 | 202 | 59 |
| PHE | CD1 | A | 322 | 998 | 176 | 191 | 58 |
| PHE | CD2 | A | 322 | 1007 | 180 | 213 | 58 |
| PHE | CE1 | A | 322 | 1003 | 162 | 192 | 58 |
| PHE | CE2 | A | 322 | 1012 | 167 | 214 | 58 |
| PHE | CZ | A | 322 | 1010 | 158 | 203 | 58 |
| PHE | C | A | 322 | 974 | 190 | 214 | 60 |
| PHE | O | A | 322 | 969 | 179 | 212 | 59 |
| TRP | N | A | 323 | 977 | 195 | 226 | 60 |
| TRP | CA | A | 323 | 973 | 187 | 238 | 61 |
| TRP | CB | A | 323 | 980 | 193 | 250 | 61 |
| TRP | CG | A | 323 | 995 | 194 | 248 | 61 |
| TRP | CD2 | A | 323 | 1005 | 184 | 249 | 61 |
| TRP | CE2 | A | 323 | 1017 | 190 | 245 | 61 |
| TRP | CE3 | A | 323 | 1005 | 171 | 252 | 61 |
| TRP | CD1 | A | 323 | 1002 | 206 | 243 | 61 |
| TRP | NE1 | A | 323 | 1015 | 203 | 241 | 61 |
| TRP | CZ2 | A | 323 | 1029 | 183 | 244 | 61 |
| TRP | CZ3 | A | 323 | 1017 | 163 | 252 | 61 |
| TRP | CH2 | A | 323 | 1029 | 169 | 248 | 61 |
| TRP | C | A | 323 | 958 | 187 | 240 | 61 |
| TRP | O | A | 323 | 953 | 180 | 249 | 61 |
| LEU | N | A | 324 | 951 | 195 | 232 | 61 |
| LEU | CA | A | 324 | 936 | 196 | 233 | 62 |
| LEU | CB | A | 324 | 932 | 210 | 232 | 62 |
| LEU | CG | A | 324 | 936 | 220 | 243 | 62 |
| LEU | CD1 | A | 324 | 933 | 234 | 240 | 62 |
| LEU | CD2 | A | 324 | 930 | 215 | 256 | 62 |
| LEU | C | A | 324 | 930 | 187 | 223 | 62 |
| LEU | O | A | 324 | 917 | 186 | 222 | 62 |
| GLY | N | A | 325 | 938 | 181 | 214 | 62 |
| GLY | CA | A | 325 | 932 | 172 | 204 | 64 |
| GLY | C | A | 325 | 926 | 180 | 192 | 64 |
| GLY | O | A | 325 | 916 | 175 | 187 | 65 |
| GLU | N | A | 326 | 932 | 191 | 188 | 65 |
| GLU | CA | A | 326 | 926 | 199 | 177 | 65 |
| GLU | CB | A | 326 | 924 | 213 | 182 | 65 |
| GLU | CG | A | 326 | 915 | 215 | 194 | 66 |
| GLU | CD | A | 326 | 914 | 229 | 200 | 66 |
| GLU | OE1 | A | 326 | 907 | 231 | 210 | 66 |
| GLU | OE2 | A | 326 | 920 | 238 | 193 | 67 |
| GLU | C | A | 326 | 935 | 199 | 165 | 65 |
| GLU | O | A | 326 | 931 | 194 | 154 | 66 |
| GLN | N | A | 327 | 947 | 203 | 167 | 65 |
| GLN | CA | A | 327 | 957 | 204 | 156 | 65 |
| GLN | CB | A | 327 | 965 | 216 | 156 | 66 |
| GLN | CG | A | 327 | 971 | 220 | 169 | 66 |
| GLN | CD | A | 327 | 965 | 231 | 176 | 67 |
| GLN | OE1 | A | 327 | 953 | 232 | 177 | 67 |
| GLN | NE2 | A | 327 | 973 | 241 | 181 | 67 |
| GLN | C | A | 327 | 966 | 191 | 157 | 65 |
| GLN | O | A | 327 | 968 | 186 | 168 | 65 |
| LEU | N | A | 328 | 971 | 187 | 145 | 64 |
| LEU | CA | A | 328 | 980 | 175 | 146 | 64 |
| LEU | CB | A | 328 | 975 | 165 | 135 | 64 |
| LEU | CG | A | 328 | 973 | 170 | 121 | 64 |
| LEU | CD1 | A | 328 | 986 | 171 | 114 | 65 |
| LEU | CD2 | A | 328 | 964 | 160 | 113 | 64 |
| LEU | C | A | 328 | 995 | 179 | 143 | 64 |
| LEU | O | A | 328 | 998 | 188 | 135 | 64 |
| VAL | N | A | 329 | 1004 | 172 | 149 | 63 |
| VAL | CA | A | 329 | 1018 | 174 | 148 | 62 |
| VAL | CB | A | 329 | 1026 | 171 | 161 | 62 |
| VAL | CG1 | A | 329 | 1041 | 171 | 158 | 62 |
| VAL | CG2 | A | 329 | 1023 | 182 | 171 | 62 |
| VAL | C | A | 329 | 1023 | 164 | 137 | 61 |
| VAL | O | A | 329 | 1019 | 153 | 136 | 61 |
| CYS | N | A | 330 | 1032 | 169 | 129 | 60 |
| CYS | CA | A | 330 | 1038 | 160 | 118 | 58 |
| CYS | C | A | 330 | 1053 | 160 | 120 | 58 |
| CYS | O | A | 330 | 1059 | 168 | 127 | 58 |
| CYS | CB | A | 330 | 1035 | 166 | 104 | 58 |
| CYS | SG | A | 330 | 1017 | 168 | 101 | 58 |
| TRP | N | A | 331 | 1060 | 151 | 113 | 57 |
| TRP | CA | A | 331 | 1074 | 149 | 113 | 57 |
| TRP | CB | A | 331 | 1078 | 140 | 125 | 56 |
| TRP | CG | A | 331 | 1079 | 147 | 138 | 56 |
| TRP | CD2 | A | 331 | 1070 | 144 | 149 | 55 |
| TRP | CE2 | A | 331 | 1075 | 152 | 160 | 55 |
| TRP | CE3 | A | 331 | 1059 | 136 | 151 | 55 |
| TRP | CD1 | A | 331 | 1088 | 156 | 142 | 55 |
| TRP | NE1 | A | 331 | 1086 | 159 | 155 | 55 |
| TRP | CZ2 | A | 331 | 1069 | 152 | 172 | 55 |
| TRP | CZ3 | A | 331 | 1053 | 136 | 163 | 55 |
| TRP | CH2 | A | 331 | 1058 | 144 | 174 | 55 |
| TRP | C | A | 331 | 1079 | 143 | 100 | 57 |
| TRP | O | A | 331 | 1071 | 136 | 93 | 58 |
| GLN | N | A | 332 | 1091 | 146 | 96 | 58 |
| GLN | CA | A | 332 | 1097 | 141 | 84 | 58 |
| GLN | CB | A | 332 | 1112 | 143 | 84 | 59 |
| GLN | CG | A | 332 | 1117 | 156 | 88 | 60 |
| GLN | CD | A | 332 | 1117 | 158 | 103 | 60 |
| GLN | OE1 | A | 332 | 1123 | 151 | 111 | 60 |
| GLN | NE2 | A | 332 | 1109 | 168 | 108 | 60 |
| GLN | C | A | 332 | 1094 | 126 | 84 | 57 |
| GLN | O | A | 332 | 1097 | 118 | 93 | 57 |
| ALA | N | A | 333 | 1088 | 121 | 73 | 56 |
| ALA | CA | A | 333 | 1084 | 107 | 71 | 55 |

TABLE 1-continued

Structure Coordinates for uncomplexed BACE

| | | | | | | | |
|---|---|---|---|---|---|---|---|
| ALA | CB | A | 333 | 1082 | 104 | 56 | 55 |
| ALA | C | A | 333 | 1094 | 98 | 77 | 54 |
| ALA | O | A | 333 | 1106 | 97 | 73 | 54 |
| GLY | N | A | 334 | 1090 | 90 | 87 | 53 |
| GLY | CA | A | 334 | 1098 | 80 | 93 | 52 |
| GLY | C | A | 334 | 1108 | 85 | 104 | 51 |
| GLY | O | A | 334 | 1117 | 78 | 108 | 51 |
| THR | N | A | 335 | 1106 | 97 | 109 | 49 |
| THR | CA | A | 335 | 1115 | 103 | 119 | 48 |
| THR | CB | A | 335 | 1122 | 116 | 113 | 48 |
| THR | OG1 | A | 335 | 1112 | 126 | 111 | 48 |
| THR | CG2 | A | 335 | 1129 | 113 | 100 | 49 |
| THR | C | A | 335 | 1108 | 108 | 132 | 46 |
| THR | O | A | 335 | 1113 | 116 | 139 | 46 |
| THR | N | A | 336 | 1096 | 102 | 134 | 45 |
| THR | CA | A | 336 | 1088 | 105 | 146 | 43 |
| THR | CB | A | 336 | 1076 | 97 | 148 | 43 |
| THR | OG1 | A | 336 | 1068 | 98 | 136 | 43 |
| THR | CG2 | A | 336 | 1068 | 102 | 160 | 43 |
| THR | C | A | 336 | 1098 | 103 | 158 | 42 |
| THR | O | A | 336 | 1104 | 92 | 159 | 42 |
| PRO | N | A | 337 | 1099 | 112 | 167 | 41 |
| PRO | CD | A | 337 | 1095 | 126 | 166 | 41 |
| PRO | CA | A | 337 | 1108 | 110 | 179 | 40 |
| PRO | CB | A | 337 | 1113 | 125 | 182 | 41 |
| PRO | CG | A | 337 | 1100 | 132 | 179 | 41 |
| PRO | C | A | 337 | 1101 | 104 | 190 | 39 |
| PRO | O | A | 337 | 1099 | 110 | 201 | 38 |
| TRP | N | A | 338 | 1098 | 91 | 189 | 37 |
| TRP | CA | A | 338 | 1091 | 84 | 199 | 36 |
| TRP | CB | A | 338 | 1090 | 69 | 196 | 36 |
| TRP | CG | A | 338 | 1084 | 66 | 182 | 37 |
| TRP | CD2 | A | 338 | 1070 | 67 | 179 | 36 |
| TRP | CE2 | A | 338 | 1069 | 63 | 166 | 37 |
| TRP | CE3 | A | 338 | 1059 | 71 | 186 | 37 |
| TRP | CD1 | A | 338 | 1091 | 61 | 171 | 37 |
| TRP | NE1 | A | 338 | 1082 | 59 | 161 | 37 |
| TRP | CZ2 | A | 338 | 1057 | 63 | 159 | 36 |
| TRP | CZ3 | A | 338 | 1047 | 71 | 179 | 37 |
| TRP | CH2 | A | 338 | 1046 | 67 | 166 | 37 |
| TRP | C | A | 338 | 1098 | 85 | 213 | 35 |
| TRP | O | A | 338 | 1092 | 88 | 223 | 35 |
| ASN | N | A | 339 | 1112 | 83 | 213 | 34 |
| ASN | CA | A | 339 | 1120 | 84 | 225 | 34 |
| ASN | CB | A | 339 | 1134 | 81 | 221 | 34 |
| ASN | CG | A | 339 | 1141 | 94 | 217 | 34 |
| ASN | OD1 | A | 339 | 1147 | 101 | 225 | 34 |
| ASN | ND2 | A | 339 | 1142 | 96 | 204 | 33 |
| ASN | C | A | 339 | 1118 | 96 | 234 | 34 |
| ASN | O | A | 339 | 1120 | 96 | 246 | 33 |
| ILE | N | A | 340 | 1114 | 108 | 228 | 33 |
| ILE | CA | A | 340 | 1113 | 120 | 236 | 33 |
| ILE | CB | A | 340 | 1113 | 133 | 227 | 34 |
| ILE | CG2 | A | 340 | 1125 | 133 | 218 | 33 |
| ILE | CG1 | A | 340 | 1100 | 134 | 218 | 34 |
| ILE | CD1 | A | 340 | 1099 | 146 | 210 | 35 |
| ILE | C | A | 340 | 1100 | 120 | 243 | 33 |
| ILE | O | A | 340 | 1098 | 126 | 253 | 32 |
| PHE | N | A | 341 | 1090 | 112 | 239 | 32 |
| PHE | CA | A | 341 | 1077 | 110 | 245 | 32 |
| PHE | CB | A | 341 | 1066 | 106 | 235 | 33 |
| PHE | CG | A | 341 | 1063 | 116 | 225 | 34 |
| PHE | CD1 | A | 341 | 1056 | 128 | 228 | 34 |
| PHE | CD2 | A | 341 | 1068 | 115 | 212 | 34 |
| PHE | CE1 | A | 341 | 1054 | 138 | 219 | 34 |
| PHE | CE2 | A | 341 | 1065 | 125 | 202 | 35 |
| PHE | CZ | A | 341 | 1058 | 136 | 206 | 34 |
| PHE | C | A | 341 | 1079 | 99 | 256 | 31 |
| PHE | O | A | 341 | 1086 | 89 | 254 | 31 |
| PRO | N | A | 342 | 1073 | 101 | 268 | 30 |
| PRO | CD | A | 342 | 1065 | 114 | 271 | 29 |
| PRO | CA | A | 342 | 1073 | 92 | 279 | 29 |
| PRO | CB | A | 342 | 1070 | 101 | 291 | 28 |
| PRO | CG | A | 342 | 1060 | 110 | 285 | 29 |
| PRO | C | A | 342 | 1063 | 81 | 278 | 29 |
| PRO | O | A | 342 | 1053 | 81 | 270 | 29 |
| VAL | N | A | 343 | 1065 | 70 | 286 | 29 |
| VAL | CA | A | 343 | 1056 | 59 | 286 | 29 |
| VAL | CB | A | 343 | 1063 | 45 | 290 | 29 |
| VAL | CG1 | A | 343 | 1074 | 42 | 279 | 28 |
| VAL | CG2 | A | 343 | 1069 | 46 | 304 | 28 |
| VAL | C | A | 343 | 1046 | 62 | 297 | 29 |
| VAL | O | A | 343 | 1049 | 70 | 306 | 29 |
| ILE | N | A | 344 | 1034 | 57 | 296 | 28 |
| ILE | CA | A | 344 | 1024 | 59 | 306 | 29 |
| ILE | CB | A | 344 | 1011 | 65 | 300 | 29 |
| ILE | CG2 | A | 344 | 1000 | 65 | 309 | 29 |
| ILE | CG1 | A | 344 | 1014 | 79 | 295 | 29 |
| ILE | CD1 | A | 344 | 1004 | 85 | 285 | 29 |
| ILE | C | A | 344 | 1020 | 46 | 313 | 29 |
| ILE | O | A | 344 | 1017 | 36 | 307 | 30 |
| SER | N | A | 345 | 1020 | 46 | 327 | 29 |
| SER | CA | A | 345 | 1017 | 34 | 334 | 29 |
| SER | CB | A | 345 | 1029 | 29 | 342 | 29 |
| SER | OG | A | 345 | 1040 | 27 | 334 | 30 |
| SER | C | A | 345 | 1005 | 35 | 344 | 29 |
| SER | O | A | 345 | 1004 | 45 | 352 | 30 |
| LEU | N | A | 346 | 996 | 26 | 343 | 29 |
| LEU | CA | A | 346 | 984 | 26 | 351 | 29 |
| LEU | CB | A | 346 | 971 | 25 | 343 | 29 |
| LEU | CG | A | 346 | 968 | 35 | 332 | 29 |
| LEU | CD1 | A | 346 | 954 | 32 | 326 | 29 |
| LEU | CD2 | A | 346 | 968 | 50 | 338 | 29 |
| LEU | C | A | 346 | 985 | 13 | 360 | 29 |
| LEU | O | A | 346 | 987 | 2 | 354 | 29 |
| TYR | N | A | 347 | 984 | 15 | 373 | 28 |
| TYR | CA | A | 347 | 985 | 3 | 382 | 29 |
| TYR | CB | A | 347 | 993 | 7 | 395 | 28 |
| TYR | CG | A | 347 | 1008 | 8 | 393 | 27 |
| TYR | CD1 | A | 347 | 1013 | 19 | 386 | 28 |
| TYR | CE1 | A | 347 | 1027 | 20 | 385 | 27 |
| TYR | CD2 | A | 347 | 1016 | −1 | 400 | 28 |
| TYR | CE2 | A | 347 | 1030 | 1 | 399 | 28 |
| TYR | CZ | A | 347 | 1036 | 11 | 392 | 28 |
| TYR | OH | A | 347 | 1049 | 13 | 391 | 28 |
| TYR | C | A | 347 | 970 | 0 | 385 | 29 |
| TYR | O | A | 347 | 962 | 9 | 389 | 29 |
| LEU | N | A | 348 | 967 | −13 | 384 | 30 |
| LEU | CA | A | 348 | 953 | −17 | 386 | 30 |
| LEU | CB | A | 348 | 948 | −25 | 374 | 30 |
| LEU | CG | A | 348 | 949 | −17 | 360 | 31 |
| LEU | CD1 | A | 348 | 944 | −26 | 349 | 31 |
| LEU | CD2 | A | 348 | 939 | −5 | 361 | 31 |
| LEU | C | A | 348 | 953 | −26 | 398 | 31 |
| LEU | O | A | 348 | 962 | −33 | 401 | 30 |
| MET | N | A | 349 | 942 | −26 | 405 | 31 |
| MET | CA | A | 349 | 940 | −34 | 417 | 33 |
| MET | CB | A | 349 | 927 | −32 | 424 | 34 |
| MET | CG | A | 349 | 924 | −41 | 436 | 35 |
| MET | SD | A | 349 | 907 | −38 | 442 | 37 |
| MET | CE | A | 349 | 909 | −23 | 451 | 36 |
| MET | C | A | 349 | 941 | −49 | 412 | 33 |
| MET | O | A | 349 | 935 | −53 | 402 | 32 |
| GLY | N | A | 350 | 949 | −57 | 420 | 33 |
| GLY | CA | A | 350 | 950 | −71 | 416 | 34 |
| GLY | C | A | 350 | 940 | −80 | 423 | 35 |
| GLY | O | A | 350 | 932 | −74 | 431 | 36 |
| GLU | N | A | 351 | 940 | −93 | 421 | 37 |
| GLU | CA | A | 351 | 931 | −102 | 428 | 39 |
| GLU | CB | A | 351 | 929 | −114 | 419 | 39 |
| GLU | CG | A | 351 | 918 | −113 | 408 | 40 |
| GLU | CD | A | 351 | 914 | −126 | 402 | 40 |
| GLU | OE1 | A | 351 | 923 | −133 | 396 | 39 |
| GLU | OE2 | A | 351 | 902 | −130 | 403 | 40 |
| GLU | C | A | 351 | 935 | −106 | 442 | 40 |
| GLU | O | A | 351 | 927 | −111 | 449 | 41 |
| VAL | N | A | 352 | 948 | −104 | 445 | 41 |
| VAL | CA | A | 352 | 952 | −107 | 458 | 42 |
| VAL | CB | A | 352 | 966 | −114 | 458 | 42 |
| VAL | CG1 | A | 352 | 971 | −118 | 472 | 42 |
| VAL | CG2 | A | 352 | 966 | −126 | 449 | 42 |
| VAL | C | A | 352 | 953 | −95 | 467 | 42 |
| VAL | O | A | 352 | 955 | −84 | 462 | 42 |
| THR | N | A | 353 | 950 | −96 | 480 | 43 |

TABLE 1-continued

Structure Coordinates for uncomplexed BACE

| | | | | | | | |
|---|---|---|---|---|---|---|---|
| THR | CA | A | 353 | 950 | −85 | 489 | 43 |
| THR | CB | A | 353 | 948 | −90 | 504 | 43 |
| THR | OG1 | A | 353 | 937 | −99 | 504 | 43 |
| THR | CG2 | A | 353 | 945 | −78 | 513 | 43 |
| THR | C | A | 353 | 963 | −77 | 489 | 42 |
| THR | O | A | 353 | 974 | −83 | 488 | 43 |
| ASN | N | A | 354 | 962 | −64 | 489 | 42 |
| ASN | CA | A | 354 | 973 | −55 | 489 | 42 |
| ASN | CB | A | 354 | 981 | −56 | 502 | 43 |
| ASN | CG | A | 354 | 972 | −54 | 515 | 44 |
| ASN | OD1 | A | 354 | 965 | −45 | 515 | 44 |
| ASN | ND2 | A | 354 | 974 | −63 | 524 | 45 |
| ASN | C | A | 354 | 983 | −57 | 478 | 41 |
| ASN | O | A | 354 | 995 | −53 | 479 | 41 |
| GLN | N | A | 355 | 978 | −63 | 467 | 40 |
| GLN | CA | A | 355 | 987 | −65 | 455 | 39 |
| GLN | CB | A | 355 | 987 | −81 | 453 | 39 |
| GLN | CG | A | 355 | 997 | −85 | 442 | 40 |
| GLN | CD | A | 355 | 1002 | −100 | 445 | 41 |
| GLN | OE1 | A | 355 | 1001 | −108 | 436 | 41 |
| GLN | NE2 | A | 355 | 1006 | −102 | 457 | 40 |
| GLN | C | A | 355 | 981 | −58 | 443 | 38 |
| GLN | O | A | 355 | 969 | −58 | 441 | 38 |
| SER | N | A | 356 | 990 | −53 | 435 | 35 |
| SER | CA | A | 356 | 985 | −46 | 422 | 34 |
| SER | CB | A | 356 | 984 | −31 | 424 | 34 |
| SER | OG | A | 356 | 997 | −25 | 426 | 33 |
| SER | C | A | 356 | 995 | −50 | 411 | 32 |
| SER | O | A | 356 | 1005 | −56 | 413 | 32 |
| PHE | N | A | 357 | 992 | −45 | 399 | 31 |
| PHE | CA | A | 357 | 1001 | −47 | 388 | 29 |
| PHE | CB | A | 357 | 998 | −60 | 380 | 29 |
| PHE | CG | A | 357 | 985 | −60 | 373 | 29 |
| PHE | CD1 | A | 357 | 984 | −56 | 359 | 28 |
| PHE | CD2 | A | 357 | 973 | −65 | 378 | 29 |
| PHE | CE1 | A | 357 | 972 | −55 | 352 | 28 |
| PHE | CE2 | A | 357 | 961 | −64 | 371 | 29 |
| PHE | CZ | A | 357 | 961 | −60 | 358 | 28 |
| PHE | C | A | 357 | 999 | −35 | 378 | 29 |
| PHE | O | A | 357 | 990 | −27 | 380 | 29 |
| ARG | N | A | 358 | 1009 | −33 | 369 | 29 |
| ARG | CA | A | 358 | 1007 | −22 | 360 | 28 |
| ARG | CB | A | 358 | 1018 | −12 | 364 | 29 |
| ARG | CG | A | 358 | 1032 | −15 | 359 | 29 |
| ARG | CD | A | 358 | 1043 | −6 | 363 | 30 |
| ARG | NE | A | 358 | 1056 | −11 | 360 | 30 |
| ARG | CZ | A | 358 | 1067 | −9 | 367 | 31 |
| ARG | NH1 | A | 358 | 1067 | −2 | 378 | 30 |
| ARG | NH2 | A | 358 | 1079 | −15 | 363 | 31 |
| ARG | C | A | 358 | 1008 | −25 | 346 | 28 |
| ARG | O | A | 358 | 1015 | −35 | 341 | 27 |
| ILE | N | A | 359 | 1001 | −17 | 338 | 27 |
| ILE | CA | A | 359 | 1002 | −19 | 323 | 27 |
| ILE | CB | A | 359 | 987 | −20 | 317 | 27 |
| ILE | CG2 | A | 359 | 980 | −32 | 324 | 26 |
| ILE | CG1 | A | 359 | 979 | −8 | 320 | 26 |
| ILE | CD1 | A | 359 | 965 | −9 | 314 | 26 |
| ILE | C | A | 359 | 1008 | −6 | 319 | 27 |
| ILE | O | A | 359 | 1005 | 5 | 324 | 27 |
| THR | N | A | 360 | 1017 | −7 | 309 | 27 |
| THR | CA | A | 360 | 1024 | 5 | 304 | 27 |
| THR | CB | A | 360 | 1039 | 4 | 307 | 27 |
| THR | OG1 | A | 360 | 1041 | 3 | 322 | 28 |
| THR | CG2 | A | 360 | 1047 | 16 | 302 | 27 |
| THR | C | A | 360 | 1023 | 6 | 289 | 27 |
| THR | O | A | 360 | 1025 | −4 | 282 | 27 |
| ILE | N | A | 361 | 1018 | 18 | 284 | 27 |
| ILE | CA | A | 361 | 1017 | 20 | 270 | 28 |
| ILE | CB | A | 361 | 1003 | 25 | 266 | 28 |
| ILE | CG2 | A | 361 | 993 | 13 | 269 | 28 |
| ILE | CG1 | A | 361 | 999 | 37 | 274 | 28 |
| ILE | CD1 | A | 361 | 987 | 44 | 268 | 28 |
| ILE | C | A | 361 | 1027 | 30 | 265 | 29 |
| ILE | O | A | 361 | 1033 | 37 | 273 | 29 |
| LEU | N | A | 362 | 1029 | 30 | 252 | 29 |
| LEU | CA | A | 362 | 1039 | 39 | 246 | 30 |
| LEU | CB | A | 362 | 1048 | 31 | 236 | 30 |
| LEU | CG | A | 362 | 1052 | 17 | 241 | 30 |
| LEU | CD1 | A | 362 | 1058 | 9 | 230 | 29 |
| LEU | CD2 | A | 362 | 1061 | 18 | 253 | 30 |
| LEU | C | A | 362 | 1032 | 50 | 238 | 30 |
| LEU | O | A | 362 | 1020 | 50 | 235 | 30 |
| PRO | N | A | 363 | 1040 | 60 | 233 | 30 |
| PRO | CD | A | 363 | 1055 | 62 | 235 | 31 |
| PRO | CA | A | 363 | 1035 | 71 | 225 | 31 |
| PRO | CB | A | 363 | 1047 | 80 | 223 | 31 |
| PRO | CG | A | 363 | 1058 | 71 | 223 | 31 |
| PRO | C | A | 363 | 1028 | 65 | 213 | 31 |
| PRO | O | A | 363 | 1019 | 71 | 207 | 31 |
| GLN | N | A | 364 | 1033 | 54 | 208 | 32 |
| GLN | CA | A | 364 | 1028 | 48 | 196 | 32 |
| GLN | CB | A | 364 | 1036 | 35 | 193 | 32 |
| GLN | CG | A | 364 | 1049 | 38 | 186 | 33 |
| GLN | CD | A | 364 | 1061 | 39 | 196 | 33 |
| GLN | OE1 | A | 364 | 1059 | 44 | 207 | 34 |
| GLN | NE2 | A | 364 | 1073 | 35 | 192 | 33 |
| GLN | C | A | 364 | 1013 | 44 | 199 | 32 |
| GLN | O | A | 364 | 1006 | 41 | 189 | 33 |
| GLN | N | A | 365 | 1009 | 44 | 212 | 32 |
| GLN | CA | A | 365 | 995 | 41 | 215 | 32 |
| GLN | CB | A | 365 | 995 | 33 | 228 | 31 |
| GLN | CG | A | 365 | 995 | 18 | 226 | 30 |
| GLN | CD | A | 365 | 1009 | 12 | 224 | 29 |
| GLN | OE1 | A | 365 | 1012 | 6 | 213 | 30 |
| GLN | NE2 | A | 365 | 1018 | 15 | 233 | 28 |
| GLN | C | A | 365 | 987 | 54 | 217 | 33 |
| GLN | O | A | 365 | 976 | 54 | 213 | 32 |
| TYR | N | A | 366 | 993 | 64 | 224 | 34 |
| TYR | CA | A | 366 | 985 | 76 | 226 | 36 |
| TYR | CB | A | 366 | 988 | 81 | 240 | 36 |
| TYR | CG | A | 366 | 1002 | 85 | 243 | 36 |
| TYR | CD1 | A | 366 | 1007 | 97 | 238 | 36 |
| TYR | CE1 | A | 366 | 1020 | 102 | 242 | 36 |
| TYR | CD2 | A | 366 | 1010 | 78 | 252 | 36 |
| TYR | CE2 | A | 366 | 1023 | 82 | 255 | 36 |
| TYR | CZ | A | 366 | 1028 | 94 | 250 | 37 |
| TYR | OH | A | 366 | 1040 | 99 | 254 | 37 |
| TYR | C | A | 366 | 987 | 87 | 216 | 37 |
| TYR | O | A | 366 | 980 | 97 | 217 | 38 |
| LEU | N | A | 367 | 995 | 85 | 206 | 39 |
| LEU | CA | A | 367 | 996 | 94 | 195 | 41 |
| LEU | CB | A | 367 | 1011 | 97 | 192 | 40 |
| LEU | CG | A | 367 | 1019 | 105 | 202 | 40 |
| LEU | CD1 | A | 367 | 1033 | 107 | 197 | 40 |
| LEU | CD2 | A | 367 | 1012 | 118 | 205 | 40 |
| LEU | C | A | 367 | 990 | 87 | 183 | 43 |
| LEU | O | A | 367 | 997 | 78 | 177 | 43 |
| ARG | N | A | 368 | 978 | 90 | 180 | 45 |
| ARG | CA | A | 368 | 971 | 83 | 169 | 47 |
| ARG | CB | A | 368 | 956 | 82 | 171 | 48 |
| ARG | CG | A | 368 | 948 | 75 | 161 | 49 |
| ARG | CD | A | 368 | 934 | 72 | 166 | 49 |
| ARG | NE | A | 368 | 927 | 84 | 170 | 50 |
| ARG | CZ | A | 368 | 921 | 93 | 162 | 50 |
| ARG | NH1 | A | 368 | 922 | 92 | 149 | 50 |
| ARG | NH2 | A | 368 | 916 | 104 | 167 | 50 |
| ARG | C | A | 368 | 974 | 89 | 155 | 49 |
| ARG | O | A | 368 | 972 | 101 | 153 | 50 |
| PRO | N | A | 369 | 979 | 81 | 146 | 51 |
| PRO | CD | A | 369 | 983 | 67 | 148 | 51 |
| PRO | CA | A | 369 | 982 | 85 | 132 | 52 |
| PRO | CB | A | 369 | 987 | 72 | 126 | 51 |
| PRO | CG | A | 369 | 993 | 64 | 137 | 52 |
| PRO | C | A | 369 | 971 | 91 | 124 | 53 |
| PRO | O | A | 369 | 959 | 85 | 125 | 53 |
| VAL | N | A | 370 | 973 | 101 | 117 | 54 |
| VAL | CA | A | 370 | 963 | 108 | 109 | 56 |
| VAL | CB | A | 370 | 957 | 120 | 116 | 56 |
| VAL | CG1 | A | 370 | 949 | 115 | 128 | 56 |
| VAL | CG2 | A | 370 | 968 | 129 | 121 | 56 |
| VAL | C | A | 370 | 969 | 112 | 95 | 57 |
| VAL | O | A | 370 | 981 | 112 | 93 | 57 |
| GLU | N | A | 371 | 960 | 116 | 86 | 58 |
| GLU | CA | A | 371 | 965 | 120 | 73 | 59 |

TABLE 1-continued

Structure Coordinates for uncomplexed BACE

| | | | | | | | |
|---|---|---|---|---|---|---|---|
| GLU | CB | A | 371 | 954 | 117 | 62 | 59 |
| GLU | CG | A | 371 | 960 | 116 | 48 | 60 |
| GLU | CD | A | 371 | 970 | 104 | 47 | 60 |
| GLU | OE1 | A | 371 | 977 | 104 | 36 | 61 |
| GLU | OE2 | A | 371 | 971 | 96 | 56 | 61 |
| GLU | C | A | 371 | 968 | 135 | 72 | 59 |
| GLU | O | A | 371 | 966 | 143 | 81 | 59 |
| GLN | N | A | 372 | 1053 | 137 | 17 | 64 |
| GLN | CA | A | 372 | 1054 | 125 | 26 | 64 |
| GLN | CB | A | 372 | 1065 | 116 | 22 | 65 |
| GLN | CG | A | 372 | 1063 | 109 | 8 | 66 |
| GLN | CD | A | 372 | 1075 | 100 | 4 | 66 |
| GLN | OE1 | A | 372 | 1078 | 91 | 12 | 66 |
| GLN | NE2 | A | 372 | 1080 | 102 | −7 | 66 |
| GLN | C | A | 372 | 1057 | 130 | 40 | 64 |
| GLN | O | A | 372 | 1068 | 135 | 43 | 64 |
| ASP | N | A | 378 | 1047 | 129 | 49 | 63 |
| ASP | CA | A | 378 | 1048 | 133 | 62 | 62 |
| ASP | CB | A | 378 | 1044 | 148 | 64 | 62 |
| ASP | CG | A | 378 | 1056 | 156 | 66 | 62 |
| ASP | OD1 | A | 378 | 1066 | 155 | 58 | 62 |
| ASP | OD2 | A | 378 | 1056 | 165 | 75 | 62 |
| ASP | C | A | 378 | 1039 | 125 | 72 | 61 |
| ASP | O | A | 378 | 1027 | 122 | 68 | 61 |
| ASP | N | A | 379 | 1044 | 121 | 83 | 59 |
| ASP | CA | A | 379 | 1037 | 114 | 93 | 58 |
| ASP | CB | A | 379 | 1046 | 103 | 99 | 58 |
| ASP | CG | A | 379 | 1051 | 93 | 89 | 58 |
| ASP | OD1 | A | 379 | 1059 | 84 | 93 | 58 |
| ASP | OD2 | A | 379 | 1047 | 94 | 77 | 58 |
| ASP | C | A | 379 | 1032 | 123 | 104 | 57 |
| ASP | O | A | 379 | 1039 | 131 | 110 | 56 |
| CYS | N | A | 380 | 1019 | 123 | 105 | 56 |
| CYS | CA | A | 380 | 1012 | 132 | 115 | 55 |
| CYS | C | A | 380 | 1004 | 124 | 125 | 53 |
| CYS | O | A | 380 | 1001 | 113 | 123 | 53 |
| CYS | CB | A | 380 | 1003 | 142 | 108 | 56 |
| CYS | SG | A | 380 | 1010 | 150 | 93 | 57 |
| TYR | N | A | 381 | 1001 | 130 | 137 | 51 |
| TYR | CA | A | 381 | 994 | 123 | 147 | 50 |
| TYR | CB | A | 381 | 1004 | 116 | 157 | 50 |
| TYR | CG | A | 381 | 1014 | 108 | 150 | 49 |
| TYR | CD1 | A | 381 | 1026 | 113 | 144 | 49 |
| TYR | CE1 | A | 381 | 1036 | 106 | 138 | 48 |
| TYR | CD2 | A | 381 | 1013 | 94 | 149 | 49 |
| TYR | CE2 | A | 381 | 1022 | 86 | 142 | 49 |
| TYR | CZ | A | 381 | 1034 | 92 | 137 | 49 |
| TYR | OH | A | 381 | 1043 | 84 | 130 | 48 |
| TYR | C | A | 381 | 986 | 133 | 156 | 49 |
| TYR | O | A | 381 | 988 | 145 | 155 | 49 |
| LYS | N | A | 382 | 977 | 128 | 163 | 48 |
| LYS | CA | A | 382 | 968 | 135 | 172 | 47 |
| LYS | CB | A | 382 | 953 | 133 | 169 | 48 |
| LYS | CG | A | 382 | 949 | 137 | 155 | 50 |
| LYS | CD | A | 382 | 934 | 134 | 153 | 51 |
| LYS | CE | A | 382 | 928 | 139 | 140 | 51 |
| LYS | NZ | A | 382 | 913 | 136 | 138 | 50 |
| LYS | C | A | 382 | 970 | 130 | 186 | 46 |
| LYS | O | A | 382 | 972 | 118 | 188 | 45 |
| PHE | N | A | 383 | 971 | 139 | 196 | 44 |
| PHE | CA | A | 383 | 972 | 135 | 210 | 42 |
| PHE | CB | A | 383 | 974 | 147 | 219 | 42 |
| PHE | CG | A | 383 | 977 | 144 | 233 | 41 |
| PHE | CD1 | A | 383 | 989 | 137 | 237 | 41 |
| PHE | CD2 | A | 383 | 969 | 149 | 243 | 41 |
| PHE | CE1 | A | 383 | 992 | 134 | 250 | 41 |
| PHE | CE2 | A | 383 | 972 | 146 | 257 | 41 |
| PHE | CZ | A | 383 | 983 | 139 | 260 | 41 |
| PHE | C | A | 383 | 959 | 128 | 213 | 42 |
| PHE | O | A | 383 | 949 | 134 | 214 | 42 |
| ALA | N | A | 384 | 960 | 114 | 215 | 41 |
| ALA | CA | A | 384 | 948 | 107 | 218 | 40 |
| ALA | CB | A | 384 | 949 | 93 | 211 | 40 |
| ALA | C | A | 384 | 944 | 105 | 232 | 39 |
| ALA | O | A | 384 | 937 | 96 | 236 | 39 |
| ILE | N | A | 385 | 948 | 114 | 240 | 39 |
| ILE | CA | A | 385 | 945 | 114 | 255 | 39 |
| ILE | CB | A | 385 | 957 | 116 | 264 | 39 |
| ILE | CG2 | A | 385 | 953 | 117 | 278 | 39 |
| ILE | CG1 | A | 385 | 966 | 103 | 263 | 39 |
| ILE | CD1 | A | 385 | 978 | 104 | 271 | 39 |
| ILE | C | A | 385 | 936 | 127 | 256 | 40 |
| ILE | O | A | 385 | 939 | 137 | 250 | 41 |
| SER | N | A | 386 | 925 | 126 | 264 | 40 |
| SER | CA | A | 386 | 917 | 137 | 265 | 41 |
| SER | CB | A | 386 | 907 | 138 | 254 | 41 |
| SER | OG | A | 386 | 898 | 127 | 253 | 42 |
| SER | C | A | 386 | 909 | 137 | 278 | 41 |
| SER | O | A | 386 | 910 | 126 | 285 | 41 |
| GLN | N | A | 387 | 902 | 147 | 282 | 42 |
| GLN | CA | A | 387 | 894 | 148 | 294 | 42 |
| GLN | CB | A | 387 | 895 | 162 | 300 | 43 |
| GLN | CG | A | 387 | 889 | 172 | 291 | 44 |
| GLN | CD | A | 387 | 892 | 186 | 296 | 45 |
| GLN | OE1 | A | 387 | 887 | 190 | 307 | 45 |
| GLN | NE2 | A | 387 | 899 | 194 | 288 | 46 |
| GLN | C | A | 387 | 880 | 143 | 293 | 42 |
| GLN | O | A | 387 | 874 | 142 | 282 | 42 |
| SER | N | A | 388 | 874 | 139 | 304 | 42 |
| SER | CA | A | 388 | 860 | 135 | 305 | 43 |
| SER | CB | A | 388 | 860 | 120 | 304 | 42 |
| SER | OG | A | 388 | 862 | 114 | 317 | 42 |
| SER | C | A | 388 | 855 | 139 | 319 | 43 |
| SER | O | A | 388 | 863 | 141 | 328 | 43 |
| SER | N | A | 389 | 842 | 140 | 320 | 43 |
| SER | CA | A | 389 | 836 | 144 | 332 | 43 |
| SER | CB | A | 389 | 826 | 156 | 330 | 44 |
| SER | OG | A | 389 | 817 | 152 | 320 | 44 |
| SER | C | A | 389 | 828 | 132 | 338 | 44 |
| SER | O | A | 389 | 822 | 132 | 348 | 44 |
| THR | N | A | 390 | 830 | 121 | 330 | 43 |
| THR | CA | A | 390 | 823 | 108 | 334 | 42 |
| THR | CB | A | 390 | 815 | 102 | 323 | 42 |
| THR | OG1 | A | 390 | 824 | 99 | 312 | 42 |
| THR | CG2 | A | 390 | 805 | 113 | 317 | 43 |
| THR | C | A | 390 | 833 | 97 | 339 | 41 |
| THR | O | A | 390 | 830 | 85 | 338 | 41 |
| GLY | N | A | 391 | 844 | 101 | 344 | 40 |
| GLY | CA | A | 391 | 854 | 92 | 349 | 38 |
| GLY | C | A | 391 | 864 | 87 | 338 | 36 |
| GLY | O | A | 391 | 863 | 91 | 327 | 36 |
| THR | N | A | 392 | 873 | 78 | 343 | 36 |
| THR | CA | A | 392 | 883 | 73 | 334 | 34 |
| THR | CB | A | 392 | 894 | 65 | 342 | 34 |
| THR | OG1 | A | 392 | 901 | 75 | 350 | 35 |
| THR | CG2 | A | 392 | 904 | 59 | 333 | 34 |
| THR | C | A | 392 | 878 | 63 | 324 | 34 |
| THR | O | A | 392 | 870 | 54 | 327 | 33 |
| VAL | N | A | 393 | 881 | 65 | 311 | 32 |
| VAL | CA | A | 393 | 877 | 56 | 301 | 32 |
| VAL | CB | A | 393 | 868 | 62 | 290 | 32 |
| VAL | CG1 | A | 393 | 863 | 51 | 281 | 31 |
| VAL | CG2 | A | 393 | 856 | 68 | 297 | 32 |
| VAL | C | A | 393 | 890 | 50 | 293 | 32 |
| VAL | O | A | 393 | 896 | 58 | 286 | 32 |
| MET | N | A | 394 | 893 | 38 | 296 | 32 |
| MET | CA | A | 394 | 904 | 31 | 290 | 31 |
| MET | CB | A | 394 | 909 | 20 | 298 | 32 |
| MET | CG | A | 394 | 914 | 24 | 312 | 33 |
| MET | SD | A | 394 | 916 | 11 | 324 | 35 |
| MET | CE | A | 394 | 933 | 6 | 321 | 34 |
| MET | C | A | 394 | 899 | 27 | 276 | 31 |
| MET | O | A | 394 | 894 | 16 | 275 | 31 |
| GLY | N | A | 395 | 901 | 35 | 266 | 30 |
| GLY | CA | A | 395 | 896 | 31 | 253 | 29 |
| GLY | C | A | 395 | 907 | 24 | 244 | 29 |
| GLY | O | A | 395 | 916 | 18 | 250 | 29 |
| ALA | N | A | 396 | 906 | 26 | 231 | 29 |
| ALA | CA | A | 396 | 915 | 19 | 222 | 30 |
| ALA | CB | A | 396 | 911 | 23 | 207 | 30 |
| ALA | C | A | 396 | 930 | 23 | 224 | 30 |
| ALA | O | A | 396 | 938 | 14 | 222 | 31 |
| VAL | N | A | 397 | 933 | 35 | 228 | 30 |
| VAL | CA | A | 397 | 947 | 38 | 231 | 30 |

TABLE 1-continued

Structure Coordinates for uncomplexed BACE

| | | | | | | | |
|---|---|---|---|---|---|---|---|
| VAL | CB | A | 397 | 948 | 53 | 235 | 31 |
| VAL | CG1 | A | 397 | 945 | 62 | 224 | 31 |
| VAL | CG2 | A | 397 | 939 | 56 | 247 | 32 |
| VAL | C | A | 397 | 953 | 29 | 242 | 30 |
| VAL | O | A | 397 | 964 | 26 | 241 | 31 |
| ILE | N | A | 398 | 944 | 25 | 251 | 29 |
| ILE | CA | A | 398 | 949 | 16 | 261 | 28 |
| ILE | CB | A | 398 | 941 | 16 | 274 | 28 |
| ILE | CG2 | A | 398 | 943 | 4 | 283 | 28 |
| ILE | CG1 | A | 398 | 943 | 29 | 282 | 28 |
| ILE | CD1 | A | 398 | 958 | 30 | 287 | 29 |
| ILE | C | A | 398 | 949 | 1 | 256 | 28 |
| ILE | O | A | 398 | 959 | −6 | 256 | 28 |
| MET | N | A | 399 | 937 | −3 | 251 | 28 |
| MET | CA | A | 399 | 935 | −16 | 246 | 28 |
| MET | CB | A | 399 | 921 | −18 | 241 | 27 |
| MET | CG | A | 399 | 911 | −16 | 253 | 27 |
| MET | SD | A | 399 | 894 | −19 | 250 | 26 |
| MET | CE | A | 399 | 893 | −37 | 249 | 27 |
| MET | C | A | 399 | 945 | −20 | 234 | 28 |
| MET | O | A | 399 | 949 | −32 | 234 | 29 |
| GLU | N | A | 400 | 948 | −11 | 225 | 27 |
| GLU | CA | A | 400 | 957 | −15 | 214 | 28 |
| GLU | CB | A | 400 | 958 | −3 | 204 | 29 |
| GLU | CG | A | 400 | 944 | −1 | 197 | 30 |
| GLU | CD | A | 400 | 944 | 10 | 186 | 31 |
| GLU | OE1 | A | 400 | 934 | 11 | 179 | 32 |
| GLU | OE2 | A | 400 | 954 | 17 | 185 | 31 |
| GLU | C | A | 400 | 971 | −19 | 219 | 27 |
| GLU | O | A | 400 | 979 | −23 | 211 | 27 |
| GLY | N | A | 401 | 973 | −17 | 232 | 26 |
| GLY | CA | A | 401 | 986 | −21 | 237 | 25 |
| GLY | C | A | 401 | 986 | −35 | 243 | 23 |
| GLY | O | A | 401 | 996 | −42 | 245 | 23 |
| PHE | N | A | 402 | 974 | −40 | 246 | 22 |
| PHE | CA | A | 402 | 973 | −54 | 252 | 22 |
| PHE | CB | A | 402 | 971 | −52 | 267 | 21 |
| PHE | CG | A | 402 | 978 | −40 | 273 | 21 |
| PHE | CD1 | A | 402 | 973 | −27 | 273 | 21 |
| PHE | CD2 | A | 402 | 991 | −42 | 278 | 21 |
| PHE | CE1 | A | 402 | 980 | −16 | 278 | 21 |
| PHE | CE2 | A | 402 | 999 | −31 | 283 | 21 |
| PHE | CZ | A | 402 | 993 | −18 | 283 | 20 |
| PHE | C | A | 402 | 962 | −63 | 247 | 22 |
| PHE | O | A | 402 | 954 | −59 | 239 | 22 |
| TYR | N | A | 403 | 963 | −75 | 252 | 22 |
| TYR | CA | A | 403 | 953 | −85 | 249 | 21 |
| TYR | CB | A | 403 | 960 | −99 | 247 | 21 |
| TYR | CG | A | 403 | 950 | −110 | 243 | 21 |
| TYR | CD1 | A | 403 | 939 | −108 | 235 | 21 |
| TYR | CE1 | A | 403 | 930 | −118 | 231 | 21 |
| TYR | CD2 | A | 403 | 952 | −123 | 248 | 21 |
| TYR | CE2 | A | 403 | 943 | −133 | 245 | 20 |
| TYR | CZ | A | 403 | 932 | −131 | 236 | 21 |
| TYR | OH | A | 403 | 924 | −141 | 233 | 21 |
| TYR | C | A | 403 | 945 | −85 | 261 | 21 |
| TYR | O | A | 403 | 950 | −87 | 272 | 22 |
| VAL | N | A | 404 | 932 | −81 | 260 | 22 |
| VAL | CA | A | 404 | 923 | −79 | 271 | 21 |
| VAL | CB | A | 404 | 916 | −65 | 270 | 22 |
| VAL | CG1 | A | 404 | 909 | −62 | 282 | 20 |
| VAL | CG2 | A | 404 | 927 | −55 | 266 | 21 |
| VAL | C | A | 404 | 913 | −90 | 272 | 21 |
| VAL | O | A | 404 | 905 | −93 | 263 | 21 |
| VAL | N | A | 405 | 913 | −97 | 284 | 21 |
| VAL | CA | A | 405 | 903 | −108 | 286 | 21 |
| VAL | CB | A | 405 | 910 | −120 | 293 | 21 |
| VAL | CG1 | A | 405 | 900 | −131 | 294 | 20 |
| VAL | CG2 | A | 405 | 922 | −124 | 285 | 20 |
| VAL | C | A | 405 | 892 | −103 | 295 | 22 |
| VAL | O | A | 405 | 894 | −100 | 307 | 23 |
| PHE | N | A | 406 | 880 | −104 | 290 | 23 |
| PHE | CA | A | 406 | 868 | −101 | 297 | 23 |
| PHE | CB | A | 406 | 858 | −94 | 288 | 23 |
| PHE | CG | A | 406 | 863 | −80 | 283 | 23 |
| PHE | CD1 | A | 406 | 859 | −68 | 290 | 22 |
| PHE | CD2 | A | 406 | 871 | −79 | 272 | 23 |
| PHE | CE1 | A | 406 | 864 | −56 | 286 | 23 |
| PHE | CE2 | A | 406 | 876 | −67 | 268 | 23 |
| PHE | CZ | A | 406 | 872 | −55 | 275 | 23 |
| PHE | C | A | 406 | 862 | −113 | 303 | 23 |
| PHE | O | A | 406 | 853 | −120 | 298 | 23 |
| ASP | N | A | 407 | 868 | −117 | 315 | 24 |
| ASP | CA | A | 407 | 865 | −130 | 322 | 25 |
| ASP | CB | A | 407 | 877 | −134 | 330 | 25 |
| ASP | CG | A | 407 | 875 | −148 | 336 | 26 |
| ASP | OD1 | A | 407 | 863 | −153 | 336 | 26 |
| ASP | OD2 | A | 407 | 885 | −154 | 341 | 26 |
| ASP | C | A | 407 | 853 | −127 | 331 | 26 |
| ASP | O | A | 407 | 854 | −126 | 343 | 26 |
| ARG | N | A | 408 | 841 | −127 | 324 | 26 |
| ARG | CA | A | 408 | 829 | −125 | 332 | 27 |
| ARG | CB | A | 408 | 817 | −124 | 322 | 26 |
| ARG | CG | A | 408 | 818 | −112 | 313 | 27 |
| ARG | CD | A | 408 | 811 | −114 | 300 | 27 |
| ARG | NE | A | 408 | 797 | −117 | 302 | 27 |
| ARG | CZ | A | 408 | 787 | −109 | 300 | 27 |
| ARG | NH1 | A | 408 | 789 | −96 | 297 | 26 |
| ARG | NH2 | A | 408 | 774 | −113 | 302 | 27 |
| ARG | C | A | 408 | 825 | −136 | 342 | 27 |
| ARG | O | A | 408 | 820 | −133 | 352 | 27 |
| ALA | N | A | 409 | 829 | −148 | 338 | 28 |
| ALA | CA | A | 409 | 826 | −160 | 347 | 28 |
| ALA | CB | A | 409 | 831 | −173 | 341 | 27 |
| ALA | C | A | 409 | 833 | −158 | 361 | 29 |
| ALA | O | A | 409 | 828 | −161 | 371 | 29 |
| ARG | N | A | 410 | 845 | −152 | 360 | 30 |
| ARG | CA | A | 410 | 853 | −150 | 373 | 31 |
| ARG | CB | A | 410 | 867 | −155 | 372 | 32 |
| ARG | CG | A | 410 | 866 | −170 | 370 | 33 |
| ARG | CD | A | 410 | 880 | −176 | 367 | 34 |
| ARG | NE | A | 410 | 888 | −178 | 378 | 36 |
| ARG | CZ | A | 410 | 899 | −187 | 379 | 37 |
| ARG | NH1 | A | 410 | 901 | −194 | 368 | 38 |
| ARG | NH2 | A | 410 | 906 | −188 | 389 | 37 |
| ARG | C | A | 410 | 853 | −135 | 377 | 32 |
| ARG | O | A | 410 | 861 | −131 | 385 | 32 |
| LYS | N | A | 411 | 844 | −127 | 371 | 32 |
| LYS | CA | A | 411 | 843 | −113 | 374 | 33 |
| LYS | CB | A | 411 | 836 | −112 | 388 | 34 |
| LYS | CG | A | 411 | 829 | −98 | 391 | 36 |
| LYS | CD | A | 411 | 819 | −100 | 403 | 37 |
| LYS | CE | A | 411 | 814 | −86 | 408 | 38 |
| LYS | NZ | A | 411 | 806 | −87 | 420 | 39 |
| LYS | C | A | 411 | 856 | −106 | 375 | 32 |
| LYS | O | A | 411 | 860 | −99 | 384 | 32 |
| ARG | N | A | 412 | 864 | −108 | 364 | 30 |
| ARG | CA | A | 412 | 877 | −102 | 363 | 28 |
| ARG | CB | A | 412 | 888 | −111 | 369 | 28 |
| ARG | CG | A | 412 | 889 | −124 | 362 | 28 |
| ARG | CD | A | 412 | 898 | −133 | 369 | 27 |
| ARG | NE | A | 412 | 901 | −145 | 361 | 27 |
| ARG | CZ | A | 412 | 911 | −154 | 363 | 28 |
| ARG | NH1 | A | 412 | 918 | −153 | 374 | 27 |
| ARG | NH2 | A | 412 | 913 | −164 | 355 | 27 |
| ARG | C | A | 412 | 881 | −98 | 349 | 27 |
| ARG | O | A | 412 | 875 | −103 | 339 | 26 |
| ILE | N | A | 413 | 891 | −90 | 348 | 26 |
| ILE | CA | A | 413 | 896 | −85 | 335 | 25 |
| ILE | CB | A | 413 | 893 | −71 | 332 | 25 |
| ILE | CG2 | A | 413 | 900 | −66 | 320 | 25 |
| ILE | CG1 | A | 413 | 878 | −69 | 331 | 26 |
| ILE | CD1 | A | 413 | 873 | −55 | 331 | 27 |
| ILE | C | A | 413 | 911 | −87 | 335 | 25 |
| ILE | O | A | 413 | 918 | −83 | 344 | 25 |
| GLY | N | A | 414 | 916 | −95 | 325 | 24 |
| GLY | CA | A | 414 | 930 | −97 | 324 | 24 |
| GLY | C | A | 414 | 937 | −89 | 313 | 24 |
| GLY | O | A | 414 | 931 | −86 | 303 | 23 |
| PHE | N | A | 415 | 950 | −86 | 315 | 23 |
| PHE | CA | A | 415 | 958 | −78 | 306 | 24 |
| PHE | CB | A | 415 | 961 | −64 | 312 | 23 |
| PHE | CG | A | 415 | 950 | −55 | 313 | 23 |
| PHE | CD1 | A | 415 | 941 | −56 | 324 | 23 |

TABLE 1-continued

Structure Coordinates for uncomplexed BACE

| | | | | | | | |
|---|---|---|---|---|---|---|---|
| PHE | CD2 | A | 415 | 947 | −45 | 303 | 23 |
| PHE | CE1 | A | 415 | 930 | −47 | 325 | 23 |
| PHE | CE2 | A | 415 | 937 | −37 | 304 | 24 |
| PHE | CZ | A | 415 | 928 | −38 | 315 | 23 |
| PHE | C | A | 415 | 971 | −86 | 303 | 23 |
| PHE | O | A | 415 | 977 | −91 | 312 | 23 |
| ALA | N | A | 416 | 975 | −86 | 291 | 23 |
| ALA | CA | A | 416 | 988 | −92 | 287 | 23 |
| ALA | CB | A | 416 | 986 | −107 | 283 | 23 |
| ALA | C | A | 416 | 994 | −84 | 275 | 24 |
| ALA | O | A | 416 | 986 | −77 | 268 | 24 |
| VAL | N | A | 417 | 1007 | −85 | 273 | 25 |
| VAL | CA | A | 417 | 1013 | −77 | 262 | 26 |
| VAL | CB | A | 417 | 1028 | −79 | 262 | 26 |
| VAL | CG1 | A | 417 | 1034 | −72 | 250 | 25 |
| VAL | CG2 | A | 417 | 1034 | −73 | 275 | 25 |
| VAL | C | A | 417 | 1007 | −83 | 250 | 26 |
| VAL | O | A | 417 | 1007 | −95 | 248 | 26 |
| SER | N | A | 418 | 1002 | −74 | 241 | 27 |
| SER | CA | A | 418 | 996 | −79 | 228 | 28 |
| SER | CB | A | 418 | 987 | −68 | 222 | 29 |
| SER | OG | A | 418 | 984 | −70 | 209 | 29 |
| SER | C | A | 418 | 1007 | −82 | 218 | 29 |
| SER | O | A | 418 | 1016 | −75 | 216 | 28 |
| ALA | N | A | 419 | 1005 | −94 | 211 | 29 |
| ALA | CA | A | 419 | 1015 | −98 | 202 | 31 |
| ALA | CB | A | 419 | 1013 | −112 | 198 | 30 |
| ALA | C | A | 419 | 1015 | −89 | 189 | 32 |
| ALA | O | A | 419 | 1024 | −90 | 181 | 32 |
| CYS | N | A | 420 | 1005 | −80 | 188 | 32 |
| CYS | CA | A | 420 | 1004 | −71 | 176 | 33 |
| CYS | C | A | 420 | 1005 | −57 | 180 | 33 |
| CYS | O | A | 420 | 1003 | −48 | 171 | 33 |
| CYS | CB | A | 420 | 990 | −73 | 169 | 34 |
| CYS | SG | A | 420 | 976 | −66 | 178 | 37 |
| HIS | N | A | 421 | 1008 | −53 | 192 | 31 |
| HIS | CA | A | 421 | 1009 | −39 | 195 | 31 |
| HIS | CB | A | 421 | 1010 | −37 | 211 | 29 |
| HIS | CG | A | 421 | 1024 | −38 | 216 | 28 |
| HIS | CD2 | A | 421 | 1032 | −28 | 220 | 28 |
| HIS | ND1 | A | 421 | 1030 | −50 | 219 | 27 |
| HIS | CE1 | A | 421 | 1042 | −48 | 224 | 27 |
| HIS | NE2 | A | 421 | 1044 | −34 | 225 | 27 |
| HIS | C | A | 421 | 1021 | −32 | 188 | 31 |
| HIS | O | A | 421 | 1031 | −38 | 186 | 30 |
| VAL | N | A | 422 | 1019 | −19 | 185 | 32 |
| VAL | CA | A | 422 | 1029 | −11 | 178 | 32 |
| VAL | CB | A | 422 | 1022 | 1 | 171 | 33 |
| VAL | CG1 | A | 422 | 1032 | 9 | 163 | 33 |
| VAL | CG2 | A | 422 | 1011 | −4 | 162 | 33 |
| VAL | C | A | 422 | 1039 | −5 | 188 | 33 |
| VAL | O | A | 422 | 1035 | 2 | 198 | 33 |
| HIS | N | A | 423 | 1051 | −8 | 185 | 33 |
| HIS | CA | A | 423 | 1062 | −3 | 194 | 34 |
| HIS | CB | A | 423 | 1066 | −13 | 205 | 34 |
| HIS | CG | A | 423 | 1070 | −26 | 199 | 34 |
| HIS | CD2 | A | 423 | 1083 | −31 | 198 | 34 |
| HIS | ND1 | A | 423 | 1062 | −36 | 194 | 34 |
| HIS | CE1 | A | 423 | 1069 | −46 | 190 | 35 |
| HIS | NE2 | A | 423 | 1082 | −44 | 192 | 35 |
| HIS | C | A | 423 | 1075 | −1 | 185 | 35 |
| HIS | O | A | 423 | 1074 | −3 | 173 | 35 |
| ASP | N | A | 424 | 1086 | 2 | 191 | 35 |
| ASP | CA | A | 424 | 1098 | 4 | 183 | 36 |
| ASP | CB | A | 424 | 1103 | 18 | 185 | 36 |
| ASP | CG | A | 424 | 1104 | 23 | 199 | 37 |
| ASP | OD1 | A | 424 | 1112 | 16 | 206 | 36 |
| ASP | OD2 | A | 424 | 1097 | 33 | 203 | 37 |
| ASP | C | A | 424 | 1109 | −6 | 188 | 37 |
| ASP | O | A | 424 | 1106 | −15 | 196 | 36 |
| GLU | N | A | 425 | 1121 | −4 | 183 | 37 |
| GLU | CA | A | 425 | 1133 | −12 | 186 | 38 |
| GLU | CB | A | 425 | 1144 | −8 | 177 | 39 |
| GLU | CG | A | 425 | 1158 | −10 | 183 | 41 |
| GLU | CD | A | 425 | 1165 | −22 | 179 | 42 |
| GLU | OE1 | A | 425 | 1160 | −33 | 180 | 43 |
| GLU | OE2 | A | 425 | 1177 | −21 | 174 | 43 |
| GLU | C | A | 425 | 1137 | −11 | 201 | 37 |
| GLU | O | A | 425 | 1144 | −20 | 206 | 37 |
| PHE | N | A | 426 | 1134 | 0 | 208 | 36 |
| PHE | CA | A | 426 | 1139 | 1 | 221 | 35 |
| PHE | CB | A | 426 | 1145 | 15 | 223 | 35 |
| PHE | CG | A | 426 | 1156 | 18 | 212 | 36 |
| PHE | CD1 | A | 426 | 1153 | 25 | 201 | 36 |
| PHE | CD2 | A | 426 | 1169 | 12 | 213 | 36 |
| PHE | CE1 | A | 426 | 1162 | 28 | 191 | 36 |
| PHE | CE2 | A | 426 | 1178 | 15 | 203 | 36 |
| PHE | CZ | A | 426 | 1175 | 22 | 192 | 36 |
| PHE | C | A | 426 | 1128 | 0 | 232 | 34 |
| PHE | O | A | 426 | 1132 | −5 | 243 | 34 |
| ARG | N | A | 427 | 1116 | 3 | 230 | 33 |
| ARG | CA | A | 427 | 1105 | 1 | 240 | 32 |
| ARG | CB | A | 427 | 1100 | 15 | 244 | 32 |
| ARG | CG | A | 427 | 1110 | 24 | 250 | 32 |
| ARG | CD | A | 427 | 1104 | 36 | 257 | 32 |
| ARG | NE | A | 427 | 1097 | 45 | 247 | 30 |
| ARG | CZ | A | 427 | 1095 | 58 | 250 | 30 |
| ARG | NH1 | A | 427 | 1098 | 63 | 262 | 29 |
| ARG | NH2 | A | 427 | 1089 | 66 | 241 | 30 |
| ARG | C | A | 427 | 1093 | −7 | 235 | 32 |
| ARG | O | A | 427 | 1090 | −7 | 223 | 32 |
| THR | N | A | 428 | 1087 | −14 | 245 | 31 |
| THR | CA | A | 428 | 1076 | −23 | 242 | 30 |
| THR | CB | A | 428 | 1080 | −38 | 243 | 30 |
| THR | OG1 | A | 428 | 1069 | −46 | 240 | 32 |
| THR | CG2 | A | 428 | 1086 | −41 | 256 | 31 |
| THR | C | A | 428 | 1065 | −20 | 253 | 29 |
| THR | O | A | 428 | 1069 | −16 | 264 | 29 |
| ALA | N | A | 429 | 1053 | −23 | 250 | 29 |
| ALA | CA | A | 429 | 1042 | −21 | 260 | 28 |
| ALA | CB | A | 429 | 1029 | −23 | 254 | 28 |
| ALA | C | A | 429 | 1045 | −32 | 270 | 28 |
| ALA | O | A | 429 | 1053 | −41 | 267 | 27 |
| ALA | N | A | 430 | 1040 | −31 | 282 | 27 |
| ALA | CA | A | 430 | 1043 | −41 | 292 | 28 |
| ALA | CB | A | 430 | 1056 | −37 | 299 | 28 |
| ALA | C | A | 430 | 1032 | −43 | 303 | 28 |
| ALA | O | A | 430 | 1024 | −34 | 305 | 28 |
| VAL | N | A | 431 | 1032 | −54 | 309 | 29 |
| VAL | CA | A | 431 | 1023 | −58 | 320 | 30 |
| VAL | CB | A | 431 | 1012 | −68 | 315 | 30 |
| VAL | CG1 | A | 431 | 1003 | −70 | 327 | 29 |
| VAL | CG2 | A | 431 | 1005 | −62 | 303 | 28 |
| VAL | C | A | 431 | 1032 | −65 | 330 | 31 |
| VAL | O | A | 431 | 1038 | −75 | 328 | 32 |
| GLU | N | A | 432 | 1034 | −58 | 342 | 32 |
| GLU | CA | A | 432 | 1042 | −64 | 352 | 34 |
| GLU | CB | A | 432 | 1056 | −57 | 352 | 35 |
| GLU | CG | A | 432 | 1062 | −56 | 338 | 38 |
| GLU | CD | A | 432 | 1076 | −49 | 338 | 40 |
| GLU | OE1 | A | 432 | 1085 | −54 | 345 | 41 |
| GLU | OE2 | A | 432 | 1077 | −38 | 331 | 41 |
| GLU | C | A | 432 | 1036 | −63 | 366 | 33 |
| GLU | O | A | 432 | 1027 | −55 | 368 | 32 |
| GLY | N | A | 433 | 1042 | −71 | 375 | 33 |
| GLY | CA | A | 433 | 1037 | −72 | 388 | 33 |
| GLY | C | A | 433 | 1044 | −83 | 396 | 34 |
| GLY | O | A | 433 | 1052 | −90 | 389 | 34 |
| PRO | N | A | 434 | 1041 | −85 | 409 | 33 |
| PRO | CD | A | 434 | 1046 | −97 | 416 | 33 |
| PRO | CA | A | 434 | 1032 | −77 | 416 | 34 |
| PRO | CB | A | 434 | 1027 | −87 | 426 | 34 |
| PRO | CG | A | 434 | 1039 | −95 | 430 | 34 |
| PRO | C | A | 434 | 1039 | −65 | 423 | 34 |
| PRO | O | A | 434 | 1051 | −64 | 424 | 33 |
| PHE | N | A | 435 | 1031 | −56 | 429 | 35 |
| PHE | CA | A | 435 | 1035 | −44 | 436 | 36 |
| PHE | CB | A | 435 | 1033 | −32 | 428 | 35 |
| PHE | CG | A | 435 | 1040 | −31 | 415 | 35 |
| PHE | CD1 | A | 435 | 1034 | −34 | 403 | 35 |
| PHE | CD2 | A | 435 | 1054 | −28 | 414 | 35 |
| PHE | CE1 | A | 435 | 1040 | −34 | 391 | 35 |
| PHE | CE2 | A | 435 | 1061 | −29 | 402 | 35 |
| PHE | CZ | A | 435 | 1054 | −32 | 390 | 35 |

TABLE 1-continued

Structure Coordinates for uncomplexed BACE

| | | | | | | | |
|---|---|---|---|---|---|---|---|
| PHE | C | A | 435 | 1028 | −44 | 449 | 37 |
| PHE | O | A | 435 | 1016 | −47 | 449 | 36 |
| VAL | N | A | 436 | 1035 | −41 | 460 | 39 |
| VAL | CA | A | 436 | 1028 | −40 | 473 | 41 |
| VAL | CB | A | 436 | 1039 | −40 | 485 | 41 |
| VAL | CG1 | A | 436 | 1031 | −39 | 498 | 41 |
| VAL | CG2 | A | 436 | 1047 | −52 | 484 | 41 |
| VAL | C | A | 436 | 1021 | −27 | 474 | 42 |
| VAL | O | A | 436 | 1026 | −16 | 472 | 42 |
| THR | N | A | 437 | 1007 | −28 | 475 | 43 |
| THR | CA | A | 437 | 999 | −16 | 475 | 45 |
| THR | CB | A | 437 | 992 | −14 | 462 | 45 |
| THR | OG1 | A | 437 | 1001 | −16 | 451 | 45 |
| THR | CG2 | A | 437 | 986 | 0 | 461 | 45 |
| THR | C | A | 437 | 989 | −18 | 486 | 46 |
| THR | O | A | 437 | 982 | −28 | 487 | 46 |
| LEU | N | A | 438 | 987 | −7 | 495 | 47 |
| LEU | CA | A | 438 | 977 | −8 | 505 | 48 |
| LEU | CB | A | 438 | 984 | −4 | 519 | 48 |
| LEU | CG | A | 438 | 998 | −11 | 521 | 48 |
| LEU | CD1 | A | 438 | 1003 | −7 | 535 | 48 |
| LEU | CD2 | A | 438 | 996 | −26 | 520 | 48 |
| LEU | C | A | 438 | 966 | 2 | 503 | 49 |
| LEU | O | A | 438 | 967 | 11 | 495 | 49 |
| ASP | N | A | 439 | 955 | 0 | 510 | 49 |
| ASP | CA | A | 439 | 943 | 9 | 509 | 50 |
| ASP | CB | A | 439 | 947 | 23 | 515 | 51 |
| ASP | CG | A | 439 | 949 | 22 | 530 | 51 |
| ASP | OD1 | A | 439 | 955 | 32 | 536 | 52 |
| ASP | OD2 | A | 439 | 946 | 11 | 537 | 51 |
| ASP | C | A | 439 | 938 | 11 | 495 | 51 |
| ASP | O | A | 439 | 934 | 22 | 491 | 51 |
| MET | N | A | 440 | 938 | 0 | 487 | 51 |
| MET | CA | A | 440 | 934 | 1 | 473 | 51 |
| MET | CB | A | 440 | 938 | −11 | 466 | 49 |
| MET | CG | A | 440 | 952 | −13 | 463 | 49 |
| MET | SD | A | 440 | 956 | −26 | 452 | 47 |
| MET | CE | A | 440 | 955 | −40 | 463 | 47 |
| MET | C | A | 440 | 919 | 4 | 472 | 52 |
| MET | O | A | 440 | 915 | 12 | 464 | 52 |
| GLU | N | A | 441 | 911 | −3 | 480 | 53 |
| GLU | CA | A | 441 | 896 | −1 | 479 | 55 |
| GLU | CB | A | 441 | 888 | −11 | 487 | 55 |
| GLU | CG | A | 441 | 874 | −13 | 483 | 55 |
| GLU | CD | A | 441 | 872 | −16 | 468 | 56 |
| GLU | OE1 | A | 441 | 875 | −27 | 464 | 56 |
| GLU | OE2 | A | 441 | 867 | −8 | 460 | 55 |
| GLU | C | A | 441 | 893 | 13 | 483 | 55 |
| GLU | O | A | 441 | 881 | 17 | 481 | 56 |
| ASP | N | A | 442 | 902 | 20 | 488 | 56 |
| ASP | CA | A | 442 | 900 | 34 | 492 | 56 |
| ASP | CB | A | 442 | 911 | 40 | 501 | 57 |
| ASP | CG | A | 442 | 909 | 37 | 516 | 57 |
| ASP | OD1 | A | 442 | 898 | 39 | 521 | 58 |
| ASP | OD2 | A | 442 | 919 | 32 | 522 | 58 |
| ASP | C | A | 442 | 900 | 42 | 479 | 56 |
| ASP | O | A | 442 | 894 | 53 | 479 | 55 |
| CYS | N | A | 443 | 906 | 37 | 469 | 55 |
| CYS | CA | A | 443 | 906 | 44 | 456 | 55 |
| CYS | C | A | 443 | 893 | 44 | 449 | 56 |
| CYS | O | A | 443 | 890 | 51 | 439 | 55 |
| CYS | CB | A | 443 | 917 | 38 | 447 | 54 |
| CYS | SG | A | 443 | 933 | 37 | 454 | 53 |
| GLY | N | A | 444 | 884 | 35 | 453 | 57 |
| GLY | CA | A | 444 | 871 | 34 | 447 | 59 |
| GLY | C | A | 444 | 861 | 45 | 451 | 60 |
| GLY | O | A | 444 | 859 | 48 | 463 | 60 |
| TYR | N | A | 445 | 858 | 52 | 441 | 61 |
| TYR | CA | A | 445 | 846 | 63 | 443 | 62 |
| TYR | CB | A | 445 | 847 | 73 | 432 | 62 |
| TYR | CG | A | 445 | 837 | 84 | 434 | 63 |
| TYR | CD1 | A | 445 | 838 | 93 | 445 | 63 |
| TYR | CD2 | A | 445 | 826 | 85 | 425 | 63 |
| TYR | CE1 | A | 445 | 828 | 103 | 446 | 63 |
| TYR | CE2 | A | 445 | 816 | 95 | 427 | 63 |
| TYR | CZ | A | 445 | 818 | 104 | 438 | 63 |
| TYR | OH | A | 445 | 808 | 114 | 440 | 63 |
| TYR | C | A | 445 | 832 | 57 | 444 | 62 |
| TYR | O | A | 445 | 830 | 47 | 438 | 63 |
| ASN | N | A | 446 | 823 | 63 | 451 | 63 |
| ASN | CA | A | 446 | 810 | 58 | 452 | 64 |
| ASN | CB | A | 446 | 807 | 54 | 467 | 64 |
| ASN | CG | A | 446 | 816 | 43 | 472 | 65 |
| ASN | OD1 | A | 446 | 816 | 32 | 467 | 65 |
| ASN | ND2 | A | 446 | 824 | 46 | 482 | 65 |
| ASN | C | A | 446 | 800 | 68 | 447 | 64 |
| ASN | O | A | 446 | 792 | 74 | 456 | 65 |
| ASN | OXT | A | 446 | 799 | 70 | 435 | 65 |
| GLY | C | B | 56 | 446 | 445 | 306 | 47 |
| GLY | O | B | 56 | 449 | 453 | 315 | 47 |
| GLY | N | B | 56 | 435 | 444 | 284 | 46 |
| GLY | CA | B | 56 | 446 | 450 | 292 | 47 |
| ARG | N | B | 57 | 441 | 433 | 308 | 46 |
| ARG | CA | B | 57 | 439 | 427 | 321 | 45 |
| ARG | CB | B | 57 | 436 | 412 | 319 | 46 |
| ARG | CG | B | 57 | 424 | 407 | 327 | 46 |
| ARG | CD | B | 57 | 411 | 412 | 321 | 46 |
| ARG | NE | B | 57 | 400 | 404 | 325 | 47 |
| ARG | CZ | B | 57 | 387 | 407 | 322 | 47 |
| ARG | NH1 | B | 57 | 384 | 417 | 315 | 47 |
| ARG | NH2 | B | 57 | 377 | 399 | 327 | 47 |
| ARG | C | B | 57 | 451 | 428 | 330 | 44 |
| ARG | O | B | 57 | 463 | 425 | 326 | 45 |
| GLY | N | B | 58 | 449 | 431 | 342 | 42 |
| GLY | CA | B | 58 | 460 | 432 | 352 | 39 |
| GLY | C | B | 58 | 455 | 423 | 363 | 37 |
| GLY | O | B | 58 | 462 | 418 | 372 | 38 |
| SER | N | B | 59 | 442 | 420 | 363 | 35 |
| SER | CA | B | 59 | 435 | 411 | 373 | 33 |
| SER | CB | B | 59 | 425 | 420 | 381 | 32 |
| SER | OG | B | 59 | 418 | 412 | 390 | 31 |
| SER | C | B | 59 | 428 | 400 | 367 | 32 |
| SER | O | B | 59 | 418 | 401 | 360 | 31 |
| PHE | N | B | 60 | 433 | 388 | 369 | 32 |
| PHE | CA | B | 60 | 428 | 376 | 363 | 32 |
| PHE | CB | B | 60 | 438 | 368 | 356 | 32 |
| PHE | CG | B | 60 | 446 | 375 | 345 | 32 |
| PHE | CD1 | B | 60 | 455 | 385 | 349 | 32 |
| PHE | CD2 | B | 60 | 443 | 373 | 332 | 32 |
| PHE | CE1 | B | 60 | 461 | 393 | 339 | 32 |
| PHE | CE2 | B | 60 | 449 | 380 | 322 | 32 |
| PHE | CZ | B | 60 | 458 | 390 | 325 | 32 |
| PHE | C | B | 60 | 421 | 368 | 374 | 31 |
| PHE | O | B | 60 | 425 | 357 | 378 | 32 |
| VAL | N | B | 61 | 410 | 374 | 379 | 31 |
| VAL | CA | B | 61 | 402 | 369 | 389 | 31 |
| VAL | CB | B | 61 | 388 | 376 | 389 | 31 |
| VAL | CG1 | B | 61 | 380 | 373 | 402 | 32 |
| VAL | CG2 | B | 61 | 390 | 391 | 389 | 32 |
| VAL | C | B | 61 | 399 | 354 | 389 | 30 |
| VAL | O | B | 61 | 401 | 347 | 399 | 29 |
| GLU | N | B | 62 | 393 | 349 | 378 | 29 |
| GLU | CA | B | 62 | 390 | 335 | 377 | 29 |
| GLU | CB | B | 62 | 382 | 332 | 364 | 29 |
| GLU | CG | B | 62 | 367 | 335 | 365 | 29 |
| GLU | CD | B | 62 | 365 | 350 | 366 | 30 |
| GLU | OE1 | B | 62 | 369 | 358 | 357 | 30 |
| GLU | OE2 | B | 62 | 358 | 354 | 376 | 29 |
| GLU | C | B | 62 | 402 | 325 | 378 | 28 |
| GLU | O | B | 62 | 400 | 314 | 382 | 29 |
| MET | N | B | 63 | 413 | 329 | 373 | 28 |
| MET | CA | B | 63 | 425 | 321 | 373 | 28 |
| MET | CB | B | 63 | 434 | 325 | 361 | 29 |
| MET | CG | B | 63 | 427 | 323 | 348 | 30 |
| MET | SD | B | 63 | 439 | 325 | 334 | 31 |
| MET | CE | B | 63 | 432 | 340 | 327 | 30 |
| MET | C | B | 63 | 433 | 320 | 386 | 28 |
| MET | O | B | 63 | 440 | 310 | 388 | 28 |
| VAL | N | B | 64 | 432 | 330 | 394 | 27 |
| VAL | CA | B | 64 | 439 | 331 | 407 | 27 |
| VAL | CB | B | 64 | 435 | 344 | 415 | 26 |
| VAL | CG1 | B | 64 | 439 | 342 | 430 | 26 |
| VAL | CG2 | B | 64 | 443 | 356 | 410 | 26 |
| VAL | C | B | 64 | 436 | 318 | 415 | 27 |

TABLE 1-continued

Structure Coordinates for uncomplexed BACE

| | | | | | | | |
|---|---|---|---|---|---|---|---|
| VAL | O | B | 64 | 424 | 314 | 417 | 26 |
| ASP | N | B | 65 | 446 | 312 | 421 | 27 |
| ASP | CA | B | 65 | 445 | 301 | 430 | 28 |
| ASP | CB | B | 65 | 436 | 304 | 442 | 28 |
| ASP | CG | B | 65 | 438 | 294 | 453 | 29 |
| ASP | OD1 | B | 65 | 428 | 291 | 460 | 30 |
| ASP | OD2 | B | 65 | 449 | 290 | 456 | 30 |
| ASP | C | B | 65 | 439 | 288 | 423 | 28 |
| ASP | O | B | 65 | 431 | 280 | 429 | 27 |
| ASN | N | B | 66 | 442 | 286 | 410 | 29 |
| ASN | CA | B | 66 | 437 | 275 | 403 | 29 |
| ASN | CB | B | 66 | 435 | 278 | 388 | 27 |
| ASN | CG | B | 66 | 447 | 283 | 381 | 26 |
| ASN | OD1 | B | 66 | 458 | 284 | 387 | 25 |
| ASN | ND2 | B | 66 | 446 | 287 | 368 | 24 |
| ASN | C | B | 66 | 446 | 263 | 404 | 31 |
| ASN | O | B | 66 | 443 | 252 | 398 | 31 |
| LEU | N | B | 67 | 457 | 264 | 441 | 32 |
| LEU | CA | B | 67 | 466 | 253 | 413 | 34 |
| LEU | CB | B | 67 | 481 | 258 | 411 | 32 |
| LEU | CG | B | 67 | 483 | 265 | 397 | 32 |
| LEU | CD1 | B | 67 | 498 | 269 | 296 | 31 |
| LEU | CD2 | B | 67 | 479 | 256 | 386 | 31 |
| LEU | C | B | 67 | 465 | 247 | 427 | 36 |
| LEU | O | B | 67 | 463 | 253 | 437 | 36 |
| ARG | N | B | 68 | 466 | 233 | 427 | 38 |
| ARG | CA | B | 68 | 466 | 226 | 440 | 40 |
| ARG | CB | B | 68 | 452 | 219 | 442 | 41 |
| ARG | CG | B | 68 | 445 | 224 | 454 | 42 |
| ARG | CD | B | 68 | 446 | 239 | 455 | 43 |
| ARG | NE | B | 68 | 437 | 245 | 465 | 44 |
| ARG | CZ | B | 68 | 436 | 258 | 467 | 44 |
| ARG | NH1 | B | 68 | 443 | 266 | 459 | 44 |
| ARG | NH2 | B | 68 | 428 | 263 | 476 | 45 |
| ARG | C | B | 68 | 476 | 214 | 439 | 41 |
| ARG | O | B | 68 | 483 | 213 | 428 | 41 |
| GLY | N | B | 69 | 478 | 207 | 450 | 42 |
| GLY | CA | B | 69 | 487 | 196 | 450 | 44 |
| GLY | C | B | 69 | 492 | 192 | 463 | 45 |
| GLY | O | B | 69 | 489 | 198 | 473 | 45 |
| LYS | N | B | 70 | 499 | 181 | 464 | 47 |
| LYS | CA | B | 70 | 505 | 176 | 477 | 48 |
| LYS | CB | B | 70 | 503 | 161 | 478 | 49 |
| LYS | CG | B | 70 | 489 | 157 | 482 | 50 |
| LYS | CD | B | 70 | 489 | 142 | 487 | 51 |
| LYS | CE | B | 70 | 475 | 138 | 493 | 52 |
| LYS | NZ | B | 70 | 475 | 124 | 499 | 52 |
| LYS | C | B | 70 | 520 | 179 | 476 | 48 |
| LYS | O | B | 70 | 526 | 177 | 466 | 49 |
| SER | N | B | 71 | 525 | 184 | 488 | 49 |
| SER | CA | B | 71 | 540 | 187 | 489 | 49 |
| SER | CB | B | 71 | 544 | 189 | 503 | 49 |
| SER | OG | B | 71 | 536 | 200 | 509 | 51 |
| SER | C | B | 71 | 549 | 177 | 482 | 48 |
| SER | O | B | 71 | 548 | 165 | 485 | 49 |
| GLY | N | B | 72 | 558 | 182 | 474 | 48 |
| GLY | CA | B | 72 | 568 | 174 | 467 | 47 |
| GLY | C | B | 72 | 562 | 164 | 457 | 47 |
| GLY | O | B | 72 | 569 | 156 | 452 | 46 |
| GLN | N | B | 73 | 549 | 166 | 454 | 46 |
| GLN | CA | B | 73 | 542 | 158 | 444 | 46 |
| GLN | CB | B | 73 | 531 | 150 | 450 | 47 |
| GLN | CG | B | 73 | 535 | 141 | 462 | 28 |
| GLN | CD | B | 73 | 525 | 131 | 466 | 48 |
| GLN | OE1 | B | 73 | 513 | 133 | 465 | 49 |
| GLN | NE2 | B | 73 | 530 | 120 | 471 | 49 |
| GLN | C | B | 73 | 538 | 165 | 431 | 46 |
| GLN | O | B | 73 | 531 | 159 | 423 | 46 |
| GLY | N | B | 74 | 541 | 178 | 431 | 45 |
| GLY | CA | B | 74 | 537 | 186 | 419 | 43 |
| GLY | C | B | 74 | 524 | 194 | 420 | 42 |
| GLY | O | B | 74 | 514 | 190 | 426 | 43 |
| TYR | N | B | 75 | 524 | 205 | 413 | 41 |
| TYR | CA | B | 75 | 512 | 214 | 412 | 39 |
| TYR | CB | B | 75 | 516 | 228 | 411 | 38 |
| TYR | CG | B | 75 | 523 | 234 | 423 | 38 |
| TYR | CD1 | B | 75 | 537 | 232 | 426 | 38 |
| TYR | CE1 | B | 75 | 543 | 238 | 437 | 38 |
| TYR | CD2 | B | 75 | 516 | 243 | 432 | 38 |
| TYR | CE2 | B | 75 | 522 | 248 | 443 | 38 |
| TYR | CZ | B | 75 | 535 | 246 | 445 | 38 |
| TYR | OH | B | 75 | 541 | 252 | 456 | 37 |
| TYR | C | B | 75 | 504 | 209 | 400 | 38 |
| TYR | O | B | 75 | 509 | 206 | 390 | 38 |
| TYR | N | B | 76 | 491 | 209 | 402 | 37 |
| TYR | CA | B | 76 | 482 | 205 | 391 | 35 |
| TYR | CB | B | 76 | 477 | 191 | 393 | 36 |
| TYR | CG | B | 76 | 469 | 189 | 406 | 36 |
| TYR | CD1 | B | 76 | 456 | 194 | 407 | 36 |
| TYR | CE1 | B | 76 | 449 | 192 | 419 | 36 |
| TYR | CD2 | B | 76 | 475 | 182 | 417 | 36 |
| TYR | CE2 | B | 76 | 467 | 180 | 429 | 36 |
| TYR | CZ | B | 76 | 454 | 185 | 430 | 37 |
| TYR | OH | B | 76 | 447 | 183 | 441 | 37 |
| TYR | C | B | 76 | 470 | 215 | 390 | 34 |
| TYR | O | B | 76 | 466 | 222 | 399 | 33 |
| VAL | N | B | 77 | 465 | 215 | 377 | 33 |
| VAL | CA | B | 77 | 454 | 223 | 374 | 32 |
| VAL | CB | B | 77 | 458 | 233 | 363 | 32 |
| VAL | CG1 | B | 77 | 461 | 226 | 350 | 31 |
| VAL | CG2 | B | 77 | 448 | 244 | 361 | 31 |
| VAL | C | B | 77 | 443 | 214 | 368 | 32 |
| VAL | O | B | 77 | 446 | 204 | 362 | 32 |
| GLU | N | B | 78 | 430 | 218 | 370 | 32 |
| GLU | CA | B | 78 | 419 | 211 | 365 | 32 |
| GLU | CB | B | 78 | 407 | 214 | 373 | 33 |
| GLU | CG | B | 78 | 394 | 208 | 368 | 34 |
| GLU | CD | B | 78 | 381 | 212 | 376 | 35 |
| GLU | OE1 | B | 78 | 381 | 208 | 387 | 37 |
| GLU | OE2 | B | 78 | 373 | 219 | 371 | 36 |
| GLU | C | B | 78 | 417 | 213 | 351 | 32 |
| GLU | O | B | 78 | 417 | 225 | 346 | 32 |
| MET | N | B | 79 | 415 | 203 | 343 | 32 |
| MET | CA | B | 79 | 412 | 204 | 328 | 33 |
| MET | CB | B | 79 | 425 | 200 | 320 | 33 |
| MET | CG | B | 79 | 437 | 209 | 323 | 34 |
| MET | SD | B | 79 | 452 | 205 | 313 | 35 |
| MET | CE | B | 79 | 448 | 215 | 298 | 34 |
| MET | C | B | 79 | 401 | 194 | 324 | 33 |
| MET | O | B | 79 | 397 | 186 | 332 | 32 |
| THR | N | B | 80 | 396 | 196 | 312 | 33 |
| THR | CA | B | 80 | 385 | 187 | 307 | 33 |
| THR | CB | B | 80 | 372 | 194 | 306 | 33 |
| THR | OG1 | B | 80 | 372 | 204 | 296 | 34 |
| THR | CG2 | B | 80 | 368 | 200 | 319 | 34 |
| THR | C | B | 80 | 390 | 182 | 294 | 34 |
| THR | O | B | 80 | 396 | 190 | 286 | 34 |
| VAL | N | B | 81 | 386 | 170 | 290 | 34 |
| VAL | CA | B | 81 | 390 | 165 | 277 | 34 |
| VAL | CB | B | 81 | 401 | 154 | 278 | 34 |
| VAL | CG1 | B | 81 | 415 | 161 | 281 | 34 |
| VAL | CG2 | B | 81 | 398 | 143 | 288 | 34 |
| VAL | C | B | 81 | 377 | 158 | 271 | 35 |
| VAL | O | B | 81 | 369 | 152 | 278 | 35 |
| GLY | N | B | 82 | 376 | 159 | 257 | 35 |
| GLY | CA | B | 82 | 365 | 153 | 250 | 36 |
| GLY | C | B | 82 | 351 | 159 | 251 | 36 |
| GLY | O | B | 82 | 349 | 170 | 257 | 36 |
| SER | N | B | 83 | 341 | 152 | 246 | 36 |
| SER | CA | B | 83 | 327 | 156 | 246 | 36 |
| SER | CB | B | 83 | 324 | 163 | 233 | 36 |
| SER | OG | B | 83 | 335 | 172 | 229 | 35 |
| SER | C | B | 83 | 318 | 144 | 248 | 36 |
| SER | O | B | 83 | 318 | 135 | 240 | 36 |
| PRO | N | B | 84 | 310 | 144 | 259 | 36 |
| PRO | CD | B | 84 | 301 | 133 | 262 | 36 |
| PRO | CA | B | 84 | 309 | 155 | 269 | 36 |
| PRO | CB | B | 84 | 298 | 150 | 278 | 36 |
| PRO | CG | B | 84 | 299 | 135 | 277 | 36 |
| PRO | C | B | 84 | 323 | 156 | 276 | 36 |
| PRO | O | B | 84 | 331 | 146 | 276 | 36 |
| PRO | N | B | 85 | 326 | 168 | 282 | 36 |
| PRO | CD | B | 85 | 317 | 179 | 283 | 36 |
| PRO | CA | B | 85 | 339 | 170 | 289 | 35 |

TABLE 1-continued

Structure Coordinates for uncomplexed BACE

| | | | | | | | |
|---|---|---|---|---|---|---|---|
| PRO | CB | B | 85 | 338 | 184 | 294 | 36 |
| PRO | CG | B | 85 | 327 | 190 | 285 | 36 |
| PRO | C | B | 85 | 341 | 160 | 300 | 35 |
| PRO | O | B | 85 | 332 | 157 | 308 | 35 |
| GLN | N | B | 86 | 353 | 155 | 301 | 35 |
| GLN | CA | B | 86 | 358 | 146 | 312 | 34 |
| GLN | CB | B | 86 | 364 | 134 | 306 | 34 |
| GLN | CG | B | 86 | 355 | 124 | 299 | 34 |
| GLN | CD | B | 86 | 362 | 113 | 291 | 34 |
| GLN | OE1 | B | 86 | 371 | 107 | 296 | 34 |
| GLN | NE2 | B | 86 | 357 | 110 | 279 | 33 |
| GLN | C | B | 86 | 368 | 154 | 320 | 34 |
| GLN | O | B | 86 | 378 | 159 | 314 | 34 |
| THR | N | B | 87 | 365 | 155 | 333 | 34 |
| THR | CA | B | 87 | 374 | 163 | 341 | 34 |
| THR | CB | B | 87 | 366 | 169 | 353 | 34 |
| THR | OG1 | B | 87 | 356 | 178 | 349 | 34 |
| THR | CG2 | B | 87 | 376 | 177 | 362 | 34 |
| THR | C | B | 87 | 386 | 155 | 346 | 34 |
| THR | O | B | 87 | 384 | 144 | 351 | 35 |
| LEU | N | B | 88 | 398 | 161 | 345 | 34 |
| LEU | CA | B | 88 | 410 | 155 | 350 | 33 |
| LEU | CB | B | 88 | 417 | 148 | 338 | 34 |
| LEU | CG | B | 88 | 410 | 137 | 331 | 34 |
| LEU | CD1 | B | 88 | 418 | 134 | 318 | 34 |
| LEU | CD2 | B | 88 | 410 | 125 | 340 | 34 |
| LEU | C | B | 88 | 419 | 165 | 356 | 33 |
| LEU | O | B | 88 | 419 | 177 | 352 | 33 |
| ASN | N | B | 89 | 427 | 161 | 367 | 33 |
| ASN | CA | B | 89 | 436 | 170 | 373 | 32 |
| ASN | CB | B | 89 | 438 | 166 | 388 | 32 |
| ASN | CG | B | 89 | 427 | 173 | 397 | 33 |
| ASN | OD1 | B | 89 | 425 | 169 | 408 | 33 |
| ASN | ND2 | B | 89 | 421 | 183 | 392 | 33 |
| ASN | C | B | 89 | 449 | 167 | 366 | 32 |
| ASN | O | B | 89 | 454 | 156 | 364 | 32 |
| ILE | N | B | 90 | 456 | 178 | 361 | 31 |
| ILE | CA | B | 90 | 468 | 177 | 353 | 30 |
| ILE | CB | B | 90 | 465 | 182 | 339 | 29 |
| ILE | CG2 | B | 90 | 477 | 180 | 330 | 28 |
| ILE | CG1 | B | 90 | 452 | 176 | 333 | 28 |
| ILE | CD1 | B | 90 | 453 | 161 | 331 | 28 |
| ILE | C | B | 90 | 480 | 184 | 359 | 31 |
| ILE | O | B | 90 | 479 | 196 | 362 | 30 |
| LEU | N | B | 91 | 491 | 177 | 360 | 31 |
| LEU | CA | B | 91 | 503 | 183 | 366 | 32 |
| LEU | CB | B | 91 | 514 | 172 | 368 | 33 |
| LEU | CG | B | 91 | 528 | 175 | 372 | 33 |
| LEU | CD1 | B | 91 | 527 | 180 | 387 | 34 |
| LEU | CD2 | B | 91 | 537 | 164 | 371 | 33 |
| LEU | C | B | 91 | 509 | 194 | 357 | 32 |
| LEU | O | B | 91 | 510 | 192 | 345 | 32 |
| VAL | N | B | 92 | 512 | 205 | 363 | 33 |
| VAL | CA | B | 92 | 518 | 216 | 355 | 33 |
| VAL | CB | B | 92 | 514 | 230 | 361 | 33 |
| VAL | CG1 | B | 92 | 521 | 241 | 354 | 33 |
| VAL | CG2 | B | 92 | 499 | 231 | 359 | 33 |
| VAL | C | B | 92 | 533 | 215 | 355 | 33 |
| VAL | O | B | 92 | 540 | 217 | 365 | 33 |
| ASP | N | B | 93 | 539 | 212 | 343 | 33 |
| ASP | CA | B | 93 | 553 | 210 | 342 | 33 |
| ASP | CB | B | 93 | 556 | 195 | 340 | 34 |
| ASP | CG | B | 93 | 570 | 192 | 336 | 35 |
| ASP | OD1 | B | 93 | 579 | 199 | 341 | 36 |
| ASP | OD2 | B | 93 | 573 | 181 | 330 | 36 |
| ASP | C | B | 93 | 559 | 218 | 330 | 32 |
| ASP | O | B | 93 | 558 | 215 | 318 | 33 |
| THR | N | B | 94 | 567 | 228 | 334 | 31 |
| THR | CA | B | 94 | 574 | 236 | 324 | 30 |
| THR | CB | B | 94 | 578 | 250 | 330 | 30 |
| THR | OG1 | B | 94 | 586 | 248 | 341 | 28 |
| THR | CG2 | B | 94 | 566 | 258 | 333 | 30 |
| THR | C | B | 94 | 586 | 229 | 319 | 30 |
| THR | O | B | 94 | 594 | 234 | 310 | 29 |
| GLY | N | B | 95 | 589 | 217 | 324 | 29 |
| GLY | CA | B | 95 | 600 | 209 | 321 | 31 |
| GLY | C | B | 95 | 598 | 199 | 309 | 30 |
| GLY | O | B | 95 | 608 | 193 | 305 | 30 |
| SER | N | B | 96 | 586 | 198 | 304 | 31 |
| SER | CA | B | 96 | 584 | 189 | 293 | 30 |
| SER | CB | B | 96 | 579 | 176 | 298 | 30 |
| SER | OG | B | 96 | 567 | 177 | 306 | 30 |
| SER | C | B | 96 | 574 | 195 | 283 | 31 |
| SER | O | B | 96 | 569 | 206 | 285 | 31 |
| SER | N | B | 97 | 571 | 188 | 272 | 31 |
| SER | CA | B | 97 | 562 | 193 | 262 | 32 |
| SER | CB | B | 97 | 571 | 197 | 249 | 32 |
| SER | OG | B | 97 | 582 | 205 | 254 | 34 |
| SER | C | B | 97 | 550 | 185 | 257 | 32 |
| SER | O | B | 97 | 544 | 189 | 247 | 31 |
| ASN | N | B | 98 | 547 | 174 | 264 | 31 |
| ASN | CA | B | 98 | 536 | 166 | 260 | 31 |
| ASN | CB | B | 98 | 540 | 151 | 259 | 31 |
| ASN | CG | B | 98 | 548 | 148 | 247 | 32 |
| ASN | OD1 | B | 98 | 560 | 150 | 247 | 32 |
| ASN | ND2 | B | 98 | 541 | 144 | 236 | 31 |
| ASN | C | B | 98 | 524 | 167 | 269 | 31 |
| ASN | O | B | 98 | 526 | 168 | 281 | 30 |
| PHE | N | B | 99 | 512 | 167 | 263 | 30 |
| PHE | CA | B | 99 | 500 | 167 | 271 | 30 |
| PHE | CB | B | 99 | 489 | 174 | 264 | 31 |
| PHE | CG | B | 99 | 476 | 174 | 272 | 31 |
| PHE | CD1 | B | 99 | 463 | 175 | 265 | 30 |
| PHE | CD2 | B | 99 | 476 | 173 | 286 | 30 |
| PHE | CE1 | B | 99 | 451 | 175 | 272 | 31 |
| PHE | CE2 | B | 99 | 464 | 173 | 293 | 30 |
| PHE | CZ | B | 99 | 452 | 174 | 286 | 31 |
| PHE | C | B | 99 | 497 | 152 | 271 | 31 |
| PHE | O | B | 99 | 495 | 146 | 261 | 30 |
| ALA | N | B | 100 | 497 | 146 | 283 | 31 |
| ALA | CA | B | 100 | 494 | 132 | 284 | 32 |
| ALA | CB | B | 100 | 508 | 124 | 285 | 31 |
| ALA | C | B | 100 | 486 | 129 | 297 | 32 |
| ALA | O | B | 100 | 489 | 133 | 308 | 31 |
| VAL | N | B | 101 | 476 | 121 | 295 | 32 |
| VAL | CA | B | 101 | 467 | 117 | 306 | 33 |
| VAL | CB | B | 101 | 453 | 124 | 304 | 33 |
| VAL | CG1 | B | 101 | 455 | 139 | 301 | 33 |
| VAL | CG2 | B | 101 | 445 | 117 | 293 | 33 |
| VAL | C | B | 101 | 465 | 102 | 306 | 34 |
| VAL | O | B | 101 | 466 | 95 | 296 | 34 |
| GLY | N | B | 102 | 461 | 97 | 318 | 34 |
| GLY | CA | B | 102 | 458 | 83 | 320 | 36 |
| GLY | C | B | 102 | 446 | 80 | 311 | 37 |
| GLY | O | B | 102 | 436 | 87 | 311 | 37 |
| ALA | N | B | 103 | 447 | 69 | 302 | 37 |
| ALA | CA | B | 103 | 436 | 66 | 294 | 39 |
| ALA | CB | B | 103 | 440 | 68 | 279 | 39 |
| ALA | C | B | 103 | 432 | 51 | 295 | 40 |
| ALA | O | B | 103 | 426 | 45 | 286 | 39 |
| ALA | N | B | 104 | 436 | 46 | 307 | 42 |
| ALA | CA | B | 104 | 432 | 32 | 310 | 43 |
| ALA | CB | B | 104 | 442 | 22 | 303 | 44 |
| ALA | C | B | 104 | 434 | 30 | 325 | 44 |
| ALA | O | B | 104 | 441 | 38 | 332 | 45 |
| PRO | N | B | 105 | 426 | 20 | 331 | 45 |
| PRO | CD | B | 105 | 418 | 10 | 324 | 45 |
| PRO | CA | B | 105 | 427 | 18 | 345 | 46 |
| PRO | CB | B | 105 | 418 | 6 | 347 | 46 |
| PRO | CG | B | 105 | 418 | −1 | 334 | 46 |
| PRO | C | B | 105 | 441 | 16 | 351 | 47 |
| PRO | O | B | 105 | 450 | 12 | 344 | 47 |
| HIS | N | B | 106 | 443 | 20 | 364 | 47 |
| HIS | CA | B | 106 | 455 | 19 | 370 | 48 |
| HIS | CB | B | 106 | 465 | 30 | 366 | 49 |
| HIS | CG | B | 106 | 478 | 30 | 372 | 49 |
| HIS | CD2 | B | 106 | 491 | 26 | 368 | 49 |
| HIS | ND1 | B | 106 | 480 | 33 | 386 | 49 |
| HIS | CE1 | B | 106 | 493 | 31 | 389 | 49 |
| HIS | NE2 | B | 106 | 499 | 27 | 378 | 49 |
| HIS | C | B | 106 | 453 | 21 | 385 | 49 |
| HIS | O | B | 106 | 445 | 29 | 390 | 49 |
| PRO | N | B | 107 | 460 | 13 | 394 | 50 |
| PRO | CD | B | 107 | 470 | 3 | 390 | 50 |

TABLE 1-continued

Structure Coordinates for uncomplexed BACE

| | | | | | | | |
|---|---|---|---|---|---|---|---|
| PRO | CA | B | 107 | 458 | 13 | 408 | 50 |
| PRO | CB | B | 107 | 469 | 4 | 414 | 50 |
| PRO | CG | B | 107 | 471 | −6 | 403 | 50 |
| PRO | C | B | 107 | 458 | 27 | 415 | 50 |
| PRO | O | B | 107 | 452 | 30 | 425 | 51 |
| PHE | N | B | 108 | 466 | 36 | 409 | 51 |
| PHE | CA | B | 108 | 467 | 50 | 414 | 51 |
| PHE | CB | B | 108 | 482 | 54 | 414 | 52 |
| PHE | CG | B | 108 | 490 | 44 | 423 | 53 |
| PHE | CD1 | B | 108 | 504 | 43 | 421 | 53 |
| PHE | CD2 | B | 108 | 484 | 36 | 433 | 53 |
| PHE | CE1 | B | 108 | 512 | 35 | 428 | 53 |
| PHE | CE2 | B | 108 | 492 | 28 | 441 | 53 |
| PHE | CZ | B | 108 | 506 | 27 | 438 | 53 |
| PHE | C | B | 108 | 459 | 61 | 407 | 51 |
| PHE | O | B | 108 | 461 | 73 | 410 | 51 |
| LEU | N | B | 109 | 449 | 57 | 399 | 51 |
| LEU | CA | B | 109 | 441 | 67 | 392 | 50 |
| LEU | CB | B | 109 | 441 | 64 | 377 | 50 |
| LEU | CG | B | 109 | 455 | 65 | 370 | 50 |
| LEU | CD1 | B | 109 | 453 | 63 | 355 | 49 |
| LEU | CD2 | B | 109 | 461 | 79 | 372 | 50 |
| LEU | C | B | 109 | 426 | 66 | 396 | 50 |
| LEU | O | B | 109 | 420 | 55 | 395 | 50 |
| HIS | N | B | 110 | 421 | 77 | 402 | 49 |
| HIS | CA | B | 110 | 407 | 77 | 406 | 48 |
| HIS | CB | B | 110 | 404 | 89 | 415 | 50 |
| HIS | CG | B | 110 | 415 | 92 | 426 | 51 |
| HIS | CD2 | B | 110 | 421 | 103 | 430 | 51 |
| HIS | ND1 | B | 110 | 419 | 81 | 434 | 51 |
| HIS | CE1 | B | 110 | 428 | 86 | 443 | 52 |
| HIS | NE2 | B | 110 | 429 | 99 | 440 | 52 |
| HIS | C | B | 110 | 398 | 78 | 394 | 47 |
| HIS | O | B | 110 | 386 | 76 | 395 | 46 |
| ARG | N | B | 111 | 404 | 82 | 382 | 45 |
| ARG | CA | B | 111 | 397 | 84 | 370 | 43 |
| ARG | CB | B | 111 | 388 | 96 | 371 | 43 |
| ARG | CG | B | 111 | 395 | 109 | 374 | 43 |
| ARG | CD | B | 111 | 386 | 121 | 377 | 43 |
| ARG | NE | B | 111 | 394 | 133 | 380 | 44 |
| ARG | CZ | B | 111 | 388 | 144 | 385 | 44 |
| ARG | NH1 | B | 111 | 375 | 145 | 387 | 44 |
| ARG | NH2 | B | 111 | 396 | 154 | 387 | 44 |
| ARG | C | B | 111 | 406 | 84 | 358 | 42 |
| ARG | O | B | 111 | 418 | 86 | 360 | 41 |
| TYR | N | B | 112 | 401 | 83 | 346 | 40 |
| TYR | CA | B | 112 | 409 | 84 | 334 | 39 |
| TYR | CB | B | 112 | 417 | 70 | 332 | 40 |
| TYR | CG | B | 112 | 408 | 58 | 332 | 41 |
| TYR | CD1 | B | 112 | 403 | 54 | 319 | 41 |
| TYR | CE1 | B | 112 | 394 | 43 | 319 | 42 |
| TYR | CD2 | B | 112 | 404 | 51 | 343 | 42 |
| TYR | CE2 | B | 112 | 396 | 40 | 343 | 42 |
| TYR | CZ | B | 112 | 391 | 36 | 330 | 43 |
| TYR | OH | B | 112 | 383 | 25 | 330 | 44 |
| TYR | C | B | 112 | 402 | 87 | 321 | 38 |
| TYR | O | B | 112 | 390 | 85 | 320 | 38 |
| TYR | N | B | 113 | 409 | 91 | 311 | 38 |
| TYR | CA | B | 113 | 404 | 95 | 298 | 37 |
| TYR | CB | B | 113 | 415 | 102 | 290 | 37 |
| TYR | CG | B | 113 | 412 | 106 | 276 | 36 |
| TYR | CD1 | B | 113 | 399 | 110 | 272 | 36 |
| TYR | CE1 | B | 113 | 396 | 114 | 259 | 35 |
| TYR | CD2 | B | 113 | 421 | 106 | 266 | 36 |
| TYR | CE2 | B | 113 | 419 | 110 | 253 | 36 |
| TYR | CZ | B | 113 | 406 | 114 | 250 | 36 |
| TYR | OH | B | 113 | 404 | 118 | 237 | 36 |
| TYR | C | B | 113 | 398 | 84 | 290 | 38 |
| TYR | O | B | 113 | 406 | 75 | 286 | 38 |
| GLN | N | B | 114 | 385 | 84 | 288 | 38 |
| GLN | CA | B | 114 | 378 | 73 | 281 | 39 |
| GLN | CB | B | 114 | 365 | 69 | 289 | 40 |
| GLN | CG | B | 114 | 368 | 62 | 302 | 41 |
| GLN | CD | B | 114 | 355 | 56 | 308 | 42 |
| GLN | OE1 | B | 114 | 350 | 63 | 317 | 42 |
| GLN | NE2 | B | 114 | 351 | 45 | 303 | 41 |
| GLN | C | B | 114 | 375 | 78 | 267 | 39 |
| GLN | O | B | 114 | 365 | 84 | 264 | 38 |
| ARG | N | B | 115 | 384 | 75 | 258 | 40 |
| ARG | CA | B | 115 | 382 | 79 | 244 | 41 |
| ARG | CB | B | 115 | 395 | 74 | 236 | 41 |
| ARG | CG | B | 115 | 408 | 80 | 241 | 41 |
| ARG | CD | B | 115 | 420 | 73 | 235 | 40 |
| ARG | NE | B | 115 | 422 | 60 | 242 | 39 |
| ARG | CZ | B | 115 | 431 | 51 | 238 | 39 |
| ARG | NH1 | B | 115 | 439 | 54 | 228 | 39 |
| ARG | NH2 | B | 115 | 432 | 40 | 245 | 39 |
| ARG | C | B | 115 | 369 | 74 | 237 | 42 |
| ARG | O | B | 115 | 364 | 80 | 229 | 42 |
| GLN | N | B | 116 | 365 | 62 | 241 | 43 |
| GLN | CA | B | 116 | 353 | 56 | 236 | 43 |
| GLN | CB | B | 116 | 351 | 42 | 241 | 44 |
| GLN | CG | B | 116 | 347 | 41 | 256 | 45 |
| GLN | CD | B | 116 | 359 | 42 | 265 | 45 |
| GLN | OE1 | B | 116 | 357 | 40 | 277 | 46 |
| GLN | NE2 | B | 116 | 371 | 44 | 260 | 45 |
| GLN | C | B | 116 | 340 | 65 | 239 | 43 |
| GLN | O | B | 116 | 330 | 64 | 232 | 43 |
| LEU | N | B | 117 | 341 | 73 | 249 | 43 |
| LEU | CA | B | 117 | 330 | 81 | 253 | 43 |
| LEU | CB | B | 117 | 329 | 82 | 269 | 43 |
| LEU | CG | B | 117 | 327 | 68 | 276 | 43 |
| LEU | CD1 | B | 117 | 325 | 71 | 291 | 43 |
| LEU | CD2 | B | 117 | 316 | 60 | 270 | 43 |
| LEU | C | B | 117 | 330 | 95 | 248 | 42 |
| LEU | O | B | 117 | 321 | 103 | 250 | 43 |
| SER | N | B | 118 | 341 | 99 | 240 | 42 |
| SER | CA | B | 118 | 342 | 112 | 234 | 42 |
| SER | CB | B | 118 | 356 | 118 | 236 | 42 |
| SER | OG | B | 118 | 358 | 130 | 229 | 42 |
| SER | C | B | 118 | 338 | 112 | 220 | 42 |
| SER | O | B | 118 | 345 | 105 | 212 | 42 |
| SER | N | B | 119 | 329 | 120 | 216 | 42 |
| SER | CA | B | 119 | 324 | 121 | 202 | 42 |
| SER | CB | B | 119 | 310 | 127 | 201 | 43 |
| SER | OG | B | 119 | 309 | 139 | 207 | 43 |
| SER | C | B | 119 | 334 | 130 | 193 | 42 |
| SER | O | B | 119 | 334 | 130 | 181 | 42 |
| THR | N | B | 120 | 343 | 137 | 200 | 42 |
| THR | CA | B | 120 | 352 | 146 | 194 | 41 |
| THR | CB | B | 120 | 352 | 160 | 200 | 41 |
| THR | OG1 | B | 120 | 351 | 159 | 214 | 40 |
| THR | CG2 | B | 120 | 340 | 167 | 195 | 41 |
| THR | C | B | 120 | 367 | 140 | 194 | 41 |
| THR | O | B | 120 | 376 | 147 | 189 | 41 |
| TYR | N | B | 121 | 368 | 127 | 198 | 42 |
| TYR | CA | B | 121 | 381 | 121 | 198 | 42 |
| TYR | CB | B | 121 | 380 | 108 | 207 | 43 |
| TYR | CG | B | 121 | 391 | 98 | 205 | 43 |
| TYR | CD1 | B | 121 | 404 | 101 | 209 | 43 |
| TYR | CE1 | B | 121 | 415 | 92 | 206 | 43 |
| TYR | CD2 | B | 121 | 389 | 86 | 198 | 43 |
| TYR | CE2 | B | 121 | 399 | 78 | 195 | 43 |
| TYR | CZ | B | 121 | 412 | 81 | 199 | 43 |
| TYR | OH | B | 121 | 423 | 72 | 196 | 43 |
| TYR | C | B | 121 | 385 | 116 | 184 | 43 |
| TYR | O | B | 121 | 376 | 112 | 177 | 43 |
| ARG | N | B | 122 | 397 | 118 | 181 | 44 |
| ARG | CA | B | 122 | 402 | 114 | 168 | 44 |
| ARG | CB | B | 122 | 405 | 126 | 159 | 45 |
| ARG | CG | B | 122 | 393 | 135 | 156 | 45 |
| ARG | CD | B | 122 | 397 | 147 | 148 | 46 |
| ARG | NE | B | 122 | 386 | 157 | 147 | 47 |
| ARG | CZ | B | 122 | 387 | 169 | 141 | 47 |
| ARG | NH1 | B | 122 | 399 | 173 | 137 | 47 |
| ARG | NH2 | B | 122 | 379 | 176 | 141 | 47 |
| ARG | C | B | 122 | 416 | 106 | 170 | 45 |
| ARG | O | B | 122 | 425 | 112 | 175 | 44 |
| ASP | N | B | 123 | 416 | 94 | 165 | 45 |
| ASP | CA | B | 123 | 428 | 86 | 166 | 46 |
| ASP | CB | B | 123 | 425 | 71 | 164 | 47 |
| ASP | CG | B | 123 | 435 | 62 | 171 | 47 |
| ASP | OD1 | B | 123 | 447 | 65 | 171 | 47 |
| ASP | OD2 | B | 123 | 430 | 52 | 177 | 48 |

TABLE 1-continued

Structure Coordinates for uncomplexed BACE

| | | | | | | |
|---|---|---|---|---|---|---|
| ASP | C | B | 123 | 439 | 91 | 156 | 46 |
| ASP | O | B | 123 | 436 | 94 | 145 | 46 |
| LEU | N | B | 124 | 451 | 92 | 161 | 46 |
| LEU | CA | B | 124 | 462 | 96 | 152 | 47 |
| LEU | CB | B | 124 | 472 | 105 | 159 | 47 |
| LEU | CG | B | 124 | 467 | 119 | 161 | 47 |
| LEU | CD1 | B | 124 | 478 | 127 | 168 | 47 |
| LEU | CD2 | B | 124 | 464 | 126 | 147 | 47 |
| LEU | C | B | 124 | 469 | 83 | 147 | 47 |
| LEU | O | B | 124 | 479 | 83 | 139 | 46 |
| ARG | N | B | 125 | 465 | 71 | 152 | 48 |
| ARG | CA | B | 125 | 471 | 58 | 149 | 49 |
| ARG | CB | B | 125 | 465 | 54 | 136 | 50 |
| ARG | CG | B | 125 | 450 | 50 | 136 | 52 |
| ARG | CD | B | 125 | 443 | 53 | 123 | 53 |
| ARG | NE | B | 125 | 450 | 46 | 112 | 55 |
| ARG | CZ | B | 125 | 448 | 49 | 99 | 56 |
| ARG | NH1 | B | 125 | 440 | 59 | 95 | 56 |
| ARG | NH2 | B | 125 | 454 | 42 | 89 | 56 |
| ARG | C | B | 125 | 486 | 59 | 149 | 49 |
| ARG | O | B | 125 | 492 | 58 | 138 | 48 |
| LYS | N | B | 126 | 492 | 62 | 160 | 48 |
| LYS | CA | B | 126 | 506 | 63 | 162 | 47 |
| LYS | CB | B | 126 | 510 | 77 | 156 | 48 |
| LYS | CG | B | 126 | 525 | 80 | 158 | 49 |
| LYS | CD | B | 126 | 530 | 90 | 148 | 50 |
| LYS | CE | B | 126 | 522 | 104 | 150 | 50 |
| LYS | NZ | B | 126 | 528 | 114 | 141 | 50 |
| LYS | C | B | 126 | 509 | 62 | 177 | 47 |
| LYS | O | B | 126 | 502 | 67 | 185 | 46 |
| GLY | N | B | 127 | 520 | 55 | 180 | 46 |
| GLY | CA | B | 127 | 523 | 53 | 194 | 44 |
| GLY | C | B | 127 | 532 | 63 | 199 | 44 |
| GLY | O | B | 127 | 539 | 70 | 191 | 44 |
| VAL | N | B | 128 | 533 | 65 | 212 | 42 |
| VAL | CA | B | 128 | 541 | 75 | 219 | 41 |
| VAL | CB | B | 128 | 534 | 88 | 220 | 41 |
| VAL | CG1 | B | 128 | 523 | 87 | 230 | 41 |
| VAL | CG2 | B | 128 | 544 | 99 | 225 | 41 |
| VAL | C | B | 128 | 546 | 70 | 232 | 41 |
| VAL | O | B | 128 | 538 | 63 | 239 | 40 |
| TYR | N | B | 129 | 558 | 73 | 236 | 41 |
| TYR | CA | B | 129 | 564 | 68 | 249 | 41 |
| TYR | CB | B | 129 | 570 | 54 | 248 | 40 |
| TYR | CG | B | 129 | 582 | 53 | 239 | 40 |
| TYR | CD1 | B | 129 | 595 | 53 | 244 | 41 |
| TYR | CE1 | B | 129 | 606 | 52 | 236 | 40 |
| TYR | CD2 | B | 129 | 580 | 52 | 225 | 40 |
| TYR | CE2 | B | 129 | 591 | 51 | 216 | 41 |
| TYR | CZ | B | 129 | 604 | 51 | 222 | 41 |
| TYR | OH | B | 129 | 615 | 51 | 213 | 41 |
| TYR | C | B | 129 | 576 | 78 | 252 | 41 |
| TYR | O | B | 129 | 581 | 85 | 244 | 41 |
| VAL | N | B | 130 | 579 | 78 | 265 | 42 |
| VAL | CA | B | 130 | 590 | 86 | 270 | 44 |
| VAL | CB | B | 130 | 585 | 97 | 280 | 43 |
| VAL | CG1 | B | 130 | 576 | 107 | 273 | 43 |
| VAL | CG2 | B | 130 | 579 | 90 | 292 | 43 |
| VAL | C | B | 130 | 600 | 77 | 277 | 46 |
| VAL | O | B | 130 | 596 | 66 | 281 | 46 |
| PRO | N | B | 131 | 613 | 81 | 279 | 47 |
| PRO | CD | B | 131 | 619 | 94 | 274 | 48 |
| PRO | CA | B | 131 | 622 | 73 | 286 | 49 |
| PRO | CB | B | 131 | 636 | 79 | 282 | 49 |
| PRO | CG | B | 131 | 632 | 94 | 282 | 48 |
| PRO | C | B | 131 | 620 | 73 | 301 | 51 |
| PRO | O | B | 131 | 611 | 79 | 306 | 51 |
| TYR | N | B | 132 | 629 | 66 | 308 | 53 |
| TYR | CA | B | 132 | 627 | 65 | 323 | 56 |
| TYR | CB | B | 132 | 633 | 52 | 328 | 56 |
| TYR | CG | B | 132 | 624 | 40 | 328 | 58 |
| TYR | CD1 | B | 132 | 624 | 31 | 317 | 58 |
| TYR | CE1 | B | 132 | 616 | 19 | 316 | 58 |
| TYR | CD2 | B | 132 | 615 | 37 | 338 | 58 |
| TYR | CE2 | B | 132 | 607 | 25 | 338 | 58 |
| TYR | CZ | B | 132 | 608 | 17 | 327 | 59 |
| TYR | OH | B | 132 | 600 | 5 | 327 | 59 |
| TYR | C | B | 132 | 634 | 76 | 331 | 56 |
| TYR | O | B | 132 | 646 | 75 | 334 | 57 |
| THR | N | B | 133 | 627 | 87 | 334 | 57 |
| THR | CA | B | 133 | 633 | 97 | 342 | 58 |
| THR | CB | B | 133 | 628 | 111 | 338 | 58 |
| THR | OG1 | B | 133 | 614 | 112 | 337 | 58 |
| THR | CG2 | B | 133 | 634 | 115 | 324 | 58 |
| THR | C | B | 133 | 628 | 94 | 356 | 58 |
| THR | O | B | 133 | 632 | 85 | 362 | 58 |
| GLN | N | B | 134 | 617 | 101 | 360 | 58 |
| GLN | CA | B | 134 | 611 | 99 | 373 | 58 |
| GLN | CB | B | 134 | 607 | 112 | 380 | 59 |
| GLN | CG | B | 134 | 619 | 118 | 387 | 60 |
| GLN | CD | B | 134 | 625 | 109 | 397 | 61 |
| GLN | OE1 | B | 134 | 632 | 99 | 394 | 61 |
| GLN | NE2 | B | 134 | 624 | 113 | 410 | 61 |
| GLN | C | B | 134 | 599 | 91 | 369 | 58 |
| GLN | O | B | 134 | 587 | 96 | 369 | 58 |
| GLY | N | B | 135 | 601 | 78 | 365 | 57 |
| GLY | CA | B | 135 | 590 | 70 | 361 | 55 |
| GLY | C | B | 135 | 589 | 70 | 346 | 55 |
| GLY | O | B | 135 | 596 | 78 | 339 | 55 |
| LYS | N | B | 136 | 581 | 61 | 340 | 53 |
| LYS | CA | B | 136 | 580 | 61 | 325 | 52 |
| LYS | CB | B | 136 | 590 | 52 | 319 | 53 |
| LYS | CG | B | 136 | 589 | 50 | 304 | 53 |
| LYS | CD | B | 136 | 598 | 40 | 298 | 54 |
| LYS | CE | B | 136 | 596 | 37 | 283 | 54 |
| LYS | NZ | B | 136 | 605 | 27 | 278 | 54 |
| LYS | C | B | 136 | 566 | 56 | 321 | 50 |
| LYS | O | B | 136 | 559 | 48 | 327 | 50 |
| TRP | N | B | 137 | 561 | 62 | 309 | 48 |
| TRP | CA | B | 137 | 548 | 58 | 304 | 46 |
| TRP | CB | B | 137 | 537 | 68 | 308 | 45 |
| TRP | CG | B | 137 | 540 | 82 | 303 | 44 |
| TRP | CD2 | B | 137 | 538 | 88 | 290 | 44 |
| TRP | CE2 | B | 137 | 542 | 101 | 290 | 43 |
| TRP | CE3 | B | 137 | 532 | 83 | 278 | 44 |
| TRP | CD1 | B | 137 | 546 | 93 | 310 | 44 |
| TRP | NE1 | B | 137 | 547 | 104 | 303 | 44 |
| TRP | CZ2 | B | 137 | 541 | 110 | 279 | 43 |
| TRP | CZ3 | B | 137 | 531 | 91 | 267 | 43 |
| TRP | CH2 | B | 137 | 536 | 104 | 267 | 43 |
| TRP | C | B | 137 | 549 | 56 | 289 | 46 |
| TRP | O | B | 137 | 558 | 60 | 282 | 46 |
| GLU | N | B | 138 | 538 | 50 | 284 | 45 |
| GLU | CA | B | 138 | 537 | 47 | 270 | 44 |
| GLU | CB | B | 138 | 542 | 33 | 267 | 45 |
| GLU | CG | B | 138 | 543 | 28 | 252 | 47 |
| GLU | CD | B | 138 | 551 | 16 | 250 | 48 |
| GLU | OE1 | B | 138 | 550 | 7 | 259 | 48 |
| GLU | OE2 | B | 138 | 559 | 16 | 240 | 48 |
| GLU | C | B | 138 | 522 | 48 | 266 | 43 |
| GLU | O | B | 138 | 514 | 45 | 274 | 43 |
| GLY | N | B | 139 | 520 | 53 | 254 | 42 |
| GLY | CA | B | 139 | 506 | 55 | 250 | 41 |
| GLY | C | B | 139 | 502 | 57 | 236 | 40 |
| GLY | O | B | 139 | 511 | 54 | 227 | 41 |
| GLU | N | B | 140 | 490 | 61 | 233 | 40 |
| GLU | CA | B | 140 | 485 | 63 | 219 | 40 |
| GLU | CB | B | 140 | 473 | 53 | 217 | 40 |
| GLU | CG | B | 140 | 477 | 39 | 222 | 42 |
| GLU | CD | B | 140 | 465 | 30 | 223 | 42 |
| GLU | OE1 | B | 140 | 467 | 18 | 227 | 43 |
| GLU | OE2 | B | 140 | 453 | 34 | 220 | 43 |
| GLU | C | B | 140 | 481 | 77 | 216 | 39 |
| GLU | O | B | 140 | 474 | 83 | 224 | 40 |
| LEU | N | B | 141 | 487 | 82 | 205 | 38 |
| LEU | CA | B | 141 | 484 | 96 | 201 | 37 |
| LEU | CB | B | 141 | 495 | 101 | 191 | 37 |
| LEU | CG | B | 141 | 509 | 103 | 196 | 37 |
| LEU | CD1 | B | 141 | 517 | 108 | 184 | 37 |
| LEU | CD2 | B | 141 | 509 | 113 | 207 | 37 |
| LEU | C | B | 141 | 470 | 98 | 195 | 37 |
| LEU | O | B | 141 | 465 | 88 | 189 | 37 |
| GLY | N | B | 142 | 465 | 110 | 196 | 36 |
| GLY | CA | B | 142 | 452 | 113 | 191 | 34 |

TABLE 1-continued

Structure Coordinates for uncomplexed BACE

| | | | | | | |
|---|---|---|---|---|---|---|
| GLY | C | B | 142 | 449 | 128 | 195 | 33 |
| GLY | O | B | 142 | 457 | 134 | 201 | 32 |
| THR | N | B | 143 | 438 | 133 | 191 | 32 |
| THR | CA | B | 143 | 434 | 147 | 194 | 32 |
| THR | CB | B | 143 | 435 | 156 | 182 | 32 |
| THR | OG1 | B | 143 | 425 | 153 | 173 | 32 |
| THR | CG2 | B | 143 | 449 | 155 | 175 | 31 |
| THR | C | B | 143 | 420 | 147 | 200 | 32 |
| THR | O | B | 143 | 413 | 138 | 198 | 31 |
| ASP | N | B | 144 | 417 | 159 | 206 | 32 |
| ASP | CA | B | 144 | 404 | 161 | 211 | 32 |
| ASP | CB | B | 144 | 401 | 151 | 223 | 32 |
| ASP | CG | B | 144 | 387 | 147 | 224 | 33 |
| ASP | OD1 | B | 144 | 378 | 155 | 221 | 32 |
| ASP | OD2 | B | 144 | 384 | 135 | 229 | 33 |
| ASP | C | B | 144 | 402 | 175 | 216 | 33 |
| ASP | O | B | 144 | 412 | 183 | 216 | 33 |
| LEU | N | B | 145 | 390 | 178 | 221 | 32 |
| LEU | CA | B | 145 | 388 | 192 | 226 | 32 |
| LEU | CB | B | 145 | 373 | 195 | 225 | 31 |
| LEU | CG | B | 145 | 368 | 196 | 210 | 31 |
| LEU | CD1 | B | 145 | 353 | 200 | 210 | 31 |
| LEU | CD2 | B | 145 | 376 | 206 | 202 | 31 |
| LEU | C | B | 145 | 392 | 192 | 240 | 33 |
| LEU | O | B | 145 | 390 | 182 | 248 | 33 |
| VAL | N | B | 146 | 400 | 202 | 244 | 33 |
| VAL | CA | B | 146 | 405 | 203 | 258 | 34 |
| VAL | CB | B | 146 | 420 | 202 | 258 | 33 |
| VAL | CG1 | B | 146 | 425 | 201 | 272 | 33 |
| VAL | CG2 | B | 146 | 424 | 189 | 250 | 33 |
| VAL | C | B | 146 | 401 | 217 | 263 | 34 |
| VAL | O | B | 146 | 402 | 227 | 256 | 35 |
| SER | N | B | 147 | 398 | 217 | 276 | 35 |
| SER | CA | B | 147 | 395 | 230 | 283 | 35 |
| SER | CB | B | 147 | 380 | 231 | 284 | 36 |
| SER | OG | B | 147 | 374 | 233 | 272 | 38 |
| SER | C | B | 147 | 401 | 231 | 297 | 35 |
| SER | O | B | 147 | 405 | 221 | 303 | 33 |
| ILE | N | B | 148 | 403 | 244 | 301 | 35 |
| ILE | CA | B | 148 | 408 | 247 | 314 | 35 |
| ILE | CB | B | 148 | 421 | 256 | 313 | 35 |
| ILE | CG2 | B | 148 | 426 | 259 | 327 | 34 |
| ILE | CG1 | B | 148 | 431 | 248 | 305 | 35 |
| ILE | CD1 | B | 148 | 445 | 255 | 303 | 35 |
| ILE | C | B | 148 | 397 | 255 | 321 | 35 |
| ILE | O | B | 148 | 396 | 267 | 320 | 34 |
| PRO | N | B | 149 | 388 | 248 | 329 | 35 |
| PRO | CD | B | 149 | 390 | 234 | 332 | 34 |
| PRO | CA | B | 149 | 377 | 254 | 336 | 35 |
| PRO | CB | B | 149 | 373 | 244 | 346 | 34 |
| PRO | CG | B | 149 | 376 | 231 | 339 | 35 |
| PRO | C | B | 149 | 381 | 268 | 343 | 35 |
| PRO | O | B | 149 | 374 | 277 | 342 | 35 |
| HIS | N | B | 150 | 392 | 268 | 350 | 36 |
| HIS | CA | B | 150 | 397 | 279 | 357 | 37 |
| HIS | CB | B | 150 | 400 | 276 | 372 | 37 |
| HIS | CG | B | 150 | 389 | 269 | 379 | 37 |
| HIS | CD2 | B | 150 | 387 | 256 | 382 | 37 |
| HIS | ND1 | B | 150 | 379 | 277 | 385 | 38 |
| HIS | CE1 | B | 150 | 370 | 268 | 390 | 38 |
| HIS | NE2 | B | 150 | 375 | 256 | 389 | 38 |
| HIS | C | B | 150 | 409 | 286 | 350 | 38 |
| HIS | O | B | 150 | 418 | 291 | 357 | 37 |
| GLY | N | B | 151 | 408 | 286 | 337 | 39 |
| GLY | CA | B | 151 | 419 | 293 | 329 | 41 |
| GLY | C | B | 151 | 411 | 300 | 319 | 42 |
| GLY | O | B | 151 | 399 | 304 | 322 | 42 |
| PRO | N | B | 152 | 416 | 303 | 307 | 44 |
| PRO | CD | B | 152 | 428 | 300 | 301 | 44 |
| PRO | CA | B | 152 | 407 | 311 | 298 | 45 |
| PRO | CB | B | 152 | 416 | 312 | 285 | 44 |
| PRO | CG | B | 152 | 425 | 301 | 286 | 44 |
| PRO | C | B | 152 | 394 | 302 | 295 | 46 |
| PRO | O | B | 152 | 395 | 290 | 295 | 46 |
| ASN | N | B | 153 | 383 | 309 | 293 | 48 |
| ASN | CA | B | 153 | 371 | 302 | 290 | 50 |
| ASN | CB | B | 153 | 359 | 312 | 290 | 51 |
| ASN | CG | B | 153 | 356 | 318 | 304 | 52 |
| ASN | OD1 | B | 153 | 352 | 311 | 313 | 52 |
| ASN | ND2 | B | 153 | 359 | 331 | 305 | 53 |
| ASN | C | B | 153 | 370 | 293 | 278 | 50 |
| ASN | O | B | 153 | 362 | 284 | 277 | 50 |
| VAL | N | B | 154 | 378 | 296 | 268 | 49 |
| VAL | CA | B | 154 | 378 | 288 | 255 | 49 |
| VAL | CB | B | 154 | 389 | 294 | 246 | 49 |
| VAL | CG1 | B | 154 | 385 | 309 | 242 | 49 |
| VAL | CG2 | B | 154 | 403 | 293 | 252 | 49 |
| VAL | C | B | 154 | 381 | 273 | 256 | 48 |
| VAL | O | B | 154 | 384 | 268 | 266 | 49 |
| THR | N | B | 155 | 380 | 267 | 244 | 47 |
| THR | CA | B | 155 | 382 | 253 | 243 | 46 |
| THR | CB | B | 155 | 369 | 245 | 241 | 46 |
| THR | OG1 | B | 155 | 362 | 245 | 254 | 45 |
| THR | CG2 | B | 155 | 372 | 231 | 237 | 46 |
| THR | C | B | 155 | 390 | 253 | 230 | 44 |
| THR | O | B | 155 | 388 | 260 | 220 | 45 |
| VAL | N | B | 156 | 399 | 242 | 229 | 43 |
| VAL | CA | B | 156 | 407 | 240 | 217 | 41 |
| VAL | CB | B | 156 | 421 | 247 | 218 | 41 |
| VAL | CG1 | B | 156 | 419 | 262 | 221 | 42 |
| VAL | CG2 | B | 156 | 429 | 241 | 229 | 41 |
| VAL | C | B | 156 | 410 | 226 | 214 | 40 |
| VAL | O | B | 156 | 408 | 217 | 222 | 39 |
| ARG | N | B | 157 | 413 | 223 | 201 | 39 |
| ARG | CA | B | 157 | 416 | 209 | 197 | 38 |
| ARG | CB | B | 157 | 413 | 206 | 183 | 38 |
| ARG | CG | B | 157 | 416 | 192 | 178 | 38 |
| ARG | CD | B | 157 | 409 | 188 | 166 | 37 |
| ARG | NE | B | 157 | 395 | 185 | 168 | 37 |
| ARG | CZ | B | 157 | 390 | 174 | 174 | 37 |
| ARG | NH1 | B | 157 | 398 | 165 | 178 | 36 |
| ARG | NH2 | B | 157 | 377 | 173 | 176 | 37 |
| ARG | C | B | 157 | 431 | 207 | 199 | 38 |
| ARG | O | B | 157 | 439 | 215 | 194 | 37 |
| ALA | N | B | 158 | 435 | 197 | 207 | 37 |
| ALA | CA | B | 158 | 449 | 195 | 210 | 36 |
| ALA | CB | B | 158 | 452 | 201 | 224 | 37 |
| ALA | C | B | 158 | 453 | 181 | 209 | 36 |
| ALA | O | B | 158 | 444 | 172 | 210 | 36 |
| ASN | N | B | 159 | 466 | 178 | 208 | 35 |
| ASN | CA | B | 159 | 471 | 165 | 208 | 35 |
| ASN | CB | B | 159 | 486 | 165 | 203 | 35 |
| ASN | CG | B | 159 | 486 | 169 | 188 | 35 |
| ASN | OD1 | B | 159 | 479 | 163 | 180 | 35 |
| ASN | ND2 | B | 159 | 495 | 178 | 184 | 35 |
| ASN | C | B | 159 | 471 | 160 | 222 | 35 |
| ASN | O | B | 159 | 473 | 167 | 232 | 35 |
| ILE | N | B | 160 | 468 | 147 | 223 | 35 |
| ILE | CA | B | 160 | 467 | 140 | 236 | 34 |
| ILE | CB | B | 160 | 453 | 138 | 241 | 34 |
| ILE | CG2 | B | 160 | 452 | 131 | 254 | 33 |
| ILE | CG1 | B | 160 | 446 | 152 | 242 | 34 |
| ILE | CD1 | B | 160 | 431 | 151 | 245 | 34 |
| ILE | C | B | 160 | 474 | 127 | 236 | 35 |
| ILE | O | B | 160 | 470 | 118 | 228 | 35 |
| ALA | N | B | 161 | 483 | 125 | 245 | 35 |
| ALA | CA | B | 161 | 490 | 112 | 246 | 36 |
| ALA | CB | B | 161 | 504 | 113 | 251 | 36 |
| ALA | C | B | 161 | 482 | 104 | 256 | 36 |
| ALA | O | B | 161 | 482 | 106 | 268 | 36 |
| ALA | N | B | 162 | 474 | 94 | 250 | 36 |
| ALA | CA | B | 162 | 465 | 86 | 259 | 37 |
| ALA | CB | B | 162 | 454 | 80 | 250 | 37 |
| ALA | C | B | 162 | 474 | 75 | 264 | 38 |
| ALA | O | B | 162 | 478 | 65 | 257 | 38 |
| ILE | N | B | 163 | 477 | 76 | 277 | 39 |
| ILE | CA | B | 163 | 486 | 66 | 284 | 40 |
| ILE | CB | B | 163 | 491 | 72 | 298 | 39 |
| ILE | CG2 | B | 163 | 500 | 62 | 305 | 39 |
| ILE | CG1 | B | 163 | 499 | 85 | 295 | 39 |
| ILE | CD1 | B | 163 | 503 | 92 | 308 | 39 |
| ILE | C | B | 163 | 479 | 53 | 287 | 40 |
| ILE | O | B | 163 | 469 | 52 | 294 | 40 |
| THR | N | B | 164 | 485 | 42 | 281 | 42 |

TABLE 1-continued

Structure Coordinates for uncomplexed BACE

| | | | | | | | |
|---|---|---|---|---|---|---|---|
| THR | CA | B | 164 | 479 | 29 | 282 | 43 |
| THR | CB | B | 164 | 478 | 22 | 269 | 42 |
| THR | OG1 | B | 164 | 490 | 24 | 261 | 41 |
| THR | CG2 | B | 164 | 466 | 28 | 261 | 42 |
| THR | C | B | 164 | 487 | 20 | 292 | 44 |
| THR | O | B | 164 | 482 | 10 | 297 | 44 |
| GLU | N | B | 165 | 500 | 23 | 293 | 45 |
| GLU | CA | B | 165 | 509 | 15 | 302 | 47 |
| GLU | CB | B | 165 | 516 | 4 | 294 | 48 |
| GLU | CG | B | 165 | 508 | −9 | 292 | 50 |
| GLU | CD | B | 165 | 517 | −20 | 286 | 51 |
| GLU | OE1 | B | 165 | 527 | −23 | 292 | 52 |
| GLU | OE2 | B | 165 | 513 | −26 | 276 | 52 |
| GLU | C | B | 165 | 519 | 24 | 308 | 47 |
| GLU | O | B | 165 | 524 | 34 | 301 | 47 |
| SER | N | B | 166 | 523 | 22 | 320 | 48 |
| SER | CA | B | 166 | 532 | 31 | 327 | 49 |
| SER | CB | B | 166 | 525 | 43 | 333 | 48 |
| SER | OG | B | 166 | 515 | 38 | 342 | 48 |
| SER | C | B | 166 | 540 | 23 | 337 | 49 |
| SER | O | B | 166 | 537 | 12 | 341 | 49 |
| ASP | N | B | 167 | 551 | 29 | 342 | 50 |
| ASP | CA | B | 167 | 560 | 24 | 353 | 51 |
| ASP | CB | B | 167 | 571 | 16 | 346 | 52 |
| ASP | CG | B | 167 | 581 | 11 | 356 | 53 |
| ASP | OD1 | B | 167 | 588 | 19 | 363 | 53 |
| ASP | OD2 | B | 167 | 583 | −2 | 357 | 53 |
| ASP | C | B | 167 | 565 | 35 | 361 | 51 |
| ASP | O | B | 167 | 571 | 44 | 357 | 51 |
| LYS | N | B | 168 | 561 | 34 | 374 | 52 |
| LYS | CA | B | 168 | 566 | 44 | 384 | 53 |
| LYS | CB | B | 168 | 581 | 44 | 386 | 54 |
| LYS | CG | B | 168 | 587 | 30 | 389 | 55 |
| LYS | CD | B | 168 | 602 | 31 | 388 | 55 |
| LYS | CE | B | 168 | 608 | 17 | 388 | 56 |
| LYS | NZ | B | 168 | 623 | 17 | 386 | 56 |
| LYS | C | B | 168 | 561 | 59 | 381 | 53 |
| LYS | O | B | 168 | 566 | 68 | 387 | 53 |
| PHE | N | B | 169 | 553 | 60 | 370 | 53 |
| PHE | CA | B | 169 | 549 | 74 | 367 | 53 |
| PHE | CB | B | 169 | 542 | 73 | 353 | 53 |
| PHE | CG | B | 169 | 539 | 87 | 348 | 53 |
| PHE | CD1 | B | 169 | 549 | 96 | 344 | 53 |
| PHE | CD2 | B | 169 | 526 | 91 | 346 | 53 |
| PHE | CE1 | B | 169 | 546 | 109 | 340 | 53 |
| PHE | CE2 | B | 169 | 523 | 104 | 342 | 53 |
| PHE | CZ | B | 169 | 533 | 113 | 338 | 53 |
| PHE | C | B | 169 | 539 | 79 | 377 | 53 |
| PHE | O | B | 169 | 542 | 89 | 384 | 53 |
| PHE | N | B | 170 | 527 | 74 | 377 | 52 |
| PHE | CA | B | 170 | 516 | 79 | 386 | 52 |
| PHE | CB | B | 170 | 503 | 73 | 383 | 52 |
| PHE | CG | B | 170 | 498 | 75 | 369 | 51 |
| PHE | CD1 | B | 170 | 500 | 65 | 359 | 51 |
| PHE | CD2 | B | 170 | 493 | 87 | 365 | 51 |
| PHE | CE1 | B | 170 | 496 | 66 | 346 | 51 |
| PHE | CE2 | B | 170 | 489 | 89 | 352 | 51 |
| PHE | CZ | B | 170 | 490 | 79 | 342 | 51 |
| PHE | C | B | 170 | 520 | 77 | 400 | 53 |
| PHE | O | B | 170 | 528 | 67 | 403 | 52 |
| ILE | N | B | 171 | 516 | 85 | 409 | 53 |
| ILE | CA | B | 171 | 519 | 84 | 423 | 53 |
| ILE | CB | B | 171 | 526 | 97 | 429 | 53 |
| ILE | CG2 | B | 171 | 529 | 96 | 444 | 53 |
| ILE | CG1 | B | 171 | 539 | 100 | 421 | 53 |
| ILE | CD1 | B | 171 | 545 | 113 | 424 | 53 |
| ILE | C | B | 171 | 506 | 82 | 431 | 54 |
| ILE | O | B | 171 | 496 | 88 | 428 | 54 |
| ASN | N | B | 172 | 507 | 73 | 441 | 54 |
| ASN | CA | B | 172 | 495 | 70 | 449 | 54 |
| ASN | CB | B | 172 | 498 | 58 | 458 | 55 |
| ASN | CG | B | 172 | 485 | 52 | 464 | 55 |
| ASN | OD1 | B | 172 | 486 | 42 | 471 | 55 |
| ASN | ND2 | B | 172 | 474 | 59 | 462 | 55 |
| ASN | C | B | 172 | 491 | 82 | 458 | 54 |
| ASN | O | B | 172 | 499 | 87 | 466 | 54 |
| GLY | N | B | 173 | 479 | 87 | 456 | 54 |
| GLY | CA | B | 173 | 474 | 99 | 463 | 53 |
| GLY | C | B | 173 | 478 | 112 | 459 | 53 |
| GLY | O | B | 173 | 477 | 122 | 467 | 53 |
| SER | N | B | 174 | 484 | 114 | 447 | 52 |
| SER | CA | B | 174 | 488 | 127 | 442 | 51 |
| SER | CB | B | 174 | 497 | 125 | 430 | 51 |
| SER | OG | B | 174 | 490 | 120 | 419 | 51 |
| SER | C | B | 174 | 476 | 135 | 438 | 49 |
| SER | O | B | 174 | 476 | 148 | 439 | 50 |
| ASN | N | B | 175 | 466 | 129 | 434 | 48 |
| ASN | CA | B | 175 | 453 | 135 | 430 | 46 |
| ASN | CB | B | 175 | 449 | 146 | 439 | 46 |
| ASN | CG | B | 175 | 434 | 150 | 438 | 46 |
| ASN | OD1 | B | 175 | 426 | 141 | 437 | 45 |
| ASN | ND2 | B | 175 | 431 | 163 | 438 | 45 |
| ASN | C | B | 175 | 453 | 140 | 415 | 44 |
| ASN | O | B | 175 | 444 | 146 | 411 | 44 |
| TRP | N | B | 176 | 464 | 138 | 408 | 42 |
| TRP | CA | B | 176 | 464 | 142 | 394 | 41 |
| TRP | CB | B | 176 | 476 | 151 | 391 | 40 |
| TRP | CG | B | 176 | 490 | 147 | 395 | 40 |
| TRP | CD2 | B | 176 | 499 | 139 | 388 | 40 |
| TRP | CE2 | B | 176 | 511 | 139 | 396 | 40 |
| TRP | CE3 | B | 176 | 498 | 132 | 376 | 40 |
| TRP | CD1 | B | 176 | 496 | 151 | 407 | 40 |
| TRP | NE1 | B | 176 | 509 | 146 | 407 | 40 |
| TRP | CZ2 | B | 176 | 522 | 132 | 391 | 40 |
| TRP | CZ3 | B | 176 | 510 | 125 | 372 | 40 |
| TRP | CH2 | B | 176 | 522 | 125 | 379 | 40 |
| TRP | C | B | 176 | 465 | 130 | 385 | 39 |
| TRP | O | B | 176 | 471 | 120 | 388 | 39 |
| GLU | N | B | 177 | 459 | 131 | 373 | 38 |
| GLU | CA | B | 177 | 458 | 120 | 364 | 36 |
| ALA | CA | B | 188 | 581 | 168 | 225 | 40 |
| ALA | CB | B | 188 | 569 | 176 | 218 | 40 |
| ALA | C | B | 188 | 583 | 155 | 218 | 41 |
| ALA | O | B | 188 | 591 | 154 | 209 | 40 |
| ARG | N | B | 189 | 576 | 144 | 223 | 41 |
| ARG | CA | B | 189 | 578 | 131 | 217 | 42 |
| ARG | CB | B | 189 | 581 | 121 | 228 | 43 |
| ARG | CG | B | 189 | 596 | 122 | 232 | 44 |
| ARG | CD | B | 189 | 600 | 110 | 240 | 45 |
| ARG | NE | B | 189 | 601 | 98 | 232 | 46 |
| ARG | CZ | B | 189 | 609 | 96 | 222 | 46 |
| ARG | NH1 | B | 189 | 618 | 105 | 219 | 46 |
| ARG | NH2 | B | 189 | 609 | 84 | 216 | 45 |
| ARG | C | B | 189 | 564 | 128 | 210 | 42 |
| ARG | O | B | 189 | 554 | 133 | 214 | 41 |
| PRO | N | B | 190 | 565 | 119 | 200 | 43 |
| PRO | CD | B | 190 | 553 | 115 | 193 | 43 |
| PRO | CA | B | 190 | 577 | 113 | 194 | 43 |
| PRO | CB | B | 190 | 570 | 104 | 182 | 43 |
| PRO | CG | B | 190 | 556 | 102 | 187 | 43 |
| PRO | C | B | 190 | 587 | 123 | 188 | 43 |
| PRO | O | B | 190 | 599 | 119 | 187 | 44 |
| ASP | N | B | 191 | 583 | 135 | 184 | 44 |
| ASP | CA | B | 191 | 592 | 144 | 178 | 45 |
| ASP | CB | B | 191 | 595 | 140 | 164 | 45 |
| ASP | CG | B | 191 | 583 | 136 | 156 | 46 |
| ASP | OD1 | B | 191 | 583 | 125 | 150 | 47 |
| ASP | OD2 | B | 191 | 574 | 144 | 155 | 46 |
| ASP | C | B | 191 | 585 | 158 | 178 | 45 |
| ASP | O | B | 191 | 574 | 160 | 181 | 44 |
| ASP | N | B | 192 | 593 | 168 | 173 | 44 |
| ASP | CA | B | 192 | 588 | 182 | 173 | 45 |
| ASP | CB | B | 192 | 599 | 192 | 169 | 46 |
| ASP | CG | B | 192 | 605 | 189 | 156 | 46 |
| ASP | OD1 | B | 192 | 598 | 185 | 146 | 46 |
| ASP | OD2 | B | 192 | 618 | 190 | 155 | 46 |
| ASP | C | B | 192 | 576 | 185 | 164 | 45 |
| ASP | O | B | 192 | 570 | 196 | 165 | 45 |
| SER | N | B | 193 | 572 | 175 | 156 | 44 |
| SER | CA | B | 193 | 560 | 177 | 148 | 44 |
| SER | CB | B | 193 | 559 | 168 | 136 | 44 |
| SER | OG | B | 193 | 557 | 154 | 141 | 45 |
| SER | C | B | 193 | 547 | 176 | 156 | 43 |
| SER | O | B | 193 | 536 | 180 | 152 | 42 |

TABLE 1-continued

Structure Coordinates for uncomplexed BACE

| | | | | | | | |
|---|---|---|---|---|---|---|---|
| LEU | N | B | 194 | 548 | 171 | 168 | 42 |
| LEU | CA | B | 194 | 537 | 170 | 177 | 41 |
| LEU | CB | B | 194 | 538 | 158 | 187 | 41 |
| LEU | CG | B | 194 | 526 | 155 | 195 | 41 |
| LEU | CD1 | B | 194 | 515 | 150 | 186 | 41 |
| LEU | CD2 | B | 194 | 529 | 144 | 206 | 41 |
| LEU | C | B | 194 | 535 | 183 | 185 | 41 |
| LEU | O | B | 194 | 541 | 185 | 195 | 41 |
| GLU | N | B | 195 | 527 | 192 | 179 | 40 |
| GLU | CA | B | 195 | 524 | 205 | 185 | 39 |
| GLU | CB | B | 195 | 514 | 212 | 176 | 40 |
| GLU | CG | B | 195 | 508 | 225 | 182 | 40 |
| GLU | CD | B | 195 | 500 | 233 | 171 | 41 |
| GLU | OE1 | B | 195 | 506 | 239 | 162 | 41 |
| GLU | OE2 | B | 195 | 488 | 233 | 172 | 40 |
| GLU | C | B | 195 | 519 | 205 | 199 | 37 |
| GLU | O | B | 195 | 509 | 199 | 202 | 37 |
| PRO | N | B | 196 | 527 | 211 | 208 | 36 |
| PRO | CD | B | 196 | 541 | 216 | 206 | 36 |
| PRO | CA | B | 196 | 524 | 211 | 223 | 35 |
| PRO | CB | B | 196 | 536 | 219 | 229 | 36 |
| PRO | CG | B | 196 | 547 | 215 | 219 | 36 |
| PRO | C | B | 196 | 511 | 219 | 225 | 35 |
| PRO | O | B | 196 | 507 | 227 | 217 | 34 |
| PHE | N | B | 197 | 505 | 216 | 237 | 34 |
| PHE | CA | B | 197 | 492 | 222 | 240 | 34 |
| PHE | CB | B | 197 | 488 | 218 | 255 | 32 |
| PHE | CG | B | 197 | 475 | 225 | 259 | 32 |
| PHE | CD1 | B | 197 | 463 | 221 | 255 | 32 |
| PHE | CD2 | B | 197 | 476 | 236 | 268 | 32 |
| PHE | CE1 | B | 197 | 451 | 227 | 259 | 32 |
| PHE | CE2 | B | 197 | 465 | 243 | 272 | 32 |
| PHE | CZ | B | 197 | 452 | 238 | 267 | 32 |
| PHE | C | B | 197 | 492 | 237 | 240 | 34 |
| PHE | O | B | 197 | 482 | 243 | 234 | 33 |
| PHE | N | B | 198 | 502 | 244 | 246 | 34 |
| PHE | CA | B | 198 | 502 | 259 | 246 | 35 |
| PHE | CB | B | 198 | 513 | 264 | 255 | 34 |
| PHE | CG | B | 198 | 510 | 278 | 260 | 34 |
| PHE | CD1 | B | 198 | 501 | 279 | 271 | 34 |
| PHE | CD2 | B | 198 | 515 | 289 | 254 | 33 |
| PHE | CE1 | B | 198 | 498 | 292 | 276 | 34 |
| PHE | CE2 | B | 198 | 512 | 302 | 259 | 34 |
| PHE | CZ | B | 198 | 503 | 303 | 270 | 34 |
| PHE | C | B | 198 | 503 | 264 | 232 | 35 |
| PHE | O | B | 198 | 496 | 275 | 229 | 35 |
| ASP | N | B | 199 | 511 | 258 | 223 | 36 |
| ASP | CA | B | 199 | 512 | 263 | 210 | 37 |
| ASP | CB | B | 199 | 522 | 254 | 202 | 38 |
| ASP | CG | B | 199 | 537 | 258 | 205 | 39 |
| ASP | OD1 | B | 199 | 542 | 268 | 199 | 40 |
| ASP | OD2 | B | 199 | 543 | 252 | 214 | 39 |
| ASP | C | B | 199 | 498 | 262 | 203 | 37 |
| ASP | O | B | 199 | 494 | 271 | 195 | 37 |
| SER | N | B | 200 | 491 | 251 | 206 | 37 |
| SER | CA | B | 200 | 478 | 249 | 200 | 38 |
| SER | CB | B | 200 | 472 | 236 | 204 | 38 |
| SER | OG | B | 200 | 479 | 225 | 199 | 38 |
| SER | C | B | 200 | 468 | 260 | 205 | 39 |
| SER | O | B | 200 | 462 | 267 | 197 | 38 |
| LEU | N | B | 201 | 468 | 262 | 218 | 39 |
| LEU | CA | B | 201 | 459 | 272 | 224 | 39 |
| LEU | CB | B | 201 | 462 | 273 | 239 | 39 |
| LEU | CG | B | 201 | 456 | 285 | 247 | 39 |
| LEU | CD1 | B | 201 | 441 | 284 | 246 | 39 |
| LEU | CD2 | B | 201 | 460 | 283 | 262 | 39 |
| LEU | C | B | 201 | 462 | 286 | 218 | 39 |
| LEU | O | B | 201 | 452 | 293 | 214 | 39 |
| VAL | N | B | 202 | 474 | 290 | 217 | 40 |
| VAL | CA | B | 202 | 478 | 303 | 211 | 41 |
| VAL | CB | B | 202 | 493 | 305 | 212 | 41 |
| VAL | CG1 | B | 202 | 498 | 317 | 204 | 40 |
| VAL | CG2 | B | 202 | 497 | 307 | 227 | 41 |
| VAL | C | B | 202 | 474 | 304 | 196 | 42 |
| VAL | O | B | 202 | 469 | 315 | 192 | 42 |
| LYS | N | B | 203 | 476 | 294 | 188 | 43 |
| LYS | CA | B | 203 | 473 | 294 | 174 | 44 |
| LYS | CB | B | 203 | 479 | 282 | 167 | 45 |
| LYS | CG | B | 203 | 485 | 285 | 154 | 47 |
| LYS | CD | B | 203 | 495 | 274 | 149 | 48 |
| LYS | CE | B | 203 | 501 | 277 | 136 | 49 |
| LYS | NZ | B | 203 | 512 | 267 | 132 | 49 |
| LYS | C | B | 203 | 458 | 294 | 171 | 44 |
| LYS | O | B | 203 | 453 | 300 | 162 | 44 |
| GLN | N | B | 204 | 450 | 288 | 180 | 43 |
| GLN | CA | B | 204 | 436 | 288 | 178 | 42 |
| GLN | CB | B | 204 | 430 | 274 | 183 | 42 |
| GLN | CG | B | 204 | 435 | 262 | 174 | 41 |
| GLN | CD | B | 204 | 432 | 249 | 180 | 41 |
| GLN | OE1 | B | 204 | 422 | 246 | 186 | 41 |
| GLN | NE2 | B | 204 | 442 | 240 | 179 | 40 |
| GLN | C | B | 204 | 427 | 298 | 185 | 42 |
| GLN | O | B | 204 | 415 | 300 | 183 | 42 |
| THR | N | B | 205 | 433 | 306 | 194 | 42 |
| THR | CA | B | 205 | 426 | 316 | 201 | 42 |
| THR | CB | B | 205 | 423 | 312 | 216 | 43 |
| THR | OG1 | B | 205 | 436 | 313 | 223 | 43 |
| THR | CG2 | B | 205 | 417 | 298 | 217 | 43 |
| THR | C | B | 205 | 433 | 330 | 202 | 43 |
| THR | O | B | 205 | 444 | 331 | 196 | 42 |
| HIS | N | B | 206 | 428 | 339 | 209 | 43 |
| HIS | CA | B | 206 | 434 | 352 | 210 | 43 |
| HIS | CB | B | 206 | 424 | 364 | 210 | 44 |
| HIS | CG | B | 206 | 416 | 365 | 198 | 46 |
| HIS | CD2 | B | 206 | 418 | 372 | 187 | 46 |
| HIS | ND1 | B | 206 | 404 | 358 | 195 | 46 |
| HIS | CE1 | B | 206 | 400 | 360 | 183 | 46 |
| HIS | NE2 | B | 206 | 408 | 369 | 178 | 46 |
| HIS | C | B | 206 | 443 | 353 | 222 | 41 |
| HIS | O | B | 206 | 449 | 363 | 225 | 41 |
| VAL | N | B | 207 | 444 | 342 | 230 | 39 |
| VAL | CA | B | 207 | 452 | 341 | 242 | 38 |
| VAL | CB | B | 207 | 452 | 327 | 248 | 37 |
| VAL | CG1 | B | 207 | 463 | 326 | 258 | 37 |
| VAL | CG2 | B | 207 | 439 | 324 | 254 | 38 |
| VAL | C | B | 207 | 466 | 346 | 238 | 36 |
| VAL | O | B | 207 | 472 | 340 | 229 | 36 |
| PRO | N | B | 208 | 472 | 355 | 245 | 35 |
| PRO | CD | B | 208 | 465 | 364 | 255 | 35 |
| PRO | CA | B | 208 | 485 | 360 | 243 | 34 |
| PRO | CB | B | 208 | 488 | 371 | 253 | 34 |
| PRO | CG | B | 208 | 474 | 377 | 255 | 35 |
| PRO | C | B | 208 | 495 | 348 | 244 | 34 |
| PRO | O | B | 208 | 492 | 338 | 252 | 33 |
| ASN | N | B | 209 | 507 | 349 | 238 | 32 |
| ASN | CA | B | 209 | 516 | 338 | 239 | 31 |
| ASN | CB | B | 209 | 525 | 338 | 226 | 31 |
| ASN | CG | B | 209 | 535 | 327 | 226 | 31 |
| ASN | OD1 | B | 209 | 532 | 316 | 232 | 31 |
| ASN | ND2 | B | 209 | 546 | 328 | 220 | 31 |
| ASN | C | B | 209 | 525 | 340 | 251 | 30 |
| ASN | O | B | 209 | 537 | 343 | 251 | 29 |
| LEU | N | B | 210 | 519 | 338 | 263 | 30 |
| LEU | CA | B | 210 | 526 | 340 | 275 | 30 |
| LEU | CB | B | 210 | 529 | 355 | 278 | 29 |
| LEU | CG | B | 210 | 533 | 360 | 291 | 30 |
| LEU | CD1 | B | 210 | 540 | 374 | 289 | 30 |
| LEU | CD2 | B | 210 | 521 | 361 | 301 | 30 |
| LEU | C | B | 210 | 517 | 335 | 287 | 29 |
| LEU | O | B | 210 | 505 | 334 | 286 | 29 |
| PHE | N | B | 211 | 524 | 330 | 297 | 29 |
| PHE | CA | B | 211 | 517 | 325 | 309 | 29 |
| PHE | CB | B | 211 | 513 | 310 | 308 | 29 |
| PHE | CG | B | 211 | 525 | 301 | 309 | 30 |
| PHE | CD1 | B | 211 | 532 | 298 | 297 | 31 |
| PHE | CD2 | B | 211 | 530 | 296 | 320 | 30 |
| PHE | CE1 | B | 211 | 543 | 289 | 297 | 31 |
| PHE | CE2 | B | 211 | 541 | 287 | 321 | 30 |
| PHE | CZ | B | 211 | 547 | 284 | 309 | 30 |
| PHE | C | B | 211 | 526 | 328 | 321 | 28 |
| PHE | O | B | 211 | 538 | 329 | 319 | 27 |
| SER | N | B | 212 | 521 | 328 | 333 | 27 |
| SER | CA | B | 212 | 529 | 331 | 345 | 26 |
| SER | CB | B | 212 | 527 | 346 | 349 | 25 |

TABLE 1-continued

Structure Coordinates for uncomplexed BACE

| | | | | | | |
|---|---|---|---|---|---|---|
| SER | OG | B | 212 | 514 | 349 | 350 | 25 |
| SER | C | B | 212 | 525 | 322 | 356 | 25 |
| SER | O | B | 212 | 514 | 317 | 357 | 24 |
| LEU | N | B | 213 | 534 | 319 | 365 | 25 |
| LEU | CA | B | 213 | 532 | 310 | 376 | 25 |
| LEU | CB | B | 213 | 540 | 297 | 374 | 25 |
| LEU | CG | B | 213 | 535 | 288 | 363 | 25 |
| LEU | CD1 | B | 213 | 545 | 276 | 362 | 25 |
| LEU | CD2 | B | 213 | 521 | 283 | 366 | 24 |
| LEU | C | B | 213 | 536 | 316 | 390 | 26 |
| LEU | O | B | 213 | 547 | 322 | 391 | 25 |
| GLN | N | B | 214 | 528 | 314 | 400 | 26 |
| GLN | CA | B | 214 | 530 | 318 | 413 | 27 |
| GLN | CB | B | 214 | 521 | 329 | 419 | 28 |
| GLN | CG | B | 214 | 524 | 333 | 433 | 28 |
| GLN | CD | B | 214 | 513 | 339 | 441 | 28 |
| GLN | OE1 | B | 214 | 502 | 334 | 443 | 28 |
| GLN | NE2 | B | 214 | 516 | 352 | 446 | 28 |
| GLN | C | B | 214 | 528 | 305 | 421 | 28 |
| GLN | O | B | 214 | 516 | 301 | 423 | 29 |
| LEU | N | B | 215 | 539 | 298 | 426 | 28 |
| LEU | CA | B | 215 | 537 | 286 | 433 | 29 |
| LEU | CB | B | 215 | 548 | 276 | 429 | 28 |
| LEU | CG | B | 215 | 548 | 273 | 414 | 29 |
| LEU | CD1 | B | 215 | 559 | 263 | 410 | 28 |
| LEU | CD2 | B | 215 | 534 | 268 | 409 | 28 |
| LEU | C | B | 215 | 540 | 290 | 448 | 31 |
| LEU | O | B | 215 | 550 | 294 | 452 | 30 |
| CYS | N | B | 216 | 529 | 287 | 456 | 32 |
| CYS | CA | B | 216 | 530 | 291 | 471 | 35 |
| CYS | C | B | 216 | 534 | 279 | 480 | 35 |
| CYS | O | B | 216 | 527 | 269 | 481 | 36 |
| CYS | CB | B | 216 | 517 | 297 | 475 | 35 |
| CYS | SG | B | 216 | 512 | 311 | 464 | 37 |
| GLY | N | B | 232 | 476 | 263 | 466 | 34 |
| GLY | CA | B | 232 | 490 | 261 | 465 | 32 |
| GLY | C | B | 232 | 496 | 271 | 455 | 31 |
| GLY | O | B | 232 | 508 | 274 | 456 | 32 |
| GLY | N | B | 233 | 488 | 275 | 446 | 30 |
| GLY | CA | B | 233 | 493 | 285 | 436 | 29 |
| GLY | C | B | 233 | 484 | 289 | 425 | 28 |
| GLY | O | B | 233 | 472 | 285 | 424 | 27 |
| SER | N | B | 234 | 489 | 297 | 416 | 27 |
| SER | CA | B | 234 | 482 | 303 | 404 | 27 |
| SER | CB | B | 234 | 479 | 318 | 406 | 26 |
| SER | OG | B | 234 | 471 | 320 | 418 | 26 |
| SER | C | B | 234 | 289 | 302 | 391 | 27 |
| SER | O | B | 234 | 501 | 304 | 391 | 27 |
| MET | N | B | 235 | 482 | 298 | 380 | 27 |
| MET | CA | B | 235 | 488 | 298 | 367 | 27 |
| MET | CB | B | 235 | 487 | 284 | 361 | 27 |
| MET | CG | B | 235 | 491 | 284 | 346 | 28 |
| MET | SD | B | 235 | 494 | 268 | 338 | 29 |
| MET | CE | B | 235 | 477 | 263 | 336 | 29 |
| MET | C | B | 235 | 480 | 307 | 359 | 27 |
| MET | O | B | 235 | 468 | 304 | 356 | 27 |
| ILE | N | B | 236 | 485 | 319 | 355 | 27 |
| ILE | CA | B | 236 | 478 | 329 | 348 | 28 |
| ILE | CB | B | 236 | 482 | 343 | 352 | 27 |
| ILE | CG2 | B | 236 | 472 | 353 | 346 | 27 |
| ILE | CG1 | B | 236 | 481 | 344 | 367 | 27 |
| ILE | CD1 | B | 236 | 468 | 341 | 373 | 27 |
| ILE | C | B | 236 | 482 | 327 | 333 | 29 |
| ILE | O | B | 236 | 493 | 329 | 329 | 29 |
| ILE | N | B | 237 | 472 | 323 | 325 | 29 |
| ILE | CA | B | 237 | 474 | 320 | 311 | 30 |
| ILE | CB | B | 237 | 465 | 308 | 306 | 30 |
| ILE | CG2 | B | 237 | 466 | 307 | 291 | 29 |
| ILE | CG1 | B | 237 | 470 | 296 | 314 | 30 |
| ILE | CD1 | B | 237 | 461 | 283 | 311 | 31 |
| ILE | C | B | 237 | 470 | 333 | 303 | 30 |
| ILE | O | B | 237 | 459 | 337 | 302 | 29 |
| GLY | N | B | 238 | 480 | 338 | 296 | 31 |
| GLY | CA | B | 238 | 479 | 349 | 287 | 31 |
| GLY | C | B | 238 | 481 | 363 | 294 | 32 |
| GLY | O | B | 238 | 478 | 373 | 287 | 32 |
| GLY | N | B | 239 | 486 | 363 | 306 | 32 |
| GLY | CA | B | 239 | 488 | 376 | 312 | 32 |
| GLY | C | B | 239 | 496 | 376 | 325 | 32 |
| GLY | O | B | 239 | 501 | 365 | 330 | 31 |
| ILE | N | B | 240 | 498 | 388 | 331 | 31 |
| ILE | CA | B | 240 | 505 | 390 | 343 | 32 |
| ILE | CB | B | 240 | 517 | 400 | 340 | 32 |
| ILE | CG2 | B | 240 | 525 | 402 | 353 | 31 |
| ILE | CG1 | B | 240 | 526 | 394 | 329 | 31 |
| ILE | CD1 | B | 240 | 537 | 403 | 324 | 31 |
| ILE | C | B | 240 | 496 | 396 | 353 | 32 |
| ILE | O | B | 240 | 491 | 407 | 351 | 32 |
| ASP | N | B | 241 | 494 | 389 | 364 | 32 |
| ASP | CA | B | 241 | 485 | 394 | 374 | 32 |
| ASP | CB | B | 241 | 477 | 383 | 381 | 31 |
| ASP | CG | B | 241 | 466 | 388 | 391 | 31 |
| ASP | OD1 | B | 241 | 454 | 386 | 387 | 30 |
| ASP | OD2 | B | 241 | 470 | 394 | 401 | 30 |
| ASP | C | B | 241 | 493 | 402 | 385 | 32 |
| ASP | O | B | 241 | 501 | 396 | 391 | 32 |
| HIS | N | B | 242 | 491 | 415 | 385 | 33 |
| HIS | CA | B | 242 | 498 | 423 | 395 | 33 |
| HIS | CB | B | 242 | 496 | 438 | 391 | 36 |
| HIS | CG | B | 242 | 501 | 442 | 378 | 39 |
| HIS | CD2 | B | 242 | 506 | 435 | 368 | 40 |
| HIS | ND1 | B | 242 | 502 | 456 | 374 | 40 |
| HIS | CE1 | B | 242 | 507 | 456 | 362 | 40 |
| HIS | NE2 | B | 242 | 510 | 444 | 358 | 40 |
| HIS | C | B | 242 | 496 | 421 | 409 | 32 |
| HIS | O | B | 242 | 503 | 426 | 418 | 33 |
| SER | N | B | 243 | 486 | 413 | 413 | 31 |
| SER | CA | B | 243 | 483 | 410 | 427 | 30 |
| SER | CB | B | 243 | 468 | 407 | 429 | 30 |
| SER | OG | B | 243 | 465 | 394 | 425 | 29 |
| SER | C | B | 243 | 492 | 398 | 431 | 30 |
| SER | O | B | 243 | 490 | 394 | 443 | 30 |
| LEU | N | B | 244 | 500 | 393 | 422 | 29 |
| LEU | CA | B | 244 | 508 | 381 | 426 | 29 |
| LEU | CB | B | 244 | 507 | 371 | 414 | 29 |
| LEU | CG | B | 244 | 493 | 367 | 411 | 30 |
| LEU | CD1 | B | 244 | 493 | 355 | 401 | 29 |
| LEU | CD2 | B | 244 | 486 | 362 | 424 | 29 |
| LEU | C | B | 244 | 523 | 384 | 429 | 28 |
| LEU | O | B | 244 | 530 | 375 | 434 | 28 |
| TYR | N | B | 245 | 527 | 396 | 427 | 27 |
| TYR | CA | B | 245 | 541 | 400 | 430 | 27 |
| TYR | CB | B | 245 | 550 | 399 | 418 | 26 |
| TYR | CG | B | 245 | 547 | 409 | 407 | 26 |
| TYR | CD1 | B | 245 | 536 | 408 | 399 | 26 |
| TYR | CE1 | B | 245 | 533 | 417 | 388 | 26 |
| TYR | CD2 | B | 245 | 556 | 419 | 405 | 26 |
| TYR | CE2 | B | 245 | 553 | 429 | 395 | 26 |
| TYR | CZ | B | 245 | 542 | 427 | 387 | 26 |
| TYR | OH | B | 245 | 541 | 437 | 377 | 27 |
| TYR | C | B | 245 | 542 | 415 | 435 | 27 |
| TYR | O | B | 245 | 532 | 422 | 434 | 27 |
| THR | N | B | 246 | 553 | 418 | 441 | 28 |
| THR | CA | B | 246 | 556 | 432 | 445 | 30 |
| THR | CB | B | 246 | 557 | 433 | 460 | 30 |
| THR | OG1 | B | 246 | 569 | 425 | 464 | 30 |
| THR | CG2 | B | 246 | 545 | 429 | 468 | 29 |
| THR | C | B | 246 | 569 | 435 | 439 | 30 |
| THR | O | B | 246 | 577 | 426 | 435 | 29 |
| GLY | N | B | 247 | 572 | 448 | 438 | 30 |
| GLY | CA | B | 247 | 585 | 452 | 432 | 31 |
| GLY | C | B | 247 | 585 | 451 | 417 | 32 |
| GLY | O | B | 247 | 574 | 450 | 411 | 32 |
| SER | N | B | 248 | 597 | 451 | 411 | 33 |
| SER | CA | B | 248 | 598 | 450 | 396 | 34 |
| SER | CB | B | 248 | 610 | 459 | 392 | 34 |
| SER | OG | B | 248 | 609 | 473 | 395 | 36 |
| SER | C | B | 248 | 601 | 436 | 391 | 33 |
| SER | O | B | 248 | 605 | 428 | 399 | 33 |
| LEU | N | B | 249 | 597 | 434 | 379 | 33 |
| LEU | CA | B | 249 | 599 | 422 | 372 | 33 |
| LEU | CB | B | 249 | 588 | 419 | 362 | 32 |
| LEU | CG | B | 249 | 575 | 412 | 367 | 32 |
| LEU | CD1 | B | 249 | 564 | 414 | 357 | 32 |

TABLE 1-continued

Structure Coordinates for uncomplexed BACE

| | | | | | | | |
|---|---|---|---|---|---|---|---|
| LEU | CD2 | B | 249 | 578 | 398 | 369 | 31 |
| LEU | C | B | 249 | 612 | 423 | 365 | 33 |
| LEU | O | B | 249 | 615 | 433 | 358 | 34 |
| TRP | N | B | 250 | 621 | 413 | 366 | 34 |
| TRP | CA | B | 250 | 634 | 413 | 359 | 35 |
| TRP | CB | B | 250 | 645 | 412 | 369 | 36 |
| TRP | CG | B | 250 | 648 | 426 | 376 | 37 |
| TRP | CD2 | B | 250 | 658 | 435 | 371 | 38 |
| TRP | CE2 | B | 250 | 657 | 446 | 380 | 38 |
| TRP | CE3 | B | 250 | 666 | 436 | 359 | 38 |
| TRP | CD1 | B | 250 | 643 | 430 | 387 | 38 |
| TRP | NE1 | B | 250 | 648 | 443 | 390 | 38 |
| TRP | CZ2 | B | 250 | 665 | 458 | 378 | 38 |
| TRP | CZ3 | B | 250 | 674 | 448 | 358 | 38 |
| TRP | CH2 | B | 250 | 673 | 458 | 367 | 38 |
| TRP | C | B | 250 | 635 | 402 | 349 | 35 |
| TRP | O | B | 250 | 633 | 390 | 353 | 35 |
| TYR | N | B | 251 | 638 | 405 | 337 | 34 |
| TYR | CA | B | 251 | 639 | 395 | 326 | 35 |
| TYR | CB | B | 251 | 631 | 400 | 314 | 34 |
| TYR | CG | B | 251 | 616 | 402 | 316 | 35 |
| TYR | CD1 | B | 251 | 612 | 414 | 322 | 35 |
| TYR | CE1 | B | 251 | 598 | 416 | 324 | 34 |
| TYR | CD2 | B | 251 | 607 | 392 | 312 | 35 |
| TYR | CE2 | B | 251 | 593 | 394 | 314 | 34 |
| TYR | CZ | B | 251 | 589 | 406 | 320 | 34 |
| TYR | OH | B | 251 | 575 | 408 | 322 | 34 |
| TYR | C | B | 251 | 652 | 389 | 322 | 35 |
| TYR | O | B | 251 | 662 | 397 | 320 | 34 |
| THR | N | B | 252 | 653 | 376 | 321 | 35 |
| THR | CA | B | 252 | 665 | 369 | 317 | 36 |
| THR | CB | B | 252 | 669 | 358 | 327 | 36 |
| THR | OG1 | B | 252 | 682 | 354 | 324 | 36 |
| THR | CG2 | B | 252 | 660 | 347 | 327 | 35 |
| THR | C | B | 252 | 661 | 362 | 303 | 37 |
| THR | O | B | 252 | 651 | 356 | 303 | 36 |
| PRO | N | B | 253 | 669 | 364 | 293 | 38 |
| PRO | CD | B | 253 | 682 | 371 | 292 | 38 |
| PRO | CA | B | 253 | 666 | 358 | 280 | 38 |
| PRO | CB | B | 253 | 677 | 362 | 271 | 38 |
| PRO | CG | B | 253 | 683 | 375 | 278 | 38 |
| PRO | C | B | 253 | 665 | 343 | 280 | 38 |
| PRO | O | B | 253 | 671 | 336 | 288 | 38 |
| ILE | N | B | 254 | 656 | 337 | 272 | 38 |
| ILE | CA | B | 254 | 654 | 323 | 271 | 39 |
| ILE | CB | B | 254 | 641 | 319 | 264 | 39 |
| ILE | CG2 | B | 254 | 640 | 304 | 261 | 39 |
| ILE | CG1 | B | 254 | 629 | 322 | 274 | 39 |
| ILE | CD1 | B | 254 | 615 | 321 | 269 | 38 |
| ILE | C | B | 254 | 665 | 320 | 260 | 40 |
| ILE | O | B | 254 | 665 | 325 | 249 | 39 |
| ARG | N | B | 255 | 676 | 313 | 265 | 41 |
| ARG | CA | B | 255 | 687 | 310 | 256 | 42 |
| ARG | CB | B | 255 | 697 | 302 | 263 | 42 |
| ARG | CG | B | 255 | 711 | 302 | 256 | 43 |
| ARG | CD | B | 255 | 720 | 292 | 262 | 43 |
| ARG | NE | B | 255 | 733 | 292 | 255 | 45 |
| ARG | CZ | B | 255 | 742 | 282 | 256 | 45 |
| ARG | NH1 | B | 255 | 739 | 271 | 264 | 45 |
| ARG | NH2 | B | 255 | 753 | 282 | 249 | 45 |
| ARG | C | B | 255 | 683 | 302 | 243 | 42 |
| ARG | O | B | 255 | 686 | 306 | 232 | 42 |
| ARG | N | B | 256 | 675 | 292 | 245 | 43 |
| ARG | CA | B | 256 | 671 | 283 | 233 | 43 |
| ARG | CB | B | 256 | 681 | 272 | 231 | 44 |
| ARG | CG | B | 256 | 677 | 262 | 220 | 45 |
| ARG | CD | B | 256 | 687 | 250 | 220 | 46 |
| ARG | NE | B | 256 | 681 | 238 | 215 | 47 |
| ARG | CZ | B | 256 | 686 | 226 | 216 | 47 |
| ARG | NH1 | B | 256 | 697 | 224 | 222 | 47 |
| ARG | NH2 | B | 256 | 679 | 216 | 211 | 47 |
| ARG | C | B | 256 | 657 | 278 | 236 | 43 |
| ARG | O | B | 256 | 654 | 273 | 247 | 42 |
| GLU | N | B | 257 | 648 | 279 | 226 | 43 |
| GLU | CA | B | 257 | 634 | 274 | 228 | 43 |
| GLU | CB | B | 257 | 625 | 282 | 218 | 44 |
| GLU | CG | B | 257 | 623 | 296 | 221 | 45 |
| GLU | CD | B | 257 | 619 | 304 | 209 | 45 |
| GLU | OE1 | B | 257 | 626 | 305 | 199 | 46 |
| GLU | OE2 | B | 257 | 607 | 310 | 209 | 46 |
| GLU | C | B | 257 | 632 | 259 | 227 | 43 |
| GLU | O | B | 257 | 626 | 255 | 217 | 43 |
| TRP | N | B | 258 | 636 | 252 | 238 | 42 |
| TRP | CA | B | 258 | 634 | 238 | 239 | 42 |
| TRP | CB | B | 258 | 646 | 230 | 235 | 43 |
| TRP | CG | B | 258 | 659 | 232 | 243 | 44 |
| TRP | CD2 | B | 258 | 669 | 223 | 246 | 45 |
| TRP | CE2 | B | 258 | 679 | 230 | 253 | 45 |
| TRP | CE3 | B | 258 | 672 | 210 | 242 | 45 |
| TRP | CD1 | B | 258 | 662 | 244 | 249 | 44 |
| TRP | NE1 | B | 258 | 674 | 243 | 256 | 45 |
| TRP | CZ2 | B | 258 | 691 | 224 | 258 | 45 |
| TRP | CZ3 | B | 258 | 683 | 203 | 246 | 46 |
| TRP | CH2 | B | 258 | 693 | 210 | 254 | 45 |
| TRP | C | B | 258 | 629 | 235 | 253 | 41 |
| TRP | O | B | 258 | 618 | 232 | 256 | 41 |
| TYR | N | B | 259 | 638 | 238 | 262 | 41 |
| TYR | CA | B | 259 | 635 | 237 | 277 | 39 |
| TYR | CB | B | 259 | 647 | 231 | 285 | 40 |
| TYR | CG | B | 259 | 648 | 216 | 285 | 41 |
| TYR | CD1 | B | 259 | 640 | 208 | 293 | 41 |
| TYR | CE1 | B | 259 | 641 | 195 | 293 | 41 |
| TYR | CD2 | B | 259 | 658 | 210 | 277 | 41 |
| TYR | CE2 | B | 259 | 659 | 196 | 277 | 41 |
| TYR | CZ | B | 259 | 651 | 188 | 285 | 41 |
| TYR | OH | B | 259 | 652 | 175 | 285 | 42 |
| TYR | C | B | 259 | 634 | 252 | 279 | 38 |
| TYR | O | B | 259 | 639 | 260 | 270 | 38 |
| TYR | N | B | 260 | 629 | 256 | 290 | 37 |
| TYR | CA | B | 260 | 629 | 271 | 293 | 36 |
| TYR | CB | B | 260 | 618 | 275 | 303 | 35 |
| TYR | CG | B | 260 | 604 | 275 | 296 | 33 |
| TYR | CD1 | B | 260 | 595 | 266 | 299 | 32 |
| TYR | CE1 | B | 260 | 582 | 266 | 293 | 31 |
| TYR | CD2 | B | 260 | 601 | 285 | 287 | 32 |
| TYR | CE2 | B | 260 | 589 | 285 | 281 | 32 |
| TYR | CZ | B | 260 | 579 | 276 | 283 | 31 |
| TYR | OH | B | 260 | 567 | 275 | 278 | 30 |
| TYR | C | B | 260 | 643 | 273 | 299 | 37 |
| TYR | O | B | 260 | 645 | 273 | 311 | 38 |
| GLU | N | B | 261 | 653 | 273 | 290 | 38 |
| GLU | CA | B | 261 | 667 | 274 | 294 | 38 |
| GLU | CB | B | 261 | 676 | 267 | 284 | 38 |
| GLU | CG | B | 261 | 691 | 270 | 286 | 39 |
| GLU | CD | B | 261 | 700 | 264 | 275 | 39 |
| GLU | OE1 | B | 261 | 695 | 262 | 264 | 40 |
| GLU | OE2 | B | 261 | 712 | 261 | 278 | 39 |
| GLU | C | B | 261 | 672 | 289 | 296 | 38 |
| GLU | O | B | 261 | 669 | 297 | 288 | 37 |
| VAL | N | B | 262 | 680 | 290 | 307 | 38 |
| VAL | CA | B | 262 | 685 | 304 | 310 | 39 |
| VAL | CB | B | 262 | 678 | 310 | 322 | 38 |
| VAL | CG1 | B | 262 | 663 | 311 | 319 | 38 |
| VAL | CG2 | B | 262 | 679 | 300 | 334 | 38 |
| VAL | C | B | 262 | 700 | 302 | 314 | 40 |
| VAL | O | B | 262 | 705 | 291 | 314 | 41 |
| ILE | N | B | 263 | 706 | 314 | 316 | 41 |
| ILE | CA | B | 263 | 721 | 314 | 320 | 42 |
| ILE | CB | B | 263 | 728 | 321 | 309 | 42 |
| ILE | CG2 | B | 263 | 743 | 323 | 313 | 43 |
| ILE | CG1 | B | 263 | 728 | 312 | 296 | 43 |
| ILE | CD1 | B | 263 | 733 | 320 | 283 | 43 |
| ILE | C | B | 263 | 724 | 320 | 333 | 43 |
| ILE | O | B | 263 | 721 | 332 | 335 | 43 |
| ILE | N | B | 264 | 729 | 313 | 342 | 43 |
| ILE | CA | B | 264 | 733 | 317 | 356 | 44 |
| ILE | CB | B | 264 | 732 | 306 | 366 | 44 |
| ILE | CG2 | B | 264 | 739 | 310 | 379 | 44 |
| ILE | CG1 | B | 264 | 718 | 301 | 368 | 43 |
| ILE | CD1 | B | 264 | 716 | 289 | 376 | 43 |
| ILE | C | B | 264 | 748 | 322 | 355 | 44 |
| ILE | O | B | 264 | 757 | 313 | 354 | 44 |
| VAL | N | B | 265 | 750 | 335 | 357 | 44 |
| VAL | CA | B | 265 | 764 | 340 | 356 | 44 |

TABLE 1-continued

Structure Coordinates for uncomplexed BACE

| | | | | | | |
|---|---|---|---|---|---|---|
| VAL | CB | B | 265 | 764 | 354 | 349 | 44 |
| VAL | CG1 | B | 265 | 758 | 353 | 335 | 44 |
| VAL | CG2 | B | 265 | 756 | 364 | 357 | 44 |
| VAL | C | B | 265 | 771 | 342 | 369 | 44 |
| VAL | O | B | 265 | 782 | 347 | 369 | 45 |
| ARG | N | B | 266 | 765 | 338 | 380 | 44 |
| ARG | CA | B | 266 | 772 | 340 | 393 | 43 |
| ARG | CB | B | 266 | 774 | 354 | 396 | 44 |
| ARG | CG | B | 266 | 781 | 357 | 410 | 45 |
| ARG | CD | B | 266 | 780 | 372 | 413 | 45 |
| ARG | NE | B | 266 | 784 | 375 | 427 | 46 |
| ARG | CZ | B | 266 | 797 | 377 | 431 | 46 |
| ARG | NH1 | B | 266 | 807 | 377 | 422 | 46 |
| ARG | NH2 | B | 266 | 800 | 379 | 444 | 46 |
| ARG | C | B | 266 | 763 | 334 | 404 | 43 |
| ARG | O | B | 266 | 751 | 335 | 404 | 43 |
| VAL | N | B | 267 | 769 | 328 | 415 | 42 |
| VAL | CA | B | 267 | 762 | 322 | 426 | 42 |
| VAL | CB | B | 267 | 763 | 307 | 426 | 41 |
| VAL | CG1 | B | 267 | 754 | 301 | 437 | 41 |
| VAL | CG2 | B | 267 | 757 | 302 | 413 | 41 |
| VAL | C | B | 267 | 768 | 327 | 439 | 42 |
| VAL | O | B | 267 | 780 | 328 | 441 | 42 |
| GLU | N | B | 268 | 759 | 330 | 449 | 42 |
| GLU | CA | B | 268 | 763 | 335 | 462 | 43 |
| GLU | CB | B | 268 | 760 | 350 | 463 | 42 |
| GLU | CG | B | 268 | 770 | 360 | 456 | 40 |
| GLU | CD | B | 268 | 766 | 374 | 459 | 40 |
| GLU | OE1 | B | 268 | 758 | 377 | 468 | 40 |
| GLU | OE2 | B | 268 | 770 | 383 | 451 | 40 |
| GLU | C | B | 268 | 756 | 328 | 473 | 43 |
| GLU | O | B | 268 | 745 | 323 | 471 | 44 |
| ILE | N | B | 269 | 763 | 326 | 484 | 43 |
| ILE | CA | B | 269 | 758 | 319 | 496 | 44 |
| ILE | CB | B | 269 | 765 | 306 | 499 | 44 |
| ILE | CG2 | B | 269 | 758 | 299 | 510 | 44 |
| ILE | CG1 | B | 269 | 767 | 298 | 486 | 44 |
| ILE | CD1 | B | 269 | 753 | 293 | 480 | 44 |
| ILE | C | B | 269 | 760 | 330 | 507 | 44 |
| ILE | O | B | 269 | 772 | 332 | 511 | 44 |
| ASN | N | B | 270 | 750 | 336 | 511 | 44 |
| ASN | CA | B | 270 | 751 | 347 | 522 | 44 |
| ASN | CB | B | 270 | 755 | 341 | 535 | 44 |
| ASN | CG | B | 270 | 743 | 341 | 545 | 45 |
| ASN | OD1 | B | 270 | 731 | 343 | 541 | 45 |
| ASN | ND2 | B | 270 | 746 | 339 | 558 | 45 |
| ASN | C | B | 270 | 761 | 357 | 517 | 45 |
| ASN | O | B | 270 | 769 | 362 | 525 | 45 |
| GLY | N | B | 271 | 760 | 361 | 504 | 45 |
| GLY | CA | B | 271 | 769 | 371 | 499 | 46 |
| GLY | C | B | 271 | 783 | 365 | 494 | 47 |
| GLY | O | B | 271 | 789 | 371 | 485 | 46 |
| GLN | N | B | 272 | 787 | 354 | 500 | 48 |
| GLN | CA | B | 272 | 800 | 348 | 496 | 49 |
| GLN | CB | B | 272 | 805 | 338 | 506 | 49 |
| GLN | CG | B | 272 | 818 | 332 | 503 | 50 |
| GLN | CD | B | 272 | 825 | 325 | 515 | 50 |
| GLN | OE1 | B | 272 | 819 | 316 | 521 | 50 |
| GLN | NE2 | B | 272 | 837 | 330 | 518 | 50 |
| GLN | C | B | 272 | 799 | 341 | 482 | 50 |
| GLN | O | B | 272 | 793 | 331 | 480 | 50 |
| ASP | N | B | 273 | 806 | 347 | 472 | 51 |
| ASP | CA | B | 273 | 807 | 342 | 459 | 53 |
| ASP | CB | B | 273 | 815 | 352 | 450 | 53 |
| ASP | CG | B | 273 | 820 | 346 | 437 | 53 |
| ASP | OD1 | B | 273 | 812 | 339 | 431 | 54 |
| ASP | OD2 | B | 273 | 831 | 349 | 433 | 54 |
| ASP | C | B | 273 | 813 | 328 | 458 | 54 |
| ASP | O | B | 273 | 824 | 325 | 463 | 54 |
| LEU | N | B | 274 | 805 | 318 | 453 | 55 |
| LEU | CA | B | 274 | 809 | 304 | 452 | 56 |
| LEU | CB | B | 274 | 799 | 296 | 445 | 56 |
| LEU | CG | B | 274 | 791 | 287 | 454 | 56 |
| LEU | CD1 | B | 274 | 781 | 278 | 446 | 56 |
| LEU | CD2 | B | 274 | 800 | 278 | 462 | 55 |
| LEU | C | B | 274 | 823 | 304 | 444 | 57 |
| LEU | O | B | 274 | 831 | 295 | 447 | 57 |
| LYS | N | B | 275 | 824 | 313 | 435 | 58 |
| LYS | CA | B | 275 | 836 | 314 | 427 | 60 |
| LYS | CB | B | 275 | 848 | 318 | 436 | 60 |
| LYS | CG | B | 275 | 861 | 321 | 429 | 60 |
| LYS | CD | B | 275 | 873 | 323 | 439 | 61 |
| LYS | CE | B | 275 | 870 | 335 | 449 | 61 |
| LYS | NZ | B | 275 | 881 | 336 | 459 | 61 |
| LYS | C | B | 275 | 840 | 301 | 420 | 60 |
| LYS | O | B | 275 | 848 | 293 | 424 | 60 |
| MET | N | B | 276 | 833 | 300 | 408 | 60 |
| MET | CA | B | 276 | 836 | 288 | 399 | 62 |
| MET | CB | B | 276 | 825 | 278 | 402 | 61 |
| MET | CG | B | 276 | 827 | 270 | 415 | 61 |
| MET | SD | B | 276 | 814 | 257 | 416 | 62 |
| MET | CE | B | 276 | 820 | 245 | 404 | 62 |
| MET | C | B | 276 | 834 | 294 | 385 | 62 |
| MET | O | B | 276 | 828 | 304 | 383 | 62 |
| ASP | N | B | 277 | 839 | 286 | 376 | 63 |
| ASP | CA | B | 277 | 838 | 291 | 362 | 63 |
| ASP | CB | B | 277 | 843 | 280 | 352 | 64 |
| ASP | CG | B | 277 | 844 | 285 | 338 | 64 |
| ASP | OD1 | B | 277 | 833 | 289 | 333 | 64 |
| ASP | OD2 | B | 277 | 854 | 284 | 331 | 65 |
| ASP | C | B | 277 | 823 | 291 | 361 | 64 |
| ASP | O | B | 277 | 816 | 282 | 365 | 64 |
| CYS | N | B | 278 | 817 | 302 | 356 | 65 |
| CYS | CA | B | 278 | 803 | 304 | 354 | 65 |
| CYS | C | B | 278 | 797 | 293 | 345 | 64 |
| CYS | O | B | 278 | 785 | 292 | 343 | 64 |
| CYS | CB | B | 278 | 799 | 318 | 350 | 66 |
| CYS | SG | B | 278 | 805 | 322 | 333 | 67 |
| LYS | N | B | 279 | 806 | 286 | 338 | 64 |
| LYS | CA | B | 279 | 802 | 276 | 329 | 63 |
| LYS | CB | B | 279 | 813 | 272 | 319 | 63 |
| LYS | CG | B | 279 | 810 | 272 | 305 | 64 |
| LYS | CD | B | 279 | 822 | 268 | 296 | 64 |
| LYS | CE | B | 279 | 818 | 268 | 281 | 64 |
| LYS | NZ | B | 279 | 815 | 282 | 276 | 64 |
| LYS | C | B | 279 | 798 | 263 | 337 | 62 |
| LYS | O | B | 279 | 789 | 256 | 332 | 62 |
| GLU | N | B | 280 | 803 | 262 | 348 | 61 |
| GLU | CA | B | 280 | 800 | 251 | 357 | 60 |
| GLU | CB | B | 280 | 810 | 250 | 369 | 61 |
| GLU | CG | B | 280 | 824 | 249 | 365 | 62 |
| GLU | CD | B | 280 | 827 | 235 | 359 | 62 |
| GLU | OE1 | B | 280 | 823 | 225 | 364 | 62 |
| GLU | OE2 | B | 280 | 834 | 235 | 348 | 62 |
| GLU | C | B | 280 | 786 | 252 | 362 | 60 |
| GLU | O | B | 280 | 779 | 242 | 365 | 59 |
| TYR | N | B | 281 | 781 | 264 | 364 | 59 |
| TYR | CA | B | 281 | 768 | 267 | 369 | 58 |
| TYR | CB | B | 281 | 766 | 282 | 371 | 58 |
| TYR | CG | B | 281 | 775 | 288 | 382 | 57 |
| TYR | CD1 | B | 281 | 780 | 301 | 380 | 57 |
| TYR | CE1 | B | 281 | 788 | 307 | 390 | 57 |
| TYR | CD2 | B | 281 | 778 | 281 | 393 | 57 |
| TYR | CE2 | B | 281 | 786 | 287 | 403 | 57 |
| TYR | CZ | B | 281 | 791 | 300 | 401 | 57 |
| TYR | OH | B | 281 | 799 | 305 | 411 | 58 |
| TYR | C | B | 281 | 757 | 262 | 359 | 58 |
| TYR | O | B | 281 | 746 | 258 | 363 | 57 |
| ASN | N | B | 282 | 760 | 262 | 346 | 57 |
| ASN | CA | B | 282 | 751 | 258 | 336 | 57 |
| ASN | CB | B | 282 | 749 | 269 | 326 | 57 |
| ASN | CG | B | 282 | 746 | 282 | 332 | 57 |
| ASN | OD1 | B | 282 | 736 | 284 | 339 | 57 |
| ASN | ND2 | B | 282 | 754 | 292 | 329 | 57 |
| ASN | C | B | 282 | 757 | 245 | 329 | 56 |
| ASN | O | B | 282 | 754 | 242 | 318 | 56 |
| TYR | N | B | 283 | 764 | 237 | 337 | 56 |
| TYR | CA | B | 283 | 770 | 225 | 332 | 55 |
| TYR | CB | B | 283 | 778 | 217 | 343 | 56 |
| TYR | CG | B | 283 | 782 | 203 | 338 | 57 |
| TYR | CD1 | B | 283 | 787 | 200 | 326 | 57 |
| TYR | CE1 | B | 283 | 790 | 187 | 322 | 57 |
| TYR | CD2 | B | 283 | 780 | 192 | 347 | 57 |
| TYR | CE2 | B | 283 | 783 | 179 | 344 | 57 |

TABLE 1-continued

Structure Coordinates for uncomplexed BACE

| | | | | | | | |
|---|---|---|---|---|---|---|---|
| TYR | CZ | B | 283 | 788 | 177 | 331 | 57 |
| TYR | OH | B | 283 | 790 | 164 | 327 | 58 |
| TYR | C | B | 283 | 760 | 216 | 325 | 54 |
| TYR | O | B | 283 | 753 | 208 | 332 | 53 |
| ASP | N | B | 284 | 759 | 217 | 312 | 53 |
| ASP | CA | B | 284 | 750 | 210 | 303 | 52 |
| ASP | CB | B | 284 | 744 | 197 | 310 | 53 |
| ASP | CG | B | 284 | 735 | 190 | 301 | 54 |
| ASP | OD1 | B | 284 | 723 | 193 | 300 | 54 |
| ASP | OD2 | B | 284 | 740 | 181 | 293 | 54 |
| ASP | C | B | 284 | 738 | 220 | 300 | 51 |
| ASP | O | B | 284 | 736 | 223 | 289 | 51 |
| LYS | N | B | 285 | 732 | 225 | 311 | 49 |
| LYS | CA | B | 285 | 721 | 235 | 309 | 47 |
| LYS | CB | B | 285 | 710 | 229 | 300 | 47 |
| LYS | CG | B | 285 | 702 | 217 | 306 | 47 |
| LYS | CD | B | 285 | 692 | 212 | 296 | 47 |
| LYS | CE | B | 285 | 683 | 201 | 302 | 47 |
| LYS | NZ | B | 285 | 690 | 190 | 308 | 47 |
| LYS | C | B | 285 | 715 | 239 | 322 | 46 |
| LYS | O | B | 285 | 716 | 232 | 332 | 46 |
| SER | N | B | 286 | 708 | 250 | 322 | 44 |
| SER | CA | B | 286 | 700 | 255 | 333 | 42 |
| SER | CB | B | 286 | 707 | 268 | 339 | 43 |
| SER | OG | B | 286 | 720 | 265 | 344 | 43 |
| SER | C | B | 286 | 686 | 258 | 329 | 41 |
| SER | O | B | 286 | 684 | 266 | 320 | 41 |
| ILE | N | B | 287 | 676 | 252 | 335 | 40 |
| ILE | CA | B | 287 | 663 | 253 | 332 | 39 |
| ILE | CB | B | 287 | 657 | 240 | 325 | 39 |
| ILE | CG2 | B | 287 | 666 | 237 | 313 | 38 |
| ILE | CG1 | B | 287 | 656 | 229 | 335 | 38 |
| ILE | CD1 | B | 287 | 650 | 217 | 329 | 38 |
| ILE | C | B | 287 | 653 | 257 | 343 | 38 |
| ILE | O | B | 287 | 656 | 253 | 355 | 38 |
| VAL | N | B | 288 | 642 | 263 | 340 | 38 |
| VAL | CA | B | 288 | 632 | 266 | 350 | 37 |
| VAL | CB | B | 288 | 626 | 280 | 347 | 37 |
| VAL | CG1 | B | 288 | 614 | 283 | 356 | 37 |
| VAL | CG2 | B | 288 | 636 | 291 | 347 | 37 |
| VAL | C | B | 288 | 621 | 256 | 348 | 36 |
| VAL | O | B | 288 | 614 | 255 | 338 | 37 |
| ASP | N | B | 289 | 620 | 247 | 358 | 36 |
| ASP | CA | B | 289 | 610 | 236 | 357 | 36 |
| ASP | CB | B | 289 | 618 | 223 | 354 | 36 |
| ASP | CG | B | 289 | 610 | 210 | 356 | 37 |
| ASP | OD1 | B | 289 | 598 | 210 | 354 | 36 |
| ASP | OD2 | B | 289 | 617 | 200 | 360 | 37 |
| ASP | C | B | 289 | 601 | 233 | 369 | 35 |
| ASP | O | B | 289 | 605 | 229 | 379 | 35 |
| SER | N | B | 290 | 588 | 237 | 367 | 34 |
| SER | CA | B | 290 | 578 | 235 | 377 | 34 |
| SER | CB | B | 290 | 565 | 243 | 373 | 34 |
| SER | OG | B | 290 | 560 | 237 | 361 | 33 |
| SER | C | B | 290 | 575 | 221 | 380 | 35 |
| SER | O | B | 290 | 568 | 218 | 390 | 35 |
| GLY | N | B | 291 | 581 | 212 | 372 | 36 |
| GLY | CA | B | 291 | 578 | 197 | 374 | 37 |
| GLY | C | B | 291 | 588 | 191 | 384 | 38 |
| GLY | O | B | 291 | 587 | 180 | 388 | 38 |
| THR | N | B | 292 | 599 | 199 | 387 | 38 |
| THR | CA | B | 292 | 609 | 194 | 396 | 39 |
| THR | CB | B | 292 | 623 | 196 | 390 | 39 |
| THR | OG1 | B | 292 | 625 | 188 | 379 | 39 |
| THR | CG2 | B | 292 | 634 | 194 | 400 | 39 |
| THR | C | B | 292 | 608 | 201 | 410 | 40 |
| THR | O | B | 292 | 608 | 213 | 411 | 39 |
| THR | N | B | 293 | 607 | 193 | 420 | 40 |
| THR | CA | B | 293 | 605 | 198 | 434 | 41 |
| THR | CB | B | 293 | 603 | 187 | 444 | 41 |
| THR | OG1 | B | 293 | 591 | 181 | 441 | 41 |
| THR | CG2 | B | 293 | 603 | 193 | 458 | 41 |
| THR | C | B | 293 | 617 | 206 | 438 | 42 |
| THR | O | B | 293 | 617 | 218 | 441 | 42 |
| ASN | N | B | 294 | 629 | 199 | 440 | 43 |
| ASN | CA | B | 294 | 641 | 205 | 444 | 44 |
| ASN | CB | B | 294 | 651 | 194 | 448 | 43 |
| ASN | CG | B | 294 | 646 | 185 | 459 | 43 |
| ASN | OD1 | B | 294 | 636 | 188 | 465 | 44 |
| ASN | ND2 | B | 294 | 654 | 174 | 461 | 44 |
| ASN | C | B | 294 | 648 | 215 | 435 | 44 |
| ASN | O | B | 294 | 644 | 216 | 423 | 43 |
| LEU | N | B | 295 | 659 | 221 | 440 | 45 |
| LEU | CA | B | 295 | 668 | 229 | 432 | 45 |
| LEU | CB | B | 295 | 673 | 241 | 441 | 45 |
| LEU | CG | B | 295 | 684 | 250 | 437 | 46 |
| LEU | CD1 | B | 295 | 697 | 243 | 440 | 46 |
| LEU | CD2 | B | 295 | 684 | 254 | 422 | 45 |
| LEU | C | B | 295 | 679 | 220 | 428 | 46 |
| LEU | O | B | 295 | 685 | 214 | 437 | 46 |
| ARG | N | B | 296 | 681 | 217 | 416 | 47 |
| ARG | CA | B | 296 | 691 | 208 | 411 | 48 |
| ARG | CB | B | 296 | 686 | 197 | 402 | 49 |
| ARG | CG | B | 296 | 676 | 188 | 408 | 50 |
| ARG | CD | B | 296 | 673 | 176 | 399 | 51 |
| ARG | NE | B | 296 | 664 | 166 | 406 | 52 |
| ARG | CZ | B | 296 | 669 | 157 | 415 | 53 |
| ARG | NH1 | B | 296 | 661 | 149 | 420 | 53 |
| ARG | NH2 | B | 296 | 682 | 158 | 419 | 53 |
| ARG | C | B | 296 | 703 | 215 | 405 | 49 |
| ARG | O | B | 296 | 702 | 223 | 396 | 49 |
| LEU | N | B | 297 | 715 | 211 | 410 | 49 |
| LEU | CA | B | 297 | 728 | 217 | 405 | 49 |
| LEU | CB | B | 297 | 734 | 225 | 416 | 49 |
| LEU | CG | B | 297 | 725 | 237 | 423 | 49 |
| LEU | CD1 | B | 297 | 731 | 241 | 436 | 49 |
| LEU | CD2 | B | 297 | 725 | 248 | 413 | 49 |
| LEU | C | B | 297 | 738 | 206 | 400 | 50 |
| LEU | O | B | 297 | 738 | 195 | 405 | 50 |
| PRO | N | B | 298 | 746 | 210 | 391 | 51 |
| PRO | CD | B | 298 | 747 | 223 | 383 | 51 |
| PRO | CA | B | 298 | 756 | 200 | 385 | 52 |
| PRO | CB | B | 298 | 764 | 209 | 376 | 52 |
| PRO | CG | B | 298 | 754 | 219 | 371 | 51 |
| PRO | C | B | 298 | 764 | 195 | 397 | 53 |
| PRO | O | B | 298 | 768 | 203 | 406 | 53 |
| LYS | N | B | 299 | 767 | 182 | 397 | 53 |
| LYS | CA | B | 299 | 774 | 176 | 408 | 54 |
| LYS | CB | B | 299 | 780 | 163 | 404 | 54 |
| LYS | CG | B | 299 | 788 | 156 | 415 | 55 |
| LYS | CD | B | 299 | 779 | 153 | 427 | 55 |
| LYS | CE | B | 299 | 786 | 147 | 439 | 55 |
| LYS | NZ | B | 299 | 778 | 145 | 451 | 55 |
| LYS | C | B | 299 | 786 | 185 | 415 | 54 |
| LYS | O | B | 299 | 786 | 186 | 427 | 54 |
| LYS | N | B | 300 | 794 | 191 | 406 | 54 |
| LYS | CA | B | 300 | 805 | 199 | 412 | 55 |
| LYS | CB | B | 300 | 814 | 204 | 400 | 56 |
| LYS | CG | B | 300 | 821 | 193 | 393 | 57 |
| LYS | CD | B | 300 | 828 | 198 | 380 | 58 |
| LYS | CE | B | 300 | 839 | 207 | 383 | 58 |
| LYS | NZ | B | 300 | 847 | 210 | 370 | 58 |
| LYS | C | B | 300 | 799 | 211 | 420 | 55 |
| LYS | O | B | 300 | 800 | 211 | 432 | 54 |
| VAL | N | B | 301 | 792 | 220 | 413 | 54 |
| VAL | CA | B | 301 | 786 | 231 | 419 | 54 |
| VAL | CB | B | 301 | 775 | 238 | 409 | 54 |
| VAL | CG1 | B | 301 | 768 | 249 | 416 | 54 |
| VAL | CG2 | B | 301 | 783 | 243 | 397 | 54 |
| VAL | C | B | 301 | 778 | 227 | 432 | 54 |
| VAL | O | B | 301 | 779 | 234 | 442 | 54 |
| PHE | N | B | 302 | 772 | 215 | 431 | 54 |
| PHE | CA | B | 302 | 764 | 211 | 443 | 54 |
| PHE | CB | B | 302 | 758 | 197 | 440 | 54 |
| PHE | CG | B | 302 | 751 | 191 | 452 | 53 |
| PHE | CD1 | B | 302 | 739 | 197 | 457 | 53 |
| PHE | CD2 | B | 302 | 756 | 180 | 459 | 53 |
| PHE | CE1 | B | 302 | 732 | 191 | 468 | 53 |
| PHE | CE2 | B | 302 | 749 | 174 | 470 | 53 |
| PHE | CZ | B | 302 | 738 | 180 | 474 | 53 |
| PHE | C | B | 302 | 774 | 210 | 455 | 55 |
| PHE | O | B | 302 | 771 | 216 | 465 | 55 |
| GLU | N | B | 303 | 784 | 202 | 454 | 56 |
| GLU | CA | B | 303 | 794 | 200 | 465 | 57 |

TABLE 1-continued

Structure Coordinates for uncomplexed BACE

| | | | | | | | |
|---|---|---|---|---|---|---|---|
| GLU | CB | B | 303 | 806 | 192 | 460 | 58 |
| GLU | CG | B | 303 | 802 | 177 | 457 | 58 |
| GLU | CD | B | 303 | 796 | 170 | 468 | 59 |
| GLU | OE1 | B | 303 | 803 | 169 | 479 | 59 |
| GLU | OE2 | B | 303 | 785 | 165 | 467 | 59 |
| GLU | C | B | 303 | 799 | 213 | 471 | 58 |
| GLU | O | B | 303 | 799 | 215 | 483 | 58 |
| ALA | N | B | 304 | 803 | 222 | 462 | 58 |
| ALA | CA | B | 304 | 808 | 235 | 466 | 58 |
| ALA | CB | B | 304 | 813 | 243 | 454 | 58 |
| ALA | C | B | 304 | 797 | 243 | 473 | 59 |
| ALA | O | B | 304 | 800 | 251 | 482 | 59 |
| ALA | N | B | 305 | 785 | 241 | 469 | 60 |
| ALA | CA | B | 305 | 773 | 248 | 475 | 60 |
| ALA | CB | B | 305 | 761 | 248 | 466 | 60 |
| ALA | C | B | 305 | 770 | 242 | 489 | 60 |
| ALA | O | B | 305 | 766 | 249 | 498 | 61 |
| VAL | N | B | 306 | 771 | 228 | 489 | 61 |
| VAL | CA | B | 306 | 767 | 221 | 501 | 61 |
| VAL | CB | B | 306 | 767 | 206 | 499 | 61 |
| VAL | CG1 | B | 306 | 761 | 199 | 511 | 61 |
| VAL | CG2 | B | 306 | 760 | 202 | 486 | 61 |
| VAL | C | B | 306 | 776 | 224 | 513 | 61 |
| VAL | O | B | 306 | 772 | 226 | 524 | 61 |
| LYS | N | B | 307 | 789 | 225 | 510 | 61 |
| LYS | CA | B | 307 | 799 | 229 | 521 | 61 |
| LYS | CB | B | 307 | 813 | 229 | 515 | 62 |
| LYS | CG | B | 307 | 818 | 215 | 509 | 63 |
| LYS | CD | B | 307 | 818 | 203 | 518 | 63 |
| LYS | CE | B | 307 | 804 | 196 | 517 | 63 |
| LYS | NZ | B | 307 | 803 | 185 | 527 | 63 |
| LYS | C | B | 307 | 796 | 242 | 526 | 61 |
| LYS | O | B | 307 | 793 | 244 | 538 | 60 |
| SER | N | B | 308 | 797 | 252 | 517 | 60 |
| SER | CA | B | 308 | 794 | 266 | 521 | 60 |
| SER | CB | B | 308 | 793 | 275 | 509 | 60 |
| SER | OG | B | 308 | 792 | 289 | 512 | 60 |
| SER | C | B | 308 | 782 | 268 | 530 | 60 |
| SER | O | B | 308 | 782 | 275 | 539 | 60 |
| ILE | N | B | 309 | 771 | 260 | 526 | 60 |
| ILE | CA | B | 309 | 759 | 260 | 534 | 60 |
| ILE | CB | B | 309 | 747 | 254 | 526 | 59 |
| ILE | CG2 | B | 309 | 735 | 254 | 534 | 59 |
| ILE | CG1 | B | 309 | 745 | 262 | 513 | 59 |
| ILE | CD1 | B | 309 | 734 | 256 | 504 | 59 |
| ILE | C | B | 309 | 761 | 253 | 547 | 60 |
| ILE | O | B | 309 | 754 | 256 | 557 | 60 |
| LYS | N | B | 310 | 770 | 243 | 547 | 61 |
| LYS | CA | B | 310 | 772 | 235 | 559 | 61 |
| LYS | CB | B | 310 | 782 | 224 | 556 | 62 |
| LYS | CG | B | 310 | 775 | 211 | 550 | 62 |
| LYS | CD | B | 310 | 785 | 200 | 549 | 62 |
| LYS | CE | B | 310 | 779 | 187 | 544 | 63 |
| LYS | NZ | B | 310 | 769 | 182 | 553 | 63 |
| LYS | C | B | 310 | 779 | 245 | 569 | 61 |
| LYS | O | B | 310 | 775 | 246 | 581 | 61 |
| ALA | N | B | 311 | 789 | 252 | 564 | 61 |
| ALA | CA | B | 311 | 797 | 261 | 573 | 61 |
| ALA | CB | B | 311 | 807 | 269 | 564 | 61 |
| ALA | C | B | 311 | 787 | 271 | 579 | 62 |
| ALA | O | B | 311 | 785 | 271 | 591 | 61 |
| ALA | N | B | 312 | 781 | 280 | 571 | 62 |
| ALA | CA | B | 312 | 772 | 290 | 575 | 62 |
| ALA | CB | B | 312 | 764 | 296 | 563 | 62 |
| ALA | C | B | 312 | 762 | 286 | 586 | 62 |
| ALA | O | B | 312 | 759 | 293 | 595 | 62 |
| SER | N | B | 313 | 758 | 273 | 586 | 63 |
| SER | CA | B | 313 | 749 | 268 | 596 | 64 |
| SER | CB | B | 313 | 738 | 260 | 589 | 64 |
| SER | OG | B | 313 | 743 | 250 | 580 | 64 |
| SER | C | B | 313 | 755 | 260 | 607 | 64 |
| SER | O | B | 313 | 748 | 254 | 615 | 64 |
| SER | N | B | 314 | 768 | 259 | 607 | 65 |
| SER | CA | B | 314 | 776 | 252 | 617 | 67 |
| SER | CB | B | 314 | 791 | 255 | 617 | 66 |
| SER | OG | B | 314 | 793 | 269 | 620 | 67 |
| SER | C | B | 314 | 770 | 253 | 631 | 68 |
| SER | O | B | 314 | 771 | 244 | 639 | 68 |
| THR | N | B | 315 | 766 | 265 | 635 | 69 |
| THR | CA | B | 315 | 760 | 267 | 648 | 70 |
| THR | CB | B | 315 | 753 | 281 | 649 | 70 |
| THR | OG1 | B | 315 | 762 | 292 | 646 | 70 |
| THR | CG2 | B | 315 | 746 | 283 | 662 | 70 |
| THR | C | B | 315 | 751 | 256 | 652 | 70 |
| THR | O | B | 315 | 750 | 253 | 664 | 71 |
| GLU | N | B | 316 | 744 | 250 | 643 | 71 |
| GLU | CA | B | 316 | 735 | 239 | 645 | 72 |
| GLU | CB | B | 316 | 721 | 242 | 640 | 72 |
| GLU | CG | B | 316 | 711 | 244 | 650 | 72 |
| GLU | CD | B | 316 | 706 | 231 | 656 | 72 |
| GLU | OE1 | B | 316 | 714 | 222 | 658 | 72 |
| GLU | OE2 | B | 316 | 693 | 230 | 658 | 72 |
| GLU | C | B | 316 | 741 | 227 | 636 | 73 |
| GLU | O | B | 316 | 749 | 228 | 629 | 72 |
| LYS | N | B | 317 | 736 | 215 | 642 | 73 |
| LYS | CA | B | 317 | 741 | 203 | 636 | 74 |
| LYS | CB | B | 317 | 752 | 196 | 645 | 74 |
| LYS | CG | B | 317 | 766 | 201 | 641 | 74 |
| LYS | CD | B | 317 | 770 | 198 | 626 | 74 |
| LYS | CE | B | 317 | 784 | 201 | 623 | 74 |
| LYS | NZ | B | 317 | 787 | 215 | 625 | 74 |
| LYS | C | B | 317 | 731 | 192 | 632 | 74 |
| LYS | O | B | 317 | 721 | 190 | 640 | 74 |
| PHE | N | B | 318 | 733 | 185 | 621 | 75 |
| PHE | CA | B | 318 | 725 | 175 | 616 | 75 |
| PHE | CB | B | 318 | 713 | 181 | 608 | 75 |
| PHE | CG | B | 318 | 714 | 196 | 606 | 75 |
| PHE | CD1 | B | 318 | 725 | 201 | 598 | 75 |
| PHE | CD2 | B | 318 | 705 | 204 | 612 | 75 |
| PHE | CE1 | B | 318 | 726 | 215 | 596 | 75 |
| PHE | CE2 | B | 318 | 706 | 218 | 610 | 75 |
| PHE | CZ | B | 318 | 716 | 223 | 602 | 75 |
| PHE | C | B | 318 | 733 | 165 | 608 | 75 |
| PHE | O | B | 318 | 742 | 169 | 601 | 75 |
| PRO | N | B | 319 | 730 | 152 | 609 | 76 |
| PRO | CD | B | 319 | 718 | 146 | 616 | 76 |
| PRO | CA | B | 319 | 737 | 142 | 602 | 76 |
| PRO | CB | B | 319 | 730 | 129 | 605 | 76 |
| PRO | CG | B | 319 | 716 | 133 | 608 | 76 |
| PRO | C | B | 319 | 736 | 144 | 587 | 76 |
| PRO | O | B | 319 | 726 | 149 | 581 | 76 |
| ASP | N | B | 320 | 747 | 141 | 579 | 76 |
| ASP | CA | B | 320 | 748 | 143 | 565 | 76 |
| ASP | CB | B | 320 | 762 | 140 | 559 | 76 |
| ASP | CG | B | 320 | 763 | 144 | 545 | 75 |
| ASP | OD1 | B | 320 | 756 | 138 | 536 | 75 |
| ASP | OD2 | B | 320 | 771 | 153 | 542 | 75 |
| ASP | C | B | 320 | 737 | 135 | 558 | 76 |
| ASP | O | B | 320 | 734 | 138 | 546 | 76 |
| GLY | N | B | 321 | 730 | 126 | 565 | 76 |
| GLY | CA | B | 321 | 720 | 119 | 559 | 76 |
| GLY | C | B | 321 | 708 | 128 | 557 | 76 |
| GLY | O | B | 321 | 699 | 125 | 550 | 76 |
| PHE | N | B | 322 | 709 | 140 | 563 | 76 |
| PHE | CA | B | 322 | 700 | 151 | 562 | 76 |
| PHE | CB | B | 322 | 700 | 160 | 574 | 76 |
| PHE | CG | B | 322 | 694 | 173 | 572 | 76 |
| PHE | CD1 | B | 322 | 681 | 175 | 570 | 76 |
| PHE | CD2 | B | 322 | 703 | 185 | 572 | 76 |
| PHE | CE1 | B | 322 | 675 | 188 | 569 | 76 |
| PHE | CE2 | B | 322 | 697 | 197 | 571 | 76 |
| PHE | CZ | B | 322 | 684 | 199 | 569 | 76 |
| PHE | C | B | 322 | 703 | 159 | 550 | 76 |
| PHE | O | B | 322 | 694 | 163 | 542 | 76 |
| TRP | N | B | 323 | 715 | 162 | 547 | 77 |
| TRP | CA | B | 323 | 720 | 169 | 536 | 77 |
| TRP | CB | B | 323 | 734 | 174 | 537 | 77 |
| TRP | CG | B | 323 | 736 | 183 | 549 | 78 |
| TRP | CD2 | B | 323 | 737 | 197 | 549 | 78 |
| TRP | CE2 | B | 323 | 738 | 201 | 562 | 78 |
| TRP | CE3 | B | 323 | 735 | 207 | 539 | 78 |
| TRP | CD1 | B | 323 | 738 | 179 | 562 | 78 |
| TRP | NE1 | B | 323 | 739 | 190 | 570 | 78 |
| TRP | CZ2 | B | 323 | 739 | 215 | 566 | 78 |

TABLE 1-continued

Structure Coordinates for uncomplexed BACE

| | | | | | | | |
|---|---|---|---|---|---|---|---|
| TRP | CZ3 | B | 323 | 736 | 220 | 542 | 78 |
| TRP | CH2 | B | 323 | 738 | 224 | 556 | 78 |
| TRP | C | B | 323 | 718 | 162 | 523 | 77 |
| TRP | O | B | 323 | 721 | 167 | 512 | 77 |
| LEU | N | B | 324 | 713 | 149 | 524 | 77 |
| LEU | CA | B | 324 | 711 | 141 | 512 | 77 |
| LEU | CB | B | 324 | 719 | 128 | 513 | 77 |
| LEU | CG | B | 324 | 734 | 128 | 513 | 77 |
| LEU | CD1 | B | 324 | 740 | 114 | 514 | 77 |
| LEU | CD2 | B | 324 | 738 | 134 | 500 | 77 |
| LEU | C | B | 324 | 696 | 138 | 510 | 77 |
| LEU | O | B | 324 | 693 | 130 | 501 | 77 |
| GLY | N | B | 325 | 688 | 145 | 517 | 77 |
| GLY | CA | B | 325 | 674 | 143 | 516 | 78 |
| GLY | C | B | 325 | 668 | 131 | 523 | 78 |
| GLY | O | B | 325 | 656 | 129 | 523 | 78 |
| GLU | N | B | 326 | 677 | 122 | 528 | 79 |
| GLU | CA | B | 326 | 672 | 110 | 534 | 79 |
| GLU | CB | B | 326 | 684 | 101 | 537 | 79 |
| GLU | CG | B | 326 | 691 | 95 | 525 | 80 |
| GLU | CD | B | 326 | 702 | 85 | 528 | 80 |
| GLU | OE1 | B | 326 | 708 | 80 | 519 | 80 |
| GLU | OE2 | B | 326 | 703 | 81 | 540 | 80 |
| GLU | C | B | 326 | 665 | 113 | 547 | 79 |
| GLU | O | B | 326 | 652 | 113 | 547 | 79 |
| GLN | N | B | 327 | 672 | 115 | 558 | 79 |
| GLN | CA | B | 327 | 666 | 119 | 571 | 79 |
| GLN | CB | B | 327 | 675 | 114 | 582 | 79 |
| GLN | CG | B | 327 | 690 | 116 | 580 | 79 |
| GLN | CD | B | 327 | 699 | 110 | 591 | 79 |
| GLN | OE1 | B | 327 | 711 | 110 | 589 | 79 |
| GLN | NE2 | B | 327 | 692 | 104 | 601 | 79 |
| GLN | C | B | 327 | 663 | 133 | 572 | 78 |
| GLN | O | B | 327 | 671 | 142 | 568 | 78 |
| LEU | N | B | 328 | 652 | 137 | 579 | 78 |
| LEU | CA | B | 328 | 648 | 150 | 581 | 77 |
| LEU | CB | B | 328 | 633 | 152 | 578 | 77 |
| LEU | CG | B | 328 | 623 | 142 | 585 | 77 |
| LEU | CD1 | B | 328 | 622 | 145 | 599 | 77 |
| LEU | CD2 | B | 328 | 609 | 143 | 578 | 77 |
| LEU | C | B | 328 | 651 | 156 | 595 | 77 |
| LEU | O | B | 328 | 652 | 148 | 605 | 77 |
| VAL | N | B | 329 | 652 | 169 | 596 | 76 |
| VAL | CA | B | 329 | 655 | 175 | 609 | 75 |
| VAL | CB | B | 329 | 666 | 186 | 607 | 75 |
| VAL | CG1 | B | 329 | 668 | 193 | 621 | 75 |
| VAL | CG2 | B | 329 | 678 | 179 | 603 | 75 |
| VAL | C | B | 329 | 642 | 182 | 614 | 75 |
| VAL | O | B | 329 | 634 | 188 | 606 | 75 |
| CYS | N | B | 330 | 640 | 182 | 627 | 74 |
| CYS | CA | B | 330 | 629 | 188 | 633 | 73 |
| CYS | C | B | 330 | 633 | 198 | 644 | 73 |
| CYS | O | B | 330 | 645 | 199 | 648 | 73 |
| CYS | CB | B | 330 | 619 | 178 | 640 | 72 |
| CYS | SG | B | 330 | 615 | 163 | 629 | 72 |
| TRP | N | B | 331 | 623 | 206 | 649 | 73 |
| TRP | CA | B | 331 | 625 | 215 | 660 | 73 |
| TRP | CB | B | 331 | 630 | 229 | 654 | 73 |
| TRP | CG | B | 331 | 645 | 229 | 650 | 72 |
| TRP | CD2 | B | 331 | 650 | 230 | 636 | 72 |
| TRP | CE2 | B | 331 | 664 | 230 | 638 | 72 |
| TRP | CE3 | B | 331 | 644 | 230 | 624 | 72 |
| TRP | CD1 | B | 331 | 655 | 229 | 658 | 72 |
| TRP | NE1 | B | 331 | 667 | 230 | 651 | 72 |
| TRP | CZ2 | B | 331 | 672 | 231 | 626 | 72 |
| TRP | CZ3 | B | 331 | 656 | 231 | 613 | 72 |
| TRP | CH2 | B | 331 | 666 | 231 | 614 | 72 |
| TRP | C | B | 331 | 612 | 217 | 667 | 73 |
| TRP | O | B | 331 | 602 | 214 | 662 | 73 |
| GLN | N | B | 332 | 613 | 223 | 679 | 73 |
| GLN | CA | B | 332 | 601 | 225 | 687 | 73 |
| GLN | CB | B | 332 | 604 | 232 | 700 | 73 |
| GLN | CG | B | 332 | 614 | 224 | 709 | 74 |
| GLN | CD | B | 332 | 627 | 221 | 702 | 74 |
| GLN | OE1 | B | 332 | 634 | 230 | 697 | 74 |
| GLN | NE2 | B | 332 | 630 | 208 | 701 | 75 |
| GLN | C | B | 332 | 591 | 234 | 679 | 72 |
| GLN | O | B | 332 | 596 | 245 | 673 | 72 |
| ALA | N | B | 333 | 579 | 231 | 678 | 71 |
| ALA | CA | B | 333 | 569 | 238 | 671 | 71 |
| ALA | CB | B | 333 | 555 | 236 | 677 | 71 |
| ALA | C | B | 333 | 572 | 253 | 670 | 70 |
| ALA | O | B | 333 | 573 | 260 | 680 | 70 |
| GLY | N | B | 334 | 574 | 258 | 657 | 69 |
| GLY | CA | B | 334 | 577 | 272 | 655 | 68 |
| GLY | C | B | 334 | 589 | 278 | 661 | 67 |
| GLY | O | B | 334 | 590 | 290 | 663 | 67 |
| THR | N | B | 335 | 599 | 269 | 664 | 65 |
| THR | CA | B | 335 | 612 | 274 | 669 | 64 |
| THR | CB | B | 335 | 615 | 267 | 683 | 64 |
| THR | OG1 | B | 335 | 618 | 253 | 680 | 64 |
| THR | CG2 | B | 335 | 604 | 268 | 692 | 64 |
| THR | C | B | 335 | 623 | 273 | 660 | 63 |
| THR | O | B | 335 | 635 | 273 | 663 | 63 |
| THR | N | B | 336 | 620 | 270 | 647 | 61 |
| THR | CA | B | 336 | 630 | 269 | 636 | 60 |
| THR | CB | B | 336 | 623 | 267 | 623 | 60 |
| THR | OG1 | B | 336 | 613 | 256 | 623 | 59 |
| THR | CG2 | B | 336 | 633 | 263 | 612 | 60 |
| THR | C | B | 336 | 639 | 280 | 636 | 58 |
| THR | O | B | 336 | 635 | 292 | 634 | 58 |
| PRO | N | B | 337 | 653 | 278 | 637 | 57 |
| PRO | CD | B | 337 | 658 | 265 | 641 | 57 |
| PRO | CA | B | 337 | 663 | 288 | 636 | 56 |
| PRO | CB | B | 337 | 675 | 281 | 643 | 56 |
| PRO | CG | B | 337 | 673 | 267 | 639 | 56 |
| PRO | C | B | 337 | 666 | 293 | 622 | 54 |
| PRO | O | B | 337 | 678 | 292 | 618 | 54 |
| TRP | N | B | 338 | 656 | 299 | 615 | 52 |
| TRP | CA | B | 338 | 658 | 303 | 602 | 51 |
| TRP | CB | B | 338 | 646 | 311 | 597 | 50 |
| TRP | CG | B | 338 | 634 | 303 | 597 | 49 |
| TRP | CD2 | B | 338 | 630 | 292 | 589 | 49 |
| TRP | CE2 | B | 338 | 617 | 288 | 593 | 49 |
| TRP | CE3 | B | 338 | 637 | 286 | 578 | 49 |
| TRP | CD1 | B | 338 | 623 | 305 | 606 | 49 |
| TRP | NE1 | B | 338 | 613 | 296 | 603 | 49 |
| TRP | CZ2 | B | 338 | 611 | 277 | 586 | 48 |
| TRP | CZ3 | B | 338 | 630 | 275 | 572 | 49 |
| TRP | CH2 | B | 338 | 617 | 271 | 576 | 48 |
| TRP | C | B | 338 | 671 | 312 | 600 | 50 |
| TRP | O | B | 338 | 678 | 311 | 589 | 50 |
| ASN | N | B | 339 | 674 | 321 | 610 | 50 |
| ASN | CA | B | 339 | 685 | 330 | 609 | 49 |
| ASN | CB | B | 339 | 685 | 339 | 621 | 49 |
| ASN | CG | B | 339 | 688 | 333 | 634 | 49 |
| ASN | OD1 | B | 339 | 700 | 330 | 637 | 49 |
| ASN | ND2 | B | 339 | 678 | 329 | 642 | 48 |
| ASN | C | B | 339 | 699 | 323 | 607 | 49 |
| ASN | O | B | 339 | 708 | 329 | 602 | 49 |
| ILE | N | B | 340 | 700 | 311 | 612 | 49 |
| ILE | CA | B | 340 | 713 | 304 | 611 | 48 |
| ILE | CB | B | 340 | 714 | 292 | 621 | 49 |
| ILE | CG2 | B | 340 | 711 | 296 | 635 | 49 |
| ILE | CG1 | B | 340 | 705 | 281 | 616 | 49 |
| ILE | CD1 | B | 340 | 705 | 269 | 625 | 50 |
| ILE | C | B | 340 | 716 | 299 | 597 | 48 |
| ILE | O | B | 340 | 728 | 298 | 593 | 47 |
| PHE | N | B | 341 | 706 | 296 | 589 | 47 |
| PHE | CA | B | 341 | 707 | 292 | 576 | 46 |
| PHE | CB | B | 341 | 695 | 284 | 571 | 46 |
| PHE | CG | B | 341 | 693 | 271 | 578 | 45 |
| PHE | CD1 | B | 341 | 701 | 260 | 573 | 46 |
| PHE | CD2 | B | 341 | 685 | 268 | 589 | 45 |
| PHE | CE1 | B | 341 | 700 | 247 | 579 | 45 |
| PHE | CE2 | B | 341 | 685 | 256 | 595 | 45 |
| PHE | CZ | B | 341 | 692 | 245 | 590 | 45 |
| PHE | C | B | 341 | 709 | 304 | 567 | 45 |
| PHE | O | B | 341 | 703 | 315 | 569 | 45 |
| PRO | N | B | 342 | 718 | 303 | 557 | 44 |
| PRO | CD | B | 342 | 726 | 291 | 554 | 44 |
| PRO | CA | B | 342 | 721 | 314 | 547 | 43 |
| PRO | CB | B | 342 | 735 | 310 | 542 | 43 |
| PRO | CG | B | 342 | 733 | 295 | 541 | 43 |

TABLE 1-continued

Structure Coordinates for uncomplexed BACE

| | | | | | | |
|---|---|---|---|---|---|---|
| PRO | C | B | 342 | 711 | 315 | 536 | 43 |
| PRO | O | B | 342 | 703 | 307 | 533 | 43 |
| VAL | N | B | 343 | 712 | 327 | 529 | 43 |
| VAL | CA | B | 343 | 704 | 329 | 517 | 42 |
| VAL | CB | B | 343 | 699 | 343 | 516 | 42 |
| VAL | CG1 | B | 343 | 691 | 347 | 529 | 43 |
| VAL | CG2 | B | 343 | 710 | 353 | 513 | 42 |
| VAL | C | B | 343 | 712 | 325 | 505 | 42 |
| VAL | O | B | 343 | 724 | 327 | 505 | 41 |
| ILE | N | B | 344 | 705 | 321 | 494 | 41 |
| ILE | CA | B | 344 | 712 | 317 | 482 | 41 |
| ILE | CB | B | 344 | 709 | 303 | 477 | 40 |
| ILE | CG2 | B | 344 | 716 | 300 | 465 | 40 |
| ILE | CG1 | B | 344 | 713 | 293 | 489 | 40 |
| ILE | CD1 | B | 344 | 708 | 279 | 487 | 41 |
| ILE | C | B | 344 | 707 | 327 | 471 | 41 |
| ILE | O | B | 344 | 695 | 329 | 469 | 41 |
| SER | N | B | 345 | 717 | 332 | 464 | 40 |
| SER | CA | B | 345 | 714 | 342 | 453 | 40 |
| SER | CB | B | 345 | 720 | 355 | 455 | 40 |
| SER | OG | B | 345 | 716 | 361 | 468 | 41 |
| SER | C | B | 345 | 719 | 336 | 440 | 41 |
| SER | O | B | 345 | 730 | 331 | 439 | 41 |
| LEU | N | B | 346 | 711 | 337 | 429 | 41 |
| LEU | CA | B | 346 | 715 | 333 | 416 | 41 |
| LEU | CB | B | 346 | 706 | 322 | 411 | 41 |
| LEU | CG | B | 346 | 705 | 308 | 418 | 41 |
| LEU | CD1 | B | 346 | 695 | 299 | 412 | 40 |
| LEU | CD2 | B | 346 | 719 | 302 | 418 | 40 |
| LEU | C | B | 346 | 714 | 345 | 407 | 41 |
| LEU | O | B | 346 | 704 | 351 | 405 | 41 |
| TYR | N | B | 347 | 726 | 348 | 401 | 41 |
| TYR | CA | B | 347 | 726 | 360 | 391 | 42 |
| TYR | CB | B | 347 | 739 | 366 | 391 | 43 |
| TYR | CG | B | 347 | 743 | 374 | 404 | 43 |
| TYR | CD1 | B | 347 | 744 | 367 | 416 | 43 |
| TYR | CE1 | B | 347 | 747 | 374 | 428 | 43 |
| TYR | CD2 | B | 347 | 745 | 388 | 404 | 43 |
| TYR | CE2 | B | 347 | 748 | 394 | 415 | 43 |
| TYR | CZ | B | 347 | 749 | 388 | 427 | 43 |
| TYR | OH | B | 347 | 752 | 394 | 439 | 44 |
| TYR | C | B | 347 | 722 | 354 | 378 | 43 |
| TYR | O | B | 347 | 728 | 344 | 374 | 43 |
| LEU | N | B | 348 | 713 | 360 | 371 | 43 |
| LEU | CA | B | 348 | 709 | 356 | 358 | 44 |
| LEU | CB | B | 348 | 694 | 352 | 358 | 44 |
| LEU | CG | B | 348 | 689 | 344 | 369 | 44 |
| LEU | CD1 | B | 348 | 673 | 344 | 369 | 44 |
| LEU | CD2 | B | 348 | 694 | 330 | 368 | 44 |
| LEU | C | B | 348 | 712 | 366 | 347 | 45 |
| LEU | O | B | 348 | 712 | 378 | 350 | 45 |
| MET | N | B | 349 | 715 | 362 | 335 | 46 |
| MET | CA | B | 349 | 718 | 371 | 324 | 48 |
| MET | CB | B | 349 | 720 | 363 | 311 | 48 |
| MET | CG | B | 349 | 724 | 372 | 299 | 49 |
| MET | SD | B | 349 | 727 | 362 | 285 | 50 |
| MET | CE | B | 349 | 743 | 355 | 289 | 50 |
| MET | C | B | 349 | 706 | 380 | 322 | 48 |
| MET | O | B | 349 | 694 | 376 | 324 | 48 |
| GLY | N | B | 350 | 709 | 393 | 320 | 49 |
| GLY | CA | B | 350 | 698 | 403 | 318 | 50 |
| GLY | C | B | 350 | 695 | 405 | 304 | 51 |
| GLY | O | B | 350 | 702 | 400 | 295 | 51 |
| GLU | N | B | 351 | 686 | 414 | 301 | 52 |
| GLU | CA | B | 351 | 682 | 417 | 287 | 53 |
| GLU | CB | B | 351 | 668 | 421 | 285 | 53 |
| GLU | CG | B | 351 | 658 | 409 | 284 | 53 |
| GLU | CD | B | 351 | 645 | 414 | 277 | 54 |
| GLU | OE1 | B | 351 | 638 | 423 | 282 | 54 |
| GLU | OE2 | B | 351 | 642 | 408 | 266 | 54 |
| GLU | C | B | 351 | 691 | 427 | 281 | 53 |
| GLU | O | B | 351 | 691 | 430 | 269 | 53 |
| VAL | N | B | 352 | 700 | 433 | 289 | 54 |
| VAL | CA | B | 352 | 709 | 444 | 284 | 55 |
| VAL | CB | B | 352 | 708 | 457 | 293 | 55 |
| VAL | CG1 | B | 352 | 718 | 467 | 287 | 54 |
| VAL | CG2 | B | 352 | 694 | 462 | 293 | 55 |
| VAL | C | B | 352 | 723 | 438 | 285 | 55 |
| VAL | O | B | 352 | 726 | 429 | 292 | 55 |
| THR | N | B | 353 | 732 | 444 | 276 | 55 |
| THR | CA | B | 353 | 746 | 439 | 275 | 56 |
| THR | CB | B | 353 | 753 | 446 | 263 | 56 |
| THR | OG1 | B | 353 | 746 | 443 | 251 | 57 |
| THR | CG2 | B | 353 | 767 | 441 | 262 | 56 |
| THR | C | B | 353 | 754 | 442 | 288 | 56 |
| THR | O | B | 353 | 754 | 452 | 294 | 56 |
| ASN | N | B | 354 | 760 | 431 | 292 | 56 |
| ASN | CA | B | 354 | 769 | 431 | 304 | 56 |
| ASN | CB | B | 354 | 781 | 441 | 302 | 57 |
| ASN | CG | B | 354 | 791 | 436 | 292 | 57 |
| ASN | OD1 | B | 354 | 797 | 426 | 294 | 57 |
| ASN | ND2 | B | 354 | 792 | 443 | 281 | 57 |
| ASN | C | B | 354 | 761 | 436 | 317 | 55 |
| ASN | O | B | 354 | 766 | 440 | 327 | 56 |
| GLN | N | B | 355 | 748 | 434 | 316 | 54 |
| GLN | CA | B | 355 | 739 | 437 | 327 | 52 |
| GLN | CB | B | 355 | 728 | 448 | 322 | 53 |
| GLN | CG | B | 355 | 719 | 453 | 333 | 53 |
| GLN | CD | B | 355 | 713 | 467 | 329 | 53 |
| GLN | OE1 | B | 355 | 701 | 470 | 332 | 53 |
| GLN | NE2 | B | 355 | 722 | 476 | 324 | 53 |
| GLN | C | B | 355 | 732 | 425 | 331 | 51 |
| GLN | O | B | 355 | 725 | 418 | 324 | 51 |
| SER | N | B | 356 | 733 | 422 | 344 | 49 |
| SER | CA | B | 356 | 727 | 410 | 350 | 48 |
| SER | CB | B | 356 | 737 | 400 | 354 | 48 |
| SER | OG | B | 356 | 745 | 404 | 365 | 48 |
| SER | C | B | 356 | 719 | 414 | 362 | 46 |
| SER | O | B | 356 | 719 | 426 | 366 | 46 |
| PHE | N | B | 357 | 711 | 405 | 368 | 44 |
| PHE | CA | B | 357 | 703 | 407 | 380 | 42 |
| PHE | CB | B | 357 | 689 | 411 | 376 | 42 |
| PHE | CG | B | 357 | 680 | 400 | 372 | 41 |
| PHE | CD1 | B | 357 | 674 | 392 | 381 | 41 |
| PHE | CD2 | B | 357 | 679 | 397 | 358 | 41 |
| PHE | CE1 | B | 357 | 665 | 381 | 376 | 41 |
| PHE | CE2 | B | 357 | 671 | 387 | 354 | 41 |
| PHE | CZ | B | 357 | 664 | 379 | 363 | 41 |
| PHE | C | B | 357 | 704 | 395 | 388 | 41 |
| PHE | O | B | 357 | 708 | 384 | 383 | 41 |
| ARG | N | B | 358 | 699 | 395 | 401 | 40 |
| ARG | CA | B | 358 | 699 | 383 | 409 | 39 |
| ARG | CB | B | 358 | 710 | 385 | 420 | 40 |
| ARG | CG | B | 358 | 707 | 394 | 431 | 41 |
| ARG | CD | B | 358 | 718 | 398 | 440 | 42 |
| ARG | NE | B | 358 | 714 | 407 | 450 | 42 |
| ARG | CZ | B | 358 | 722 | 416 | 457 | 43 |
| ARG | NH1 | B | 358 | 735 | 416 | 454 | 42 |
| ARG | NH2 | B | 358 | 717 | 424 | 466 | 42 |
| ARG | C | B | 358 | 686 | 381 | 416 | 38 |
| ARG | O | B | 358 | 678 | 390 | 418 | 38 |
| ILE | N | B | 359 | 684 | 368 | 420 | 37 |
| ILE | CA | B | 359 | 672 | 364 | 427 | 36 |
| ILE | CB | B | 359 | 664 | 354 | 419 | 36 |
| ILE | CG2 | B | 359 | 658 | 361 | 407 | 35 |
| ILE | CG1 | B | 359 | 672 | 342 | 415 | 35 |
| ILE | CD1 | B | 359 | 664 | 331 | 408 | 35 |
| ILE | C | B | 359 | 678 | 357 | 440 | 35 |
| ILE | O | B | 359 | 688 | 351 | 439 | 36 |
| THR | N | B | 360 | 671 | 359 | 451 | 35 |
| THR | CA | B | 360 | 675 | 353 | 464 | 34 |
| THR | CB | B | 360 | 681 | 364 | 473 | 34 |
| THR | OG1 | B | 360 | 692 | 371 | 466 | 34 |
| THR | CG2 | B | 360 | 687 | 358 | 486 | 33 |
| THR | C | B | 360 | 664 | 346 | 471 | 35 |
| THR | O | B | 360 | 653 | 352 | 473 | 34 |
| ILE | N | B | 361 | 667 | 334 | 475 | 35 |
| ILE | CA | B | 361 | 657 | 326 | 483 | 35 |
| ILE | CB | B | 361 | 655 | 312 | 476 | 35 |
| ILE | CG2 | B | 361 | 653 | 314 | 461 | 35 |
| ILE | CG1 | B | 361 | 666 | 303 | 479 | 35 |
| ILE | CD1 | B | 361 | 663 | 288 | 475 | 34 |
| ILE | C | B | 361 | 662 | 324 | 497 | 35 |
| ILE | O | B | 361 | 674 | 325 | 500 | 35 |

TABLE 1-continued

Structure Coordinates for uncomplexed BACE

| | | | | | | | |
|---|---|---|---|---|---|---|---|
| LEU | N | B | 362 | 653 | 321 | 506 | 36 |
| LEU | CA | B | 362 | 655 | 319 | 520 | 38 |
| LEU | CB | B | 362 | 645 | 327 | 528 | 38 |
| LEU | CG | B | 362 | 643 | 341 | 525 | 38 |
| LEU | CD1 | B | 362 | 631 | 347 | 533 | 39 |
| LEU | CD2 | B | 362 | 655 | 349 | 527 | 38 |
| LEU | C | B | 362 | 654 | 304 | 524 | 40 |
| LEU | O | B | 362 | 649 | 296 | 517 | 40 |
| PRO | N | B | 363 | 659 | 300 | 536 | 41 |
| PRO | CD | B | 363 | 665 | 309 | 547 | 41 |
| PRO | CA | B | 363 | 659 | 287 | 540 | 41 |
| PRO | CB | B | 363 | 664 | 287 | 554 | 41 |
| PRO | CG | B | 363 | 661 | 301 | 559 | 41 |
| PRO | C | B | 363 | 644 | 282 | 540 | 41 |
| PRO | O | B | 363 | 641 | 270 | 539 | 41 |
| GLN | N | B | 364 | 635 | 291 | 540 | 42 |
| GLN | CA | B | 364 | 621 | 288 | 540 | 42 |
| GLN | CB | B | 364 | 612 | 300 | 543 | 42 |
| GLN | CG | B | 364 | 611 | 304 | 557 | 43 |
| GLN | CD | B | 364 | 622 | 314 | 561 | 43 |
| GLN | OE1 | B | 364 | 633 | 313 | 556 | 43 |
| GLN | NE2 | B | 364 | 620 | 322 | 571 | 43 |
| GLN | C | B | 364 | 617 | 281 | 526 | 42 |
| GLN | O | B | 364 | 607 | 275 | 525 | 41 |
| GLN | N | B | 365 | 626 | 283 | 516 | 42 |
| GLN | CA | B | 365 | 624 | 278 | 503 | 43 |
| GLN | CB | B | 365 | 628 | 288 | 492 | 42 |
| GLN | CG | B | 365 | 617 | 297 | 488 | 42 |
| GLN | CD | B | 365 | 615 | 309 | 498 | 41 |
| GLN | OE1 | B | 365 | 604 | 311 | 502 | 41 |
| GLN | NE2 | B | 365 | 625 | 316 | 501 | 41 |
| GLN | C | B | 365 | 631 | 265 | 501 | 44 |
| GLN | O | B | 365 | 625 | 255 | 496 | 45 |
| TYR | N | B | 366 | 644 | 264 | 505 | 46 |
| TYR | CA | B | 366 | 651 | 252 | 503 | 47 |
| TYR | CB | B | 366 | 666 | 255 | 500 | 47 |
| TYR | CG | B | 366 | 674 | 262 | 511 | 48 |
| TYR | CD1 | B | 366 | 676 | 256 | 524 | 48 |
| TYR | CE1 | B | 366 | 684 | 262 | 533 | 49 |
| TYR | CD2 | B | 366 | 679 | 274 | 509 | 48 |
| TYR | CE2 | B | 366 | 687 | 281 | 519 | 48 |
| TYR | CZ | B | 366 | 689 | 275 | 531 | 48 |
| TYR | OH | B | 366 | 697 | 281 | 540 | 49 |
| TYR | C | B | 366 | 650 | 241 | 515 | 48 |
| TYR | O | B | 366 | 650 | 241 | 515 | 48 |
| LEU | N | B | 367 | 657 | 231 | 514 | 49 |
| LEU | CA | B | 367 | 642 | 244 | 524 | 49 |
| LEU | CB | B | 367 | 639 | 234 | 535 | 50 |
| LEU | CG | B | 367 | 643 | 240 | 549 | 51 |
| LEU | CD1 | B | 367 | 658 | 245 | 550 | 51 |
| LEU | CD2 | B | 367 | 659 | 252 | 564 | 51 |
| LEU | C | B | 367 | 667 | 233 | 548 | 51 |
| LEU | O | B | 367 | 624 | 232 | 535 | 51 |
| ARG | N | B | 368 | 616 | 240 | 540 | 51 |
| ARG | CA | B | 368 | 620 | 221 | 528 | 53 |
| ARG | CB | B | 368 | 606 | 217 | 527 | 54 |
| ARG | CG | B | 368 | 604 | 209 | 514 | 54 |
| ARG | CD | B | 368 | 590 | 204 | 512 | 55 |
| ARG | NE | B | 368 | 588 | 199 | 497 | 55 |
| ARG | CZ | B | 368 | 598 | 189 | 494 | 56 |
| ARG | NH1 | B | 368 | 597 | 176 | 498 | 56 |
| ARG | NH2 | B | 368 | 587 | 172 | 506 | 56 |
| ARG | C | B | 368 | 606 | 167 | 494 | 56 |
| ARG | O | B | 368 | 600 | 210 | 539 | 54 |
| PRO | N | B | 369 | 605 | 200 | 544 | 54 |
| PRO | CD | B | 369 | 589 | 215 | 544 | 55 |
| PRO | CA | B | 369 | 582 | 228 | 540 | 55 |
| PRO | CB | B | 369 | 571 | 221 | 559 | 55 |
| PRO | CG | B | 369 | 576 | 233 | 553 | 55 |
| PRO | C | B | 369 | 575 | 197 | 553 | 56 |
| PRO | O | B | 369 | 572 | 194 | 541 | 56 |
| VAL | N | B | 370 | 573 | 188 | 563 | 56 |
| VAL | CA | B | 370 | 567 | 175 | 561 | 57 |
| VAL | CB | B | 370 | 578 | 164 | 562 | 57 |
| VAL | CG1 | B | 370 | 588 | 166 | 551 | 57 |
| VAL | CG2 | B | 370 | 584 | 165 | 576 | 57 |
| VAL | C | B | 370 | 556 | 172 | 571 | 57 |
| VAL | O | B | 370 | 558 | 171 | 583 | 57 |
| ASP | N | B | 379 | 576 | 206 | 639 | 68 |
| ASP | CA | B | 379 | 580 | 211 | 626 | 68 |
| ASP | CB | B | 379 | 582 | 226 | 626 | 67 |
| ASP | CG | B | 379 | 569 | 234 | 629 | 67 |
| ASP | OD1 | B | 379 | 570 | 246 | 630 | 67 |
| ASP | OD2 | B | 379 | 559 | 227 | 631 | 67 |
| ASP | C | B | 379 | 592 | 204 | 621 | 68 |
| ASP | O | B | 379 | 603 | 205 | 627 | 68 |
| CYS | N | B | 380 | 591 | 197 | 610 | 68 |
| CYS | CA | B | 380 | 603 | 190 | 604 | 68 |
| CYS | C | B | 380 | 605 | 194 | 590 | 67 |
| CYS | O | B | 380 | 595 | 197 | 583 | 67 |
| CYS | CB | B | 380 | 601 | 174 | 605 | 69 |
| CYS | SG | B | 380 | 597 | 168 | 621 | 71 |
| TYR | N | B | 381 | 617 | 193 | 585 | 66 |
| TYR | CA | B | 381 | 620 | 197 | 571 | 65 |
| TYR | CB | B | 381 | 626 | 211 | 571 | 65 |
| TYR | CG | B | 381 | 618 | 221 | 579 | 65 |
| TYR | CD1 | B | 381 | 618 | 221 | 593 | 65 |
| TYR | CE1 | B | 381 | 611 | 230 | 600 | 65 |
| TYR | CD2 | B | 381 | 610 | 231 | 573 | 65 |
| TYR | CE2 | B | 381 | 603 | 240 | 580 | 65 |
| TYR | CZ | B | 381 | 604 | 240 | 594 | 65 |
| TYR | OH | B | 381 | 596 | 249 | 601 | 65 |
| TYR | C | B | 381 | 630 | 188 | 564 | 64 |
| TYR | O | B | 381 | 637 | 180 | 571 | 64 |
| LYS | N | B | 382 | 631 | 189 | 551 | 63 |
| LYS | CA | B | 382 | 640 | 181 | 543 | 62 |
| LYS | CB | B | 382 | 633 | 171 | 534 | 62 |
| LYS | CG | B | 382 | 629 | 158 | 541 | 63 |
| LYS | CD | B | 382 | 625 | 147 | 531 | 63 |
| LYS | CE | B | 382 | 623 | 133 | 538 | 63 |
| LYS | NZ | B | 382 | 618 | 123 | 529 | 63 |
| LYS | C | B | 382 | 648 | 190 | 534 | 60 |
| LYS | O | B | 382 | 642 | 200 | 529 | 61 |
| PHE | N | B | 383 | 661 | 188 | 533 | 59 |
| PHE | CA | B | 383 | 669 | 196 | 524 | 57 |
| PHE | CB | B | 383 | 684 | 192 | 527 | 56 |
| PHE | CG | B | 383 | 694 | 202 | 521 | 55 |
| PHE | CD1 | B | 383 | 693 | 215 | 524 | 55 |
| PHE | CD2 | B | 383 | 704 | 197 | 513 | 55 |
| PHE | CE1 | B | 383 | 703 | 224 | 520 | 55 |
| PHE | CE2 | B | 383 | 714 | 206 | 508 | 55 |
| PHE | CZ | B | 383 | 713 | 220 | 512 | 55 |
| PHE | C | B | 383 | 665 | 194 | 510 | 56 |
| PHE | O | B | 383 | 668 | 184 | 504 | 56 |
| ALA | N | B | 384 | 658 | 204 | 504 | 55 |
| ALA | CA | B | 384 | 653 | 203 | 491 | 54 |
| ALA | CB | B | 384 | 640 | 211 | 490 | 54 |
| ALA | C | B | 384 | 663 | 208 | 480 | 53 |
| ALA | O | B | 384 | 659 | 213 | 470 | 53 |
| ILE | N | B | 385 | 676 | 206 | 482 | 53 |
| ILE | CA | B | 385 | 686 | 209 | 472 | 53 |
| ILE | CB | B | 385 | 696 | 220 | 478 | 53 |
| ILE | CG2 | B | 385 | 707 | 223 | 468 | 52 |
| ILE | CG1 | B | 385 | 689 | 233 | 482 | 53 |
| ILE | CD1 | B | 385 | 698 | 244 | 486 | 52 |
| ILE | C | B | 385 | 693 | 196 | 469 | 53 |
| ILE | O | B | 385 | 696 | 188 | 478 | 53 |
| SER | N | B | 386 | 696 | 194 | 456 | 53 |
| SER | CA | B | 386 | 703 | 182 | 452 | 53 |
| SER | CB | B | 386 | 692 | 171 | 451 | 53 |
| SER | OG | B | 386 | 682 | 175 | 442 | 53 |
| SER | C | B | 386 | 711 | 182 | 440 | 53 |
| SER | O | B | 386 | 710 | 191 | 432 | 53 |
| GLN | N | B | 387 | 720 | 173 | 439 | 54 |
| GLN | CA | B | 387 | 729 | 171 | 428 | 54 |
| GLN | CB | B | 387 | 741 | 162 | 432 | 54 |
| GLN | CG | B | 387 | 737 | 150 | 439 | 55 |
| GLN | CD | B | 387 | 748 | 142 | 445 | 55 |
| GLN | OE1 | B | 387 | 757 | 137 | 438 | 56 |
| GLN | NE2 | B | 387 | 749 | 141 | 458 | 55 |
| GLN | C | B | 387 | 723 | 166 | 415 | 54 |
| GLN | O | B | 387 | 713 | 159 | 415 | 53 |
| SER | N | B | 388 | 729 | 170 | 403 | 54 |
| SER | CA | B | 388 | 724 | 166 | 390 | 54 |

TABLE 1-continued

Structure Coordinates for uncomplexed BACE

| SER | CB  | B | 388 | 714 | 176 | 385 | 54 |
| --- | --- | - | --- | --- | --- | --- | -- |
| SER | OG  | B | 388 | 712 | 175 | 371 | 54 |
| SER | C   | B | 388 | 736 | 165 | 380 | 54 |
| SER | O   | B | 388 | 747 | 170 | 383 | 55 |
| SER | N   | B | 389 | 734 | 158 | 369 | 55 |
| SER | CA  | B | 389 | 745 | 157 | 359 | 55 |
| SER | CB  | B | 389 | 750 | 142 | 358 | 55 |
| SER | OG  | B | 389 | 739 | 134 | 354 | 55 |
| SER | C   | B | 389 | 739 | 162 | 343 | 54 |
| SER | O   | B | 389 | 746 | 161 | 335 | 55 |
| THR | N   | B | 390 | 727 | 166 | 346 | 54 |
| THR | CA  | B | 390 | 720 | 170 | 334 | 53 |
| THR | CB  | B | 390 | 706 | 163 | 332 | 53 |
| THR | OG1 | B | 390 | 698 | 165 | 344 | 53 |
| THR | CG2 | B | 390 | 708 | 149 | 329 | 53 |
| THR | C   | B | 390 | 717 | 185 | 335 | 52 |
| THR | O   | B | 390 | 707 | 191 | 330 | 51 |
| GLY | N   | B | 391 | 726 | 192 | 342 | 50 |
| GLY | CA  | B | 391 | 725 | 207 | 344 | 49 |
| GLY | C   | B | 391 | 717 | 211 | 356 | 47 |
| GLY | O   | B | 391 | 712 | 203 | 363 | 47 |
| THR | N   | B | 392 | 716 | 224 | 357 | 46 |
| THR | CA  | B | 392 | 709 | 230 | 368 | 45 |
| THR | CB  | B | 392 | 713 | 245 | 370 | 46 |
| THR | OG1 | B | 392 | 727 | 246 | 374 | 46 |
| THR | CG2 | B | 392 | 704 | 252 | 381 | 45 |
| THR | C   | B | 392 | 694 | 230 | 365 | 44 |
| THR | O   | B | 392 | 689 | 233 | 354 | 43 |
| VAL | N   | B | 393 | 686 | 226 | 376 | 43 |
| VAL | CA  | B | 393 | 672 | 226 | 374 | 43 |
| VAL | CB  | B | 393 | 666 | 212 | 376 | 42 |
| VAL | CG1 | B | 393 | 650 | 213 | 375 | 42 |
| VAL | CG2 | B | 393 | 671 | 203 | 365 | 42 |
| VAL | C   | B | 393 | 666 | 235 | 385 | 42 |
| VAL | O   | B | 393 | 665 | 231 | 397 | 42 |
| MET | N   | B | 394 | 661 | 247 | 381 | 42 |
| MET | CA  | B | 394 | 655 | 256 | 391 | 41 |
| MET | CB  | B | 394 | 656 | 270 | 385 | 41 |
| MET | CG  | B | 394 | 670 | 275 | 384 | 42 |
| MET | SD  | B | 394 | 671 | 290 | 374 | 43 |
| MET | CE  | B | 394 | 662 | 301 | 385 | 43 |
| MET | C   | B | 394 | 640 | 252 | 392 | 41 |
| MET | O   | B | 394 | 632 | 256 | 385 | 41 |
| GLY | N   | B | 395 | 638 | 243 | 402 | 40 |
| GLY | CA  | B | 395 | 625 | 238 | 405 | 40 |
| GLY | C   | B | 395 | 617 | 246 | 415 | 40 |
| GLY | O   | B | 395 | 619 | 258 | 417 | 39 |
| ALA | N   | B | 396 | 608 | 239 | 422 | 39 |
| ALA | CA  | B | 396 | 599 | 245 | 432 | 40 |
| ALA | CB  | B | 396 | 590 | 234 | 438 | 40 |
| ALA | C   | B | 396 | 605 | 254 | 442 | 40 |
| ALA | O   | B | 396 | 600 | 264 | 446 | 40 |
| VAL | N   | B | 397 | 617 | 249 | 448 | 41 |
| VAL | CA  | B | 397 | 623 | 257 | 458 | 40 |
| VAL | CB  | B | 397 | 636 | 250 | 464 | 40 |
| VAL | CG1 | B | 397 | 633 | 235 | 465 | 39 |
| VAL | CG2 | B | 397 | 648 | 253 | 455 | 40 |
| VAL | C   | B | 397 | 627 | 271 | 453 | 40 |
| VAL | O   | B | 397 | 627 | 281 | 460 | 40 |
| ILE | N   | B | 398 | 631 | 272 | 440 | 39 |
| ILE | CA  | B | 398 | 634 | 285 | 434 | 39 |
| ILE | CB  | B | 398 | 642 | 283 | 421 | 39 |
| ILE | CG2 | B | 398 | 640 | 296 | 413 | 39 |
| ILE | CG1 | B | 398 | 657 | 281 | 424 | 39 |
| ILE | CD1 | B | 398 | 664 | 294 | 430 | 39 |
| ILE | C   | B | 398 | 621 | 292 | 432 | 39 |
| ILE | O   | B | 398 | 619 | 304 | 436 | 39 |
| MET | N   | B | 399 | 612 | 286 | 424 | 38 |
| MET | CA  | B | 399 | 600 | 292 | 420 | 38 |
| MET | CB  | B | 399 | 592 | 283 | 410 | 38 |
| MET | CG  | B | 399 | 600 | 280 | 397 | 38 |
| MET | SD  | B | 399 | 591 | 270 | 386 | 38 |
| MET | CE  | B | 399 | 578 | 281 | 380 | 38 |
| MET | C   | B | 399 | 590 | 297 | 431 | 37 |
| MET | O   | B | 399 | 583 | 306 | 429 | 37 |
| GLU | N   | B | 400 | 590 | 289 | 442 | 36 |
| GLU | CA  | B | 400 | 581 | 293 | 453 | 36 |
| GLU | CB  | B | 400 | 580 | 282 | 463 | 36 |
| GLU | CG  | B | 400 | 573 | 269 | 458 | 37 |
| GLU | CD  | B | 400 | 572 | 258 | 468 | 37 |
| GLU | OE1 | B | 400 | 565 | 248 | 465 | 37 |
| GLU | OE2 | B | 400 | 578 | 259 | 479 | 37 |
| GLU | C   | B | 400 | 584 | 306 | 460 | 35 |
| GLU | O   | B | 400 | 578 | 310 | 470 | 35 |
| GLY | N   | B | 401 | 594 | 313 | 455 | 35 |
| GLY | CA  | B | 401 | 598 | 326 | 461 | 34 |
| GLY | C   | B | 401 | 595 | 337 | 452 | 34 |
| GLY | O   | B | 401 | 596 | 349 | 455 | 34 |
| PHE | N   | B | 402 | 592 | 334 | 439 | 33 |
| PHE | CA  | B | 402 | 589 | 344 | 429 | 32 |
| PHE | CB  | B | 402 | 601 | 346 | 420 | 33 |
| PHE | CG  | B | 402 | 614 | 345 | 427 | 33 |
| PHE | CD1 | B | 402 | 621 | 333 | 429 | 33 |
| PHE | CD2 | B | 402 | 619 | 357 | 433 | 34 |
| PHE | CE1 | B | 402 | 633 | 333 | 436 | 34 |
| PHE | CE2 | B | 402 | 631 | 356 | 440 | 34 |
| PHE | CZ  | B | 402 | 638 | 344 | 442 | 34 |
| PHE | C   | B | 402 | 577 | 342 | 421 | 31 |
| PHE | O   | B | 402 | 570 | 332 | 421 | 30 |
| TYR | N   | B | 403 | 573 | 353 | 413 | 30 |
| TYR | CA  | B | 403 | 562 | 352 | 404 | 29 |
| TYR | CB  | B | 403 | 554 | 365 | 404 | 28 |
| TYR | CG  | B | 403 | 542 | 365 | 395 | 27 |
| TYR | CD1 | B | 403 | 534 | 354 | 393 | 26 |
| TYR | CE1 | B | 403 | 523 | 354 | 385 | 26 |
| TYR | CD2 | B | 403 | 539 | 376 | 387 | 26 |
| TYR | CE2 | B | 403 | 528 | 377 | 378 | 26 |
| TYR | CZ  | B | 403 | 520 | 366 | 377 | 26 |
| TYR | OH  | B | 403 | 509 | 366 | 369 | 25 |
| TYR | C   | B | 403 | 570 | 351 | 392 | 29 |
| TYR | O   | B | 403 | 578 | 359 | 389 | 29 |
| VAL | N   | B | 404 | 568 | 340 | 385 | 29 |
| VAL | CA  | B | 404 | 576 | 337 | 373 | 29 |
| VAL | CB  | B | 404 | 582 | 323 | 373 | 29 |
| VAL | CG1 | B | 404 | 591 | 320 | 361 | 29 |
| VAL | CG2 | B | 404 | 590 | 321 | 386 | 28 |
| VAL | C   | B | 404 | 568 | 338 | 360 | 29 |
| VAL | O   | B | 404 | 558 | 332 | 358 | 29 |
| VAL | N   | B | 405 | 572 | 348 | 351 | 29 |
| VAL | CA  | B | 405 | 566 | 351 | 339 | 29 |
| VAL | CB  | B | 405 | 565 | 366 | 337 | 29 |
| VAL | CG1 | B | 405 | 559 | 369 | 323 | 28 |
| VAL | CG2 | B | 405 | 557 | 373 | 348 | 29 |
| VAL | C   | B | 405 | 572 | 344 | 327 | 30 |
| VAL | O   | B | 405 | 584 | 347 | 324 | 31 |
| PHE | N   | B | 406 | 565 | 335 | 320 | 30 |
| PHE | CA  | B | 406 | 571 | 328 | 309 | 30 |
| PHE | CB  | B | 406 | 566 | 313 | 309 | 29 |
| PHE | CG  | B | 406 | 572 | 305 | 320 | 29 |
| PHE | CD1 | B | 406 | 583 | 297 | 317 | 29 |
| PHE | CD2 | B | 406 | 567 | 305 | 333 | 28 |
| PHE | CE1 | B | 406 | 589 | 290 | 328 | 28 |
| PHE | CE2 | B | 406 | 573 | 298 | 343 | 28 |
| PHE | CZ  | B | 406 | 584 | 290 | 341 | 28 |
| PHE | C   | B | 406 | 566 | 335 | 296 | 31 |
| PHE | O   | B | 406 | 557 | 332 | 290 | 31 |
| ASP | N   | B | 407 | 574 | 346 | 293 | 31 |
| ASP | CA  | B | 407 | 571 | 355 | 282 | 32 |
| ASP | CB  | B | 407 | 577 | 368 | 285 | 32 |
| ASP | CG  | B | 407 | 572 | 379 | 276 | 33 |
| ASP | OD1 | B | 407 | 566 | 376 | 265 | 33 |
| ASP | OD2 | B | 407 | 575 | 391 | 278 | 34 |
| ASP | C   | B | 407 | 576 | 349 | 269 | 33 |
| ASP | O   | B | 407 | 586 | 354 | 264 | 33 |
| ARG | N   | B | 408 | 569 | 339 | 264 | 34 |
| ARG | CA  | B | 408 | 573 | 332 | 251 | 34 |
| ARG | CB  | B | 408 | 564 | 321 | 248 | 34 |
| ARG | CG  | B | 408 | 564 | 309 | 258 | 34 |
| ARG | CD  | B | 408 | 551 | 302 | 259 | 34 |
| ARG | NE  | B | 408 | 546 | 297 | 246 | 35 |
| ARG | CZ  | B | 408 | 549 | 284 | 242 | 35 |
| ARG | NH1 | B | 408 | 556 | 276 | 249 | 35 |
| ARG | NH2 | B | 408 | 544 | 281 | 230 | 35 |
| ARG | C   | B | 408 | 574 | 342 | 240 | 35 |

TABLE 1-continued

Structure Coordinates for uncomplexed BACE

| | | | | | | | |
|---|---|---|---|---|---|---|---|
| ARG | O | B | 408 | 583 | 341 | 231 | 36 |
| ALA | N | B | 409 | 564 | 351 | 239 | 36 |
| ALA | CA | B | 409 | 563 | 360 | 228 | 38 |
| ALA | CB | B | 409 | 551 | 369 | 229 | 38 |
| ALA | C | B | 409 | 576 | 369 | 227 | 39 |
| ALA | O | B | 409 | 580 | 372 | 216 | 39 |
| ARG | N | B | 410 | 582 | 372 | 238 | 40 |
| ARG | CA | B | 410 | 594 | 380 | 238 | 41 |
| ARG | CB | B | 410 | 592 | 392 | 247 | 42 |
| ARG | CG | B | 410 | 582 | 402 | 241 | 43 |
| ARG | CD | B | 410 | 580 | 415 | 249 | 44 |
| ARG | NE | B | 410 | 593 | 423 | 249 | 46 |
| ARG | CZ | B | 410 | 594 | 435 | 254 | 46 |
| ARG | NH1 | B | 410 | 583 | 442 | 258 | 46 |
| ARG | NH2 | B | 410 | 606 | 441 | 254 | 47 |
| ARG | C | B | 410 | 606 | 372 | 242 | 41 |
| ARG | O | B | 410 | 617 | 378 | 244 | 41 |
| LYS | N | B | 411 | 605 | 359 | 242 | 41 |
| LYS | CA | B | 411 | 616 | 350 | 245 | 41 |
| LYS | CB | B | 411 | 625 | 349 | 232 | 42 |
| LYS | CG | B | 411 | 635 | 338 | 232 | 43 |
| LYS | CD | B | 411 | 642 | 337 | 219 | 44 |
| LYS | CE | B | 411 | 652 | 325 | 218 | 44 |
| LYS | NZ | B | 411 | 660 | 325 | 205 | 45 |
| LYS | C | B | 411 | 623 | 354 | 257 | 40 |
| LYS | O | B | 411 | 636 | 355 | 257 | 40 |
| ARG | N | B | 412 | 616 | 355 | 268 | 39 |
| ARG | CA | B | 412 | 623 | 358 | 281 | 38 |
| ARG | CB | B | 412 | 625 | 373 | 281 | 38 |
| ARG | CG | B | 412 | 611 | 381 | 281 | 37 |
| ARG | CD | B | 412 | 613 | 396 | 281 | 37 |
| ARG | NE | B | 412 | 601 | 403 | 283 | 37 |
| ARG | CZ | B | 412 | 599 | 416 | 284 | 37 |
| ARG | NH1 | B | 412 | 610 | 424 | 284 | 37 |
| ARG | NH2 | B | 412 | 587 | 422 | 285 | 37 |
| ARG | C | B | 412 | 615 | 353 | 293 | 37 |
| ARG | O | B | 412 | 603 | 350 | 292 | 37 |
| ILE | N | B | 413 | 622 | 352 | 304 | 36 |
| ILE | CA | B | 413 | 615 | 348 | 317 | 35 |
| ILE | CB | B | 413 | 621 | 335 | 322 | 35 |
| ILE | CG2 | B | 413 | 615 | 332 | 336 | 35 |
| ILE | CG1 | B | 413 | 619 | 323 | 312 | 35 |
| ILE | CD1 | B | 413 | 624 | 310 | 317 | 36 |
| ILE | C | B | 413 | 617 | 359 | 327 | 35 |
| ILE | O | B | 413 | 629 | 363 | 330 | 35 |
| GLY | N | B | 414 | 606 | 364 | 332 | 34 |
| GLY | CA | B | 414 | 607 | 374 | 342 | 33 |
| GLY | C | B | 414 | 605 | 369 | 356 | 33 |
| GLY | O | B | 414 | 598 | 359 | 359 | 33 |
| PHE | N | B | 415 | 612 | 375 | 366 | 32 |
| PHE | CA | B | 415 | 611 | 371 | 380 | 32 |
| PHE | CB | B | 415 | 625 | 366 | 385 | 31 |
| PHE | CG | B | 415 | 628 | 352 | 379 | 31 |
| PHE | CD1 | B | 415 | 634 | 351 | 367 | 31 |
| PHE | CD2 | B | 415 | 626 | 341 | 387 | 31 |
| PHE | CE1 | B | 415 | 638 | 339 | 362 | 31 |
| PHE | CE2 | B | 415 | 630 | 328 | 382 | 32 |
| PHE | CZ | B | 415 | 636 | 327 | 369 | 32 |
| PHE | C | B | 415 | 608 | 384 | 388 | 32 |
| PHE | O | B | 415 | 612 | 395 | 385 | 32 |
| ALA | N | B | 416 | 600 | 382 | 398 | 31 |
| ALA | CA | B | 416 | 596 | 392 | 408 | 31 |
| ALA | CB | B | 416 | 584 | 400 | 403 | 30 |
| ALA | C | B | 416 | 593 | 386 | 421 | 30 |
| ALA | O | B | 416 | 590 | 374 | 421 | 30 |
| VAL | N | B | 417 | 594 | 393 | 432 | 31 |
| VAL | CA | B | 417 | 592 | 388 | 445 | 31 |
| VAL | CB | B | 417 | 594 | 398 | 456 | 31 |
| VAL | CG1 | B | 417 | 591 | 392 | 470 | 30 |
| VAL | CG2 | B | 417 | 609 | 403 | 455 | 30 |
| VAL | C | B | 417 | 577 | 383 | 445 | 31 |
| VAL | O | B | 417 | 568 | 390 | 440 | 31 |
| SER | N | B | 418 | 574 | 371 | 451 | 31 |
| SER | CA | B | 418 | 561 | 366 | 452 | 31 |
| SER | CB | B | 418 | 561 | 351 | 452 | 30 |
| SER | OG | B | 418 | 548 | 346 | 454 | 30 |
| SER | C | B | 418 | 554 | 372 | 464 | 31 |
| SER | O | B | 418 | 560 | 372 | 475 | 31 |
| ALA | N | B | 419 | 541 | 375 | 463 | 31 |
| ALA | CA | B | 419 | 533 | 380 | 474 | 32 |
| ALA | CB | B | 419 | 521 | 388 | 468 | 31 |
| ALA | C | B | 419 | 529 | 369 | 483 | 33 |
| ALA | O | B | 419 | 524 | 372 | 494 | 34 |
| CYS | N | B | 420 | 531 | 357 | 480 | 34 |
| CYS | CA | B | 420 | 527 | 346 | 489 | 36 |
| CYS | C | B | 420 | 539 | 338 | 494 | 36 |
| CYS | O | B | 420 | 537 | 329 | 502 | 36 |
| CYS | CB | B | 420 | 518 | 336 | 481 | 36 |
| CYS | SG | B | 420 | 526 | 326 | 468 | 38 |
| HIS | N | B | 421 | 551 | 342 | 490 | 37 |
| HIS | CA | B | 421 | 563 | 334 | 495 | 37 |
| HIS | CB | B | 421 | 576 | 338 | 488 | 37 |
| HIS | CG | B | 421 | 583 | 350 | 494 | 37 |
| HIS | CD2 | B | 421 | 592 | 351 | 503 | 37 |
| HIS | ND1 | B | 421 | 580 | 363 | 490 | 37 |
| HIS | CE1 | B | 421 | 588 | 371 | 497 | 37 |
| HIS | NE2 | B | 421 | 595 | 364 | 505 | 37 |
| HIS | C | B | 421 | 565 | 335 | 510 | 38 |
| HIS | O | B | 421 | 562 | 345 | 516 | 38 |
| VAL | N | B | 422 | 569 | 324 | 516 | 39 |
| VAL | CA | B | 422 | 571 | 323 | 530 | 40 |
| VAL | CB | B | 422 | 572 | 308 | 534 | 40 |
| VAL | CG1 | B | 422 | 573 | 307 | 550 | 40 |
| VAL | CG2 | B | 422 | 561 | 300 | 529 | 40 |
| VAL | C | B | 422 | 584 | 330 | 534 | 40 |
| VAL | O | B | 422 | 594 | 329 | 527 | 40 |
| HIS | N | B | 423 | 584 | 336 | 545 | 41 |
| HIS | CA | B | 423 | 596 | 344 | 550 | 42 |
| HIS | CB | B | 423 | 598 | 356 | 541 | 43 |
| HIS | CG | B | 423 | 587 | 366 | 543 | 44 |
| HIS | CD2 | B | 423 | 586 | 377 | 551 | 44 |
| HIS | ND1 | B | 423 | 575 | 365 | 536 | 44 |
| HIS | CE1 | B | 423 | 567 | 375 | 539 | 45 |
| HIS | NE2 | B | 423 | 574 | 383 | 548 | 45 |
| HIS | C | B | 423 | 594 | 348 | 564 | 42 |
| HIS | O | B | 423 | 584 | 345 | 570 | 42 |
| ASP | N | B | 424 | 604 | 354 | 570 | 42 |
| ASP | CA | B | 424 | 602 | 359 | 584 | 43 |
| ASP | CB | B | 424 | 613 | 352 | 593 | 42 |
| ASP | CG | B | 424 | 627 | 354 | 588 | 42 |
| ASP | OD1 | B | 424 | 631 | 365 | 585 | 42 |
| ASP | OD2 | B | 424 | 634 | 343 | 587 | 43 |
| ASP | C | B | 424 | 603 | 374 | 585 | 43 |
| ASP | O | B | 424 | 606 | 380 | 575 | 43 |
| GLU | N | B | 425 | 600 | 379 | 596 | 43 |
| GLU | CA | B | 425 | 601 | 394 | 598 | 44 |
| GLU | CB | B | 425 | 597 | 397 | 613 | 45 |
| GLU | CG | B | 425 | 605 | 390 | 624 | 47 |
| GLU | CD | B | 425 | 601 | 376 | 626 | 48 |
| GLU | OE1 | B | 425 | 601 | 368 | 617 | 49 |
| GLU | OE2 | B | 425 | 597 | 373 | 638 | 49 |
| GLU | C | B | 425 | 614 | 400 | 595 | 43 |
| GLU | O | B | 425 | 615 | 412 | 591 | 43 |
| PHE | N | B | 426 | 625 | 392 | 595 | 43 |
| PHE | CA | B | 426 | 638 | 397 | 593 | 42 |
| PHE | CB | B | 426 | 648 | 391 | 602 | 43 |
| PHE | CG | B | 426 | 644 | 392 | 617 | 43 |
| PHE | CD1 | B | 426 | 639 | 382 | 623 | 43 |
| PHE | CD2 | B | 426 | 646 | 405 | 623 | 44 |
| PHE | CE1 | B | 426 | 634 | 383 | 636 | 44 |
| PHE | CE2 | B | 426 | 641 | 406 | 636 | 44 |
| PHE | CZ | B | 426 | 636 | 395 | 643 | 44 |
| PHE | C | B | 426 | 643 | 396 | 578 | 41 |
| PHE | O | B | 426 | 650 | 406 | 573 | 41 |
| ARG | N | B | 427 | 640 | 386 | 571 | 41 |
| ARG | CA | B | 427 | 644 | 384 | 557 | 40 |
| ARG | CB | B | 427 | 655 | 373 | 556 | 41 |
| ARG | CG | B | 427 | 668 | 376 | 563 | 42 |
| ARG | CD | B | 427 | 679 | 366 | 560 | 42 |
| ARG | NE | B | 427 | 675 | 353 | 564 | 43 |
| ARG | CZ | B | 427 | 684 | 343 | 566 | 43 |
| ARG | NH1 | B | 427 | 697 | 345 | 564 | 43 |
| ARG | NH2 | B | 427 | 680 | 331 | 570 | 43 |
| ARG | C | B | 427 | 633 | 381 | 548 | 39 |

TABLE 1-continued

Structure Coordinates for uncomplexed BACE

| | | | | | | | |
|---|---|---|---|---|---|---|---|
| ARG | O | B | 427 | 623 | 376 | 552 | 38 |
| THR | N | B | 428 | 635 | 384 | 535 | 38 |
| THR | CA | B | 428 | 625 | 382 | 525 | 37 |
| THR | CB | B | 428 | 616 | 394 | 523 | 37 |
| THR | OG1 | B | 428 | 610 | 394 | 510 | 38 |
| THR | CG2 | B | 428 | 625 | 407 | 524 | 38 |
| THR | C | B | 428 | 632 | 378 | 512 | 37 |
| THR | O | B | 428 | 644 | 382 | 509 | 36 |
| ALA | N | B | 429 | 625 | 371 | 503 | 35 |
| ALA | CA | B | 429 | 631 | 367 | 490 | 34 |
| ALA | CB | B | 429 | 621 | 359 | 482 | 35 |
| ALA | C | B | 429 | 633 | 380 | 483 | 34 |
| ALA | O | B | 429 | 626 | 390 | 487 | 34 |
| ALA | N | B | 430 | 642 | 381 | 473 | 34 |
| ALA | CA | B | 430 | 645 | 393 | 466 | 35 |
| ALA | CB | B | 430 | 656 | 401 | 474 | 34 |
| ALA | C | B | 430 | 649 | 392 | 451 | 35 |
| ALA | O | B | 430 | 654 | 382 | 447 | 34 |
| VAL | N | B | 431 | 646 | 403 | 444 | 36 |
| VAL | CA | B | 431 | 650 | 403 | 430 | 37 |
| VAL | CB | B | 431 | 638 | 401 | 421 | 37 |
| VAL | CG1 | B | 431 | 643 | 402 | 406 | 37 |
| VAL | CG2 | B | 431 | 631 | 388 | 424 | 37 |
| VAL | C | B | 431 | 656 | 417 | 428 | 39 |
| VAL | O | B | 431 | 648 | 427 | 429 | 39 |
| GLU | N | B | 432 | 669 | 418 | 426 | 41 |
| GLU | CA | B | 432 | 675 | 431 | 425 | 42 |
| GLU | CB | B | 432 | 683 | 434 | 438 | 43 |
| GLU | CG | B | 432 | 673 | 436 | 450 | 44 |
| GLU | CD | B | 432 | 680 | 432 | 463 | 45 |
| GLU | OE1 | B | 432 | 674 | 436 | 473 | 46 |
| GLU | OE2 | B | 432 | 690 | 425 | 463 | 46 |
| GLU | C | B | 432 | 684 | 433 | 413 | 43 |
| GLU | O | B | 432 | 688 | 423 | 407 | 43 |
| GLY | N | B | 433 | 687 | 445 | 409 | 43 |
| GLY | CA | B | 433 | 696 | 448 | 398 | 44 |
| GLY | C | B | 433 | 696 | 463 | 395 | 46 |
| GLY | O | B | 433 | 689 | 470 | 401 | 45 |
| PRO | N | B | 434 | 704 | 467 | 385 | 47 |
| PRO | CD | B | 434 | 703 | 480 | 379 | 48 |
| PRO | CA | B | 434 | 713 | 458 | 377 | 49 |
| PRO | CB | B | 434 | 712 | 465 | 363 | 48 |
| PRO | CG | B | 434 | 712 | 480 | 367 | 48 |
| PRO | C | B | 434 | 727 | 457 | 382 | 50 |
| PRO | O | B | 434 | 731 | 466 | 390 | 50 |
| PHE | N | B | 435 | 734 | 447 | 378 | 52 |
| PHE | CA | B | 435 | 748 | 445 | 382 | 54 |
| PHE | CB | B | 435 | 750 | 432 | 389 | 54 |
| PHE | CG | B | 435 | 742 | 431 | 402 | 54 |
| PHE | CD1 | B | 435 | 728 | 428 | 402 | 54 |
| PHE | CD2 | B | 435 | 748 | 434 | 414 | 54 |
| PHE | CE1 | B | 435 | 721 | 427 | 414 | 54 |
| PHE | CE2 | B | 435 | 741 | 434 | 426 | 54 |
| PHE | CZ | B | 435 | 728 | 430 | 426 | 54 |
| PHE | C | B | 435 | 757 | 445 | 369 | 55 |
| PHE | O | B | 435 | 752 | 440 | 358 | 55 |
| VAL | N | B | 436 | 769 | 449 | 371 | 57 |
| VAL | CA | B | 436 | 778 | 449 | 359 | 58 |
| VAL | CB | B | 436 | 790 | 459 | 361 | 58 |
| VAL | CG1 | B | 436 | 799 | 459 | 349 | 58 |
| VAL | CG2 | B | 436 | 784 | 473 | 364 | 58 |
| VAL | C | B | 436 | 784 | 435 | 358 | 59 |
| VAL | O | B | 436 | 789 | 429 | 368 | 59 |
| THR | N | B | 437 | 783 | 429 | 347 | 61 |
| THR | CA | B | 437 | 788 | 415 | 344 | 62 |
| THR | CB | B | 437 | 777 | 405 | 347 | 62 |
| THR | OG1 | B | 437 | 770 | 407 | 359 | 62 |
| THR | CG2 | B | 437 | 783 | 391 | 346 | 62 |
| THR | C | B | 437 | 793 | 414 | 330 | 63 |
| THR | O | B | 437 | 786 | 416 | 321 | 63 |
| LEU | N | B | 438 | 806 | 410 | 329 | 65 |
| LEU | CA | B | 438 | 813 | 409 | 316 | 66 |
| LEU | CB | B | 438 | 827 | 415 | 318 | 66 |
| LEU | CG | B | 438 | 828 | 428 | 325 | 66 |
| LEU | CD1 | B | 438 | 843 | 432 | 327 | 66 |
| LEU | CD2 | B | 438 | 821 | 439 | 317 | 66 |
| LEU | C | B | 438 | 814 | 395 | 311 | 67 |
| LEU | O | B | 438 | 815 | 385 | 319 | 66 |
| ASP | N | B | 439 | 813 | 394 | 298 | 68 |
| ASP | CA | B | 439 | 814 | 381 | 291 | 69 |
| ASP | CB | B | 439 | 828 | 375 | 292 | 70 |
| ASP | CG | B | 439 | 839 | 384 | 285 | 71 |
| ASP | OD1 | B | 439 | 840 | 396 | 289 | 71 |
| ASP | OD2 | B | 439 | 846 | 379 | 276 | 71 |
| ASP | C | B | 439 | 804 | 370 | 296 | 70 |
| ASP | O | B | 439 | 808 | 359 | 299 | 70 |
| MET | N | B | 440 | 792 | 374 | 298 | 70 |
| MET | CA | B | 440 | 781 | 365 | 303 | 70 |
| MET | CB | B | 440 | 768 | 373 | 305 | 69 |
| MET | CG | B | 440 | 769 | 383 | 316 | 69 |
| MET | SD | B | 440 | 753 | 389 | 321 | 68 |
| MET | CE | B | 440 | 751 | 402 | 310 | 68 |
| MET | C | B | 440 | 779 | 353 | 293 | 70 |
| MET | O | B | 440 | 777 | 342 | 298 | 70 |
| GLU | N | B | 441 | 778 | 356 | 280 | 71 |
| GLU | CA | B | 441 | 775 | 345 | 271 | 71 |
| GLU | CB | B | 441 | 775 | 351 | 257 | 72 |
| GLU | CG | B | 441 | 770 | 341 | 246 | 73 |
| GLU | CD | B | 441 | 757 | 334 | 250 | 73 |
| GLU | OE1 | B | 441 | 747 | 341 | 251 | 73 |
| GLU | OE2 | B | 441 | 757 | 322 | 253 | 73 |
| GLU | C | B | 441 | 785 | 334 | 272 | 71 |
| GLU | O | B | 441 | 783 | 323 | 267 | 71 |
| ASP | N | B | 442 | 797 | 336 | 278 | 71 |
| ASP | CA | B | 442 | 807 | 326 | 279 | 71 |
| ASP | CB | B | 442 | 821 | 332 | 283 | 71 |
| ASP | CG | B | 442 | 829 | 338 | 271 | 71 |
| ASP | OD1 | B | 442 | 831 | 330 | 261 | 71 |
| ASP | OD2 | B | 442 | 833 | 349 | 271 | 71 |
| ASP | C | B | 442 | 803 | 316 | 290 | 71 |
| ASP | O | B | 442 | 810 | 305 | 291 | 70 |
| CYS | N | B | 443 | 792 | 319 | 297 | 70 |
| CYS | CA | B | 443 | 788 | 310 | 307 | 70 |
| CYS | C | B | 443 | 779 | 299 | 302 | 71 |
| CYS | O | B | 443 | 775 | 290 | 309 | 71 |
| CYS | CB | B | 443 | 780 | 318 | 318 | 69 |
| CYS | SG | B | 443 | 789 | 332 | 325 | 68 |
| GLY | N | B | 444 | 776 | 299 | 289 | 71 |
| GLY | CA | B | 444 | 768 | 288 | 283 | 73 |
| GLY | C | B | 444 | 776 | 276 | 280 | 73 |
| GLY | O | B | 444 | 789 | 277 | 278 | 73 |
| TYR | N | B | 445 | 770 | 264 | 279 | 74 |
| TYR | CA | B | 445 | 776 | 252 | 276 | 75 |
| TYR | CB | B | 445 | 770 | 241 | 284 | 76 |
| TYR | CG | B | 445 | 774 | 226 | 280 | 76 |
| TYR | CD1 | B | 445 | 787 | 222 | 282 | 77 |
| TYR | CE1 | B | 445 | 790 | 209 | 279 | 77 |
| TYR | CD2 | B | 445 | 765 | 218 | 274 | 77 |
| TYR | CE2 | B | 445 | 768 | 205 | 271 | 77 |
| TYR | CZ | B | 445 | 781 | 200 | 273 | 77 |
| TYR | OH | B | 445 | 784 | 187 | 269 | 77 |
| TYR | C | B | 445 | 774 | 249 | 261 | 75 |
| TYR | O | B | 445 | 766 | 255 | 255 | 75 |
| ASN | N | B | 446 | 782 | 239 | 256 | 75 |
| ASN | CA | B | 446 | 781 | 236 | 242 | 75 |
| ASN | CB | B | 446 | 790 | 245 | 233 | 75 |
| ASN | CG | B | 446 | 787 | 259 | 235 | 75 |
| ASN | OD1 | B | 446 | 776 | 264 | 232 | 75 |
| ASN | ND2 | B | 446 | 797 | 267 | 240 | 76 |
| ASN | C | B | 446 | 784 | 221 | 239 | 75 |
| ASN | O | B | 446 | 789 | 215 | 249 | 75 |
| ASN | OXT | B | 446 | 782 | 216 | 228 | 75 |
| GLY | C | C | 56 | 276 | 230 | 766 | 67 |
| GLY | O | C | 56 | 273 | 229 | 777 | 67 |
| GLY | N | C | 56 | 300 | 227 | 773 | 67 |
| GLY | CA | C | 56 | 291 | 231 | 762 | 67 |
| ALA | N | C | 57 | 268 | 231 | 756 | 67 |
| ALA | CA | C | 57 | 253 | 230 | 758 | 66 |
| ALA | CB | C | 57 | 247 | 243 | 753 | 66 |
| ALA | C | C | 57 | 247 | 218 | 751 | 66 |
| ALA | O | C | 57 | 247 | 217 | 738 | 66 |
| GLY | N | C | 58 | 242 | 209 | 759 | 64 |
| GLY | CA | C | 58 | 236 | 197 | 753 | 63 |
| GLY | C | C | 58 | 222 | 195 | 757 | 62 |

TABLE 1-continued

Structure Coordinates for uncomplexed BACE

| | | | | | | |
|---|---|---|---|---|---|---|
| GLY | O | C | 58 | 217 | 183 | 757 | 62 |
| SER | N | C | 59 | 215 | 205 | 762 | 61 |
| SER | CA | C | 59 | 202 | 204 | 767 | 60 |
| SER | CB | C | 59 | 201 | 206 | 782 | 60 |
| SER | OG | C | 59 | 188 | 205 | 787 | 61 |
| SER | C | C | 59 | 192 | 215 | 760 | 59 |
| SER | O | C | 59 | 196 | 227 | 759 | 59 |
| PHE | N | C | 60 | 181 | 210 | 755 | 58 |
| PHE | CA | C | 60 | 171 | 219 | 749 | 57 |
| PHE | CB | C | 60 | 170 | 216 | 734 | 56 |
| PHE | CG | C | 60 | 183 | 216 | 727 | 56 |
| PHE | CD1 | C | 60 | 192 | 206 | 729 | 56 |
| PHE | CD2 | C | 60 | 186 | 226 | 718 | 56 |
| PHE | CE1 | C | 60 | 204 | 205 | 722 | 56 |
| PHE | CE2 | C | 60 | 198 | 226 | 711 | 56 |
| PHE | CZ | C | 60 | 207 | 215 | 713 | 56 |
| PHE | C | C | 60 | 157 | 218 | 756 | 57 |
| PHE | O | C | 60 | 148 | 213 | 750 | 56 |
| VAL | N | C | 61 | 156 | 222 | 768 | 56 |
| VAL | CA | C | 61 | 144 | 221 | 776 | 56 |
| VAL | CB | C | 61 | 145 | 228 | 790 | 56 |
| VAL | CG1 | C | 61 | 134 | 224 | 799 | 56 |
| VAL | CG2 | C | 61 | 159 | 224 | 796 | 56 |
| VAL | C | C | 61 | 132 | 227 | 769 | 55 |
| VAL | O | C | 61 | 121 | 221 | 769 | 55 |
| GLU | N | C | 62 | 133 | 238 | 762 | 54 |
| GLU | CA | C | 62 | 122 | 244 | 755 | 54 |
| GLU | CB | C | 62 | 126 | 258 | 750 | 55 |
| GLU | CG | C | 62 | 126 | 269 | 761 | 56 |
| GLU | CD | C | 62 | 128 | 283 | 755 | 56 |
| GLU | OE1 | C | 62 | 138 | 285 | 747 | 57 |
| GLU | OE2 | C | 62 | 120 | 292 | 758 | 57 |
| GLU | C | C | 62 | 116 | 236 | 744 | 53 |
| GLU | O | C | 62 | 105 | 239 | 740 | 53 |
| MET | N | C | 63 | 123 | 226 | 740 | 51 |
| MET | CA | C | 63 | 117 | 217 | 729 | 50 |
| MET | CB | C | 63 | 127 | 216 | 718 | 49 |
| MET | CG | C | 63 | 129 | 229 | 710 | 49 |
| MET | SD | C | 63 | 140 | 227 | 696 | 48 |
| MET | CE | C | 63 | 152 | 239 | 700 | 48 |
| MET | C | C | 63 | 113 | 203 | 734 | 49 |
| MET | O | C | 63 | 106 | 196 | 727 | 49 |
| VAL | N | C | 64 | 119 | 199 | 745 | 49 |
| VAL | CA | C | 64 | 115 | 186 | 751 | 48 |
| VAL | CB | C | 64 | 122 | 183 | 764 | 48 |
| VAL | CG1 | C | 64 | 117 | 170 | 770 | 47 |
| VAL | CG2 | C | 64 | 137 | 183 | 763 | 47 |
| VAL | C | C | 64 | 100 | 185 | 752 | 47 |
| VAL | O | C | 64 | 94 | 194 | 757 | 47 |
| ASP | N | C | 65 | 95 | 173 | 748 | 47 |
| ASP | CA | C | 65 | 80 | 171 | 749 | 47 |
| ASP | CB | C | 65 | 76 | 172 | 764 | 47 |
| ASP | CG | C | 65 | 62 | 166 | 766 | 47 |
| ASP | OD1 | C | 65 | 55 | 173 | 774 | 48 |
| ASP | OD2 | C | 65 | 59 | 156 | 761 | 47 |
| ASP | C | C | 65 | 72 | 181 | 741 | 47 |
| ASP | O | C | 65 | 61 | 184 | 745 | 47 |
| ASN | N | C | 66 | 76 | 184 | 729 | 47 |
| ASN | CA | C | 66 | 69 | 193 | 720 | 47 |
| ASN | CB | C | 66 | 78 | 203 | 713 | 45 |
| ASN | CG | C | 66 | 89 | 196 | 704 | 44 |
| ASN | OD1 | C | 66 | 89 | 183 | 703 | 43 |
| ASN | ND2 | C | 66 | 97 | 203 | 697 | 44 |
| ASN | C | C | 66 | 60 | 186 | 710 | 48 |
| ASN | O | C | 66 | 53 | 192 | 702 | 48 |
| LEU | N | C | 67 | 60 | 173 | 711 | 48 |
| LEU | CA | C | 67 | 52 | 164 | 702 | 50 |
| LEU | CB | C | 67 | 61 | 153 | 696 | 49 |
| LEU | CG | C | 67 | 74 | 157 | 689 | 49 |
| LEU | CD1 | C | 67 | 79 | 144 | 681 | 49 |
| LEU | CD2 | C | 67 | 71 | 168 | 678 | 49 |
| LEU | C | C | 67 | 41 | 158 | 709 | 52 |
| LEU | O | C | 67 | 42 | 154 | 721 | 52 |
| ARG | N | C | 68 | 29 | 157 | 702 | 54 |
| ARG | CA | C | 68 | 17 | 151 | 708 | 56 |
| ARG | CB | C | 68 | 8 | 161 | 714 | 57 |
| ARG | CG | C | 68 | 15 | 169 | 725 | 58 |
| ARG | CD | C | 68 | 6 | 181 | 729 | 59 |
| ARG | NE | C | 68 | 2 | 190 | 718 | 60 |
| ARG | CZ | C | 68 | -3 | 202 | 719 | 61 |
| ARG | NH1 | C | 68 | -6 | 207 | 731 | 61 |
| ARG | NH2 | C | 68 | -6 | 208 | 708 | 61 |
| ARG | C | C | 68 | 10 | 143 | 697 | 57 |
| ARG | O | C | 68 | 15 | 140 | 686 | 57 |
| GLY | N | C | 69 | -3 | 140 | 700 | 58 |
| GLY | CA | C | 69 | -11 | 133 | 690 | 59 |
| GLY | C | C | 69 | -19 | 121 | 695 | 59 |
| GLY | O | C | 69 | -20 | 119 | 707 | 59 |
| LYS | N | C | 70 | -26 | 114 | 686 | 60 |
| LYS | CA | C | 70 | -34 | 103 | 690 | 61 |
| LYS | CB | C | 70 | -48 | 104 | 685 | 61 |
| LYS | CG | C | 70 | -55 | 116 | 690 | 62 |
| LYS | CD | C | 70 | -70 | 116 | 687 | 63 |
| LYS | CE | C | 70 | -78 | 106 | 694 | 63 |
| LYS | NZ | C | 70 | -92 | 106 | 692 | 63 |
| LYS | C | C | 70 | -27 | 90 | 684 | 61 |
| LYS | O | C | 70 | -23 | 90 | 672 | 61 |
| SER | N | C | 71 | -27 | 79 | 691 | 60 |
| SER | CA | C | 71 | -21 | 67 | 687 | 60 |
| SER | CB | C | 71 | -25 | 55 | 696 | 60 |
| SER | OG | C | 71 | -22 | 58 | 710 | 61 |
| SER | C | C | 71 | -24 | 63 | 672 | 59 |
| SER | O | C | 71 | -36 | 61 | 669 | 59 |
| GLY | N | C | 72 | -14 | 61 | 664 | 59 |
| GLY | CA | C | 72 | -16 | 57 | 651 | 58 |
| GLY | C | C | 72 | -19 | 69 | 641 | 57 |
| GLY | O | C | 72 | -20 | 67 | 629 | 57 |
| GLN | N | C | 73 | -21 | 81 | 647 | 56 |
| GLN | CA | C | 73 | -25 | 92 | 638 | 56 |
| GLN | CB | C | 73 | -36 | 100 | 645 | 56 |
| GLN | CG | C | 73 | -48 | 90 | 649 | 56 |
| GLN | CD | C | 73 | -61 | 98 | 651 | 56 |
| GLN | OE1 | C | 73 | -61 | 108 | 658 | 57 |
| GLN | NE2 | C | 73 | -71 | 92 | 646 | 57 |
| GLN | C | C | 73 | -12 | 101 | 637 | 55 |
| GLN | O | C | 73 | -14 | 113 | 635 | 55 |
| GLY | N | C | 74 | -1 | 95 | 637 | 54 |
| GLY | CA | C | 74 | 12 | 103 | 636 | 52 |
| GLY | C | C | 74 | 14 | 113 | 646 | 50 |
| GLY | O | C | 74 | 5 | 118 | 653 | 51 |
| TYR | N | C | 75 | 27 | 117 | 648 | 49 |
| TYR | CA | C | 75 | 30 | 128 | 658 | 47 |
| TYR | CB | C | 75 | 44 | 125 | 664 | 47 |
| TYR | CG | C | 75 | 45 | 112 | 671 | 47 |
| TYR | CD1 | C | 75 | 47 | 100 | 664 | 47 |
| TYR | CE1 | C | 75 | 49 | 88 | 671 | 47 |
| TYR | CD2 | C | 75 | 45 | 111 | 685 | 47 |
| TYR | CE2 | C | 75 | 46 | 99 | 692 | 47 |
| TYR | CZ | C | 75 | 48 | 87 | 685 | 47 |
| TYR | OH | C | 75 | 50 | 76 | 692 | 48 |
| TYR | C | C | 75 | 30 | 141 | 651 | 47 |
| TYR | O | C | 75 | 33 | 142 | 639 | 47 |
| TYR | N | C | 76 | 28 | 152 | 659 | 46 |
| TYR | CA | C | 76 | 28 | 165 | 653 | 45 |
| TYR | CB | C | 76 | 13 | 169 | 649 | 45 |
| TYR | CG | C | 76 | 3 | 169 | 660 | 45 |
| TYR | CD1 | C | 76 | 3 | 180 | 669 | 46 |
| TYR | CE1 | C | 76 | -6 | 180 | 680 | 46 |
| TYR | CD2 | C | 76 | -6 | 159 | 662 | 46 |
| TYR | CE2 | C | 76 | -15 | 159 | 673 | 46 |
| TYR | CZ | C | 76 | -15 | 170 | 682 | 46 |
| TYR | OH | C | 76 | -23 | 170 | 692 | 46 |
| TYR | C | C | 76 | 33 | 175 | 663 | 44 |
| TYR | O | C | 76 | 34 | 173 | 675 | 44 |
| VAL | N | C | 77 | 37 | 187 | 657 | 44 |
| VAL | CA | C | 77 | 43 | 198 | 665 | 43 |
| VAL | CB | C | 77 | 58 | 201 | 661 | 43 |
| VAL | CG1 | C | 77 | 59 | 207 | 648 | 43 |
| VAL | CG2 | C | 77 | 64 | 210 | 672 | 43 |
| VAL | C | C | 77 | 35 | 210 | 662 | 44 |
| VAL | O | C | 77 | 28 | 211 | 652 | 43 |
| GLU | N | C | 78 | 35 | 220 | 671 | 44 |
| GLU | CA | C | 78 | 27 | 233 | 669 | 45 |
| GLU | CB | C | 78 | 23 | 239 | 682 | 45 |

TABLE 1-continued

Structure Coordinates for uncomplexed BACE

| | | | | | | |
|---|---|---|---|---|---|---|
| GLU | CG | C | 78 | 18 | 253 | 681 | 47 |
| GLU | CD | C | 78 | 13 | 259 | 695 | 47 |
| GLU | OE1 | C | 78 | 4 | 254 | 701 | 48 |
| GLU | OE2 | C | 78 | 19 | 269 | 699 | 47 |
| GLU | C | C | 78 | 36 | 243 | 661 | 45 |
| GLU | O | C | 78 | 47 | 246 | 665 | 45 |
| MET | N | C | 79 | 30 | 248 | 650 | 45 |
| MET | CA | C | 79 | 37 | 258 | 642 | 45 |
| MET | CB | C | 79 | 41 | 252 | 628 | 44 |
| MET | CG | C | 79 | 52 | 241 | 629 | 44 |
| MET | SD | C | 79 | 55 | 233 | 614 | 44 |
| MET | CE | C | 79 | 67 | 243 | 607 | 43 |
| MET | C | C | 79 | 28 | 270 | 640 | 45 |
| MET | O | C | 79 | 16 | 269 | 643 | 46 |
| THR | N | C | 80 | 34 | 280 | 634 | 46 |
| THR | CA | C | 80 | 26 | 292 | 631 | 46 |
| THR | CB | C | 80 | 27 | 303 | 641 | 46 |
| THR | OG1 | C | 80 | 41 | 308 | 640 | 46 |
| THR | CG2 | C | 80 | 25 | 298 | 655 | 46 |
| THR | C | C | 80 | 30 | 297 | 617 | 46 |
| THR | O | C | 80 | 42 | 298 | 614 | 46 |
| VAL | N | C | 81 | 20 | 300 | 608 | 46 |
| VAL | CA | C | 81 | 22 | 304 | 595 | 45 |
| VAL | CB | C | 81 | 17 | 295 | 584 | 45 |
| VAL | CG1 | C | 81 | 24 | 282 | 585 | 45 |
| VAL | CG2 | C | 81 | 2 | 292 | 586 | 45 |
| VAL | C | C | 81 | 15 | 318 | 593 | 45 |
| VAL | O | C | 81 | 3 | 319 | 598 | 45 |
| GLY | N | C | 82 | 21 | 327 | 587 | 45 |
| GLY | CA | C | 82 | 14 | 340 | 585 | 46 |
| GLY | C | C | 82 | 17 | 351 | 595 | 47 |
| GLY | O | C | 82 | 24 | 349 | 605 | 47 |
| SER | N | C | 83 | 12 | 363 | 592 | 47 |
| SER | CA | C | 83 | 14 | 375 | 601 | 47 |
| SER | CB | C | 83 | 26 | 383 | 595 | 47 |
| SER | OG | C | 83 | 37 | 375 | 593 | 48 |
| SER | C | C | 83 | 2 | 383 | 601 | 47 |
| SER | O | C | 83 | -2 | 389 | 590 | 48 |
| PRO | N | C | 84 | -5 | 384 | 612 | 47 |
| PRO | CD | C | 84 | -17 | 393 | 614 | 47 |
| PRO | CA | C | 84 | -1 | 378 | 625 | 47 |
| PRO | CB | C | 84 | -12 | 384 | 635 | 46 |
| PRO | CG | C | 84 | -24 | 387 | 626 | 47 |
| PRO | C | C | 84 | -2 | 363 | 625 | 46 |
| PRO | O | C | 84 | -8 | 357 | 617 | 46 |
| PRO | N | C | 85 | 6 | 357 | 634 | 45 |
| PRO | CD | C | 85 | 13 | 363 | 645 | 45 |
| PRO | CA | C | 85 | 7 | 342 | 635 | 45 |
| PRO | CB | C | 85 | 15 | 340 | 647 | 45 |
| PRO | CG | C | 85 | 23 | 352 | 649 | 45 |
| PRO | C | C | 85 | -6 | 334 | 635 | 45 |
| PRO | O | C | 85 | -15 | 338 | 642 | 45 |
| GLN | N | C | 86 | -7 | 324 | 627 | 44 |
| GLN | CA | C | 86 | -18 | 315 | 627 | 44 |
| GLN | CB | C | 86 | -24 | 313 | 613 | 43 |
| GLN | CG | C | 86 | -33 | 325 | 608 | 43 |
| GLN | CD | C | 86 | -37 | 324 | 594 | 42 |
| GLN | OE1 | C | 86 | -41 | 313 | 589 | 42 |
| GLN | NE2 | C | 86 | -36 | 335 | 587 | 42 |
| GLN | C | C | 86 | -13 | 301 | 632 | 44 |
| GLN | O | C | 86 | -5 | 295 | 625 | 45 |
| THR | N | C | 87 | -17 | 297 | 644 | 44 |
| THR | CA | C | 87 | -13 | 285 | 650 | 44 |
| THR | CB | C | 87 | -15 | 285 | 665 | 44 |
| THR | OG1 | C | 87 | -12 | 298 | 670 | 45 |
| THR | CG2 | C | 87 | -6 | 275 | 672 | 44 |
| THR | C | C | 87 | -19 | 273 | 644 | 44 |
| THR | O | C | 87 | -31 | 272 | 642 | 45 |
| LEU | N | C | 88 | -11 | 263 | 641 | 44 |
| LEU | CA | C | 88 | -16 | 250 | 635 | 44 |
| LEU | CB | C | 88 | -14 | 250 | 620 | 44 |
| LEU | CG | C | 88 | -23 | 260 | 611 | 45 |
| LEU | CD1 | C | 88 | -16 | 261 | 597 | 45 |
| LEU | CD2 | C | 88 | -37 | 255 | 610 | 45 |
| LEU | C | C | 88 | -8 | 239 | 640 | 44 |
| LEU | O | C | 88 | 4 | 240 | 644 | 45 |
| ASN | N | C | 89 | -14 | 227 | 640 | 44 |
| ASN | CA | C | 89 | -7 | 215 | 645 | 44 |
| ASN | CB | C | 89 | -17 | 205 | 652 | 44 |
| ASN | CG | C | 89 | -20 | 210 | 666 | 45 |
| ASN | OD1 | C | 89 | -30 | 205 | 671 | 46 |
| ASN | ND2 | C | 89 | -12 | 219 | 671 | 45 |
| ASN | C | C | 89 | -2 | 208 | 632 | 43 |
| ASN | O | C | 89 | -10 | 206 | 623 | 43 |
| ILE | N | C | 90 | 11 | 205 | 631 | 43 |
| ILE | CA | C | 90 | 17 | 199 | 619 | 42 |
| ILE | CB | C | 90 | 27 | 208 | 613 | 41 |
| ILE | CG2 | C | 90 | 33 | 202 | 600 | 41 |
| ILE | CG1 | C | 90 | 21 | 222 | 610 | 41 |
| ILE | CD1 | C | 90 | 9 | 221 | 601 | 41 |
| ILE | C | C | 90 | 23 | 185 | 621 | 41 |
| ILE | O | C | 90 | 31 | 184 | 630 | 42 |
| LEU | N | C | 91 | 19 | 176 | 613 | 41 |
| LEU | CA | C | 91 | 25 | 162 | 614 | 41 |
| LEU | CB | C | 91 | 17 | 154 | 604 | 42 |
| LEU | CG | C | 91 | 20 | 139 | 603 | 42 |
| LEU | CD1 | C | 91 | 14 | 132 | 615 | 43 |
| LEU | CD2 | C | 91 | 15 | 133 | 590 | 43 |
| LEU | C | C | 91 | 40 | 162 | 610 | 41 |
| LEU | O | C | 91 | 44 | 168 | 601 | 40 |
| VAL | N | C | 92 | 47 | 154 | 618 | 41 |
| VAL | CA | C | 92 | 61 | 152 | 616 | 40 |
| VAL | CB | C | 92 | 69 | 151 | 629 | 41 |
| VAL | CG1 | C | 92 | 84 | 148 | 626 | 40 |
| VAL | CG2 | C | 92 | 68 | 163 | 637 | 40 |
| VAL | C | C | 92 | 64 | 140 | 607 | 40 |
| VAL | O | C | 92 | 61 | 129 | 611 | 40 |
| ASP | N | C | 93 | 70 | 142 | 595 | 39 |
| ASP | CA | C | 93 | 72 | 131 | 586 | 38 |
| ASP | CB | C | 93 | 60 | 131 | 576 | 39 |
| ASP | CG | C | 93 | 62 | 120 | 565 | 39 |
| ASP | OD1 | C | 93 | 70 | 111 | 567 | 40 |
| ASP | OD2 | C | 93 | 55 | 122 | 554 | 40 |
| ASP | C | C | 93 | 85 | 131 | 579 | 38 |
| ASP | O | C | 93 | 88 | 139 | 570 | 39 |
| THR | N | C | 94 | 94 | 121 | 583 | 37 |
| THR | CA | C | 94 | 107 | 120 | 577 | 35 |
| THR | CB | C | 94 | 118 | 114 | 586 | 36 |
| THR | OG1 | C | 94 | 115 | 100 | 587 | 36 |
| THR | CG2 | C | 94 | 117 | 120 | 600 | 35 |
| THR | C | C | 94 | 106 | 112 | 564 | 35 |
| THR | O | C | 94 | 117 | 108 | 558 | 34 |
| GLY | N | C | 95 | 94 | 109 | 560 | 35 |
| GLY | CA | C | 95 | 92 | 101 | 548 | 35 |
| GLY | C | C | 95 | 88 | 109 | 535 | 35 |
| GLY | O | C | 95 | 85 | 103 | 525 | 36 |
| SER | N | C | 96 | 87 | 122 | 537 | 35 |
| SER | CA | C | 96 | 84 | 131 | 526 | 36 |
| SER | CB | C | 96 | 69 | 133 | 525 | 35 |
| SER | OG | C | 96 | 64 | 139 | 537 | 34 |
| SER | C | C | 96 | 91 | 144 | 527 | 36 |
| SER | O | C | 96 | 98 | 147 | 536 | 36 |
| SER | N | C | 97 | 90 | 153 | 517 | 36 |
| SER | CA | C | 97 | 97 | 166 | 517 | 36 |
| SER | CB | C | 97 | 108 | 165 | 507 | 36 |
| SER | OG | C | 97 | 115 | 153 | 508 | 36 |
| SER | C | C | 97 | 89 | 178 | 515 | 35 |
| SER | O | C | 97 | 95 | 189 | 512 | 35 |
| ASN | N | C | 98 | 76 | 178 | 516 | 35 |
| ASN | CA | C | 98 | 68 | 189 | 514 | 35 |
| ASN | CB | C | 98 | 56 | 187 | 504 | 34 |
| ASN | CG | C | 98 | 61 | 189 | 489 | 33 |
| ASN | OD1 | C | 98 | 66 | 179 | 483 | 33 |
| ASN | ND2 | C | 98 | 58 | 200 | 484 | 33 |
| ASN | C | C | 98 | 62 | 195 | 526 | 35 |
| ASN | O | C | 98 | 58 | 187 | 535 | 35 |
| PHE | N | C | 99 | 61 | 208 | 527 | 35 |
| PHE | CA | C | 99 | 55 | 214 | 539 | 35 |
| PHE | CB | C | 99 | 63 | 226 | 543 | 35 |
| PHE | CG | C | 99 | 56 | 234 | 554 | 35 |
| PHE | CD1 | C | 99 | 56 | 248 | 554 | 35 |
| PHE | CD2 | C | 99 | 50 | 228 | 565 | 35 |
| PHE | CE1 | C | 99 | 50 | 255 | 565 | 35 |
| PHE | CE2 | C | 99 | 43 | 235 | 575 | 35 |

TABLE 1-continued

Structure Coordinates for uncomplexed BACE

| | | | | | | | |
|---|---|---|---|---|---|---|---|
| PHE | CZ | C | 99 | 44 | 249 | 575 | 35 |
| PHE | C | C | 99 | 41 | 218 | 533 | 37 |
| PHE | O | C | 99 | 41 | 227 | 524 | 36 |
| ALA | N | C | 100 | 31 | 212 | 537 | 38 |
| ALA | CA | C | 100 | 17 | 215 | 532 | 40 |
| ALA | CB | C | 100 | 13 | 204 | 522 | 39 |
| ALA | C | C | 100 | 8 | 216 | 544 | 41 |
| ALA | O | C | 100 | 8 | 208 | 553 | 41 |
| VAL | N | C | 101 | −2 | 225 | 543 | 42 |
| VAL | CA | C | 101 | −12 | 227 | 553 | 44 |
| VAL | CB | C | 101 | −7 | 238 | 562 | 45 |
| VAL | CG1 | C | 101 | 7 | 236 | 567 | 45 |
| VAL | CG2 | C | 101 | −9 | 252 | 555 | 45 |
| VAL | C | C | 101 | −26 | 229 | 548 | 45 |
| VAL | O | C | 101 | −28 | 234 | 537 | 45 |
| GLY | N | C | 102 | −36 | 226 | 556 | 46 |
| GLY | CA | C | 102 | −50 | 228 | 553 | 46 |
| GLY | C | C | 102 | −52 | 242 | 550 | 47 |
| GLY | O | C | 102 | −50 | 251 | 558 | 47 |
| ALA | N | C | 103 | −57 | 245 | 538 | 48 |
| ALA | CA | C | 103 | −60 | 259 | 534 | 49 |
| ALA | CB | C | 103 | −51 | 263 | 522 | 49 |
| ALA | C | C | 103 | −74 | 262 | 531 | 50 |
| ALA | O | C | 103 | −77 | 273 | 526 | 50 |
| ALA | N | C | 104 | −83 | 253 | 534 | 51 |
| ALA | CA | C | 104 | −97 | 255 | 532 | 52 |
| ALA | CB | C | 104 | −101 | 252 | 518 | 51 |
| ALA | C | C | 104 | −105 | 244 | 541 | 52 |
| ALA | O | C | 104 | −100 | 234 | 544 | 52 |
| PRO | N | C | 105 | −117 | 248 | 545 | 53 |
| PRO | CD | C | 105 | −126 | 259 | 540 | 54 |
| PRO | CA | C | 105 | −125 | 239 | 553 | 54 |
| PRO | CB | C | 105 | −139 | 246 | 554 | 54 |
| PRO | CG | C | 105 | −140 | 254 | 542 | 54 |
| PRO | C | C | 105 | −127 | 224 | 548 | 54 |
| PRO | O | C | 105 | −127 | 222 | 536 | 54 |
| HIS | N | C | 106 | −127 | 215 | 557 | 55 |
| HIS | CA | C | 106 | −129 | 201 | 554 | 55 |
| HIS | CB | C | 106 | −115 | 194 | 552 | 55 |
| HIS | CG | C | 106 | −115 | 179 | 550 | 54 |
| HIS | CD2 | C | 106 | −114 | 172 | 538 | 54 |
| HIS | ND1 | C | 106 | −117 | 170 | 560 | 55 |
| HIS | CE1 | C | 106 | −117 | 158 | 555 | 55 |
| HIS | NE2 | C | 106 | −115 | 159 | 542 | 55 |
| HIS | C | C | 106 | −136 | 194 | 566 | 56 |
| HIS | O | C | 106 | −135 | 199 | 577 | 56 |
| PRO | N | C | 107 | −144 | 184 | 564 | 57 |
| PRO | CD | C | 107 | −147 | 177 | 552 | 57 |
| PRO | CA | C | 107 | −151 | 178 | 575 | 58 |
| PRO | CB | C | 107 | −159 | 166 | 568 | 58 |
| PRO | CG | C | 107 | −150 | 163 | 556 | 58 |
| PRO | C | C | 107 | −142 | 173 | 586 | 58 |
| PRO | O | C | 107 | −147 | 167 | 596 | 59 |
| PHE | N | C | 108 | −129 | 175 | 585 | 59 |
| PHE | CA | C | 108 | −120 | 170 | 596 | 59 |
| PHE | CB | C | 108 | −113 | 158 | 592 | 59 |
| PHE | CG | C | 108 | −122 | 145 | 591 | 59 |
| PHE | CD1 | C | 108 | −120 | 135 | 582 | 59 |
| PHE | CD2 | C | 108 | −132 | 144 | 660 | 60 |
| PHE | CE1 | C | 108 | −128 | 124 | 581 | 60 |
| PHE | CE2 | C | 108 | −141 | 133 | 599 | 60 |
| PHE | CZ | C | 108 | −138 | 123 | 590 | 60 |
| PHE | C | C | 108 | −110 | 181 | 600 | 59 |
| PHE | O | C | 108 | −98 | 177 | 603 | 59 |
| LEU | N | C | 109 | −113 | 194 | 600 | 58 |
| LEU | CA | C | 109 | −104 | 204 | 604 | 58 |
| LEU | CB | C | 109 | −98 | 211 | 592 | 58 |
| LEU | CG | C | 109 | −88 | 203 | 583 | 58 |
| LEU | CD1 | C | 109 | −86 | 211 | 570 | 58 |
| LEU | CD2 | C | 109 | −75 | 200 | 590 | 58 |
| LEU | C | C | 109 | −110 | 215 | 614 | 58 |
| LEU | O | C | 109 | −119 | 222 | 610 | 58 |
| HIS | N | C | 110 | −104 | 216 | 625 | 57 |
| HIS | CA | C | 110 | −109 | 226 | 635 | 57 |
| HIS | CB | C | 110 | −103 | 223 | 649 | 58 |
| HIS | CG | C | 110 | −110 | 212 | 656 | 58 |
| HIS | CD2 | C | 110 | −105 | 200 | 661 | 58 |
| HIS | ND1 | C | 110 | −123 | 211 | 659 | 58 |
| HIS | CE1 | C | 110 | −126 | 200 | 665 | 59 |
| HIS | NE2 | C | 110 | −115 | 193 | 667 | 58 |
| HIS | C | C | 110 | −104 | 240 | 631 | 56 |
| HIS | O | C | 110 | −108 | 250 | 636 | 56 |
| ARG | N | C | 111 | −94 | 240 | 621 | 55 |
| ARG | CA | C | 111 | −89 | 252 | 616 | 53 |
| ARG | CB | C | 111 | −81 | 259 | 627 | 53 |
| ARG | CG | C | 111 | −71 | 250 | 634 | 53 |
| ARG | CD | C | 111 | −64 | 257 | 646 | 52 |
| ARG | NE | C | 111 | −55 | 247 | 653 | 53 |
| ARG | CZ | C | 111 | −47 | 251 | 663 | 52 |
| ARG | NH1 | C | 111 | −47 | 263 | 667 | 52 |
| ARG | NH2 | C | 111 | −39 | 242 | 668 | 52 |
| ARG | C | C | 111 | −80 | 250 | 604 | 52 |
| ARG | O | C | 111 | −75 | 238 | 602 | 52 |
| TYR | N | C | 112 | −78 | 260 | 596 | 51 |
| TYR | CA | C | 112 | −70 | 259 | 584 | 50 |
| TYR | CB | C | 112 | −78 | 255 | 572 | 51 |
| TYR | CG | C | 112 | −90 | 264 | 570 | 52 |
| TYR | CD1 | C | 112 | −89 | 277 | 565 | 52 |
| TYR | CE1 | C | 112 | −100 | 285 | 563 | 52 |
| TYR | CD2 | C | 112 | −103 | 260 | 575 | 52 |
| TYR | CE2 | C | 112 | −114 | 269 | 573 | 52 |
| TYR | CZ | C | 112 | −112 | 281 | 567 | 52 |
| TYR | OH | C | 112 | −123 | 290 | 566 | 52 |
| TYR | C | C | 112 | −63 | 272 | 581 | 49 |
| TYR | O | C | 112 | −66 | 282 | 587 | 48 |
| TYR | N | C | 113 | −52 | 271 | 573 | 47 |
| TYR | CA | C | 113 | −44 | 283 | 569 | 45 |
| TYR | CB | C | 113 | −32 | 278 | 561 | 44 |
| TYR | CG | C | 113 | −23 | 289 | 556 | 43 |
| TYR | CD1 | C | 113 | −21 | 301 | 562 | 42 |
| TYR | CE1 | C | 113 | −13 | 311 | 557 | 42 |
| TYR | CD2 | C | 113 | −16 | 286 | 544 | 42 |
| TYR | CE2 | C | 113 | −7 | 296 | 539 | 41 |
| TYR | CZ | C | 113 | −5 | 308 | 546 | 41 |
| TYR | OH | C | 113 | 4 | 317 | 541 | 41 |
| TYR | C | C | 113 | −53 | 292 | 560 | 46 |
| TYR | O | C | 113 | −57 | 288 | 550 | 46 |
| GLN | N | C | 114 | −55 | 304 | 565 | 46 |
| GLN | CA | C | 114 | −63 | 314 | 558 | 46 |
| GLN | CB | C | 114 | −73 | 321 | 567 | 47 |
| GLN | CG | C | 114 | −82 | 311 | 574 | 48 |
| GLN | CD | C | 114 | −94 | 317 | 580 | 49 |
| GLN | OE1 | C | 114 | −93 | 326 | 589 | 49 |
| GLN | NE2 | C | 114 | −106 | 313 | 575 | 49 |
| GLN | C | C | 114 | −53 | 325 | 552 | 46 |
| GLN | O | C | 114 | −50 | 335 | 559 | 45 |
| ARG | N | C | 115 | −49 | 322 | 540 | 45 |
| ARG | CA | C | 115 | −39 | 331 | 533 | 45 |
| ARG | CB | C | 115 | −37 | 326 | 519 | 44 |
| ARG | CG | C | 115 | −29 | 314 | 519 | 44 |
| ARG | CD | C | 115 | −30 | 307 | 505 | 44 |
| ARG | NE | C | 115 | −43 | 302 | 502 | 43 |
| ARG | CZ | C | 115 | −47 | 297 | 491 | 43 |
| ARG | NH1 | C | 115 | −38 | 295 | 481 | 43 |
| ARG | NH2 | C | 115 | −59 | 292 | 490 | 43 |
| ARG | C | C | 115 | −43 | 346 | 533 | 45 |
| ARG | O | C | 115 | −34 | 355 | 534 | 45 |
| GLN | N | C | 116 | −56 | 349 | 531 | 45 |
| GLN | CA | C | 116 | −60 | 363 | 530 | 45 |
| GLN | CB | C | 116 | −75 | 364 | 527 | 46 |
| GLN | CG | C | 116 | −85 | 357 | 537 | 47 |
| GLN | CD | C | 116 | −88 | 343 | 534 | 47 |
| GLN | OE1 | C | 116 | −80 | 334 | 537 | 46 |
| GLN | NE2 | C | 116 | −100 | 341 | 529 | 47 |
| GLN | C | C | 116 | −58 | 372 | 543 | 45 |
| GLN | O | C | 116 | −58 | 384 | 542 | 45 |
| LEU | N | C | 117 | −56 | 365 | 554 | 45 |
| LEU | CA | C | 117 | −54 | 373 | 566 | 44 |
| LEU | CB | C | 117 | −61 | 366 | 578 | 45 |
| LEU | CG | C | 117 | −76 | 365 | 578 | 45 |
| LEU | CD1 | C | 117 | −81 | 358 | 590 | 45 |
| LEU | CD2 | C | 117 | −82 | 379 | 577 | 45 |
| LEU | C | C | 117 | −39 | 375 | 570 | 44 |
| LEU | O | C | 117 | −36 | 382 | 579 | 43 |

TABLE 1-continued

Structure Coordinates for uncomplexed BACE

| | | | | | | |
|---|---|---|---|---|---|---|
| SER | N | C | 118 | −30 | 369 | 562 | 42 |
| SER | CA | C | 118 | −16 | 370 | 564 | 41 |
| SER | CB | C | 118 | −8 | 357 | 562 | 41 |
| SER | OG | C | 118 | 6 | 359 | 562 | 41 |
| SER | C | C | 118 | −10 | 381 | 556 | 41 |
| SER | O | C | 118 | −10 | 380 | 543 | 41 |
| SER | N | C | 119 | −4 | 392 | 562 | 40 |
| SER | CA | C | 119 | 2 | 403 | 554 | 39 |
| SER | CB | C | 119 | 4 | 415 | 563 | 39 |
| SER | OG | C | 119 | 15 | 412 | 572 | 40 |
| SER | C | C | 119 | 15 | 399 | 547 | 37 |
| SER | O | C | 119 | 20 | 406 | 539 | 37 |
| THR | N | C | 120 | 20 | 387 | 551 | 36 |
| THR | CA | C | 120 | 33 | 383 | 546 | 34 |
| THR | CB | C | 120 | 43 | 378 | 557 | 34 |
| THR | OG1 | C | 120 | 36 | 369 | 566 | 34 |
| THR | CG2 | C | 120 | 48 | 390 | 564 | 34 |
| THR | C | C | 120 | 32 | 371 | 536 | 33 |
| THR | O | C | 120 | 42 | 366 | 531 | 33 |
| TYR | N | C | 121 | 19 | 368 | 532 | 32 |
| TYR | CA | C | 121 | 17 | 357 | 523 | 32 |
| TYR | CB | C | 121 | 2 | 353 | 523 | 32 |
| TYR | CG | C | 121 | −2 | 345 | 511 | 32 |
| TYR | CD1 | C | 121 | 1 | 332 | 510 | 31 |
| TYR | CE1 | C | 121 | −3 | 324 | 498 | 32 |
| TYR | CD2 | C | 121 | −9 | 351 | 500 | 32 |
| TYR | CE2 | C | 121 | −13 | 344 | 489 | 32 |
| TYR | CZ | C | 121 | −10 | 331 | 488 | 32 |
| TYR | OH | C | 121 | −13 | 323 | 477 | 32 |
| TYR | C | C | 121 | 21 | 361 | 509 | 32 |
| TYR | O | C | 121 | 19 | 372 | 504 | 31 |
| ARG | N | C | 122 | 27 | 352 | 501 | 32 |
| ARG | CA | C | 122 | 30 | 354 | 487 | 33 |
| ARG | CB | C | 122 | 45 | 357 | 486 | 33 |
| ARG | CG | C | 122 | 50 | 369 | 493 | 32 |
| ARG | CD | C | 122 | 63 | 375 | 488 | 33 |
| ARG | NE | C | 122 | 70 | 383 | 497 | 33 |
| ARG | CZ | C | 122 | 77 | 394 | 494 | 33 |
| ARG | NH1 | C | 122 | 79 | 397 | 481 | 33 |
| ARG | NH2 | C | 122 | 84 | 401 | 503 | 34 |
| ARG | C | C | 122 | 26 | 342 | 479 | 33 |
| ARG | O | C | 122 | 29 | 331 | 482 | 34 |
| ASP | N | C | 123 | 19 | 345 | 468 | 33 |
| ASP | CA | C | 123 | 13 | 336 | 459 | 32 |
| ASP | CB | C | 123 | 1 | 342 | 452 | 32 |
| ASP | CG | C | 123 | −8 | 332 | 446 | 32 |
| ASP | OD1 | C | 123 | −4 | 321 | 442 | 32 |
| ASP | OD2 | C | 123 | −20 | 335 | 443 | 33 |
| ASP | C | C | 123 | 23 | 332 | 448 | 31 |
| ASP | O | C | 123 | 28 | 340 | 441 | 31 |
| LEU | N | C | 124 | 27 | 319 | 448 | 31 |
| LEU | CA | C | 124 | 36 | 314 | 438 | 31 |
| LEU | CB | C | 124 | 44 | 301 | 443 | 30 |
| LEU | CG | C | 124 | 56 | 303 | 452 | 30 |
| LEU | CD1 | C | 124 | 60 | 290 | 458 | 29 |
| LEU | CD2 | C | 124 | 67 | 310 | 444 | 29 |
| LEU | C | C | 124 | 29 | 311 | 424 | 32 |
| LEU | O | C | 124 | 35 | 307 | 414 | 31 |
| ARG | N | C | 125 | 16 | 312 | 425 | 33 |
| ARG | CA | C | 125 | 7 | 310 | 413 | 35 |
| ARG | CB | C | 125 | 9 | 322 | 403 | 36 |
| ARG | CG | C | 125 | 6 | 336 | 409 | 37 |
| ARG | CD | C | 125 | 16 | 346 | 404 | 39 |
| ARG | NE | C | 125 | 16 | 348 | 389 | 40 |
| ARG | CZ | C | 125 | 26 | 352 | 382 | 40 |
| ARG | NH1 | C | 125 | 37 | 356 | 387 | 40 |
| ARG | NH2 | C | 125 | 24 | 354 | 369 | 41 |
| ARG | C | C | 125 | 11 | 297 | 406 | 35 |
| ARG | O | C | 125 | 13 | 297 | 394 | 35 |
| LYS | N | C | 126 | 10 | 286 | 413 | 36 |
| LYS | CA | C | 126 | 13 | 273 | 407 | 37 |
| LYS | CB | C | 126 | 28 | 271 | 406 | 38 |
| LYS | CG | C | 126 | 32 | 258 | 399 | 38 |
| LYS | CD | C | 126 | 47 | 256 | 398 | 38 |
| LYS | CE | C | 126 | 51 | 243 | 390 | 39 |
| LYS | NZ | C | 126 | 66 | 240 | 390 | 39 |
| LYS | C | C | 126 | 7 | 262 | 415 | 38 |
| LYS | O | C | 126 | 6 | 263 | 427 | 38 |
| GLY | N | C | 127 | 1 | 252 | 408 | 38 |
| GLY | CA | C | 127 | −5 | 241 | 415 | 39 |
| GLY | C | C | 127 | 4 | 229 | 418 | 39 |
| GLY | O | C | 127 | 14 | 228 | 411 | 38 |
| VAL | N | C | 128 | 0 | 221 | 428 | 41 |
| VAL | CA | C | 128 | 8 | 210 | 431 | 42 |
| VAL | CB | C | 128 | 18 | 213 | 443 | 42 |
| VAL | CG1 | C | 128 | 10 | 218 | 455 | 41 |
| VAL | CG2 | C | 128 | 26 | 200 | 446 | 41 |
| VAL | C | C | 128 | −2 | 199 | 435 | 44 |
| VAL | O | C | 128 | −12 | 201 | 441 | 43 |
| TYR | N | C | 129 | 2 | 186 | 432 | 47 |
| TYR | CA | C | 129 | −6 | 175 | 434 | 49 |
| TYR | CB | C | 129 | −13 | 170 | 421 | 51 |
| TYR | CG | C | 129 | −19 | 157 | 421 | 52 |
| TYR | CD1 | C | 129 | −30 | 154 | 430 | 52 |
| TYR | CE1 | C | 129 | −36 | 141 | 430 | 53 |
| TYR | CD2 | C | 129 | −15 | 147 | 413 | 53 |
| TYR | CE2 | C | 129 | −21 | 134 | 413 | 53 |
| TYR | CZ | C | 129 | −32 | 132 | 421 | 53 |
| TYR | OH | C | 129 | −38 | 119 | 420 | 54 |
| TYR | C | C | 129 | 2 | 164 | 440 | 51 |
| TYR | O | C | 129 | 12 | 160 | 434 | 50 |
| VAL | N | C | 130 | −2 | 159 | 452 | 52 |
| VAL | CA | C | 130 | 6 | 148 | 458 | 54 |
| VAL | CB | C | 130 | 13 | 153 | 471 | 54 |
| VAL | CG1 | C | 130 | 20 | 142 | 478 | 54 |
| VAL | CG2 | C | 130 | 22 | 165 | 468 | 54 |
| VAL | C | C | 130 | −4 | 136 | 462 | 55 |
| VAL | O | C | 130 | −12 | 138 | 471 | 55 |
| PRO | N | C | 131 | −3 | 125 | 455 | 57 |
| PRO | CD | C | 131 | 4 | 123 | 442 | 57 |
| PRO | CA | C | 131 | −11 | 114 | 458 | 58 |
| PRO | CB | C | 131 | −14 | 108 | 444 | 57 |
| PRO | CG | C | 131 | −1 | 110 | 438 | 57 |
| PRO | C | C | 131 | −4 | 104 | 467 | 59 |
| PRO | O | C | 131 | 8 | 101 | 464 | 59 |
| TYR | N | C | 132 | −10 | 98 | 477 | 60 |
| TYR | CA | C | 132 | −4 | 88 | 486 | 62 |
| TYR | CB | C | 132 | −6 | 91 | 500 | 61 |
| TYR | CG | C | 132 | −1 | 105 | 505 | 62 |
| TYR | CD1 | C | 132 | −8 | 116 | 503 | 62 |
| TYR | CE1 | C | 132 | −4 | 129 | 507 | 62 |
| TYR | CD2 | C | 132 | 12 | 106 | 511 | 62 |
| TYR | CE2 | C | 132 | 16 | 118 | 515 | 62 |
| TYR | CZ | C | 132 | 9 | 130 | 513 | 62 |
| TYR | OH | C | 132 | 14 | 142 | 517 | 62 |
| TYR | C | C | 132 | −9 | 74 | 482 | 62 |
| TYR | O | C | 132 | −14 | 72 | 471 | 62 |
| THR | N | C | 133 | −8 | 65 | 492 | 63 |
| THR | CA | C | 133 | −13 | 52 | 490 | 64 |
| THR | CB | C | 133 | −5 | 42 | 500 | 64 |
| THR | OG1 | C | 133 | 9 | 43 | 498 | 64 |
| THR | CG2 | C | 133 | −10 | 27 | 497 | 64 |
| THR | C | C | 133 | −28 | 52 | 493 | 64 |
| THR | O | C | 133 | −36 | 46 | 486 | 65 |
| GLN | N | C | 134 | −31 | 58 | 504 | 65 |
| GLN | CA | C | 134 | −45 | 59 | 509 | 65 |
| GLN | CB | C | 134 | −47 | 56 | 523 | 65 |
| GLN | CG | C | 134 | −49 | 41 | 526 | 66 |
| GLN | CD | C | 134 | −52 | 38 | 541 | 66 |
| GLN | OE1 | C | 134 | −61 | 43 | 547 | 66 |
| GLN | NE2 | C | 134 | −43 | 29 | 547 | 66 |
| GLN | C | C | 134 | −50 | 74 | 507 | 64 |
| GLN | O | C | 134 | −62 | 76 | 505 | 65 |
| GLY | N | C | 135 | −40 | 83 | 507 | 64 |
| GLY | CA | C | 135 | −43 | 97 | 505 | 62 |
| GLY | C | C | 135 | −42 | 103 | 492 | 61 |
| GLY | O | C | 135 | −37 | 97 | 482 | 62 |
| LYS | N | C | 136 | −45 | 116 | 491 | 60 |
| LYS | CA | C | 136 | −43 | 124 | 479 | 59 |
| LYS | CB | C | 136 | −52 | 117 | 468 | 59 |
| LYS | CG | C | 136 | −53 | 125 | 455 | 59 |
| LYS | CD | C | 136 | −64 | 121 | 445 | 60 |
| LYS | CE | C | 136 | −61 | 107 | 439 | 60 |
| LYS | NZ | C | 136 | −72 | 103 | 430 | 60 |

TABLE 1-continued

Structure Coordinates for uncomplexed BACE

| | | | | | | |
|---|---|---|---|---|---|---|
| LYS | C | C | 136 | −48 | 138 | 481 | 57 |
| LYS | O | C | 136 | −60 | 140 | 485 | 57 |
| TRP | N | C | 137 | −39 | 147 | 480 | 56 |
| TRP | CA | C | 137 | −43 | 161 | 482 | 54 |
| TRP | CB | C | 137 | −38 | 167 | 495 | 54 |
| TRP | CG | C | 137 | −23 | 167 | 497 | 55 |
| TRP | CD2 | C | 137 | −14 | 177 | 493 | 55 |
| TRP | CE2 | C | 137 | −1 | 172 | 497 | 55 |
| TRP | CE3 | C | 137 | −15 | 189 | 486 | 55 |
| TRP | CD1 | C | 137 | −16 | 157 | 503 | 55 |
| TRP | NE1 | C | 137 | −3 | 160 | 503 | 55 |
| TRP | CZ2 | C | 137 | 11 | 180 | 494 | 55 |
| TRP | CZ3 | C | 137 | −3 | 196 | 484 | 55 |
| TRP | CH2 | C | 137 | 9 | 192 | 488 | 55 |
| TRP | C | C | 137 | −39 | 170 | 470 | 52 |
| TRP | O | C | 137 | −30 | 166 | 462 | 52 |
| GLU | N | C | 138 | −45 | 182 | 469 | 51 |
| GLU | CA | C | 138 | −42 | 191 | 458 | 49 |
| GLU | CB | C | 138 | −54 | 191 | 449 | 50 |
| GLU | CG | C | 138 | −51 | 196 | 435 | 51 |
| GLU | CD | C | 138 | −56 | 187 | 424 | 52 |
| GLU | OE1 | C | 138 | −68 | 182 | 426 | 52 |
| GLU | OE2 | C | 138 | −50 | 185 | 413 | 53 |
| GLU | C | C | 138 | −41 | 204 | 465 | 47 |
| GLU | O | C | 138 | −48 | 207 | 475 | 46 |
| GLY | N | C | 139 | −31 | 212 | 461 | 45 |
| GLY | CA | C | 139 | −29 | 225 | 467 | 43 |
| GLY | C | C | 139 | −23 | 236 | 458 | 42 |
| GLY | O | C | 139 | −20 | 234 | 446 | 41 |
| GLU | N | C | 140 | −21 | 248 | 464 | 40 |
| GLU | CA | C | 140 | −16 | 259 | 457 | 39 |
| GLU | CB | C | 140 | −26 | 271 | 457 | 39 |
| GLU | CG | C | 140 | −39 | 266 | 450 | 40 |
| GLU | CD | C | 140 | −50 | 277 | 452 | 40 |
| GLU | OE1 | C | 140 | −61 | 275 | 446 | 41 |
| GLU | OE2 | C | 140 | −48 | 286 | 459 | 41 |
| GLU | C | C | 140 | −3 | 264 | 464 | 37 |
| GLU | O | C | 140 | −3 | 266 | 476 | 37 |
| LEU | N | C | 141 | 8 | 264 | 456 | 36 |
| LEU | CA | C | 141 | 21 | 268 | 462 | 34 |
| LEU | CB | C | 141 | 32 | 265 | 452 | 33 |
| LEU | CG | C | 141 | 35 | 250 | 451 | 33 |
| LEU | CD1 | C | 141 | 44 | 247 | 439 | 34 |
| LEU | CD2 | C | 141 | 41 | 244 | 464 | 33 |
| LEU | C | C | 141 | 21 | 282 | 466 | 33 |
| LEU | O | C | 141 | 14 | 290 | 460 | 34 |
| GLY | N | C | 142 | 29 | 286 | 476 | 32 |
| GLY | CA | C | 142 | 30 | 299 | 480 | 31 |
| GLY | C | C | 142 | 41 | 300 | 491 | 30 |
| GLY | O | C | 142 | 48 | 290 | 493 | 30 |
| THR | N | C | 143 | 43 | 311 | 497 | 30 |
| THR | CA | C | 143 | 53 | 313 | 508 | 30 |
| THR | CB | C | 143 | 67 | 319 | 502 | 30 |
| THR | OG1 | C | 143 | 64 | 333 | 499 | 29 |
| THR | CG2 | C | 143 | 72 | 312 | 490 | 30 |
| THR | C | C | 143 | 48 | 322 | 519 | 30 |
| THR | O | C | 143 | 39 | 330 | 516 | 29 |
| ASP | N | C | 144 | 54 | 320 | 531 | 30 |
| ASP | CA | C | 144 | 50 | 329 | 542 | 31 |
| ASP | CB | C | 144 | 36 | 324 | 547 | 30 |
| ASP | CG | C | 144 | 28 | 336 | 552 | 29 |
| ASP | OD1 | C | 144 | 34 | 346 | 558 | 28 |
| ASP | OD2 | C | 144 | 15 | 336 | 551 | 29 |
| ASP | C | C | 144 | 60 | 327 | 553 | 32 |
| ASP | O | C | 144 | 68 | 318 | 553 | 32 |
| LEU | N | C | 145 | 59 | 336 | 564 | 33 |
| LEU | CA | C | 145 | 68 | 335 | 575 | 35 |
| LEU | CB | C | 145 | 68 | 348 | 583 | 34 |
| LEU | CG | C | 145 | 73 | 360 | 576 | 34 |
| LEU | CD1 | C | 145 | 73 | 372 | 585 | 34 |
| LEU | CD2 | C | 145 | 87 | 358 | 571 | 35 |
| LEU | C | C | 145 | 62 | 323 | 584 | 36 |
| LEU | O | C | 145 | 50 | 322 | 586 | 36 |
| VAL | N | C | 146 | 72 | 315 | 588 | 37 |
| VAL | CA | C | 146 | 68 | 303 | 596 | 38 |
| VAL | CB | C | 146 | 71 | 290 | 587 | 38 |
| VAL | CG1 | C | 146 | 68 | 278 | 596 | 37 |
| VAL | CG2 | C | 146 | 64 | 290 | 574 | 38 |
| VAL | C | C | 146 | 77 | 303 | 608 | 39 |
| VAL | O | C | 146 | 88 | 307 | 608 | 38 |
| SER | N | C | 147 | 71 | 298 | 619 | 40 |
| SER | CA | C | 147 | 78 | 297 | 632 | 42 |
| SER | CB | C | 147 | 74 | 309 | 641 | 42 |
| SER | OG | C | 147 | 82 | 320 | 637 | 44 |
| SER | C | C | 147 | 74 | 284 | 639 | 42 |
| SER | O | C | 147 | 64 | 278 | 636 | 42 |
| ILE | N | C | 148 | 81 | 281 | 650 | 43 |
| ILE | CA | C | 148 | 79 | 269 | 658 | 43 |
| ILE | CB | C | 148 | 89 | 258 | 655 | 43 |
| ILE | CG2 | C | 148 | 85 | 245 | 661 | 43 |
| ILE | CG1 | C | 148 | 92 | 256 | 640 | 43 |
| ILE | CD1 | C | 148 | 103 | 246 | 637 | 42 |
| ILE | C | C | 148 | 79 | 273 | 672 | 44 |
| ILE | O | C | 148 | 90 | 274 | 678 | 44 |
| PRO | N | C | 149 | 67 | 276 | 678 | 45 |
| PRO | CD | C | 149 | 54 | 274 | 672 | 45 |
| PRO | CA | C | 149 | 66 | 280 | 692 | 45 |
| PRO | CB | C | 149 | 51 | 278 | 695 | 45 |
| PRO | CG | C | 149 | 45 | 281 | 682 | 45 |
| PRO | C | C | 149 | 75 | 273 | 701 | 46 |
| PRO | O | C | 149 | 84 | 279 | 708 | 46 |
| HIS | N | C | 150 | 74 | 260 | 702 | 46 |
| HIS | CA | C | 150 | 82 | 251 | 710 | 47 |
| HIS | CB | C | 150 | 74 | 240 | 717 | 48 |
| HIS | CG | C | 150 | 63 | 246 | 725 | 48 |
| HIS | CD2 | C | 150 | 49 | 246 | 724 | 48 |
| HIS | ND1 | C | 150 | 65 | 254 | 736 | 48 |
| HIS | CE1 | C | 150 | 54 | 259 | 741 | 48 |
| HIS | NE2 | C | 150 | 44 | 254 | 734 | 49 |
| HIS | C | C | 150 | 94 | 245 | 703 | 48 |
| HIS | O | C | 150 | 96 | 233 | 703 | 48 |
| GLY | N | C | 151 | 102 | 254 | 697 | 48 |
| GLY | CA | C | 151 | 114 | 250 | 690 | 48 |
| GLY | C | C | 151 | 123 | 262 | 690 | 48 |
| GLY | O | C | 151 | 122 | 271 | 699 | 48 |
| PRO | N | C | 152 | 132 | 264 | 680 | 49 |
| PRO | CD | C | 152 | 135 | 255 | 669 | 49 |
| PRO | CA | C | 152 | 141 | 276 | 681 | 49 |
| PRO | CB | C | 152 | 150 | 273 | 669 | 49 |
| PRO | CG | C | 152 | 142 | 264 | 660 | 49 |
| PRO | C | C | 152 | 133 | 289 | 679 | 50 |
| PRO | O | C | 152 | 123 | 289 | 672 | 50 |
| ASN | N | C | 153 | 137 | 299 | 686 | 51 |
| ASN | CA | C | 153 | 131 | 312 | 685 | 52 |
| ASN | CB | C | 153 | 134 | 321 | 697 | 53 |
| ASN | CG | C | 153 | 132 | 314 | 711 | 54 |
| ASN | OD1 | C | 153 | 121 | 310 | 714 | 54 |
| ASN | ND2 | C | 153 | 143 | 312 | 718 | 54 |
| ASN | C | C | 153 | 134 | 319 | 672 | 51 |
| ASN | O | C | 153 | 140 | 330 | 673 | 51 |
| VAL | N | C | 154 | 131 | 313 | 661 | 50 |
| VAL | CA | C | 154 | 134 | 319 | 648 | 49 |
| VAL | CB | C | 154 | 145 | 311 | 641 | 49 |
| VAL | CG1 | C | 154 | 158 | 312 | 649 | 49 |
| VAL | CG2 | C | 154 | 141 | 297 | 640 | 49 |
| VAL | C | C | 154 | 121 | 319 | 639 | 48 |
| VAL | O | C | 154 | 112 | 311 | 641 | 48 |
| THR | N | C | 155 | 121 | 328 | 630 | 46 |
| THR | CA | C | 155 | 110 | 330 | 620 | 45 |
| THR | CB | C | 155 | 102 | 343 | 622 | 45 |
| THR | OG1 | C | 155 | 96 | 342 | 635 | 46 |
| THR | CG2 | C | 155 | 92 | 345 | 611 | 45 |
| THR | C | C | 155 | 116 | 330 | 606 | 43 |
| THR | O | C | 155 | 124 | 338 | 603 | 44 |
| VAL | N | C | 156 | 112 | 320 | 598 | 41 |
| VAL | CA | C | 156 | 118 | 319 | 585 | 40 |
| VAL | CB | C | 156 | 126 | 306 | 583 | 40 |
| VAL | CG1 | C | 156 | 138 | 306 | 593 | 41 |
| VAL | CG2 | C | 156 | 118 | 294 | 585 | 40 |
| VAL | C | C | 156 | 107 | 319 | 574 | 39 |
| VAL | O | C | 156 | 96 | 315 | 577 | 39 |
| ARG | N | C | 157 | 111 | 322 | 562 | 37 |
| ARG | CA | C | 157 | 102 | 322 | 551 | 35 |
| ARG | CB | C | 157 | 105 | 333 | 540 | 35 |

TABLE 1-continued

Structure Coordinates for uncomplexed BACE

| | | | | | | | |
|---|---|---|---|---|---|---|---|
| ARG | CG | C | 157 | 95 | 332 | 528 | 36 |
| ARG | CD | C | 157 | 97 | 345 | 520 | 36 |
| ARG | NE | C | 157 | 93 | 357 | 527 | 37 |
| ARG | CZ | C | 157 | 81 | 361 | 529 | 38 |
| ARG | NH1 | C | 157 | 70 | 355 | 523 | 37 |
| ARG | NH2 | C | 157 | 79 | 372 | 536 | 39 |
| ARG | C | C | 157 | 104 | 308 | 544 | 33 |
| ARG | O | C | 157 | 115 | 304 | 542 | 32 |
| ALA | N | C | 158 | 93 | 301 | 541 | 31 |
| ALA | CA | C | 158 | 94 | 288 | 535 | 30 |
| ALA | CB | C | 158 | 93 | 277 | 546 | 29 |
| ALA | C | C | 158 | 83 | 286 | 525 | 29 |
| ALA | O | C | 158 | 73 | 292 | 525 | 28 |
| ASN | N | C | 159 | 85 | 276 | 517 | 28 |
| ASN | CA | C | 159 | 75 | 272 | 507 | 28 |
| ASN | CB | C | 159 | 81 | 262 | 497 | 27 |
| ASN | CG | C | 159 | 91 | 269 | 488 | 27 |
| ASN | OD1 | C | 159 | 88 | 279 | 482 | 26 |
| ASN | ND2 | C | 159 | 103 | 263 | 487 | 26 |
| ASN | C | C | 159 | 63 | 265 | 514 | 29 |
| ASN | O | C | 159 | 66 | 258 | 524 | 28 |
| ILE | N | C | 160 | 51 | 268 | 510 | 30 |
| ILE | CA | C | 160 | 39 | 262 | 516 | 31 |
| ILE | CB | C | 160 | 33 | 273 | 526 | 30 |
| ILE | CG2 | C | 160 | 20 | 267 | 531 | 30 |
| ILE | CG1 | C | 160 | 42 | 277 | 537 | 30 |
| ILE | CD1 | C | 160 | 36 | 287 | 546 | 30 |
| ILE | C | C | 160 | 29 | 258 | 506 | 32 |
| ILE | O | C | 160 | 24 | 266 | 498 | 31 |
| ALA | N | C | 161 | 26 | 245 | 506 | 33 |
| ALA | CA | C | 161 | 16 | 239 | 497 | 34 |
| ALA | CB | C | 161 | 19 | 225 | 494 | 34 |
| ALA | C | C | 161 | 2 | 241 | 504 | 36 |
| ALA | O | C | 161 | −1 | 232 | 513 | 35 |
| ALA | N | C | 162 | −5 | 251 | 500 | 37 |
| ALA | CA | C | 162 | −19 | 253 | 506 | 39 |
| ALA | CB | C | 162 | −23 | 267 | 504 | 38 |
| ALA | C | C | 162 | −29 | 243 | 500 | 40 |
| ALA | O | C | 162 | −33 | 245 | 489 | 40 |
| ILE | N | C | 163 | −32 | 233 | 508 | 41 |
| ILE | CA | C | 163 | −42 | 223 | 504 | 43 |
| ILE | CB | C | 163 | −41 | 211 | 514 | 43 |
| ILE | CG2 | C | 163 | −53 | 202 | 511 | 43 |
| ILE | CG1 | C | 163 | −28 | 204 | 512 | 43 |
| ILE | CD1 | C | 163 | −26 | 192 | 521 | 44 |
| ILE | C | C | 163 | −56 | 229 | 503 | 44 |
| ILE | O | C | 163 | −61 | 234 | 512 | 44 |
| THR | N | C | 164 | −62 | 227 | 491 | 44 |
| THR | CA | C | 164 | −75 | 232 | 489 | 46 |
| THR | CB | C | 164 | −75 | 242 | 477 | 45 |
| THR | OG1 | C | 164 | −68 | 236 | 466 | 45 |
| THR | CG2 | C | 164 | −69 | 255 | 480 | 45 |
| THR | C | C | 164 | −85 | 221 | 486 | 48 |
| THR | O | C | 164 | −97 | 222 | 488 | 48 |
| GLU | N | C | 165 | −79 | 209 | 482 | 50 |
| GLU | CA | C | 165 | −87 | 197 | 480 | 53 |
| GLU | CB | C | 165 | −90 | 196 | 465 | 54 |
| GLU | CG | C | 165 | −100 | 207 | 459 | 56 |
| GLU | CD | C | 165 | −99 | 208 | 444 | 57 |
| GLU | OE1 | C | 165 | −97 | 198 | 437 | 58 |
| GLU | OE2 | C | 165 | −99 | 220 | 440 | 58 |
| GLU | C | C | 165 | −80 | 185 | 485 | 54 |
| GLU | O | C | 165 | −68 | 183 | 482 | 54 |
| SER | N | C | 166 | −87 | 176 | 492 | 55 |
| SER | CA | C | 166 | −81 | 164 | 497 | 56 |
| SER | CB | C | 166 | −76 | 167 | 512 | 56 |
| SER | OG | C | 166 | −86 | 174 | 519 | 56 |
| SER | C | C | 166 | −90 | 152 | 497 | 58 |
| SER | O | C | 166 | −102 | 154 | 500 | 58 |
| ASP | N | C | 167 | −85 | 141 | 494 | 59 |
| ASP | CA | C | 167 | −92 | 128 | 494 | 60 |
| ASP | CB | C | 167 | −92 | 122 | 480 | 60 |
| ASP | CG | C | 167 | −100 | 110 | 479 | 60 |
| ASP | OD1 | C | 167 | −97 | 101 | 470 | 60 |
| ASP | OD2 | C | 167 | −110 | 108 | 487 | 60 |
| ASP | C | C | 167 | −87 | 118 | 504 | 60 |
| ASP | O | C | 167 | −77 | 112 | 501 | 60 |
| LYS | N | C | 168 | −94 | 117 | 515 | 61 |
| LYS | CA | C | 168 | −90 | 107 | 525 | 62 |
| LYS | CB | C | 168 | −91 | 93 | 520 | 62 |
| LYS | CG | C | 168 | −105 | 89 | 516 | 63 |
| LYS | CD | C | 168 | −106 | 74 | 512 | 63 |
| LYS | CE | C | 168 | −97 | 71 | 500 | 64 |
| LYS | NZ | C | 168 | −96 | 57 | 497 | 64 |
| LYS | C | C | 168 | −75 | 110 | 530 | 62 |
| LYS | O | C | 168 | −67 | 100 | 532 | 62 |
| PHE | N | C | 169 | −72 | 122 | 532 | 62 |
| PHE | CA | C | 169 | −59 | 126 | 536 | 62 |
| PHE | CB | C | 169 | −54 | 139 | 529 | 61 |
| PHE | CG | C | 169 | −40 | 143 | 533 | 60 |
| PHE | CD1 | C | 169 | −29 | 135 | 531 | 60 |
| PHE | CD2 | C | 169 | −39 | 156 | 539 | 60 |
| PHE | CE1 | C | 169 | −16 | 139 | 536 | 60 |
| PHE | CE2 | C | 169 | −26 | 160 | 544 | 60 |
| PHE | CZ | C | 169 | −15 | 152 | 542 | 60 |
| PHE | C | C | 169 | −59 | 129 | 551 | 62 |
| PHE | O | C | 169 | −51 | 123 | 558 | 62 |
| PHE | N | C | 170 | −68 | 138 | 555 | 62 |
| PHE | CA | C | 170 | −68 | 142 | 569 | 63 |
| PHE | CB | C | 170 | −76 | 155 | 570 | 63 |
| PHE | CG | C | 170 | −69 | 166 | 564 | 63 |
| PHE | CD1 | C | 170 | −72 | 170 | 551 | 63 |
| PHE | CD2 | C | 170 | −59 | 173 | 570 | 63 |
| PHE | CE1 | C | 170 | −66 | 181 | 545 | 63 |
| PHE | CE2 | C | 170 | −52 | 183 | 564 | 63 |
| PHE | CZ | C | 170 | −55 | 187 | 551 | 63 |
| PHE | C | C | 170 | −75 | 131 | 577 | 64 |
| PHE | O | C | 170 | −85 | 125 | 574 | 64 |
| ILE | N | C | 171 | −68 | 128 | 589 | 65 |
| ILE | CA | C | 171 | −73 | 118 | 598 | 66 |
| ILE | CB | C | 171 | −60 | 114 | 607 | 66 |
| ILE | CG2 | C | 171 | −65 | 106 | 619 | 66 |
| ILE | CG1 | C | 171 | −51 | 105 | 598 | 66 |
| ILE | CD1 | C | 171 | −38 | 101 | 606 | 66 |
| ILE | C | C | 171 | −84 | 122 | 607 | 66 |
| ILE | O | C | 171 | −85 | 134 | 611 | 66 |
| ASN | N | C | 172 | −92 | 112 | 610 | 66 |
| ASN | CA | C | 172 | −104 | 114 | 619 | 67 |
| ASN | CB | C | 172 | −112 | 101 | 619 | 67 |
| ASN | CG | C | 172 | −127 | 102 | 622 | 67 |
| ASN | OD1 | C | 172 | −134 | 93 | 624 | 67 |
| ASN | ND2 | C | 172 | −131 | 115 | 623 | 67 |
| ASN | C | C | 172 | −101 | 118 | 633 | 66 |
| ASN | O | C | 172 | −97 | 110 | 642 | 67 |
| GLY | N | C | 173 | −102 | 132 | 636 | 66 |
| GLY | CA | C | 173 | −99 | 137 | 649 | 65 |
| GLY | C | C | 173 | −84 | 138 | 653 | 64 |
| GLY | O | C | 173 | −82 | 140 | 665 | 64 |
| SER | N | C | 174 | −75 | 136 | 644 | 64 |
| SER | CA | C | 174 | −61 | 136 | 647 | 63 |
| SER | CB | C | 174 | −53 | 135 | 634 | 63 |
| SER | OG | C | 174 | −54 | 147 | 626 | 63 |
| SER | C | C | 174 | −56 | 148 | 654 | 62 |
| SER | O | C | 174 | −47 | 148 | 662 | 62 |
| ASN | N | C | 175 | −63 | 160 | 651 | 61 |
| ASN | CA | C | 175 | −60 | 173 | 657 | 60 |
| ASN | CB | C | 175 | −58 | 171 | 672 | 60 |
| ASN | CG | C | 175 | −59 | 185 | 679 | 60 |
| ASN | OD1 | C | 175 | −67 | 193 | 677 | 60 |
| ASN | ND2 | C | 175 | −49 | 187 | 689 | 60 |
| ASN | C | C | 175 | −48 | 180 | 651 | 58 |
| ASN | O | C | 175 | =43 | 189 | 656 | 58 |
| TRP | N | C | 176 | −44 | 175 | 639 | 57 |
| TRP | CA | C | 176 | −33 | 182 | 632 | 56 |
| TRP | CB | C | 176 | −21 | 173 | 630 | 56 |
| TRP | CG | C | 176 | −23 | 159 | 624 | 55 |
| TRP | CD2 | C | 176 | −23 | 156 | 610 | 55 |
| TRP | CE2 | C | 176 | −23 | 142 | 609 | 55 |
| TRP | CE3 | C | 176 | −23 | 164 | 598 | 55 |
| TRP | CD1 | C | 176 | −23 | 147 | 630 | 55 |
| TRP | NE1 | C | 176 | −23 | 137 | 621 | 55 |
| TRP | CZ2 | C | 176 | −24 | 136 | 596 | 55 |
| TRP | CZ3 | C | 176 | −24 | 158 | 586 | 55 |
| TRP | CH2 | C | 176 | −24 | 144 | 585 | 55 |

TABLE 1-continued

Structure Coordinates for uncomplexed BACE

| | | | | | | | |
|---|---|---|---|---|---|---|---|
| TRP | C | C | 176 | −38 | 186 | 618 | 56 |
| TRP | O | C | 176 | −44 | 179 | 610 | 56 |
| GLU | N | C | 177 | −35 | 199 | 615 | 55 |
| GLU | CA | C | 177 | −39 | 205 | 602 | 54 |
| GLU | CB | C | 177 | −44 | 219 | 605 | 54 |
| GLU | CG | C | 177 | −55 | 220 | 615 | 55 |
| GLU | CD | C | 177 | −51 | 219 | 630 | 56 |
| GLU | OE1 | C | 177 | −59 | 218 | 639 | 56 |
| GLU | OE2 | C | 177 | −38 | 218 | 632 | 56 |
| GLU | C | C | 177 | −29 | 206 | 591 | 52 |
| GLU | O | C | 177 | −31 | 213 | 581 | 52 |
| GLY | N | C | 178 | −18 | 198 | 592 | 51 |
| GLY | CA | C | 178 | −8 | 199 | 581 | 48 |
| GLY | C | C | 178 | 3 | 188 | 582 | 46 |
| GLY | O | C | 178 | 3 | 180 | 591 | 47 |
| ILE | N | C | 179 | 13 | 189 | 572 | 44 |
| ILE | CA | C | 179 | 24 | 179 | 572 | 42 |
| ILE | CB | C | 179 | 21 | 169 | 561 | 42 |
| ILE | CG2 | C | 179 | 21 | 175 | 547 | 42 |
| ILE | CG1 | C | 179 | 32 | 158 | 561 | 42 |
| ILE | CD1 | C | 179 | 30 | 147 | 551 | 42 |
| ILE | C | C | 179 | 37 | 186 | 569 | 41 |
| ILE | O | C | 179 | 38 | 195 | 561 | 41 |
| LEU | N | C | 180 | 47 | 181 | 576 | 40 |
| LEU | CA | C | 180 | 61 | 186 | 575 | 38 |
| LEU | CB | C | 180 | 65 | 191 | 588 | 39 |
| LEU | CG | C | 180 | 80 | 196 | 590 | 39 |
| LEU | CD1 | C | 180 | 82 | 209 | 582 | 39 |
| LEU | CD2 | C | 180 | 81 | 199 | 605 | 39 |
| LEU | C | C | 180 | 71 | 176 | 569 | 38 |
| LEU | O | C | 180 | 76 | 168 | 577 | 37 |
| GLY | N | C | 181 | 73 | 176 | 556 | 36 |
| GLY | CA | C | 181 | 83 | 167 | 550 | 36 |
| GLY | C | C | 181 | 97 | 171 | 554 | 36 |
| GLY | O | C | 181 | 101 | 182 | 550 | 35 |
| LEU | N | C | 182 | 104 | 162 | 561 | 34 |
| LEU | CA | C | 182 | 117 | 166 | 566 | 34 |
| LEU | CB | C | 182 | 119 | 162 | 580 | 34 |
| LEU | CG | C | 182 | 111 | 170 | 590 | 34 |
| LEU | CD1 | C | 182 | 110 | 163 | 604 | 34 |
| LEU | CD2 | C | 182 | 117 | 184 | 591 | 34 |
| LEU | C | C | 182 | 128 | 159 | 557 | 33 |
| LEU | O | C | 182 | 140 | 160 | 560 | 34 |
| ALA | N | C | 183 | 123 | 151 | 547 | 33 |
| ALA | CA | C | 183 | 133 | 144 | 538 | 32 |
| ALA | CB | C | 183 | 125 | 133 | 531 | 33 |
| ALA | C | C | 183 | 138 | 154 | 528 | 32 |
| ALA | O | C | 183 | 135 | 166 | 529 | 31 |
| TYR | N | C | 184 | 147 | 149 | 519 | 32 |
| TYR | CA | C | 184 | 153 | 158 | 510 | 33 |
| TYR | CB | C | 184 | 167 | 152 | 505 | 33 |
| TYR | CG | C | 184 | 176 | 149 | 517 | 34 |
| TYR | CD1 | C | 184 | 175 | 137 | 524 | 34 |
| TYR | CE1 | C | 184 | 183 | 134 | 535 | 34 |
| TYR | CD2 | C | 184 | 186 | 158 | 521 | 34 |
| TYR | CE2 | C | 184 | 194 | 155 | 532 | 34 |
| TYR | CZ | C | 184 | 193 | 143 | 539 | 34 |
| TYR | OH | C | 184 | 201 | 141 | 550 | 34 |
| TYR | C | C | 184 | 145 | 162 | 497 | 33 |
| TYR | O | C | 184 | 135 | 156 | 493 | 32 |
| ALA | N | C | 185 | 150 | 173 | 491 | 34 |
| ALA | CA | C | 185 | 144 | 179 | 479 | 34 |
| ALA | CB | C | 185 | 153 | 191 | 474 | 34 |
| ALA | C | C | 185 | 141 | 169 | 468 | 35 |
| ALA | O | C | 185 | 131 | 171 | 461 | 34 |
| GLU | N | C | 186 | 150 | 160 | 466 | 36 |
| GLU | CA | C | 186 | 148 | 150 | 455 | 37 |
| GLU | CB | C | 186 | 159 | 139 | 456 | 38 |
| GLU | CG | C | 186 | 158 | 130 | 444 | 40 |
| GLU | CD | C | 186 | 169 | 119 | 444 | 42 |
| GLU | OE1 | C | 186 | 180 | 122 | 448 | 42 |
| GLU | OE2 | C | 186 | 166 | 108 | 439 | 43 |
| GLU | C | C | 186 | 134 | 144 | 454 | 38 |
| GLU | O | C | 186 | 130 | 140 | 443 | 38 |
| ILE | N | C | 187 | 127 | 143 | 465 | 37 |
| ILE | CA | C | 187 | 114 | 137 | 464 | 37 |
| ILE | CB | C | 187 | 112 | 125 | 474 | 37 |
| ILE | CG2 | C | 187 | 122 | 114 | 469 | 38 |
| ILE | CG1 | C | 187 | 115 | 129 | 488 | 38 |
| ILE | CD1 | C | 187 | 114 | 117 | 498 | 38 |
| ILE | C | C | 187 | 103 | 147 | 467 | 37 |
| ILE | O | C | 187 | 91 | 144 | 469 | 38 |
| ALA | N | C | 188 | 106 | 160 | 466 | 38 |
| ALA | CA | C | 188 | 97 | 171 | 468 | 38 |
| ALA | CB | C | 188 | 104 | 184 | 470 | 38 |
| ALA | C | C | 188 | 88 | 172 | 455 | 39 |
| ALA | O | C | 188 | 93 | 169 | 444 | 38 |
| ARG | N | C | 189 | 76 | 177 | 456 | 40 |
| ARG | CA | C | 189 | 67 | 179 | 445 | 41 |
| ARG | CB | C | 189 | 54 | 172 | 447 | 43 |
| ARG | CG | C | 189 | 54 | 157 | 449 | 45 |
| ARG | CD | C | 189 | 62 | 150 | 438 | 47 |
| ARG | NE | C | 189 | 59 | 136 | 437 | 49 |
| ARG | CZ | C | 189 | 49 | 132 | 431 | 50 |
| ARG | NH1 | C | 189 | 40 | 140 | 425 | 50 |
| ARG | NH2 | C | 189 | 46 | 118 | 430 | 50 |
| ARG | C | C | 189 | 65 | 194 | 445 | 40 |
| ARG | O | C | 189 | 65 | 200 | 456 | 40 |
| PRO | N | C | 190 | 64 | 200 | 433 | 40 |
| PRO | CD | C | 190 | 60 | 214 | 432 | 40 |
| PRO | CA | C | 190 | 63 | 193 | 420 | 40 |
| PRO | CB | C | 190 | 59 | 205 | 411 | 40 |
| PRO | CG | C | 190 | 51 | 214 | 420 | 40 |
| PRO | C | C | 190 | 76 | 187 | 416 | 40 |
| PRO | O | C | 190 | 77 | 178 | 408 | 41 |
| ASP | N | C | 191 | 87 | 193 | 420 | 39 |
| ASP | CA | C | 191 | 100 | 188 | 417 | 39 |
| ASP | CB | C | 191 | 104 | 193 | 402 | 40 |
| ASP | CG | C | 191 | 105 | 208 | 401 | 41 |
| ASP | OD1 | C | 191 | 101 | 213 | 391 | 42 |
| ASP | OD2 | C | 191 | 110 | 214 | 411 | 41 |
| ASP | C | C | 191 | 111 | 192 | 427 | 38 |
| ASP | O | C | 191 | 109 | 199 | 436 | 38 |
| ASP | N | C | 192 | 123 | 187 | 424 | 38 |
| ASP | CA | C | 192 | 134 | 189 | 434 | 38 |
| ASP | CB | C | 192 | 147 | 181 | 429 | 39 |
| ASP | CG | C | 192 | 154 | 187 | 418 | 40 |
| ASP | OD1 | C | 192 | 148 | 193 | 409 | 41 |
| ASP | OD2 | C | 192 | 167 | 186 | 418 | 41 |
| ASP | C | C | 192 | 138 | 204 | 435 | 37 |
| ASP | O | C | 192 | 148 | 207 | 442 | 37 |
| SER | N | C | 193 | 131 | 213 | 428 | 36 |
| SER | CA | C | 193 | 134 | 227 | 429 | 35 |
| SER | CB | C | 193 | 132 | 234 | 415 | 35 |
| SER | OG | C | 193 | 119 | 239 | 414 | 35 |
| SER | C | C | 193 | 126 | 234 | 440 | 34 |
| SER | O | C | 193 | 129 | 246 | 443 | 33 |
| LEU | N | C | 194 | 117 | 227 | 445 | 32 |
| LEU | CA | C | 194 | 109 | 233 | 456 | 31 |
| LEU | CB | C | 194 | 94 | 227 | 456 | 31 |
| LEU | CG | C | 194 | 85 | 234 | 465 | 31 |
| LEU | CD1 | C | 194 | 81 | 248 | 459 | 31 |
| LEU | CD2 | C | 194 | 72 | 226 | 468 | 31 |
| LEU | C | C | 194 | 116 | 229 | 469 | 30 |
| LEU | O | C | 194 | 115 | 218 | 474 | 30 |
| GLU | N | C | 195 | 123 | 239 | 474 | 30 |
| GLU | CA | C | 195 | 131 | 237 | 486 | 29 |
| GLU | CB | C | 195 | 139 | 250 | 489 | 30 |
| GLU | CG | C | 195 | 146 | 250 | 502 | 31 |
| GLU | CD | C | 195 | 157 | 261 | 503 | 31 |
| GLU | OE1 | C | 195 | 168 | 259 | 498 | 33 |
| GLU | OE2 | C | 195 | 154 | 272 | 509 | 32 |
| GLU | C | C | 195 | 123 | 233 | 499 | 28 |
| GLU | O | C | 195 | 114 | 240 | 503 | 27 |
| PRO | N | C | 196 | 127 | 222 | 505 | 27 |
| PRO | CD | C | 196 | 137 | 212 | 500 | 27 |
| PRO | CA | C | 196 | 120 | 217 | 517 | 28 |
| PRO | CB | C | 196 | 127 | 203 | 520 | 28 |
| PRO | CG | C | 196 | 131 | 199 | 506 | 28 |
| PRO | C | C | 196 | 121 | 227 | 528 | 27 |
| PRO | O | C | 196 | 131 | 235 | 528 | 27 |
| PHE | N | C | 197 | 113 | 226 | 538 | 27 |
| PHE | CA | C | 197 | 113 | 235 | 550 | 27 |
| PHE | CB | C | 197 | 101 | 231 | 560 | 27 |

TABLE 1-continued

Structure Coordinates for uncomplexed BACE

| | | | | | | | |
|---|---|---|---|---|---|---|---|
| PHE | CG | C | 197 | 102 | 240 | 572 | 26 |
| PHE | CD1 | C | 197 | 95 | 252 | 572 | 26 |
| PHE | CD2 | C | 197 | 108 | 235 | 584 | 27 |
| PHE | CE1 | C | 197 | 96 | 260 | 584 | 27 |
| PHE | CE2 | C | 197 | 109 | 243 | 595 | 26 |
| PHE | CZ | C | 197 | 103 | 256 | 595 | 27 |
| PHE | C | C | 197 | 126 | 235 | 558 | 27 |
| PHE | O | C | 197 | 131 | 246 | 561 | 27 |
| PHE | N | C | 198 | 131 | 223 | 561 | 27 |
| PHE | CA | C | 198 | 143 | 223 | 569 | 27 |
| PHE | CB | C | 198 | 147 | 209 | 573 | 28 |
| PHE | CG | C | 198 | 156 | 208 | 585 | 29 |
| PHE | CD1 | C | 198 | 150 | 210 | 598 | 29 |
| PHE | CD2 | C | 198 | 169 | 205 | 584 | 29 |
| PHE | CE1 | C | 198 | 159 | 210 | 610 | 30 |
| PHE | CE2 | C | 198 | 177 | 204 | 595 | 30 |
| PHE | CZ | C | 198 | 172 | 207 | 608 | 30 |
| PHE | C | C | 198 | 155 | 229 | 562 | 27 |
| PHE | O | C | 198 | 163 | 236 | 569 | 26 |
| ASP | N | C | 199 | 156 | 227 | 549 | 28 |
| ASP | CA | C | 199 | 167 | 233 | 542 | 30 |
| ASP | CB | C | 199 | 166 | 229 | 527 | 31 |
| ASP | CG | C | 199 | 171 | 215 | 524 | 32 |
| ASP | OD1 | C | 199 | 183 | 213 | 522 | 34 |
| ASP | OD2 | C | 199 | 162 | 206 | 526 | 34 |
| ASP | C | C | 199 | 167 | 248 | 543 | 29 |
| ASP | O | C | 199 | 177 | 255 | 546 | 28 |
| SER | N | C | 200 | 155 | 254 | 542 | 29 |
| SER | CA | C | 200 | 153 | 269 | 543 | 30 |
| SER | CB | C | 200 | 139 | 273 | 539 | 29 |
| SER | OG | C | 200 | 136 | 269 | 526 | 29 |
| SER | C | C | 200 | 156 | 273 | 558 | 31 |
| SER | O | C | 200 | 162 | 283 | 560 | 30 |
| LEU | N | C | 201 | 152 | 264 | 567 | 32 |
| LEU | CA | C | 201 | 154 | 267 | 581 | 33 |
| LEU | CB | C | 201 | 149 | 256 | 590 | 33 |
| LEU | CG | C | 201 | 152 | 257 | 605 | 33 |
| LEU | CD1 | C | 201 | 146 | 270 | 611 | 33 |
| LEU | CD2 | C | 201 | 147 | 245 | 612 | 34 |
| LEU | C | C | 201 | 169 | 269 | 584 | 33 |
| LEU | O | C | 201 | 174 | 280 | 588 | 33 |
| VAL | N | C | 202 | 177 | 259 | 580 | 33 |
| VAL | CA | C | 202 | 191 | 259 | 582 | 33 |
| VAL | CB | C | 202 | 198 | 246 | 577 | 33 |
| VAL | CG1 | C | 202 | 213 | 247 | 576 | 32 |
| VAL | CG2 | C | 202 | 194 | 234 | 586 | 33 |
| VAL | C | C | 202 | 198 | 271 | 575 | 34 |
| VAL | O | C | 202 | 206 | 278 | 581 | 35 |
| LYS | N | C | 203 | 194 | 273 | 563 | 35 |
| LYS | CA | C | 203 | 200 | 284 | 555 | 35 |
| LYS | CB | C | 203 | 195 | 284 | 541 | 36 |
| LYS | CG | C | 203 | 202 | 274 | 532 | 37 |
| LYS | CD | C | 203 | 194 | 272 | 519 | 37 |
| LYS | CE | C | 203 | 203 | 267 | 508 | 38 |
| LYS | NZ | C | 203 | 212 | 256 | 513 | 38 |
| LYS | C | C | 203 | 197 | 298 | 560 | 36 |
| LYS | O | C | 203 | 206 | 307 | 560 | 35 |
| GLN | N | C | 204 | 186 | 300 | 566 | 35 |
| GLN | CA | C | 204 | 182 | 313 | 571 | 36 |
| GLN | CB | C | 204 | 167 | 315 | 569 | 35 |
| GLN | CG | C | 204 | 162 | 315 | 555 | 34 |
| GLN | CD | C | 204 | 147 | 317 | 553 | 33 |
| GLN | OE1 | C | 204 | 141 | 326 | 560 | 33 |
| GLN | NE2 | C | 204 | 141 | 309 | 544 | 33 |
| GLN | C | C | 204 | 185 | 316 | 586 | 37 |
| GLN | O | C | 204 | 185 | 328 | 590 | 38 |
| THR | N | C | 205 | 188 | 306 | 593 | 38 |
| THR | CA | C | 205 | 191 | 308 | 607 | 39 |
| THR | CB | C | 205 | 181 | 301 | 616 | 39 |
| THR | OG1 | C | 205 | 182 | 287 | 616 | 38 |
| THR | CG2 | C | 205 | 167 | 305 | 612 | 39 |
| THR | C | C | 205 | 205 | 302 | 612 | 40 |
| THR | O | C | 205 | 213 | 298 | 604 | 40 |
| HIS | N | C | 206 | 207 | 302 | 625 | 41 |
| HIS | CA | C | 206 | 219 | 298 | 631 | 42 |
| HIS | CB | C | 206 | 220 | 305 | 644 | 44 |
| HIS | CG | C | 206 | 207 | 308 | 651 | 45 |
| HIS | CD2 | C | 206 | 200 | 301 | 661 | 45 |
| HIS | ND1 | C | 206 | 199 | 319 | 648 | 45 |
| HIS | CE1 | C | 206 | 188 | 319 | 655 | 45 |
| HIS | NE2 | C | 206 | 189 | 308 | 663 | 45 |
| HIS | C | C | 206 | 218 | 283 | 634 | 42 |
| HIS | O | C | 206 | 228 | 276 | 638 | 42 |
| VAL | N | C | 207 | 206 | 277 | 633 | 40 |
| VAL | CA | C | 207 | 203 | 263 | 636 | 39 |
| VAL | CB | C | 207 | 188 | 260 | 633 | 40 |
| VAL | CG1 | C | 207 | 186 | 245 | 637 | 39 |
| VAL | CG2 | C | 207 | 180 | 269 | 642 | 39 |
| VAL | C | C | 207 | 212 | 253 | 628 | 39 |
| VAL | O | C | 207 | 212 | 253 | 616 | 38 |
| PRO | N | C | 208 | 219 | 244 | 636 | 38 |
| PRO | CD | C | 208 | 220 | 244 | 651 | 38 |
| PRO | CA | C | 208 | 227 | 233 | 630 | 37 |
| PRO | CB | C | 208 | 232 | 226 | 643 | 37 |
| PRO | CG | C | 208 | 233 | 237 | 653 | 38 |
| PRO | C | C | 208 | 219 | 224 | 621 | 37 |
| PRO | O | C | 208 | 207 | 222 | 624 | 36 |
| ASN | N | C | 209 | 225 | 219 | 611 | 35 |
| ASN | CA | C | 209 | 218 | 211 | 601 | 35 |
| ASN | CB | C | 209 | 226 | 210 | 588 | 35 |
| ASN | CG | C | 209 | 218 | 204 | 577 | 35 |
| ASN | OD1 | C | 209 | 205 | 203 | 577 | 35 |
| ASN | ND2 | C | 209 | 225 | 199 | 566 | 35 |
| ASN | C | C | 209 | 216 | 197 | 607 | 34 |
| ASN | O | C | 209 | 223 | 187 | 603 | 34 |
| LEU | N | C | 210 | 207 | 195 | 616 | 34 |
| LEU | CA | C | 210 | 204 | 183 | 622 | 33 |
| LEU | CB | C | 210 | 217 | 178 | 630 | 34 |
| LEU | CG | C | 210 | 217 | 167 | 640 | 35 |
| LEU | CD1 | C | 210 | 232 | 163 | 643 | 35 |
| LEU | CD2 | C | 210 | 210 | 170 | 653 | 34 |
| LEU | C | C | 210 | 192 | 184 | 632 | 33 |
| LEU | O | C | 210 | 190 | 195 | 637 | 33 |
| PHE | N | C | 211 | 185 | 173 | 633 | 32 |
| PHE | CA | C | 211 | 173 | 173 | 642 | 32 |
| PHE | CB | C | 211 | 160 | 177 | 635 | 32 |
| PHE | CG | C | 211 | 155 | 168 | 625 | 32 |
| PHE | CD1 | C | 211 | 159 | 169 | 611 | 32 |
| PHE | CD2 | C | 211 | 147 | 157 | 628 | 32 |
| PHE | CE1 | C | 211 | 154 | 160 | 601 | 32 |
| PHE | CE2 | C | 211 | 142 | 148 | 618 | 32 |
| PHE | CZ | C | 211 | 146 | 150 | 605 | 33 |
| PHE | C | C | 211 | 173 | 159 | 647 | 31 |
| PHE | O | C | 211 | 177 | 150 | 641 | 32 |
| SER | N | C | 212 | 167 | 157 | 659 | 31 |
| SER | CA | C | 212 | 166 | 144 | 665 | 31 |
| SER | CB | C | 212 | 176 | 143 | 676 | 31 |
| SER | OG | C | 212 | 175 | 154 | 685 | 31 |
| SER | C | C | 212 | 151 | 142 | 669 | 32 |
| SER | O | C | 212 | 144 | 151 | 672 | 31 |
| LEU | N | C | 213 | 148 | 129 | 670 | 33 |
| LEU | CA | C | 213 | 134 | 126 | 674 | 34 |
| LEU | CB | C | 213 | 126 | 121 | 662 | 35 |
| LEU | CG | C | 213 | 123 | 132 | 651 | 35 |
| LEU | CD1 | C | 213 | 116 | 125 | 639 | 35 |
| LEU | CD2 | C | 213 | 114 | 143 | 657 | 35 |
| LEU | C | C | 213 | 133 | 115 | 684 | 35 |
| LEU | O | C | 213 | 139 | 104 | 683 | 35 |
| GLN | N | C | 214 | 125 | 118 | 695 | 36 |
| GLN | CA | C | 214 | 123 | 108 | 705 | 38 |
| GLN | CB | C | 214 | 127 | 113 | 719 | 38 |
| GLN | CG | C | 214 | 125 | 103 | 730 | 38 |
| GLN | CD | C | 214 | 124 | 109 | 744 | 38 |
| GLN | OE1 | C | 214 | 116 | 118 | 746 | 38 |
| GLN | NE2 | C | 214 | 133 | 104 | 753 | 38 |
| GLN | C | C | 214 | 108 | 106 | 705 | 38 |
| GLN | O | C | 214 | 100 | 114 | 711 | 38 |
| LEU | N | C | 215 | 103 | 95 | 699 | 39 |
| LEU | CA | C | 215 | 89 | 92 | 698 | 41 |
| LEU | CB | C | 215 | 86 | 86 | 685 | 40 |
| LEU | CG | C | 215 | 89 | 96 | 673 | 41 |
| LEU | CD1 | C | 215 | 86 | 90 | 660 | 40 |
| LEU | CD2 | C | 215 | 81 | 109 | 675 | 41 |
| LEU | C | C | 215 | 85 | 82 | 710 | 42 |

TABLE 1-continued

Structure Coordinates for uncomplexed BACE

| | | | | | | | |
|---|---|---|---|---|---|---|---|
| LEU | O | C | 215 | 90 | 71 | 710 | 42 |
| CYS | N | C | 216 | 77 | 87 | 719 | 43 |
| CYS | CA | C | 216 | 72 | 79 | 730 | 45 |
| CYS | C | C | 216 | 58 | 75 | 728 | 45 |
| CYS | O | C | 216 | 54 | 66 | 720 | 46 |
| CYS | CB | C | 216 | 74 | 87 | 743 | 46 |
| CYS | SG | C | 216 | 90 | 95 | 745 | 47 |
| GLY | N | C | 232 | 63 | 126 | 725 | 36 |
| GLY | CA | C | 232 | 77 | 126 | 723 | 36 |
| GLY | C | C | 232 | 83 | 139 | 721 | 37 |
| GLY | O | C | 232 | 78 | 150 | 724 | 36 |
| GLY | N | C | 233 | 96 | 139 | 716 | 37 |
| GLY | CA | C | 233 | 103 | 152 | 714 | 36 |
| GLY | C | C | 233 | 114 | 153 | 724 | 37 |
| GLY | O | C | 233 | 109 | 154 | 737 | 38 |
| SER | N | C | 234 | 110 | 153 | 700 | 36 |
| SER | CA | C | 234 | 115 | 143 | 695 | 36 |
| SER | CB | C | 234 | 110 | 165 | 695 | 35 |
| SER | OG | C | 234 | 116 | 168 | 682 | 35 |
| SER | C | C | 234 | 107 | 173 | 671 | 35 |
| SER | O | C | 234 | 115 | 179 | 659 | 35 |
| MET | N | C | 235 | 106 | 180 | 644 | 36 |
| MET | CA | C | 235 | 97 | 195 | 646 | 35 |
| MET | CB | C | 235 | 126 | 179 | 686 | 34 |
| MET | CG | C | 235 | 122 | 190 | 688 | 34 |
| MET | SD | C | 235 | 139 | 176 | 686 | 34 |
| MET | CE | C | 235 | 149 | 186 | 689 | 33 |
| MET | C | C | 235 | 160 | 181 | 698 | 32 |
| MET | O | C | 235 | 170 | 192 | 702 | 32 |
| ILE | N | C | 236 | 155 | 173 | 710 | 32 |
| ILE | CA | C | 236 | 147 | 182 | 720 | 32 |
| ILE | CB | C | 236 | 154 | 192 | 676 | 32 |
| ILE | CG2 | C | 236 | 161 | 185 | 669 | 31 |
| ILE | CG1 | C | 236 | 152 | 205 | 674 | 33 |
| ILE | CD1 | C | 236 | 157 | 212 | 662 | 34 |
| ILE | C | C | 236 | 147 | 223 | 658 | 34 |
| ILE | O | C | 236 | 161 | 185 | 669 | 31 |
| ILE | N | C | 237 | 152 | 205 | 674 | 33 |
| ILE | CA | C | 237 | 157 | 212 | 662 | 34 |
| ILE | CB | C | 237 | 147 | 223 | 658 | 34 |
| ILE | CG2 | C | 237 | 152 | 229 | 645 | 34 |
| ILE | CG1 | C | 237 | 133 | 217 | 655 | 34 |
| ILE | CD1 | C | 237 | 132 | 206 | 645 | 34 |
| ILE | C | C | 237 | 170 | 218 | 664 | 35 |
| ILE | O | C | 237 | 172 | 227 | 672 | 34 |
| GLY | N | C | 238 | 180 | 213 | 656 | 35 |
| GLY | CA | C | 238 | 193 | 219 | 657 | 37 |
| GLY | C | C | 238 | 203 | 213 | 667 | 38 |
| GLY | O | C | 238 | 213 | 219 | 670 | 39 |
| GLY | N | C | 239 | 200 | 201 | 673 | 38 |
| GLY | CA | C | 239 | 209 | 195 | 682 | 39 |
| GLY | C | C | 239 | 204 | 182 | 688 | 39 |
| GLY | O | C | 239 | 194 | 177 | 684 | 40 |
| ILE | N | C | 240 | 211 | 177 | 698 | 39 |
| ILE | CA | C | 240 | 209 | 165 | 705 | 40 |
| ILE | CB | C | 240 | 220 | 155 | 702 | 40 |
| ILE | CG2 | C | 240 | 218 | 142 | 710 | 39 |
| ILE | CG1 | C | 240 | 221 | 152 | 687 | 40 |
| ILE | CD1 | C | 240 | 235 | 146 | 683 | 40 |
| ILE | C | C | 240 | 207 | 167 | 720 | 41 |
| ILE | O | C | 240 | 216 | 173 | 726 | 40 |
| ASP | N | C | 241 | 196 | 162 | 725 | 42 |
| ASP | CA | C | 241 | 194 | 164 | 740 | 43 |
| ASP | CB | C | 241 | 179 | 168 | 742 | 44 |
| ASP | CG | C | 241 | 177 | 171 | 757 | 44 |
| ASP | OD1 | C | 241 | 168 | 179 | 760 | 45 |
| ASP | OD2 | C | 241 | 185 | 167 | 766 | 45 |
| ASP | C | C | 241 | 197 | 150 | 746 | 43 |
| ASP | O | C | 241 | 189 | 141 | 746 | 44 |
| HIS | N | C | 242 | 208 | 150 | 753 | 44 |
| HIS | CA | C | 242 | 213 | 138 | 760 | 44 |
| HIS | CB | C | 242 | 227 | 141 | 765 | 46 |
| HIS | CG | C | 242 | 237 | 144 | 754 | 47 |
| HIS | CD2 | C | 242 | 241 | 155 | 748 | 48 |
| HIS | ND1 | C | 242 | 244 | 134 | 747 | 48 |
| HIS | CE1 | C | 242 | 251 | 139 | 738 | 48 |
| HIS | NE2 | C | 242 | 249 | 152 | 738 | 48 |

TABLE 1-continued

Structure Coordinates for uncomplexed BACE

| | | | | | | | |
|---|---|---|---|---|---|---|---|
| HIS | C | C | 242 | 204 | 132 | 771 | 44 |
| HIS | O | C | 242 | 205 | 120 | 774 | 43 |
| SER | N | C | 243 | 196 | 141 | 777 | 43 |
| SER | CA | C | 243 | 187 | 135 | 787 | 43 |
| SER | CB | C | 243 | 181 | 147 | 795 | 42 |
| SER | OG | C | 243 | 169 | 152 | 789 | 43 |
| SER | C | C | 243 | 176 | 127 | 781 | 42 |
| SER | O | C | 243 | 167 | 122 | 788 | 43 |
| LEU | N | C | 244 | 176 | 126 | 768 | 41 |
| LEU | CA | C | 244 | 165 | 118 | 761 | 40 |
| LEU | CB | C | 244 | 161 | 125 | 748 | 40 |
| LEU | CG | C | 244 | 154 | 139 | 750 | 40 |
| LEU | CD1 | C | 244 | 150 | 144 | 736 | 40 |
| LEU | CD2 | C | 244 | 142 | 138 | 759 | 40 |
| LEU | C | C | 244 | 169 | 104 | 757 | 39 |
| LEU | O | C | 244 | 161 | 96 | 752 | 39 |
| TYR | N | C | 245 | 182 | 100 | 760 | 39 |
| TYR | CA | C | 245 | 186 | 87 | 758 | 38 |
| TYR | CB | C | 245 | 192 | 86 | 743 | 38 |
| TYR | CG | C | 245 | 205 | 93 | 742 | 37 |
| TYR | CD1 | C | 245 | 206 | 106 | 738 | 38 |
| TYR | CE1 | C | 245 | 218 | 113 | 736 | 38 |
| TYR | CD2 | C | 245 | 217 | 86 | 743 | 37 |
| TYR | CE2 | C | 245 | 230 | 92 | 741 | 37 |
| TYR | CZ | C | 245 | 230 | 106 | 738 | 38 |
| TYR | OH | C | 245 | 242 | 112 | 736 | 39 |
| TYR | C | C | 245 | 197 | 82 | 768 | 38 |
| TYR | O | C | 245 | 203 | 91 | 775 | 37 |
| THR | N | C | 246 | 200 | 70 | 768 | 38 |
| THR | CA | C | 246 | 211 | 64 | 776 | 38 |
| THR | CB | C | 246 | 205 | 56 | 788 | 39 |
| THR | OG1 | C | 246 | 197 | 45 | 783 | 39 |
| THR | CG2 | C | 246 | 196 | 65 | 797 | 38 |
| THR | C | C | 246 | 220 | 55 | 768 | 38 |
| THR | O | C | 246 | 216 | 51 | 757 | 37 |
| GLY | N | C | 247 | 232 | 53 | 774 | 38 |
| GLY | CA | C | 247 | 241 | 44 | 766 | 39 |
| GLY | C | C | 247 | 247 | 53 | 756 | 39 |
| GLY | O | C | 247 | 247 | 65 | 757 | 39 |
| SER | N | C | 248 | 252 | 47 | 745 | 39 |
| SER | CA | C | 248 | 259 | 55 | 734 | 40 |
| SER | CB | C | 248 | 272 | 49 | 731 | 41 |
| SER | OG | C | 248 | 281 | 51 | 742 | 43 |
| SER | C | C | 248 | 250 | 56 | 721 | 40 |
| SER | O | C | 248 | 241 | 48 | 719 | 40 |
| LEU | N | C | 249 | 254 | 65 | 713 | 39 |
| LEU | CA | C | 249 | 248 | 67 | 700 | 38 |
| LEU | CB | C | 249 | 247 | 82 | 697 | 38 |
| LEU | CG | C | 249 | 236 | 90 | 702 | 38 |
| LEU | CD1 | C | 249 | 239 | 105 | 701 | 38 |
| LEU | CD2 | C | 249 | 223 | 87 | 695 | 38 |
| LEU | C | C | 249 | 256 | 60 | 690 | 38 |
| LEU | O | C | 249 | 268 | 61 | 690 | 38 |
| TRP | N | C | 250 | 250 | 52 | 681 | 38 |
| TRP | CA | C | 250 | 257 | 45 | 670 | 37 |
| TRP | CB | C | 250 | 255 | 30 | 671 | 38 |
| TRP | CG | C | 250 | 264 | 24 | 681 | 38 |
| TRP | CD2 | C | 250 | 277 | 17 | 679 | 38 |
| TRP | CE2 | C | 250 | 281 | 12 | 691 | 38 |
| TRP | CE3 | C | 250 | 284 | 15 | 667 | 38 |
| TRP | CD1 | C | 250 | 262 | 22 | 695 | 38 |
| TRP | NE1 | C | 250 | 272 | 16 | 701 | 39 |
| TRP | CZ2 | C | 250 | 294 | 6 | 693 | 38 |
| TRP | CZ3 | C | 250 | 297 | 9 | 669 | 39 |
| TRP | CH2 | C | 250 | 301 | 4 | 681 | 39 |
| TRP | C | C | 250 | 251 | 51 | 657 | 36 |
| TRP | O | C | 250 | 239 | 52 | 655 | 36 |
| TYR | N | C | 251 | 260 | 54 | 648 | 35 |
| TYR | CA | C | 251 | 256 | 60 | 635 | 35 |
| TYR | CB | C | 251 | 264 | 73 | 632 | 34 |
| TYR | CG | C | 251 | 261 | 84 | 642 | 33 |
| TYR | CD1 | C | 251 | 269 | 85 | 654 | 33 |
| TYR | CE1 | C | 251 | 266 | 96 | 662 | 33 |
| TYR | CD2 | C | 251 | 251 | 93 | 639 | 33 |
| TYR | CE2 | C | 251 | 248 | 103 | 648 | 33 |
| TYR | CZ | C | 251 | 256 | 105 | 660 | 33 |
| TYR | OH | C | 251 | 253 | 115 | 669 | 33 |

TABLE 1-continued

Structure Coordinates for uncomplexed BACE

| | | | | | | | |
|---|---|---|---|---|---|---|---|
| TYR | C   | C | 251 | 258 | 51  | 622 | 35 |
| TYR | O   | C | 251 | 268 | 44  | 620 | 35 |
| THR | N   | C | 252 | 247 | 51  | 614 | 36 |
| THR | CA  | C | 252 | 247 | 44  | 602 | 37 |
| THR | CB  | C | 252 | 235 | 34  | 601 | 37 |
| THR | OG1 | C | 252 | 236 | 26  | 589 | 38 |
| THR | CG2 | C | 252 | 222 | 43  | 600 | 37 |
| THR | C   | C | 252 | 247 | 54  | 591 | 38 |
| THR | O   | C | 252 | 241 | 65  | 593 | 38 |
| PRO | N   | C | 253 | 254 | 52  | 580 | 38 |
| PRO | CD  | C | 253 | 264 | 42  | 577 | 39 |
| PRO | CA  | C | 253 | 254 | 62  | 569 | 39 |
| PRO | CB  | C | 253 | 266 | 57  | 560 | 39 |
| PRO | CG  | C | 253 | 274 | 48  | 569 | 39 |
| PRO | C   | C | 253 | 241 | 64  | 561 | 39 |
| PRO | O   | C | 253 | 235 | 54  | 558 | 39 |
| ILE | N   | C | 254 | 238 | 76  | 557 | 40 |
| ILE | CA  | C | 254 | 226 | 79  | 549 | 41 |
| ILE | CB  | C | 254 | 222 | 93  | 550 | 41 |
| ILE | CG2 | C | 254 | 211 | 96  | 539 | 41 |
| ILE | CG1 | C | 254 | 217 | 97  | 564 | 40 |
| ILE | CD1 | C | 254 | 211 | 111 | 565 | 40 |
| ILE | C   | C | 254 | 232 | 75  | 535 | 41 |
| ILE | O   | C | 254 | 242 | 81  | 531 | 41 |
| ARG | N   | C | 255 | 226 | 66  | 528 | 42 |
| ARG | CA  | C | 255 | 231 | 61  | 515 | 43 |
| ARG | CB  | C | 255 | 224 | 49  | 511 | 44 |
| ARG | CG  | C | 255 | 232 | 41  | 500 | 44 |
| ARG | CD  | C | 255 | 224 | 31  | 493 | 45 |
| ARG | NE  | C | 255 | 232 | 23  | 484 | 45 |
| ARG | CZ  | C | 255 | 226 | 15  | 474 | 46 |
| ARG | NH1 | C | 255 | 213 | 14  | 473 | 45 |
| ARG | NH2 | C | 255 | 234 | 8   | 466 | 46 |
| ARG | C   | C | 255 | 230 | 72  | 504 | 44 |
| ARG | O   | C | 255 | 240 | 74  | 497 | 44 |
| ARG | N   | C | 256 | 218 | 78  | 503 | 44 |
| ARG | CA  | C | 256 | 216 | 88  | 493 | 45 |
| ARG | CB  | C | 256 | 210 | 82  | 480 | 46 |
| ARG | CG  | C | 256 | 210 | 93  | 468 | 48 |
| ARG | CD  | C | 256 | 198 | 90  | 459 | 49 |
| ARG | NE  | C | 256 | 199 | 78  | 451 | 50 |
| ARG | CZ  | C | 256 | 189 | 72  | 446 | 50 |
| ARG | NH1 | C | 256 | 176 | 77  | 447 | 50 |
| ARG | NH2 | C | 256 | 190 | 61  | 438 | 51 |
| ARG | C   | C | 256 | 207 | 98  | 499 | 44 |
| ARG | O   | C | 256 | 197 | 94  | 505 | 45 |
| GLU | N   | C | 257 | 209 | 111 | 496 | 44 |
| GLU | CA  | C | 257 | 200 | 121 | 501 | 43 |
| GLU | CB  | C | 257 | 208 | 134 | 503 | 43 |
| GLU | CG  | C | 257 | 218 | 134 | 514 | 44 |
| GLU | CD  | C | 257 | 229 | 144 | 513 | 45 |
| GLU | OE1 | C | 257 | 237 | 144 | 503 | 45 |
| GLU | OE2 | C | 257 | 230 | 153 | 522 | 45 |
| GLU | C   | C | 257 | 187 | 123 | 493 | 43 |
| GLU | O   | C | 257 | 186 | 132 | 485 | 42 |
| TRP | N   | C | 258 | 177 | 115 | 496 | 42 |
| TRP | CA  | C | 258 | 164 | 116 | 490 | 41 |
| TRP | CB  | C | 258 | 163 | 107 | 478 | 43 |
| TRP | CG  | C | 258 | 165 | 92  | 479 | 44 |
| TRP | CD2 | C | 258 | 158 | 82  | 472 | 44 |
| TRP | CE2 | C | 258 | 163 | 69  | 476 | 44 |
| TRP | CE3 | C | 258 | 149 | 82  | 462 | 44 |
| TRP | CD1 | C | 258 | 173 | 86  | 488 | 44 |
| TRP | NE1 | C | 258 | 173 | 72  | 486 | 44 |
| TRP | CZ2 | C | 258 | 159 | 57  | 471 | 44 |
| TRP | CZ3 | C | 258 | 144 | 69  | 457 | 44 |
| TRP | CH2 | C | 258 | 150 | 57  | 461 | 44 |
| TRP | C   | C | 258 | 155 | 112 | 501 | 40 |
| TRP | O   | C | 258 | 149 | 121 | 508 | 40 |
| TYR | N   | C | 259 | 153 | 100 | 504 | 40 |
| TYR | CA  | C | 259 | 145 | 95  | 516 | 39 |
| TYR | CB  | C | 259 | 139 | 81  | 513 | 39 |
| TYR | CG  | C | 259 | 127 | 80  | 505 | 39 |
| TYR | CD1 | C | 259 | 115 | 84  | 509 | 39 |
| TYR | CE1 | C | 259 | 104 | 84  | 501 | 39 |
| TYR | CD2 | C | 259 | 128 | 76  | 491 | 39 |
| TYR | CE2 | C | 259 | 117 | 75  | 483 | 39 |
| TYR | CZ  | C | 259 | 105 | 79  | 488 | 39 |
| TYR | OH  | C | 259 | 93  | 79  | 480 | 41 |
| TYR | C   | C | 259 | 157 | 94  | 525 | 38 |
| TYR | O   | C | 259 | 168 | 95  | 521 | 37 |
| TYR | N   | C | 260 | 154 | 92  | 538 | 38 |
| TYR | CA  | C | 260 | 166 | 90  | 547 | 38 |
| TYR | CB  | C | 260 | 162 | 93  | 561 | 37 |
| TYR | CG  | C | 260 | 162 | 108 | 564 | 36 |
| TYR | CD1 | C | 260 | 149 | 115 | 565 | 36 |
| TYR | CE1 | C | 260 | 149 | 128 | 567 | 35 |
| TYR | CD2 | C | 260 | 173 | 115 | 565 | 36 |
| TYR | CE2 | C | 260 | 173 | 129 | 567 | 35 |
| TYR | CZ  | C | 260 | 161 | 136 | 568 | 35 |
| TYR | OH  | C | 260 | 160 | 149 | 570 | 34 |
| TYR | C   | C | 260 | 169 | 75  | 545 | 39 |
| TYR | O   | C | 260 | 165 | 67  | 553 | 39 |
| GLU | N   | C | 261 | 176 | 72  | 535 | 40 |
| GLU | CA  | C | 261 | 180 | 58  | 532 | 42 |
| GLU | CB  | C | 261 | 182 | 56  | 517 | 42 |
| GLU | CG  | C | 261 | 188 | 42  | 513 | 43 |
| GLU | CD  | C | 261 | 190 | 41  | 498 | 44 |
| GLU | OE1 | C | 261 | 193 | 51  | 491 | 44 |
| GLU | OE2 | C | 261 | 190 | 30  | 492 | 44 |
| GLU | C   | C | 261 | 192 | 52  | 539 | 42 |
| GLU | O   | C | 261 | 202 | 59  | 540 | 42 |
| VAL | N   | C | 262 | 191 | 40  | 544 | 43 |
| VAL | CA  | C | 262 | 202 | 33  | 551 | 44 |
| VAL | CB  | C | 262 | 199 | 33  | 566 | 43 |
| VAL | CG1 | C | 262 | 198 | 47  | 572 | 43 |
| VAL | CG2 | C | 262 | 186 | 25  | 569 | 44 |
| VAL | C   | C | 262 | 203 | 19  | 545 | 45 |
| VAL | O   | C | 262 | 194 | 15  | 538 | 45 |
| ILE | N   | C | 263 | 213 | 12  | 549 | 45 |
| ILE | CA  | C | 263 | 215 | −2  | 545 | 46 |
| ILE | CB  | C | 263 | 229 | −3  | 537 | 46 |
| ILE | CG2 | C | 263 | 231 | −17 | 534 | 46 |
| ILE | CG1 | C | 263 | 228 | 6   | 525 | 46 |
| ILE | CD1 | C | 263 | 242 | 6   | 517 | 46 |
| ILE | C   | C | 263 | 215 | −12 | 556 | 45 |
| ILE | O   | C | 263 | 222 | −10 | 566 | 45 |
| ILE | N   | C | 264 | 207 | −22 | 555 | 46 |
| ILE | CA  | C | 264 | 207 | −32 | 566 | 46 |
| ILE | CB  | C | 264 | 192 | −37 | 568 | 46 |
| ILE | CG2 | C | 264 | 192 | −49 | 578 | 46 |
| ILE | CG1 | C | 264 | 184 | −26 | 574 | 45 |
| ILE | CD1 | C | 264 | 170 | −29 | 576 | 46 |
| ILE | C   | C | 264 | 215 | −44 | 561 | 46 |
| ILE | O   | C | 264 | 214 | −48 | 549 | 47 |
| VAL | N   | C | 265 | 224 | −49 | 569 | 46 |
| VAL | CA  | C | 265 | 233 | −60 | 565 | 45 |
| VAL | CB  | C | 265 | 248 | −56 | 569 | 45 |
| VAL | CG1 | C | 265 | 251 | −43 | 562 | 45 |
| VAL | CG2 | C | 265 | 250 | −56 | 583 | 45 |
| VAL | C   | C | 265 | 230 | −74 | 571 | 45 |
| VAL | O   | C | 265 | 234 | −84 | 566 | 45 |
| ARG | N   | C | 266 | 223 | −74 | 583 | 45 |
| ARG | CA  | C | 266 | 219 | −86 | 589 | 46 |
| ARG | CB  | C | 266 | 231 | −90 | 599 | 46 |
| ARG | CG  | C | 266 | 228 | −102| 608 | 47 |
| ARG | CD  | C | 266 | 239 | −104| 619 | 47 |
| ARG | NE  | C | 266 | 236 | −114| 629 | 48 |
| ARG | CZ  | C | 266 | 239 | −127| 627 | 49 |
| ARG | NH1 | C | 266 | 244 | −131| 616 | 49 |
| ARG | NH2 | C | 266 | 237 | −135| 637 | 49 |
| ARG | C   | C | 266 | 206 | −85 | 597 | 45 |
| ARG | O   | C | 266 | 203 | −74 | 602 | 45 |
| VAL | N   | C | 267 | 199 | −96 | 598 | 45 |
| VAL | CA  | C | 267 | 186 | −96 | 605 | 45 |
| VAL | CB  | C | 267 | 174 | −96 | 595 | 45 |
| VAL | CG1 | C | 267 | 161 | −97 | 603 | 45 |
| VAL | CG2 | C | 267 | 174 | −84 | 586 | 45 |
| VAL | C   | C | 267 | 185 | −107| 615 | 45 |
| VAL | O   | C | 267 | 189 | −119| 611 | 46 |
| GLU | N   | C | 268 | 181 | −104| 627 | 45 |
| GLU | CA  | C | 268 | 180 | −114| 637 | 45 |
| GLU | CB  | C | 268 | 191 | −112| 648 | 45 |
| GLU | CG  | C | 268 | 202 | −121| 647 | 44 |

TABLE 1-continued

Structure Coordinates for uncomplexed BACE

| | | | | | | |
|---|---|---|---|---|---|---|
| GLU | CD | C | 268 | 213 | −117 | 656 | 43 |
| GLU | OE1 | C | 268 | 210 | −113 | 668 | 43 |
| GLU | OE2 | C | 268 | 225 | −118 | 653 | 42 |
| GLU | C | C | 268 | 167 | −114 | 644 | 46 |
| GLU | O | C | 268 | 160 | −104 | 646 | 46 |
| ILE | N | C | 269 | 162 | −126 | 648 | 47 |
| ILE | CA | C | 269 | 150 | −127 | 655 | 48 |
| ILE | CB | C | 269 | 139 | −134 | 646 | 48 |
| ILE | CG2 | C | 269 | 144 | −148 | 642 | 48 |
| ILE | CG1 | C | 269 | 126 | −134 | 653 | 48 |
| ILE | CD1 | C | 269 | 120 | −121 | 656 | 48 |
| ILE | C | C | 269 | 153 | −136 | 668 | 48 |
| ILE | O | C | 269 | 156 | −147 | 667 | 47 |
| ASN | N | C | 270 | 152 | −129 | 679 | 49 |
| ASN | CA | C | 270 | 156 | −135 | 692 | 50 |
| ASN | CB | C | 270 | 146 | −146 | 696 | 50 |
| ASN | CG | C | 270 | 140 | −144 | 709 | 50 |
| ASN | OD1 | C | 270 | 141 | −133 | 715 | 51 |
| ASN | ND2 | C | 270 | 132 | −154 | 714 | 50 |
| ASN | C | C | 270 | 170 | −141 | 692 | 50 |
| ASN | O | C | 270 | 173 | −150 | 699 | 51 |
| GLY | N | C | 271 | 178 | −136 | 683 | 51 |
| GLY | CA | C | 271 | 192 | −141 | 682 | 52 |
| GLY | C | C | 271 | 195 | −150 | 670 | 52 |
| GLY | O | C | 271 | 206 | −152 | 666 | 52 |
| GLN | N | C | 272 | 184 | −155 | 664 | 53 |
| GLN | CA | C | 272 | 186 | −164 | 652 | 54 |
| GLN | CB | C | 272 | 174 | −174 | 652 | 55 |
| GLN | CG | C | 272 | 175 | −185 | 641 | 55 |
| GLN | CD | C | 272 | 166 | −196 | 643 | 56 |
| GLN | OE1 | C | 272 | 154 | −194 | 645 | 56 |
| GLN | NE2 | C | 272 | 171 | −208 | 643 | 56 |
| GLN | C | C | 272 | 186 | −157 | 639 | 55 |
| GLN | O | C | 272 | 177 | −149 | 635 | 55 |
| ASP | N | C | 273 | 197 | −159 | 632 | 55 |
| ASP | CA | C | 273 | 199 | −153 | 619 | 57 |
| ASP | CB | C | 273 | 213 | −156 | 613 | 57 |
| ASP | CG | C | 273 | 216 | −151 | 600 | 57 |
| ASP | OD1 | C | 273 | 209 | −141 | 596 | 57 |
| ASP | OD2 | C | 273 | 224 | −156 | 592 | 57 |
| ASP | C | C | 273 | 189 | −156 | 609 | 58 |
| ASP | O | C | 273 | 187 | −168 | 605 | 57 |
| LEU | N | C | 274 | 182 | −146 | 603 | 58 |
| LEU | CA | C | 274 | 171 | −148 | 593 | 59 |
| LEU | CB | C | 274 | 165 | −134 | 589 | 59 |
| LEU | CG | C | 274 | 151 | −134 | 585 | 59 |
| LEU | CD1 | C | 274 | 142 | −140 | 596 | 59 |
| LEU | CD2 | C | 274 | 146 | −120 | 582 | 59 |
| LEU | C | C | 274 | 178 | −154 | 581 | 60 |
| LEU | O | C | 274 | 171 | −161 | 574 | 60 |
| LYS | N | C | 275 | 191 | −152 | 580 | 61 |
| LYS | CA | C | 275 | 199 | −159 | 569 | 62 |
| LYS | CB | C | 275 | 200 | −173 | 573 | 62 |
| LYS | CG | C | 275 | 212 | −181 | 566 | 63 |
| LYS | CD | C | 275 | 212 | −195 | 571 | 63 |
| LYS | CE | C | 275 | 224 | −203 | 565 | 63 |
| LYS | NZ | C | 275 | 224 | −217 | 570 | 64 |
| LYS | C | C | 275 | 193 | −157 | 555 | 63 |
| LYS | O | C | 275 | 190 | −167 | 548 | 63 |
| MET | N | C | 276 | 192 | −145 | 550 | 64 |
| MET | CA | C | 276 | 188 | −142 | 537 | 65 |
| MET | CB | C | 276 | 175 | −133 | 537 | 65 |
| MET | CG | C | 276 | 163 | −140 | 542 | 64 |
| MET | SD | C | 276 | 148 | −129 | 542 | 64 |
| MET | CE | C | 276 | 147 | −125 | 526 | 64 |
| MET | C | C | 276 | 199 | −134 | 530 | 66 |
| MET | O | C | 276 | 208 | −129 | 536 | 66 |
| ASP | N | C | 277 | 198 | −133 | 516 | 67 |
| ASP | CA | C | 277 | 208 | −126 | 509 | 68 |
| ASP | CB | C | 277 | 205 | −126 | 494 | 69 |
| ASP | CG | C | 277 | 216 | −120 | 485 | 69 |
| ASP | OD1 | C | 277 | 219 | −108 | 486 | 69 |
| ASP | OD2 | C | 277 | 222 | −128 | 477 | 69 |
| ASP | C | C | 277 | 207 | −111 | 514 | 69 |
| ASP | O | C | 277 | 196 | −106 | 514 | 69 |
| CYS | N | C | 278 | 218 | −105 | 517 | 69 |
| CYS | CA | C | 278 | 219 | −92 | 522 | 70 |
| CYS | C | C | 278 | 210 | −82 | 515 | 69 |
| CYS | O | C | 278 | 204 | −73 | 521 | 69 |
| CYS | CB | C | 278 | 233 | −87 | 523 | 70 |
| CYS | SG | C | 278 | 235 | −74 | 536 | 72 |
| LYS | N | C | 279 | 210 | −82 | 502 | 69 |
| LYS | CA | C | 279 | 202 | −73 | 494 | 68 |
| LYS | CB | C | 279 | 204 | −75 | 479 | 68 |
| LYS | CG | C | 279 | 219 | −75 | 475 | 68 |
| LYS | CD | C | 279 | 221 | −78 | 460 | 68 |
| LYS | CE | C | 279 | 217 | −66 | 451 | 68 |
| LYS | NZ | C | 279 | 227 | −56 | 452 | 69 |
| LYS | C | C | 279 | 187 | −73 | 497 | 68 |
| LYS | O | C | 279 | 181 | −63 | 499 | 68 |
| GLU | N | C | 280 | 182 | −85 | 498 | 67 |
| GLU | CA | C | 280 | 167 | −87 | 501 | 66 |
| GLU | CB | C | 280 | 165 | −101 | 505 | 66 |
| GLU | CG | C | 280 | 167 | −111 | 493 | 66 |
| GLU | CD | C | 280 | 157 | −109 | 482 | 66 |
| GLU | OE1 | C | 280 | 145 | −106 | 484 | 66 |
| GLU | OE2 | C | 280 | 162 | −109 | 470 | 66 |
| GLU | C | C | 280 | 162 | −78 | 512 | 66 |
| GLU | O | C | 280 | 151 | −73 | 512 | 66 |
| TYR | N | C | 281 | 171 | −76 | 522 | 66 |
| TYR | CA | C | 281 | 167 | −67 | 634 | 65 |
| TYR | CB | C | 281 | 178 | −67 | 544 | 65 |
| TYR | CG | C | 281 | 180 | −81 | 550 | 66 |
| TYR | CD1 | C | 281 | 193 | −85 | 553 | 66 |
| TYR | CE1 | C | 281 | 196 | −98 | 559 | 66 |
| TYR | CD2 | C | 281 | 170 | −90 | 553 | 66 |
| TYR | CE2 | C | 281 | 172 | −103 | 558 | 66 |
| TYR | CZ | C | 281 | 185 | −106 | 561 | 66 |
| TYR | OH | C | 281 | 188 | −119 | 566 | 66 |
| TYR | C | C | 281 | 164 | −53 | 529 | 65 |
| TYR | O | C | 281 | 155 | −46 | 535 | 65 |
| ASN | N | C | 282 | 171 | −49 | 519 | 65 |
| ASN | CA | C | 282 | 170 | −35 | 514 | 65 |
| ASN | CB | C | 282 | 183 | −28 | 515 | 64 |
| ASN | CG | C | 282 | 190 | −29 | 528 | 64 |
| ASN | OD1 | C | 282 | 185 | −25 | 538 | 63 |
| ASN | ND2 | C | 282 | 202 | −35 | 528 | 63 |
| ASN | C | C | 282 | 165 | −36 | 499 | 65 |
| ASN | O | C | 282 | 169 | −27 | 491 | 65 |
| TYR | N | C | 283 | 157 | −46 | 496 | 66 |
| TYR | CA | C | 283 | 152 | −47 | 483 | 66 |
| TYR | CB | C | 283 | 144 | −60 | 481 | 67 |
| TYR | CG | C | 283 | 141 | −62 | 466 | 67 |
| TYR | CD1 | C | 283 | 151 | −67 | 458 | 68 |
| TYR | CE1 | C | 283 | 149 | −69 | 444 | 68 |
| TYR | CD2 | C | 283 | 129 | −60 | 460 | 68 |
| TYR | CE2 | C | 283 | 126 | −62 | 447 | 68 |
| TYR | CZ | C | 283 | 137 | −67 | 439 | 68 |
| TYR | OH | C | 283 | 135 | −68 | 425 | 68 |
| TYR | C | C | 283 | 144 | −35 | 479 | 65 |
| TYR | O | C | 283 | 133 | −33 | 485 | 65 |
| ASP | N | C | 284 | 149 | −27 | 470 | 64 |
| ASP | CA | C | 284 | 143 | −15 | 465 | 63 |
| ASP | CB | C | 284 | 128 | −14 | 469 | 63 |
| ASP | CG | C | 284 | 122 | −2 | 462 | 64 |
| ASP | OD1 | C | 284 | 126 | 9 | 465 | 64 |
| ASP | OD2 | C | 284 | 112 | −4 | 455 | 64 |
| ASP | C | C | 284 | 151 | −5 | 474 | 62 |
| ASP | O | C | 284 | 160 | 2 | 469 | 62 |
| LYS | N | C | 285 | 148 | −4 | 487 | 60 |
| LYS | CA | C | 285 | 154 | 5 | 496 | 59 |
| LYS | CB | C | 285 | 151 | 20 | 492 | 59 |
| LYS | CG | C | 285 | 136 | 23 | 493 | 58 |
| LYS | CD | C | 285 | 133 | 37 | 488 | 58 |
| LYS | CE | C | 285 | 118 | 40 | 490 | 58 |
| LYS | NZ | C | 285 | 109 | 31 | 481 | 58 |
| LYS | C | C | 285 | 150 | 3 | 510 | 58 |
| LYS | O | C | 285 | 140 | −4 | 513 | 58 |
| SER | N | C | 286 | 157 | 9 | 519 | 56 |
| SER | CA | C | 286 | 154 | 8 | 534 | 55 |
| SER | CB | C | 286 | 164 | 0 | 541 | 55 |
| SER | OG | C | 286 | 163 | −14 | 538 | 55 |
| SER | C | C | 286 | 155 | 23 | 539 | 54 |
| SER | O | C | 286 | 164 | 30 | 536 | 54 |

TABLE 1-continued

Structure Coordinates for uncomplexed BACE

| | | | | | | | |
|---|---|---|---|---|---|---|---|
| ILE | N | C | 287 | 144 | 27 | 546 | 52 |
| ILE | CA | C | 287 | 144 | 41 | 551 | 51 |
| ILE | CB | C | 287 | 135 | 50 | 541 | 51 |
| ILE | CG2 | C | 287 | 141 | 49 | 527 | 51 |
| ILE | CG1 | C | 287 | 121 | 45 | 542 | 51 |
| ILE | CD1 | C | 287 | 111 | 54 | 534 | 51 |
| ILE | C | C | 287 | 138 | 42 | 565 | 51 |
| ILE | O | C | 287 | 131 | 33 | 570 | 50 |
| VAL | N | C | 288 | 141 | 54 | 571 | 50 |
| VAL | CA | C | 288 | 137 | 57 | 584 | 49 |
| VAL | CB | C | 288 | 148 | 63 | 593 | 49 |
| VAL | CG1 | C | 288 | 143 | 66 | 607 | 49 |
| VAL | CG2 | C | 288 | 160 | 54 | 593 | 48 |
| VAL | C | C | 288 | 125 | 67 | 583 | 49 |
| VAL | O | C | 288 | 128 | 78 | 579 | 49 |
| ASP | N | C | 289 | 113 | 62 | 585 | 50 |
| ASP | CA | C | 289 | 102 | 71 | 583 | 50 |
| ASP | CB | C | 289 | 94 | 67 | 571 | 50 |
| ASP | CG | C | 289 | 81 | 75 | 569 | 50 |
| ASP | OD1 | C | 289 | 80 | 87 | 572 | 50 |
| ASP | OD2 | C | 289 | 71 | 68 | 565 | 50 |
| ASP | C | C | 289 | 92 | 72 | 595 | 50 |
| ASP | O | C | 289 | 85 | 63 | 598 | 51 |
| SER | N | C | 290 | 92 | 84 | 601 | 51 |
| SER | CA | C | 290 | 83 | 87 | 612 | 51 |
| SER | CB | C | 290 | 87 | 100 | 619 | 51 |
| SER | OG | C | 290 | 85 | 111 | 611 | 51 |
| SER | C | C | 290 | 68 | 89 | 608 | 52 |
| SER | O | C | 290 | 59 | 91 | 616 | 52 |
| GLY | N | C | 291 | 66 | 88 | 595 | 53 |
| GLY | CA | C | 291 | 53 | 90 | 589 | 55 |
| GLY | C | C | 291 | 46 | 76 | 588 | 56 |
| GLY | O | C | 291 | 34 | 76 | 586 | 56 |
| THR | N | C | 292 | 53 | 66 | 589 | 56 |
| THR | CA | C | 292 | 48 | 52 | 589 | 57 |
| THR | CB | C | 292 | 57 | 43 | 580 | 57 |
| THR | OG1 | C | 292 | 57 | 48 | 567 | 56 |
| THR | CG2 | C | 292 | 52 | 29 | 580 | 57 |
| THR | C | C | 292 | 47 | 46 | 603 | 57 |
| THR | O | C | 292 | 57 | 46 | 610 | 57 |
| THR | N | C | 293 | 35 | 41 | 606 | 57 |
| THR | CA | C | 293 | 32 | 36 | 619 | 58 |
| THR | CB | C | 293 | 17 | 34 | 622 | 57 |
| THR | OG1 | C | 293 | 11 | 46 | 622 | 58 |
| THR | CG2 | C | 293 | 15 | 27 | 635 | 58 |
| THR | C | C | 293 | 39 | 22 | 622 | 58 |
| THR | O | C | 293 | 46 | 20 | 632 | 58 |
| ASN | N | C | 294 | 38 | 13 | 612 | 58 |
| ASN | CA | C | 294 | 44 | 0 | 613 | 58 |
| ASN | CB | C | 294 | 34 | −10 | 605 | 58 |
| ASN | CG | C | 294 | 22 | −13 | 613 | 58 |
| ASN | OD1 | C | 294 | 17 | −5 | 620 | 57 |
| ASN | ND2 | C | 294 | 16 | −25 | 610 | 58 |
| ASN | C | C | 294 | 58 | −2 | 608 | 59 |
| ASN | O | C | 294 | 65 | 8 | 605 | 59 |
| LEU | N | C | 295 | 62 | −14 | 608 | 59 |
| LEU | CA | C | 295 | 76 | −18 | 603 | 59 |
| LEU | CB | C | 295 | 83 | −26 | 614 | 59 |
| LEU | CG | C | 295 | 97 | −31 | 611 | 59 |
| LEU | CD1 | C | 295 | 102 | −38 | 624 | 59 |
| LEU | CD2 | C | 295 | 99 | −39 | 599 | 59 |
| LEU | C | C | 295 | 73 | −27 | 591 | 60 |
| LEU | O | C | 295 | 67 | −37 | 592 | 60 |
| ARG | N | C | 296 | 77 | −22 | 579 | 60 |
| ARG | CA | C | 296 | 75 | −29 | 567 | 60 |
| ARG | CB | C | 296 | 69 | −19 | 557 | 60 |
| ARG | CG | C | 296 | 56 | −13 | 561 | 61 |
| ARG | CD | C | 296 | 53 | 1 | 557 | 61 |
| ARG | NE | C | 296 | 40 | 3 | 551 | 61 |
| ARG | CZ | C | 296 | 37 | −1 | 538 | 61 |
| ARG | NH1 | C | 296 | 25 | 1 | 534 | 61 |
| ARG | NH2 | C | 296 | 46 | −7 | 531 | 61 |
| ARG | C | C | 296 | 88 | −35 | 561 | 60 |
| ARG | O | C | 296 | 99 | −29 | 562 | 60 |
| LEU | N | C | 297 | 86 | −47 | 555 | 60 |
| LEU | CA | C | 297 | 97 | −54 | 549 | 60 |
| LEU | CB | C | 297 | 101 | −66 | 557 | 60 |
| LEU | CG | C | 297 | 103 | −64 | 572 | 60 |
| LEU | CD1 | C | 297 | 102 | −77 | 580 | 60 |
| LEU | CD2 | C | 297 | 117 | −58 | 574 | 60 |
| LEU | C | C | 297 | 93 | −58 | 535 | 61 |
| LEU | O | C | 297 | 81 | −59 | 532 | 61 |
| PRO | N | C | 298 | 103 | −61 | 526 | 61 |
| PRO | CD | C | 298 | 117 | −58 | 528 | 61 |
| PRO | CA | C | 298 | 100 | −65 | 512 | 62 |
| PRO | CB | C | 298 | 114 | −68 | 507 | 61 |
| PRO | CG | C | 298 | 123 | −58 | 514 | 61 |
| PRO | C | C | 298 | 91 | −77 | 511 | 62 |
| PRO | O | C | 298 | 82 | −79 | 519 | 62 |
| LYS | N | C | 299 | 94 | −86 | 502 | 63 |
| LYS | CA | C | 299 | 86 | −98 | 499 | 63 |
| LYS | CB | C | 299 | 84 | −100 | 484 | 64 |
| LYS | CG | C | 299 | 79 | −114 | 480 | 64 |
| LYS | CD | C | 299 | 66 | −118 | 487 | 65 |
| LYS | CE | C | 299 | 61 | −132 | 484 | 65 |
| LYS | NZ | C | 299 | 49 | −136 | 490 | 65 |
| LYS | C | C | 299 | 92 | −110 | 506 | 63 |
| LYS | O | C | 299 | 87 | −116 | 516 | 62 |
| LYS | N | C | 300 | 104 | −115 | 500 | 63 |
| LYS | CA | C | 300 | 111 | −127 | 505 | 63 |
| LYS | CB | C | 300 | 123 | −130 | 497 | 62 |
| LYS | CG | C | 300 | 132 | −142 | 502 | 61 |
| LYS | CD | C | 300 | 146 | −141 | 497 | 60 |
| LYS | CE | C | 300 | 156 | −151 | 505 | 58 |
| LYS | NZ | C | 300 | 170 | −150 | 501 | 57 |
| LYS | C | C | 300 | 115 | −125 | 520 | 63 |
| LYS | O | C | 300 | 117 | −134 | 527 | 64 |
| VAL | N | C | 301 | 116 | −112 | 524 | 64 |
| VAL | CA | C | 301 | 120 | −109 | 537 | 65 |
| VAL | CB | C | 301 | 126 | −94 | 538 | 65 |
| VAL | CG1 | C | 301 | 129 | −91 | 552 | 65 |
| VAL | CG2 | C | 301 | 138 | −94 | 529 | 65 |
| VAL | C | C | 301 | 108 | −109 | 547 | 65 |
| VAL | O | C | 301 | 110 | −115 | 558 | 65 |
| PHE | N | C | 302 | 97 | −104 | 544 | 66 |
| PHE | CA | C | 302 | 85 | −104 | 553 | 66 |
| PHE | CB | C | 302 | 73 | −97 | 547 | 66 |
| PHE | CG | C | 302 | 61 | −97 | 556 | 66 |
| PHE | CD1 | C | 302 | 62 | −90 | 569 | 66 |
| PHE | CD2 | C | 302 | 50 | −104 | 553 | 66 |
| PHE | CE1 | C | 302 | 51 | −90 | 577 | 66 |
| PHE | CE2 | C | 302 | 39 | −104 | 562 | 66 |
| PHE | CZ | C | 302 | 39 | −97 | 574 | 66 |
| PHE | C | C | 302 | 81 | −118 | 556 | 67 |
| PHE | O | C | 302 | 77 | −121 | 568 | 67 |
| GLU | N | C | 303 | 83 | −127 | 547 | 68 |
| GLU | CA | C | 303 | 79 | −141 | 549 | 69 |
| GLU | CB | C | 303 | 83 | −149 | 536 | 69 |
| GLU | CG | C | 303 | 77 | −144 | 523 | 70 |
| GLU | CD | C | 303 | 62 | −145 | 523 | 70 |
| GLU | OE1 | C | 303 | 55 | −142 | 533 | 70 |
| GLU | OE2 | C | 303 | 56 | −150 | 513 | 70 |
| GLU | C | C | 303 | 87 | −147 | 561 | 69 |
| GLU | O | C | 303 | 81 | −149 | 571 | 69 |
| ALA | N | C | 304 | 100 | −148 | 559 | 69 |
| ALA | CA | C | 304 | 109 | −153 | 570 | 69 |
| ALA | CB | C | 304 | 123 | −150 | 566 | 69 |
| ALA | C | C | 304 | 106 | −147 | 583 | 69 |
| ALA | O | C | 304 | 106 | −154 | 594 | 69 |
| ALA | N | C | 305 | 104 | −134 | 584 | 68 |
| ALA | CA | C | 305 | 101 | −127 | 596 | 68 |
| ALA | CB | C | 305 | 100 | −112 | 593 | 68 |
| ALA | C | C | 305 | 88 | −132 | 603 | 68 |
| ALA | O | C | 305 | 88 | −133 | 615 | 68 |
| VAL | N | C | 306 | 78 | −135 | 595 | 67 |
| VAL | CA | C | 306 | 66 | −140 | 601 | 66 |
| VAL | CB | C | 306 | 54 | −139 | 590 | 67 |
| VAL | CG1 | C | 306 | 41 | −144 | 597 | 67 |
| VAL | CG2 | C | 306 | 53 | −126 | 584 | 67 |
| VAL | C | C | 306 | 67 | −154 | 606 | 66 |
| VAL | O | C | 306 | 63 | −156 | 617 | 66 |
| LYS | N | C | 307 | 73 | −163 | 598 | 65 |
| LYS | CA | C | 307 | 74 | −176 | 602 | 65 |
| LYS | CB | C | 307 | 82 | −184 | 591 | 65 |

TABLE 1-continued

Structure Coordinates for uncomplexed BACE

| | | | | | | | |
|---|---|---|---|---|---|---|---|
| LYS | CG | C | 307 | 89 | −197 | 595 | 66 |
| LYS | CD | C | 307 | 103 | −194 | 600 | 66 |
| LYS | CE | C | 307 | 110 | −207 | 604 | 66 |
| LYS | NZ | C | 307 | 125 | −205 | 605 | 66 |
| LYS | C | C | 307 | 82 | −177 | 615 | 65 |
| LYS | O | C | 307 | 77 | −183 | 625 | 65 |
| SER | N | C | 308 | 94 | −172 | 615 | 65 |
| SER | CA | C | 308 | 103 | −172 | 627 | 64 |
| SER | CB | C | 308 | 116 | −165 | 624 | 65 |
| SER | OG | C | 308 | 125 | −167 | 635 | 65 |
| SER | C | C | 308 | 97 | −166 | 639 | 64 |
| SER | O | C | 308 | 99 | −171 | 650 | 65 |
| ILE | N | C | 309 | 89 | −156 | 638 | 63 |
| ILE | CA | C | 309 | 83 | −150 | 650 | 63 |
| ILE | CB | C | 309 | 76 | −136 | 647 | 63 |
| ILE | CG2 | C | 309 | 69 | −131 | 659 | 63 |
| ILE | CG1 | C | 309 | 87 | −126 | 643 | 63 |
| ILE | CD1 | C | 309 | 82 | −112 | 640 | 63 |
| ILE | C | C | 309 | 72 | −159 | 655 | 63 |
| ILE | O | C | 309 | 69 | −160 | 667 | 63 |
| LYS | N | C | 310 | 66 | −167 | 646 | 63 |
| LYS | CA | C | 310 | 56 | −176 | 650 | 64 |
| LYS | CB | C | 310 | 49 | −182 | 637 | 64 |
| LYS | CG | C | 310 | 39 | −172 | 631 | 64 |
| LYS | CD | C | 310 | 32 | −178 | 618 | 64 |
| LYS | CE | C | 310 | 22 | −169 | 612 | 65 |
| LYS | NZ | C | 310 | 17 | −173 | 599 | 65 |
| LYS | C | C | 310 | 62 | −188 | 657 | 64 |
| LYS | O | C | 310 | 59 | −190 | 669 | 63 |
| ALA | N | C | 311 | 72 | −194 | 651 | 64 |
| ALA | CA | C | 311 | 79 | −205 | 657 | 64 |
| ALA | CB | C | 311 | 90 | −210 | 648 | 64 |
| ALA | C | C | 311 | 85 | −202 | 671 | 65 |
| ALA | O | C | 311 | 85 | −210 | 680 | 65 |
| ALA | N | C | 312 | 90 | −189 | 672 | 65 |
| ALA | CA | C | 312 | 96 | −185 | 685 | 66 |
| ALA | CB | C | 312 | 104 | −173 | 683 | 65 |
| ALA | C | C | 312 | 86 | −183 | 695 | 66 |
| ALA | O | C | 312 | 88 | −183 | 707 | 65 |
| SER | N | C | 313 | 73 | −180 | 691 | 67 |
| SER | CA | C | 313 | 62 | −178 | 701 | 68 |
| SER | CB | C | 313 | 56 | −164 | 698 | 68 |
| SER | OG | C | 313 | 50 | −164 | 685 | 68 |
| SER | C | C | 313 | 52 | −189 | 700 | 68 |
| SER | O | C | 313 | 41 | −188 | 705 | 68 |
| SER | N | C | 314 | 56 | −200 | 693 | 69 |
| SER | CA | C | 314 | 47 | −211 | 691 | 70 |
| SER | CB | C | 314 | 55 | −223 | 685 | 70 |
| SER | OG | C | 314 | 65 | −228 | 695 | 70 |
| SER | C | C | 314 | 40 | −216 | 703 | 71 |
| SER | O | C | 314 | 29 | −222 | 702 | 71 |
| THR | N | C | 315 | 45 | −214 | 715 | 71 |
| THR | CA | C | 315 | 38 | −218 | 728 | 72 |
| THR | CB | C | 315 | 44 | −211 | 740 | 72 |
| THR | OG1 | C | 315 | 42 | −197 | 739 | 73 |
| THR | CG2 | C | 315 | 59 | −214 | 742 | 72 |
| THR | C | C | 315 | 23 | −214 | 726 | 73 |
| THR | O | C | 315 | 15 | −223 | 727 | 73 |
| GLU | N | C | 316 | 21 | −202 | 724 | 74 |
| GLU | CA | C | 316 | 7 | −197 | 722 | 75 |
| GLU | CB | C | 316 | 4 | −184 | 729 | 75 |
| GLU | CG | C | 316 | 1 | −185 | 743 | 75 |
| GLU | CD | C | 316 | −4 | −172 | 749 | 76 |
| GLU | OE1 | C | 316 | −13 | −165 | 743 | 76 |
| GLU | OE2 | C | 316 | 1 | −168 | 760 | 76 |
| GLU | C | C | 316 | 4 | −196 | 707 | 76 |
| GLU | O | C | 316 | 13 | −192 | 699 | 76 |
| LYS | N | C | 317 | −8 | −199 | 702 | 77 |
| LYS | CA | C | 317 | −12 | −198 | 688 | 78 |
| LYS | CB | C | 317 | −18 | −211 | 684 | 78 |
| LYS | CG | C | 317 | −8 | −222 | 682 | 78 |
| LYS | CD | C | 317 | 2 | −219 | 671 | 78 |
| LYS | CE | C | 317 | 12 | −231 | 669 | 78 |
| LYS | NZ | C | 317 | 21 | −232 | 681 | 78 |
| LYS | C | C | 317 | −21 | −186 | 686 | 78 |
| LYS | O | C | 317 | −30 | −183 | 694 | 78 |
| PHE | N | C | 318 | −20 | −180 | 674 | 79 |
| PHE | CA | C | 318 | −29 | −169 | 670 | 79 |
| PHE | CB | C | 318 | −21 | −156 | 671 | 79 |
| PHE | CG | C | 318 | −14 | −153 | 684 | 80 |
| PHE | CD1 | C | 318 | −2 | −160 | 686 | 80 |
| PHE | CD2 | C | 318 | −19 | −145 | 693 | 80 |
| PHE | CE1 | C | 318 | 5 | −157 | 699 | 80 |
| PHE | CE2 | C | 318 | −13 | −142 | 705 | 80 |
| PHE | CZ | C | 318 | −1 | −149 | 708 | 80 |
| PHE | C | C | 318 | −35 | −171 | 656 | 80 |
| PHE | O | C | 318 | −29 | −178 | 648 | 80 |
| PRO | N | C | 319 | −46 | −164 | 653 | 80 |
| PRO | CD | C | 319 | −54 | −156 | 663 | 80 |
| PRO | CA | C | 319 | −53 | −165 | 640 | 81 |
| PRO | CB | C | 319 | −67 | −159 | 644 | 81 |
| PRO | CG | C | 319 | −64 | −149 | 654 | 81 |
| PRO | C | C | 319 | −45 | −156 | 630 | 82 |
| PRO | O | C | 319 | −42 | −145 | 633 | 82 |
| ASP | N | C | 320 | −44 | −162 | 618 | 82 |
| ASP | CA | C | 320 | −36 | −154 | 608 | 83 |
| ASP | CB | C | 320 | −38 | −162 | 594 | 83 |
| ASP | CG | C | 320 | −33 | −176 | 595 | 83 |
| ASP | OD1 | C | 320 | −31 | −183 | 585 | 83 |
| ASP | OD2 | C | 320 | −31 | −181 | 607 | 83 |
| ASP | C | C | 320 | −42 | −140 | 606 | 83 |
| ASP | O | C | 320 | −35 | −131 | 601 | 83 |
| GLY | N | C | 321 | −54 | −138 | 611 | 83 |
| GLY | CA | C | 321 | −60 | −125 | 610 | 83 |
| GLY | C | C | 321 | −53 | −115 | 619 | 83 |
| GLY | O | C | 321 | −54 | −103 | 618 | 83 |
| PHE | N | C | 322 | −45 | −121 | 629 | 83 |
| PHE | CA | C | 322 | −37 | −113 | 638 | 83 |
| PHE | CB | C | 322 | −34 | −121 | 651 | 83 |
| PHE | CG | C | 322 | −25 | −114 | 660 | 83 |
| PHE | CD1 | C | 322 | −28 | −101 | 665 | 83 |
| PHE | CD2 | C | 322 | −13 | −120 | 664 | 83 |
| PHE | CE1 | C | 322 | −19 | −95 | 674 | 83 |
| PHE | CE2 | C | 322 | −4 | −114 | 673 | 83 |
| PHE | CZ | C | 322 | −8 | −102 | 678 | 83 |
| PHE | C | C | 322 | −24 | −109 | 631 | 83 |
| PHE | O | C | 322 | −19 | −98 | 631 | 83 |
| TRP | N | C | 323 | −18 | −120 | 625 | 83 |
| TRP | CA | C | 323 | −5 | −118 | 618 | 83 |
| TRP | CB | C | 323 | 2 | −132 | 616 | 83 |
| TRP | CG | C | 323 | 5 | −138 | 629 | 83 |
| TRP | CD2 | C | 323 | 18 | −140 | 635 | 83 |
| TRP | CE2 | C | 323 | 16 | −146 | 648 | 83 |
| TRP | CE3 | C | 323 | 31 | −137 | 630 | 83 |
| TRP | CD1 | C | 323 | −4 | −143 | 639 | 83 |
| TRP | NE1 | C | 323 | 3 | −147 | 650 | 83 |
| TRP | CZ2 | C | 323 | 27 | −149 | 656 | 83 |
| TRP | CZ3 | C | 323 | 42 | −140 | 638 | 83 |
| TRP | CH2 | C | 323 | 40 | −146 | 651 | 83 |
| TRP | C | C | 323 | −7 | −111 | 605 | 83 |
| TRP | O | C | 323 | 1 | −113 | 595 | 83 |
| LEU | N | C | 324 | −17 | −103 | 604 | 83 |
| LEU | CA | C | 324 | −20 | −95 | 592 | 83 |
| LEU | CB | C | 324 | −30 | −102 | 583 | 83 |
| LEU | CG | C | 324 | −25 | −116 | 577 | 83 |
| LEU | CD1 | C | 324 | −36 | −123 | 570 | 82 |
| LEU | CD2 | C | 324 | −13 | −114 | 568 | 83 |
| LEU | C | C | 324 | −26 | −82 | 596 | 83 |
| LEU | O | C | 324 | −31 | −74 | 588 | 83 |
| GLY | N | C | 325 | −25 | −79 | 609 | 83 |
| GLY | CA | C | 325 | −31 | −67 | 614 | 83 |
| GLY | C | C | 325 | −46 | −65 | 613 | 83 |
| GLY | O | C | 325 | −51 | −55 | 616 | 83 |
| GLU | N | C | 326 | −52 | −76 | 608 | 83 |
| GLU | CA | C | 326 | −67 | −76 | 606 | 84 |
| GLU | CB | C | 326 | −71 | −88 | 597 | 84 |
| GLU | CG | C | 326 | −65 | −87 | 583 | 85 |
| GLU | CD | C | 326 | −68 | −100 | 575 | 85 |
| GLU | OE1 | C | 326 | −64 | −100 | 563 | 85 |
| GLU | OE2 | C | 326 | −75 | −109 | 581 | 85 |
| GLU | C | C | 326 | −74 | −77 | 620 | 84 |
| GLU | O | C | 326 | −83 | −68 | 622 | 84 |
| GLN | N | C | 327 | −71 | −86 | 628 | 83 |
| GLN | CA | C | 327 | −78 | −88 | 641 | 83 |

TABLE 1-continued

Structure Coordinates for uncomplexed BACE

| | | | | | | | |
|---|---|---|---|---|---|---|---|
| GLN | CB | C | 327 | −86 | −101 | 641 | 83 |
| GLN | CG | C | 327 | −78 | −113 | 637 | 83 |
| GLN | CD | C | 327 | −86 | −125 | 632 | 84 |
| GLN | OE1 | C | 327 | −92 | −124 | 621 | 84 |
| GLN | NE2 | C | 327 | −87 | −136 | 639 | 84 |
| GLN | C | C | 327 | −68 | −88 | 652 | 82 |
| GLN | O | C | 327 | −58 | −94 | 652 | 82 |
| LEU | N | C | 328 | −72 | −80 | 663 | 81 |
| LEU | CA | C | 328 | −63 | −78 | 674 | 80 |
| LEU | CB | C | 328 | −66 | −64 | 680 | 80 |
| LEU | CG | C | 328 | −80 | −60 | 680 | 80 |
| LEU | CD1 | C | 328 | −89 | −68 | 690 | 80 |
| LEU | CD2 | C | 328 | −81 | −45 | 684 | 80 |
| LEU | C | C | 328 | −65 | −89 | 685 | 80 |
| LEU | O | C | 328 | −76 | −93 | 688 | 80 |
| VAL | N | C | 329 | −53 | −93 | 691 | 79 |
| VAL | CA | C | 329 | −53 | −103 | 702 | 77 |
| VAL | CB | C | 329 | −40 | −112 | 701 | 78 |
| VAL | CG1 | C | 329 | −40 | −121 | 713 | 78 |
| VAL | CG2 | C | 329 | −40 | −120 | 688 | 77 |
| VAL | C | C | 329 | −54 | −96 | 715 | 76 |
| VAL | O | C | 329 | −49 | −85 | 717 | 76 |
| CYS | N | C | 330 | −60 | −103 | 725 | 75 |
| CYS | CA | C | 330 | −62 | −97 | 738 | 74 |
| CYS | C | C | 330 | −57 | −106 | 750 | 73 |
| CYS | O | C | 330 | −54 | −118 | 747 | 73 |
| CYS | CB | C | 330 | −77 | −94 | 741 | 74 |
| CYS | SG | C | 330 | −85 | −85 | 728 | 74 |
| TRP | N | C | 331 | −56 | −101 | 762 | 72 |
| TRP | CA | C | 331 | −51 | −107 | 774 | 71 |
| TRP | CB | C | 331 | −36 | −108 | 774 | 71 |
| TRP | CG | C | 331 | −29 | −117 | 765 | 70 |
| TRP | CD2 | C | 331 | −21 | −114 | 753 | 70 |
| TRP | CE2 | C | 331 | −17 | −126 | 747 | 70 |
| TRP | CE3 | C | 331 | −17 | −102 | 748 | 70 |
| TRP | CD1 | C | 331 | −30 | −131 | 765 | 70 |
| TRP | NE1 | C | 331 | −23 | −136 | 755 | 70 |
| TRP | CZ2 | C | 331 | −9 | −126 | 736 | 70 |
| TRP | CZ3 | C | 331 | −9 | −102 | 736 | 70 |
| TRP | CH2 | C | 331 | −6 | −114 | 730 | 70 |
| TRP | C | C | 331 | −57 | −100 | 786 | 71 |
| TRP | O | C | 331 | −59 | −88 | 785 | 71 |
| GLN | N | C | 332 | −58 | −107 | 797 | 70 |
| GLN | CA | C | 332 | −63 | −101 | 809 | 70 |
| GLN | CB | C | 332 | −64 | −111 | 820 | 70 |
| GLN | CG | C | 332 | −75 | −121 | 819 | 71 |
| GLN | CD | C | 332 | −76 | −128 | 805 | 71 |
| GLN | OE1 | C | 332 | −65 | −133 | 801 | 71 |
| GLN | NE2 | C | 332 | −87 | −127 | 798 | 71 |
| GLN | C | C | 332 | −54 | −89 | 813 | 70 |
| GLN | O | C | 332 | −41 | −91 | 812 | 70 |
| ALA | N | C | 333 | −59 | −78 | 817 | 69 |
| ALA | CA | C | 333 | −51 | −66 | 821 | 69 |
| ALA | CB | C | 333 | −60 | −57 | 830 | 69 |
| ALA | C | C | 333 | −39 | −70 | 828 | 69 |
| ALA | O | C | 333 | −39 | −78 | 838 | 69 |
| GLY | N | C | 334 | −27 | −65 | 823 | 68 |
| GLY | CA | C | 334 | −15 | −67 | 829 | 67 |
| GLY | C | C | 334 | −10 | −81 | 830 | 66 |
| GLY | O | C | 334 | −1 | −85 | 838 | 67 |
| THR | N | C | 335 | −15 | −90 | 821 | 65 |
| THR | CA | C | 335 | −11 | −104 | 821 | 64 |
| THR | CB | C | 335 | −23 | −114 | 823 | 64 |
| THR | OG1 | C | 335 | −31 | −115 | 812 | 64 |
| THR | CG2 | C | 335 | −31 | −108 | 835 | 64 |
| THR | C | C | 335 | −5 | −107 | 807 | 63 |
| THR | O | C | 335 | −3 | −119 | 803 | 63 |
| THR | N | C | 336 | −2 | −96 | 800 | 62 |
| THR | CA | C | 336 | 4 | −98 | 786 | 60 |
| THR | CB | C | 336 | 7 | −84 | 780 | 60 |
| THR | OG1 | C | 336 | −5 | −76 | 782 | 60 |
| THR | CG2 | C | 336 | 10 | −85 | 765 | 60 |
| THR | C | C | 336 | 17 | −106 | 787 | 60 |
| THR | O | C | 336 | 26 | −101 | 794 | 60 |
| PRO | N | C | 337 | 18 | −117 | 780 | 59 |
| PRO | CD | C | 337 | 7 | −123 | 772 | 59 |
| PRO | CA | C | 337 | 30 | −126 | 780 | 59 |
| PRO | CB | C | 337 | 24 | −139 | 774 | 59 |
| PRO | CG | C | 337 | 14 | −134 | 764 | 59 |
| PRO | C | C | 337 | 41 | −120 | 772 | 58 |
| PRO | O | C | 337 | 46 | −127 | 762 | 58 |
| TRP | N | C | 338 | 46 | −108 | 775 | 57 |
| TRP | CA | C | 338 | 57 | −102 | 768 | 56 |
| TRP | CB | C | 338 | 62 | −90 | 777 | 57 |
| TRP | CG | C | 338 | 53 | −79 | 778 | 57 |
| TRP | CD2 | C | 338 | 46 | −72 | 767 | 57 |
| TRP | CE2 | C | 338 | 38 | −62 | 773 | 57 |
| TRP | CE3 | C | 338 | 46 | −74 | 753 | 57 |
| TRP | CD1 | C | 338 | 49 | −73 | 789 | 57 |
| TRP | NE1 | C | 338 | 40 | −62 | 786 | 57 |
| TRP | CZ2 | C | 338 | 31 | −53 | 765 | 57 |
| TRP | CZ3 | C | 338 | 38 | −66 | 746 | 57 |
| TRP | CH2 | C | 338 | 31 | −55 | 752 | 57 |
| TRP | C | C | 338 | 69 | −112 | 765 | 55 |
| TRP | O | C | 338 | 74 | −112 | 754 | 55 |
| ASN | N | C | 339 | 73 | −119 | 776 | 54 |
| ASN | CA | C | 339 | 84 | −128 | 774 | 54 |
| ASN | CB | C | 339 | 88 | −134 | 788 | 53 |
| ASN | CG | C | 339 | 77 | −143 | 794 | 54 |
| ASN | OD1 | C | 339 | 76 | −154 | 790 | 53 |
| ASN | ND2 | C | 339 | 69 | −137 | 803 | 53 |
| ASN | C | C | 339 | 83 | −140 | 764 | 53 |
| ASN | O | C | 339 | 93 | −146 | 762 | 52 |
| ILE | N | C | 340 | 72 | −142 | 759 | 52 |
| ILE | CA | C | 340 | 70 | −153 | 749 | 52 |
| ILE | CB | C | 340 | 57 | −160 | 750 | 52 |
| ILE | CG2 | C | 340 | 54 | −165 | 764 | 52 |
| ILE | CG1 | C | 340 | 46 | −150 | 745 | 52 |
| ILE | CD1 | C | 340 | 32 | −155 | 746 | 53 |
| ILE | C | C | 340 | 73 | −148 | 735 | 51 |
| ILE | O | C | 340 | 76 | −156 | 726 | 52 |
| PHE | N | C | 341 | 72 | −135 | 733 | 51 |
| PHE | CA | C | 341 | 75 | −130 | 720 | 50 |
| PHE | CB | C | 341 | 66 | −117 | 717 | 51 |
| PHE | CG | C | 341 | 52 | −120 | 716 | 51 |
| PHE | CD1 | C | 341 | 46 | −125 | 705 | 51 |
| PHE | CD2 | C | 341 | 43 | −116 | 726 | 51 |
| PHE | CE1 | C | 341 | 33 | −128 | 703 | 51 |
| PHE | CE2 | C | 341 | 29 | −118 | 725 | 51 |
| PHE | CZ | C | 341 | 24 | −124 | 714 | 51 |
| PHE | C | C | 341 | 90 | −126 | 719 | 48 |
| PHE | O | C | 341 | 95 | −121 | 728 | 49 |
| PRO | N | C | 342 | 96 | −130 | 707 | 47 |
| PRO | CD | C | 342 | 90 | −136 | 696 | 47 |
| PRO | CA | C | 342 | 110 | −127 | 705 | 46 |
| PRO | CB | C | 342 | 113 | −136 | 693 | 46 |
| PRO | CG | C | 342 | 101 | −134 | 685 | 47 |
| PRO | C | C | 342 | 114 | −113 | 703 | 46 |
| PRO | O | C | 342 | 105 | −104 | 700 | 46 |
| VAL | N | C | 343 | 126 | −109 | 705 | 45 |
| VAL | CA | C | 343 | 131 | −96 | 703 | 44 |
| VAL | CB | C | 343 | 143 | −92 | 713 | 44 |
| VAL | CG1 | C | 343 | 139 | −93 | 727 | 43 |
| VAL | CG2 | C | 343 | 154 | −102 | 711 | 43 |
| VAL | C | C | 343 | 136 | −95 | 689 | 44 |
| VAL | O | C | 343 | 140 | −106 | 684 | 44 |
| ILE | N | C | 344 | 136 | −84 | 683 | 44 |
| ILE | CA | C | 344 | 140 | −83 | 669 | 44 |
| ILE | CB | C | 344 | 128 | −78 | 660 | 44 |
| ILE | CG2 | C | 344 | 132 | −79 | 645 | 44 |
| ILE | CG1 | C | 344 | 116 | −86 | 662 | 44 |
| ILE | CD1 | C | 344 | 104 | −83 | 654 | 44 |
| ILE | C | C | 344 | 152 | −73 | 668 | 44 |
| ILE | O | C | 344 | 152 | −62 | 673 | 44 |
| SER | N | C | 345 | 162 | −77 | 660 | 44 |
| SER | CA | C | 345 | 174 | −69 | 658 | 44 |
| SER | CB | C | 345 | 186 | −76 | 665 | 44 |
| SER | OG | C | 345 | 184 | −76 | 679 | 45 |
| SER | C | C | 345 | 177 | −67 | 643 | 44 |
| SER | O | C | 345 | 177 | −76 | 635 | 44 |
| LEU | N | C | 346 | 181 | −55 | 640 | 44 |
| LEU | CA | C | 346 | 185 | −51 | 627 | 44 |
| LEU | CB | C | 346 | 177 | −40 | 621 | 44 |
| LEU | CG | C | 346 | 162 | −42 | 621 | 44 |

TABLE 1-continued

Structure Coordinates for uncomplexed BACE

| | | | | | | | |
|---|---|---|---|---|---|---|---|
| LEU | CD1 | C | 346 | 154 | −29 | 617 | 43 |
| LEU | CD2 | C | 346 | 158 | −53 | 611 | 44 |
| LEU | C | C | 346 | 200 | −47 | 628 | 44 |
| LEU | O | C | 346 | 203 | −39 | 637 | 44 |
| TYR | N | C | 347 | 208 | −52 | 619 | 45 |
| TYR | CA | C | 347 | 222 | −48 | 619 | 46 |
| TYR | CB | C | 347 | 231 | −60 | 616 | 46 |
| TYR | CG | C | 347 | 233 | −69 | 628 | 47 |
| TYR | CD1 | C | 347 | 222 | −76 | 634 | 47 |
| TYR | CE1 | C | 347 | 224 | −85 | 645 | 47 |
| TYR | CD2 | C | 347 | 246 | −71 | 633 | 47 |
| TYR | CE2 | C | 347 | 248 | −80 | 644 | 47 |
| TYR | CZ | C | 347 | 237 | −86 | 650 | 47 |
| TYR | OH | C | 347 | 239 | −95 | 660 | 47 |
| TYR | C | C | 347 | 224 | −37 | 608 | 46 |
| TYR | O | C | 347 | 221 | −40 | 596 | 46 |
| LEU | N | C | 348 | 228 | −26 | 612 | 46 |
| LEU | CA | C | 348 | 230 | −15 | 602 | 46 |
| LEU | CB | C | 348 | 225 | −2 | 608 | 46 |
| LEU | CG | C | 348 | 210 | −2 | 613 | 46 |
| LEU | CD1 | C | 348 | 206 | 10 | 620 | 46 |
| LEU | CD2 | C | 348 | 201 | −4 | 600 | 46 |
| LEU | C | C | 348 | 245 | −13 | 599 | 47 |
| LEU | O | C | 348 | 254 | −16 | 607 | 46 |
| MET | N | C | 349 | 248 | −8 | 587 | 48 |
| MET | CA | C | 349 | 261 | −5 | 583 | 49 |
| MET | CB | C | 349 | 261 | −1 | 568 | 50 |
| MET | CG | C | 349 | 275 | 3 | 562 | 51 |
| MET | SD | C | 349 | 274 | 8 | 545 | 52 |
| MET | CE | C | 349 | 284 | −4 | 537 | 52 |
| MET | C | C | 349 | 267 | 6 | 591 | 48 |
| MET | O | C | 349 | 261 | 16 | 594 | 48 |
| GLY | N | C | 350 | 279 | 4 | 596 | 48 |
| GLY | CA | C | 350 | 285 | 14 | 605 | 48 |
| GLY | C | C | 350 | 293 | 24 | 597 | 48 |
| GLY | O | C | 350 | 292 | 24 | 585 | 49 |
| GLU | N | C | 351 | 300 | 33 | 604 | 49 |
| GLU | CA | C | 351 | 308 | 44 | 596 | 49 |
| GLU | CB | C | 351 | 308 | 57 | 604 | 49 |
| GLU | CG | C | 351 | 295 | 65 | 602 | 49 |
| GLU | CD | C | 351 | 296 | 79 | 607 | 49 |
| GLU | OE1 | C | 351 | 297 | 81 | 619 | 48 |
| GLU | OE2 | C | 351 | 297 | 88 | 598 | 50 |
| GLU | C | C | 351 | 322 | 39 | 594 | 50 |
| GLU | O | C | 351 | 329 | 45 | 586 | 50 |
| VAL | N | C | 352 | 326 | 28 | 600 | 50 |
| VAL | CA | C | 352 | 339 | 23 | 599 | 51 |
| VAL | CB | C | 352 | 345 | 18 | 612 | 51 |
| VAL | CG1 | C | 352 | 359 | 12 | 610 | 51 |
| VAL | CG2 | C | 352 | 345 | 29 | 622 | 51 |
| VAL | C | C | 352 | 339 | 11 | 589 | 51 |
| VAL | O | C | 352 | 329 | 3 | 589 | 51 |
| THR | N | C | 353 | 349 | 10 | 581 | 52 |
| THR | CA | C | 353 | 350 | −1 | 571 | 52 |
| THR | CB | C | 353 | 364 | −1 | 564 | 52 |
| THR | OG1 | C | 353 | 367 | 12 | 559 | 53 |
| THR | CG2 | C | 353 | 365 | −12 | 553 | 52 |
| THR | C | C | 353 | 347 | −14 | 577 | 52 |
| THR | O | C | 353 | 353 | −18 | 587 | 52 |
| ASN | N | C | 354 | 338 | −22 | 570 | 52 |
| ASN | CA | C | 354 | 334 | −35 | 575 | 52 |
| ASN | CB | C | 354 | 345 | −46 | 571 | 53 |
| ASN | CG | C | 354 | 345 | −47 | 556 | 53 |
| ASN | OD1 | C | 354 | 335 | −48 | 549 | 54 |
| ASN | ND2 | C | 354 | 357 | −49 | 550 | 53 |
| ASN | C | C | 354 | 332 | −36 | 590 | 51 |
| ASN | O | C | 354 | 338 | −44 | 597 | 51 |
| GLN | N | C | 355 | 323 | −28 | 595 | 49 |
| GLN | CA | C | 355 | 319 | −27 | 609 | 47 |
| GLN | CB | C | 355 | 328 | −17 | 616 | 47 |
| GLN | CG | C | 355 | 323 | −13 | 630 | 48 |
| GLN | CD | C | 355 | 335 | −8 | 639 | 48 |
| GLN | OE1 | C | 355 | 333 | 0 | 648 | 48 |
| GLN | NE2 | C | 355 | 347 | −13 | 636 | 47 |
| GLN | C | C | 355 | 304 | −23 | 609 | 47 |
| GLN | O | C | 355 | 300 | −14 | 602 | 46 |
| SER | N | C | 356 | 297 | −31 | 617 | 45 |
| SER | CA | C | 356 | 282 | −28 | 618 | 43 |
| SER | CB | C | 356 | 274 | −38 | 611 | 43 |
| SER | OG | C | 356 | 276 | −51 | 616 | 44 |
| SER | C | C | 356 | 278 | −27 | 633 | 42 |
| SER | O | C | 356 | 286 | −30 | 642 | 42 |
| PHE | N | C | 357 | 266 | −24 | 635 | 40 |
| PHE | CA | C | 357 | 260 | −24 | 649 | 39 |
| PHE | CB | C | 357 | 261 | −10 | 655 | 39 |
| PHE | CG | C | 357 | 252 | 1 | 649 | 38 |
| PHE | CD1 | C | 357 | 240 | 4 | 654 | 38 |
| PHE | CD2 | C | 357 | 256 | 8 | 638 | 38 |
| PHE | CE1 | C | 357 | 231 | 13 | 649 | 38 |
| PHE | CE2 | C | 357 | 248 | 18 | 632 | 38 |
| PHE | CZ | C | 357 | 236 | 21 | 638 | 38 |
| PHE | C | C | 357 | 245 | −28 | 648 | 39 |
| PHE | O | C | 357 | 240 | −28 | 637 | 39 |
| ARG | N | C | 358 | 239 | −32 | 659 | 39 |
| ARG | CA | C | 358 | 225 | −36 | 659 | 39 |
| ARG | CB | C | 358 | 225 | −51 | 662 | 40 |
| ARG | CG | C | 358 | 226 | −54 | 677 | 40 |
| ARG | CD | C | 358 | 229 | −69 | 680 | 41 |
| ARG | NE | C | 358 | 230 | −72 | 694 | 41 |
| ARG | CZ | C | 358 | 236 | −83 | 699 | 41 |
| ARG | NH1 | C | 358 | 241 | −92 | 690 | 40 |
| ARG | NH2 | C | 358 | 237 | −85 | 712 | 41 |
| ARG | C | C | 358 | 216 | −28 | 668 | 38 |
| ARG | O | C | 358 | 221 | −23 | 679 | 38 |
| ILE | N | C | 359 | 204 | −28 | 665 | 38 |
| ILE | CA | C | 359 | 194 | −21 | 673 | 38 |
| ILE | CB | C | 359 | 186 | −10 | 665 | 38 |
| ILE | CG2 | C | 359 | 195 | 2 | 664 | 38 |
| ILE | CG1 | C | 359 | 182 | −15 | 652 | 38 |
| ILE | CD1 | C | 359 | 174 | −5 | 644 | 38 |
| ILE | C | C | 359 | 184 | −33 | 676 | 38 |
| ILE | O | C | 359 | 182 | −41 | 668 | 38 |
| THR | N | C | 360 | 178 | −33 | 688 | 38 |
| THR | CA | C | 360 | 169 | −44 | 692 | 39 |
| THR | CB | C | 360 | 175 | −53 | 702 | 39 |
| THR | OG1 | C | 360 | 187 | −60 | 696 | 38 |
| THR | CG2 | C | 360 | 165 | −64 | 706 | 39 |
| THR | C | C | 360 | 156 | −38 | 698 | 40 |
| THR | O | C | 360 | 156 | −31 | 707 | 40 |
| ILE | N | C | 361 | 145 | −42 | 692 | 41 |
| ILE | CA | C | 361 | 132 | −38 | 697 | 43 |
| ILE | CB | C | 361 | 122 | −33 | 686 | 43 |
| ILE | CG2 | C | 361 | 129 | −21 | 679 | 44 |
| ILE | CG1 | C | 361 | 120 | −44 | 676 | 43 |
| ILE | CD1 | C | 361 | 110 | −40 | 665 | 44 |
| ILE | C | C | 361 | 125 | −50 | 704 | 44 |
| ILE | O | C | 361 | 128 | −61 | 701 | 43 |
| LEU | N | C | 362 | 117 | −46 | 714 | 44 |
| LEU | CA | C | 362 | 109 | −56 | 721 | 45 |
| LEU | CB | C | 362 | 108 | −52 | 736 | 45 |
| LEU | CG | C | 362 | 122 | −47 | 742 | 44 |
| LEU | CD1 | C | 362 | 119 | −42 | 756 | 44 |
| LEU | CD2 | C | 362 | 131 | −59 | 743 | 44 |
| LEU | C | C | 362 | 95 | −58 | 716 | 47 |
| LEU | O | C | 362 | 91 | −50 | 707 | 47 |
| PRO | N | C | 363 | 88 | −68 | 721 | 48 |
| PRO | CD | C | 363 | 91 | −78 | 731 | 48 |
| PRO | CA | C | 363 | 74 | −70 | 716 | 48 |
| PRO | CB | C | 363 | 69 | −82 | 724 | 49 |
| PRO | CG | C | 363 | 78 | −82 | 736 | 48 |
| PRO | C | C | 363 | 66 | −57 | 720 | 48 |
| PRO | O | C | 363 | 56 | −54 | 714 | 49 |
| GLN | N | C | 364 | 70 | −50 | 731 | 49 |
| GLN | CA | C | 364 | 64 | −38 | 735 | 50 |
| GLN | CB | C | 364 | 70 | −33 | 748 | 49 |
| GLN | CG | C | 364 | 66 | −40 | 761 | 49 |
| GLN | CD | C | 364 | 75 | −51 | 764 | 48 |
| GLN | OE1 | C | 364 | 80 | −59 | 756 | 48 |
| GLN | NE2 | C | 364 | 77 | −53 | 777 | 48 |
| GLN | C | C | 364 | 64 | −27 | 724 | 50 |
| GLN | O | C | 364 | 56 | −18 | 725 | 50 |
| GLN | N | C | 365 | 72 | −29 | 714 | 51 |
| GLN | CA | C | 365 | 73 | −20 | 703 | 52 |
| GLN | CB | C | 365 | 88 | −19 | 698 | 51 |

TABLE 1-continued

Structure Coordinates for uncomplexed BACE

| | | | | | | | |
|---|---|---|---|---|---|---|---|
| GLN | CG | C | 365 | 97 | −9 | 705 | 51 |
| GLN | CD | C | 365 | 100 | −13 | 719 | 50 |
| GLN | OE1 | C | 365 | 94 | −8 | 729 | 50 |
| GLN | NE2 | C | 365 | 109 | −22 | 721 | 50 |
| GLN | C | C | 365 | 64 | −24 | 692 | 53 |
| GLN | O | C | 365 | 56 | −16 | 688 | 53 |
| TYR | N | C | 366 | 66 | −36 | 687 | 54 |
| TYR | CA | C | 366 | 58 | −41 | 675 | 56 |
| TYR | CB | C | 366 | 67 | −51 | 667 | 56 |
| TYR | CG | C | 366 | 70 | −64 | 674 | 58 |
| TYR | CD1 | C | 366 | 61 | −74 | 675 | 58 |
| TYR | CE1 | C | 366 | 64 | −86 | 681 | 59 |
| TYR | CD2 | C | 366 | 83 | −66 | 680 | 58 |
| TYR | CE2 | C | 366 | 86 | −77 | 687 | 58 |
| TYR | CZ | C | 366 | 77 | −88 | 687 | 59 |
| TYR | OH | C | 366 | 80 | −100 | 693 | 58 |
| TYR | C | C | 366 | 44 | −47 | 679 | 56 |
| TYR | O | C | 366 | 39 | −55 | 671 | 56 |
| LEU | N | C | 367 | 38 | −43 | 690 | 57 |
| LEU | CA | C | 367 | 25 | −47 | 693 | 57 |
| LEU | CB | C | 367 | 26 | −58 | 704 | 58 |
| LEU | CG | C | 367 | 32 | −72 | 701 | 57 |
| LEU | CD1 | C | 367 | 31 | −80 | 714 | 58 |
| LEU | CD2 | C | 367 | 25 | −78 | 690 | 57 |
| LEU | C | C | 367 | 17 | −35 | 698 | 58 |
| LEU | O | C | 367 | 19 | −31 | 710 | 58 |
| ARG | N | C | 368 | 9 | −29 | 690 | 59 |
| ARG | CA | C | 368 | 1 | −17 | 692 | 60 |
| ARG | CB | C | 368 | −3 | −11 | 679 | 61 |
| ARG | CG | C | 368 | 7 | −3 | 672 | 61 |
| ARG | CD | C | 368 | 5 | −2 | 657 | 62 |
| ARG | NE | C | 368 | −9 | 1 | 654 | 62 |
| ARG | CZ | C | 368 | −16 | 12 | 658 | 62 |
| ARG | NH1 | C | 368 | −10 | 20 | 666 | 62 |
| ARG | NH2 | C | 368 | −29 | 13 | 655 | 62 |
| ARG | C | C | 368 | −11 | −19 | 702 | 61 |
| ARG | O | C | 368 | −20 | −26 | 699 | 61 |
| PRO | N | C | 369 | −10 | −12 | 713 | 61 |
| PRO | CD | C | 369 | 2 | −4 | 718 | 61 |
| PRO | CA | C | 369 | −21 | −11 | 723 | 61 |
| PRO | CB | C | 369 | −15 | −3 | 735 | 61 |
| PRO | CG | C | 369 | 0 | −6 | 733 | 61 |
| PRO | C | C | 369 | −34 | −5 | 718 | 62 |
| PRO | O | C | 369 | −36 | 7 | 720 | 61 |
| VAL | N | C | 370 | −42 | −13 | 712 | 62 |
| VAL | CA | C | 370 | −55 | −8 | 706 | 62 |
| VAL | CB | C | 370 | −62 | −19 | 699 | 62 |
| VAL | CG1 | C | 370 | −53 | −24 | 688 | 62 |
| VAL | CG2 | C | 370 | −65 | −31 | 709 | 62 |
| VAL | C | C | 370 | −64 | −3 | 717 | 62 |
| VAL | O | C | 370 | −65 | −9 | 728 | 62 |
| ASP | N | C | 379 | −66 | −57 | 781 | 72 |
| ASP | CA | C | 379 | −55 | −53 | 772 | 71 |
| ASP | CB | C | 379 | −42 | −54 | 780 | 71 |
| ASP | CG | C | 379 | −41 | −44 | 791 | 72 |
| ASP | OD1 | C | 379 | −31 | −45 | 799 | 72 |
| ASP | OD2 | C | 379 | −49 | −35 | 793 | 72 |
| ASP | C | C | 379 | −54 | −61 | 759 | 71 |
| ASP | O | C | 379 | −52 | −73 | 759 | 71 |
| CYS | N | C | 380 | −57 | −54 | 748 | 71 |
| CYS | CA | C | 380 | −56 | −60 | 735 | 71 |
| CYS | C | C | 380 | −45 | −54 | 727 | 70 |
| CYS | O | C | 380 | −41 | −42 | 730 | 70 |
| CYS | CB | C | 380 | −69 | −58 | 728 | 72 |
| CYS | SG | C | 380 | −84 | −65 | 736 | 73 |
| TYR | N | C | 381 | −40 | −61 | 717 | 69 |
| TYR | CA | C | 381 | −29 | −56 | 709 | 68 |
| TYR | CB | C | 381 | −15 | −61 | 714 | 68 |
| TYR | CG | C | 381 | −13 | −58 | 728 | 68 |
| TYR | CD1 | C | 381 | −18 | −65 | 739 | 68 |
| TYR | CE1 | C | 381 | −16 | −62 | 752 | 68 |
| TYR | CD2 | C | 381 | −5 | −47 | 732 | 68 |
| TYR | CE2 | C | 381 | −2 | −44 | 745 | 68 |
| TYR | CZ | C | 381 | −8 | −51 | 755 | 68 |
| TYR | OH | C | 381 | −6 | −48 | 769 | 68 |
| TYR | C | C | 381 | −31 | −60 | 694 | 67 |
| TYR | O | C | 381 | −38 | −70 | 691 | 67 |
| LYS | N | C | 382 | −24 | −53 | 685 | 66 |
| LYS | CA | C | 382 | −25 | −56 | 671 | 65 |
| LYS | CB | C | 382 | −32 | −45 | 664 | 66 |
| LYS | CG | C | 382 | −34 | −47 | 649 | 66 |
| LYS | CD | C | 382 | −43 | −37 | 642 | 67 |
| LYS | CE | C | 382 | −57 | −36 | 647 | 67 |
| LYS | NZ | C | 382 | −66 | −26 | 641 | 67 |
| LYS | C | C | 382 | −11 | −57 | 666 | 64 |
| LYS | O | C | 382 | −2 | −49 | 670 | 64 |
| PHE | N | C | 383 | −8 | −67 | 658 | 63 |
| PHE | CA | C | 383 | 5 | −69 | 652 | 61 |
| PHE | CB | C | 383 | 5 | −81 | 643 | 61 |
| PHE | CG | C | 383 | 19 | −86 | 640 | 60 |
| PHE | CD1 | C | 383 | 28 | −89 | 650 | 60 |
| PHE | CD2 | C | 383 | 22 | −89 | 626 | 60 |
| PHE | CE1 | C | 383 | 41 | −94 | 647 | 59 |
| PHE | CE2 | C | 383 | 35 | −95 | 623 | 60 |
| PHE | CZ | C | 383 | 44 | −97 | 634 | 59 |
| PHE | C | C | 383 | 9 | −56 | 645 | 61 |
| PHE | O | C | 383 | 0 | −50 | 639 | 61 |
| ALA | N | C | 384 | 21 | −52 | 645 | 61 |
| ALA | CA | C | 384 | 25 | −39 | 638 | 61 |
| ALA | CB | C | 384 | 29 | −29 | 648 | 61 |
| ALA | C | C | 384 | 37 | −41 | 628 | 61 |
| ALA | O | C | 384 | 45 | −32 | 626 | 61 |
| ILE | N | C | 385 | 37 | −53 | 622 | 60 |
| ILE | CA | C | 385 | 48 | −56 | 612 | 60 |
| ILE | CB | C | 385 | 58 | −66 | 617 | 60 |
| ILE | CG2 | C | 385 | 68 | −70 | 606 | 60 |
| ILE | CG1 | C | 385 | 65 | −61 | 629 | 60 |
| ILE | CD1 | C | 385 | 75 | −71 | 635 | 60 |
| ILE | C | C | 385 | 41 | −61 | 599 | 61 |
| ILE | O | C | 385 | 40 | −73 | 597 | 61 |
| SER | N | C | 386 | 37 | −52 | 591 | 61 |
| SER | CA | C | 386 | 31 | −55 | 578 | 61 |
| SER | CB | C | 386 | 21 | −44 | 574 | 61 |
| SER | OG | C | 386 | 28 | −32 | 573 | 61 |
| SER | C | C | 386 | 41 | −57 | 567 | 61 |
| SER | O | C | 386 | 53 | −56 | 570 | 61 |
| GLN | N | C | 387 | 37 | −60 | 555 | 61 |
| GLN | CA | C | 387 | 47 | −62 | 544 | 61 |
| GLN | CB | C | 387 | 44 | −74 | 536 | 62 |
| GLN | CG | C | 387 | 30 | −74 | 530 | 63 |
| GLN | CD | C | 387 | 27 | −87 | 522 | 63 |
| GLN | OE1 | C | 387 | 33 | −89 | 512 | 63 |
| GLN | NE2 | C | 387 | 17 | −95 | 527 | 63 |
| GLN | C | C | 387 | 47 | −49 | 535 | 61 |
| GLN | O | C | 387 | 39 | −40 | 537 | 61 |
| SER | N | C | 388 | 56 | −49 | 526 | 61 |
| SER | CA | C | 388 | 57 | −37 | 517 | 62 |
| SER | CB | C | 388 | 66 | −27 | 523 | 62 |
| SER | OG | C | 388 | 67 | −15 | 515 | 62 |
| SER | C | C | 388 | 63 | −41 | 503 | 62 |
| SER | O | C | 388 | 70 | −51 | 502 | 62 |
| SER | N | C | 389 | 60 | −32 | 493 | 62 |
| SER | CA | C | 389 | 65 | −34 | 480 | 61 |
| SER | CB | C | 389 | 53 | −34 | 470 | 62 |
| SER | OG | C | 389 | 47 | −21 | 470 | 62 |
| SER | C | C | 389 | 75 | −23 | 476 | 61 |
| SER | O | C | 389 | 82 | −24 | 466 | 61 |
| THR | N | C | 390 | 76 | −13 | 485 | 60 |
| THR | CA | C | 390 | 85 | −2 | 483 | 60 |
| THR | CB | C | 390 | 77 | 11 | 485 | 60 |
| THR | OG1 | C | 390 | 70 | 12 | 497 | 60 |
| THR | CG2 | C | 390 | 66 | 12 | 473 | 59 |
| THR | C | C | 390 | 96 | −1 | 493 | 59 |
| THR | O | C | 390 | 100 | 9 | 498 | 59 |
| GLY | N | C | 391 | 102 | −13 | 496 | 58 |
| GLY | CA | C | 391 | 113 | −14 | 505 | 56 |
| GLY | C | C | 391 | 110 | −14 | 520 | 55 |
| GLY | O | C | 391 | 98 | −13 | 524 | 55 |
| THR | N | C | 392 | 120 | −15 | 528 | 54 |
| THR | CA | C | 392 | 119 | −16 | 543 | 53 |
| THR | CB | C | 392 | 132 | −21 | 550 | 53 |
| THR | OG1 | C | 392 | 135 | −34 | 545 | 52 |
| THR | CG2 | C | 392 | 130 | −21 | 565 | 52 |
| THR | C | C | 392 | 116 | −2 | 548 | 52 |

TABLE 1-continued

Structure Coordinates for uncomplexed BACE

| | | | | | | | |
|---|---|---|---|---|---|---|---|
| THR | O | C | 392 | 122 | 8 | 545 | 52 |
| VAL | N | C | 393 | 106 | −1 | 557 | 51 |
| VAL | CA | C | 393 | 102 | 11 | 563 | 50 |
| VAL | CB | C | 393 | 87 | 15 | 559 | 50 |
| VAL | CG1 | C | 393 | 84 | 29 | 565 | 49 |
| VAL | CG2 | C | 393 | 86 | 16 | 544 | 50 |
| VAL | C | C | 393 | 102 | 11 | 578 | 50 |
| VAL | O | C | 393 | 93 | 6 | 585 | 49 |
| MET | N | C | 394 | 113 | 17 | 584 | 49 |
| MET | CA | C | 394 | 115 | 17 | 598 | 49 |
| MET | CB | C | 394 | 129 | 19 | 601 | 49 |
| MET | CG | C | 394 | 138 | 8 | 596 | 50 |
| MET | SD | C | 394 | 156 | 11 | 598 | 50 |
| MET | CE | C | 394 | 156 | 15 | 615 | 50 |
| MET | C | C | 394 | 106 | 28 | 604 | 48 |
| MET | O | C | 394 | 110 | 40 | 605 | 48 |
| GLY | N | C | 395 | 94 | 25 | 608 | 47 |
| GLY | CA | C | 395 | 84 | 34 | 613 | 46 |
| GLY | C | C | 395 | 85 | 36 | 628 | 46 |
| GLY | O | C | 395 | 95 | 34 | 635 | 47 |
| ALA | N | C | 396 | 73 | 41 | 633 | 46 |
| ALA | CA | C | 396 | 72 | 43 | 648 | 46 |
| ALA | CB | C | 396 | 58 | 49 | 651 | 46 |
| ALA | C | C | 396 | 75 | 31 | 656 | 46 |
| ALA | O | C | 396 | 80 | 33 | 667 | 47 |
| VAL | N | C | 397 | 72 | 19 | 651 | 46 |
| VAL | CA | C | 397 | 74 | 7 | 659 | 47 |
| VAL | CB | C | 397 | 69 | −5 | 652 | 47 |
| VAL | CG1 | C | 397 | 53 | −6 | 653 | 47 |
| VAL | CG2 | C | 397 | 73 | −6 | 638 | 47 |
| VAL | C | C | 397 | 89 | 6 | 662 | 46 |
| VAL | O | C | 397 | 93 | 1 | 673 | 47 |
| ILE | N | C | 398 | 97 | 11 | 653 | 46 |
| ILE | CA | C | 398 | 112 | 10 | 655 | 45 |
| ILE | CB | C | 398 | 119 | 11 | 641 | 45 |
| ILE | CG2 | C | 398 | 133 | 16 | 643 | 45 |
| ILE | CG1 | C | 398 | 120 | −3 | 635 | 45 |
| ILE | CD1 | C | 398 | 129 | −13 | 642 | 45 |
| ILE | C | C | 398 | 116 | 23 | 663 | 45 |
| ILE | O | C | 398 | 122 | 22 | 673 | 45 |
| MET | N | C | 399 | 113 | 34 | 657 | 44 |
| MET | CA | C | 399 | 116 | 47 | 663 | 43 |
| MET | CB | C | 399 | 112 | 59 | 654 | 42 |
| MET | CG | C | 399 | 118 | 58 | 640 | 42 |
| MET | SD | C | 399 | 114 | 71 | 630 | 43 |
| MET | CE | C | 399 | 121 | 85 | 639 | 42 |
| MET | C | C | 399 | 111 | 50 | 678 | 42 |
| MET | O | C | 399 | 116 | 58 | 685 | 42 |
| GLU | N | C | 400 | 101 | 42 | 682 | 42 |
| GLU | CA | C | 400 | 96 | 44 | 695 | 41 |
| GLU | CB | C | 400 | 82 | 39 | 697 | 42 |
| GLU | CG | C | 400 | 72 | 48 | 690 | 43 |
| GLU | CD | C | 400 | 58 | 43 | 691 | 44 |
| GLU | OE1 | C | 400 | 48 | 52 | 691 | 45 |
| GLU | OE2 | C | 400 | 56 | 31 | 691 | 44 |
| GLU | C | C | 400 | 105 | 38 | 706 | 41 |
| GLU | O | C | 400 | 103 | 41 | 718 | 40 |
| GLY | N | C | 401 | 114 | 30 | 701 | 40 |
| GLY | CA | C | 401 | 124 | 24 | 711 | 40 |
| GLY | C | C | 401 | 137 | 31 | 712 | 39 |
| GLY | O | C | 401 | 144 | 29 | 722 | 39 |
| PHE | N | C | 402 | 140 | 40 | 702 | 38 |
| PHE | CA | C | 402 | 152 | 47 | 703 | 36 |
| PHE | CB | C | 402 | 162 | 42 | 692 | 37 |
| PHE | CG | C | 402 | 161 | 27 | 690 | 37 |
| PHE | CD1 | C | 402 | 152 | 21 | 682 | 38 |
| PHE | CD2 | C | 402 | 170 | 19 | 697 | 37 |
| PHE | CE1 | C | 402 | 151 | 7 | 680 | 37 |
| PHE | CE2 | C | 402 | 170 | 5 | 695 | 38 |
| PHE | CZ | C | 402 | 160 | −1 | 687 | 38 |
| PHE | C | C | 402 | 151 | 62 | 701 | 36 |
| PHE | O | C | 402 | 141 | 68 | 697 | 36 |
| TYR | N | C | 403 | 162 | 69 | 704 | 35 |
| TYR | CA | C | 403 | 163 | 83 | 702 | 35 |
| TYR | CB | C | 403 | 172 | 90 | 712 | 35 |
| TYR | CG | C | 403 | 174 | 105 | 711 | 35 |
| TYR | CD1 | C | 403 | 163 | 113 | 709 | 35 |
| TYR | CE1 | C | 403 | 164 | 127 | 708 | 35 |
| TYR | CD2 | C | 403 | 186 | 111 | 712 | 35 |
| TYR | CE2 | C | 403 | 188 | 125 | 712 | 35 |
| TYR | CZ | C | 403 | 177 | 133 | 710 | 35 |
| TYR | OH | C | 403 | 178 | 146 | 709 | 34 |
| TYR | C | C | 403 | 170 | 83 | 688 | 34 |
| TYR | O | C | 403 | 180 | 77 | 687 | 34 |
| VAL | N | C | 404 | 164 | 89 | 678 | 33 |
| VAL | CA | C | 404 | 170 | 89 | 665 | 32 |
| VAL | CB | C | 404 | 160 | 84 | 655 | 31 |
| VAL | CG1 | C | 404 | 166 | 83 | 641 | 31 |
| VAL | CG2 | C | 404 | 155 | 70 | 659 | 31 |
| VAL | C | C | 404 | 175 | 103 | 661 | 31 |
| VAL | O | C | 404 | 168 | 113 | 662 | 31 |
| VAL | N | C | 405 | 187 | 103 | 656 | 30 |
| VAL | CA | C | 405 | 194 | 115 | 652 | 30 |
| VAL | CB | C | 405 | 208 | 116 | 659 | 30 |
| VAL | CG1 | C | 405 | 215 | 129 | 656 | 29 |
| VAL | CG2 | C | 405 | 206 | 115 | 674 | 29 |
| VAL | C | C | 405 | 196 | 115 | 637 | 29 |
| VAL | O | C | 405 | 204 | 107 | 631 | 29 |
| PHE | N | C | 406 | 189 | 125 | 631 | 30 |
| PHE | CA | C | 406 | 191 | 127 | 617 | 31 |
| PHE | CB | C | 406 | 177 | 132 | 611 | 31 |
| PHE | CG | C | 406 | 166 | 122 | 613 | 32 |
| PHE | CD1 | C | 406 | 162 | 113 | 602 | 31 |
| PHE | CD2 | C | 406 | 160 | 120 | 625 | 32 |
| PHE | CE1 | C | 406 | 152 | 104 | 604 | 32 |
| PHE | CE2 | C | 406 | 150 | 111 | 627 | 32 |
| PHE | CZ | C | 406 | 146 | 102 | 617 | 32 |
| PHE | C | C | 406 | 201 | 138 | 615 | 31 |
| PHE | O | C | 406 | 198 | 150 | 615 | 32 |
| ASP | N | C | 407 | 214 | 133 | 614 | 32 |
| ASP | CA | C | 407 | 225 | 142 | 613 | 33 |
| ASP | CB | C | 407 | 237 | 135 | 619 | 33 |
| ASP | CG | C | 407 | 250 | 144 | 620 | 33 |
| ASP | OD1 | C | 407 | 250 | 154 | 613 | 33 |
| ASP | OD2 | C | 407 | 259 | 140 | 628 | 33 |
| ASP | C | C | 407 | 228 | 145 | 598 | 33 |
| ASP | O | C | 407 | 237 | 139 | 592 | 32 |
| ARG | N | C | 408 | 220 | 154 | 593 | 33 |
| ARG | CA | C | 408 | 222 | 158 | 579 | 34 |
| ARG | CB | C | 408 | 211 | 168 | 574 | 34 |
| ARG | CG | C | 408 | 197 | 162 | 573 | 34 |
| ARG | CD | C | 408 | 186 | 172 | 577 | 34 |
| ARG | NE | C | 408 | 186 | 183 | 567 | 34 |
| ARG | CZ | C | 408 | 178 | 184 | 557 | 34 |
| ARG | NH1 | C | 408 | 169 | 174 | 554 | 33 |
| ARG | NH2 | C | 408 | 179 | 195 | 549 | 33 |
| ARG | C | C | 408 | 235 | 163 | 575 | 34 |
| ARG | O | C | 408 | 241 | 160 | 565 | 34 |
| ALA | N | C | 409 | 241 | 171 | 584 | 35 |
| ALA | CA | C | 409 | 254 | 177 | 582 | 35 |
| ALA | CB | C | 409 | 258 | 185 | 595 | 35 |
| ALA | C | C | 409 | 265 | 166 | 579 | 36 |
| ALA | O | C | 409 | 274 | 168 | 571 | 36 |
| ARG | N | C | 410 | 264 | 155 | 586 | 37 |
| ARG | CA | C | 410 | 274 | 144 | 584 | 37 |
| ARG | CB | C | 410 | 280 | 140 | 597 | 38 |
| ARG | CG | C | 410 | 287 | 151 | 605 | 39 |
| ARG | CD | C | 410 | 294 | 147 | 617 | 41 |
| ARG | NE | C | 410 | 305 | 137 | 614 | 43 |
| ARG | CZ | C | 410 | 314 | 133 | 623 | 43 |
| ARG | NH1 | C | 410 | 314 | 138 | 636 | 43 |
| ARG | NH2 | C | 410 | 323 | 124 | 620 | 44 |
| ARG | C | C | 410 | 268 | 132 | 577 | 37 |
| ARG | O | C | 410 | 273 | 121 | 577 | 37 |
| LYS | N | C | 411 | 257 | 135 | 570 | 36 |
| LYS | CA | C | 411 | 251 | 124 | 562 | 35 |
| LYS | CB | C | 411 | 259 | 123 | 549 | 37 |
| LYS | CG | C | 411 | 251 | 115 | 538 | 38 |
| LYS | CD | C | 411 | 260 | 114 | 525 | 39 |
| LYS | CE | C | 411 | 253 | 108 | 513 | 39 |
| LYS | NZ | C | 411 | 263 | 103 | 503 | 40 |
| LYS | C | C | 411 | 250 | 111 | 570 | 34 |
| LYS | O | C | 411 | 255 | 101 | 565 | 33 |
| ARG | N | C | 412 | 244 | 111 | 582 | 33 |

TABLE 1-continued

Structure Coordinates for uncomplexed BACE

| | | | | | | | |
|---|---|---|---|---|---|---|---|
| ARG | CA | C | 412 | 243 | 99 | 589 | 33 |
| ARG | CB | C | 412 | 256 | 96 | 597 | 33 |
| ARG | CG | C | 412 | 259 | 108 | 607 | 33 |
| ARG | CD | C | 412 | 272 | 105 | 615 | 33 |
| ARG | NE | C | 412 | 274 | 115 | 626 | 34 |
| ARG | CZ | C | 412 | 283 | 114 | 635 | 34 |
| ARG | NH1 | C | 412 | 292 | 105 | 635 | 34 |
| ARG | NH2 | C | 412 | 283 | 124 | 645 | 34 |
| ARG | C | C | 412 | 232 | 99 | 599 | 33 |
| ARG | O | C | 412 | 227 | 110 | 603 | 33 |
| ILE | N | C | 413 | 227 | 88 | 603 | 33 |
| ILE | CA | C | 413 | 216 | 87 | 613 | 32 |
| ILE | CB | C | 413 | 204 | 80 | 606 | 33 |
| ILE | CG2 | C | 413 | 193 | 76 | 617 | 32 |
| ILE | CG1 | C | 413 | 198 | 89 | 596 | 33 |
| ILE | CD1 | C | 413 | 186 | 83 | 588 | 33 |
| ILE | C | C | 413 | 220 | 79 | 625 | 32 |
| ILE | O | C | 413 | 226 | 68 | 625 | 31 |
| GLY | N | C | 414 | 218 | 85 | 637 | 32 |
| GLY | CA | C | 414 | 222 | 79 | 649 | 32 |
| GLY | C | C | 414 | 211 | 73 | 657 | 32 |
| GLY | O | C | 414 | 199 | 78 | 657 | 32 |
| PHE | N | C | 415 | 214 | 62 | 664 | 32 |
| PHE | CA | C | 415 | 204 | 55 | 672 | 33 |
| PHE | CB | C | 415 | 202 | 41 | 666 | 32 |
| PHE | CG | C | 415 | 195 | 41 | 653 | 32 |
| PHE | CD1 | C | 415 | 202 | 43 | 641 | 32 |
| PHE | CD2 | C | 415 | 181 | 39 | 652 | 32 |
| PHE | CE1 | C | 415 | 196 | 43 | 629 | 32 |
| PHE | CE2 | C | 415 | 175 | 39 | 640 | 32 |
| PHE | CZ | C | 415 | 182 | 41 | 628 | 31 |
| PHE | C | C | 415 | 210 | 53 | 686 | 34 |
| PHE | O | C | 415 | 221 | 50 | 688 | 34 |
| ALA | N | C | 416 | 201 | 54 | 696 | 35 |
| ALA | CA | C | 416 | 204 | 53 | 710 | 36 |
| ALA | CB | C | 416 | 209 | 66 | 716 | 36 |
| ALA | C | C | 416 | 192 | 48 | 717 | 37 |
| ALA | O | C | 416 | 181 | 52 | 714 | 36 |
| VAL | N | C | 417 | 194 | 41 | 728 | 37 |
| VAL | CA | C | 417 | 183 | 36 | 736 | 38 |
| VAL | CB | C | 417 | 188 | 27 | 748 | 38 |
| VAL | CG1 | C | 417 | 176 | 23 | 756 | 38 |
| VAL | CG2 | C | 417 | 195 | 15 | 742 | 37 |
| VAL | C | C | 417 | 175 | 48 | 742 | 38 |
| VAL | O | C | 417 | 181 | 57 | 749 | 38 |
| SER | N | C | 418 | 162 | 49 | 739 | 39 |
| SER | CA | C | 418 | 154 | 60 | 743 | 40 |
| SER | CB | C | 418 | 141 | 60 | 735 | 40 |
| SER | OG | C | 418 | 132 | 69 | 741 | 41 |
| SER | C | C | 418 | 150 | 59 | 758 | 41 |
| SER | O | C | 418 | 147 | 49 | 763 | 41 |
| ALA | N | C | 419 | 152 | 71 | 765 | 42 |
| ALA | CA | C | 419 | 149 | 72 | 779 | 44 |
| ALA | CB | C | 419 | 154 | 84 | 785 | 43 |
| ALA | C | C | 419 | 134 | 71 | 782 | 45 |
| ALA | O | C | 419 | 129 | 72 | 793 | 45 |
| CYS | N | C | 420 | 126 | 69 | 771 | 46 |
| CYS | CA | C | 420 | 111 | 68 | 773 | 47 |
| CYS | C | C | 420 | 105 | 55 | 767 | 48 |
| CYS | O | C | 420 | 93 | 53 | 769 | 48 |
| CYS | CB | C | 420 | 104 | 80 | 767 | 47 |
| CYS | SG | C | 420 | 104 | 81 | 749 | 48 |
| HIS | N | C | 421 | 113 | 47 | 760 | 48 |
| HIS | CA | C | 421 | 108 | 35 | 754 | 49 |
| HIS | CB | C | 421 | 118 | 28 | 746 | 49 |
| HIS | CG | C | 421 | 127 | 19 | 754 | 49 |
| HIS | CD2 | C | 421 | 129 | 6 | 753 | 49 |
| HIS | ND1 | C | 421 | 136 | 24 | 763 | 49 |
| HIS | CE1 | C | 421 | 143 | 14 | 768 | 49 |
| HIS | NE2 | C | 421 | 139 | 3 | 762 | 49 |
| HIS | C | C | 421 | 101 | 26 | 764 | 50 |
| HIS | O | C | 421 | 106 | 26 | 776 | 50 |
| VAL | N | C | 422 | 91 | 19 | 760 | 51 |
| VAL | CA | C | 422 | 84 | 9 | 769 | 52 |
| VAL | CB | C | 422 | 70 | 8 | 764 | 52 |
| VAL | CG1 | C | 422 | 62 | -3 | 772 | 52 |
| VAL | CG2 | C | 422 | 62 | 21 | 765 | 52 |
| VAL | C | C | 422 | 91 | -5 | 769 | 52 |
| VAL | O | C | 422 | 95 | -10 | 759 | 52 |
| HIS | N | C | 423 | 92 | -10 | 781 | 53 |
| HIS | CA | C | 423 | 98 | -23 | 784 | 53 |
| HIS | CB | C | 423 | 113 | -22 | 783 | 54 |
| HIS | CG | C | 423 | 119 | -13 | 793 | 54 |
| HIS | CD2 | C | 423 | 125 | -15 | 805 | 54 |
| HIS | ND1 | C | 423 | 119 | 1 | 791 | 55 |
| HIS | CE1 | C | 423 | 124 | 6 | 802 | 55 |
| HIS | NE2 | C | 423 | 128 | -3 | 810 | 55 |
| HIS | C | C | 423 | 93 | -28 | 797 | 53 |
| HIS | O | C | 423 | 85 | -23 | 804 | 54 |
| ASP | N | C | 424 | 100 | -39 | 802 | 53 |
| ASP | CA | C | 424 | 97 | -45 | 815 | 53 |
| ASP | CB | C | 424 | 90 | -59 | 813 | 53 |
| ASP | CG | C | 424 | 98 | -68 | 804 | 52 |
| ASP | OD1 | C | 424 | 110 | -71 | 807 | 52 |
| ASP | OD2 | C | 424 | 92 | -72 | 793 | 52 |
| ASP | C | C | 424 | 110 | -46 | 823 | 53 |
| ASP | O | C | 424 | 120 | -41 | 819 | 53 |
| GLU | N | C | 425 | 109 | -52 | 835 | 53 |
| GLU | CA | C | 425 | 120 | -53 | 843 | 53 |
| GLU | CB | C | 425 | 117 | -55 | 858 | 54 |
| GLU | CG | C | 425 | 108 | -67 | 860 | 55 |
| GLU | CD | C | 425 | 93 | -64 | 862 | 56 |
| GLU | OE1 | C | 425 | 87 | -57 | 852 | 56 |
| GLU | OE2 | C | 425 | 87 | -67 | 872 | 56 |
| GLU | C | C | 425 | 130 | -63 | 839 | 51 |
| GLU | O | C | 425 | 141 | -65 | 845 | 51 |
| PHE | N | C | 426 | 127 | -71 | 828 | 50 |
| PHE | CA | C | 426 | 136 | -81 | 824 | 49 |
| PHE | CB | C | 426 | 129 | -94 | 823 | 49 |
| PHE | CG | C | 426 | 123 | -99 | 836 | 50 |
| PHE | CD1 | C | 426 | 109 | -98 | 838 | 50 |
| PHE | CD2 | C | 426 | 131 | -104 | 846 | 50 |
| PHE | CE1 | C | 426 | 104 | -102 | 850 | 50 |
| PHE | CE2 | C | 426 | 126 | -108 | 858 | 50 |
| PHE | CZ | C | 426 | 112 | -107 | 860 | 50 |
| PHE | C | C | 426 | 143 | -78 | 810 | 49 |
| PHE | O | C | 426 | 154 | -83 | 807 | 49 |
| ARG | N | C | 427 | 137 | -69 | 802 | 48 |
| ARG | CA | C | 427 | 143 | -66 | 789 | 47 |
| ARG | CB | C | 427 | 136 | -75 | 778 | 47 |
| ARG | CG | C | 427 | 139 | -89 | 779 | 47 |
| ARG | CD | C | 427 | 135 | -97 | 767 | 46 |
| ARG | NE | C | 427 | 121 | -96 | 764 | 45 |
| ARG | CZ | C | 427 | 114 | -103 | 755 | 45 |
| ARG | NH1 | C | 427 | 121 | -112 | 748 | 44 |
| ARG | NH2 | C | 427 | 101 | -101 | 753 | 45 |
| ARG | C | C | 427 | 140 | -51 | 786 | 47 |
| ARG | O | C | 427 | 131 | -45 | 791 | 47 |
| THR | N | C | 428 | 149 | -46 | 777 | 46 |
| THR | CA | C | 428 | 148 | -33 | 772 | 46 |
| THR | CB | C | 428 | 157 | -24 | 781 | 46 |
| THR | OG1 | C | 428 | 171 | -27 | 778 | 46 |
| THR | CG2 | C | 428 | 155 | -25 | 795 | 46 |
| THR | C | C | 428 | 154 | -33 | 758 | 45 |
| THR | O | C | 428 | 160 | -42 | 753 | 44 |
| ALA | N | C | 429 | 151 | -22 | 751 | 44 |
| ALA | CA | C | 429 | 156 | -20 | 737 | 44 |
| ALA | CB | C | 429 | 149 | -8 | 731 | 44 |
| ALA | C | C | 429 | 171 | -18 | 739 | 43 |
| ALA | O | C | 429 | 175 | -14 | 749 | 43 |
| ALA | N | C | 430 | 178 | -21 | 728 | 43 |
| ALA | CA | C | 430 | 193 | -19 | 729 | 42 |
| ALA | CB | C | 430 | 199 | -31 | 735 | 43 |
| ALA | C | C | 430 | 199 | -15 | 716 | 42 |
| ALA | O | C | 430 | 195 | -19 | 705 | 42 |
| VAL | N | C | 431 | 211 | -8 | 717 | 42 |
| VAL | CA | C | 431 | 219 | -5 | 705 | 41 |
| VAL | CB | C | 431 | 219 | 10 | 703 | 41 |
| VAL | CG1 | C | 431 | 228 | 13 | 690 | 41 |
| VAL | CG2 | C | 431 | 205 | 15 | 701 | 41 |
| VAL | C | C | 431 | 233 | -10 | 710 | 42 |
| VAL | O | C | 431 | 238 | -5 | 719 | 41 |
| GLU | N | C | 432 | 238 | -20 | 703 | 42 |
| GLU | CA | C | 432 | 251 | -26 | 706 | 42 |

TABLE 1-continued

Structure Coordinates for uncomplexed BACE

| | | | | | | | |
|---|---|---|---|---|---|---|---|
| GLU | CB | C | 432 | 248 | −39 | 712 | 43 |
| GLU | CG | C | 432 | 240 | −39 | 725 | 44 |
| GLU | CD | C | 432 | 234 | −53 | 728 | 45 |
| GLU | OE1 | C | 432 | 228 | −54 | 739 | 46 |
| GLU | OE2 | C | 432 | 233 | −62 | 720 | 45 |
| GLU | C | C | 432 | 260 | −27 | 694 | 42 |
| GLU | O | C | 432 | 256 | −29 | 682 | 42 |
| GLY | N | C | 433 | 273 | −26 | 696 | 43 |
| GLY | CA | C | 433 | 283 | −27 | 686 | 43 |
| GLY | C | C | 433 | 297 | −28 | 692 | 44 |
| GLY | O | C | 433 | 298 | −26 | 704 | 44 |
| PRO | N | C | 434 | 307 | −30 | 684 | 45 |
| PRO | CD | C | 434 | 321 | −28 | 688 | 45 |
| PRO | CA | C | 434 | 307 | −33 | 670 | 46 |
| PRO | CB | C | 434 | 319 | −26 | 665 | 46 |
| PRO | CG | C | 434 | 329 | −29 | 675 | 46 |
| PRO | C | C | 434 | 307 | −48 | 666 | 48 |
| PRO | O | C | 434 | 311 | −56 | 674 | 48 |
| PHE | N | C | 435 | 303 | −51 | 654 | 49 |
| PHE | CA | C | 435 | 303 | −64 | 649 | 51 |
| PHE | CB | C | 435 | 289 | −70 | 647 | 50 |
| PHE | CG | C | 435 | 281 | −70 | 660 | 51 |
| PHE | CD1 | C | 435 | 274 | −59 | 664 | 51 |
| PHE | CD2 | C | 435 | 281 | −81 | 668 | 51 |
| PHE | CE1 | C | 435 | 267 | −59 | 676 | 51 |
| PHE | CE2 | C | 435 | 274 | −81 | 680 | 50 |
| PHE | CZ | C | 435 | 267 | −70 | 684 | 51 |
| PHE | C | C | 435 | 310 | −64 | 636 | 52 |
| PHE | O | C | 435 | 307 | −56 | 627 | 52 |
| VAL | N | C | 436 | 320 | −72 | 634 | 53 |
| VAL | CA | C | 436 | 328 | −72 | 622 | 55 |
| VAL | CB | C | 436 | 341 | −81 | 623 | 55 |
| VAL | CG1 | C | 436 | 347 | −82 | 609 | 55 |
| VAL | CG2 | C | 436 | 350 | −74 | 633 | 55 |
| VAL | C | C | 436 | 319 | −78 | 611 | 56 |
| VAL | O | C | 436 | 315 | −90 | 611 | 57 |
| THR | N | C | 437 | 316 | −70 | 601 | 58 |
| THR | CA | C | 437 | 307 | −74 | 590 | 60 |
| THR | CB | C | 437 | 294 | −67 | 590 | 59 |
| THR | OG1 | C | 437 | 287 | −69 | 602 | 59 |
| THR | CG2 | C | 437 | 285 | −72 | 579 | 60 |
| THR | C | C | 437 | 314 | −71 | 577 | 61 |
| THR | O | C | 437 | 319 | −60 | 574 | 61 |
| LEU | N | C | 438 | 316 | −81 | 568 | 62 |
| LEU | CA | C | 438 | 323 | −79 | 555 | 63 |
| LEU | CB | C | 438 | 331 | −91 | 552 | 63 |
| LEU | CG | C | 438 | 343 | −94 | 561 | 63 |
| LEU | CD1 | C | 438 | 350 | −107 | 557 | 63 |
| LEU | CD2 | C | 438 | 353 | −82 | 560 | 63 |
| LEU | C | C | 438 | 314 | −76 | 544 | 64 |
| LEU | O | C | 438 | 302 | −79 | 544 | 64 |
| ASP | N | C | 439 | 320 | −69 | 533 | 66 |
| ASP | CA | C | 439 | 313 | −65 | 521 | 67 |
| ASP | CB | C | 439 | 313 | −77 | 512 | 67 |
| ASP | CG | C | 439 | 327 | −82 | 507 | 68 |
| ASP | OD1 | C | 439 | 334 | −86 | 516 | 68 |
| ASP | OD2 | C | 439 | 329 | −82 | 495 | 68 |
| ASP | C | C | 439 | 299 | −60 | 523 | 67 |
| ASP | O | C | 439 | 290 | −64 | 516 | 67 |
| MET | N | C | 440 | 297 | −51 | 533 | 68 |
| MET | CA | C | 440 | 284 | −45 | 536 | 68 |
| MET | CB | C | 440 | 285 | −36 | 548 | 68 |
| MET | CG | C | 440 | 288 | −43 | 561 | 68 |
| MET | SD | C | 440 | 287 | −32 | 575 | 67 |
| MET | CE | C | 440 | 302 | −23 | 573 | 68 |
| MET | C | C | 440 | 278 | −37 | 524 | 69 |
| MET | O | C | 440 | 266 | −37 | 523 | 69 |
| GLU | N | C | 441 | 287 | −31 | 516 | 70 |
| GLU | CA | C | 441 | 281 | −24 | 505 | 71 |
| GLU | CB | C | 441 | 293 | −15 | 498 | 71 |
| GLU | CG | C | 441 | 288 | −3 | 491 | 71 |
| GLU | CD | C | 441 | 281 | 7 | 501 | 72 |
| GLU | OE1 | C | 441 | 288 | 12 | 510 | 72 |
| GLU | OE2 | C | 441 | 269 | 9 | 499 | 71 |
| GLU | C | C | 441 | 274 | −32 | 494 | 71 |
| GLU | O | C | 441 | 266 | −28 | 487 | 71 |
| ASP | N | C | 442 | 278 | −45 | 494 | 72 |

TABLE 1-continued

Structure Coordinates for uncomplexed BACE

| | | | | | | | |
|---|---|---|---|---|---|---|---|
| ASP | CA | C | 442 | 272 | −55 | 485 | 72 |
| ASP | CB | C | 442 | 279 | −68 | 485 | 73 |
| ASP | CG | C | 442 | 292 | −68 | 478 | 73 |
| ASP | OD1 | C | 442 | 293 | −65 | 466 | 73 |
| ASP | OD2 | C | 442 | 302 | −71 | 485 | 73 |
| ASP | C | C | 442 | 257 | −56 | 488 | 72 |
| ASP | O | C | 442 | 249 | −63 | 481 | 72 |
| CYS | N | C | 443 | 253 | −51 | 500 | 73 |
| CYS | CA | C | 443 | 239 | −52 | 504 | 73 |
| CYS | C | C | 443 | 231 | −42 | 497 | 74 |
| CYS | O | C | 443 | 219 | −44 | 495 | 74 |
| CYS | CB | C | 443 | 239 | −49 | 520 | 73 |
| CYS | SG | C | 443 | 249 | −61 | 529 | 72 |
| GLY | N | C | 444 | 237 | −30 | 494 | 75 |
| GLY | CA | C | 444 | 230 | −20 | 487 | 76 |
| GLY | C | C | 444 | 223 | −25 | 474 | 76 |
| GLY | O | C | 444 | 230 | −32 | 466 | 77 |
| TYR | N | C | 445 | 211 | −21 | 472 | 77 |
| TYR | CA | C | 445 | 203 | −25 | 460 | 78 |
| TYR | CB | C | 445 | 189 | −30 | 464 | 79 |
| TYR | CG | C | 445 | 180 | −32 | 452 | 79 |
| TYR | CD1 | C | 445 | 183 | −43 | 443 | 80 |
| TYR | CE1 | C | 445 | 175 | −46 | 433 | 80 |
| TYR | CD2 | C | 445 | 169 | −25 | 449 | 80 |
| TYR | CE2 | C | 445 | 161 | −27 | 439 | 80 |
| TYR | CZ | C | 445 | 164 | −38 | 430 | 80 |
| TYR | OH | C | 445 | 155 | −41 | 420 | 80 |
| TYR | C | C | 445 | 202 | −13 | 450 | 78 |
| TYR | O | C | 445 | 199 | −2 | 455 | 78 |
| ASN | N | C | 446 | 205 | −15 | 438 | 79 |
| ASN | CA | C | 446 | 204 | −5 | 428 | 79 |
| ASN | CB | C | 446 | 217 | −4 | 420 | 79 |
| ASN | CG | C | 446 | 230 | −3 | 428 | 79 |
| ASN | OD1 | C | 446 | 231 | 7 | 436 | 80 |
| ASN | ND2 | C | 446 | 239 | −12 | 427 | 80 |
| ASN | C | C | 446 | 192 | −6 | 419 | 79 |
| ASN | O | C | 446 | 185 | −17 | 420 | 79 |
| ASN | OXT | C | 446 | 190 | 3 | 410 | 79 |
| I | I | I | 1 | 404 | 358 | 341 | 35 |
| I | I | I | 2 | 873 | −212 | 166 | 37 |
| I | I | I | 3 | 636 | 40 | 266 | 43 |
| I | I | I | 4 | 768 | −171 | 170 | 48 |
| I | I | I | 5 | 28 | 182 | 408 | 54 |
| I | I | I | 6 | 559 | 17 | 304 | 60 |
| I | I | I | 7 | 412 | 267 | 275 | 58 |
| I | I | I | 8 | 606 | −58 | 262 | 50 |
| I | I | I | 9 | 970 | −247 | 214 | 47 |
| I | I | I | 10 | 855 | 159 | 364 | 73 |
| I | I | I | 11 | −79 | 157 | 457 | 73 |
| I | I | I | 12 | 1130 | 62 | 185 | 66 |
| I | I | I | 13 | 949 | 153 | 444 | 78 |
| I | I | I | 14 | 496 | −48 | 189 | 83 |
| I | I | I | 15 | 644 | 338 | 630 | 87 |
| I | I | I | 16 | 1113 | 122 | 318 | 84 |
| I | I | I | 17 | 871 | 98 | 222 | 84 |
| I | I | I | 18 | 857 | 258 | 389 | 99 |
| I | I | I | 19 | 438 | −13 | 381 | 99 |
| I | I | I | 20 | −167 | 216 | 557 | 99 |
| I | I | I | 21 | 159 | 254 | 736 | 99 |
| WAT | OH2 | W | 1 | 1057 | −158 | 260 | 17 |
| WAT | OH2 | W | 2 | 636 | 166 | 429 | 22 |
| WAT | OH2 | W | 3 | 976 | −96 | 418 | 18 |
| WAT | OH2 | W | 4 | 562 | 203 | 446 | 27 |
| WAT | OH2 | W | 5 | 880 | −200 | 291 | 21 |
| WAT | OH2 | W | 6 | 270 | 99 | 732 | 20 |
| WAT | OH2 | W | 7 | 399 | 341 | 228 | 29 |
| WAT | OH2 | W | 8 | 682 | 82 | 35 | 26 |
| WAT | OH2 | W | 9 | 80 | 224 | 510 | 21 |
| WAT | OH2 | W | 10 | 820 | −126 | 120 | 24 |
| WAT | OH2 | W | 11 | 1047 | 180 | 364 | 32 |
| WAT | OH2 | W | 12 | 827 | −9 | 300 | 22 |
| WAT | OH2 | W | 13 | 791 | 30 | 422 | 26 |
| WAT | OH2 | W | 14 | 487 | 189 | 233 | 24 |
| WAT | OH2 | W | 15 | 412 | 246 | 359 | 26 |
| WAT | OH2 | W | 16 | 745 | −8 | 230 | 23 |
| WAT | OH2 | W | 17 | 762 | −85 | 254 | 24 |
| WAT | OH2 | W | 18 | 606 | −134 | 206 | 29 |

TABLE 1-continued

Structure Coordinates for uncomplexed BACE

| | | | | | | | |
|---|---|---|---|---|---|---|---|
| WAT | OH2 | W | 19 | 937 | −252 | 206 | 34 |
| WAT | OH2 | W | 20 | 114 | 286 | 642 | 35 |
| WAT | OH2 | W | 21 | 1083 | 42 | 222 | 29 |
| WAT | OH2 | W | 22 | 525 | 235 | 258 | 27 |
| WAT | OH2 | W | 23 | 660 | −121 | 59 | 29 |
| WAT | OH2 | W | 24 | 821 | −203 | 319 | 33 |
| WAT | OH2 | W | 25 | 203 | 237 | 539 | 28 |
| WAT | OH2 | W | 26 | 736 | −65 | 237 | 22 |
| WAT | OH2 | W | 27 | 690 | 439 | 327 | 38 |
| WAT | OH2 | W | 28 | 946 | −193 | 164 | 28 |
| WAT | OH2 | W | 29 | 123 | 198 | 553 | 28 |
| WAT | OH2 | W | 30 | 841 | −207 | 217 | 25 |
| WAT | OH2 | W | 31 | 924 | −248 | 171 | 23 |
| WAT | OH2 | W | 32 | 696 | −109 | 239 | 21 |
| WAT | OH2 | W | 33 | 1021 | −101 | 294 | 24 |
| WAT | OH2 | W | 34 | 852 | 19 | 116 | 36 |
| WAT | OH2 | W | 35 | −3 | 252 | 381 | 37 |
| WAT | OH2 | W | 36 | 239 | 193 | 705 | 30 |
| WAT | OH2 | W | 37 | 768 | −142 | 305 | 25 |
| WAT | OH2 | W | 38 | 961 | −57 | 213 | 25 |
| WAT | OH2 | W | 39 | −144 | 97 | 567 | 38 |
| WAT | OH2 | W | 40 | 121 | 84 | 682 | 33 |
| WAT | OH2 | W | 41 | 927 | −52 | 228 | 23 |
| WAT | OH2 | W | 42 | 145 | 186 | 542 | 27 |
| WAT | OH2 | W | 43 | 472 | 64 | 183 | 34 |
| WAT | OH2 | W | 44 | 883 | −144 | 113 | 26 |
| WAT | OH2 | W | 45 | 995 | −173 | 306 | 35 |
| WAT | OH2 | W | 46 | 614 | −46 | 158 | 28 |
| WAT | OH2 | W | 47 | 499 | 109 | 397 | 38 |
| WAT | OH2 | W | 48 | 631 | −33 | 90 | 28 |
| WAT | OH2 | W | 49 | 1059 | −100 | 269 | 26 |
| WAT | OH2 | W | 50 | 621 | 241 | 311 | 32 |
| WAT | OH2 | W | 51 | 512 | 145 | 238 | 35 |
| WAT | OH2 | W | 52 | 1062 | −122 | 390 | 39 |
| WAT | OH2 | W | 53 | 246 | 191 | 671 | 37 |
| WAT | OH2 | W | 54 | 486 | 202 | 210 | 30 |
| WAT | OH2 | W | 55 | 989 | −119 | 170 | 38 |
| WAT | OH2 | W | 56 | 578 | 83 | 205 | 33 |
| WAT | OH2 | W | 57 | 624 | −142 | 173 | 32 |
| WAT | OH2 | W | 58 | 55 | 163 | 525 | 27 |
| WAT | OH2 | W | 59 | 965 | −176 | 157 | 23 |
| WAT | OH2 | W | 60 | 741 | −90 | 318 | 27 |
| WAT | OH2 | W | 61 | 840 | −105 | 112 | 23 |
| WAT | OH2 | W | 62 | 650 | −103 | 275 | 28 |
| WAT | OH2 | W | 63 | 554 | 320 | 441 | 26 |
| WAT | OH2 | W | 64 | 87 | 242 | 528 | 26 |
| WAT | OH2 | W | 65 | 636 | 425 | 460 | 25 |
| WAT | OH2 | W | 66 | 501 | 167 | 441 | 34 |
| WAT | OH2 | W | 67 | 575 | 303 | 495 | 28 |
| WAT | OH2 | W | 68 | 256 | 139 | 653 | 36 |
| WAT | OH2 | W | 69 | 253 | 224 | 608 | 30 |
| WAT | OH2 | W | 70 | 710 | −150 | 108 | 35 |
| WAT | OH2 | W | 71 | 727 | 86 | 122 | 33 |
| WAT | OH2 | W | 72 | 765 | −88 | 282 | 30 |
| WAT | OH2 | W | 73 | 390 | 41 | 376 | 34 |
| WAT | OH2 | W | 74 | 53 | 223 | 499 | 31 |
| WAT | OH2 | W | 75 | 740 | 365 | 484 | 35 |
| WAT | OH2 | W | 76 | 877 | −91 | 99 | 35 |
| WAT | OH2 | W | 77 | 594 | 436 | 468 | 30 |
| WAT | OH2 | W | 78 | 614 | −129 | 235 | 24 |
| WAT | OH2 | W | 79 | 531 | 180 | 223 | 35 |
| WAT | OH2 | W | 80 | 643 | −84 | 155 | 23 |
| WAT | OH2 | W | 81 | 220 | −13 | 743 | 41 |
| WAT | OH2 | W | 82 | 651 | 293 | 197 | 42 |
| WAT | OH2 | W | 83 | 1058 | −71 | 304 | 24 |
| WAT | OH2 | W | 84 | 812 | 32 | 245 | 29 |
| WAT | OH2 | W | 85 | 440 | 227 | 410 | 29 |
| WAT | OH2 | W | 86 | 683 | 34 | 101 | 33 |
| WAT | OH2 | W | 87 | 1072 | 24 | 162 | 30 |
| WAT | OH2 | W | 88 | 850 | 78 | 208 | 35 |
| WAT | OH2 | W | 89 | 736 | 458 | 460 | 47 |
| WAT | OH2 | W | 90 | 341 | 143 | 341 | 43 |
| WAT | OH2 | W | 91 | 1120 | 157 | 257 | 34 |
| WAT | OH2 | W | 92 | 747 | −180 | 317 | 30 |
| WAT | OH2 | W | 93 | 702 | −53 | 260 | 24 |
| WAT | OH2 | W | 94 | 1107 | −24 | 161 | 39 |
| WAT | OH2 | W | 95 | 1024 | −153 | 211 | 28 |
| WAT | OH2 | W | 96 | −88 | 171 | 646 | 59 |
| WAT | OH2 | W | 97 | 217 | 184 | 540 | 35 |
| WAT | OH2 | W | 98 | 107 | 259 | 519 | 27 |
| WAT | OH2 | W | 99 | 982 | 201 | 371 | 35 |
| WAT | OH2 | W | 100 | 465 | 45 | 323 | 30 |
| WAT | OH2 | W | 101 | 615 | 436 | 444 | 30 |
| WAT | OH2 | W | 102 | 852 | −6 | 187 | 31 |
| WAT | OH2 | W | 103 | 288 | 50 | 651 | 31 |
| WAT | OH2 | W | 104 | 259 | 212 | 572 | 44 |
| WAT | OH2 | W | 105 | 536 | −90 | 182 | 25 |
| WAT | OH2 | W | 106 | 993 | 78 | 418 | 37 |
| WAT | OH2 | W | 107 | 781 | −128 | 337 | 30 |
| WAT | OH2 | W | 108 | 226 | −45 | 427 | 47 |
| WAT | OH2 | W | 109 | 1047 | −97 | 298 | 33 |
| WAT | OH2 | W | 110 | 705 | 166 | 490 | 46 |
| WAT | OH2 | W | 111 | 88 | 259 | 753 | 41 |
| WAT | OH2 | W | 112 | 733 | −142 | 322 | 30 |
| WAT | OH2 | W | 113 | 795 | −85 | 34 | 50 |
| WAT | OH2 | W | 114 | 298 | −70 | 710 | 55 |
| WAT | OH2 | W | 115 | 1089 | −97 | 407 | 59 |
| WAT | OH2 | W | 116 | 172 | 189 | 504 | 34 |
| WAT | OH2 | W | 117 | −61 | 287 | 671 | 50 |
| WAT | OH2 | W | 118 | 788 | 76 | 167 | 40 |
| WAT | OH2 | W | 119 | 421 | 244 | 384 | 26 |
| WAT | OH2 | W | 120 | 690 | −216 | 268 | 42 |
| WAT | OH2 | W | 121 | −62 | 303 | 525 | 40 |
| WAT | OH2 | W | 122 | 20 | 304 | 516 | 32 |
| WAT | OH2 | W | 123 | −103 | −123 | 779 | 56 |
| WAT | OH2 | W | 124 | 803 | −75 | 61 | 37 |
| WAT | OH2 | W | 125 | 779 | 42 | 91 | 44 |
| WAT | OH2 | W | 126 | 1073 | −79 | 264 | 29 |
| WAT | OH2 | W | 127 | 429 | 156 | 143 | 37 |
| WAT | OH2 | W | 128 | −4 | 292 | 440 | 34 |
| WAT | OH2 | W | 129 | 646 | −190 | 220 | 23 |
| WAT | OH2 | W | 130 | −90 | 294 | 615 | 53 |
| WAT | OH2 | W | 131 | 1070 | −60 | 280 | 39 |
| WAT | OH2 | W | 132 | 907 | 207 | 383 | 48 |
| WAT | OH2 | W | 133 | 904 | −206 | 262 | 33 |
| WAT | OH2 | W | 134 | 744 | −158 | 304 | 31 |
| WAT | OH2 | W | 135 | 1060 | 45 | 343 | 38 |
| WAT | OH2 | W | 136 | 637 | −55 | 160 | 27 |
| WAT | OH2 | W | 137 | 991 | −11 | 192 | 35 |
| WAT | OH2 | W | 138 | 364 | 101 | 319 | 42 |
| WAT | OH2 | W | 139 | 1142 | 28 | 256 | 29 |
| WAT | OH2 | W | 140 | 563 | 306 | 409 | 25 |
| WAT | OH2 | W | 141 | 557 | −147 | 179 | 35 |
| WAT | OH2 | W | 142 | 587 | −28 | 184 | 28 |
| WAT | OH2 | W | 143 | −8 | 296 | 480 | 40 |
| WAT | OH2 | W | 144 | 1030 | −44 | 150 | 53 |
| WAT | OH2 | W | 145 | 519 | 198 | 256 | 23 |
| WAT | OH2 | W | 146 | 793 | −173 | 346 | 32 |
| WAT | OH2 | W | 147 | 620 | −77 | 287 | 35 |
| WAT | OH2 | W | 148 | 942 | −98 | 157 | 23 |
| WAT | OH2 | W | 149 | 529 | −68 | 152 | 45 |
| WAT | OH2 | W | 150 | 225 | 37 | 737 | 39 |
| WAT | OH2 | W | 151 | 685 | −90 | 314 | 32 |
| WAT | OH2 | W | 152 | −120 | 131 | 522 | 60 |
| WAT | OH2 | W | 153 | 684 | 397 | 583 | 32 |
| WAT | OH2 | W | 154 | 763 | 28 | 276 | 38 |
| WAT | OH2 | W | 155 | 76 | −75 | 837 | 50 |
| WAT | OH2 | W | 156 | 669 | −114 | 32 | 32 |
| WAT | OH2 | W | 157 | 704 | −241 | 265 | 43 |
| WAT | OH2 | W | 158 | 516 | 382 | 228 | 43 |
| WAT | OH2 | W | 159 | 409 | 295 | 401 | 35 |
| WAT | OH2 | W | 160 | 333 | 120 | 267 | 35 |
| WAT | OH2 | W | 161 | 687 | −39 | 220 | 23 |
| WAT | OH2 | W | 162 | 644 | 432 | 334 | 41 |
| WAT | OH2 | W | 163 | 934 | −182 | 359 | 44 |
| WAT | OH2 | W | 164 | 6 | 287 | 502 | 36 |
| WAT | OH2 | W | 165 | 858 | 26 | 391 | 37 |
| WAT | OH2 | W | 166 | 504 | 395 | 277 | 42 |
| WAT | OH2 | W | 167 | 1026 | 47 | 145 | 39 |
| WAT | OH2 | W | 168 | 601 | 185 | 344 | 34 |
| WAT | OH2 | W | 169 | 714 | 370 | 553 | 46 |
| WAT | OH2 | W | 170 | 1018 | −176 | 292 | 56 |
| WAT | OH2 | W | 171 | 492 | 31 | 332 | 43 |
| WAT | OH2 | W | 172 | 707 | −86 | 224 | 23 |

TABLE 1-continued

Structure Coordinates for uncomplexed BACE

| | | | | | | | |
|---|---|---|---|---|---|---|---|
| WAT | OH2 | W | 173 | 1104 | −12 | 273 | 41 |
| WAT | OH2 | W | 174 | 670 | 463 | 429 | 41 |
| WAT | OH2 | W | 175 | 575 | 259 | 586 | 40 |
| WAT | OH2 | W | 176 | 1126 | −29 | 260 | 45 |
| WAT | OH2 | W | 177 | 851 | −224 | 192 | 45 |
| WAT | OH2 | W | 178 | 672 | 419 | 326 | 37 |
| WAT | OH2 | W | 179 | 217 | 24 | 773 | 42 |
| WAT | OH2 | W | 180 | 1083 | −56 | 387 | 45 |
| WAT | OH2 | W | 181 | 465 | 242 | 167 | 37 |
| WAT | OH2 | W | 182 | 945 | −169 | 324 | 35 |
| WAT | OH2 | W | 183 | 934 | −55 | 487 | 51 |
| WAT | OH2 | W | 184 | 820 | 40 | 404 | 37 |
| WAT | OH2 | W | 185 | 563 | 308 | 211 | 40 |
| WAT | OH2 | W | 186 | 864 | −103 | 412 | 33 |
| WAT | OH2 | W | 187 | 362 | 166 | 400 | 44 |
| WAT | OH2 | W | 188 | 167 | −138 | 737 | 43 |
| WAT | OH2 | W | 189 | 562 | 400 | 298 | 34 |
| WAT | OH2 | W | 190 | −100 | −109 | 755 | 53 |
| WAT | OH2 | W | 191 | 446 | 77 | 213 | 32 |
| WAT | OH2 | W | 192 | 628 | 416 | 482 | 24 |
| WAT | OH2 | W | 193 | 247 | 258 | 587 | 46 |
| WAT | OH2 | W | 194 | 76 | 144 | 492 | 40 |
| WAT | OH2 | W | 195 | 376 | 109 | 409 | 50 |
| WAT | OH2 | W | 196 | 912 | −79 | 84 | 51 |
| WAT | OH2 | W | 197 | 987 | −226 | 230 | 35 |
| WAT | OH2 | W | 198 | −142 | 128 | 542 | 48 |
| WAT | OH2 | W | 199 | 1040 | 144 | 388 | 61 |
| WAT | OH2 | W | 200 | 842 | 61 | 327 | 26 |
| WAT | OH2 | W | 201 | 80 | 218 | 744 | 39 |
| WAT | OH2 | W | 202 | 588 | −105 | 91 | 30 |
| WAT | OH2 | W | 203 | 930 | 164 | 252 | 41 |
| WAT | OH2 | W | 204 | 870 | −165 | 61 | 41 |
| WAT | OH2 | W | 205 | 543 | 247 | 247 | 41 |
| WAT | OH2 | W | 206 | 426 | 252 | 424 | 39 |
| WAT | OH2 | W | 207 | 342 | 207 | 263 | 51 |
| WAT | OH2 | W | 208 | 303 | 112 | 583 | 58 |
| WAT | OH2 | W | 209 | 420 | 30 | 265 | 45 |
| WAT | OH2 | W | 210 | 484 | 164 | 152 | 43 |
| WAT | OH2 | W | 211 | 224 | 328 | 588 | 41 |
| WAT | OH2 | W | 212 | 415 | 136 | 409 | 38 |
| WAT | OH2 | W | 213 | 94 | 210 | 494 | 25 |
| WAT | OH2 | W | 214 | 780 | −65 | 403 | 43 |
| WAT | OH2 | W | 215 | 708 | −107 | 320 | 35 |
| WAT | OH2 | W | 216 | 834 | −207 | 127 | 51 |
| WAT | OH2 | W | 217 | 510 | 423 | 479 | 29 |
| WAT | OH2 | W | 218 | 426 | 125 | 222 | 43 |
| WAT | OH2 | W | 219 | 199 | 215 | 552 | 37 |
| WAT | OH2 | W | 220 | −28 | 208 | 402 | 66 |
| WAT | OH2 | W | 221 | 721 | 272 | 302 | 35 |
| WAT | OH2 | W | 222 | 76 | 184 | 375 | 51 |
| WAT | OH2 | W | 223 | 350 | 78 | 204 | 44 |
| WAT | OH2 | W | 224 | 125 | −198 | 642 | 39 |
| WAT | OH2 | W | 225 | 1059 | −90 | 360 | 42 |
| WAT | OH2 | W | 226 | 502 | 191 | 512 | 40 |
| WAT | OH2 | W | 227 | 407 | 346 | 251 | 50 |
| WAT | OH2 | W | 228 | 602 | 262 | 545 | 32 |
| WAT | OH2 | W | 229 | 866 | −180 | 334 | 49 |
| WAT | OH2 | W | 230 | 56 | 214 | 374 | 39 |
| WAT | OH2 | W | 231 | 1113 | −34 | 218 | 34 |
| WAT | OH2 | W | 232 | 1091 | −43 | 292 | 43 |
| WAT | OH2 | W | 233 | 393 | 174 | 425 | 42 |
| WAT | OH2 | W | 234 | 395 | 278 | 413 | 41 |
| WAT | OH2 | W | 235 | 1012 | 54 | 165 | 31 |
| WAT | OH2 | W | 236 | 337 | −18 | 718 | 57 |
| WAT | OH2 | W | 237 | 537 | 13 | 400 | 44 |
| WAT | OH2 | W | 238 | −123 | 288 | 601 | 52 |
| WAT | OH2 | W | 239 | 552 | 164 | 288 | 28 |
| WAT | OH2 | W | 240 | −27 | 365 | 361 | 60 |
| WAT | OH2 | W | 241 | 303 | 188 | 247 | 38 |
| WAT | OH2 | W | 242 | 701 | −62 | 235 | 27 |
| WAT | OH2 | W | 243 | 694 | −34 | 27 | 46 |
| WAT | OH2 | W | 244 | 242 | 328 | 621 | 47 |
| WAT | OH2 | W | 245 | 192 | −189 | 618 | 34 |
| WAT | OH2 | W | 246 | 202 | 227 | 516 | 40 |
| WAT | OH2 | W | 247 | 574 | −79 | 95 | 34 |
| WAT | OH2 | W | 248 | 233 | 27 | 562 | 34 |
| WAT | OH2 | W | 249 | 949 | −189 | 301 | 42 |
| WAT | OH2 | W | 250 | 585 | −47 | 118 | 38 |
| WAT | OH2 | W | 251 | 369 | 51 | 199 | 54 |
| WAT | OH2 | W | 252 | 678 | −208 | 299 | 51 |
| WAT | OH2 | W | 253 | −129 | 224 | 582 | 49 |
| WAT | OH2 | W | 254 | 226 | 271 | 596 | 38 |
| WAT | OH2 | W | 255 | 807 | −111 | 352 | 44 |
| WAT | OH2 | W | 256 | 670 | −213 | 251 | 31 |
| WAT | OH2 | W | 257 | 1154 | 117 | 185 | 37 |
| WAT | OH2 | W | 258 | 1061 | −156 | 209 | 35 |
| WAT | OH2 | W | 259 | 895 | 137 | 393 | 53 |
| WAT | OH2 | W | 260 | 229 | 51 | 459 | 43 |
| WAT | OH2 | W | 261 | 991 | −134 | 375 | 39 |
| WAT | OH2 | W | 262 | 866 | −6 | 70 | 35 |
| WAT | OH2 | W | 263 | 965 | −118 | 383 | 26 |
| WAT | OH2 | W | 264 | 552 | −23 | 256 | 44 |
| WAT | OH2 | W | 265 | 1059 | −22 | 155 | 52 |
| WAT | OH2 | W | 266 | 697 | −177 | 105 | 39 |
| WAT | OH2 | W | 267 | 1040 | −63 | 182 | 30 |
| WAT | OH2 | W | 268 | 851 | −74 | 104 | 31 |
| WAT | OH2 | W | 269 | 743 | 259 | 294 | 42 |
| WAT | OH2 | W | 270 | 913 | −163 | 110 | 28 |
| WAT | OH2 | W | 271 | 938 | 209 | 378 | 49 |
| WAT | OH2 | W | 272 | 356 | 235 | 392 | 51 |
| WAT | OH2 | W | 273 | 880 | −215 | 266 | 31 |
| WAT | OH2 | W | 274 | 1094 | 28 | 147 | 44 |
| WAT | OH2 | W | 275 | 400 | 45 | 216 | 53 |
| WAT | OH2 | W | 276 | 822 | 134 | 242 | 56 |
| WAT | OH2 | W | 277 | −134 | 263 | 614 | 41 |
| WAT | OH2 | W | 278 | 819 | 256 | 252 | 57 |
| WAT | OH2 | W | 279 | 531 | 255 | 164 | 49 |
| WAT | OH2 | W | 280 | 66 | −42 | 835 | 51 |
| WAT | OH2 | W | 281 | 294 | 101 | 286 | 43 |
| WAT | OH2 | W | 282 | 71 | 112 | 498 | 40 |
| WAT | OH2 | W | 283 | 706 | 11 | 16 | 39 |
| WAT | OH2 | W | 284 | 303 | 71 | 641 | 33 |
| WAT | OH2 | W | 285 | 92 | −70 | 471 | 38 |
| WAT | OH2 | W | 286 | 901 | −160 | 324 | 30 |
| WAT | OH2 | W | 287 | 359 | 155 | 157 | 45 |
| WAT | OH2 | W | 288 | 373 | 71 | 164 | 42 |
| WAT | OH2 | W | 289 | 562 | −200 | 196 | 23 |
| WAT | OH2 | W | 290 | 751 | 187 | 352 | 46 |
| WAT | OH2 | W | 291 | 669 | −208 | 221 | 38 |
| WAT | OH2 | W | 292 | 376 | 205 | 162 | 42 |
| WAT | OH2 | W | 293 | 360 | 266 | 301 | 41 |
| WAT | OH2 | W | 294 | 737 | 19 | 227 | 40 |
| WAT | OH2 | W | 295 | 965 | 164 | 189 | 32 |
| WAT | OH2 | W | 296 | 532 | 440 | 336 | 55 |
| WAT | OH2 | W | 297 | 428 | 135 | 122 | 49 |
| WAT | OH2 | W | 298 | 611 | −169 | 153 | 36 |
| WAT | OH2 | W | 299 | 840 | 79 | 478 | 46 |
| WAT | OH2 | W | 300 | 405 | 56 | 265 | 39 |
| WAT | OH2 | W | 301 | 1000 | 222 | 307 | 42 |
| WAT | OH2 | W | 302 | 783 | −192 | 112 | 45 |
| WAT | OH2 | W | 303 | 943 | −30 | 495 | 45 |
| WAT | OH2 | W | 304 | −135 | 137 | 636 | 31 |
| WAT | OH2 | W | 305 | 476 | 203 | 160 | 55 |
| WAT | OH2 | W | 306 | 849 | 123 | 363 | 36 |
| WAT | OH2 | W | 307 | 312 | 101 | 660 | 54 |
| WAT | OH2 | W | 308 | 489 | 410 | 313 | 42 |
| WAT | OH2 | W | 309 | 897 | −235 | 156 | 35 |
| WAT | OH2 | W | 310 | 654 | −133 | 283 | 34 |
| WAT | OH2 | W | 311 | 189 | −184 | 689 | 44 |
| WAT | OH2 | W | 312 | 1015 | 168 | 376 | 41 |
| WAT | OH2 | W | 313 | 1134 | 49 | 242 | 43 |
| WAT | OH2 | W | 314 | 555 | 31 | 217 | 41 |
| WAT | OH2 | W | 315 | 542 | 414 | 290 | 55 |
| WAT | OH2 | W | 316 | 1016 | 54 | 449 | 42 |
| WAT | OH2 | W | 317 | 711 | 147 | 361 | 55 |
| WAT | OH2 | W | 318 | 968 | −277 | 222 | 39 |
| WAT | OH2 | W | 319 | 323 | 81 | 203 | 43 |
| WAT | OH2 | W | 320 | 656 | 350 | 599 | 40 |
| WAT | OH2 | W | 321 | 1115 | 90 | 271 | 46 |
| WAT | OH2 | W | 322 | 298 | 125 | 672 | 55 |
| WAT | OH2 | W | 323 | 406 | 277 | 440 | 35 |
| WAT | OH2 | W | 324 | 305 | −109 | 576 | 48 |
| WAT | OH2 | W | 325 | 407 | 251 | 406 | 50 |
| WAT | OH2 | W | 326 | 1109 | 74 | 140 | 36 |

TABLE 1-continued

Structure Coordinates for uncomplexed BACE

| | | | | | | | |
|---|---|---|---|---|---|---|---|
| WAT | OH2 | W | 327 | 1148 | −49 | 199 | 49 |
| WAT | OH2 | W | 328 | 803 | −142 | 372 | 57 |
| WAT | OH2 | W | 329 | 779 | 77 | 195 | 56 |
| WAT | OH2 | W | 330 | 58 | 88 | 551 | 42 |
| WAT | OH2 | W | 331 | 595 | 318 | 583 | 42 |
| WAT | OH2 | W | 332 | 1031 | 200 | 390 | 55 |
| WAT | OH2 | W | 333 | 1160 | 67 | 193 | 34 |
| WAT | OH2 | W | 334 | 445 | 377 | 281 | 43 |
| WAT | OH2 | W | 335 | 783 | 158 | 506 | 61 |
| WAT | OH2 | W | 336 | 57 | 353 | 629 | 61 |
| WAT | OH2 | W | 337 | 1089 | 6 | 285 | 47 |
| WAT | OH2 | W | 338 | 1051 | −116 | 316 | 35 |
| WAT | OH2 | W | 339 | 906 | −126 | 83 | 51 |
| WAT | OH2 | W | 340 | 723 | −73 | 45 | 36 |
| WAT | OH2 | W | 341 | 828 | 47 | 170 | 45 |
| WAT | OH2 | W | 342 | 579 | 456 | 367 | 38 |
| WAT | OH2 | W | 343 | 586 | 220 | 148 | 46 |
| WAT | OH2 | W | 344 | 1122 | 167 | 279 | 33 |
| WAT | OH2 | W | 345 | 630 | −139 | 20 | 41 |
| WAT | OH2 | W | 346 | 848 | −84 | 423 | 45 |
| WAT | OH2 | W | 347 | 574 | −214 | 177 | 37 |
| WAT | OH2 | W | 348 | 630 | 421 | 553 | 58 |
| WAT | OH2 | W | 349 | 867 | 144 | 444 | 59 |
| WAT | OH2 | W | 350 | 237 | 100 | 773 | 55 |
| WAT | OH2 | W | 351 | 949 | −87 | 134 | 36 |
| WAT | OH2 | W | 352 | 200 | −13 | 768 | 49 |
| WAT | OH2 | W | 353 | 204 | 175 | 790 | 43 |
| WAT | OH2 | W | 354 | 981 | 14 | 182 | 34 |
| WAT | OH2 | W | 355 | 1038 | 200 | 131 | 45 |
| WAT | OH2 | W | 356 | 951 | 187 | 381 | 57 |
| WAT | OH2 | W | 357 | 853 | 47 | 413 | 27 |
| WAT | OH2 | W | 358 | 1133 | 32 | 163 | 50 |
| WAT | OH2 | W | 359 | 68 | 121 | 464 | 46 |
| WAT | OH2 | W | 360 | 983 | 25 | 149 | 47 |
| WAT | OH2 | W | 361 | 568 | 124 | 319 | 47 |
| WAT | OH2 | W | 362 | 274 | 116 | 689 | 52 |
| WAT | OH2 | W | 363 | 851 | −196 | 316 | 45 |
| WAT | OH2 | W | 364 | 59 | 241 | 687 | 49 |
| WAT | OH2 | W | 365 | 623 | 160 | 170 | 45 |
| WAT | OH2 | W | 366 | 319 | 111 | 292 | 47 |
| WAT | OH2 | W | 367 | 143 | −45 | 881 | 45 |
| WAT | OH2 | W | 368 | 464 | −51 | 171 | 43 |
| WAT | OH2 | W | 369 | 1139 | 83 | 159 | 53 |
| WAT | OH2 | W | 370 | 46 | 34 | 544 | 50 |
| WAT | OH2 | W | 371 | 571 | 204 | 414 | 46 |
| WAT | OH2 | W | 372 | 618 | 159 | 203 | 38 |
| WAT | OH2 | W | 373 | 587 | 36 | 160 | 48 |
| WAT | OH2 | W | 374 | 555 | −85 | 115 | 43 |
| WAT | OH2 | W | 375 | 546 | 354 | 201 | 49 |
| WAT | OH2 | W | 376 | −85 | 90 | 580 | 50 |
| WAT | OH2 | W | 377 | 307 | 89 | 221 | 59 |
| WAT | OH2 | W | 378 | 76 | 143 | 401 | 52 |
| WAT | OH2 | W | 379 | 1115 | −45 | 171 | 48 |
| WAT | OH2 | W | 380 | 567 | 46 | 149 | 44 |
| WAT | OH2 | W | 381 | 102 | −21 | 842 | 53 |
| WAT | OH2 | W | 382 | 749 | −96 | 350 | 53 |
| WAT | OH2 | W | 383 | 983 | 75 | 447 | 55 |
| WAT | OH2 | W | 384 | 1074 | −123 | 275 | 45 |
| WAT | OH2 | W | 385 | 804 | 335 | 402 | 44 |
| WAT | OH2 | W | 386 | 153 | 32 | 791 | 45 |
| WAT | OH2 | W | 387 | 529 | 46 | 366 | 40 |
| WAT | OH2 | W | 388 | 204 | −51 | 763 | 56 |
| WAT | OH2 | W | 389 | 249 | 172 | 523 | 52 |
| WAT | OH2 | W | 390 | 554 | −12 | 287 | 47 |
| WAT | OH2 | W | 391 | −19 | 243 | 692 | 44 |
| WAT | OH2 | W | 392 | 838 | 76 | 261 | 40 |
| WAT | OH2 | W | 393 | 510 | −4 | 408 | 49 |
| WAT | OH2 | W | 394 | 1075 | 147 | 334 | 47 |
| WAT | OH2 | W | 395 | 732 | 441 | 498 | 45 |
| WAT | OH2 | W | 396 | −33 | 377 | 515 | 48 |
| WAT | OH2 | W | 397 | 192 | 194 | 402 | 48 |
| WAT | OH2 | W | 398 | 279 | −19 | 729 | 47 |
| WAT | OH2 | W | 399 | 597 | 1 | 299 | 54 |
| WAT | OH2 | W | 400 | 853 | −226 | 234 | 45 |
| WAT | OH2 | W | 401 | 229 | 246 | 543 | 52 |
| WAT | OH2 | W | 402 | 801 | 303 | 492 | 57 |
| WAT | OH2 | W | 403 | 543 | 209 | 392 | 46 |
| WAT | OH2 | W | 404 | −54 | 347 | 613 | 59 |
| WAT | OH2 | W | 405 | 670 | −9 | 349 | 46 |
| WAT | OH2 | W | 406 | 1129 | 24 | 279 | 33 |
| WAT | OH2 | W | 407 | −92 | 180 | 415 | 61 |
| WAT | OH2 | W | 408 | 304 | 108 | 551 | 52 |
| WAT | OH2 | W | 409 | 308 | 177 | 576 | 54 |
| WAT | OH2 | W | 410 | 546 | 132 | 152 | 60 |
| WAT | OH2 | W | 411 | 25 | −145 | 560 | 52 |
| WAT | OH2 | W | 412 | 763 | −174 | 93 | 50 |
| WAT | OH2 | W | 413 | −50 | 160 | 392 | 51 |
| WAT | OH2 | W | 414 | 230 | −36 | 774 | 62 |
| WAT | OH2 | W | 415 | 420 | 238 | 492 | 59 |
| WAT | OH2 | W | 416 | 199 | 178 | 498 | 51 |
| WAT | OH2 | W | 417 | −94 | 289 | 508 | 53 |
| WAT | OH2 | W | 418 | 747 | 52 | 337 | 54 |
| WAT | OH2 | W | 419 | 1044 | 258 | 202 | 51 |
| WAT | OH2 | W | 420 | 532 | 298 | 208 | 45 |
| WAT | OH2 | W | 421 | 870 | 137 | 253 | 58 |
| WAT | OH2 | W | 422 | 14 | 300 | 691 | 55 |
| WAT | OH2 | W | 423 | 550 | 398 | 260 | 52 |
| WAT | OH2 | W | 424 | 807 | −109 | 39 | 41 |
| WAT | OH2 | W | 425 | 249 | −148 | 571 | 61 |
| WAT | OH2 | W | 426 | 1133 | 198 | 180 | 59 |
| WAT | OH2 | W | 427 | 807 | 46 | 195 | 50 |
| WAT | OH2 | W | 428 | 1064 | 194 | 249 | 52 |
| WAT | OH2 | W | 429 | 1017 | −166 | 342 | 55 |
| WAT | OH2 | W | 430 | 1044 | −176 | 312 | 58 |
| WAT | OH2 | W | 431 | 248 | −120 | 588 | 52 |
| WAT | OH2 | W | 432 | 18 | 281 | 727 | 49 |
| WAT | OH2 | W | 433 | 707 | −218 | 303 | 51 |
| WAT | OH2 | W | 434 | 692 | 10 | 324 | 52 |
| WAT | OH2 | W | 435 | 22 | 106 | 548 | 57 |
| WAT | OH2 | W | 436 | 1029 | −52 | 116 | 54 |
| WAT | OH2 | W | 437 | 567 | 63 | 191 | 51 |
| WAT | OH2 | W | 438 | 323 | 102 | 172 | 51 |
| WAT | OH2 | W | 439 | 1082 | 27 | 336 | 49 |
| WAT | OH2 | W | 440 | 838 | −73 | 78 | 41 |
| WAT | OH2 | W | 441 | 431 | 6 | 274 | 62 |
| WAT | OH2 | W | 442 | 459 | 175 | 465 | 48 |
| WAT | OH2 | W | 443 | 733 | −252 | 263 | 49 |
| WAT | OH2 | W | 444 | 712 | 265 | 230 | 48 |
| WAT | OH2 | W | 445 | 1006 | −104 | 148 | 56 |
| WAT | OH2 | W | 446 | 70 | 62 | 774 | 47 |
| WAT | OH2 | W | 447 | −19 | 269 | 709 | 47 |
| WAT | OH2 | W | 448 | 1104 | 1 | 145 | 43 |
| WAT | OH2 | W | 449 | 878 | 94 | 174 | 46 |
| WAT | OH2 | W | 450 | 548 | 367 | 513 | 42 |
| WAT | OH2 | W | 451 | 180 | −59 | 746 | 58 |
| WAT | OH2 | W | 452 | 508 | 186 | 155 | 39 |
| WAT | OH2 | W | 453 | −135 | 239 | 512 | 59 |
| WAT | OH2 | W | 454 | 292 | 100 | 261 | 52 |
| WAT | OH2 | W | 455 | 201 | 34 | 443 | 60 |
| WAT | OH2 | W | 456 | 774 | −146 | 354 | 54 |
| WAT | OH2 | W | 457 | 574 | −16 | 129 | 41 |
| WAT | OH2 | W | 458 | 591 | 200 | 125 | 45 |
| WAT | OH2 | W | 459 | 1056 | −153 | 311 | 46 |
| WAT | OH2 | W | 460 | 564 | 136 | 297 | 41 |
| WAT | OH2 | W | 461 | 1079 | 120 | 340 | 43 |
| WAT | OH2 | W | 462 | 193 | 256 | 744 | 47 |
| WAT | OH2 | W | 463 | 579 | 15 | 121 | 56 |
| WAT | OH2 | W | 464 | 1090 | 213 | 341 | 52 |
| WAT | OH2 | W | 465 | 900 | −186 | 321 | 40 |
| WAT | OH2 | W | 466 | 663 | 170 | 311 | 51 |
| WAT | OH2 | W | 467 | 918 | 153 | 458 | 48 |
| WAT | OH2 | W | 468 | 556 | −25 | 159 | 51 |
| WAT | OH2 | W | 469 | 662 | 426 | 497 | 49 |
| WAT | OH2 | W | 470 | −79 | −127 | 711 | 53 |
| WAT | OH2 | W | 471 | 563 | 103 | 389 | 59 |
| WAT | OH2 | W | 472 | 1068 | 166 | 27 | 56 |
| WAT | OH2 | W | 473 | 348 | 285 | 408 | 45 |

TABLE 2

Structure Coordinates for BACE complexed to Inhibitor

The structure coordinates for BACE (SEQ ID NO: 20 and 22 wherein disordered residues are not shown) complexed to OM-99-2 are set forth below. There are two molecules: A and B.

"Res" refers to the amino acid whose atomic coordinates have been determined.
"At" refers to the atom, of the corresponding residue, whose coordinates have been determined.
"C" refers to the chain identifier.
"#" refers to the amino acid number of the corresponding residue.
"X", "Y" and "Z" refer to the crystallographically determined atomic position determined for each atom (multiplied by a factor of 10).
"B" refers to the thermal factor that measures movement of the atom around its atomic center (multiplied by a factor of 10).

Notes:
    All occupancies are set to 1.0
    A and B refer to protein molecules A and B
    W refers to water
    S refers to inhibitor (1 and 2 are the two copies)

| Res | At | C | # | X | Y | Z | B |
|---|---|---|---|---|---|---|---|
| ALA | CB | A | 53 | 432 | −167 | 448 | 57 |
| ALA | C | A | 53 | 414 | −183 | 440 | 57 |
| ALA | O | A | 53 | 411 | −195 | 442 | 58 |
| ALA | N | A | 53 | 419 | −181 | 464 | 58 |
| ALA | CA | A | 53 | 419 | −174 | 451 | 57 |
| ALA | N | A | 54 | 414 | −178 | 428 | 54 |
| ALA | CA | A | 54 | 410 | −186 | 416 | 52 |
| ALA | CB | A | 54 | 396 | −192 | 418 | 51 |
| ALA | C | A | 54 | 411 | −177 | 404 | 50 |
| ALA | O | A | 54 | 407 | −165 | 404 | 50 |
| GLY | N | A | 55 | 415 | −182 | 393 | 48 |
| GLY | CA | A | 55 | 416 | −174 | 380 | 45 |
| GLY | C | A | 55 | 403 | −175 | 372 | 43 |
| GLY | O | A | 55 | 398 | −186 | 369 | 44 |
| ARG | N | A | 56 | 398 | −163 | 369 | 41 |
| ARG | CA | A | 56 | 385 | −163 | 361 | 40 |
| ARG | CB | A | 56 | 378 | −150 | 364 | 41 |
| ARG | CG | A | 56 | 370 | −150 | 378 | 42 |
| ARG | CD | A | 56 | 360 | −138 | 379 | 43 |
| ARG | NE | A | 56 | 365 | −127 | 386 | 44 |
| ARG | CZ | A | 56 | 373 | −118 | 381 | 45 |
| ARG | NH1 | A | 56 | 378 | −119 | 369 | 42 |
| ARG | NH2 | A | 56 | 377 | −108 | 389 | 43 |
| ARG | C | A | 56 | 387 | −164 | 346 | 38 |
| ARG | O | A | 56 | 397 | −159 | 341 | 38 |
| ARG | N | A | 57 | 379 | −172 | 340 | 34 |
| ARG | CA | A | 57 | 380 | −175 | 326 | 30 |
| ARG | CB | A | 57 | 375 | −189 | 323 | 30 |
| ARG | CG | A | 57 | 383 | −200 | 331 | 29 |
| ARG | CD | A | 57 | 377 | −213 | 330 | 30 |
| ARG | NE | A | 57 | 365 | −215 | 338 | 29 |
| ARG | CZ | A | 57 | 353 | −211 | 334 | 32 |
| ARG | NH1 | A | 57 | 350 | −206 | 322 | 32 |
| ARG | NH2 | A | 57 | 342 | −213 | 343 | 31 |
| ARG | C | A | 57 | 371 | −165 | 318 | 28 |
| ARG | O | A | 57 | 361 | −160 | 323 | 28 |
| GLY | N | A | 58 | 374 | −163 | 305 | 25 |
| GLY | CA | A | 58 | 367 | −154 | 296 | 21 |
| GLY | C | A | 58 | 359 | −164 | 287 | 22 |
| GLY | O | A | 58 | 366 | −169 | 278 | 17 |
| SER | N | A | 59 | 346 | −166 | 289 | 20 |
| SER | CA | A | 59 | 339 | −175 | 280 | 23 |
| SER | CB | A | 59 | 329 | −183 | 289 | 24 |
| SER | OG | A | 59 | 336 | −189 | 300 | 26 |
| SER | C | A | 59 | 332 | −169 | 268 | 22 |
| SER | O | A | 59 | 325 | −177 | 261 | 24 |
| PHE | N | A | 60 | 333 | −156 | 265 | 18 |
| PHE | CA | A | 60 | 327 | −151 | 253 | 16 |
| PHE | CB | A | 60 | 316 | −140 | 258 | 16 |
| PHE | CG | A | 60 | 305 | −146 | 266 | 16 |
| PHE | CD1 | A | 60 | 307 | −146 | 280 | 15 |
| PHE | CD2 | A | 60 | 293 | −150 | 260 | 16 |
| PHE | CE1 | A | 60 | 296 | −151 | 288 | 16 |
| PHE | CE2 | A | 60 | 283 | −155 | 268 | 17 |
| PHE | CZ | A | 60 | 284 | −155 | 282 | 17 |
| PHE | C | A | 60 | 337 | −145 | 244 | 17 |
| PHE | O | A | 60 | 335 | −133 | 239 | 14 |
| VAL | N | A | 61 | 347 | −152 | 240 | 16 |
| VAL | CA | A | 61 | 358 | −148 | 231 | 15 |
| VAL | CB | A | 61 | 367 | −160 | 228 | 15 |
| VAL | CG1 | A | 61 | 378 | −155 | 219 | 17 |
| VAL | CG2 | A | 61 | 373 | −165 | 241 | 16 |
| VAL | C | A | 61 | 353 | −142 | 218 | 15 |
| VAL | O | A | 61 | 359 | −133 | 213 | 18 |
| GLU | N | A | 62 | 342 | −147 | 213 | 16 |
| GLU | CA | A | 62 | 336 | −143 | 200 | 15 |
| GLU | CB | A | 62 | 325 | −152 | 196 | 23 |
| GLU | CG | A | 62 | 319 | −148 | 182 | 31 |
| GLU | CD | A | 62 | 311 | −159 | 176 | 35 |
| GLU | OE1 | A | 62 | 301 | −163 | 183 | 38 |
| GLU | OE2 | A | 62 | 313 | −163 | 165 | 37 |
| GLU | C | A | 62 | 332 | −128 | 201 | 16 |
| GLU | O | A | 62 | 331 | −121 | 191 | 14 |
| MET | N | A | 63 | 328 | −123 | 213 | 9 |
| MET | CA | A | 63 | 323 | −110 | 214 | 8 |
| MET | CB | A | 63 | 310 | −109 | 222 | 9 |
| MET | CG | A | 63 | 299 | −116 | 215 | 12 |
| MET | SD | A | 63 | 283 | −116 | 223 | 10 |
| MET | CE | A | 63 | 284 | −131 | 233 | 13 |
| MET | C | A | 63 | 334 | −100 | 221 | 11 |
| MET | O | A | 63 | 332 | −88 | 220 | 10 |
| VAL | N | A | 64 | 344 | −106 | 227 | 10 |
| VAL | CA | A | 64 | 354 | −97 | 233 | 11 |
| VAL | CB | A | 64 | 365 | −106 | 240 | 11 |
| VAL | CG1 | A | 64 | 377 | −98 | 244 | 12 |
| VAL | CG2 | A | 64 | 359 | −111 | 253 | 11 |
| VAL | C | A | 64 | 361 | −89 | 222 | 9 |
| VAL | O | A | 64 | 364 | −94 | 211 | 9 |
| ASP | N | A | 65 | 364 | −76 | 225 | 9 |
| ASP | CA | A | 65 | 371 | −67 | 216 | 6 |
| ASP | CB | A | 65 | 385 | −73 | 213 | 9 |
| ASP | CG | A | 65 | 394 | −74 | 225 | 12 |
| ASP | OD1 | A | 65 | 405 | −78 | 223 | 12 |
| ASP | OD2 | A | 65 | 390 | −70 | 236 | 11 |
| ASP | C | A | 65 | 363 | −64 | 203 | 9 |
| ASP | O | A | 65 | 369 | −62 | 193 | 10 |
| ASN | N | A | 66 | 350 | −64 | 204 | 8 |
| ASN | CA | A | 66 | 341 | −62 | 193 | 9 |
| ASN | CB | A | 66 | 329 | −70 | 193 | 8 |
| ASN | CG | A | 66 | 320 | −68 | 205 | 9 |
| ASN | OD1 | A | 66 | 323 | −60 | 214 | 9 |
| ASN | ND2 | A | 66 | 308 | −74 | 205 | 9 |
| ASN | C | A | 66 | 337 | −47 | 191 | 8 |
| ASN | O | A | 66 | 330 | −43 | 182 | 8 |
| LEU | N | A | 67 | 343 | −38 | 200 | 7 |
| LEU | CA | A | 67 | 339 | −24 | 199 | 8 |
| LEU | CB | A | 67 | 335 | −18 | 212 | 6 |
| LEU | CG | A | 67 | 322 | −24 | 219 | 5 |
| LEU | CD1 | A | 67 | 320 | −17 | 232 | 7 |
| LEU | CD2 | A | 67 | 311 | −23 | 209 | 6 |
| LEU | C | A | 67 | 351 | −16 | 194 | 9 |
| LEU | O | A | 67 | 363 | −20 | 196 | 9 |
| ARG | N | A | 68 | 348 | −4 | 188 | 6 |
| ARG | CA | A | 68 | 358 | 5 | 184 | 9 |
| ARG | CB | A | 68 | 361 | 4 | 169 | 9 |
| ARG | CG | A | 68 | 370 | −8 | 165 | 11 |
| ARG | CD | A | 68 | 374 | −8 | 151 | 13 |
| ARG | NE | A | 68 | 363 | −10 | 142 | 15 |
| ARG | CZ | A | 68 | 364 | −7 | 129 | 15 |
| ARG | NH1 | A | 68 | 375 | −2 | 123 | 16 |
| ARG | NH2 | A | 68 | 353 | −9 | 121 | 13 |
| ARG | C | A | 68 | 353 | 19 | 187 | 9 |
| ARG | O | A | 68 | 341 | 21 | 190 | 7 |
| GLY | N | A | 69 | 362 | 29 | 186 | 8 |
| GLY | CA | A | 69 | 358 | 43 | 189 | 8 |
| GLY | C | A | 69 | 365 | 49 | 201 | 9 |
| GLY | O | A | 69 | 375 | 44 | 205 | 10 |
| LYS | N | A | 70 | 359 | 60 | 206 | 7 |
| LYS | CA | A | 70 | 365 | 67 | 217 | 8 |
| LYS | CB | A | 70 | 377 | 76 | 213 | 8 |
| LYS | CG | A | 70 | 374 | 85 | 202 | 12 |
| LYS | CD | A | 70 | 387 | 92 | 197 | 14 |
| LYS | CE | A | 70 | 384 | 102 | 185 | 18 |
| LYS | NZ | A | 70 | 397 | 108 | 181 | 18 |

TABLE 2-continued

Structure Coordinates for BACE complexed to Inhibitor

| | | | | | | | |
|---|---|---|---|---|---|---|---|
| LYS | C | A | 70 | 354 | 76 | 224 | 9 |
| LYS | O | A | 70 | 344 | 79 | 217 | 8 |
| SER | N | A | 71 | 356 | 80 | 236 | 8 |
| SER | CA | A | 71 | 346 | 87 | 243 | 8 |
| SER | CB | A | 71 | 352 | 92 | 257 | 10 |
| SER | OG | A | 71 | 362 | 101 | 256 | 10 |
| SER | C | A | 71 | 341 | 100 | 236 | 7 |
| SER | O | A | 71 | 329 | 102 | 237 | 8 |
| GLY | N | A | 72 | 349 | 107 | 230 | 8 |
| GLY | CA | A | 72 | 345 | 119 | 223 | 8 |
| GLY | C | A | 72 | 336 | 118 | 211 | 11 |
| GLY | O | A | 72 | 329 | 127 | 207 | 10 |
| GLN | N | A | 73 | 337 | 106 | 204 | 9 |
| GLN | CA | A | 73 | 329 | 104 | 192 | 10 |
| GLN | CB | A | 73 | 338 | 102 | 180 | 11 |
| GLN | CG | A | 73 | 347 | 114 | 178 | 15 |
| GLN | CD | A | 73 | 353 | 114 | 164 | 18 |
| GLN | OE1 | A | 73 | 358 | 104 | 159 | 21 |
| GLN | NE2 | A | 73 | 353 | 126 | 157 | 22 |
| GLN | C | A | 73 | 320 | 92 | 194 | 11 |
| GLN | O | A | 73 | 312 | 89 | 184 | 10 |
| GLY | N | A | 74 | 321 | 85 | 205 | 8 |
| GLY | CA | A | 74 | 312 | 73 | 207 | 8 |
| GLY | C | A | 74 | 319 | 60 | 204 | 6 |
| GLY | O | A | 74 | 328 | 59 | 196 | 8 |
| TYR | N | A | 75 | 314 | 49 | 210 | 7 |
| TYR | CA | A | 75 | 318 | 36 | 208 | 7 |
| TYR | CB | A | 75 | 321 | 28 | 221 | 7 |
| TYR | CG | A | 75 | 333 | 33 | 229 | 9 |
| TYR | CD1 | A | 75 | 332 | 44 | 238 | 9 |
| TYR | CE1 | A | 75 | 343 | 49 | 244 | 8 |
| TYR | CD2 | A | 75 | 345 | 27 | 227 | 10 |
| TYR | CE2 | A | 75 | 357 | 32 | 233 | 10 |
| TYR | CZ | A | 75 | 356 | 43 | 242 | 9 |
| TYR | OH | A | 75 | 367 | 47 | 248 | 9 |
| TYR | C | A | 75 | 308 | 28 | 199 | 8 |
| TYR | O | A | 75 | 296 | 29 | 202 | 8 |
| TYR | N | A | 76 | 313 | 21 | 190 | 7 |
| TYR | CA | A | 76 | 304 | 14 | 181 | 8 |
| TYR | CB | A | 76 | 303 | 21 | 167 | 6 |
| TYR | CG | A | 76 | 316 | 21 | 160 | 8 |
| TYR | CD1 | A | 76 | 320 | 11 | 151 | 7 |
| TYR | CE1 | A | 76 | 332 | 12 | 144 | 10 |
| TYR | CD2 | A | 76 | 325 | 32 | 162 | 9 |
| TYR | CE2 | A | 76 | 337 | 33 | 155 | 10 |
| TYR | CZ | A | 76 | 341 | 22 | 146 | 11 |
| TYR | OH | A | 76 | 352 | 23 | 139 | 14 |
| TYR | C | A | 76 | 307 | −1 | 178 | 7 |
| TYR | O | A | 76 | 318 | −6 | 180 | 7 |
| VAL | N | A | 77 | 296 | −8 | 174 | 7 |
| VAL | CA | A | 77 | 298 | −23 | 171 | 8 |
| VAL | CB | A | 77 | 289 | −31 | 181 | 6 |
| VAL | CG1 | A | 77 | 274 | −28 | 179 | 7 |
| VAL | CG2 | A | 77 | 292 | −46 | 179 | 7 |
| VAL | C | A | 77 | 293 | −25 | 157 | 8 |
| VAL | O | A | 77 | 284 | −17 | 152 | 8 |
| GLU | N | A | 78 | 298 | −35 | 150 | 9 |
| GLU | CA | A | 78 | 294 | −38 | 137 | 9 |
| GLU | CB | A | 79 | 304 | −45 | 129 | 11 |
| GLU | CG | A | 78 | 301 | −49 | 115 | 13 |
| GLU | CD | A | 78 | 312 | −56 | 107 | 16 |
| GLU | OE1 | A | 78 | 322 | −50 | 104 | 17 |
| GLU | OE2 | A | 78 | 310 | −68 | 105 | 19 |
| GLU | C | A | 78 | 281 | −46 | 137 | 7 |
| GLU | O | A | 78 | 279 | −55 | 145 | 8 |
| MET | N | A | 79 | 272 | −42 | 128 | 8 |
| MET | CA | A | 79 | 259 | −49 | 127 | 9 |
| MET | CB | A | 79 | 248 | −41 | 134 | 7 |
| MET | CG | A | 79 | 250 | −40 | 149 | 8 |
| MET | SD | A | 79 | 236 | −31 | 158 | 9 |
| MET | CE | A | 79 | 224 | −44 | 159 | 11 |
| MET | C | A | 79 | 255 | −50 | 112 | 9 |
| MET | O | A | 79 | 261 | −44 | 104 | 9 |
| THR | N | A | 80 | 245 | −59 | 109 | 10 |
| THR | CA | A | 80 | 241 | −60 | 95 | 10 |
| THR | CB | A | 80 | 245 | −74 | 89 | 12 |
| THR | OG1 | A | 80 | 237 | −84 | 95 | 13 |
| THR | CG2 | A | 80 | 260 | −76 | 90 | 12 |
| THR | C | A | 80 | 226 | −59 | 95 | 10 |
| THR | O | A | 80 | 219 | −63 | 105 | 9 |
| VAL | N | A | 81 | 220 | −53 | 85 | 10 |
| VAL | CA | A | 81 | 206 | −51 | 83 | 9 |
| VAL | CB | A | 81 | 201 | −37 | 86 | 11 |
| VAL | CG1 | A | 81 | 204 | −33 | 100 | 10 |
| VAL | CG2 | A | 81 | 209 | −27 | 77 | 12 |
| VAL | C | A | 81 | 202 | −55 | 69 | 10 |
| VAL | O | A | 81 | 209 | −53 | 60 | 8 |
| GLY | N | A | 82 | 190 | −62 | 68 | 12 |
| GLY | CA | A | 82 | 185 | −66 | 55 | 10 |
| GLY | C | A | 82 | 190 | −79 | 49 | 12 |
| GLY | O | A | 82 | 199 | −85 | 54 | 9 |
| SER | N | A | 83 | 185 | −82 | 37 | 11 |
| SER | CA | A | 83 | 188 | −94 | 30 | 10 |
| SER | CB | A | 83 | 177 | −104 | 31 | 11 |
| SER | OG | A | 83 | 173 | −107 | 44 | 14 |
| SER | C | A | 83 | 190 | −90 | 15 | 12 |
| SER | O | A | 83 | 180 | −86 | 9 | 13 |
| PRO | N | A | 84 | 202 | −92 | 10 | 11 |
| PRO | CD | A | 84 | 205 | −89 | −4 | 13 |
| PRO | CA | A | 84 | 214 | −97 | 17 | 12 |
| PRO | CB | A | 84 | 224 | −98 | 6 | 13 |
| PRO | CG | A | 84 | 220 | −87 | −4 | 14 |
| PRO | C | A | 84 | 218 | −87 | 27 | 12 |
| PRO | O | A | 84 | 214 | −75 | 27 | 10 |
| PRO | N | A | 85 | 226 | −91 | 37 | 13 |
| PRO | CD | A | 85 | 231 | −105 | 39 | 13 |
| PRO | CA | A | 85 | 230 | −82 | 48 | 12 |
| PRO | CB | A | 85 | 238 | −91 | 57 | 13 |
| PRO | CG | A | 85 | 243 | −102 | 48 | 16 |
| PRO | C | A | 85 | 239 | −70 | 44 | 11 |
| PRO | O | A | 85 | 248 | −71 | 36 | 12 |
| GLN | N | A | 86 | 235 | −58 | 49 | 9 |
| GLN | CA | A | 86 | 242 | −46 | 47 | 9 |
| GLN | CB | A | 86 | 232 | −35 | 43 | 10 |
| GLN | CG | A | 86 | 225 | −37 | 30 | 10 |
| GLN | CD | A | 86 | 214 | −26 | 28 | 10 |
| GLN | OE1 | A | 86 | 216 | −14 | 30 | 10 |
| GLN | NE2 | A | 86 | 202 | −31 | 23 | 9 |
| GLN | C | A | 86 | 249 | −43 | 59 | 9 |
| GLN | O | A | 86 | 243 | −41 | 70 | 10 |
| THR | N | A | 87 | 262 | −42 | 59 | 9 |
| THR | CA | A | 87 | 270 | −39 | 70 | 10 |
| THR | CB | A | 87 | 285 | −44 | 68 | 11 |
| THR | OG1 | A | 87 | 284 | −58 | 65 | 11 |
| THR | CG2 | A | 87 | 294 | −42 | 80 | 12 |
| THR | C | A | 87 | 271 | −24 | 74 | 8 |
| THR | O | A | 87 | 273 | −16 | 65 | 9 |
| LEU | N | A | 88 | 269 | −21 | 87 | 8 |
| LEU | CA | A | 88 | 269 | −8 | 92 | 9 |
| LEU | CB | A | 88 | 255 | −2 | 92 | 9 |
| LEU | CG | A | 88 | 247 | 0 | 79 | 11 |
| LEU | CD1 | A | 88 | 233 | 5 | 82 | 14 |
| LEU | CD2 | A | 88 | 254 | 10 | 70 | 13 |
| LEU | C | A | 88 | 275 | −8 | 106 | 9 |
| LEU | O | A | 88 | 273 | −17 | 113 | 11 |
| ASN | N | A | 89 | 282 | 3 | 109 | 9 |
| ASN | CA | A | 89 | 287 | 5 | 123 | 7 |
| ASN | CB | A | 89 | 301 | 12 | 122 | 9 |
| ASN | CG | A | 89 | 312 | 3 | 117 | 10 |
| ASN | OD1 | A | 89 | 312 | −9 | 120 | 11 |
| ASN | ND2 | A | 89 | 321 | 8 | 110 | 12 |
| ASN | C | A | 89 | 277 | 12 | 131 | 7 |
| ASN | O | A | 89 | 272 | 23 | 127 | 8 |
| ILE | N | A | 90 | 274 | 7 | 142 | 6 |
| ILE | CA | A | 90 | 264 | 13 | 151 | 7 |
| ILE | CB | A | 90 | 252 | 2 | 152 | 8 |
| ILE | CG2 | A | 90 | 240 | 9 | 160 | 8 |
| ILE | CG1 | A | 90 | 248 | −2 | 139 | 7 |
| ILE | CD1 | A | 90 | 242 | 8 | 129 | 6 |
| ILE | C | A | 90 | 268 | 17 | 165 | 6 |
| ILE | O | A | 90 | 274 | 9 | 172 | 7 |
| LEU | N | A | 91 | 266 | 30 | 168 | 7 |
| LEU | CA | A | 91 | 270 | 35 | 181 | 9 |
| LEU | CB | A | 91 | 269 | 50 | 182 | 11 |

TABLE 2-continued

Structure Coordinates for BACE complexed to Inhibitor

| | | | | | | |
|---|---|---|---|---|---|---|
| LEU | CG | A | 91 | 272 | 57 | 195 | 11 |
| LEU | CD1 | A | 91 | 276 | 71 | 192 | 12 |
| LEU | CD2 | A | 91 | 260 | 57 | 204 | 10 |
| LEU | C | A | 91 | 262 | 28 | 192 | 9 |
| LEU | O | A | 91 | 249 | 28 | 191 | 8 |
| VAL | N | A | 92 | 268 | 23 | 203 | 7 |
| VAL | CA | A | 92 | 261 | 17 | 214 | 7 |
| VAL | CB | A | 92 | 270 | 7 | 221 | 10 |
| VAL | CG1 | A | 92 | 263 | 1 | 233 | 12 |
| VAL | CG2 | A | 92 | 275 | −4 | 212 | 11 |
| VAL | C | A | 92 | 257 | 28 | 224 | 9 |
| VAL | O | A | 92 | 265 | 35 | 230 | 9 |
| ASP | N | A | 93 | 244 | 30 | 225 | 7 |
| ASP | CA | A | 93 | 238 | 40 | 234 | 8 |
| ASP | CB | A | 93 | 231 | 50 | 225 | 9 |
| ASP | CG | A | 93 | 227 | 63 | 232 | 10 |
| ASP | OD1 | A | 93 | 235 | 68 | 240 | 9 |
| ASP | OD2 | A | 93 | 215 | 68 | 230 | 8 |
| ASP | C | A | 93 | 228 | 35 | 244 | 8 |
| ASP | O | A | 93 | 217 | 33 | 242 | 8 |
| THR | N | A | 94 | 233 | 34 | 257 | 6 |
| THR | CA | A | 94 | 224 | 29 | 267 | 8 |
| THR | CB | A | 94 | 232 | 23 | 279 | 7 |
| THR | OG1 | A | 94 | 241 | 33 | 284 | 7 |
| THR | CG2 | A | 94 | 240 | 11 | 275 | 6 |
| THR | C | A | 94 | 215 | 40 | 272 | 8 |
| THR | O | A | 94 | 207 | 38 | 281 | 7 |
| GLY | N | A | 95 | 217 | 52 | 266 | 7 |
| GLY | CA | A | 95 | 209 | 63 | 270 | 7 |
| GLY | C | A | 95 | 196 | 66 | 262 | 7 |
| GLY | O | A | 95 | 189 | 75 | 264 | 7 |
| SER | N | A | 96 | 193 | 57 | 252 | 8 |
| SER | CA | A | 96 | 181 | 58 | 244 | 7 |
| SER | CB | A | 96 | 184 | 66 | 231 | 8 |
| SER | OG | A | 96 | 192 | 59 | 222 | 8 |
| SER | C | A | 96 | 176 | 45 | 240 | 7 |
| SER | O | A | 96 | 182 | 34 | 244 | 7 |
| SER | N | A | 97 | 165 | 44 | 234 | 8 |
| SER | CA | A | 97 | 159 | 31 | 231 | 8 |
| SER | CB | A | 97 | 146 | 29 | 240 | 11 |
| SER | OG | A | 97 | 150 | 32 | 253 | 7 |
| SER | C | A | 97 | 155 | 28 | 216 | 8 |
| SER | O | A | 97 | 147 | 19 | 214 | 8 |
| ASN | N | A | 98 | 159 | 37 | 207 | 8 |
| ASN | CA | A | 98 | 156 | 35 | 193 | 8 |
| ASN | CB | A | 98 | 152 | 48 | 187 | 8 |
| ASN | CG | A | 98 | 137 | 51 | 190 | 10 |
| ASN | OD1 | A | 98 | 134 | 56 | 201 | 9 |
| ASN | ND2 | A | 98 | 128 | 48 | 181 | 8 |
| ASN | C | A | 98 | 168 | 30 | 185 | 7 |
| ASN | O | A | 98 | 180 | 34 | 187 | 8 |
| PHE | N | A | 99 | 166 | 20 | 176 | 7 |
| PHE | CA | A | 99 | 176 | 15 | 168 | 8 |
| PHE | CB | A | 99 | 174 | 0 | 165 | 8 |
| PHE | CG | A | 99 | 184 | −6 | 155 | 10 |
| PHE | CD1 | A | 99 | 179 | −16 | 146 | 11 |
| PHE | CD2 | A | 99 | 197 | −2 | 155 | 8 |
| PHE | CE1 | A | 99 | 188 | −22 | 137 | 10 |
| PHE | CE2 | A | 99 | 206 | −8 | 146 | 10 |
| PHE | CZ | A | 99 | 202 | −18 | 137 | 11 |
| PHE | C | A | 99 | 174 | 23 | 155 | 8 |
| PHE | O | A | 99 | 163 | 22 | 149 | 8 |
| ALA | N | A | 100 | 184 | 30 | 150 | 7 |
| ALA | CA | A | 100 | 182 | 38 | 138 | 8 |
| ALA | CB | A | 100 | 178 | 53 | 142 | 9 |
| ALA | C | A | 100 | 195 | 39 | 130 | 8 |
| ALA | O | A | 100 | 206 | 38 | 136 | 11 |
| VAL | N | A | 101 | 193 | 40 | 117 | 8 |
| VAL | CA | A | 101 | 205 | 40 | 108 | 9 |
| VAL | CB | A | 101 | 207 | 26 | 102 | 9 |
| VAL | CG1 | A | 101 | 210 | 16 | 112 | 11 |
| VAL | CG2 | A | 101 | 195 | 22 | 94 | 9 |
| VAL | C | A | 101 | 203 | 50 | 97 | 9 |
| VAL | O | A | 101 | 192 | 53 | 93 | 10 |
| GLY | N | A | 102 | 214 | 56 | 92 | 10 |
| GLY | CA | A | 102 | 214 | 65 | 81 | 12 |
| GLY | C | A | 102 | 208 | 58 | 70 | 13 |
| GLY | O | A | 102 | 211 | 46 | 68 | 10 |
| ALA | N | A | 103 | 198 | 64 | 63 | 12 |
| ALA | CA | A | 103 | 192 | 57 | 52 | 14 |
| ALA | CB | A | 103 | 178 | 52 | 56 | 12 |
| ALA | C | A | 103 | 191 | 66 | 40 | 16 |
| ALA | O | A | 103 | 183 | 64 | 30 | 17 |
| ALA | N | A | 104 | 198 | 77 | 40 | 16 |
| ALA | CA | A | 104 | 199 | 87 | 29 | 19 |
| ALA | CB | A | 104 | 188 | 97 | 31 | 18 |
| ALA | C | A | 104 | 212 | 93 | 29 | 23 |
| ALA | O | A | 104 | 219 | 94 | 39 | 24 |
| PRO | N | A | 105 | 217 | 98 | 17 | 23 |
| PRO | CD | A | 105 | 211 | 97 | 4 | 25 |
| PRO | CA | A | 105 | 230 | 104 | 16 | 23 |
| PRO | CB | A | 105 | 230 | 110 | 2 | 24 |
| PRO | CG | A | 105 | 223 | 99 | −5 | 23 |
| PRO | C | A | 105 | 232 | 115 | 27 | 21 |
| PRO | O | A | 105 | 223 | 123 | 30 | 23 |
| HIS | N | A | 106 | 244 | 116 | 32 | 21 |
| HIS | CA | A | 106 | 248 | 126 | 42 | 21 |
| HIS | CB | A | 106 | 244 | 122 | 56 | 17 |
| HIS | CG | A | 106 | 247 | 132 | 67 | 16 |
| HIS | CD2 | A | 106 | 238 | 140 | 73 | 16 |
| HIS | ND1 | A | 106 | 260 | 135 | 71 | 14 |
| HIS | CE1 | A | 106 | 259 | 145 | 80 | 15 |
| HIS | NE2 | A | 106 | 246 | 148 | 82 | 18 |
| HIS | C | A | 106 | 263 | 128 | 41 | 19 |
| HIS | O | A | 106 | 271 | 119 | 39 | 19 |
| PRO | N | A | 107 | 267 | 141 | 42 | 21 |
| PRO | CD | A | 107 | 259 | 153 | 43 | 21 |
| PRO | CA | A | 107 | 282 | 145 | 41 | 21 |
| PRO | CB | A | 107 | 282 | 160 | 45 | 22 |
| PRO | CG | A | 107 | 269 | 164 | 39 | 22 |
| PRO | C | A | 107 | 291 | 137 | 49 | 20 |
| PRO | O | A | 107 | 303 | 134 | 45 | 22 |
| PHE | N | A | 108 | 287 | 132 | 61 | 20 |
| PHE | CA | A | 108 | 295 | 125 | 70 | 20 |
| PHE | CB | A | 108 | 292 | 129 | 84 | 19 |
| PHE | CG | A | 108 | 295 | 144 | 87 | 20 |
| PHE | CD1 | A | 108 | 291 | 150 | 99 | 19 |
| PHE | CD2 | A | 108 | 303 | 151 | 78 | 21 |
| PHE | CE1 | A | 108 | 294 | 163 | 101 | 21 |
| PHE | CE2 | A | 108 | 305 | 164 | 80 | 23 |
| PHE | CZ | A | 108 | 301 | 170 | 92 | 21 |
| PHE | C | A | 108 | 293 | 109 | 69 | 19 |
| PHE | O | A | 108 | 300 | 102 | 76 | 18 |
| LEU | N | A | 109 | 285 | 105 | 60 | 18 |
| LEU | CA | A | 109 | 282 | 90 | 58 | 18 |
| LEU | CB | A | 109 | 267 | 87 | 58 | 16 |
| LEU | CG | A | 109 | 259 | 90 | 71 | 16 |
| LEU | CD1 | A | 109 | 245 | 87 | 69 | 15 |
| LEU | CD2 | A | 109 | 265 | 82 | 83 | 16 |
| LEU | C | A | 109 | 289 | 85 | 46 | 20 |
| LEU | O | A | 109 | 287 | 91 | 35 | 20 |
| HIS | N | A | 110 | 296 | 74 | 47 | 21 |
| HIS | CA | A | 110 | 302 | 68 | 36 | 24 |
| HIS | CB | A | 110 | 316 | 62 | 40 | 31 |
| HIS | CG | A | 110 | 326 | 72 | 45 | 38 |
| HIS | CD2 | A | 110 | 332 | 73 | 57 | 40 |
| HIS | ND1 | A | 110 | 329 | 83 | 38 | 41 |
| HIS | CE1 | A | 110 | 338 | 91 | 45 | 41 |
| HIS | NE2 | A | 110 | 340 | 85 | 56 | 42 |
| HIS | C | A | 110 | 294 | 56 | 30 | 21 |
| HIS | O | A | 110 | 295 | 52 | 19 | 21 |
| ARG | N | A | 111 | 284 | 52 | 38 | 18 |
| ARG | CA | A | 111 | 274 | 42 | 35 | 17 |
| ARG | CB | A | 111 | 280 | 28 | 37 | 17 |
| ARG | CG | A | 111 | 284 | 25 | 52 | 16 |
| ARG | CD | A | 111 | 291 | 12 | 53 | 18 |
| ARG | NE | A | 111 | 296 | 10 | 67 | 16 |
| ARG | CZ | A | 111 | 302 | −1 | 71 | 16 |
| ARG | NH1 | A | 111 | 306 | −11 | 63 | 16 |
| ARG | NH2 | A | 111 | 306 | −2 | 84 | 16 |
| ARG | C | A | 111 | 262 | 44 | 43 | 16 |
| ARG | O | A | 111 | 262 | 51 | 53 | 13 |
| TYR | N | A | 112 | 251 | 38 | 38 | 14 |
| TYR | CA | A | 112 | 238 | 39 | 45 | 14 |

TABLE 2-continued

Structure Coordinates for BACE complexed to Inhibitor

| | | | | | | | |
|---|---|---|---|---|---|---|---|
| TYR | CB | A | 112 | 232 | 52 | 43 | 16 |
| TYR | CG | A | 112 | 229 | 56 | 28 | 20 |
| TYR | CD1 | A | 112 | 218 | 50 | 21 | 21 |
| TYR | CE1 | A | 112 | 216 | 53 | 8 | 24 |
| TYR | CD2 | A | 112 | 238 | 65 | 21 | 23 |
| TYR | CE2 | A | 112 | 235 | 68 | 8 | 25 |
| TYR | CZ | A | 112 | 224 | 62 | 1 | 26 |
| TYR | OH | A | 112 | 222 | 65 | -12 | 30 |
| TYR | C | A | 112 | 229 | 27 | 41 | 15 |
| TYR | O | A | 112 | 231 | 20 | 31 | 15 |
| TYR | N | A | 113 | 218 | 26 | 49 | 11 |
| TYR | CA | A | 113 | 208 | 15 | 47 | 10 |
| TYR | CB | A | 113 | 199 | 15 | 60 | 9 |
| TYR | CG | A | 113 | 188 | 5 | 60 | 9 |
| TYR | CD1 | A | 113 | 189 | -8 | 54 | 9 |
| TYR | CE1 | A | 113 | 178 | -17 | 55 | 9 |
| TYR | CD2 | A | 113 | 176 | 8 | 67 | 11 |
| TYR | CE2 | A | 113 | 166 | -1 | 68 | 10 |
| TYR | CZ | A | 113 | 167 | -13 | 62 | 9 |
| TYR | OH | A | 113 | 157 | -22 | 63 | 10 |
| TYR | C | A | 113 | 200 | 18 | 35 | 9 |
| TYR | O | A | 113 | 194 | 29 | 34 | 9 |
| GLN | N | A | 114 | 200 | 8 | 26 | 11 |
| GLN | CA | A | 114 | 192 | 10 | 13 | 12 |
| GLN | CB | A | 114 | 202 | 7 | 1 | 14 |
| GLN | CG | A | 114 | 212 | 18 | -1 | 17 |
| GLN | CD | A | 114 | 221 | 15 | -13 | 21 |
| GLN | OE1 | A | 114 | 230 | 7 | -12 | 25 |
| GLN | NE2 | A | 114 | 219 | 23 | -23 | 23 |
| GLN | C | A | 114 | 181 | 0 | 14 | 11 |
| GLN | O | A | 114 | 183 | -12 | 9 | 11 |
| ARG | N | A | 115 | 170 | 4 | 19 | 12 |
| ARG | CA | A | 115 | 158 | -4 | 20 | 10 |
| ARG | CB | A | 115 | 146 | 4 | 26 | 10 |
| ARG | CG | A | 115 | 149 | 8 | 40 | 9 |
| ARG | CD | A | 115 | 139 | 19 | 45 | 9 |
| ARG | NE | A | 115 | 142 | 32 | 38 | 11 |
| ARG | CZ | A | 115 | 135 | 43 | 39 | 12 |
| ARG | NH1 | A | 115 | 124 | 43 | 47 | 12 |
| ARG | NH2 | A | 115 | 139 | 54 | 33 | 15 |
| ARG | C | A | 115 | 153 | -11 | 7 | 11 |
| ARG | O | A | 115 | 148 | -23 | 8 | 10 |
| GLN | N | A | 116 | 155 | -4 | -4 | 13 |
| GLN | CA | A | 116 | 150 | -10 | -17 | 15 |
| GLN | CB | A | 116 | 151 | 1 | -28 | 21 |
| GLN | CG | A | 116 | 141 | 12 | -26 | 28 |
| GLN | CD | A | 116 | 141 | 22 | -37 | 33 |
| GLN | OE1 | A | 116 | 138 | 19 | -49 | 35 |
| GLN | NE2 | A | 116 | 145 | 35 | -34 | 34 |
| GLN | C | A | 116 | 158 | -22 | -21 | 15 |
| GLN | O | A | 116 | 154 | -30 | -30 | 12 |
| LEU | N | A | 117 | 170 | -24 | -15 | 11 |
| LEU | CA | A | 117 | 179 | -35 | -18 | 12 |
| LEU | CB | A | 117 | 193 | -31 | -19 | 13 |
| LEU | CG | A | 117 | 196 | -20 | -29 | 15 |
| LEU | CD1 | A | 117 | 211 | -17 | -29 | 17 |
| LEU | CD2 | A | 117 | 191 | -24 | -43 | 19 |
| LEU | C | A | 117 | 177 | -47 | -8 | 11 |
| LEU | O | A | 117 | 184 | -57 | -9 | 11 |
| SER | N | A | 118 | 168 | -46 | 1 | 10 |
| SER | CA | A | 118 | 166 | -56 | 11 | 10 |
| SER | CB | A | 118 | 165 | -50 | 25 | 9 |
| SER | OG | A | 118 | 162 | -61 | 35 | 7 |
| SER | C | A | 118 | 152 | -63 | 8 | 9 |
| SER | O | A | 118 | 142 | -57 | 9 | 11 |
| SER | N | A | 119 | 153 | -76 | 6 | 11 |
| SER | CA | A | 119 | 141 | -84 | 3 | 11 |
| SER | CB | A | 119 | 145 | -97 | -3 | 12 |
| SER | OG | A | 119 | 152 | -105 | 6 | 13 |
| SER | C | A | 119 | 132 | -86 | 15 | 12 |
| SER | O | A | 119 | 120 | -89 | 14 | 11 |
| THR | N | A | 120 | 138 | -84 | 27 | 13 |
| THR | CA | A | 120 | 131 | -86 | 39 | 10 |
| THR | CB | A | 120 | 139 | -94 | 49 | 12 |
| THR | OG1 | A | 120 | 153 | -89 | 49 | 12 |
| THR | CG2 | A | 120 | 140 | -109 | 45 | 12 |
| THR | C | A | 120 | 126 | -73 | 46 | 10 |
| THR | O | A | 120 | 120 | -74 | 57 | 11 |
| TYR | N | A | 121 | 128 | -62 | 39 | 8 |
| TYR | CA | A | 121 | 124 | -49 | 45 | 9 |
| TYR | CB | A | 121 | 129 | -38 | 36 | 10 |
| TYR | CG | A | 121 | 122 | -25 | 38 | 11 |
| TYR | CD1 | A | 121 | 124 | -18 | 50 | 12 |
| TYR | CE1 | A | 121 | 117 | -6 | 53 | 11 |
| TYR | CD2 | A | 121 | 113 | -19 | 29 | 12 |
| TYR | CE2 | A | 121 | 106 | -8 | 31 | 13 |
| TYR | CZ | A | 121 | 108 | -1 | 43 | 13 |
| TYR | OH | A | 121 | 101 | 11 | 46 | 11 |
| TYR | C | A | 121 | 109 | -49 | 45 | 11 |
| TYR | O | A | 121 | 102 | -53 | 36 | 11 |
| ARG | N | A | 122 | 103 | -43 | 56 | 9 |
| ARG | CA | A | 122 | 89 | -42 | 58 | 11 |
| ARG | CB | A | 122 | 83 | -51 | 68 | 9 |
| ARG | CG | A | 122 | 83 | -66 | 64 | 9 |
| ARG | CD | A | 122 | 78 | -74 | 76 | 10 |
| ARG | NE | A | 122 | 77 | -88 | 73 | 10 |
| ARG | CZ | A | 122 | 74 | -98 | 82 | 9 |
| ARG | NH1 | A | 122 | 72 | -94 | 94 | 10 |
| ARG | NH2 | A | 122 | 74 | -111 | 78 | 11 |
| ARG | C | A | 122 | 86 | -27 | 62 | 10 |
| ARG | O | A | 122 | 92 | -22 | 72 | 11 |
| ASP | N | A | 123 | 78 | -20 | 55 | 8 |
| ASP | CA | A | 123 | 75 | -6 | 57 | 11 |
| ASP | CB | A | 123 | 70 | 0 | 44 | 12 |
| ASP | CG | A | 123 | 68 | 15 | 46 | 13 |
| ASP | OD1 | A | 123 | 71 | 21 | 57 | 15 |
| ASP | OD2 | A | 123 | 63 | 22 | 36 | 15 |
| ASP | C | A | 123 | 64 | -5 | 68 | 11 |
| ASP | O | A | 123 | 53 | -12 | 67 | 11 |
| LEU | N | A | 124 | 66 | 3 | 78 | 10 |
| LEU | CA | A | 124 | 56 | 5 | 89 | 11 |
| LEU | CB | A | 124 | 63 | 6 | 102 | 12 |
| LEU | CG | A | 124 | 69 | -6 | 108 | 13 |
| LEU | CD1 | A | 124 | 76 | -3 | 121 | 14 |
| LEU | CD2 | A | 124 | 58 | -17 | 110 | 14 |
| LEU | C | A | 124 | 47 | 17 | 86 | 9 |
| LEU | O | A | 124 | 38 | 20 | 93 | 12 |
| ARG | N | A | 125 | 50 | 24 | 75 | 9 |
| ARG | CA | A | 125 | 42 | 36 | 71 | 11 |
| ARG | CB | A | 125 | 29 | 31 | 66 | 11 |
| ARG | CG | A | 125 | 29 | 22 | 54 | 15 |
| ARG | CD | A | 125 | 15 | 16 | 51 | 17 |
| ARG | NE | A | 125 | 15 | 5 | 41 | 21 |
| ARG | CZ | A | 125 | 6 | -4 | 39 | 23 |
| ARG | NH1 | A | 125 | -5 | -4 | 48 | 24 |
| ARG | NH2 | A | 125 | 7 | -13 | 30 | 23 |
| ARG | C | A | 125 | 40 | 46 | 82 | 14 |
| ARG | O | A | 125 | 29 | 51 | 84 | 12 |
| LYS | N | A | 126 | 51 | 49 | 89 | 12 |
| LYS | CA | A | 126 | 50 | 58 | 100 | 16 |
| LYS | CB | A | 126 | 47 | 50 | 113 | 20 |
| LYS | CG | A | 126 | 44 | 58 | 125 | 29 |
| LYS | CD | A | 126 | 45 | 50 | 138 | 32 |
| LYS | CE | A | 126 | 37 | 37 | 138 | 35 |
| LYS | NZ | A | 126 | 39 | 29 | 150 | 37 |
| LYS | C | A | 126 | 63 | 65 | 102 | 15 |
| LYS | O | A | 126 | 74 | 60 | 101 | 13 |
| GLY | N | A | 127 | 62 | 78 | 106 | 13 |
| GLY | CA | A | 127 | 74 | 86 | 108 | 10 |
| GLY | C | A | 127 | 79 | 85 | 122 | 13 |
| GLY | O | A | 127 | 71 | 80 | 131 | 13 |
| VAL | N | A | 128 | 91 | 90 | 125 | 12 |
| VAL | CA | A | 128 | 96 | 90 | 138 | 12 |
| VAL | CB | A | 128 | 103 | 76 | 141 | 13 |
| VAL | CG1 | A | 128 | 114 | 73 | 131 | 13 |
| VAL | CG2 | A | 128 | 108 | 76 | 156 | 14 |
| VAL | C | A | 128 | 106 | 101 | 140 | 11 |
| VAL | O | A | 128 | 114 | 104 | 131 | 11 |
| TYR | N | A | 129 | 106 | 107 | 152 | 13 |
| TYR | CA | A | 129 | 115 | 118 | 155 | 13 |
| TYR | CB | A | 129 | 107 | 131 | 155 | 14 |
| TYR | CG | A | 129 | 115 | 143 | 162 | 17 |
| TYR | CD1 | A | 129 | 126 | 148 | 156 | 19 |
| TYR | CE1 | A | 129 | 133 | 159 | 161 | 19 |

TABLE 2-continued

Structure Coordinates for BACE complexed to Inhibitor

| | | | | | | | |
|---|---|---|---|---|---|---|---|
| TYR | CD2 | A | 129 | 110 | 149 | 173 | 17 |
| TYR | CE2 | A | 129 | 117 | 160 | 179 | 18 |
| TYR | CZ | A | 129 | 128 | 165 | 173 | 20 |
| TYR | OH | A | 129 | 135 | 176 | 178 | 21 |
| TYR | C | A | 129 | 121 | 116 | 169 | 10 |
| TYR | O | A | 129 | 114 | 113 | 178 | 10 |
| VAL | N | A | 130 | 134 | 116 | 169 | 10 |
| VAL | CA | A | 130 | 141 | 114 | 182 | 9 |
| VAL | CB | A | 130 | 149 | 101 | 182 | 10 |
| VAL | CG1 | A | 130 | 157 | 100 | 195 | 10 |
| VAL | CG2 | A | 130 | 139 | 89 | 181 | 12 |
| VAL | C | A | 130 | 151 | 125 | 185 | 8 |
| VAL | O | A | 130 | 161 | 127 | 178 | 9 |
| PRO | N | A | 131 | 149 | 133 | 196 | 9 |
| PRO | CD | A | 131 | 135 | 135 | 202 | 11 |
| PRO | CA | A | 131 | 158 | 144 | 200 | 10 |
| PRO | CB | A | 131 | 148 | 155 | 204 | 10 |
| PRO | CG | A | 131 | 137 | 147 | 211 | 13 |
| PRO | C | A | 131 | 166 | 139 | 212 | 10 |
| PRO | O | A | 131 | 161 | 132 | 220 | 9 |
| TYR | N | A | 132 | 179 | 142 | 212 | 9 |
| TYR | CA | A | 132 | 188 | 138 | 222 | 8 |
| TYR | CB | A | 132 | 200 | 131 | 217 | 7 |
| TYR | CG | A | 132 | 197 | 118 | 209 | 8 |
| TYR | CD1 | A | 132 | 195 | 106 | 215 | 7 |
| TYR | CE1 | A | 132 | 192 | 95 | 208 | 7 |
| TYR | CD2 | A | 132 | 196 | 119 | 195 | 12 |
| TYR | CE2 | A | 132 | 193 | 107 | 188 | 12 |
| TYR | CZ | A | 132 | 192 | 95 | 194 | 10 |
| TYR | OH | A | 132 | 189 | 84 | 187 | 9 |
| TYR | C | A | 132 | 192 | 151 | 229 | 9 |
| TYR | O | A | 132 | 190 | 162 | 225 | 11 |
| THR | N | A | 133 | 200 | 149 | 240 | 10 |
| THR | CA | A | 133 | 205 | 161 | 248 | 9 |
| THR | CB | A | 133 | 214 | 157 | 259 | 8 |
| THR | OG1 | A | 133 | 207 | 150 | 269 | 9 |
| THR | CG2 | A | 133 | 221 | 169 | 265 | 10 |
| THR | C | A | 133 | 212 | 170 | 238 | 12 |
| THR | O | A | 133 | 211 | 182 | 238 | 12 |
| GLN | N | A | 134 | 219 | 164 | 229 | 10 |
| GLN | CA | A | 134 | 227 | 171 | 218 | 12 |
| GLN | CB | A | 134 | 241 | 172 | 221 | 18 |
| GLN | CG | A | 134 | 244 | 182 | 233 | 28 |
| GLN | CD | A | 134 | 241 | 196 | 230 | 33 |
| GLN | OE1 | A | 134 | 242 | 205 | 238 | 38 |
| GLN | NE2 | A | 134 | 236 | 199 | 218 | 36 |
| GLN | C | A | 134 | 225 | 162 | 205 | 12 |
| GLN | O | A | 134 | 229 | 151 | 205 | 12 |
| GLY | N | A | 135 | 219 | 168 | 195 | 12 |
| GLY | CA | A | 135 | 217 | 161 | 183 | 11 |
| GLY | C | A | 135 | 202 | 156 | 181 | 11 |
| GLY | O | A | 135 | 196 | 153 | 192 | 10 |
| LYS | N | A | 136 | 198 | 154 | 169 | 10 |
| LYS | CA | A | 136 | 184 | 149 | 167 | 11 |
| LYS | CB | A | 136 | 174 | 160 | 169 | 13 |
| LYS | CG | A | 136 | 175 | 172 | 160 | 16 |
| LYS | CD | A | 136 | 166 | 183 | 163 | 19 |
| LYS | CE | A | 136 | 169 | 189 | 177 | 25 |
| LYS | NZ | A | 136 | 160 | 201 | 180 | 31 |
| LYS | C | A | 136 | 183 | 144 | 152 | 10 |
| LYS | O | A | 136 | 191 | 147 | 144 | 11 |
| TRP | N | A | 137 | 173 | 136 | 150 | 11 |
| TRP | CA | A | 137 | 170 | 131 | 136 | 10 |
| TRP | CB | A | 137 | 179 | 119 | 133 | 10 |
| TRP | CG | A | 137 | 178 | 107 | 143 | 9 |
| TRP | CD2 | A | 137 | 168 | 97 | 144 | 9 |
| TRP | CE2 | A | 137 | 171 | 88 | 154 | 8 |
| TRP | CE3 | A | 137 | 156 | 96 | 137 | 10 |
| TRP | CD1 | A | 137 | 188 | 103 | 152 | 9 |
| TRP | NE1 | A | 137 | 183 | 92 | 159 | 7 |
| TRP | CZ2 | A | 137 | 163 | 78 | 157 | 8 |
| TRP | CZ3 | A | 137 | 147 | 85 | 140 | 9 |
| TRP | CH2 | A | 137 | 151 | 76 | 151 | 9 |
| TRP | C | A | 137 | 156 | 127 | 134 | 10 |
| TRP | O | A | 137 | 148 | 125 | 144 | 11 |
| GLU | N | A | 138 | 152 | 126 | 122 | 11 |
| GLU | CA | A | 138 | 138 | 123 | 118 | 11 |
| GLU | CB | A | 138 | 131 | 134 | 110 | 16 |
| GLU | CG | A | 138 | 129 | 146 | 119 | 27 |
| GLU | CD | A | 138 | 119 | 156 | 112 | 31 |
| GLU | OE1 | A | 138 | 123 | 160 | 101 | 34 |
| GLU | OE2 | A | 138 | 109 | 159 | 117 | 36 |
| GLU | C | A | 138 | 140 | 111 | 108 | 9 |
| GLU | O | A | 138 | 150 | 110 | 101 | 10 |
| GLY | N | A | 139 | 130 | 102 | 108 | 10 |
| GLY | CA | A | 139 | 131 | 90 | 100 | 11 |
| GLY | C | A | 139 | 118 | 84 | 97 | 12 |
| GLY | O | A | 139 | 107 | 89 | 100 | 12 |
| GLU | N | A | 140 | 119 | 72 | 90 | 12 |
| GLU | CA | A | 140 | 107 | 64 | 86 | 13 |
| GLU | CB | A | 140 | 107 | 64 | 70 | 12 |
| GLU | CG | A | 140 | 105 | 77 | 64 | 14 |
| GLU | CD | A | 140 | 107 | 77 | 49 | 16 |
| GLU | OE1 | A | 140 | 105 | 88 | 43 | 20 |
| GLU | OE2 | A | 140 | 111 | 67 | 43 | 15 |
| GLU | C | A | 140 | 109 | 51 | 92 | 11 |
| GLU | O | A | 140 | 119 | 44 | 91 | 10 |
| LEU | N | A | 141 | 99 | 46 | 99 | 9 |
| LEU | CA | A | 141 | 99 | 33 | 105 | 10 |
| LEU | CB | A | 141 | 89 | 33 | 117 | 11 |
| LEU | CG | A | 141 | 92 | 42 | 129 | 12 |
| LEU | CD1 | A | 141 | 81 | 42 | 139 | 12 |
| LEU | CD2 | A | 141 | 105 | 36 | 136 | 13 |
| LEU | C | A | 141 | 96 | 21 | 96 | 11 |
| LEU | O | A | 141 | 89 | 22 | 87 | 11 |
| GLY | N | A | 142 | 102 | 10 | 100 | 10 |
| GLY | CA | A | 142 | 101 | −3 | 93 | 11 |
| GLY | C | A | 142 | 107 | −14 | 101 | 11 |
| GLY | O | A | 142 | 112 | −11 | 112 | 9 |
| THR | N | A | 143 | 108 | −26 | 95 | 9 |
| THR | CA | A | 143 | 115 | −37 | 102 | 8 |
| THR | CB | A | 143 | 105 | −47 | 109 | 10 |
| THR | OG1 | A | 143 | 98 | −54 | 99 | 9 |
| THR | CG2 | A | 143 | 94 | −39 | 118 | 10 |
| THR | C | A | 143 | 123 | −44 | 92 | 9 |
| THR | O | A | 143 | 121 | −43 | 80 | 9 |
| ASP | N | A | 144 | 133 | −52 | 97 | 9 |
| ASP | CA | A | 144 | 141 | −60 | 88 | 9 |
| ASP | CB | A | 144 | 151 | −51 | 81 | 7 |
| ASP | CG | A | 144 | 154 | −56 | 67 | 8 |
| ASP | OD1 | A | 144 | 154 | −68 | 65 | 9 |
| ASP | OD2 | A | 144 | 157 | −48 | 58 | 10 |
| ASP | C | A | 144 | 149 | −70 | 97 | 10 |
| ASP | O | A | 144 | 148 | −69 | 109 | 8 |
| LEU | N | A | 145 | 156 | −78 | 90 | 7 |
| LEU | CA | A | 145 | 164 | −88 | 98 | 8 |
| LEU | CB | A | 145 | 166 | −101 | 89 | 7 |
| LEU | CG | A | 145 | 154 | −108 | 84 | 7 |
| LEU | CD1 | A | 145 | 157 | −121 | 77 | 10 |
| LEU | CD2 | A | 145 | 145 | −111 | 96 | 9 |
| LEU | C | A | 145 | 177 | −82 | 102 | 8 |
| LEU | O | A | 145 | 184 | −76 | 93 | 11 |
| VAL | N | A | 146 | 181 | −83 | 114 | 9 |
| VAL | CA | A | 146 | 193 | −77 | 120 | 10 |
| VAL | CB | A | 146 | 189 | −66 | 130 | 10 |
| VAL | CG1 | A | 146 | 202 | −59 | 134 | 10 |
| VAL | CG2 | A | 146 | 179 | −57 | 123 | 8 |
| VAL | C | A | 146 | 202 | −88 | 126 | 11 |
| VAL | O | A | 146 | 197 | −97 | 133 | 11 |
| SER | N | A | 147 | 215 | −86 | 125 | 11 |
| SER | CA | A | 147 | 225 | −95 | 131 | 12 |
| SER | CB | A | 147 | 229 | −105 | 121 | 14 |
| SER | OG | A | 147 | 218 | −113 | 116 | 21 |
| SER | C | A | 147 | 237 | −87 | 136 | 12 |
| SER | O | A | 147 | 238 | −75 | 132 | 11 |
| ILE | N | A | 148 | 245 | −93 | 144 | 12 |
| ILE | CA | A | 148 | 257 | −87 | 150 | 10 |
| ILE | CB | A | 148 | 255 | −85 | 165 | 9 |
| ILE | CG2 | A | 148 | 268 | −78 | 171 | 11 |
| ILE | CG1 | A | 148 | 243 | −76 | 168 | 10 |
| ILE | CD1 | A | 148 | 241 | −74 | 183 | 10 |
| ILE | C | A | 148 | 268 | −97 | 147 | 10 |
| ILE | O | A | 148 | 268 | −107 | 155 | 11 |
| PRO | N | A | 149 | 276 | −95 | 137 | 9 |

TABLE 2-continued

Structure Coordinates for BACE complexed to Inhibitor

| | | | | | | | |
|---|---|---|---|---|---|---|---|
| PRO | CD | A | 149 | 275 | −84 | 128 | 8 |
| PRO | CA | A | 149 | 286 | −104 | 133 | 12 |
| PRO | CB | A | 149 | 295 | −96 | 123 | 9 |
| PRO | CG | A | 149 | 284 | −88 | 116 | 11 |
| PRO | C | A | 149 | 295 | −109 | 145 | 13 |
| PRO | O | A | 149 | 297 | −121 | 146 | 12 |
| HIS | N | A | 150 | 299 | −100 | 153 | 11 |
| HIS | CA | A | 150 | 307 | −104 | 165 | 12 |
| HIS | CB | A | 150 | 319 | −95 | 166 | 13 |
| HIS | CG | A | 150 | 328 | −95 | 153 | 16 |
| HIS | CD2 | A | 150 | 330 | −86 | 144 | 18 |
| HIS | ND1 | A | 150 | 335 | −106 | 150 | 18 |
| HIS | CE1 | A | 150 | 341 | −104 | 138 | 19 |
| HIS | NE2 | A | 150 | 338 | −91 | 134 | 21 |
| HIS | C | A | 150 | 299 | −103 | 177 | 15 |
| HIS | O | A | 150 | 302 | −96 | 187 | 16 |
| GLY | N | A | 151 | 288 | −111 | 177 | 18 |
| GLY | CA | A | 151 | 279 | −112 | 188 | 17 |
| GLY | C | A | 151 | 272 | −125 | 188 | 18 |
| GLY | O | A | 151 | 278 | −135 | 183 | 21 |
| PRO | N | A | 152 | 260 | −127 | 194 | 17 |
| PRO | CD | A | 152 | 251 | −117 | 199 | 19 |
| PRO | CA | A | 152 | 254 | −140 | 194 | 19 |
| PRO | CB | A | 152 | 241 | −138 | 202 | 19 |
| PRO | CG | A | 152 | 238 | −123 | 198 | 21 |
| PRO | C | A | 152 | 251 | −144 | 180 | 19 |
| PRO | O | A | 152 | 248 | −136 | 171 | 22 |
| ASN | N | A | 153 | 253 | −157 | 177 | 20 |
| ASN | CA | A | 153 | 250 | −162 | 164 | 17 |
| ASN | CB | A | 153 | 258 | −175 | 162 | 22 |
| ASN | CG | A | 153 | 273 | −173 | 163 | 23 |
| ASN | OD1 | A | 153 | 279 | −165 | 156 | 24 |
| ASN | ND2 | A | 153 | 279 | −181 | 172 | 24 |
| ASN | C | A | 153 | 235 | −164 | 161 | 17 |
| ASN | O | A | 153 | 230 | −175 | 160 | 16 |
| VAL | N | A | 154 | 228 | −153 | 160 | 15 |
| VAL | CA | A | 154 | 214 | −153 | 158 | 16 |
| VAL | CB | A | 154 | 206 | −152 | 171 | 17 |
| VAL | CG1 | A | 154 | 210 | −163 | 181 | 20 |
| VAL | CG2 | A | 154 | 209 | −139 | 178 | 19 |
| VAL | C | A | 154 | 210 | −141 | 149 | 14 |
| VAL | O | A | 154 | 218 | −132 | 148 | 17 |
| THR | N | A | 155 | 198 | −142 | 143 | 13 |
| THR | CA | A | 155 | 193 | −132 | 134 | 13 |
| THR | CB | A | 155 | 193 | −136 | 120 | 16 |
| THR | OG1 | A | 155 | 206 | −138 | 115 | 19 |
| THR | CG2 | A | 155 | 186 | −125 | 111 | 17 |
| THR | C | A | 155 | 179 | −129 | 139 | 13 |
| THR | O | A | 155 | 171 | −139 | 141 | 15 |
| VAL | N | A | 156 | 175 | −116 | 141 | 10 |
| VAL | CA | A | 156 | 162 | −113 | 146 | 13 |
| VAL | CB | A | 156 | 163 | −109 | 160 | 15 |
| VAL | CG1 | A | 156 | 168 | −120 | 169 | 18 |
| VAL | CG2 | A | 156 | 171 | −96 | 162 | 14 |
| VAL | C | A | 156 | 156 | −102 | 137 | 12 |
| VAL | O | A | 156 | 162 | −94 | 131 | 13 |
| ARG | N | A | 157 | 142 | −102 | 138 | 9 |
| ARG | CA | A | 157 | 135 | −91 | 131 | 9 |
| ARG | CB | A | 157 | 122 | −97 | 125 | 12 |
| ARG | CG | A | 157 | 114 | −86 | 117 | 15 |
| ARG | CD | A | 157 | 103 | −92 | 110 | 18 |
| ARG | NE | A | 157 | 107 | −98 | 97 | 13 |
| ARG | CZ | A | 157 | 111 | −92 | 86 | 13 |
| ARG | NH1 | A | 157 | 113 | −79 | 86 | 11 |
| ARG | NH2 | A | 157 | 113 | −99 | 75 | 11 |
| ARG | C | A | 157 | 132 | −80 | 141 | 10 |
| ARG | O | A | 157 | 126 | −83 | 151 | 10 |
| ALA | N | A | 158 | 138 | −69 | 138 | 9 |
| ALA | CA | A | 158 | 136 | −57 | 147 | 10 |
| ALA | CB | A | 158 | 150 | −55 | 154 | 10 |
| ALA | C | A | 158 | 132 | −45 | 140 | 10 |
| ALA | O | A | 158 | 133 | −43 | 128 | 8 |
| ASN | N | A | 159 | 127 | −35 | 148 | 9 |
| ASN | CA | A | 159 | 123 | −22 | 143 | 8 |
| ASN | CB | A | 159 | 115 | −15 | 154 | 9 |
| ASN | CG | A | 159 | 102 | −21 | 157 | 11 |
| ASN | OD1 | A | 159 | 94 | −24 | 148 | 12 |
| ASN | ND2 | A | 159 | 99 | −23 | 170 | 8 |
| ASN | C | A | 159 | 135 | −14 | 139 | 7 |
| ASN | O | A | 159 | 145 | −15 | 146 | 8 |
| ILE | N | A | 160 | 134 | −7 | 128 | 7 |
| ILE | CA | A | 160 | 145 | 1 | 124 | 7 |
| ILE | CB | A | 160 | 153 | −6 | 112 | 9 |
| ILE | CG2 | A | 160 | 164 | 3 | 107 | 9 |
| ILE | CG1 | A | 160 | 157 | −20 | 116 | 10 |
| ILE | CD1 | A | 160 | 165 | −27 | 105 | 11 |
| ILE | C | A | 160 | 140 | 15 | 119 | 10 |
| ILE | O | A | 160 | 131 | 15 | 110 | 9 |
| ALA | N | A | 161 | 146 | 25 | 124 | 8 |
| ALA | CA | A | 161 | 142 | 39 | 120 | 7 |
| ALA | CB | A | 161 | 143 | 48 | 132 | 8 |
| ALA | C | A | 161 | 152 | 43 | 109 | 10 |
| ALA | O | A | 161 | 164 | 44 | 112 | 9 |
| ALA | N | A | 162 | 147 | 44 | 97 | 7 |
| ALA | CA | A | 162 | 156 | 48 | 86 | 9 |
| ALA | CB | A | 162 | 149 | 44 | 73 | 10 |
| ALA | C | A | 162 | 157 | 64 | 86 | 12 |
| ALA | O | A | 162 | 147 | 71 | 83 | 11 |
| ILE | N | A | 163 | 168 | 69 | 90 | 10 |
| ILE | CA | A | 163 | 171 | 83 | 92 | 11 |
| ILE | CB | A | 163 | 184 | 86 | 99 | 8 |
| ILE | CG2 | A | 163 | 186 | 101 | 101 | 10 |
| ILE | CG1 | A | 163 | 183 | 79 | 113 | 10 |
| ILE | CD1 | A | 163 | 196 | 79 | 121 | 9 |
| ILE | C | A | 163 | 171 | 90 | 78 | 12 |
| ILE | O | A | 163 | 179 | 86 | 69 | 12 |
| THR | N | A | 164 | 163 | 100 | 76 | 13 |
| THR | CA | A | 164 | 162 | 107 | 63 | 14 |
| THR | CB | A | 164 | 148 | 107 | 58 | 15 |
| THR | OG1 | A | 164 | 138 | 111 | 68 | 16 |
| THR | CG2 | A | 164 | 144 | 93 | 53 | 17 |
| THR | C | A | 164 | 167 | 122 | 65 | 15 |
| THR | O | A | 164 | 170 | 128 | 55 | 16 |
| GLU | N | A | 165 | 166 | 127 | 78 | 14 |
| GLU | CA | A | 165 | 170 | 140 | 81 | 16 |
| GLU | CB | A | 165 | 158 | 150 | 80 | 22 |
| GLU | CG | A | 165 | 153 | 153 | 66 | 29 |
| GLU | CD | A | 165 | 141 | 162 | 66 | 35 |
| GLU | OE1 | A | 165 | 142 | 173 | 72 | 39 |
| GLU | OE2 | A | 165 | 131 | 158 | 60 | 39 |
| GLU | C | A | 165 | 176 | 140 | 95 | 15 |
| GLU | O | A | 165 | 172 | 133 | 104 | 14 |
| SER | N | A | 166 | 187 | 148 | 96 | 14 |
| SER | CA | A | 166 | 193 | 149 | 109 | 12 |
| SER | CB | A | 166 | 203 | 137 | 111 | 11 |
| SER | OG | A | 166 | 214 | 138 | 101 | 13 |
| SER | C | A | 166 | 201 | 162 | 112 | 12 |
| SER | O | A | 166 | 204 | 169 | 102 | 13 |
| ASP | N | A | 167 | 204 | 165 | 124 | 13 |
| ASP | CA | A | 167 | 211 | 177 | 127 | 14 |
| ASP | CB | A | 167 | 201 | 189 | 130 | 18 |
| ASP | CG | A | 167 | 208 | 202 | 133 | 22 |
| ASP | OD1 | A | 167 | 211 | 205 | 145 | 26 |
| ASP | OD2 | A | 167 | 211 | 210 | 124 | 27 |
| ASP | C | A | 167 | 220 | 175 | 140 | 13 |
| ASP | O | A | 167 | 215 | 172 | 150 | 12 |
| LYS | N | A | 168 | 233 | 177 | 138 | 12 |
| LYS | CA | A | 168 | 242 | 176 | 148 | 14 |
| LYS | CB | A | 168 | 240 | 186 | 159 | 16 |
| LYS | CG | A | 168 | 241 | 201 | 154 | 21 |
| LYS | CD | A | 168 | 236 | 211 | 164 | 26 |
| LYS | CE | A | 168 | 237 | 225 | 158 | 29 |
| LYS | NZ | A | 168 | 233 | 235 | 168 | 32 |
| LYS | C | A | 168 | 242 | 162 | 154 | 13 |
| LYS | O | A | 168 | 245 | 160 | 166 | 12 |
| PHE | N | A | 169 | 238 | 152 | 146 | 11 |
| PHE | CA | A | 169 | 238 | 138 | 151 | 11 |
| PHE | CB | A | 169 | 225 | 131 | 145 | 10 |
| PHE | CG | A | 169 | 224 | 117 | 150 | 10 |
| PHE | CD1 | A | 169 | 222 | 114 | 163 | 9 |
| PHE | CD2 | A | 169 | 224 | 107 | 140 | 9 |
| PHE | CE1 | A | 169 | 221 | 100 | 167 | 10 |
| PHE | CE2 | A | 169 | 222 | 93 | 144 | 9 |
| PHE | CZ | A | 169 | 221 | 90 | 157 | 10 |

TABLE 2-continued

Structure Coordinates for BACE complexed to Inhibitor

| | | | | | | | |
|---|---|---|---|---|---|---|---|
| PHE | C | A | 169 | 250 | 131 | 146 | 12 |
| PHE | O | A | 169 | 258 | 126 | 154 | 12 |
| PHE | N | A | 170 | 251 | 129 | 133 | 10 |
| PHE | CA | A | 170 | 263 | 122 | 128 | 13 |
| PHE | CB | A | 170 | 261 | 120 | 113 | 11 |
| PHE | CG | A | 170 | 250 | 110 | 110 | 11 |
| PHE | CD1 | A | 170 | 238 | 114 | 102 | 11 |
| PHE | CD2 | A | 170 | 250 | 97 | 114 | 10 |
| PHE | CE1 | A | 170 | 228 | 106 | 100 | 12 |
| PHE | CE2 | A | 170 | 239 | 88 | 111 | 11 |
| PHE | CZ | A | 170 | 228 | 93 | 104 | 10 |
| PHE | C | A | 170 | 276 | 130 | 130 | 15 |
| PHE | O | A | 170 | 275 | 143 | 130 | 16 |
| ILE | N | A | 171 | 287 | 124 | 132 | 15 |
| ILE | CA | A | 171 | 299 | 130 | 135 | 17 |
| ILE | CB | A | 171 | 305 | 126 | 148 | 18 |
| ILE | CG2 | A | 171 | 319 | 132 | 150 | 20 |
| ILE | CG1 | A | 171 | 296 | 130 | 159 | 18 |
| ILE | CD1 | A | 171 | 300 | 126 | 173 | 19 |
| ILE | C | A | 171 | 309 | 127 | 123 | 18 |
| ILE | O | A | 171 | 311 | 115 | 120 | 17 |
| ASN | N | A | 172 | 316 | 137 | 118 | 20 |
| ASN | CA | A | 172 | 325 | 135 | 107 | 22 |
| ASN | CB | A | 172 | 330 | 149 | 102 | 26 |
| ASN | CG | A | 172 | 338 | 148 | 89 | 31 |
| ASN | OD1 | A | 172 | 343 | 158 | 83 | 35 |
| ASN | ND2 | A | 172 | 339 | 135 | 83 | 32 |
| ASN | C | A | 172 | 337 | 127 | 112 | 21 |
| ASN | O | A | 172 | 344 | 130 | 121 | 21 |
| GLY | N | A | 173 | 339 | 116 | 105 | 19 |
| GLY | CA | A | 173 | 351 | 107 | 108 | 19 |
| GLY | C | A | 173 | 349 | 97 | 120 | 19 |
| GLY | O | A | 173 | 358 | 91 | 125 | 21 |
| SER | N | A | 174 | 336 | 97 | 126 | 17 |
| SER | CA | A | 174 | 334 | 88 | 137 | 15 |
| SER | CB | A | 174 | 320 | 91 | 143 | 17 |
| SER | OG | A | 174 | 310 | 87 | 134 | 17 |
| SER | C | A | 174 | 334 | 73 | 133 | 16 |
| SER | O | A | 174 | 336 | 64 | 141 | 14 |
| ASN | N | A | 175 | 331 | 71 | 120 | 14 |
| ASN | CA | A | 175 | 330 | 58 | 114 | 13 |
| ASN | CB | A | 175 | 342 | 49 | 117 | 15 |
| ASN | CG | A | 175 | 345 | 38 | 107 | 18 |
| ASN | OD1 | A | 175 | 345 | 41 | 95 | 19 |
| ASN | ND2 | A | 175 | 348 | 26 | 112 | 15 |
| ASN | C | A | 175 | 317 | 50 | 117 | 14 |
| ASN | O | A | 175 | 317 | 38 | 114 | 13 |
| TRP | N | A | 176 | 307 | 56 | 123 | 12 |
| TRP | CA | A | 176 | 295 | 49 | 126 | 9 |
| TRP | CB | A | 176 | 291 | 48 | 141 | 10 |
| TRP | CG | A | 176 | 292 | 61 | 149 | 10 |
| TRP | CD2 | A | 176 | 281 | 70 | 150 | 9 |
| TRP | CE2 | A | 176 | 285 | 80 | 160 | 12 |
| TRP | CE3 | A | 176 | 268 | 72 | 145 | 9 |
| TRP | CD1 | A | 176 | 302 | 65 | 157 | 11 |
| TRP | NE1 | A | 176 | 298 | 77 | 163 | 11 |
| TRP | CZ2 | A | 176 | 278 | 91 | 163 | 10 |
| TRP | CZ3 | A | 176 | 260 | 82 | 149 | 10 |
| TRP | CH2 | A | 176 | 265 | 92 | 158 | 11 |
| TRP | C | A | 176 | 284 | 56 | 118 | 10 |
| TRP | O | A | 176 | 284 | 68 | 115 | 11 |
| GLU | N | A | 177 | 274 | 47 | 114 | 10 |
| GLU | CA | A | 177 | 263 | 52 | 106 | 10 |
| GLU | CB | A | 177 | 263 | 45 | 92 | 12 |
| GLU | CG | A | 177 | 276 | 47 | 84 | 14 |
| GLU | CD | A | 177 | 286 | 36 | 86 | 18 |
| GLU | OE1 | A | 177 | 298 | 38 | 81 | 24 |
| GLU | OE2 | A | 177 | 283 | 25 | 91 | 14 |
| GLU | C | A | 177 | 249 | 50 | 112 | 9 |
| GLU | O | A | 177 | 239 | 53 | 106 | 9 |
| GLY | N | A | 178 | 249 | 46 | 124 | 7 |
| GLY | CA | A | 178 | 236 | 44 | 131 | 8 |
| GLY | C | A | 178 | 238 | 43 | 146 | 9 |
| GLY | O | A | 178 | 249 | 45 | 151 | 8 |
| ILE | N | A | 179 | 227 | 41 | 153 | 8 |
| ILE | CA | A | 179 | 227 | 41 | 168 | 8 |
| ILE | CB | A | 179 | 222 | 55 | 173 | 7 |
| ILE | CG2 | A | 179 | 207 | 57 | 169 | 8 |
| ILE | CG1 | A | 179 | 223 | 55 | 188 | 7 |
| ILE | CD1 | A | 179 | 221 | 69 | 194 | 7 |
| ILE | C | A | 179 | 218 | 30 | 173 | 8 |
| ILE | O | A | 179 | 208 | 27 | 168 | 7 |
| LEU | N | A | 180 | 223 | 23 | 184 | 7 |
| LEU | CA | A | 180 | 216 | 12 | 190 | 8 |
| LEU | CB | A | 180 | 225 | 0 | 191 | 8 |
| LEU | CG | A | 180 | 218 | −13 | 197 | 7 |
| LEU | CD1 | A | 180 | 206 | −17 | 189 | 10 |
| LEU | CD2 | A | 180 | 229 | −24 | 198 | 8 |
| LEU | C | A | 180 | 212 | 16 | 204 | 10 |
| LEU | O | A | 180 | 220 | 16 | 213 | 8 |
| GLY | N | A | 181 | 199 | 20 | 205 | 6 |
| GLY | CA | A | 181 | 194 | 24 | 218 | 7 |
| GLY | C | A | 181 | 191 | 12 | 226 | 9 |
| GLY | O | A | 181 | 182 | 4 | 223 | 9 |
| LEU | N | A | 182 | 198 | 10 | 237 | 6 |
| LEU | CA | A | 182 | 197 | −2 | 245 | 6 |
| LEU | CB | A | 182 | 211 | −7 | 249 | 8 |
| LEU | CG | A | 182 | 219 | −13 | 238 | 8 |
| LEU | CD1 | A | 182 | 234 | −15 | 242 | 9 |
| LEU | CD2 | A | 182 | 213 | −26 | 232 | 10 |
| LEU | C | A | 182 | 188 | −1 | 258 | 6 |
| LEU | O | A | 182 | 187 | −10 | 265 | 9 |
| ALA | N | A | 183 | 183 | 11 | 260 | 8 |
| ALA | CA | A | 183 | 174 | 14 | 271 | 8 |
| ALA | CB | A | 183 | 173 | 29 | 274 | 9 |
| ALA | C | A | 183 | 160 | 8 | 269 | 8 |
| ALA | O | A | 183 | 158 | 1 | 259 | 8 |
| TYR | N | A | 184 | 151 | 10 | 278 | 7 |
| TYR | CA | A | 184 | 138 | 5 | 278 | 9 |
| TYR | CB | A | 184 | 132 | 3 | 292 | 7 |
| TYR | CG | A | 184 | 141 | −6 | 301 | 9 |
| TYR | CD1 | A | 184 | 151 | 0 | 309 | 9 |
| TYR | CE1 | A | 184 | 159 | −8 | 317 | 10 |
| TYR | CD2 | A | 184 | 140 | −20 | 301 | 9 |
| TYR | CE2 | A | 184 | 148 | −27 | 310 | 11 |
| TYR | CZ | A | 184 | 158 | −21 | 317 | 10 |
| TYR | OH | A | 184 | 165 | −29 | 326 | 11 |
| TYR | C | A | 184 | 127 | 12 | 269 | 9 |
| TYR | O | A | 184 | 129 | 24 | 266 | 10 |
| ALA | N | A | 185 | 117 | 4 | 265 | 11 |
| ALA | CA | A | 185 | 106 | 10 | 257 | 10 |
| ALA | CB | A | 185 | 96 | −1 | 255 | 10 |
| ALA | C | A | 185 | 99 | 22 | 262 | 11 |
| ALA | O | A | 185 | 94 | 30 | 254 | 10 |
| GLU | N | A | 186 | 99 | 24 | 275 | 13 |
| GLU | CA | A | 186 | 92 | 36 | 281 | 14 |
| GLU | CB | A | 186 | 95 | 37 | 296 | 18 |
| GLU | CG | A | 186 | 85 | 46 | 303 | 24 |
| GLU | CD | A | 186 | 87 | 47 | 318 | 28 |
| GLU | OE1 | A | 186 | 89 | 37 | 325 | 30 |
| GLU | OE2 | A | 186 | 88 | 59 | 322 | 34 |
| GLU | C | A | 186 | 97 | 49 | 274 | 14 |
| GLU | O | A | 186 | 89 | 58 | 273 | 14 |
| ILE | N | A | 187 | 110 | 50 | 270 | 13 |
| ILE | CA | A | 187 | 115 | 62 | 264 | 11 |
| ILE | CB | A | 187 | 128 | 67 | 271 | 11 |
| ILE | CG2 | A | 187 | 125 | 70 | 286 | 10 |
| ILE | CG1 | A | 187 | 139 | 56 | 270 | 12 |
| ILE | CD1 | A | 187 | 152 | 60 | 275 | 12 |
| ILE | C | A | 187 | 117 | 61 | 249 | 12 |
| ILE | O | A | 187 | 124 | 69 | 243 | 13 |
| ALA | N | A | 188 | 111 | 51 | 243 | 12 |
| ALA | CA | A | 188 | 113 | 49 | 228 | 12 |
| ALA | CB | A | 188 | 110 | 35 | 224 | 11 |
| ALA | C | A | 188 | 103 | 58 | 221 | 12 |
| ALA | O | A | 188 | 92 | 62 | 226 | 12 |
| ARG | N | A | 189 | 107 | 63 | 209 | 10 |
| ARG | CA | A | 189 | 98 | 71 | 201 | 10 |
| ARG | CB | A | 189 | 106 | 83 | 195 | 12 |
| ARG | CG | A | 189 | 111 | 93 | 206 | 13 |
| ARG | CD | A | 189 | 100 | 99 | 214 | 17 |
| ARG | NE | A | 189 | 105 | 109 | 224 | 18 |
| ARG | CZ | A | 189 | 106 | 122 | 221 | 20 |
| ARG | NH1 | A | 189 | 102 | 127 | 210 | 23 |

TABLE 2-continued

Structure Coordinates for BACE complexed to Inhibitor

| ARG | NH2 | A | 189 | 110 | 130 | 231 | 21 |
|---|---|---|---|---|---|---|---|
| ARG | C | A | 189 | 93 | 63 | 190 | 11 |
| ARG | O | A | 189 | 100 | 54 | 185 | 12 |
| PRO | N | A | 190 | 81 | 66 | 185 | 12 |
| PRO | CD | A | 190 | 76 | 59 | 172 | 13 |
| PRO | CA | A | 190 | 72 | 76 | 189 | 13 |
| PRO | CB | A | 190 | 61 | 76 | 178 | 14 |
| PRO | CG | A | 190 | 68 | 70 | 166 | 16 |
| PRO | C | A | 190 | 66 | 74 | 203 | 14 |
| PRO | O | A | 190 | 62 | 83 | 210 | 16 |
| ASP | N | A | 191 | 65 | 61 | 207 | 14 |
| ASP | CA | A | 191 | 60 | 57 | 220 | 16 |
| ASP | CB | A | 191 | 44 | 57 | 219 | 18 |
| ASP | CG | A | 191 | 39 | 49 | 208 | 23 |
| ASP | OD1 | A | 191 | 36 | 54 | 197 | 24 |
| ASP | OD2 | A | 191 | 38 | 37 | 210 | 22 |
| ASP | C | A | 191 | 64 | 43 | 224 | 15 |
| ASP | O | A | 191 | 72 | 37 | 216 | 15 |
| ASP | N | A | 192 | 61 | 39 | 236 | 15 |
| ASP | CA | A | 192 | 65 | 26 | 241 | 16 |
| ASP | CB | A | 192 | 62 | 24 | 256 | 17 |
| ASP | CG | A | 192 | 47 | 25 | 258 | 22 |
| ASP | OD1 | A | 192 | 39 | 22 | 249 | 19 |
| ASP | OD2 | A | 192 | 43 | 28 | 270 | 24 |
| ASP | C | A | 192 | 60 | 14 | 233 | 15 |
| ASP | O | A | 192 | 63 | 2 | 237 | 14 |
| SER | N | A | 193 | 52 | 16 | 223 | 14 |
| SER | CA | A | 193 | 47 | 4 | 215 | 15 |
| SER | CB | A | 193 | 35 | 8 | 207 | 15 |
| SER | OG | A | 193 | 37 | 16 | 196 | 18 |
| SER | C | A | 193 | 58 | 0 | 205 | 14 |
| SER | O | A | 193 | 57 | −11 | 200 | 13 |
| LEU | N | A | 194 | 68 | 8 | 203 | 13 |
| LEU | CA | A | 194 | 79 | 4 | 194 | 10 |
| LEU | CB | A | 194 | 85 | 17 | 187 | 11 |
| LEU | CG | A | 194 | 85 | 13 | 175 | 10 |
| LEU | CD1 | A | 194 | 86 | 9 | 163 | 10 |
| LEU | CD2 | A | 194 | 104 | 25 | 172 | 12 |
| LEU | C | A | 194 | 90 | −3 | 201 | 11 |
| LEU | O | A | 194 | 98 | 2 | 208 | 9 |
| GLU | N | A | 195 | 89 | −17 | 201 | 11 |
| GLU | CA | A | 195 | 98 | −26 | 208 | 9 |
| GLU | CB | A | 195 | 94 | −40 | 204 | 10 |
| GLU | CG | A | 195 | 103 | −51 | 211 | 13 |
| GLU | CD | A | 195 | 97 | −65 | 208 | 15 |
| GLU | OE1 | A | 195 | 89 | −69 | 216 | 19 |
| GLU | OE2 | A | 195 | 102 | −71 | 199 | 15 |
| GLU | C | A | 195 | 112 | −23 | 205 | 10 |
| GLU | O | A | 195 | 116 | −23 | 193 | 10 |
| PRO | N | A | 196 | 121 | −21 | 215 | 8 |
| PRO | CD | A | 196 | 117 | −17 | 229 | 7 |
| PRO | CA | A | 196 | 135 | −18 | 213 | 9 |
| PRO | CB | A | 196 | 140 | −14 | 227 | 9 |
| PRO | CG | A | 196 | 128 | −7 | 233 | 8 |
| PRO | C | A | 196 | 142 | −31 | 208 | 10 |
| PRO | O | A | 196 | 137 | −42 | 210 | 8 |
| PHE | N | A | 197 | 154 | −29 | 202 | 7 |
| PHE | CA | A | 197 | 161 | −40 | 197 | 8 |
| PHE | CB | A | 197 | 175 | −35 | 191 | 7 |
| PHE | CG | A | 197 | 184 | −47 | 186 | 8 |
| PHE | CD1 | A | 197 | 181 | −53 | 174 | 9 |
| PHE | CD2 | A | 197 | 194 | −51 | 194 | 8 |
| PHE | CE1 | A | 197 | 189 | −64 | 170 | 10 |
| PHE | CE2 | A | 197 | 202 | −62 | 190 | 10 |
| PHE | CZ | A | 197 | 199 | −68 | 178 | 10 |
| PHE | C | A | 197 | 164 | −51 | 206 | 7 |
| PHE | O | A | 197 | 162 | −63 | 204 | 8 |
| PHE | N | A | 198 | 169 | −48 | 218 | 6 |
| PHE | CA | A | 198 | 173 | −58 | 228 | 7 |
| PHE | CB | A | 198 | 180 | −52 | 240 | 8 |
| PHE | CG | A | 198 | 189 | −62 | 247 | 9 |
| PHE | CD1 | A | 198 | 202 | −65 | 242 | 11 |
| PHE | CD2 | A | 198 | 185 | −70 | 258 | 9 |
| PHE | CE1 | A | 198 | 210 | −74 | 247 | 11 |
| PHE | CE2 | A | 198 | 193 | −79 | 264 | 12 |
| PHE | CZ | A | 198 | 206 | −82 | 258 | 11 |
| PHE | C | A | 198 | 161 | −66 | 232 | 10 |
| PHE | O | A | 198 | 162 | −78 | 235 | 8 |
| ASP | N | A | 199 | 149 | −60 | 233 | 10 |
| ASP | CA | A | 199 | 137 | −67 | 237 | 10 |
| ASP | CB | A | 199 | 125 | −57 | 239 | 11 |
| ASP | CG | A | 199 | 127 | −48 | 251 | 15 |
| ASP | OD1 | A | 199 | 122 | −52 | 262 | 20 |
| ASP | OD2 | A | 199 | 134 | −38 | 250 | 16 |
| ASP | C | A | 199 | 133 | −77 | 227 | 10 |
| ASP | O | A | 199 | 130 | −88 | 230 | 12 |
| SER | N | A | 200 | 135 | −73 | 214 | 10 |
| SER | CA | A | 200 | 132 | −82 | 203 | 11 |
| SER | CB | A | 200 | 134 | −75 | 189 | 11 |
| SER | OG | A | 200 | 125 | −64 | 188 | 12 |
| SER | C | A | 200 | 142 | −94 | 203 | 12 |
| SER | O | A | 200 | 138 | −106 | 201 | 11 |
| LEU | N | A | 201 | 155 | −91 | 206 | 9 |
| LEU | CA | A | 201 | 165 | −101 | 206 | 11 |
| LEU | CB | A | 201 | 179 | −95 | 209 | 11 |
| LEU | CG | A | 201 | 191 | −104 | 211 | 12 |
| LEU | CD1 | A | 201 | 193 | −112 | 198 | 14 |
| LEU | CD2 | A | 201 | 203 | −96 | 215 | 14 |
| LEU | C | A | 201 | 162 | −112 | 216 | 12 |
| LEU | O | A | 201 | 162 | −124 | 214 | 9 |
| VAL | N | A | 202 | 159 | −107 | 229 | 10 |
| VAL | CA | A | 202 | 155 | −117 | 239 | 11 |
| VAL | CB | A | 202 | 154 | −109 | 253 | 12 |
| VAL | CG1 | A | 202 | 149 | −118 | 264 | 14 |
| VAL | CG2 | A | 202 | 168 | −104 | 257 | 11 |
| VAL | C | A | 202 | 142 | −125 | 237 | 13 |
| VAL | O | A | 202 | 142 | −136 | 240 | 14 |
| LYS | N | A | 203 | 132 | −118 | 231 | 12 |
| LYS | CA | A | 203 | 120 | −125 | 228 | 15 |
| LYS | CB | A | 203 | 109 | −115 | 225 | 18 |
| LYS | CG | A | 203 | 95 | −121 | 222 | 25 |
| LYS | CD | A | 203 | 84 | −110 | 220 | 29 |
| LYS | CE | A | 203 | 71 | −117 | 218 | 33 |
| LYS | NZ | A | 203 | 60 | −107 | 217 | 36 |
| LYS | C | A | 203 | 121 | −135 | 217 | 15 |
| LYS | O | A | 203 | 114 | −145 | 218 | 15 |
| GLN | N | A | 204 | 129 | −133 | 207 | 14 |
| GLN | CA | A | 204 | 130 | −142 | 196 | 13 |
| GLN | CB | A | 204 | 132 | −133 | 183 | 11 |
| GLN | CG | A | 204 | 120 | −125 | 179 | 11 |
| GLN | CD | A | 204 | 123 | −115 | 168 | 12 |
| GLN | OE1 | A | 204 | 130 | −119 | 158 | 11 |
| GLN | NE2 | A | 204 | 119 | −103 | 169 | 11 |
| GLN | C | A | 204 | 141 | −152 | 197 | 15 |
| GLN | O | A | 204 | 141 | −161 | 188 | 17 |
| THR | N | A | 205 | 150 | −151 | 206 | 13 |
| THR | CA | A | 205 | 161 | −161 | 208 | 14 |
| THR | CB | A | 205 | 174 | −155 | 203 | 15 |
| THR | OG1 | A | 205 | 178 | −145 | 213 | 14 |
| THR | CG2 | A | 205 | 173 | −148 | 190 | 12 |
| THR | C | A | 205 | 163 | −166 | 222 | 15 |
| THR | O | A | 205 | 155 | −163 | 231 | 17 |
| HIS | N | A | 206 | 173 | −174 | 224 | 15 |
| HIS | CA | A | 206 | 176 | −179 | 237 | 18 |
| HIS | CB | A | 206 | 182 | −193 | 236 | 24 |
| HIS | CG | A | 206 | 172 | −203 | 231 | 29 |
| HIS | CD2 | A | 206 | 160 | −208 | 237 | 31 |
| HIS | ND1 | A | 206 | 173 | −210 | 219 | 32 |
| HIS | CE1 | A | 206 | 162 | −218 | 217 | 32 |
| HIS | NE2 | A | 206 | 155 | −217 | 228 | 33 |
| HIS | C | A | 206 | 187 | −170 | 245 | 16 |
| HIS | O | A | 206 | 191 | −174 | 255 | 16 |
| VAL | N | A | 207 | 190 | −159 | 239 | 15 |
| VAL | CA | A | 207 | 199 | −150 | 245 | 11 |
| VAL | CB | A | 207 | 202 | −138 | 236 | 13 |
| VAL | CG1 | A | 207 | 212 | −128 | 243 | 14 |
| VAL | CG2 | A | 207 | 208 | −142 | 223 | 13 |
| VAL | C | A | 207 | 194 | −145 | 258 | 12 |
| VAL | O | A | 207 | 183 | −139 | 259 | 13 |
| PRO | N | A | 208 | 202 | −146 | 269 | 10 |
| PRO | CD | A | 208 | 214 | −154 | 270 | 12 |
| PRO | CA | A | 208 | 198 | −141 | 282 | 11 |
| PRO | CB | A | 208 | 210 | −145 | 291 | 12 |
| PRO | CG | A | 208 | 215 | −158 | 285 | 14 |

TABLE 2-continued

Structure Coordinates for BACE complexed to Inhibitor

| | | | | | | | |
|---|---|---|---|---|---|---|---|
| PRO | C | A | 208 | 195 | −126 | 282 | 13 |
| PRO | O | A | 208 | 202 | −119 | 275 | 11 |
| ASN | N | A | 209 | 186 | −122 | 291 | 11 |
| ASN | CA | A | 209 | 182 | −108 | 291 | 11 |
| ASN | CB | A | 209 | 168 | −107 | 298 | 12 |
| ASN | CG | A | 209 | 163 | −92 | 297 | 11 |
| ASN | OD1 | A | 209 | 167 | −85 | 288 | 9 |
| ASN | ND2 | A | 209 | 154 | −89 | 306 | 11 |
| ASN | C | A | 209 | 193 | −100 | 299 | 12 |
| ASN | O | A | 209 | 190 | −96 | 311 | 9 |
| LEU | N | A | 210 | 205 | −99 | 294 | 10 |
| LEU | CA | A | 210 | 216 | −92 | 300 | 10 |
| LEU | CB | A | 210 | 221 | −100 | 312 | 14 |
| LEU | CG | A | 210 | 233 | −96 | 320 | 13 |
| LEU | CD1 | A | 210 | 233 | −104 | 333 | 13 |
| LEU | CD2 | A | 210 | 246 | −100 | 312 | 15 |
| LEU | C | A | 210 | 227 | −89 | 290 | 10 |
| LEU | O | A | 210 | 229 | −97 | 281 | 10 |
| PHE | N | A | 211 | 234 | −78 | 292 | 8 |
| PHE | CA | A | 211 | 245 | −75 | 283 | 8 |
| PHE | CB | A | 211 | 241 | −67 | 271 | 7 |
| PHE | CG | A | 211 | 236 | −53 | 274 | 9 |
| PHE | CD1 | A | 211 | 223 | −50 | 275 | 7 |
| PHE | CD2 | A | 211 | 245 | −42 | 274 | 8 |
| PHE | CE1 | A | 211 | 218 | −37 | 278 | 7 |
| PHE | CE2 | A | 211 | 241 | −29 | 277 | 6 |
| PHE | CZ | A | 211 | 227 | −27 | 278 | 6 |
| PHE | C | A | 211 | 255 | −67 | 292 | 8 |
| PHE | O | A | 211 | 251 | −62 | 302 | 6 |
| SER | N | A | 212 | 267 | −67 | 288 | 7 |
| SER | CA | A | 212 | 278 | −60 | 296 | 6 |
| SER | CB | A | 212 | 286 | −70 | 304 | 8 |
| SER | OG | A | 212 | 291 | −81 | 296 | 8 |
| SER | C | A | 212 | 286 | −52 | 286 | 9 |
| SER | O | A | 212 | 289 | −56 | 275 | 8 |
| LEU | N | A | 213 | 291 | −41 | 291 | 7 |
| LEU | CA | A | 213 | 300 | −32 | 283 | 7 |
| LEU | CB | A | 213 | 293 | −19 | 280 | 6 |
| LEU | CG | A | 213 | 281 | −19 | 271 | 8 |
| LEU | CD1 | A | 213 | 273 | −6 | 271 | 8 |
| LEU | CD2 | A | 213 | 285 | −23 | 257 | 10 |
| LEU | C | A | 213 | 313 | −29 | 290 | 7 |
| LEU | O | A | 213 | 314 | −25 | 302 | 7 |
| GLN | N | A | 214 | 324 | −30 | 282 | 6 |
| GLN | CA | A | 214 | 337 | −26 | 286 | 5 |
| GLN | CB | A | 214 | 347 | −38 | 285 | 6 |
| GLN | CG | A | 214 | 361 | −35 | 289 | 7 |
| GLN | CD | A | 214 | 371 | −45 | 283 | 10 |
| GLN | OE1 | A | 214 | 370 | −49 | 271 | 13 |
| GLN | NE2 | A | 214 | 380 | −49 | 291 | 10 |
| GLN | C | A | 214 | 342 | −16 | 276 | 7 |
| GLN | O | A | 214 | 346 | −19 | 265 | 8 |
| LEU | N | A | 215 | 341 | −3 | 280 | 7 |
| LEU | CA | A | 215 | 345 | 8 | 271 | 7 |
| LEU | CB | A | 215 | 337 | 20 | 273 | 8 |
| LEU | CG | A | 215 | 322 | 18 | 271 | 7 |
| LEU | CD1 | A | 215 | 315 | 32 | 271 | 7 |
| LEU | CD2 | A | 215 | 319 | 12 | 257 | 7 |
| LEU | C | A | 215 | 360 | 10 | 274 | 8 |
| LEU | O | A | 215 | 363 | 13 | 286 | 9 |
| CYS | N | A | 216 | 369 | 10 | 264 | 8 |
| CYS | CA | A | 216 | 383 | 12 | 267 | 8 |
| CYS | C | A | 216 | 389 | 24 | 261 | 9 |
| CYS | O | A | 216 | 391 | 25 | 249 | 8 |
| CYS | CB | A | 216 | 391 | 0 | 261 | 8 |
| CYS | SG | A | 216 | 386 | −16 | 269 | 9 |
| GLY | N | A | 217 | 392 | 34 | 270 | 7 |
| GLY | CA | A | 217 | 398 | 46 | 265 | 7 |
| GLY | C | A | 217 | 413 | 42 | 263 | 8 |
| GLY | O | A | 217 | 418 | 34 | 270 | 9 |
| ALA | N | A | 218 | 420 | 49 | 254 | 7 |
| ALA | CA | A | 218 | 434 | 46 | 251 | 8 |
| ALA | CB | A | 218 | 437 | 50 | 237 | 11 |
| ALA | C | A | 218 | 443 | 53 | 261 | 10 |
| ALA | O | A | 218 | 454 | 48 | 264 | 11 |
| GLY | N | A | 219 | 439 | 64 | 266 | 9 |
| GLY | CA | A | 219 | 447 | 72 | 275 | 8 |
| GLY | C | A | 219 | 456 | 82 | 268 | 10 |
| GLY | O | A | 219 | 463 | 90 | 274 | 10 |
| PHE | N | A | 220 | 454 | 83 | 255 | 9 |
| PHE | CA | A | 220 | 461 | 92 | 246 | 9 |
| PHE | CB | A | 220 | 475 | 87 | 243 | 10 |
| PHE | CG | A | 220 | 476 | 73 | 238 | 12 |
| PHE | CD1 | A | 220 | 478 | 63 | 247 | 10 |
| PHE | CD2 | A | 220 | 473 | 70 | 225 | 14 |
| PHE | CE1 | A | 220 | 479 | 49 | 243 | 12 |
| PHE | CE2 | A | 220 | 474 | 56 | 221 | 13 |
| PHE | CZ | A | 220 | 477 | 46 | 230 | 13 |
| PHE | C | A | 220 | 452 | 94 | 234 | 10 |
| PHE | O | A | 220 | 443 | 87 | 231 | 10 |
| PRO | N | A | 221 | 455 | 105 | 226 | 12 |
| PRO | CD | A | 221 | 466 | 116 | 229 | 12 |
| PRO | CA | A | 221 | 448 | 108 | 214 | 14 |
| PRO | CB | A | 221 | 454 | 121 | 209 | 14 |
| PRO | CG | A | 221 | 459 | 127 | 222 | 15 |
| PRO | C | A | 221 | 449 | 97 | 204 | 15 |
| PRO | O | A | 221 | 460 | 90 | 203 | 18 |
| LEU | N | A | 222 | 439 | 95 | 196 | 14 |
| LEU | CA | A | 222 | 439 | 85 | 185 | 16 |
| LEU | CB | A | 222 | 429 | 74 | 187 | 16 |
| LEU | CG | A | 222 | 431 | 65 | 200 | 17 |
| LEU | CD1 | A | 222 | 419 | 56 | 202 | 13 |
| LEU | CD2 | A | 222 | 443 | 57 | 199 | 17 |
| LEU | C | A | 222 | 435 | 92 | 172 | 16 |
| LEU | O | A | 222 | 424 | 98 | 171 | 18 |
| ASN | N | A | 223 | 444 | 93 | 162 | 20 |
| ASN | CA | A | 223 | 441 | 99 | 149 | 23 |
| ASN | CB | A | 223 | 454 | 102 | 141 | 25 |
| ASN | CG | A | 223 | 461 | 89 | 138 | 28 |
| ASN | OD1 | A | 223 | 456 | 80 | 133 | 29 |
| ASN | ND2 | A | 223 | 474 | 89 | 141 | 32 |
| ASN | C | A | 223 | 431 | 90 | 142 | 25 |
| ASN | O | A | 223 | 428 | 80 | 146 | 21 |
| GLN | N | A | 224 | 427 | 95 | 130 | 27 |
| GLN | CA | A | 224 | 418 | 87 | 122 | 30 |
| GLN | CB | A | 224 | 414 | 94 | 109 | 34 |
| GLN | CG | A | 224 | 426 | 96 | 100 | 40 |
| GLN | CD | A | 224 | 423 | 104 | 87 | 44 |
| GLN | OE1 | A | 224 | 414 | 100 | 80 | 46 |
| GLN | NE2 | A | 224 | 430 | 115 | 85 | 45 |
| GLN | C | A | 224 | 422 | 73 | 119 | 27 |
| GLN | O | A | 224 | 414 | 63 | 121 | 28 |
| SER | N | A | 225 | 435 | 71 | 115 | 24 |
| SER | CA | A | 225 | 440 | 58 | 112 | 23 |
| SER | CB | A | 225 | 454 | 59 | 106 | 26 |
| SER | OG | A | 225 | 453 | 67 | 93 | 30 |
| SER | C | A | 225 | 441 | 49 | 124 | 22 |
| SER | O | A | 225 | 437 | 38 | 124 | 21 |
| GLU | N | A | 226 | 446 | 55 | 135 | 20 |
| GLU | CA | A | 226 | 447 | 48 | 148 | 18 |
| GLU | CB | A | 226 | 455 | 56 | 158 | 19 |
| GLU | CG | A | 226 | 470 | 57 | 154 | 20 |
| GLU | CD | A | 226 | 477 | 68 | 163 | 22 |
| GLU | OE1 | A | 226 | 489 | 67 | 164 | 25 |
| GLU | OE2 | A | 226 | 470 | 77 | 168 | 21 |
| GLU | C | A | 226 | 434 | 43 | 154 | 16 |
| GLU | O | A | 226 | 433 | 32 | 159 | 15 |
| VAL | N | A | 227 | 424 | 52 | 154 | 16 |
| VAL | CA | A | 227 | 411 | 48 | 160 | 17 |
| VAL | CB | A | 227 | 402 | 60 | 161 | 18 |
| VAL | CG1 | A | 227 | 398 | 64 | 147 | 19 |
| VAL | CG2 | A | 227 | 390 | 57 | 169 | 20 |
| VAL | C | A | 227 | 405 | 37 | 152 | 19 |
| VAL | O | A | 227 | 396 | 29 | 158 | 18 |
| LEU | N | A | 228 | 408 | 35 | 140 | 18 |
| LEU | CA | A | 228 | 402 | 25 | 132 | 17 |
| LEU | CB | A | 228 | 404 | 28 | 117 | 19 |
| LEU | CG | A | 228 | 396 | 40 | 111 | 21 |
| LEU | CD1 | A | 228 | 400 | 43 | 97 | 23 |
| LEU | CD2 | A | 228 | 381 | 38 | 112 | 21 |
| LEU | C | A | 228 | 408 | 11 | 134 | 18 |
| LEU | O | A | 228 | 402 | 1 | 133 | 19 |
| ALA | N | A | 229 | 421 | 11 | 138 | 16 |
| ALA | CA | A | 229 | 428 | −1 | 141 | 17 |

TABLE 2-continued

Structure Coordinates for BACE complexed to Inhibitor

| | | | | | | | |
|---|---|---|---|---|---|---|---|
| ALA | CB | A | 229 | 443 | 0 | 137 | 17 |
| ALA | C | A | 229 | 427 | −5 | 156 | 17 |
| ALA | O | A | 229 | 429 | −17 | 159 | 22 |
| SER | N | A | 230 | 425 | 4 | 165 | 15 |
| SER | CA | A | 230 | 425 | 2 | 179 | 13 |
| SER | CB | A | 230 | 426 | 15 | 186 | 14 |
| SER | OG | A | 230 | 426 | 13 | 200 | 15 |
| SER | C | A | 230 | 412 | −5 | 184 | 14 |
| SER | O | A | 230 | 401 | −3 | 178 | 12 |
| VAL | N | A | 231 | 414 | −13 | 194 | 13 |
| VAL | CA | A | 231 | 402 | −20 | 200 | 13 |
| VAL | CB | A | 231 | 407 | −33 | 207 | 13 |
| VAL | CG1 | A | 231 | 395 | −39 | 216 | 12 |
| VAL | CG2 | A | 231 | 412 | −43 | 197 | 16 |
| VAL | C | A | 231 | 396 | −11 | 211 | 13 |
| VAL | O | A | 231 | 403 | −7 | 220 | 13 |
| GLY | N | A | 232 | 384 | −7 | 209 | 9 |
| GLY | CA | A | 232 | 377 | 2 | 218 | 9 |
| GLY | C | A | 232 | 370 | −4 | 229 | 9 |
| GLY | O | A | 232 | 364 | 3 | 237 | 10 |
| GLY | N | A | 233 | 370 | −17 | 230 | 9 |
| GLY | CA | A | 233 | 363 | −24 | 241 | 10 |
| GLY | C | A | 233 | 355 | −36 | 237 | 10 |
| GLY | O | A | 233 | 356 | −42 | 226 | 9 |
| SER | N | A | 234 | 345 | −40 | 246 | 7 |
| SER | CA | A | 234 | 337 | −51 | 243 | 7 |
| SER | CB | A | 234 | 342 | −64 | 251 | 8 |
| SER | OG | A | 234 | 356 | −66 | 249 | 9 |
| SER | C | A | 234 | 323 | −49 | 247 | 6 |
| SER | O | A | 234 | 320 | −43 | 257 | 7 |
| MET | N | A | 235 | 314 | −55 | 239 | 6 |
| MET | CA | A | 235 | 300 | −55 | 243 | 6 |
| MET | CB | A | 235 | 291 | −48 | 232 | 6 |
| MET | CG | A | 235 | 276 | −50 | 235 | 8 |
| MET | SD | A | 235 | 264 | −40 | 227 | 10 |
| MET | CE | A | 235 | 266 | −46 | 210 | 16 |
| MET | C | A | 235 | 296 | −70 | 243 | 7 |
| MET | O | A | 235 | 295 | −77 | 233 | 8 |
| ILE | N | A | 236 | 294 | −76 | 255 | 7 |
| ILE | CA | A | 236 | 291 | −90 | 256 | 9 |
| ILE | CB | A | 236 | 297 | −96 | 269 | 9 |
| ILE | CG2 | A | 236 | 295 | −111 | 269 | 10 |
| ILE | CG1 | A | 236 | 312 | −93 | 269 | 9 |
| ILE | CD1 | A | 236 | 320 | −98 | 257 | 11 |
| ILE | C | A | 236 | 276 | −91 | 257 | 11 |
| ILE | O | A | 236 | 270 | −87 | 267 | 10 |
| ILE | N | A | 237 | 270 | −97 | 246 | 10 |
| ILE | CA | A | 237 | 255 | −98 | 246 | 10 |
| ILE | CB | A | 237 | 250 | −97 | 231 | 11 |
| ILE | CG2 | A | 237 | 235 | −100 | 230 | 11 |
| ILE | CG1 | A | 237 | 254 | −84 | 225 | 14 |
| ILE | CD1 | A | 237 | 246 | −72 | 231 | 20 |
| ILE | C | A | 237 | 251 | −111 | 252 | 12 |
| ILE | O | A | 237 | 254 | −122 | 246 | 13 |
| GLY | N | A | 238 | 243 | −111 | 262 | 10 |
| GLY | CA | A | 238 | 238 | −123 | 269 | 12 |
| GLY | C | A | 238 | 247 | −128 | 280 | 14 |
| GLY | O | A | 238 | 244 | −139 | 285 | 14 |
| GLY | N | A | 239 | 257 | −121 | 284 | 13 |
| GLY | CA | A | 239 | 266 | −127 | 295 | 13 |
| GLY | C | A | 239 | 276 | −117 | 300 | 13 |
| GLY | O | A | 239 | 277 | −106 | 296 | 10 |
| ILE | N | A | 240 | 284 | −123 | 309 | 12 |
| ILE | CA | A | 240 | 295 | −116 | 316 | 13 |
| ILE | CB | A | 240 | 293 | −116 | 331 | 12 |
| ILE | CG2 | A | 240 | 304 | −108 | 338 | 15 |
| ILE | CG1 | A | 240 | 280 | −109 | 334 | 13 |
| ILE | CD1 | A | 240 | 276 | −110 | 349 | 15 |
| ILE | C | A | 240 | 308 | −123 | 313 | 14 |
| ILE | O | A | 240 | 309 | −135 | 316 | 16 |
| ASP | N | A | 241 | 318 | −116 | 307 | 11 |
| ASP | CA | A | 241 | 331 | −123 | 304 | 11 |
| ASP | CB | A | 241 | 336 | −118 | 291 | 14 |
| ASP | CG | A | 241 | 349 | −125 | 287 | 13 |
| ASP | OD1 | A | 241 | 348 | −133 | 277 | 14 |
| ASP | OD2 | A | 241 | 359 | −124 | 294 | 14 |
| ASP | C | A | 241 | 340 | −118 | 316 | 14 |
| ASP | O | A | 241 | 344 | −107 | 317 | 12 |
| HIS | N | A | 242 | 345 | −128 | 323 | 14 |
| HIS | CA | A | 242 | 354 | −125 | 335 | 15 |
| HIS | CB | A | 242 | 354 | −138 | 344 | 19 |
| HIS | CG | A | 242 | 340 | −141 | 349 | 24 |
| HIS | CD2 | A | 242 | 332 | −152 | 346 | 28 |
| HIS | ND1 | A | 242 | 332 | −133 | 357 | 26 |
| HIS | CE1 | A | 242 | 321 | −139 | 359 | 28 |
| HIS | NE2 | A | 242 | 320 | −151 | 353 | 29 |
| HIS | C | A | 242 | 368 | −121 | 332 | 14 |
| HIS | O | A | 242 | 375 | −117 | 341 | 16 |
| SER | N | A | 243 | 372 | −121 | 319 | 10 |
| SER | CA | A | 243 | 385 | −116 | 316 | 12 |
| SER | CB | A | 243 | 390 | −123 | 303 | 14 |
| SER | OG | A | 243 | 384 | −117 | 292 | 14 |
| SER | C | A | 243 | 386 | −101 | 315 | 11 |
| SER | O | A | 243 | 397 | −95 | 314 | 12 |
| LEU | N | A | 244 | 374 | −95 | 314 | 10 |
| LEU | CA | A | 244 | 373 | −80 | 312 | 8 |
| LEU | CB | A | 244 | 361 | −77 | 305 | 9 |
| LEU | CG | A | 244 | 359 | −85 | 292 | 9 |
| LEU | CD1 | A | 244 | 346 | −80 | 285 | 9 |
| LEU | CD2 | A | 244 | 371 | −83 | 283 | 10 |
| LEU | C | A | 244 | 374 | −72 | 325 | 8 |
| LEU | O | A | 244 | 374 | −59 | 324 | 11 |
| TYR | N | A | 245 | 375 | −78 | 336 | 8 |
| TYR | CA | A | 245 | 376 | −70 | 349 | 9 |
| TYR | CB | A | 245 | 362 | −68 | 355 | 8 |
| TYR | CG | A | 245 | 355 | −80 | 360 | 11 |
| TYR | CD1 | A | 245 | 348 | −89 | 351 | 11 |
| TYR | CE1 | A | 245 | 342 | −100 | 356 | 13 |
| TYR | CD2 | A | 245 | 355 | −83 | 373 | 10 |
| TYR | CE2 | A | 245 | 348 | −94 | 378 | 14 |
| TYR | CZ | A | 245 | 341 | −103 | 370 | 14 |
| TYR | OH | A | 245 | 335 | −114 | 375 | 16 |
| TYR | C | A | 245 | 385 | −77 | 359 | 11 |
| TYR | O | A | 245 | 388 | −89 | 358 | 11 |
| THR | N | A | 246 | 388 | −70 | 370 | 12 |
| THR | CA | A | 246 | 395 | −75 | 381 | 13 |
| THR | CB | A | 246 | 409 | −68 | 382 | 13 |
| THR | OG1 | A | 246 | 407 | −54 | 384 | 13 |
| THR | CG2 | A | 246 | 417 | −70 | 370 | 14 |
| THR | C | A | 246 | 387 | −72 | 394 | 13 |
| THR | O | A | 246 | 378 | −64 | 394 | 11 |
| GLY | N | A | 247 | 390 | −80 | 404 | 14 |
| GLY | CA | A | 247 | 382 | −78 | 416 | 14 |
| GLY | C | A | 247 | 368 | −83 | 416 | 12 |
| GLY | O | A | 247 | 365 | −91 | 407 | 14 |
| SER | N | A | 248 | 359 | −78 | 425 | 12 |
| SER | CA | A | 248 | 345 | −83 | 425 | 15 |
| SER | CB | A | 248 | 341 | −84 | 440 | 17 |
| SER | OG | A | 248 | 349 | −94 | 446 | 22 |
| SER | C | A | 248 | 336 | −73 | 418 | 13 |
| SER | O | A | 248 | 338 | −61 | 417 | 14 |
| LEU | N | A | 249 | 324 | −79 | 414 | 13 |
| LEU | CA | A | 249 | 314 | −71 | 408 | 12 |
| LEU | CB | A | 249 | 306 | −79 | 398 | 13 |
| LEU | CG | A | 249 | 311 | −80 | 383 | 11 |
| LEU | CD1 | A | 249 | 305 | −92 | 376 | 11 |
| LEU | CD2 | A | 249 | 308 | −67 | 376 | 12 |
| LEU | C | A | 249 | 304 | −67 | 419 | 11 |
| LEU | O | A | 249 | 300 | −75 | 427 | 15 |
| TRP | N | A | 250 | 301 | −54 | 419 | 10 |
| TRP | CA | A | 250 | 291 | −49 | 429 | 9 |
| TRP | CB | A | 250 | 297 | −37 | 437 | 9 |
| TRP | CG | A | 250 | 306 | −43 | 448 | 10 |
| TRP | CD2 | A | 250 | 303 | −45 | 462 | 12 |
| TRP | CE2 | A | 250 | 314 | −51 | 468 | 12 |
| TRP | CE3 | A | 250 | 291 | −43 | 469 | 13 |
| TRP | CD1 | A | 250 | 319 | −47 | 447 | 10 |
| TRP | NE1 | A | 250 | 324 | −52 | 459 | 14 |
| TRP | CZ2 | A | 250 | 314 | −54 | 482 | 15 |
| TRP | CZ3 | A | 250 | 291 | −47 | 483 | 16 |
| TRP | CH2 | A | 250 | 302 | −52 | 489 | 12 |
| TRP | C | A | 250 | 279 | −43 | 421 | 9 |
| TRP | O | A | 250 | 280 | −36 | 411 | 10 |
| TYR | N | A | 251 | 267 | −47 | 426 | 9 |

TABLE 2-continued

Structure Coordinates for BACE complexed to Inhibitor

| | | | | | | | |
|---|---|---|---|---|---|---|---|
| TYR | CA | A | 251 | 255 | -43 | 419 | 9 |
| TYR | CB | A | 251 | 246 | -55 | 417 | 10 |
| TYR | CG | A | 251 | 252 | -65 | 407 | 11 |
| TYR | CD1 | A | 251 | 260 | -75 | 412 | 12 |
| TYR | CE1 | A | 251 | 266 | -84 | 403 | 11 |
| TYR | CD2 | A | 251 | 248 | -64 | 394 | 11 |
| TYR | CE2 | A | 251 | 253 | -74 | 385 | 10 |
| TYR | CZ | A | 251 | 262 | -83 | 389 | 12 |
| TYR | OH | A | 251 | 267 | -93 | 380 | 13 |
| TYR | C | A | 251 | 246 | -32 | 426 | 9 |
| TYR | O | A | 251 | 245 | -32 | 439 | 9 |
| THR | N | A | 252 | 241 | -23 | 418 | 9 |
| THR | CA | A | 252 | 232 | -13 | 423 | 10 |
| THR | CB | A | 252 | 237 | 1 | 420 | 9 |
| THR | OG1 | A | 252 | 230 | 11 | 427 | 10 |
| THR | CG2 | A | 252 | 237 | 4 | 405 | 11 |
| THR | C | A | 252 | 219 | -15 | 416 | 11 |
| THR | O | A | 252 | 218 | -19 | 404 | 9 |
| PRO | N | A | 253 | 207 | -13 | 423 | 11 |
| PRO | CD | A | 253 | 206 | -10 | 437 | 12 |
| PRO | CA | A | 253 | 194 | -15 | 417 | 11 |
| PRO | CB | A | 253 | 184 | -14 | 428 | 11 |
| PRO | CG | A | 253 | 193 | -17 | 440 | 10 |
| PRO | C | A | 253 | 191 | -6 | 405 | 11 |
| PRO | O | A | 253 | 195 | 6 | 405 | 10 |
| ILE | N | A | 254 | 184 | -10 | 395 | 11 |
| ILE | CA | A | 254 | 179 | -2 | 385 | 11 |
| ILE | CB | A | 254 | 176 | -10 | 372 | 12 |
| ILE | CG2 | A | 254 | 168 | -1 | 362 | 11 |
| ILE | CG1 | A | 254 | 189 | -14 | 365 | 10 |
| ILE | CD1 | A | 254 | 187 | -23 | 353 | 11 |
| ILE | C | A | 254 | 166 | 3 | 391 | 11 |
| ILE | O | A | 254 | 157 | -4 | 393 | 11 |
| ARG | N | A | 255 | 166 | 16 | 394 | 11 |
| ARG | CA | A | 255 | 154 | 22 | 401 | 11 |
| ARG | CB | A | 255 | 157 | 37 | 403 | 13 |
| ARG | CG | A | 255 | 147 | 43 | 412 | 14 |
| ARG | CD | A | 255 | 148 | 58 | 413 | 15 |
| ARG | NE | A | 255 | 139 | 64 | 422 | 16 |
| ARG | CZ | A | 255 | 135 | 77 | 422 | 18 |
| ARG | NH1 | A | 255 | 140 | 85 | 413 | 16 |
| ARG | NH2 | A | 255 | 127 | 82 | 431 | 16 |
| ARG | C | A | 255 | 141 | 21 | 393 | 13 |
| ARG | O | A | 255 | 131 | 18 | 399 | 13 |
| ARG | N | A | 256 | 142 | 24 | 380 | 12 |
| ARG | CA | A | 256 | 130 | 24 | 371 | 13 |
| ARG | CB | A | 256 | 123 | 37 | 371 | 15 |
| ARG | CG | A | 256 | 112 | 40 | 361 | 20 |
| ARG | CD | A | 256 | 107 | 54 | 363 | 23 |
| ARG | NE | A | 256 | 99 | 58 | 352 | 24 |
| ARG | CZ | A | 256 | 96 | 71 | 350 | 27 |
| ARG | NH1 | A | 256 | 100 | 81 | 358 | 25 |
| ARG | NH2 | A | 256 | 87 | 75 | 340 | 28 |
| ARG | C | A | 256 | 135 | 20 | 358 | 12 |
| ARG | O | A | 256 | 146 | 24 | 353 | 11 |
| GLU | N | A | 257 | 127 | 12 | 351 | 13 |
| GLU | CA | A | 257 | 131 | 7 | 337 | 12 |
| GLU | CB | A | 257 | 125 | -7 | 335 | 15 |
| GLU | CG | A | 257 | 132 | -17 | 345 | 18 |
| GLU | CD | A | 257 | 124 | -30 | 346 | 21 |
| GLU | OE1 | A | 257 | 112 | -29 | 350 | 24 |
| GLU | OE2 | A | 257 | 129 | -41 | 343 | 19 |
| GLU | C | A | 257 | 126 | 16 | 326 | 13 |
| GLU | O | A | 257 | 116 | 14 | 320 | 13 |
| TRP | N | A | 258 | 134 | 27 | 324 | 9 |
| TRP | CA | A | 258 | 132 | 36 | 313 | 9 |
| TRP | CB | A | 258 | 124 | 49 | 318 | 9 |
| TRP | CG | A | 258 | 130 | 57 | 329 | 11 |
| TRP | CD2 | A | 258 | 128 | 71 | 331 | 10 |
| TRP | CE2 | A | 258 | 134 | 75 | 343 | 12 |
| TRP | CE3 | A | 258 | 121 | 81 | 323 | 11 |
| TRP | CD1 | A | 258 | 137 | 53 | 340 | 12 |
| TRP | NE1 | A | 258 | 139 | 63 | 348 | 11 |
| TRP | CZ2 | A | 258 | 134 | 88 | 348 | 13 |
| TRP | CZ3 | A | 258 | 121 | 94 | 328 | 14 |
| TRP | CH2 | A | 258 | 127 | 97 | 340 | 14 |
| TRP | C | A | 258 | 146 | 39 | 308 | 11 |
| TRP | O | A | 258 | 151 | 33 | 299 | 11 |
| TRP | N | A | 259 | 153 | 48 | 315 | 12 |
| TYR | CA | A | 259 | 167 | 50 | 312 | 8 |
| TYR | CB | A | 259 | 172 | 64 | 317 | 9 |
| TYR | CG | A | 259 | 167 | 75 | 309 | 10 |
| TYR | CD1 | A | 259 | 174 | 79 | 298 | 8 |
| TYR | C1 | A | 259 | 169 | 90 | 290 | 8 |
| TYR | CD2 | A | 259 | 156 | 82 | 314 | 9 |
| TYR | CE2 | A | 259 | 151 | 93 | 306 | 9 |
| TYR | CZ | A | 259 | 158 | 97 | 295 | 9 |
| TYR | OH | A | 259 | 153 | 108 | 288 | 10 |
| TYR | C | A | 259 | 173 | 40 | 322 | 6 |
| TYR | O | A | 259 | 165 | 33 | 329 | 8 |
| TYR | N | A | 260 | 186 | 38 | 322 | 8 |
| TYR | CA | A | 260 | 192 | 29 | 332 | 7 |
| TYR | CB | A | 260 | 205 | 22 | 326 | 7 |
| TYR | CG | A | 260 | 202 | 11 | 317 | 8 |
| TYR | CD1 | A | 260 | 203 | 13 | 303 | 9 |
| TYR | CE1 | A | 260 | 200 | 3 | 294 | 8 |
| TYR | CD2 | A | 260 | 197 | -1 | 321 | 8 |
| TYR | CE2 | A | 260 | 194 | -12 | 312 | 10 |
| TYR | CZ | A | 260 | 195 | -10 | 299 | 10 |
| TYR | OH | A | 260 | 192 | -20 | 290 | 8 |
| TYR | C | A | 260 | 195 | 38 | 343 | 9 |
| TYR | O | A | 260 | 206 | 43 | 345 | 9 |
| GLU | N | A | 261 | 184 | 40 | 351 | 10 |
| GLU | CA | A | 261 | 185 | 49 | 363 | 9 |
| GLU | CB | A | 261 | 171 | 55 | 366 | 10 |
| GLU | CG | A | 261 | 171 | 64 | 378 | 9 |
| GLU | CD | A | 261 | 157 | 70 | 381 | 9 |
| GLU | OE1 | A | 261 | 147 | 65 | 377 | 11 |
| GLU | OE2 | A | 261 | 157 | 81 | 388 | 10 |
| GLU | C | A | 261 | 190 | 42 | 376 | 9 |
| GLU | O | A | 261 | 186 | 31 | 379 | 9 |
| VAL | N | A | 262 | 199 | 49 | 383 | 8 |
| VAL | CA | A | 262 | 205 | 44 | 395 | 8 |
| VAL | CB | A | 262 | 220 | 40 | 393 | 9 |
| VAL | CG1 | A | 262 | 220 | 29 | 383 | 9 |
| VAL | CG2 | A | 262 | 228 | 52 | 389 | 8 |
| VAL | C | A | 262 | 204 | 56 | 405 | 9 |
| VAL | O | A | 262 | 200 | 67 | 402 | 8 |
| ILE | N | A | 263 | 208 | 52 | 418 | 9 |
| ILE | CA | A | 363 | 208 | 62 | 428 | 9 |
| ILE | CB | A | 263 | 197 | 58 | 439 | 11 |
| ILE | CG2 | A | 263 | 198 | 68 | 451 | 12 |
| ILE | CG1 | A | 263 | 183 | 58 | 433 | 13 |
| ILE | CD1 | A | 263 | 172 | 54 | 443 | 14 |
| ILE | C | A | 263 | 221 | 64 | 435 | 9 |
| ILE | O | A | 263 | 227 | 54 | 440 | 9 |
| ILE | N | A | 264 | 227 | 76 | 435 | 8 |
| ILE | CA | A | 264 | 240 | 79 | 441 | 8 |
| ILE | CB | A | 264 | 247 | 90 | 433 | 8 |
| ILE | CG2 | A | 264 | 259 | 95 | 440 | 8 |
| ILE | CG1 | A | 264 | 250 | 85 | 418 | 8 |
| ILE | CD1 | A | 264 | 254 | 96 | 409 | 10 |
| ILE | C | A | 264 | 236 | 84 | 455 | 8 |
| ILE | O | A | 264 | 228 | 93 | 456 | 9 |
| VAL | N | A | 265 | 243 | 79 | 465 | 8 |
| VAL | CA | A | 265 | 241 | 83 | 479 | 10 |
| VAL | CB | A | 265 | 238 | 71 | 487 | 11 |
| VAL | CG1 | A | 265 | 226 | 63 | 482 | 11 |
| VAL | CG2 | A | 265 | 250 | 61 | 488 | 11 |
| VAL | C | A | 265 | 251 | 91 | 485 | 10 |
| VAL | O | A | 265 | 249 | 97 | 496 | 12 |
| ARG | N | A | 266 | 263 | 92 | 479 | 9 |
| ARG | CA | A | 266 | 274 | 100 | 485 | 9 |
| ARG | CB | A | 266 | 281 | 92 | 497 | 8 |
| ARG | CG | A | 266 | 293 | 98 | 503 | 8 |
| ARG | CD | A | 266 | 299 | 89 | 514 | 9 |
| ARG | NE | A | 266 | 312 | 93 | 519 | 10 |
| ARG | CZ | A | 266 | 314 | 100 | 529 | 13 |
| ARG | NH1 | A | 266 | 304 | 105 | 537 | 11 |
| ARG | NH2 | A | 266 | 327 | 103 | 533 | 11 |
| ARG | C | A | 266 | 285 | 102 | 474 | 8 |
| ARG | O | A | 266 | 286 | 94 | 465 | 8 |
| VAL | N | A | 267 | 291 | 114 | 475 | 7 |
| VAL | CA | A | 267 | 302 | 117 | 466 | 7 |

TABLE 2-continued

Structure Coordinates for BACE complexed to Inhibitor

| | | | | | | | |
|---|---|---|---|---|---|---|---|
| VAL | CB | A | 267 | 297 | 128 | 456 | 9 |
| VAL | CG1 | A | 267 | 308 | 133 | 447 | 9 |
| VAL | CG2 | A | 267 | 285 | 123 | 448 | 8 |
| VAL | C | A | 267 | 314 | 123 | 473 | 7 |
| VAL | O | A | 267 | 312 | 131 | 483 | 8 |
| GLU | N | A | 268 | 325 | 118 | 469 | 7 |
| GLU | CA | A | 268 | 338 | 122 | 476 | 7 |
| GLU | CB | A | 268 | 344 | 110 | 483 | 10 |
| GLU | CG | A | 268 | 337 | 106 | 496 | 10 |
| GLU | CD | A | 268 | 344 | 94 | 502 | 7 |
| GLU | OE1 | A | 268 | 355 | 90 | 497 | 8 |
| GLU | OE2 | A | 268 | 338 | 88 | 511 | 12 |
| GLU | C | A | 268 | 348 | 127 | 465 | 9 |
| GLU | O | A | 268 | 348 | 121 | 454 | 8 |
| ILE | N | A | 269 | 356 | 136 | 469 | 6 |
| ILE | CA | A | 269 | 367 | 141 | 461 | 7 |
| ILE | CB | A | 269 | 366 | 157 | 458 | 7 |
| ILE | CG2 | A | 269 | 377 | 161 | 448 | 7 |
| ILE | CG1 | A | 269 | 352 | 160 | 452 | 10 |
| ILE | CD1 | A | 269 | 350 | 153 | 438 | 10 |
| ILE | C | A | 269 | 379 | 139 | 469 | 6 |
| ILE | O | A | 269 | 381 | 146 | 480 | 6 |
| ASN | N | A | 270 | 388 | 129 | 465 | 6 |
| ASN | CA | A | 270 | 399 | 126 | 473 | 7 |
| ASN | CB | A | 270 | 410 | 137 | 472 | 7 |
| ASN | CG | A | 270 | 422 | 133 | 464 | 8 |
| ASN | OD1 | A | 270 | 422 | 122 | 457 | 8 |
| ASN | ND2 | A | 270 | 432 | 141 | 464 | 8 |
| ASN | C | A | 270 | 396 | 123 | 488 | 9 |
| ASN | O | A | 270 | 402 | 127 | 497 | 7 |
| GLY | N | A | 271 | 385 | 115 | 489 | 9 |
| GLY | CA | A | 271 | 381 | 111 | 503 | 8 |
| GLY | C | A | 271 | 372 | 122 | 510 | 9 |
| GLN | O | A | 271 | 367 | 118 | 521 | 7 |
| GLN | N | A | 272 | 372 | 134 | 505 | 6 |
| GLN | CA | A | 272 | 365 | 144 | 512 | 6 |
| GLN | CB | A | 272 | 371 | 158 | 509 | 7 |
| GLN | CG | A | 272 | 363 | 169 | 516 | 10 |
| GLN | CD | A | 272 | 372 | 182 | 517 | 17 |
| GLN | OE1 | A | 272 | 380 | 185 | 508 | 23 |
| GLN | NE2 | A | 272 | 369 | 190 | 528 | 19 |
| GLN | C | A | 272 | 350 | 144 | 507 | 8 |
| GLN | O | A | 272 | 347 | 146 | 495 | 8 |
| ASP | N | A | 273 | 341 | 143 | 517 | 6 |
| ASP | CA | A | 273 | 327 | 143 | 514 | 8 |
| ASP | CB | A | 273 | 319 | 140 | 527 | 9 |
| ASP | CG | A | 273 | 304 | 139 | 525 | 10 |
| ASP | OD1 | A | 273 | 299 | 138 | 513 | 9 |
| ASP | OD2 | A | 273 | 297 | 139 | 535 | 11 |
| ASP | C | A | 273 | 322 | 156 | 508 | 8 |
| ASP | O | A | 273 | 324 | 167 | 514 | 9 |
| LEU | N | A | 274 | 315 | 156 | 496 | 8 |
| LEU | CA | A | 274 | 310 | 168 | 490 | 10 |
| LEU | CB | A | 274 | 304 | 164 | 476 | 12 |
| LEU | CG | A | 274 | 304 | 176 | 466 | 14 |
| LEU | CD1 | A | 274 | 318 | 182 | 464 | 14 |
| LEU | CD2 | A | 274 | 299 | 170 | 453 | 11 |
| LEU | C | A | 274 | 299 | 174 | 499 | 12 |
| LEU | O | A | 274 | 296 | 185 | 498 | 13 |
| LYS | N | A | 275 | 294 | 165 | 508 | 12 |
| LYS | CA | A | 275 | 285 | 169 | 518 | 16 |
| LYS | CB | A | 275 | 292 | 177 | 529 | 21 |
| LYS | CG | A | 275 | 285 | 176 | 543 | 28 |
| LYS | CD | A | 275 | 294 | 183 | 553 | 34 |
| LYS | CE | A | 275 | 289 | 180 | 567 | 37 |
| LYS | NZ | A | 275 | 298 | 186 | 578 | 41 |
| LYS | C | A | 275 | 272 | 176 | 514 | 16 |
| LYS | O | A | 275 | 267 | 185 | 520 | 18 |
| MET | N | A | 276 | 266 | 171 | 503 | 14 |
| MET | CA | A | 276 | 253 | 177 | 498 | 13 |
| MET | CB | A | 276 | 254 | 179 | 483 | 14 |
| MET | CG | A | 276 | 264 | 189 | 479 | 16 |
| MET | SD | A | 276 | 264 | 191 | 461 | 15 |
| MET | CE | A | 276 | 250 | 202 | 459 | 18 |
| MET | C | A | 276 | 242 | 167 | 501 | 14 |
| MET | O | A | 276 | 244 | 155 | 503 | 14 |
| ASP | N | A | 277 | 230 | 172 | 502 | 13 |
| ASP | CA | A | 277 | 218 | 163 | 504 | 14 |
| ASP | CB | A | 277 | 205 | 172 | 504 | 16 |
| ASP | CG | A | 277 | 193 | 164 | 506 | 20 |
| ASP | OD1 | A | 277 | 191 | 153 | 501 | 19 |
| ASP | OD2 | A | 277 | 184 | 169 | 514 | 23 |
| ASP | C | A | 277 | 219 | 154 | 493 | 13 |
| ASP | O | A | 277 | 219 | 158 | 481 | 14 |
| CYS | N | A | 278 | 219 | 141 | 495 | 13 |
| CYS | CA | A | 278 | 220 | 131 | 484 | 13 |
| CYS | C | A | 278 | 210 | 132 | 474 | 14 |
| CYS | O | A | 278 | 211 | 127 | 463 | 14 |
| CYS | CB | A | 278 | 221 | 117 | 490 | 16 |
| CYS | SG | A | 278 | 205 | 111 | 498 | 17 |
| LYS | N | A | 279 | 199 | 139 | 476 | 12 |
| LYS | CA | A | 279 | 188 | 141 | 467 | 13 |
| LYS | CB | A | 279 | 176 | 147 | 473 | 16 |
| LYS | CG | A | 279 | 163 | 144 | 466 | 23 |
| LYS | CD | A | 279 | 151 | 150 | 474 | 25 |
| LYS | CE | A | 279 | 138 | 142 | 472 | 29 |
| LYS | NZ | A | 279 | 140 | 128 | 476 | 26 |
| LYS | C | A | 279 | 193 | 150 | 455 | 11 |
| LYS | O | A | 279 | 189 | 148 | 444 | 11 |
| GLU | N | A | 280 | 203 | 158 | 458 | 10 |
| GLU | CA | A | 280 | 209 | 167 | 448 | 10 |
| GLU | CB | A | 280 | 218 | 177 | 455 | 11 |
| GLU | CG | A | 280 | 211 | 186 | 465 | 13 |
| GLU | CD | A | 280 | 203 | 198 | 459 | 17 |
| GLU | OE1 | A | 280 | 202 | 198 | 447 | 15 |
| GLU | OE2 | A | 280 | 198 | 206 | 467 | 19 |
| GLU | C | A | 280 | 216 | 160 | 438 | 9 |
| GLU | O | A | 280 | 217 | 164 | 426 | 7 |
| TYR | N | A | 281 | 222 | 149 | 442 | 9 |
| TYR | CA | A | 281 | 230 | 140 | 433 | 7 |
| TYR | CB | A | 281 | 238 | 129 | 441 | 7 |
| TYR | CG | A | 281 | 247 | 135 | 452 | 7 |
| TYR | CD1 | A | 281 | 249 | 128 | 464 | 9 |
| TYR | CE1 | A | 281 | 258 | 132 | 473 | 10 |
| TYR | CD2 | A | 281 | 254 | 147 | 450 | 8 |
| TYR | CE2 | A | 281 | 263 | 151 | 460 | 9 |
| TYR | CZ | A | 281 | 265 | 144 | 471 | 9 |
| TYR | OH | A | 281 | 273 | 149 | 481 | 11 |
| TYR | C | A | 281 | 222 | 133 | 422 | 8 |
| TYR | O | A | 281 | 227 | 129 | 412 | 9 |
| ASN | N | A | 282 | 209 | 132 | 425 | 8 |
| ASN | CA | A | 282 | 200 | 125 | 416 | 10 |
| ASN | CB | A | 282 | 194 | 112 | 422 | 9 |
| ASN | CG | A | 282 | 205 | 104 | 429 | 12 |
| ASN | OD1 | A | 282 | 213 | 98 | 422 | 10 |
| ASN | ND2 | A | 282 | 206 | 104 | 442 | 10 |
| ASN | C | A | 282 | 189 | 134 | 411 | 10 |
| ASN | O | A | 282 | 178 | 129 | 407 | 10 |
| TYR | N | A | 283 | 191 | 147 | 410 | 9 |
| TYR | CA | A | 283 | 181 | 156 | 406 | 11 |
| TYR | CB | A | 283 | 182 | 169 | 414 | 12 |
| TYR | CG | A | 283 | 173 | 180 | 409 | 13 |
| TYR | CD1 | A | 283 | 159 | 179 | 408 | 15 |
| TYR | CE1 | A | 283 | 151 | 189 | 403 | 18 |
| TYR | CD2 | A | 283 | 179 | 192 | 405 | 15 |
| TYR | CE2 | A | 283 | 171 | 202 | 400 | 19 |
| TYR | CZ | A | 283 | 157 | 201 | 399 | 19 |
| TYR | OH | A | 283 | 149 | 211 | 394 | 23 |
| TYR | C | A | 283 | 183 | 160 | 391 | 9 |
| TYR | O | A | 283 | 193 | 167 | 388 | 10 |
| ASP | N | A | 284 | 174 | 156 | 382 | 10 |
| ASP | CA | A | 284 | 162 | 149 | 385 | 11 |
| ASP | CB | A | 284 | 150 | 156 | 377 | 13 |
| ASP | CG | A | 284 | 153 | 155 | 362 | 18 |
| ASP | OD1 | A | 284 | 164 | 152 | 358 | 16 |
| ASP | OD2 | A | 284 | 144 | 158 | 354 | 20 |
| ASP | C | A | 284 | 162 | 134 | 383 | 11 |
| ASP | O | A | 284 | 152 | 127 | 384 | 14 |
| LYS | N | A | 285 | 174 | 129 | 380 | 11 |
| LYS | CA | A | 285 | 176 | 115 | 378 | 9 |
| LYS | CB | A | 285 | 169 | 110 | 366 | 9 |
| LYS | CG | A | 285 | 173 | 116 | 353 | 8 |
| LYS | CD | A | 285 | 166 | 109 | 341 | 13 |
| LYS | CE | A | 285 | 170 | 116 | 328 | 17 |

TABLE 2-continued

Structure Coordinates for BACE complexed to Inhibitor

| | | | | | | | |
|---|---|---|---|---|---|---|---|
| LYS | NZ | A | 285 | 166 | 131 | 328 | 18 |
| LYS | C | A | 285 | 191 | 113 | 376 | 7 |
| LYS | O | A | 285 | 199 | 122 | 373 | 9 |
| SER | N | A | 286 | 196 | 100 | 378 | 7 |
| SER | CA | A | 286 | 210 | 97 | 375 | 7 |
| SER | CB | A | 286 | 217 | 93 | 388 | 9 |
| SER | OG | A | 286 | 219 | 104 | 396 | 9 |
| SER | C | A | 286 | 209 | 85 | 366 | 8 |
| SER | O | A | 286 | 203 | 75 | 369 | 7 |
| ILE | N | A | 287 | 216 | 86 | 355 | 8 |
| ILE | CA | A | 287 | 216 | 74 | 345 | 6 |
| ILE | CB | A | 287 | 208 | 78 | 332 | 6 |
| ILE | CG2 | A | 287 | 194 | 83 | 337 | 8 |
| ILE | CG1 | A | 287 | 215 | 89 | 324 | 8 |
| ILE | CD1 | A | 287 | 208 | 92 | 311 | 7 |
| ILE | C | A | 287 | 230 | 70 | 340 | 9 |
| ILE | O | A | 287 | 240 | 78 | 342 | 8 |
| VAL | N | A | 288 | 231 | 58 | 335 | 7 |
| VAL | CA | A | 288 | 243 | 53 | 330 | 7 |
| VAL | CB | A | 288 | 246 | 38 | 334 | 7 |
| VAL | CG1 | A | 288 | 259 | 33 | 329 | 9 |
| VAL | CG2 | A | 288 | 245 | 37 | 349 | 8 |
| VAL | C | A | 288 | 242 | 54 | 314 | 8 |
| VAL | O | A | 288 | 233 | 48 | 309 | 10 |
| ASP | N | A | 289 | 251 | 61 | 308 | 5 |
| ASP | CA | A | 289 | 249 | 63 | 294 | 5 |
| ASP | CB | A | 289 | 243 | 77 | 291 | 6 |
| ASP | CG | A | 289 | 240 | 79 | 276 | 6 |
| ASP | OD1 | A | 289 | 240 | 70 | 268 | 8 |
| ASP | OD2 | A | 289 | 238 | 91 | 273 | 8 |
| ASP | C | A | 289 | 262 | 62 | 286 | 7 |
| ASP | O | A | 289 | 271 | 72 | 286 | 7 |
| SER | N | A | 290 | 264 | 51 | 278 | 6 |
| SER | CA | A | 290 | 276 | 49 | 270 | 7 |
| SER | CB | A | 290 | 275 | 35 | 264 | 8 |
| SER | OG | A | 290 | 263 | 33 | 257 | 8 |
| SER | C | A | 290 | 277 | 59 | 258 | 7 |
| SER | O | A | 290 | 287 | 61 | 252 | 6 |
| GLY | N | A | 291 | 265 | 66 | 256 | 6 |
| GLY | CA | A | 291 | 265 | 75 | 245 | 6 |
| GLY | C | A | 291 | 268 | 90 | 248 | 7 |
| GLY | O | A | 291 | 266 | 99 | 240 | 7 |
| THR | N | A | 292 | 272 | 92 | 261 | 6 |
| THR | CA | A | 292 | 275 | 105 | 266 | 6 |
| THR | CB | A | 292 | 268 | 109 | 278 | 8 |
| THR | OG1 | A | 292 | 254 | 111 | 275 | 8 |
| THR | CG2 | A | 292 | 273 | 121 | 285 | 6 |
| THR | C | A | 292 | 290 | 105 | 269 | 7 |
| THR | O | A | 292 | 295 | 96 | 276 | 7 |
| THR | N | A | 293 | 298 | 115 | 264 | 6 |
| THR | CA | A | 293 | 312 | 116 | 267 | 7 |
| THR | CB | A | 293 | 318 | 127 | 259 | 7 |
| THR | OG1 | A | 293 | 316 | 125 | 245 | 8 |
| THR | CG2 | A | 293 | 333 | 128 | 262 | 6 |
| THR | C | A | 293 | 316 | 118 | 281 | 9 |
| THR | O | A | 293 | 324 | 110 | 287 | 8 |
| ASN | N | A | 294 | 311 | 128 | 287 | 8 |
| ASN | CA | A | 294 | 314 | 132 | 301 | 8 |
| ASN | CB | A | 294 | 311 | 147 | 303 | 8 |
| ASN | CG | A | 294 | 319 | 156 | 293 | 8 |
| ASN | OD1 | A | 294 | 328 | 151 | 285 | 8 |
| ASN | ND2 | A | 294 | 317 | 169 | 293 | 11 |
| ASN | C | A | 294 | 306 | 126 | 312 | 9 |
| ASN | O | A | 294 | 297 | 118 | 310 | 8 |
| LEU | N | A | 295 | 310 | 130 | 324 | 10 |
| LEU | CA | A | 295 | 304 | 126 | 336 | 7 |
| LEU | CB | A | 295 | 313 | 125 | 348 | 8 |
| LEU | CG | A | 295 | 307 | 127 | 362 | 9 |
| LEU | CD1 | A | 295 | 296 | 116 | 364 | 9 |
| LEU | CD2 | A | 295 | 318 | 125 | 373 | 10 |
| LEU | C | A | 295 | 296 | 140 | 338 | 8 |
| LEU | O | A | 295 | 303 | 150 | 340 | 8 |
| ARG | N | A | 296 | 283 | 140 | 336 | 7 |
| ARG | CA | A | 296 | 276 | 152 | 337 | 8 |
| ARG | CB | A | 296 | 266 | 153 | 326 | 11 |
| ARG | CG | A | 296 | 273 | 152 | 312 | 13 |
| ARG | CD | A | 296 | 265 | 158 | 300 | 14 |
| ARG | NE | A | 296 | 262 | 172 | 302 | 15 |
| ARG | CZ | A | 296 | 257 | 180 | 292 | 17 |
| ARG | NH1 | A | 296 | 255 | 193 | 295 | 19 |
| ARG | NH2 | A | 296 | 254 | 175 | 280 | 19 |
| ARG | C | A | 296 | 269 | 152 | 351 | 6 |
| ARG | O | A | 296 | 263 | 142 | 355 | 6 |
| LEU | N | A | 297 | 269 | 164 | 357 | 6 |
| LEU | CA | A | 297 | 263 | 165 | 370 | 8 |
| LEU | CB | A | 297 | 274 | 168 | 381 | 8 |
| LEU | CG | A | 297 | 286 | 158 | 381 | 7 |
| LEU | CD1 | A | 297 | 298 | 164 | 389 | 7 |
| LEU | CD2 | A | 297 | 281 | 145 | 388 | 8 |
| LEU | C | A | 297 | 253 | 177 | 371 | 9 |
| LEU | O | A | 297 | 255 | 187 | 364 | 9 |
| PRO | N | A | 298 | 243 | 175 | 380 | 10 |
| PRO | CD | A | 298 | 240 | 164 | 388 | 9 |
| PRO | CA | A | 298 | 233 | 186 | 382 | 10 |
| PRO | CB | A | 298 | 225 | 181 | 393 | 10 |
| PRO | CG | A | 298 | 226 | 166 | 392 | 10 |
| PRO | C | A | 298 | 240 | 199 | 385 | 10 |
| PRO | O | A | 298 | 251 | 198 | 392 | 9 |
| LYS | N | A | 299 | 235 | 210 | 380 | 9 |
| LYS | CA | A | 299 | 241 | 223 | 382 | 11 |
| LYS | CB | A | 299 | 231 | 234 | 380 | 11 |
| LYS | CG | A | 299 | 236 | 248 | 380 | 15 |
| LYS | CD | A | 299 | 225 | 258 | 376 | 20 |
| LYS | CE | A | 299 | 231 | 272 | 373 | 25 |
| LYS | NZ | A | 299 | 236 | 278 | 386 | 25 |
| LYS | C | A | 299 | 248 | 225 | 396 | 8 |
| LYS | O | A | 299 | 260 | 228 | 397 | 10 |
| LYS | N | A | 300 | 240 | 224 | 407 | 10 |
| LYS | CA | A | 300 | 245 | 226 | 420 | 11 |
| LYS | CB | A | 300 | 234 | 226 | 430 | 14 |
| LYS | CG | A | 300 | 224 | 237 | 429 | 21 |
| LYS | CD | A | 300 | 212 | 235 | 438 | 23 |
| LYS | CE | A | 300 | 216 | 235 | 453 | 23 |
| LYS | NZ | A | 300 | 204 | 234 | 462 | 20 |
| LYS | C | A | 300 | 256 | 217 | 424 | 10 |
| LYS | O | A | 300 | 265 | 220 | 431 | 9 |
| VAL | N | A | 301 | 255 | 204 | 419 | 8 |
| VAL | CA | A | 301 | 265 | 194 | 423 | 8 |
| VAL | CB | A | 301 | 260 | 180 | 419 | 7 |
| VAL | CG1 | A | 301 | 271 | 170 | 422 | 7 |
| VAL | CG2 | A | 301 | 247 | 177 | 426 | 8 |
| VAL | C | A | 301 | 278 | 197 | 415 | 7 |
| VAL | O | A | 301 | 289 | 196 | 420 | 7 |
| PHE | N | A | 302 | 276 | 201 | 402 | 7 |
| PHE | CA | A | 302 | 288 | 205 | 394 | 8 |
| PHE | CB | A | 302 | 283 | 209 | 380 | 9 |
| PHE | CG | A | 302 | 294 | 213 | 371 | 9 |
| PHE | CD1 | A | 302 | 303 | 204 | 365 | 11 |
| PHE | CD2 | A | 302 | 296 | 227 | 369 | 11 |
| PHE | CE1 | A | 302 | 314 | 209 | 358 | 11 |
| PHE | CE2 | A | 302 | 307 | 232 | 361 | 13 |
| PHE | CZ | A | 302 | 316 | 222 | 355 | 13 |
| PHE | C | A | 302 | 295 | 216 | 400 | 8 |
| PHE | O | A | 302 | 308 | 216 | 401 | 7 |
| GLU | N | A | 303 | 288 | 226 | 404 | 8 |
| GLU | CA | A | 303 | 294 | 238 | 411 | 8 |
| GLU | CB | A | 303 | 283 | 248 | 414 | 9 |
| GLU | CG | A | 303 | 278 | 255 | 402 | 10 |
| GLU | CD | A | 303 | 266 | 263 | 404 | 13 |
| GLU | OE1 | A | 303 | 262 | 271 | 395 | 16 |
| GLU | OE2 | A | 303 | 260 | 263 | 415 | 15 |
| GLU | C | A | 303 | 302 | 234 | 423 | 8 |
| GLU | O | A | 303 | 313 | 239 | 425 | 10 |
| ALA | N | A | 304 | 297 | 225 | 431 | 5 |
| ALA | CA | A | 304 | 304 | 221 | 443 | 7 |
| ALA | CB | A | 304 | 294 | 213 | 452 | 10 |
| ALA | C | A | 304 | 316 | 212 | 440 | 8 |
| ALA | O | A | 304 | 327 | 213 | 445 | 8 |
| ALA | N | A | 305 | 314 | 203 | 430 | 8 |
| ALA | CA | A | 305 | 325 | 194 | 426 | 9 |
| ALA | CB | A | 305 | 319 | 184 | 415 | 8 |
| ALA | C | A | 305 | 337 | 202 | 420 | 8 |
| ALA | O | A | 305 | 348 | 199 | 423 | 8 |
| VAL | N | A | 306 | 334 | 211 | 411 | 8 |

TABLE 2-continued

Structure Coordinates for BACE complexed to Inhibitor

| | | | | | | | |
|---|---|---|---|---|---|---|---|
| VAL | CA | A | 306 | 345 | 219 | 405 | 11 |
| VAL | CB | A | 306 | 340 | 228 | 394 | 14 |
| VAL | CG1 | A | 306 | 330 | 238 | 400 | 17 |
| VAL | CG2 | A | 306 | 351 | 236 | 388 | 19 |
| VAL | C | A | 306 | 352 | 227 | 416 | 9 |
| VAL | O | A | 306 | 365 | 228 | 415 | 9 |
| LYS | N | A | 307 | 345 | 232 | 425 | 10 |
| LYS | CA | A | 307 | 352 | 240 | 436 | 9 |
| LYS | CB | A | 307 | 341 | 246 | 445 | 10 |
| LYS | CG | A | 307 | 348 | 255 | 456 | 11 |
| LYS | CD | A | 307 | 337 | 261 | 465 | 13 |
| LYS | CE | A | 307 | 344 | 270 | 476 | 16 |
| LYS | NZ | A | 307 | 334 | 277 | 485 | 17 |
| LYS | C | A | 307 | 361 | 231 | 444 | 9 |
| LYS | O | A | 307 | 372 | 235 | 447 | 8 |
| SER | N | A | 308 | 357 | 219 | 446 | 8 |
| SER | CA | A | 308 | 365 | 209 | 454 | 6 |
| SER | CB | A | 308 | 357 | 197 | 458 | 8 |
| SER | OG | A | 308 | 364 | 188 | 466 | 10 |
| SER | C | A | 308 | 377 | 204 | 445 | 6 |
| SER | O | A | 308 | 388 | 202 | 450 | 7 |
| ILE | N | A | 309 | 374 | 201 | 432 | 7 |
| ILE | CA | A | 309 | 385 | 197 | 424 | 5 |
| ILE | CB | A | 309 | 379 | 192 | 410 | 5 |
| ILE | CG2 | A | 309 | 391 | 188 | 401 | 5 |
| ILE | CG1 | A | 309 | 370 | 180 | 413 | 7 |
| ILE | CD1 | A | 309 | 362 | 175 | 401 | 6 |
| ILE | C | A | 309 | 395 | 208 | 422 | 6 |
| ILE | O | A | 309 | 407 | 205 | 421 | 7 |
| LYS | N | A | 310 | 391 | 220 | 421 | 7 |
| LYS | CA | A | 310 | 400 | 231 | 420 | 8 |
| LYS | CB | A | 310 | 392 | 244 | 418 | 8 |
| LYS | CG | A | 310 | 386 | 247 | 405 | 11 |
| LYS | CD | A | 310 | 378 | 260 | 405 | 13 |
| LYS | CE | A | 310 | 373 | 264 | 391 | 14 |
| LYS | NZ | A | 310 | 365 | 277 | 392 | 17 |
| LYS | C | A | 310 | 409 | 232 | 432 | 8 |
| LYS | O | A | 310 | 421 | 234 | 431 | 10 |
| ALA | N | A | 311 | 402 | 231 | 444 | 8 |
| ALA | CA | A | 311 | 410 | 232 | 456 | 9 |
| ALA | CB | A | 311 | 400 | 231 | 468 | 8 |
| ALA | C | A | 311 | 420 | 220 | 458 | 9 |
| ALA | O | A | 311 | 431 | 223 | 462 | 9 |
| ALA | N | A | 312 | 417 | 208 | 453 | 8 |
| ALA | CA | A | 312 | 429 | 197 | 454 | 7 |
| ALA | CB | A | 312 | 418 | 184 | 451 | 7 |
| ALA | C | A | 312 | 438 | 199 | 445 | 8 |
| ALA | O | A | 312 | 449 | 194 | 448 | 9 |
| SER | N | A | 313 | 436 | 205 | 433 | 8 |
| SER | CA | A | 313 | 446 | 207 | 423 | 8 |
| SER | CB | A | 313 | 440 | 204 | 409 | 9 |
| SER | OG | A | 313 | 430 | 213 | 406 | 10 |
| SER | C | A | 313 | 452 | 221 | 423 | 9 |
| SER | O | A | 313 | 458 | 225 | 414 | 10 |
| SER | N | A | 314 | 449 | 228 | 434 | 10 |
| SER | CA | A | 314 | 454 | 242 | 435 | 12 |
| SER | CB | A | 314 | 449 | 248 | 449 | 12 |
| SER | OG | A | 314 | 457 | 243 | 459 | 15 |
| SER | C | A | 314 | 468 | 245 | 433 | 13 |
| SER | O | A | 314 | 472 | 257 | 432 | 13 |
| THR | N | A | 315 | 477 | 236 | 433 | 9 |
| THR | CA | A | 315 | 491 | 239 | 431 | 13 |
| THR | CB | A | 315 | 501 | 227 | 434 | 14 |
| THR | OG1 | A | 315 | 497 | 216 | 427 | 15 |
| THR | CG2 | A | 315 | 500 | 224 | 449 | 15 |
| THR | C | A | 315 | 494 | 243 | 416 | 13 |
| THR | O | A | 315 | 504 | 248 | 413 | 12 |
| GLU | N | A | 316 | 484 | 241 | 408 | 12 |
| GLU | CA | A | 316 | 484 | 245 | 394 | 15 |
| GLU | CB | A | 316 | 485 | 233 | 385 | 20 |
| GLU | CG | A | 316 | 486 | 236 | 370 | 28 |
| GLU | CD | A | 316 | 500 | 236 | 365 | 33 |
| GLU | OE1 | A | 316 | 508 | 243 | 370 | 36 |
| GLU | OE2 | A | 316 | 502 | 228 | 355 | 34 |
| GLU | C | A | 316 | 471 | 253 | 391 | 15 |
| GLU | O | A | 316 | 460 | 248 | 395 | 15 |
| LYS | N | A | 317 | 472 | 264 | 385 | 11 |
| LYS | CA | A | 317 | 461 | 272 | 381 | 14 |
| LYS | CB | A | 317 | 464 | 287 | 383 | 15 |
| LYS | CG | A | 317 | 452 | 297 | 382 | 22 |
| LYS | CD | A | 317 | 443 | 295 | 394 | 27 |
| LYS | CE | A | 317 | 432 | 306 | 395 | 30 |
| LYS | NZ | A | 317 | 424 | 305 | 408 | 32 |
| LYS | C | A | 317 | 456 | 270 | 367 | 11 |
| LYS | O | A | 317 | 465 | 271 | 358 | 11 |
| PHE | N | A | 318 | 444 | 267 | 364 | 12 |
| PHE | CA | A | 318 | 439 | 264 | 351 | 11 |
| PHE | CB | A | 318 | 432 | 250 | 350 | 12 |
| PHE | CG | A | 318 | 441 | 239 | 354 | 9 |
| PHE | CD1 | A | 318 | 442 | 235 | 367 | 12 |
| PHE | CD2 | A | 318 | 449 | 233 | 344 | 15 |
| PHE | CE1 | A | 318 | 451 | 225 | 371 | 13 |
| PHE | CE2 | A | 318 | 458 | 223 | 348 | 15 |
| PHE | CZ | A | 318 | 459 | 219 | 361 | 12 |
| PHE | C | A | 318 | 428 | 275 | 348 | 13 |
| PHE | O | A | 318 | 421 | 280 | 356 | 14 |
| PRO | N | A | 319 | 428 | 279 | 335 | 14 |
| PRO | CD | A | 319 | 436 | 274 | 324 | 16 |
| PRO | CA | A | 319 | 419 | 289 | 330 | 16 |
| PRO | CB | A | 319 | 423 | 291 | 315 | 15 |
| PRO | CG | A | 319 | 428 | 278 | 312 | 19 |
| PRO | C | A | 319 | 404 | 285 | 331 | 15 |
| PRO | O | A | 319 | 401 | 273 | 331 | 12 |
| ASP | N | A | 320 | 395 | 295 | 332 | 12 |
| ASP | CA | A | 320 | 381 | 292 | 333 | 13 |
| ASP | CB | A | 320 | 373 | 305 | 334 | 18 |
| ASP | CG | A | 320 | 376 | 314 | 345 | 22 |
| ASP | OD1 | A | 320 | 380 | 308 | 356 | 20 |
| ASP | OD2 | A | 320 | 374 | 326 | 344 | 23 |
| ASP | C | A | 320 | 376 | 283 | 322 | 12 |
| ASP | O | A | 320 | 368 | 274 | 324 | 13 |
| GLY | N | A | 321 | 382 | 285 | 310 | 12 |
| GLY | CA | A | 321 | 378 | 278 | 298 | 13 |
| GLY | C | A | 321 | 380 | 263 | 300 | 13 |
| GLY | O | A | 321 | 373 | 254 | 294 | 13 |
| PHE | N | A | 322 | 390 | 259 | 308 | 10 |
| PHE | CA | A | 322 | 393 | 245 | 310 | 9 |
| PHE | CB | A | 322 | 407 | 244 | 318 | 10 |
| PHE | CG | A | 322 | 410 | 230 | 323 | 7 |
| PHE | CD1 | A | 322 | 413 | 220 | 314 | 10 |
| PHE | CD2 | A | 322 | 408 | 227 | 336 | 8 |
| PHE | CE1 | A | 322 | 415 | 207 | 319 | 11 |
| PHE | CE2 | A | 322 | 411 | 214 | 341 | 9 |
| PHE | CZ | A | 322 | 414 | 204 | 332 | 9 |
| PHE | C | A | 322 | 382 | 239 | 319 | 10 |
| PHE | O | A | 322 | 377 | 228 | 316 | 8 |
| TRP | N | A | 323 | 379 | 246 | 330 | 8 |
| TRP | CA | A | 323 | 369 | 241 | 339 | 9 |
| TRP | CB | A | 323 | 368 | 249 | 352 | 10 |
| TRP | CG | A | 323 | 381 | 248 | 360 | 10 |
| TRP | CD2 | A | 323 | 387 | 236 | 366 | 10 |
| TRP | CE2 | A | 323 | 399 | 240 | 372 | 11 |
| TRP | CE3 | A | 323 | 382 | 223 | 368 | 9 |
| TRP | CD1 | A | 323 | 390 | 258 | 361 | 10 |
| TRP | NE1 | A | 323 | 401 | 253 | 369 | 10 |
| TRP | CZ2 | A | 323 | 407 | 231 | 379 | 10 |
| TRP | CZ3 | A | 323 | 390 | 214 | 375 | 11 |
| TRP | CH2 | A | 323 | 402 | 218 | 380 | 11 |
| TRP | C | A | 323 | 355 | 240 | 333 | 7 |
| TRP | O | A | 323 | 346 | 233 | 337 | 8 |
| LEU | N | A | 324 | 353 | 248 | 322 | 9 |
| LEU | CA | A | 324 | 340 | 248 | 315 | 10 |
| LEU | CB | A | 324 | 338 | 261 | 307 | 14 |
| LEU | CG | A | 324 | 335 | 273 | 316 | 18 |
| LEU | CD1 | A | 324 | 333 | 286 | 307 | 19 |
| LEU | CD2 | A | 324 | 322 | 271 | 324 | 21 |
| LEU | C | A | 324 | 340 | 236 | 304 | 11 |
| LEU | O | A | 324 | 330 | 235 | 297 | 10 |
| GLY | N | A | 325 | 351 | 229 | 303 | 8 |
| GLY | CA | A | 325 | 352 | 218 | 294 | 10 |
| GLY | C | A | 325 | 354 | 222 | 280 | 13 |
| GLY | O | A | 325 | 353 | 214 | 270 | 10 |
| GLU | N | A | 326 | 356 | 235 | 278 | 14 |
| GLU | CA | A | 326 | 358 | 241 | 264 | 15 |

TABLE 2-continued

Structure Coordinates for BACE complexed to Inhibitor

| | | | | | | | |
|---|---|---|---|---|---|---|---|
| GLU | CB | A | 326 | 352 | 255 | 264 | 16 |
| GLU | CG | A | 326 | 337 | 256 | 267 | 20 |
| GLU | CD | A | 326 | 333 | 270 | 270 | 24 |
| GLU | OE1 | A | 326 | 320 | 272 | 271 | 28 |
| GLU | OE2 | A | 326 | 341 | 279 | 270 | 26 |
| GLU | C | A | 326 | 372 | 241 | 259 | 16 |
| GLU | O | A | 326 | 374 | 239 | 247 | 18 |
| GLN | N | A | 327 | 382 | 244 | 267 | 15 |
| GLN | CA | A | 327 | 396 | 244 | 262 | 15 |
| GLN | CB | A | 327 | 402 | 258 | 264 | 21 |
| GLN | CG | A | 327 | 404 | 262 | 279 | 26 |
| GLN | CD | A | 327 | 408 | 277 | 280 | 29 |
| GLN | OE1 | A | 327 | 400 | 286 | 277 | 34 |
| GLN | NE2 | A | 327 | 420 | 279 | 284 | 32 |
| GLN | C | A | 327 | 405 | 234 | 268 | 14 |
| GLN | O | A | 327 | 404 | 230 | 280 | 13 |
| LEU | N | A | 328 | 415 | 229 | 260 | 12 |
| LEU | CA | A | 328 | 424 | 219 | 264 | 13 |
| LEU | CB | A | 328 | 429 | 211 | 252 | 18 |
| LEU | CG | A | 328 | 436 | 219 | 241 | 22 |
| LEU | CD1 | A | 328 | 450 | 224 | 246 | 24 |
| LEU | CD2 | A | 328 | 438 | 210 | 229 | 25 |
| LEU | C | A | 328 | 436 | 226 | 272 | 12 |
| LEU | O | A | 328 | 438 | 238 | 271 | 13 |
| VAL | N | A | 329 | 443 | 217 | 279 | 12 |
| VAL | CA | A | 329 | 455 | 222 | 287 | 13 |
| VAL | CB | A | 329 | 453 | 222 | 302 | 14 |
| VAL | CG1 | A | 329 | 443 | 233 | 306 | 16 |
| VAL | CG2 | A | 329 | 447 | 208 | 306 | 17 |
| VAL | C | A | 329 | 465 | 211 | 283 | 12 |
| VAL | O | A | 329 | 462 | 200 | 281 | 11 |
| CYS | N | A | 330 | 477 | 216 | 281 | 11 |
| CYS | CA | A | 330 | 488 | 207 | 277 | 11 |
| CYS | C | A | 330 | 500 | 207 | 287 | 12 |
| CYS | O | A | 330 | 502 | 217 | 294 | 12 |
| CYS | CB | A | 330 | 493 | 211 | 263 | 14 |
| CYS | SG | A | 330 | 481 | 211 | 250 | 14 |
| TRP | N | A | 331 | 508 | 196 | 286 | 11 |
| TRP | CA | A | 331 | 520 | 195 | 294 | 9 |
| TRP | CB | A | 331 | 517 | 185 | 306 | 10 |
| TRP | CG | A | 331 | 510 | 192 | 317 | 9 |
| TRP | CD2 | A | 331 | 496 | 191 | 320 | 9 |
| TRP | CE2 | A | 331 | 494 | 198 | 332 | 10 |
| TRP | CE3 | A | 331 | 486 | 184 | 314 | 9 |
| TRP | CD1 | A | 331 | 516 | 200 | 327 | 12 |
| TRP | NE1 | A | 331 | 506 | 204 | 336 | 12 |
| TRP | CZ2 | A | 331 | 481 | 199 | 338 | 10 |
| TRP | CZ3 | A | 331 | 473 | 184 | 320 | 11 |
| TRP | CH2 | A | 331 | 471 | 192 | 332 | 11 |
| TRP | C | A | 331 | 530 | 188 | 285 | 9 |
| TRP | O | A | 331 | 527 | 181 | 276 | 11 |
| GLN | N | A | 332 | 543 | 191 | 288 | 10 |
| GLN | CA | A | 332 | 554 | 185 | 280 | 13 |
| GLN | CB | A | 332 | 567 | 189 | 286 | 17 |
| GLN | CG | A | 332 | 579 | 181 | 280 | 24 |
| GLN | CD | A | 332 | 592 | 185 | 287 | 28 |
| GLN | OE1 | A | 332 | 603 | 179 | 284 | 33 |
| GLN | NE2 | A | 332 | 592 | 196 | 295 | 32 |
| GLN | C | A | 332 | 552 | 170 | 280 | 12 |
| GLN | O | A | 332 | 548 | 164 | 290 | 11 |
| ALA | N | A | 333 | 555 | 163 | 269 | 11 |
| ALA | CA | A | 333 | 554 | 149 | 268 | 10 |
| ALA | CB | A | 333 | 562 | 144 | 256 | 12 |
| ALA | C | A | 333 | 557 | 141 | 280 | 10 |
| ALA | O | A | 333 | 568 | 142 | 285 | 10 |
| GLY | N | A | 334 | 548 | 133 | 285 | 10 |
| GLY | CA | A | 334 | 550 | 124 | 296 | 10 |
| GLY | C | A | 334 | 550 | 131 | 310 | 9 |
| GLY | O | A | 334 | 551 | 124 | 320 | 10 |
| THR | N | A | 335 | 548 | 144 | 311 | 7 |
| THR | CA | A | 335 | 548 | 151 | 324 | 8 |
| THR | CB | A | 335 | 557 | 164 | 323 | 9 |
| THR | OG1 | A | 335 | 550 | 174 | 315 | 8 |
| THR | CG2 | A | 335 | 570 | 161 | 317 | 10 |
| THR | C | A | 335 | 535 | 155 | 330 | 9 |
| THR | O | A | 335 | 534 | 162 | 340 | 10 |
| THR | N | A | 336 | 524 | 149 | 324 | 8 |
| THR | CA | A | 336 | 511 | 152 | 330 | 9 |
| THR | CB | A | 336 | 500 | 144 | 324 | 9 |
| THR | OG1 | A | 336 | 500 | 146 | 309 | 9 |
| THR | CG2 | A | 336 | 486 | 148 | 329 | 8 |
| THR | C | A | 336 | 511 | 150 | 345 | 8 |
| THR | O | A | 336 | 514 | 138 | 349 | 8 |
| PRO | N | A | 337 | 508 | 160 | 353 | 9 |
| PRO | CD | A | 337 | 504 | 173 | 349 | 10 |
| PRO | CA | A | 337 | 508 | 158 | 368 | 9 |
| PRO | CB | A | 337 | 509 | 173 | 373 | 8 |
| PRO | CG | A | 337 | 500 | 180 | 363 | 10 |
| PRO | C | A | 337 | 496 | 151 | 374 | 8 |
| PRO | O | A | 337 | 488 | 157 | 382 | 7 |
| TRP | N | A | 338 | 493 | 139 | 370 | 6 |
| TRP | CA | A | 338 | 482 | 131 | 375 | 5 |
| TRP | CB | A | 338 | 484 | 117 | 371 | 6 |
| TRP | CG | A | 338 | 485 | 114 | 357 | 5 |
| TRP | CD2 | A | 338 | 475 | 116 | 347 | 6 |
| TRP | CE2 | A | 338 | 480 | 113 | 334 | 7 |
| TRP | CE3 | A | 338 | 461 | 121 | 348 | 6 |
| TRP | CD1 | A | 338 | 496 | 109 | 350 | 8 |
| TRP | NE1 | A | 338 | 493 | 108 | 337 | 9 |
| TRP | CZ2 | A | 338 | 473 | 114 | 323 | 8 |
| TRP | CZ3 | A | 338 | 454 | 122 | 336 | 6 |
| TRP | CH2 | A | 338 | 460 | 118 | 323 | 7 |
| TRP | C | A | 338 | 480 | 133 | 390 | 7 |
| TRP | O | A | 338 | 469 | 134 | 395 | 6 |
| ASN | N | A | 339 | 491 | 132 | 397 | 7 |
| ASN | CA | A | 339 | 491 | 132 | 412 | 7 |
| ASN | CB | A | 339 | 505 | 130 | 418 | 7 |
| ASN | CG | A | 339 | 513 | 142 | 417 | 8 |
| ASN | OD1 | A | 339 | 514 | 150 | 427 | 8 |
| ASN | ND2 | A | 339 | 520 | 144 | 406 | 9 |
| ASN | C | A | 339 | 484 | 145 | 418 | 7 |
| ASN | O | A | 339 | 480 | 144 | 430 | 7 |
| ILE | N | A | 340 | 484 | 156 | 411 | 5 |
| ILE | CA | A | 340 | 478 | 168 | 417 | 6 |
| ILE | CB | A | 340 | 484 | 181 | 411 | 6 |
| ILE | CG2 | A | 340 | 499 | 181 | 411 | 7 |
| ILE | CG1 | A | 340 | 479 | 183 | 397 | 7 |
| ILE | CD1 | A | 340 | 482 | 197 | 391 | 10 |
| ILE | C | A | 340 | 463 | 168 | 416 | 7 |
| ILE | O | A | 340 | 456 | 176 | 423 | 6 |
| PHE | N | A | 341 | 458 | 160 | 407 | 7 |
| PHE | CA | A | 341 | 444 | 159 | 405 | 7 |
| PHE | CB | A | 341 | 440 | 155 | 391 | 7 |
| PHE | CG | A | 341 | 441 | 167 | 381 | 9 |
| PHE | CD1 | A | 341 | 431 | 176 | 380 | 9 |
| PHE | CD2 | A | 341 | 453 | 169 | 374 | 8 |
| PHE | CE1 | A | 341 | 432 | 187 | 372 | 9 |
| PHE | CE2 | A | 341 | 454 | 180 | 366 | 10 |
| PHE | CZ | A | 341 | 443 | 189 | 364 | 11 |
| PHE | C | A | 341 | 438 | 148 | 414 | 6 |
| PHE | O | A | 341 | 444 | 137 | 416 | 7 |
| PRO | N | A | 342 | 426 | 150 | 420 | 4 |
| PRO | CD | A | 342 | 418 | 163 | 419 | 5 |
| PRO | CA | A | 342 | 420 | 141 | 429 | 6 |
| PRO | CB | A | 342 | 411 | 150 | 437 | 7 |
| PRO | CG | A | 342 | 406 | 159 | 427 | 7 |
| PRO | C | A | 342 | 412 | 129 | 423 | 7 |
| PRO | O | A | 342 | 409 | 130 | 411 | 8 |
| VAL | N | A | 343 | 410 | 119 | 430 | 8 |
| VAL | CA | A | 343 | 402 | 108 | 425 | 6 |
| VAL | CB | A | 343 | 406 | 94 | 432 | 7 |
| VAL | CG1 | A | 343 | 420 | 91 | 429 | 9 |
| VAL | CG2 | A | 343 | 403 | 95 | 447 | 10 |
| VAL | C | A | 343 | 388 | 112 | 429 | 7 |
| VAL | O | A | 343 | 386 | 120 | 438 | 7 |
| ILE | N | A | 344 | 378 | 106 | 422 | 5 |
| ILE | CA | A | 344 | 364 | 109 | 425 | 6 |
| ILE | CB | A | 344 | 357 | 116 | 413 | 7 |
| ILE | CG2 | A | 344 | 343 | 118 | 415 | 9 |
| ILE | CG1 | A | 344 | 364 | 129 | 410 | 5 |
| ILE | CD1 | A | 344 | 360 | 136 | 397 | 7 |
| ILE | C | A | 344 | 357 | 96 | 428 | 8 |
| ILE | O | A | 344 | 357 | 87 | 420 | 9 |
| SER | N | A | 345 | 349 | 96 | 439 | 7 |

TABLE 2-continued

Structure Coordinates for BACE complexed to Inhibitor

| | | | | | | | |
|---|---|---|---|---|---|---|---|
| SER | CA | A | 345 | 342 | 84 | 443 | 9 |
| SER | CB | A | 345 | 346 | 79 | 457 | 9 |
| SER | OG | A | 345 | 360 | 75 | 457 | 9 |
| SER | C | A | 345 | 327 | 87 | 443 | 8 |
| SER | O | A | 345 | 322 | 97 | 449 | 7 |
| LEU | N | A | 346 | 319 | 78 | 437 | 6 |
| LEU | CA | A | 346 | 305 | 79 | 437 | 8 |
| LEU | CB | A | 346 | 300 | 78 | 423 | 7 |
| LEU | CG | A | 346 | 304 | 89 | 413 | 9 |
| LEU | CD1 | A | 346 | 297 | 87 | 399 | 9 |
| LEU | CD2 | A | 346 | 301 | 103 | 418 | 10 |
| LEU | C | A | 346 | 300 | 66 | 444 | 7 |
| LEU | O | A | 346 | 303 | 55 | 441 | 7 |
| TYR | N | A | 347 | 292 | 69 | 455 | 7 |
| TYR | CA | A | 347 | 287 | 57 | 463 | 7 |
| TYR | CB | A | 347 | 285 | 61 | 477 | 7 |
| TYR | CG | A | 347 | 298 | 61 | 485 | 6 |
| TYR | CD1 | A | 347 | 308 | 71 | 482 | 7 |
| TYR | CE1 | A | 347 | 320 | 72 | 490 | 8 |
| TYR | CD2 | A | 347 | 301 | 52 | 495 | 9 |
| TYR | CE2 | A | 347 | 313 | 52 | 502 | 9 |
| TYR | CZ | A | 347 | 322 | 62 | 499 | 10 |
| TYR | OH | A | 347 | 334 | 63 | 507 | 9 |
| TYR | C | A | 347 | 273 | 55 | 457 | 6 |
| TYR | O | A | 347 | 265 | 64 | 455 | 8 |
| LEU | N | A | 348 | 270 | 42 | 454 | 8 |
| LEU | CA | A | 348 | 257 | 38 | 448 | 8 |
| LEU | CB | A | 348 | 260 | 30 | 435 | 8 |
| LEU | CG | A | 348 | 267 | 38 | 424 | 10 |
| LEU | CD1 | A | 348 | 271 | 29 | 413 | 11 |
| LEU | CD2 | A | 348 | 258 | 49 | 419 | 16 |
| LEU | C | A | 348 | 250 | 29 | 458 | 7 |
| LEU | O | A | 348 | 256 | 22 | 466 | 10 |
| MET | N | A | 349 | 237 | 29 | 457 | 10 |
| MET | CA | A | 349 | 228 | 21 | 466 | 12 |
| MET | CB | A | 349 | 213 | 24 | 462 | 15 |
| MET | CG | A | 349 | 204 | 15 | 470 | 19 |
| MET | SD | A | 349 | 187 | 19 | 465 | 26 |
| MET | CE | A | 349 | 185 | 35 | 472 | 18 |
| MET | C | A | 349 | 231 | 6 | 463 | 13 |
| MET | O | A | 349 | 233 | 2 | 451 | 13 |
| GLY | N | A | 350 | 233 | -2 | 474 | 11 |
| GLY | CA | A | 350 | 235 | -16 | 472 | 11 |
| GLY | C | A | 350 | 223 | -24 | 471 | 13 |
| GLY | O | A | 350 | 212 | -18 | 471 | 13 |
| GLU | N | A | 351 | 224 | -37 | 469 | 12 |
| GLU | CA | A | 351 | 212 | -46 | 467 | 17 |
| GLU | CB | A | 361 | 216 | -58 | 459 | 17 |
| GLU | CG | A | 351 | 216 | -55 | 444 | 18 |
| GLU | CD | A | 351 | 213 | -67 | 436 | 20 |
| GLU | OE1 | A | 351 | 221 | -77 | 436 | 18 |
| GLU | OE2 | A | 351 | 202 | -68 | 430 | 22 |
| GLU | C | A | 351 | 207 | -50 | 481 | 17 |
| GLU | O | A | 351 | 195 | -54 | 482 | 18 |
| VAL | N | A | 352 | 215 | -49 | 491 | 18 |
| VAL | CA | A | 352 | 211 | -52 | 505 | 21 |
| VAL | CB | A | 352 | 223 | -59 | 513 | 23 |
| VAL | CG1 | A | 352 | 219 | -62 | 527 | 24 |
| VAL | CG2 | A | 352 | 227 | -72 | 506 | 25 |
| VAL | C | A | 352 | 207 | -40 | 512 | 21 |
| VAL | O | A | 352 | 212 | -29 | 510 | 20 |
| THR | N | A | 353 | 196 | -41 | 520 | 20 |
| THR | CA | A | 353 | 191 | -30 | 528 | 21 |
| THR | CB | A | 353 | 180 | -34 | 538 | 23 |
| THR | OG1 | A | 353 | 170 | -42 | 531 | 27 |
| THR | CG2 | A | 353 | 173 | -22 | 544 | 24 |
| THR | C | A | 353 | 202 | -22 | 536 | 18 |
| THR | O | A | 353 | 210 | -29 | 542 | 17 |
| ASN | N | A | 354 | 202 | -9 | 535 | 21 |
| ASN | CA | A | 354 | 211 | -1 | 542 | 20 |
| ASN | CB | A | 354 | 210 | -2 | 557 | 22 |
| ASN | CG | A | 354 | 196 | 2 | 562 | 23 |
| ASN | OD1 | A | 354 | 191 | 13 | 558 | 25 |
| ASN | ND2 | A | 354 | 190 | -6 | 571 | 23 |
| ASN | C | A | 354 | 226 | -3 | 538 | 20 |
| ASN | O | A | 354 | 235 | 0 | 546 | 19 |
| GLN | N | A | 355 | 228 | -8 | 527 | 18 |
| GLN | CA | A | 355 | 242 | -11 | 522 | 19 |
| GLN | CB | A | 355 | 244 | -26 | 520 | 24 |
| GLN | CG | A | 355 | 258 | -31 | 521 | 30 |
| GLN | CD | A | 355 | 259 | -46 | 521 | 32 |
| GLN | OE1 | A | 355 | 258 | -52 | 510 | 35 |
| GLN | NE2 | A | 355 | 262 | -52 | 532 | 35 |
| GLN | C | A | 355 | 245 | -4 | 509 | 17 |
| GLN | O | A | 355 | 236 | -3 | 500 | 13 |
| SER | N | A | 356 | 257 | 1 | 508 | 14 |
| SER | CA | A | 356 | 261 | 8 | 496 | 12 |
| SER | CB | A | 356 | 261 | 24 | 498 | 14 |
| SER | OG | A | 356 | 270 | 28 | 507 | 13 |
| SER | C | A | 356 | 276 | 4 | 493 | 13 |
| SER | O | A | 356 | 282 | -2 | 500 | 12 |
| PHE | N | A | 357 | 280 | 8 | 481 | 10 |
| PHE | CA | A | 357 | 294 | 5 | 476 | 9 |
| PHE | CB | A | 357 | 294 | -8 | 468 | 8 |
| PHE | CG | A | 357 | 288 | -7 | 455 | 10 |
| PHE | CD1 | A | 357 | 295 | -3 | 443 | 8 |
| PHE | CD2 | A | 357 | 274 | -9 | 453 | 10 |
| PHE | CE1 | A | 357 | 288 | -2 | 431 | 9 |
| PHE | CE2 | A | 357 | 268 | -9 | 441 | 11 |
| PHE | CZ | A | 357 | 275 | -5 | 430 | 8 |
| PHE | C | A | 357 | 298 | 17 | 469 | 8 |
| PHE | O | A | 357 | 290 | 26 | 465 | 8 |
| ARG | N | A | 358 | 311 | 18 | 466 | 8 |
| ARG | CA | A | 358 | 316 | 30 | 459 | 8 |
| ARG | CB | A | 358 | 324 | 39 | 468 | 7 |
| ARG | CG | A | 358 | 338 | 33 | 473 | 9 |
| ARG | CD | A | 358 | 344 | 41 | 483 | 9 |
| ARG | NE | A | 358 | 357 | 35 | 487 | 10 |
| ARG | CZ | A | 358 | 364 | 39 | 498 | 13 |
| ARG | NH1 | A | 358 | 359 | 48 | 507 | 12 |
| ARG | NH2 | A | 358 | 376 | 33 | 501 | 14 |
| ARG | C | A | 358 | 325 | 26 | 447 | 6 |
| ARG | O | A | 358 | 331 | 16 | 446 | 7 |
| ILE | N | A | 359 | 324 | 35 | 437 | 7 |
| ILE | CA | A | 359 | 332 | 33 | 425 | 7 |
| ILE | CB | A | 359 | 324 | 32 | 412 | 7 |
| ILE | CG2 | A | 359 | 314 | 20 | 413 | 9 |
| ILE | CG1 | A | 359 | 316 | 45 | 409 | 9 |
| ILE | CD1 | A | 359 | 308 | 45 | 396 | 11 |
| ILE | C | A | 359 | 341 | 46 | 424 | 6 |
| ILE | O | A | 359 | 336 | 57 | 427 | 8 |
| THR | N | A | 360 | 354 | 44 | 422 | 5 |
| THR | CA | A | 360 | 363 | 55 | 422 | 6 |
| THR | CB | A | 360 | 374 | 53 | 433 | 8 |
| THR | OG1 | A | 360 | 367 | 52 | 446 | 8 |
| THR | CG2 | A | 360 | 383 | 64 | 434 | 9 |
| THR | C | A | 360 | 371 | 56 | 409 | 6 |
| THR | O | A | 360 | 377 | 46 | 404 | 6 |
| ILE | N | A | 361 | 371 | 68 | 403 | 6 |
| ILE | CA | A | 361 | 378 | 70 | 390 | 7 |
| ILE | CB | A | 361 | 369 | 76 | 380 | 8 |
| ILE | CG2 | A | 361 | 357 | 66 | 376 | 10 |
| ILE | CG1 | A | 361 | 363 | 90 | 384 | 9 |
| ILE | CD1 | A | 361 | 356 | 97 | 373 | 11 |
| ILE | C | A | 361 | 390 | 79 | 393 | 7 |
| ILE | O | A | 361 | 390 | 86 | 403 | 5 |
| LEU | N | A | 362 | 399 | 79 | 383 | 6 |
| LEU | CA | A | 362 | 411 | 87 | 384 | 6 |
| LEU | CB | A | 362 | 423 | 79 | 381 | 6 |
| LEU | CG | A | 362 | 424 | 65 | 388 | 8 |
| LEU | CD1 | A | 362 | 436 | 58 | 381 | 7 |
| LEU | CD2 | A | 362 | 426 | 67 | 403 | 8 |
| LEU | C | A | 362 | 410 | 98 | 374 | 6 |
| LEU | O | A | 362 | 402 | 99 | 365 | 7 |
| PRO | N | A | 363 | 420 | 108 | 375 | 6 |
| PRO | CD | A | 363 | 429 | 111 | 385 | 8 |
| PRO | CA | A | 363 | 419 | 119 | 365 | 6 |
| PRO | CB | A | 363 | 431 | 128 | 370 | 7 |
| PRO | CG | A | 363 | 440 | 119 | 378 | 6 |
| PRO | C | A | 363 | 422 | 113 | 351 | 9 |
| PRO | O | A | 363 | 419 | 119 | 341 | 7 |
| GLN | N | A | 364 | 428 | 101 | 351 | 7 |
| GLN | CA | A | 364 | 430 | 94 | 338 | 6 |
| GLN | CB | A | 364 | 439 | 82 | 340 | 8 |

TABLE 2-continued

Structure Coordinates for BACE complexed to Inhibitor

| | | | | | | | |
|---|---|---|---|---|---|---|---|
| GLN | CG | A | 364 | 454 | 84 | 341 | 6 |
| GLN | CD | A | 364 | 458 | 86 | 355 | 9 |
| GLN | OE1 | A | 364 | 450 | 89 | 364 | 6 |
| GLN | NE2 | A | 364 | 471 | 83 | 358 | 7 |
| GLN | C | A | 364 | 417 | 91 | 331 | 7 |
| GLN | O | A | 364 | 417 | 88 | 319 | 8 |
| GLN | N | A | 365 | 406 | 91 | 339 | 7 |
| GLN | CA | A | 365 | 393 | 89 | 333 | 8 |
| GLN | CB | A | 365 | 384 | 81 | 343 | 6 |
| GLN | CG | A | 365 | 385 | 66 | 342 | 6 |
| GLN | CD | A | 365 | 398 | 61 | 348 | 9 |
| GLN | OE1 | A | 365 | 406 | 55 | 340 | 10 |
| GLN | NE2 | A | 365 | 401 | 63 | 360 | 5 |
| GLN | C | A | 365 | 386 | 102 | 330 | 7 |
| GLN | O | A | 365 | 380 | 104 | 319 | 8 |
| TYR | N | A | 366 | 386 | 112 | 339 | 7 |
| TYR | CA | A | 366 | 379 | 124 | 337 | 6 |
| TYR | CB | A | 366 | 373 | 130 | 350 | 7 |
| TYR | CG | A | 366 | 383 | 134 | 361 | 7 |
| TYR | CD1 | A | 366 | 389 | 147 | 360 | 7 |
| TYR | CE1 | A | 366 | 397 | 151 | 370 | 6 |
| TYR | CD2 | A | 366 | 385 | 127 | 372 | 7 |
| TYR | CE2 | A | 366 | 393 | 131 | 383 | 6 |
| TYR | CZ | A | 366 | 399 | 144 | 382 | 6 |
| TYR | OH | A | 366 | 407 | 148 | 392 | 7 |
| TYR | C | A | 366 | 387 | 135 | 329 | 6 |
| TYR | O | A | 366 | 381 | 146 | 327 | 7 |
| LEU | N | A | 367 | 399 | 133 | 326 | 7 |
| LEU | CA | A | 367 | 407 | 142 | 318 | 5 |
| LEU | CB | A | 367 | 421 | 145 | 324 | 7 |
| LEU | CG | A | 367 | 421 | 152 | 337 | 6 |
| LEU | CD1 | A | 367 | 435 | 156 | 341 | 6 |
| LEU | CD2 | A | 367 | 412 | 165 | 336 | 8 |
| LEU | C | A | 367 | 408 | 135 | 304 | 8 |
| LEU | O | A | 367 | 415 | 125 | 303 | 8 |
| ARG | N | A | 368 | 400 | 140 | 294 | 6 |
| ARG | CA | A | 368 | 399 | 134 | 281 | 7 |
| ARG | CB | A | 368 | 386 | 137 | 275 | 7 |
| ARG | CG | A | 368 | 383 | 129 | 262 | 10 |
| ARG | CD | A | 368 | 368 | 131 | 258 | 9 |
| ARG | NE | A | 368 | 364 | 144 | 255 | 9 |
| ARG | CZ | A | 368 | 367 | 151 | 243 | 11 |
| ARG | NH1 | A | 368 | 374 | 144 | 234 | 11 |
| ARG | NH2 | A | 368 | 363 | 163 | 242 | 11 |
| ARG | C | A | 368 | 411 | 138 | 272 | 9 |
| ARG | O | A | 368 | 412 | 150 | 269 | 8 |
| PRO | N | A | 369 | 419 | 128 | 267 | 9 |
| PRO | CD | A | 369 | 419 | 114 | 271 | 10 |
| PRO | CA | A | 369 | 430 | 131 | 258 | 9 |
| PRO | CB | A | 369 | 436 | 118 | 256 | 11 |
| PRO | CG | A | 369 | 433 | 110 | 268 | 11 |
| PRO | C | A | 369 | 425 | 137 | 245 | 10 |
| PRO | O | A | 369 | 415 | 132 | 239 | 9 |
| VAL | N | A | 370 | 431 | 148 | 241 | 11 |
| VAL | CA | A | 370 | 428 | 155 | 228 | 13 |
| VAL | CB | A | 370 | 419 | 167 | 231 | 13 |
| VAL | CG1 | A | 370 | 406 | 163 | 237 | 13 |
| VAL | CG2 | A | 370 | 426 | 177 | 239 | 16 |
| VAL | C | A | 370 | 441 | 159 | 222 | 16 |
| VAL | O | A | 370 | 451 | 162 | 228 | 17 |
| GLU | N | A | 371 | 441 | 159 | 208 | 20 |
| GLU | CA | A | 371 | 453 | 163 | 201 | 28 |
| GLU | CB | A | 371 | 451 | 159 | 186 | 31 |
| GLU | CG | A | 371 | 463 | 162 | 177 | 37 |
| GLU | CD | A | 371 | 476 | 156 | 183 | 40 |
| GLU | OE1 | A | 371 | 481 | 161 | 194 | 42 |
| GLU | OE2 | A | 371 | 481 | 146 | 178 | 44 |
| GLU | C | A | 371 | 455 | 178 | 202 | 31 |
| GLU | O | A | 371 | 445 | 186 | 201 | 29 |
| ASP | N | A | 372 | 467 | 182 | 203 | 36 |
| ASP | CA | A | 372 | 471 | 196 | 204 | 42 |
| ASP | CB | A | 372 | 486 | 198 | 207 | 44 |
| ASP | CG | A | 372 | 490 | 211 | 212 | 46 |
| ASP | OD1 | A | 372 | 484 | 221 | 206 | 47 |
| ASP | OD2 | A | 372 | 498 | 212 | 221 | 47 |
| ASP | C | A | 372 | 467 | 203 | 191 | 45 |
| ASP | O | A | 372 | 469 | 196 | 180 | 44 |
| VAL | N | A | 373 | 462 | 215 | 191 | 49 |
| VAL | CA | A | 373 | 458 | 222 | 179 | 51 |
| VAL | CB | A | 373 | 453 | 236 | 183 | 53 |
| VAL | CG1 | A | 373 | 448 | 243 | 170 | 53 |
| VAL | CG2 | A | 373 | 441 | 235 | 192 | 53 |
| VAL | C | A | 373 | 471 | 224 | 170 | 53 |
| VAL | O | A | 373 | 470 | 227 | 159 | 54 |
| ALA | N | A | 374 | 482 | 221 | 176 | 53 |
| ALA | CA | A | 374 | 495 | 222 | 169 | 52 |
| ALA | CB | A | 374 | 505 | 231 | 176 | 53 |
| ALA | C | A | 374 | 501 | 208 | 166 | 52 |
| ALA | O | A | 374 | 512 | 207 | 162 | 54 |
| THR | N | A | 375 | 493 | 198 | 170 | 51 |
| THR | CA | A | 375 | 498 | 184 | 168 | 48 |
| THR | CB | A | 375 | 497 | 180 | 153 | 50 |
| THR | OG1 | A | 375 | 506 | 188 | 146 | 50 |
| THR | CG2 | A | 375 | 483 | 181 | 148 | 49 |
| THR | C | A | 375 | 512 | 182 | 173 | 46 |
| THR | O | A | 375 | 519 | 173 | 168 | 46 |
| SER | N | A | 376 | 515 | 189 | 184 | 41 |
| SER | CA | A | 376 | 529 | 188 | 190 | 35 |
| SER | CB | A | 376 | 531 | 199 | 200 | 35 |
| SER | OG | A | 376 | 521 | 199 | 210 | 33 |
| SER | C | A | 376 | 530 | 174 | 197 | 31 |
| SER | O | A | 376 | 521 | 166 | 197 | 32 |
| GLN | N | A | 377 | 541 | 173 | 204 | 25 |
| GLN | CA | A | 377 | 544 | 161 | 212 | 23 |
| GLN | CB | A | 377 | 558 | 157 | 212 | 25 |
| GLN | CG | A | 377 | 565 | 156 | 199 | 29 |
| GLN | CD | A | 377 | 579 | 150 | 199 | 28 |
| GLN | OE1 | A | 377 | 587 | 153 | 208 | 30 |
| GLN | NE2 | A | 377 | 581 | 141 | 190 | 30 |
| GLN | C | A | 377 | 538 | 162 | 226 | 19 |
| GLN | O | A | 377 | 540 | 153 | 235 | 18 |
| ASP | N | A | 378 | 532 | 173 | 229 | 16 |
| ASP | CA | A | 378 | 526 | 176 | 242 | 14 |
| ASP | CB | A | 378 | 521 | 190 | 243 | 14 |
| ASP | CG | A | 378 | 532 | 201 | 245 | 18 |
| ASP | OD1 | A | 378 | 544 | 197 | 245 | 16 |
| ASP | OD2 | A | 378 | 528 | 213 | 247 | 20 |
| ASP | C | A | 378 | 515 | 166 | 245 | 11 |
| ASP | O | A | 378 | 509 | 161 | 235 | 10 |
| ASP | N | A | 379 | 512 | 164 | 257 | 10 |
| ASP | CA | A | 379 | 501 | 155 | 261 | 9 |
| ASP | CB | A | 379 | 505 | 146 | 272 | 9 |
| ASP | CG | A | 379 | 514 | 134 | 268 | 9 |
| ASP | OD1 | A | 379 | 522 | 129 | 276 | 11 |
| ASP | OD2 | A | 379 | 513 | 131 | 256 | 12 |
| ASP | C | A | 379 | 490 | 165 | 266 | 9 |
| ASP | O | A | 379 | 492 | 172 | 276 | 9 |
| CYS | N | A | 380 | 479 | 166 | 259 | 9 |
| CYS | CA | A | 380 | 469 | 175 | 262 | 11 |
| CYS | C | A | 380 | 455 | 168 | 265 | 10 |
| CYS | O | A | 380 | 453 | 157 | 260 | 9 |
| CYS | CB | A | 380 | 466 | 185 | 250 | 10 |
| CYS | SG | A | 380 | 481 | 192 | 243 | 12 |
| TYR | N | A | 381 | 447 | 175 | 273 | 9 |
| TYR | CA | A | 381 | 434 | 170 | 277 | 9 |
| TYR | CB | A | 381 | 435 | 162 | 290 | 11 |
| TYR | CG | A | 381 | 447 | 154 | 291 | 10 |
| TYR | CD1 | A | 381 | 460 | 159 | 294 | 11 |
| TYR | CE1 | A | 381 | 471 | 152 | 296 | 12 |
| TYR | CD2 | A | 381 | 447 | 140 | 290 | 9 |
| TYR | CE2 | A | 381 | 458 | 132 | 291 | 11 |
| TYR | CZ | A | 381 | 470 | 138 | 294 | 9 |
| TYR | OH | A | 381 | 481 | 130 | 295 | 11 |
| TYR | C | A | 381 | 424 | 181 | 279 | 9 |
| TYR | O | A | 381 | 427 | 193 | 280 | 8 |
| LYS | N | A | 382 | 411 | 177 | 279 | 9 |
| LYS | CA | A | 382 | 400 | 186 | 282 | 8 |
| LYS | CB | A | 382 | 390 | 186 | 271 | 9 |
| LYS | CG | A | 382 | 393 | 196 | 260 | 11 |
| LYS | CD | A | 382 | 382 | 197 | 250 | 12 |
| LYS | CE | A | 382 | 386 | 207 | 238 | 14 |
| LYS | NZ | A | 382 | 375 | 208 | 228 | 18 |
| LYS | C | A | 382 | 393 | 180 | 295 | 8 |
| LYS | O | A | 382 | 394 | 168 | 297 | 9 |

TABLE 2-continued

Structure Coordinates for BACE complexed to Inhibitor

| | | | | | | | |
|---|---|---|---|---|---|---|---|
| PHE | N | A | 383 | 388 | 189 | 303 | 7 |
| PHE | CA | A | 383 | 381 | 185 | 315 | 6 |
| PHE | CB | A | 383 | 379 | 197 | 324 | 8 |
| PHE | CG | A | 383 | 373 | 194 | 337 | 6 |
| PHE | CD1 | A | 383 | 379 | 186 | 346 | 7 |
| PHE | CD2 | A | 383 | 361 | 201 | 341 | 7 |
| PHE | CE1 | A | 383 | 373 | 184 | 359 | 7 |
| PHE | CE2 | A | 383 | 356 | 199 | 354 | 7 |
| PHE | CZ | A | 383 | 362 | 190 | 363 | 6 |
| PHE | C | A | 383 | 368 | 179 | 311 | 8 |
| PHE | O | A | 383 | 359 | 186 | 305 | 8 |
| ALA | N | A | 384 | 366 | 166 | 313 | 7 |
| ALA | CA | A | 384 | 354 | 159 | 309 | 6 |
| ALA | CB | A | 384 | 358 | 145 | 303 | 6 |
| ALA | C | A | 384 | 343 | 157 | 319 | 8 |
| ALA | O | A | 384 | 336 | 147 | 320 | 8 |
| ILE | N | A | 385 | 341 | 167 | 327 | 7 |
| ILE | CA | A | 385 | 330 | 168 | 337 | 8 |
| ILE | CB | A | 385 | 335 | 168 | 351 | 7 |
| ILE | CG2 | A | 385 | 324 | 169 | 361 | 9 |
| ILE | CG1 | A | 385 | 344 | 156 | 354 | 8 |
| ILE | CD1 | A | 385 | 349 | 155 | 368 | 8 |
| ILE | C | A | 385 | 323 | 181 | 333 | 6 |
| ILE | O | A | 385 | 329 | 191 | 332 | 6 |
| SER | N | A | 386 | 310 | 180 | 332 | 6 |
| SER | CA | A | 386 | 302 | 193 | 328 | 7 |
| SER | CB | A | 386 | 301 | 194 | 313 | 9 |
| SER | OG | A | 386 | 294 | 182 | 308 | 9 |
| SER | C | A | 386 | 289 | 193 | 335 | 10 |
| SER | O | A | 386 | 284 | 182 | 340 | 9 |
| GLN | N | A | 387 | 282 | 204 | 336 | 10 |
| GLN | CA | A | 387 | 270 | 205 | 343 | 11 |
| GLN | CB | A | 387 | 267 | 219 | 348 | 17 |
| GLN | CG | A | 387 | 265 | 230 | 338 | 20 |
| GLN | CD | A | 387 | 260 | 243 | 344 | 23 |
| GLN | OE1 | A | 387 | 248 | 244 | 348 | 26 |
| GLN | NE2 | A | 387 | 269 | 253 | 346 | 24 |
| GLN | C | A | 387 | 258 | 200 | 334 | 9 |
| GLN | O | A | 387 | 259 | 201 | 321 | 13 |
| SER | N | A | 388 | 247 | 196 | 340 | 8 |
| SER | CA | A | 388 | 236 | 191 | 333 | 9 |
| SER | CB | A | 388 | 235 | 176 | 335 | 9 |
| SER | OG | A | 388 | 222 | 171 | 332 | 9 |
| SER | C | A | 388 | 223 | 198 | 339 | 13 |
| SER | O | A | 388 | 223 | 202 | 351 | 11 |
| SER | N | A | 389 | 213 | 198 | 331 | 11 |
| SER | CA | A | 389 | 200 | 204 | 336 | 13 |
| SER | CB | A | 389 | 195 | 215 | 326 | 15 |
| SER | OG | A | 389 | 193 | 210 | 313 | 17 |
| SER | C | A | 389 | 190 | 192 | 336 | 13 |
| SER | O | A | 389 | 178 | 194 | 339 | 13 |
| THR | N | A | 390 | 194 | 180 | 333 | 11 |
| THR | CA | A | 390 | 186 | 168 | 332 | 11 |
| THR | CB | A | 390 | 183 | 164 | 318 | 14 |
| THR | OG1 | A | 390 | 196 | 161 | 311 | 11 |
| THR | CG2 | A | 390 | 175 | 174 | 310 | 15 |
| THR | C | A | 390 | 191 | 157 | 341 | 9 |
| THR | O | A | 390 | 189 | 145 | 337 | 10 |
| GLY | N | A | 391 | 198 | 160 | 352 | 8 |
| GLY | CA | A | 391 | 203 | 150 | 360 | 9 |
| GLY | C | A | 391 | 217 | 145 | 358 | 10 |
| GLY | O | A | 391 | 224 | 150 | 349 | 10 |
| THR | N | A | 392 | 222 | 136 | 366 | 8 |
| THR | CA | A | 392 | 235 | 130 | 365 | 7 |
| THR | CB | A | 392 | 240 | 123 | 378 | 8 |
| THR | OG1 | A | 392 | 241 | 132 | 388 | 8 |
| THR | CG2 | A | 392 | 253 | 116 | 376 | 6 |
| THR | C | A | 392 | 236 | 121 | 353 | 7 |
| THR | O | A | 392 | 227 | 113 | 351 | 8 |
| VAL | N | A | 393 | 247 | 121 | 346 | 6 |
| VAL | CA | A | 393 | 249 | 112 | 335 | 7 |
| VAL | CB | A | 393 | 248 | 119 | 321 | 8 |
| VAL | CG1 | A | 393 | 250 | 108 | 310 | 7 |
| VAL | CG2 | A | 393 | 235 | 126 | 319 | 8 |
| VAL | C | A | 393 | 263 | 106 | 337 | 6 |
| VAL | O | A | 393 | 273 | 113 | 336 | 6 |
| MET | N | A | 394 | 263 | 93 | 340 | 8 |
| MET | CA | A | 394 | 275 | 86 | 341 | 8 |
| MET | CB | A | 394 | 274 | 74 | 351 | 8 |
| MET | CG | A | 394 | 271 | 79 | 365 | 10 |
| MET | SD | A | 394 | 265 | 66 | 376 | 17 |
| MET | CE | A | 394 | 279 | 55 | 376 | 16 |
| MET | C | A | 394 | 279 | 81 | 327 | 8 |
| MET | O | A | 394 | 275 | 70 | 323 | 9 |
| GLY | N | A | 395 | 286 | 90 | 320 | 6 |
| GLY | CA | A | 395 | 290 | 87 | 306 | 6 |
| GLY | C | A | 395 | 303 | 79 | 305 | 6 |
| GLY | O | A | 395 | 307 | 72 | 314 | 8 |
| ALA | N | A | 396 | 309 | 80 | 293 | 10 |
| ALA | CA | A | 396 | 321 | 73 | 290 | 14 |
| ALA | CB | A | 396 | 327 | 77 | 276 | 15 |
| ALA | C | A | 396 | 332 | 75 | 301 | 17 |
| ALA | O | A | 396 | 340 | 66 | 304 | 18 |
| VAL | N | A | 397 | 333 | 87 | 306 | 17 |
| VAL | CA | A | 397 | 342 | 91 | 316 | 19 |
| VAL | CB | A | 397 | 340 | 105 | 322 | 20 |
| VAL | CG1 | A | 397 | 347 | 107 | 335 | 20 |
| VAL | CG2 | A | 397 | 344 | 115 | 312 | 19 |
| VAL | C | A | 397 | 342 | 80 | 328 | 18 |
| VAL | O | A | 397 | 352 | 76 | 332 | 22 |
| ILE | N | A | 398 | 330 | 77 | 332 | 14 |
| ILE | CA | A | 398 | 328 | 67 | 343 | 14 |
| ILE | CB | A | 398 | 314 | 68 | 349 | 16 |
| ILE | CG2 | A | 398 | 311 | 56 | 358 | 15 |
| ILE | CG1 | A | 398 | 313 | 82 | 357 | 20 |
| ILE | CD1 | A | 398 | 322 | 82 | 369 | 19 |
| ILE | C | A | 398 | 330 | 53 | 337 | 12 |
| ILE | O | A | 398 | 338 | 45 | 343 | 11 |
| MET | N | A | 399 | 323 | 50 | 326 | 9 |
| MET | CA | A | 399 | 324 | 37 | 320 | 7 |
| MET | CB | A | 399 | 314 | 36 | 309 | 8 |
| MET | CG | A | 399 | 299 | 38 | 314 | 8 |
| MET | SD | A | 399 | 287 | 35 | 301 | 8 |
| MET | CE | A | 399 | 287 | 17 | 301 | 8 |
| MET | C | A | 399 | 338 | 32 | 316 | 8 |
| MET | O | A | 399 | 340 | 20 | 317 | 8 |
| GLU | N | A | 400 | 347 | 41 | 312 | 7 |
| GLU | CA | A | 400 | 360 | 36 | 308 | 7 |
| GLU | CB | A | 400 | 368 | 48 | 302 | 7 |
| GLU | CG | A | 400 | 363 | 50 | 287 | 7 |
| GLU | CD | A | 400 | 370 | 62 | 280 | 9 |
| GLU | OE1 | A | 400 | 368 | 64 | 268 | 9 |
| GLU | OE2 | A | 400 | 379 | 69 | 287 | 7 |
| GLU | C | A | 400 | 368 | 31 | 320 | 6 |
| GLU | O | A | 400 | 378 | 24 | 318 | 6 |
| GLY | N | A | 401 | 364 | 34 | 332 | 7 |
| GLY | CA | A | 401 | 371 | 29 | 344 | 6 |
| GLY | C | A | 401 | 365 | 15 | 348 | 7 |
| GLY | O | A | 401 | 372 | 8 | 356 | 7 |
| PHE | N | A | 402 | 354 | 11 | 344 | 8 |
| PHE | CA | A | 402 | 348 | −1 | 348 | 7 |
| PHE | CB | A | 402 | 337 | 2 | 359 | 9 |
| PHE | CG | A | 402 | 341 | 12 | 369 | 10 |
| PHE | CD1 | A | 402 | 338 | 26 | 366 | 11 |
| PHE | CD2 | A | 402 | 348 | 9 | 380 | 8 |
| PHE | CE1 | A | 402 | 342 | 36 | 375 | 8 |
| PHE | CE2 | A | 402 | 353 | 19 | 389 | 8 |
| PHE | CZ | A | 402 | 350 | 32 | 386 | 10 |
| PHE | C | A | 402 | 341 | −10 | 338 | 8 |
| PHE | O | A | 402 | 338 | −6 | 327 | 9 |
| TYR | N | A | 403 | 340 | −23 | 342 | 7 |
| TYR | CA | A | 403 | 333 | −32 | 333 | 8 |
| TYR | CB | A | 403 | 338 | −46 | 336 | 7 |
| TYR | CG | A | 403 | 331 | −57 | 328 | 8 |
| TYR | CD1 | A | 403 | 327 | −55 | 314 | 7 |
| TYR | CE1 | A | 403 | 322 | −65 | 307 | 9 |
| TYR | CD2 | A | 403 | 328 | −70 | 333 | 7 |
| TYR | CE2 | A | 403 | 322 | −80 | 326 | 8 |
| TYR | CZ | A | 403 | 319 | −77 | 312 | 9 |
| TYR | OH | A | 403 | 314 | −88 | 305 | 10 |
| TYR | C | A | 403 | 319 | −31 | 339 | 8 |
| TYR | O | A | 403 | 316 | −32 | 351 | 9 |
| VAL | N | A | 404 | 309 | −27 | 330 | 5 |
| VAL | CA | A | 404 | 295 | −25 | 335 | 7 |

TABLE 2-continued

Structure Coordinates for BACE complexed to Inhibitor

| | | | | | | | |
|---|---|---|---|---|---|---|---|
| VAL | CB | A | 404 | 290 | −11 | 330 | 7 |
| VAL | CG1 | A | 404 | 277 | −8 | 337 | 7 |
| VAL | CG2 | A | 404 | 301 | −1 | 335 | 7 |
| VAL | C | A | 404 | 286 | −36 | 330 | 7 |
| VAL | O | A | 404 | 284 | −38 | 318 | 9 |
| VAL | N | A | 405 | 279 | −42 | 339 | 7 |
| VAL | CA | A | 405 | 269 | −52 | 336 | 7 |
| VAL | CB | A | 405 | 271 | −65 | 345 | 7 |
| VAL | CG1 | A | 405 | 261 | −75 | 342 | 8 |
| VAL | CG2 | A | 405 | 285 | −70 | 344 | 10 |
| VAL | C | A | 405 | 255 | −48 | 337 | 9 |
| VAL | O | A | 405 | 250 | −44 | 348 | 9 |
| PHE | N | A | 406 | 248 | −47 | 326 | 8 |
| PHE | CA | A | 406 | 234 | −43 | 328 | 8 |
| PHE | CB | A | 406 | 231 | −36 | 312 | 6 |
| PHE | CG | A | 406 | 239 | −23 | 311 | 8 |
| PHE | CD1 | A | 406 | 232 | −10 | 314 | 7 |
| PHE | CD2 | A | 406 | 252 | −22 | 308 | 7 |
| PHE | CE1 | A | 406 | 239 | 2 | 313 | 6 |
| PHE | CE2 | A | 406 | 259 | −10 | 307 | 6 |
| PHE | CZ | A | 406 | 253 | 2 | 309 | 7 |
| PHE | C | A | 406 | 225 | −55 | 327 | 9 |
| PHE | O | A | 406 | 221 | −62 | 317 | 8 |
| ASP | N | A | 407 | 223 | −59 | 339 | 8 |
| ASP | CA | A | 407 | 215 | −71 | 343 | 10 |
| ASP | CB | A | 407 | 220 | −77 | 356 | 10 |
| ASP | CG | A | 407 | 214 | −90 | 360 | 12 |
| ASP | OD1 | A | 407 | 205 | −95 | 353 | 10 |
| ASP | OD2 | A | 407 | 220 | −97 | 369 | 10 |
| ASP | C | A | 407 | 200 | −68 | 343 | 9 |
| ASP | O | A | 407 | 195 | −66 | 353 | 10 |
| ARG | N | A | 408 | 194 | −68 | 331 | 9 |
| ARG | CA | A | 408 | 180 | −65 | 330 | 9 |
| ARG | CB | A | 408 | 177 | −64 | 315 | 9 |
| ARG | CG | A | 408 | 184 | −53 | 307 | 9 |
| ARG | CD | A | 408 | 184 | −56 | 292 | 9 |
| ARG | NE | A | 408 | 171 | −58 | 286 | 9 |
| ARG | CZ | A | 408 | 165 | −48 | 280 | 10 |
| ARG | NH1 | A | 408 | 170 | −36 | 278 | 9 |
| ARG | NH2 | A | 408 | 153 | −51 | 274 | 11 |
| ARG | C | A | 408 | 172 | −75 | 337 | 11 |
| ARG | O | A | 408 | 162 | −72 | 343 | 11 |
| ALA | N | A | 409 | 176 | −88 | 335 | 10 |
| ALA | CA | A | 409 | 168 | −99 | 341 | 12 |
| ALA | CB | A | 409 | 175 | −112 | 339 | 12 |
| ALA | C | A | 409 | 166 | −97 | 356 | 11 |
| ALA | O | A | 409 | 156 | −100 | 362 | 12 |
| ARG | N | A | 410 | 177 | −92 | 363 | 11 |
| ARG | CA | A | 410 | 176 | −90 | 378 | 13 |
| ARG | CB | A | 410 | 188 | −97 | 384 | 14 |
| ARG | CG | A | 410 | 188 | −112 | 382 | 15 |
| ARG | CD | A | 410 | 200 | −119 | 388 | 17 |
| ARG | NE | A | 410 | 201 | −118 | 403 | 22 |
| ARG | CZ | A | 410 | 209 | −125 | 410 | 26 |
| ARG | NH1 | A | 410 | 218 | −133 | 405 | 28 |
| ARG | NH2 | A | 410 | 209 | −124 | 423 | 28 |
| ARG | C | A | 410 | 175 | −75 | 382 | 12 |
| ARG | O | A | 410 | 177 | −72 | 393 | 12 |
| LYS | N | A | 411 | 171 | −67 | 372 | 11 |
| LYS | CA | A | 411 | 169 | −53 | 374 | 9 |
| LYS | CB | A | 411 | 156 | −50 | 381 | 12 |
| LYS | CG | A | 411 | 150 | −36 | 381 | 17 |
| LYS | CD | A | 411 | 136 | −36 | 386 | 21 |
| LYS | CE | A | 411 | 131 | −21 | 386 | 21 |
| LYS | NZ | A | 411 | 117 | −21 | 391 | 24 |
| LYS | C | A | 411 | 181 | −46 | 382 | 11 |
| LYS | O | A | 411 | 178 | −40 | 393 | 10 |
| ARG | N | A | 412 | 193 | −48 | 378 | 10 |
| ARG | CA | A | 412 | 204 | −43 | 385 | 9 |
| ARG | CB | A | 412 | 209 | −53 | 396 | 8 |
| ARG | CG | A | 412 | 213 | −66 | 390 | 9 |
| ARG | CD | A | 412 | 217 | −76 | 402 | 10 |
| ARG | NE | A | 412 | 223 | −88 | 396 | 12 |
| ARG | CZ | A | 412 | 229 | −97 | 403 | 14 |
| ARG | NH1 | A | 412 | 230 | −96 | 417 | 13 |
| ARG | NH2 | A | 412 | 235 | −108 | 397 | 14 |
| ARG | C | A | 412 | 216 | −40 | 376 | 9 |
| ARG | O | A | 412 | 217 | −46 | 365 | 10 |
| ILE | N | A | 413 | 225 | −31 | 380 | 8 |
| ILE | CA | A | 413 | 237 | −28 | 372 | 8 |
| ILE | CB | A | 413 | 236 | −13 | 368 | 8 |
| ILE | CG2 | A | 413 | 249 | −9 | 360 | 9 |
| ILE | CG1 | A | 413 | 224 | −10 | 359 | 11 |
| ILE | CD1 | A | 413 | 223 | 4 | 355 | 13 |
| ILE | C | A | 413 | 249 | −31 | 380 | 7 |
| ILE | O | A | 413 | 250 | −26 | 391 | 8 |
| GLY | N | A | 414 | 258 | −39 | 374 | 7 |
| GLY | CA | A | 414 | 270 | −42 | 382 | 8 |
| GLY | C | A | 414 | 282 | −34 | 377 | 8 |
| GLY | O | A | 414 | 283 | −31 | 365 | 6 |
| PHE | N | A | 415 | 291 | −31 | 387 | 6 |
| PHE | CA | A | 415 | 304 | −24 | 384 | 6 |
| PHE | CB | A | 415 | 304 | −10 | 390 | 6 |
| PHE | CG | A | 415 | 294 | −1 | 384 | 6 |
| PHE | CD1 | A | 415 | 281 | −2 | 388 | 7 |
| PHE | CD2 | A | 415 | 298 | 9 | 376 | 9 |
| PHE | CE1 | A | 415 | 271 | 7 | 383 | 9 |
| PHE | CE2 | A | 415 | 289 | 18 | 370 | 9 |
| PHE | CZ | A | 415 | 275 | 17 | 374 | 7 |
| PHE | C | A | 415 | 316 | −32 | 389 | 5 |
| PHE | O | A | 415 | 315 | −37 | 400 | 8 |
| ALA | N | A | 416 | 326 | −32 | 381 | 8 |
| ALA | CA | A | 416 | 339 | −39 | 385 | 9 |
| ALA | CB | A | 416 | 339 | −54 | 380 | 7 |
| ALA | C | A | 416 | 350 | −31 | 378 | 9 |
| ALA | O | A | 416 | 348 | −26 | 368 | 7 |
| VAL | N | A | 417 | 362 | −31 | 385 | 5 |
| VAL | CA | A | 417 | 373 | −24 | 379 | 8 |
| VAL | CB | A | 417 | 386 | −26 | 388 | 10 |
| VAL | CG1 | A | 417 | 398 | −19 | 381 | 10 |
| VAL | CG2 | A | 417 | 383 | −19 | 402 | 10 |
| VAL | C | A | 417 | 376 | −30 | 365 | 11 |
| VAL | O | A | 417 | 378 | −42 | 364 | 8 |
| SER | N | A | 418 | 377 | −21 | 355 | 7 |
| SER | CA | A | 418 | 380 | −26 | 342 | 10 |
| SER | CB | A | 418 | 376 | −15 | 331 | 9 |
| SER | OG | A | 418 | 380 | −19 | 318 | 9 |
| SER | C | A | 418 | 394 | −30 | 339 | 8 |
| SER | O | A | 418 | 404 | −24 | 344 | 8 |
| ALA | N | A | 419 | 396 | −41 | 332 | 7 |
| ALA | CA | A | 419 | 409 | −46 | 328 | 8 |
| ALA | CB | A | 419 | 408 | −60 | 322 | 8 |
| ALA | C | A | 419 | 416 | −36 | 319 | 9 |
| ALA | O | A | 419 | 428 | −38 | 316 | 12 |
| CYS | N | A | 420 | 408 | −27 | 313 | 7 |
| CYS | CA | A | 420 | 414 | −18 | 304 | 8 |
| CYS | C | A | 420 | 414 | 3 | 308 | 8 |
| CYS | O | A | 420 | 415 | 6 | 300 | 9 |
| CYS | CB | A | 420 | 408 | 19 | 290 | 8 |
| CYS | SG | A | 420 | 391 | 13 | 288 | 9 |
| HIS | N | A | 421 | 412 | 1 | 321 | 7 |
| HIS | CA | A | 421 | 412 | 13 | 326 | 7 |
| HIS | CB | A | 421 | 404 | 15 | 339 | 8 |
| HIS | CG | A | 421 | 413 | 12 | 351 | 7 |
| HIS | CD2 | A | 421 | 419 | 21 | 360 | 9 |
| HIS | ND1 | A | 421 | 416 | 3 | 356 | 8 |
| HIS | CE1 | A | 421 | 423 | 1 | 367 | 10 |
| HIS | NE2 | A | 421 | 425 | 14 | 369 | 9 |
| HIS | C | A | 421 | 426 | 19 | 326 | 7 |
| HIS | O | A | 421 | 435 | 12 | 330 | 8 |
| VAL | N | A | 422 | 427 | 32 | 323 | 8 |
| VAL | CA | A | 422 | 440 | 38 | 323 | 7 |
| VAL | CB | A | 422 | 441 | 50 | 313 | 8 |
| VAL | CG1 | A | 422 | 454 | 57 | 313 | 6 |
| VAL | CG2 | A | 422 | 437 | 45 | 299 | 8 |
| VAL | C | A | 422 | 444 | 43 | 337 | 8 |
| VAL | O | A | 422 | 435 | 48 | 344 | 9 |
| HIS | N | A | 423 | 456 | 41 | 341 | 8 |
| HIS | CA | A | 423 | 460 | 45 | 355 | 9 |
| HIS | CB | A | 423 | 456 | 34 | 365 | 8 |
| HIS | CG | A | 423 | 463 | 21 | 363 | 11 |
| HIS | CD2 | A | 423 | 474 | 16 | 368 | 12 |
| HIS | ND1 | A | 423 | 458 | 11 | 355 | 13 |
| HIS | CE1 | A | 423 | 466 | 1 | 355 | 15 |

TABLE 2-continued

Structure Coordinates for BACE complexed to Inhibitor

| | | | | | | | |
|---|---|---|---|---|---|---|---|
| HIS | NE2 | A | 423 | 476 | 3 | 363 | 15 |
| HIS | C | A | 423 | 475 | 47 | 355 | 9 |
| HIS | O | A | 423 | 482 | 46 | 345 | 12 |
| ASP | N | A | 424 | 481 | 49 | 367 | 9 |
| ASP | CA | A | 424 | 495 | 50 | 368 | 9 |
| ASP | CB | A | 424 | 499 | 65 | 372 | 9 |
| ASP | CG | A | 424 | 491 | 70 | 384 | 8 |
| ASP | OD1 | A | 424 | 491 | 63 | 394 | 9 |
| ASP | OD2 | A | 424 | 486 | 81 | 383 | 11 |
| ASP | C | A | 424 | 500 | 40 | 379 | 8 |
| ASP | O | A | 424 | 493 | 32 | 383 | 8 |
| GLU | N | A | 425 | 513 | 41 | 382 | 10 |
| GLU | CA | A | 425 | 519 | 32 | 392 | 13 |
| GLU | CB | A | 425 | 534 | 32 | 391 | 17 |
| GLU | CG | A | 425 | 540 | 46 | 395 | 21 |
| GLU | CD | A | 425 | 555 | 46 | 395 | 27 |
| GLU | OE1 | A | 425 | 561 | 38 | 402 | 28 |
| GLU | OE2 | A | 425 | 561 | 54 | 387 | 31 |
| GLU | C | A | 425 | 514 | 34 | 406 | 12 |
| GLU | O | A | 425 | 516 | 26 | 415 | 12 |
| PHE | N | A | 426 | 508 | 46 | 409 | 9 |
| PHE | CA | A | 426 | 504 | 49 | 422 | 9 |
| PHE | CB | A | 426 | 509 | 64 | 425 | 9 |
| PHE | CG | A | 426 | 523 | 66 | 423 | 11 |
| PHE | CD1 | A | 426 | 528 | 75 | 413 | 13 |
| PHE | CD2 | A | 426 | 533 | 60 | 431 | 12 |
| PHE | CE1 | A | 426 | 541 | 77 | 410 | 14 |
| PHE | CE2 | A | 426 | 547 | 62 | 429 | 13 |
| PHE | CZ | A | 426 | 551 | 70 | 418 | 13 |
| PHE | C | A | 426 | 490 | 48 | 426 | 9 |
| PHE | O | A | 426 | 486 | 46 | 438 | 10 |
| ARG | N | A | 427 | 481 | 49 | 416 | 7 |
| ARG | CA | A | 427 | 467 | 48 | 418 | 8 |
| ARG | CB | A | 427 | 460 | 62 | 419 | 9 |
| ARG | CG | A | 427 | 466 | 71 | 430 | 12 |
| ARG | CD | A | 427 | 457 | 84 | 432 | 9 |
| ARG | NE | A | 427 | 458 | 92 | 420 | 8 |
| ARG | CZ | A | 427 | 456 | 105 | 420 | 7 |
| ARG | NH1 | A | 427 | 453 | 111 | 432 | 7 |
| ARG | NH2 | A | 427 | 456 | 113 | 409 | 8 |
| ARG | C | A | 427 | 460 | 40 | 408 | 8 |
| ARG | O | A | 427 | 464 | 39 | 396 | 7 |
| THR | N | A | 428 | 448 | 34 | 412 | 8 |
| THR | CA | A | 428 | 440 | 26 | 402 | 9 |
| THR | CB | A | 428 | 443 | 11 | 404 | 13 |
| THR | OG1 | A | 428 | 435 | 3 | 395 | 19 |
| THR | CG2 | A | 428 | 439 | 7 | 419 | 12 |
| THR | C | A | 428 | 426 | 29 | 406 | 8 |
| THR | O | A | 428 | 422 | 33 | 417 | 8 |
| ALA | N | A | 429 | 417 | 26 | 396 | 7 |
| ALA | CA | A | 429 | 403 | 28 | 398 | 6 |
| ALA | CB | A | 429 | 395 | 27 | 385 | 8 |
| ALA | C | A | 429 | 399 | 17 | 408 | 9 |
| ALA | O | A | 429 | 406 | 8 | 410 | 8 |
| ALA | N | A | 430 | 387 | 19 | 414 | 8 |
| ALA | CA | A | 430 | 383 | 9 | 424 | 10 |
| ALA | CB | A | 430 | 389 | 12 | 437 | 10 |
| ALA | C | A | 430 | 368 | 7 | 425 | 9 |
| ALA | O | A | 430 | 360 | 16 | 421 | 7 |
| VAL | N | A | 431 | 364 | -4 | 430 | 8 |
| VAL | CA | A | 431 | 350 | -7 | 433 | 7 |
| VAL | CB | A | 431 | 344 | -17 | 423 | 8 |
| VAL | CG1 | A | 431 | 329 | -20 | 426 | 8 |
| VAL | CG2 | A | 431 | 344 | -11 | 409 | 9 |
| VAL | C | A | 431 | 351 | -14 | 446 | 9 |
| VAL | O | A | 431 | 356 | -25 | 447 | 9 |
| GLU | N | A | 432 | 346 | -7 | 457 | 10 |
| GLU | CA | A | 432 | 347 | -13 | 470 | 11 |
| GLU | CB | A | 432 | 358 | -4 | 478 | 11 |
| GLU | CG | A | 432 | 372 | -5 | 471 | 15 |
| GLU | CD | A | 432 | 381 | 6 | 476 | 14 |
| GLU | OE1 | A | 432 | 393 | 3 | 477 | 19 |
| GLU | OE2 | A | 432 | 377 | 17 | 478 | 14 |
| GLU | C | A | 432 | 334 | -12 | 478 | 10 |
| GLU | O | A | 432 | 326 | -4 | 476 | 10 |
| GLY | N | A | 433 | 333 | -21 | 488 | 11 |
| GLY | CA | A | 433 | 321 | -22 | 496 | 12 |
| GLY | C | A | 433 | 323 | -33 | 506 | 13 |
| GLY | O | A | 433 | 332 | -41 | 506 | 14 |
| PRO | N | A | 434 | 313 | -34 | 515 | 14 |
| PRO | CD | A | 434 | 311 | -47 | 523 | 15 |
| PRO | CA | A | 434 | 301 | -26 | 516 | 14 |
| PRO | CB | A | 434 | 290 | -36 | 520 | 14 |
| PRO | CG | A | 434 | 297 | -44 | 530 | 15 |
| PRO | C | A | 434 | 302 | -15 | 526 | 13 |
| PRO | O | A | 434 | 312 | -15 | 535 | 15 |
| PHE | N | A | 435 | 294 | -5 | 526 | 12 |
| PHE | CA | A | 435 | 293 | 6 | 536 | 14 |
| PHE | CB | A | 435 | 297 | 19 | 529 | 13 |
| PHE | CG | A | 435 | 311 | 20 | 523 | 12 |
| PHE | CD1 | A | 435 | 312 | 16 | 510 | 13 |
| PHE | CD2 | A | 435 | 322 | 23 | 530 | 13 |
| PHE | CE1 | A | 435 | 325 | 16 | 504 | 12 |
| PHE | CE2 | A | 435 | 334 | 23 | 525 | 13 |
| PHE | CZ | A | 435 | 336 | 19 | 511 | 13 |
| PHE | C | A | 435 | 279 | 7 | 541 | 14 |
| PHE | O | A | 435 | 270 | 5 | 534 | 18 |
| VAL | N | A | 436 | 278 | 10 | 554 | 19 |
| VAL | CA | A | 436 | 265 | 11 | 560 | 21 |
| VAL | CB | A | 436 | 266 | 9 | 576 | 24 |
| VAL | CG1 | A | 436 | 252 | 11 | 582 | 22 |
| VAL | CG2 | A | 436 | 271 | -5 | 579 | 22 |
| VAL | C | A | 436 | 260 | 25 | 557 | 26 |
| VAL | O | A | 436 | 264 | 35 | 563 | 27 |
| THR | N | A | 437 | 249 | 25 | 549 | 28 |
| THR | CA | A | 437 | 243 | 38 | 545 | 27 |
| THR | CB | A | 437 | 245 | 41 | 530 | 29 |
| THR | OG1 | A | 437 | 259 | 40 | 527 | 30 |
| THR | CG2 | A | 437 | 241 | 55 | 526 | 29 |
| THR | C | A | 437 | 228 | 38 | 548 | 27 |
| THR | O | A | 437 | 221 | 29 | 543 | 26 |
| LEU | N | A | 438 | 223 | 47 | 555 | 27 |
| LEU | CA | A | 438 | 209 | 48 | 559 | 27 |
| LEU | CB | A | 438 | 208 | 52 | 573 | 28 |
| LEU | CG | A | 438 | 215 | 44 | 584 | 28 |
| LEU | CD1 | A | 438 | 213 | 50 | 598 | 28 |
| LEU | CD2 | A | 438 | 209 | 30 | 584 | 28 |
| LEU | C | A | 438 | 201 | 57 | 550 | 27 |
| LEU | O | A | 438 | 206 | 66 | 543 | 24 |
| ASP | N | A | 439 | 188 | 55 | 550 | 28 |
| ASP | CA | A | 439 | 178 | 63 | 543 | 30 |
| ASP | CB | A | 439 | 175 | 76 | 550 | 33 |
| ASP | CG | A | 439 | 170 | 74 | 564 | 35 |
| ASP | OD1 | A | 439 | 160 | 66 | 566 | 36 |
| ASP | OD2 | A | 439 | 177 | 79 | 574 | 37 |
| ASP | C | A | 439 | 182 | 66 | 528 | 29 |
| ASP | O | A | 439 | 181 | 78 | 524 | 29 |
| MET | N | A | 440 | 187 | 56 | 521 | 28 |
| MET | CA | A | 440 | 191 | 58 | 507 | 28 |
| MET | CB | A | 440 | 199 | 46 | 502 | 25 |
| MET | CG | A | 440 | 212 | 44 | 510 | 25 |
| MET | SD | A | 440 | 223 | 31 | 504 | 22 |
| MET | CE | A | 440 | 215 | 17 | 511 | 21 |
| MET | C | A | 440 | 179 | 61 | 498 | 28 |
| MET | O | A | 440 | 181 | 67 | 487 | 23 |
| GLU | N | A | 441 | 168 | 56 | 501 | 30 |
| GLU | CA | A | 441 | 156 | 59 | 493 | 33 |
| GLU | CB | A | 441 | 144 | 51 | 499 | 36 |
| GLU | CG | A | 441 | 144 | 36 | 497 | 40 |
| GLU | CD | A | 441 | 146 | 32 | 483 | 44 |
| GLU | OE1 | A | 441 | 138 | 37 | 474 | 46 |
| GLU | OE2 | A | 441 | 154 | 23 | 480 | 46 |
| GLU | C | A | 441 | 153 | 73 | 492 | 32 |
| GLU | O | A | 441 | 148 | 78 | 482 | 33 |
| ASP | N | A | 442 | 156 | 81 | 502 | 29 |
| ASP | CA | A | 442 | 154 | 95 | 503 | 29 |
| ASP | CB | A | 442 | 157 | 101 | 516 | 33 |
| ASP | CG | A | 442 | 147 | 96 | 527 | 37 |
| ASP | OD1 | A | 442 | 134 | 98 | 525 | 39 |
| ASP | OD2 | A | 442 | 151 | 91 | 537 | 41 |
| ASP | C | A | 442 | 163 | 103 | 492 | 25 |
| ASP | O | A | 442 | 160 | 114 | 489 | 24 |
| CYS | N | A | 443 | 173 | 96 | 487 | 20 |
| CYS | CA | A | 443 | 182 | 101 | 477 | 19 |

TABLE 2-continued

Structure Coordinates for BACE complexed to Inhibitor

| | | | | | | | |
|---|---|---|---|---|---|---|---|
| CYS | C | A | 443 | 175 | 102 | 464 | 18 |
| CYS | O | A | 443 | 180 | 110 | 455 | 16 |
| CYS | CB | A | 443 | 195 | 93 | 477 | 18 |
| CYS | SG | A | 443 | 203 | 92 | 493 | 18 |
| GLY | N | A | 444 | 165 | 94 | 461 | 17 |
| GLY | CA | A | 444 | 158 | 94 | 449 | 18 |
| GLY | C | A | 444 | 149 | 106 | 447 | 19 |
| GLY | O | A | 444 | 142 | 110 | 456 | 20 |
| TYR | N | A | 445 | 149 | 111 | 435 | 18 |
| TYR | CA | A | 445 | 140 | 123 | 432 | 21 |
| TYR | CB | A | 445 | 147 | 132 | 422 | 20 |
| TYR | CG | A | 445 | 139 | 145 | 418 | 22 |
| TYR | CD1 | A | 445 | 138 | 155 | 428 | 23 |
| TYR | CE1 | A | 445 | 130 | 166 | 425 | 23 |
| TYR | CD2 | A | 445 | 133 | 146 | 406 | 20 |
| TYR | CE2 | A | 445 | 126 | 157 | 403 | 22 |
| TYR | CZ | A | 445 | 125 | 167 | 412 | 22 |
| TYR | OH | A | 445 | 117 | 179 | 409 | 24 |
| TYR | C | A | 445 | 127 | 119 | 426 | 22 |
| TYR | O | A | 425 | 126 | 110 | 418 | 22 |
| ASN | N | A | 446 | 116 | 126 | 430 | 24 |
| ASN | CA | A | 446 | 103 | 123 | 426 | 29 |
| ASN | CB | A | 446 | 94 | 117 | 437 | 29 |
| ASN | CG | A | 446 | 99 | 104 | 441 | 30 |
| ASN | OD1 | A | 446 | 100 | 95 | 433 | 32 |
| ASN | ND2 | A | 446 | 102 | 103 | 454 | 30 |
| ASN | C | A | 446 | 97 | 137 | 421 | 32 |
| ASN | O | A | 446 | 98 | 147 | 428 | 32 |
| ILE | N | A | 447 | 90 | 136 | 409 | 37 |
| ILE | CA | A | 447 | 84 | 148 | 404 | 42 |
| ILE | CB | A | 447 | 75 | 145 | 391 | 44 |
| ILE | CG2 | A | 447 | 69 | 157 | 386 | 45 |
| ILE | CG1 | A | 447 | 84 | 138 | 381 | 46 |
| ILE | CD1 | A | 447 | 77 | 134 | 368 | 46 |
| ILE | C | A | 447 | 75 | 155 | 414 | 43 |
| ILE | O | A | 447 | 67 | 149 | 420 | 45 |
| GLY | N | B | 58 | 333 | 265 | 1329 | 42 |
| GLY | CA | B | 58 | 326 | 269 | 1317 | 39 |
| GLY | C | B | 58 | 335 | 277 | 1307 | 38 |
| GLY | O | B | 58 | 341 | 286 | 1311 | 34 |
| SER | N | B | 59 | 335 | 272 | 1294 | 38 |
| SER | CA | B | 59 | 343 | 279 | 1284 | 37 |
| SER | CB | B | 59 | 356 | 271 | 1282 | 40 |
| SER | OG | B | 59 | 354 | 258 | 1278 | 42 |
| SER | C | B | 59 | 335 | 279 | 1271 | 35 |
| SER | O | B | 59 | 330 | 268 | 1266 | 36 |
| PHE | N | B | 60 | 335 | 290 | 1264 | 32 |
| PHE | CA | B | 60 | 328 | 292 | 1252 | 27 |
| PHE | CB | B | 60 | 316 | 301 | 1253 | 26 |
| PHE | CG | B | 60 | 306 | 297 | 1263 | 24 |
| PHE | CD1 | B | 60 | 309 | 297 | 1277 | 24 |
| PHE | CD2 | B | 60 | 293 | 292 | 1259 | 24 |
| PHE | CE1 | B | 60 | 299 | 292 | 1286 | 23 |
| PHE | CE2 | B | 60 | 284 | 288 | 1269 | 24 |
| PHE | CZ | B | 60 | 287 | 288 | 1282 | 24 |
| PHE | C | B | 60 | 338 | 298 | 1242 | 27 |
| PHE | O | B | 60 | 336 | 309 | 1237 | 23 |
| VAL | N | B | 61 | 348 | 290 | 1238 | 26 |
| VAL | CA | B | 61 | 358 | 294 | 1229 | 27 |
| VAL | CB | B | 61 | 368 | 282 | 1225 | 29 |
| VAL | CG1 | B | 61 | 379 | 287 | 1216 | 30 |
| VAL | CG2 | B | 61 | 374 | 276 | 1238 | 30 |
| VAL | C | B | 61 | 353 | 300 | 1216 | 26 |
| VAL | O | B | 61 | 359 | 309 | 1211 | 28 |
| GLU | N | B | 62 | 342 | 295 | 1211 | 23 |
| GLU | CA | B | 62 | 337 | 301 | 1198 | 23 |
| GLU | CB | B | 62 | 325 | 292 | 1193 | 27 |
| GLU | CG | B | 62 | 312 | 292 | 1202 | 35 |
| GLU | CD | B | 62 | 314 | 284 | 1215 | 37 |
| GLU | OE1 | B | 62 | 323 | 277 | 1216 | 40 |
| GLU | OE2 | B | 62 | 305 | 286 | 1224 | 41 |
| GLU | C | B | 62 | 332 | 315 | 1199 | 20 |
| GLU | O | B | 62 | 331 | 322 | 1189 | 19 |
| MET | N | B | 63 | 329 | 320 | 1212 | 14 |
| MET | CA | B | 63 | 325 | 333 | 1214 | 12 |
| MET | CB | B | 63 | 312 | 334 | 1222 | 13 |
| MET | CG | B | 63 | 300 | 326 | 1214 | 13 |
| MET | SD | B | 63 | 285 | 327 | 1223 | 14 |
| MET | CE | B | 63 | 285 | 312 | 1232 | 17 |
| MET | C | B | 63 | 335 | 343 | 1220 | 13 |
| MET | O | B | 63 | 333 | 355 | 1220 | 11 |
| VAL | N | B | 64 | 346 | 337 | 1225 | 11 |
| VAL | CA | B | 64 | 356 | 345 | 1232 | 13 |
| VAL | CB | B | 64 | 367 | 336 | 1238 | 13 |
| VAL | CG1 | B | 64 | 378 | 345 | 1243 | 14 |
| VAL | CG2 | B | 64 | 361 | 329 | 1250 | 15 |
| VAL | C | B | 64 | 363 | 354 | 1221 | 11 |
| VAL | O | B | 64 | 365 | 349 | 1210 | 12 |
| ASP | N | B | 65 | 365 | 366 | 1224 | 10 |
| ASP | CA | B | 65 | 372 | 376 | 1215 | 10 |
| ASP | CB | B | 65 | 386 | 371 | 1211 | 11 |
| ASP | CG | B | 65 | 395 | 370 | 1223 | 14 |
| ASP | OD1 | B | 65 | 406 | 366 | 1221 | 13 |
| ASP | OD2 | B | 65 | 391 | 374 | 1234 | 13 |
| ASP | C | B | 65 | 364 | 379 | 1202 | 9 |
| ASP | O | B | 65 | 369 | 381 | 1192 | 11 |
| ASN | N | B | 66 | 350 | 379 | 1203 | 8 |
| ASN | CA | B | 66 | 342 | 382 | 1192 | 7 |
| ASN | CB | B | 66 | 329 | 373 | 1192 | 8 |
| ASN | CG | B | 66 | 320 | 375 | 1204 | 9 |
| ASN | OD1 | B | 66 | 324 | 383 | 1213 | 9 |
| ASN | ND2 | B | 66 | 309 | 369 | 1204 | 9 |
| ASN | C | B | 66 | 338 | 396 | 1190 | 8 |
| ASN | O | B | 66 | 329 | 400 | 1182 | 10 |
| LEU | N | B | 67 | 343 | 405 | 1199 | 8 |
| LEU | CA | B | 67 | 340 | 419 | 1198 | 8 |
| LEU | CB | B | 67 | 335 | 424 | 1212 | 7 |
| LEU | CG | B | 67 | 323 | 419 | 1218 | 6 |
| LEU | CD1 | B | 67 | 320 | 426 | 1231 | 7 |
| LEU | CD2 | B | 67 | 311 | 419 | 1209 | 8 |
| LEU | C | B | 67 | 352 | 427 | 1193 | 8 |
| LEU | O | B | 67 | 363 | 424 | 1195 | 9 |
| ARG | N | B | 68 | 348 | 439 | 1188 | 9 |
| ARG | CA | B | 68 | 358 | 449 | 1183 | 8 |
| ARG | CB | B | 68 | 361 | 447 | 1168 | 8 |
| ARG | CG | B | 68 | 370 | 435 | 1165 | 11 |
| ARG | CD | B | 68 | 374 | 436 | 1150 | 13 |
| ARG | NE | B | 68 | 363 | 434 | 1141 | 15 |
| ARG | CZ | B | 68 | 363 | 437 | 1128 | 18 |
| ARG | NH1 | B | 68 | 374 | 442 | 1122 | 17 |
| ARG | NH2 | B | 68 | 352 | 434 | 1121 | 15 |
| ARG | C | B | 68 | 353 | 463 | 1186 | 9 |
| ARG | O | B | 68 | 341 | 464 | 1189 | 7 |
| GLY | N | B | 69 | 362 | 473 | 1186 | 8 |
| GLY | CA | B | 69 | 357 | 486 | 1188 | 9 |
| GLY | C | B | 69 | 365 | 492 | 1200 | 9 |
| GLY | O | B | 69 | 375 | 487 | 1205 | 9 |
| LYS | N | B | 70 | 359 | 503 | 1205 | 7 |
| LYS | CA | B | 70 | 365 | 510 | 1217 | 9 |
| LYS | CB | B | 70 | 377 | 519 | 1212 | 10 |
| LYS | CG | B | 70 | 374 | 528 | 1201 | 10 |
| LYS | CD | B | 70 | 387 | 535 | 1196 | 14 |
| LYS | CE | B | 70 | 385 | 545 | 1185 | 15 |
| LYS | NZ | B | 70 | 397 | 551 | 1180 | 17 |
| LYS | C | B | 70 | 354 | 519 | 1223 | 9 |
| LYS | O | B | 70 | 344 | 522 | 1217 | 10 |
| SER | N | B | 71 | 357 | 523 | 1236 | 8 |
| SER | CA | B | 71 | 346 | 530 | 1243 | 7 |
| SER | CB | B | 71 | 352 | 534 | 1257 | 9 |
| SER | OG | B | 71 | 363 | 543 | 1256 | 11 |
| SER | C | B | 71 | 341 | 543 | 1236 | 7 |
| SER | O | B | 71 | 329 | 545 | 1237 | 8 |
| GLY | N | B | 72 | 350 | 550 | 1230 | 6 |
| GLY | CA | B | 72 | 345 | 562 | 1223 | 10 |
| GLY | C | B | 72 | 336 | 561 | 1211 | 9 |
| GLY | O | B | 72 | 329 | 570 | 1207 | 10 |
| GLN | N | B | 73 | 337 | 549 | 1204 | 9 |
| GLN | CA | B | 73 | 328 | 547 | 1193 | 9 |
| GLN | CB | B | 73 | 337 | 546 | 1180 | 12 |
| GLN | CG | B | 73 | 346 | 558 | 1178 | 15 |
| GLN | CD | B | 73 | 353 | 558 | 1164 | 20 |
| GLN | OE1 | B | 73 | 358 | 548 | 1160 | 21 |
| GLN | NE2 | B | 73 | 352 | 569 | 1158 | 22 |
| GLN | C | B | 73 | 319 | 535 | 1194 | 9 |

TABLE 2-continued

Structure Coordinates for BACE complexed to Inhibitor

| | | | | | | | |
|---|---|---|---|---|---|---|---|
| GLN | O | B | 73 | 311 | 532 | 1185 | 11 |
| GLY | N | B | 74 | 320 | 528 | 1205 | 9 |
| GLY | CA | B | 74 | 312 | 516 | 1207 | 9 |
| GLY | C | B | 74 | 318 | 503 | 1204 | 6 |
| GLY | O | B | 74 | 328 | 502 | 1195 | 8 |
| TYR | N | B | 75 | 314 | 492 | 1210 | 8 |
| TYR | CA | B | 75 | 319 | 478 | 1207 | 7 |
| TYR | CB | B | 75 | 321 | 471 | 1221 | 10 |
| TYR | CG | B | 75 | 333 | 476 | 1228 | 10 |
| TYR | CD1 | B | 75 | 332 | 487 | 1237 | 10 |
| TYR | CE1 | B | 75 | 343 | 492 | 1244 | 10 |
| TYR | CD2 | B | 75 | 346 | 470 | 1226 | 11 |
| TYR | CE2 | B | 75 | 357 | 475 | 1233 | 10 |
| TYR | CZ | B | 75 | 356 | 486 | 1242 | 11 |
| TYR | OH | B | 75 | 367 | 490 | 1248 | 10 |
| TYR | C | B | 75 | 308 | 471 | 1199 | 9 |
| TYR | O | B | 75 | 296 | 472 | 1202 | 8 |
| TYR | N | B | 76 | 313 | 463 | 1189 | 7 |
| TYR | CA | B | 76 | 303 | 457 | 1180 | 6 |
| TYR | CB | B | 76 | 303 | 464 | 1167 | 7 |
| TYR | CG | B | 76 | 316 | 464 | 1160 | 8 |
| TYR | CD1 | B | 76 | 320 | 454 | 1151 | 8 |
| TYR | CE1 | B | 76 | 332 | 455 | 1144 | 10 |
| TYR | CD2 | B | 76 | 324 | 475 | 1161 | 9 |
| TYR | CE2 | B | 76 | 337 | 476 | 1154 | 10 |
| TYR | CZ | B | 76 | 340 | 465 | 1146 | 9 |
| TYR | OH | B | 76 | 352 | 466 | 1139 | 13 |
| TYR | C | B | 76 | 307 | 442 | 1178 | 7 |
| TYR | O | B | 76 | 318 | 437 | 1180 | 6 |
| VAL | N | B | 77 | 296 | 434 | 1174 | 7 |
| VAL | CA | B | 77 | 298 | 420 | 1171 | 7 |
| VAL | CB | B | 77 | 289 | 412 | 1181 | 6 |
| VAL | CG1 | B | 77 | 274 | 414 | 1178 | 9 |
| VAL | CG2 | B | 77 | 292 | 397 | 1179 | 7 |
| VAL | C | B | 77 | 292 | 418 | 1157 | 9 |
| VAL | O | B | 77 | 284 | 426 | 1152 | 11 |
| GLU | N | B | 78 | 298 | 408 | 1150 | 9 |
| GLU | CA | B | 78 | 293 | 405 | 1136 | 8 |
| GLU | CB | B | 78 | 304 | 398 | 1129 | 11 |
| GLU | CG | B | 78 | 300 | 394 | 1114 | 12 |
| GLU | CD | B | 78 | 311 | 387 | 1107 | 16 |
| GLU | OE1 | B | 78 | 321 | 394 | 1103 | 18 |
| GLU | OE2 | B | 78 | 310 | 375 | 1104 | 19 |
| GLU | C | B | 78 | 280 | 397 | 1137 | 7 |
| GLU | O | B | 78 | 279 | 388 | 1145 | 7 |
| MET | N | B | 79 | 271 | 401 | 1128 | 7 |
| MET | CA | B | 79 | 258 | 394 | 1127 | 8 |
| MET | CB | B | 79 | 247 | 402 | 1134 | 7 |
| MET | CG | B | 79 | 250 | 404 | 1149 | 6 |
| MET | SD | B | 79 | 236 | 412 | 1157 | 10 |
| MET | CE | B | 79 | 224 | 399 | 1159 | 11 |
| MET | C | B | 79 | 255 | 392 | 1112 | 9 |
| MET | O | B | 79 | 261 | 399 | 1104 | 9 |
| THR | N | B | 80 | 245 | 384 | 1109 | 10 |
| THR | CA | B | 80 | 241 | 383 | 1095 | 11 |
| THR | CB | B | 80 | 245 | 369 | 1089 | 14 |
| THR | OG1 | B | 80 | 237 | 358 | 1095 | 15 |
| THR | CG2 | B | 80 | 260 | 366 | 1090 | 15 |
| THR | C | B | 80 | 226 | 384 | 1095 | 11 |
| THR | O | B | 80 | 219 | 379 | 1104 | 10 |
| VAL | N | B | 81 | 221 | 390 | 1085 | 10 |
| VAL | CA | B | 81 | 206 | 392 | 1083 | 11 |
| VAL | CB | B | 81 | 202 | 406 | 1086 | 13 |
| VAL | CG1 | B | 81 | 205 | 410 | 1100 | 13 |
| VAL | CG2 | B | 81 | 208 | 416 | 1076 | 14 |
| VAL | C | B | 81 | 202 | 388 | 1069 | 10 |
| VAL | O | B | 81 | 209 | 390 | 1060 | 8 |
| GLY | N | B | 82 | 190 | 382 | 1068 | 10 |
| GLY | CA | B | 82 | 185 | 378 | 1055 | 10 |
| GLY | C | B | 82 | 190 | 365 | 1048 | 10 |
| GLY | O | B | 82 | 199 | 358 | 1054 | 11 |
| SER | N | B | 83 | 184 | 362 | 1037 | 10 |
| SER | CA | B | 83 | 188 | 350 | 1029 | 10 |
| SER | CB | B | 83 | 176 | 340 | 1030 | 12 |
| SER | OG | B | 83 | 173 | 337 | 1044 | 13 |
| SER | C | B | 83 | 189 | 354 | 1014 | 11 |
| SER | O | B | 83 | 180 | 359 | 1008 | 11 |
| PRO | N | B | 84 | 201 | 353 | 1009 | 11 |
| PRO | CD | B | 84 | 204 | 356 | 995 | 13 |
| PRO | CA | B | 84 | 213 | 347 | 1015 | 12 |
| PRO | CB | B | 84 | 223 | 346 | 1004 | 12 |
| PRO | CG | B | 84 | 219 | 358 | 995 | 13 |
| PRO | C | B | 84 | 218 | 357 | 1026 | 12 |
| PRO | O | B | 84 | 214 | 369 | 1027 | 11 |
| PRO | N | B | 85 | 226 | 352 | 1036 | 12 |
| PRO | CD | B | 85 | 231 | 339 | 1037 | 14 |
| PRO | CA | B | 85 | 231 | 361 | 1047 | 13 |
| PRO | CB | B | 85 | 240 | 351 | 1055 | 14 |
| PRO | CG | B | 85 | 234 | 338 | 1052 | 18 |
| PRO | C | B | 85 | 239 | 373 | 1042 | 11 |
| PRO | O | B | 85 | 247 | 373 | 1034 | 13 |
| GLN | N | B | 86 | 235 | 384 | 1049 | 10 |
| GLN | CA | B | 86 | 241 | 397 | 1046 | 11 |
| GLN | CB | B | 86 | 231 | 408 | 1043 | 11 |
| GLN | CG | B | 86 | 224 | 407 | 1030 | 10 |
| GLN | CD | B | 86 | 213 | 418 | 1028 | 9 |
| GLN | OE1 | B | 86 | 216 | 430 | 1030 | 11 |
| GLN | NE2 | B | 86 | 202 | 414 | 1023 | 9 |
| GLN | C | B | 86 | 249 | 400 | 1059 | 10 |
| GLN | O | B | 86 | 243 | 401 | 1070 | 10 |
| THR | N | B | 87 | 262 | 401 | 1058 | 9 |
| THR | CA | B | 87 | 270 | 404 | 1070 | 9 |
| THR | CB | B | 87 | 285 | 399 | 1068 | 10 |
| THR | OG1 | B | 87 | 284 | 385 | 1065 | 11 |
| THR | CG2 | B | 87 | 293 | 401 | 1080 | 12 |
| THR | C | B | 87 | 270 | 419 | 1074 | 9 |
| THR | O | B | 87 | 272 | 428 | 1065 | 10 |
| LEU | N | B | 88 | 269 | 422 | 1087 | 8 |
| LEU | CA | B | 88 | 269 | 435 | 1092 | 8 |
| LEU | CB | B | 88 | 255 | 441 | 1093 | 9 |
| LEU | CG | B | 88 | 246 | 442 | 1080 | 11 |
| LEU | CD1 | B | 88 | 232 | 447 | 1084 | 13 |
| LEU | CD2 | B | 88 | 252 | 452 | 1070 | 13 |
| LEU | C | B | 88 | 275 | 435 | 1106 | 9 |
| LEU | O | B | 88 | 273 | 426 | 1113 | 11 |
| ASN | N | B | 89 | 282 | 446 | 1109 | 8 |
| ASN | CA | B | 89 | 287 | 448 | 1122 | 10 |
| ASN | CB | B | 89 | 301 | 456 | 1121 | 10 |
| ASN | CG | B | 89 | 312 | 447 | 1116 | 11 |
| ASN | OD1 | B | 89 | 322 | 452 | 1111 | 16 |
| ASN | ND2 | B | 89 | 311 | 434 | 1118 | 11 |
| ASN | C | B | 89 | 277 | 455 | 1131 | 8 |
| ASN | O | B | 89 | 272 | 466 | 1127 | 8 |
| ILE | N | B | 90 | 274 | 450 | 1142 | 7 |
| ILE | CA | B | 90 | 264 | 456 | 1151 | 8 |
| ILE | CB | B | 90 | 252 | 446 | 1152 | 8 |
| ILE | CG2 | B | 90 | 240 | 452 | 1160 | 8 |
| ILE | CG1 | B | 90 | 247 | 441 | 1138 | 7 |
| ILE | CD1 | B | 90 | 241 | 452 | 1130 | 6 |
| ILE | C | B | 90 | 268 | 460 | 1165 | 8 |
| ILE | O | B | 90 | 273 | 451 | 1172 | 7 |
| LEU | N | B | 91 | 266 | 472 | 1168 | 7 |
| LEU | CA | B | 91 | 270 | 478 | 1181 | 7 |
| LEU | CB | B | 91 | 268 | 493 | 1182 | 9 |
| LEU | CG | B | 91 | 271 | 500 | 1195 | 8 |
| LEU | CD1 | B | 91 | 276 | 514 | 1192 | 11 |
| LEU | CD2 | B | 91 | 259 | 500 | 1204 | 10 |
| LEU | C | B | 91 | 262 | 471 | 1192 | 8 |
| LEU | O | B | 91 | 249 | 470 | 1191 | 8 |
| VAL | N | B | 92 | 268 | 466 | 1203 | 7 |
| VAL | CA | B | 92 | 262 | 460 | 1214 | 8 |
| VAL | CB | B | 92 | 271 | 450 | 1221 | 12 |
| VAL | CG1 | B | 92 | 264 | 443 | 1233 | 14 |
| VAL | CG2 | B | 92 | 276 | 439 | 1211 | 14 |
| VAL | C | B | 92 | 257 | 470 | 1224 | 8 |
| VAL | O | B | 92 | 265 | 477 | 1230 | 7 |
| ASP | N | B | 93 | 244 | 472 | 1225 | 7 |
| ASP | CA | B | 93 | 238 | 482 | 1234 | 6 |
| ASP | CB | B | 93 | 231 | 493 | 1225 | 8 |
| ASP | CG | B | 93 | 227 | 505 | 1232 | 8 |
| ASP | OD1 | B | 93 | 235 | 510 | 1240 | 10 |
| ASP | OD2 | B | 93 | 216 | 510 | 1230 | 8 |
| ASP | C | B | 93 | 229 | 477 | 1244 | 7 |
| ASP | O | B | 93 | 217 | 475 | 1242 | 7 |

TABLE 2-continued

Structure Coordinates for BACE complexed to Inhibitor

| | | | | | | | |
|---|---|---|---|---|---|---|---|
| THR | N | B | 94 | 234 | 476 | 1257 | 7 |
| THR | CA | B | 94 | 225 | 471 | 1267 | 5 |
| THR | CB | B | 94 | 233 | 466 | 1279 | 6 |
| THR | OG1 | B | 94 | 242 | 476 | 1285 | 7 |
| THR | CG2 | B | 94 | 242 | 454 | 1275 | 5 |
| THR | C | B | 94 | 216 | 482 | 1272 | 7 |
| THR | O | B | 94 | 208 | 480 | 1281 | 7 |
| GLY | N | B | 95 | 217 | 494 | 1266 | 6 |
| GLY | CA | B | 95 | 209 | 506 | 1270 | 8 |
| GLY | C | B | 95 | 197 | 508 | 1262 | 10 |
| GLY | O | B | 95 | 189 | 518 | 1265 | 9 |
| SER | N | B | 96 | 194 | 500 | 1252 | 10 |
| SER | CA | B | 96 | 182 | 501 | 1244 | 9 |
| SER | CB | B | 96 | 184 | 509 | 1232 | 9 |
| SER | OG | B | 96 | 193 | 502 | 1223 | 7 |
| SER | C | B | 96 | 176 | 487 | 1241 | 8 |
| SER | O | B | 96 | 183 | 477 | 1244 | 7 |
| SER | N | B | 97 | 165 | 486 | 1234 | 9 |
| SER | CA | B | 97 | 159 | 473 | 1231 | 9 |
| SER | CB | B | 97 | 147 | 471 | 1240 | 11 |
| SER | OG | B | 97 | 150 | 474 | 1254 | 10 |
| SER | C | B | 97 | 155 | 471 | 1217 | 8 |
| SER | O | B | 97 | 148 | 461 | 1214 | 8 |
| ASN | N | B | 98 | 160 | 479 | 1208 | 8 |
| ASN | CA | B | 98 | 156 | 477 | 1194 | 8 |
| ASN | CB | B | 98 | 151 | 491 | 1187 | 8 |
| ASN | CG | B | 98 | 137 | 494 | 1191 | 10 |
| ASN | OD1 | B | 98 | 134 | 499 | 1202 | 10 |
| ASN | ND2 | B | 98 | 128 | 491 | 1182 | 10 |
| ASN | C | B | 98 | 168 | 472 | 1185 | 7 |
| ASN | O | B | 98 | 180 | 477 | 1187 | 7 |
| PHE | N | B | 99 | 166 | 463 | 1176 | 7 |
| PHE | CA | B | 99 | 176 | 458 | 1168 | 8 |
| PHE | CB | B | 99 | 174 | 443 | 1165 | 8 |
| PHE | CG | B | 99 | 183 | 437 | 1155 | 10 |
| PHE | CD1 | B | 99 | 179 | 426 | 1147 | 11 |
| PHE | CD2 | B | 99 | 197 | 441 | 1154 | 11 |
| PHE | CE1 | B | 99 | 188 | 421 | 1138 | 12 |
| PHE | CE2 | B | 99 | 206 | 435 | 1145 | 10 |
| PHE | CZ | B | 99 | 202 | 425 | 1137 | 12 |
| PHE | C | B | 99 | 173 | 466 | 1155 | 7 |
| PHE | O | B | 99 | 162 | 465 | 1149 | 8 |
| ALA | N | B | 100 | 183 | 473 | 1150 | 6 |
| ALA | CA | B | 100 | 182 | 482 | 1138 | 7 |
| ALA | CB | B | 100 | 178 | 496 | 1142 | 9 |
| ALA | C | B | 100 | 195 | 482 | 1130 | 8 |
| ALA | O | B | 100 | 206 | 481 | 1136 | 9 |
| VAL | N | B | 101 | 193 | 484 | 1117 | 8 |
| VAL | CA | B | 101 | 204 | 484 | 1108 | 8 |
| VAL | CB | B | 101 | 207 | 470 | 1102 | 10 |
| VAL | CG1 | B | 101 | 210 | 460 | 1113 | 11 |
| VAL | CG2 | B | 101 | 195 | 466 | 1094 | 11 |
| VAL | C | B | 101 | 203 | 494 | 1097 | 8 |
| VAL | O | B | 101 | 191 | 496 | 1092 | 8 |
| GLY | N | B | 102 | 214 | 500 | 1093 | 9 |
| GLY | CA | B | 102 | 213 | 509 | 1082 | 10 |
| GLY | C | B | 102 | 207 | 502 | 1070 | 9 |
| GLY | O | B | 102 | 211 | 490 | 1068 | 9 |
| ALA | N | B | 103 | 198 | 508 | 1063 | 13 |
| ALA | CA | B | 103 | 191 | 501 | 1052 | 14 |
| ALA | CB | B | 103 | 177 | 497 | 1055 | 12 |
| ALA | C | B | 103 | 191 | 510 | 1039 | 19 |
| ALA | O | B | 103 | 183 | 507 | 1030 | 19 |
| ALA | N | B | 104 | 199 | 520 | 1039 | 21 |
| ALA | CA | B | 104 | 200 | 529 | 1028 | 26 |
| ALA | CB | B | 104 | 189 | 540 | 1030 | 25 |
| ALA | C | B | 104 | 214 | 536 | 1028 | 29 |
| ALA | O | B | 104 | 220 | 536 | 1038 | 29 |
| PRO | N | B | 105 | 218 | 540 | 1016 | 31 |
| PRO | CD | B | 105 | 212 | 539 | 1003 | 33 |
| PRO | CA | B | 105 | 232 | 546 | 1015 | 31 |
| PRO | CB | B | 105 | 232 | 552 | 1001 | 33 |
| PRO | CG | B | 105 | 224 | 541 | 994 | 33 |
| PRO | C | B | 105 | 233 | 557 | 1026 | 30 |
| PRO | O | B | 105 | 224 | 565 | 1029 | 29 |
| HIS | N | B | 106 | 246 | 558 | 1031 | 29 |
| HIS | CA | B | 106 | 249 | 568 | 1041 | 28 |
| HIS | CB | B | 106 | 245 | 563 | 1055 | 26 |
| HIS | CG | B | 106 | 247 | 574 | 1066 | 24 |
| HIS | CD2 | B | 106 | 238 | 581 | 1073 | 24 |
| HIS | ND1 | B | 106 | 260 | 578 | 1070 | 24 |
| HIS | CE1 | B | 106 | 258 | 587 | 1079 | 23 |
| HIS | NE2 | B | 106 | 245 | 589 | 1081 | 25 |
| HIS | C | B | 106 | 264 | 570 | 1040 | 26 |
| HIS | O | B | 106 | 272 | 561 | 1039 | 27 |
| PRO | N | B | 107 | 268 | 583 | 1040 | 26 |
| PRO | CD | B | 107 | 260 | 595 | 1044 | 28 |
| PRO | CA | B | 107 | 283 | 586 | 1039 | 27 |
| PRO | CB | B | 107 | 283 | 602 | 1041 | 28 |
| PRO | CG | B | 107 | 271 | 604 | 1050 | 29 |
| PRO | C | B | 107 | 292 | 579 | 1049 | 25 |
| PRO | O | B | 107 | 304 | 577 | 1046 | 27 |
| PHE | N | B | 108 | 287 | 575 | 1060 | 22 |
| PHE | CA | B | 108 | 295 | 568 | 1070 | 22 |
| PHE | CB | B | 108 | 291 | 572 | 1084 | 21 |
| PHE | CG | B | 108 | 293 | 586 | 1088 | 21 |
| PHE | CD1 | B | 108 | 289 | 592 | 1099 | 21 |
| PHE | CD2 | B | 108 | 300 | 595 | 1079 | 21 |
| PHE | CE1 | B | 108 | 291 | 605 | 1103 | 21 |
| PHE | CE2 | B | 108 | 303 | 608 | 1082 | 22 |
| PHE | CZ | B | 108 | 298 | 613 | 1094 | 22 |
| PHE | C | B | 108 | 294 | 553 | 1069 | 21 |
| PHE | O | B | 108 | 301 | 545 | 1076 | 21 |
| LEU | N | B | 109 | 285 | 548 | 1060 | 21 |
| LEU | CA | B | 109 | 284 | 533 | 1059 | 21 |
| LEU | CB | B | 109 | 269 | 530 | 1060 | 20 |
| LEU | CG | B | 109 | 261 | 534 | 1072 | 19 |
| LEU | CD1 | B | 109 | 246 | 530 | 1071 | 20 |
| LEU | CD2 | B | 109 | 267 | 528 | 1084 | 20 |
| LEU | C | B | 109 | 289 | 528 | 1045 | 23 |
| LEU | O | B | 109 | 287 | 535 | 1035 | 24 |
| HIS | N | B | 110 | 296 | 517 | 1045 | 24 |
| HIS | CA | B | 110 | 301 | 512 | 1033 | 27 |
| HIS | CB | B | 110 | 316 | 508 | 1034 | 31 |
| HIS | CG | B | 110 | 319 | 498 | 1045 | 36 |
| HIS | CD2 | B | 110 | 319 | 485 | 1046 | 39 |
| HIS | ND1 | B | 110 | 323 | 503 | 1058 | 40 |
| HIS | CE1 | B | 110 | 326 | 492 | 1066 | 41 |
| HIS | NE2 | B | 110 | 323 | 481 | 1059 | 41 |
| HIS | C | B | 110 | 293 | 499 | 1029 | 25 |
| HIS | O | B | 110 | 295 | 493 | 1019 | 27 |
| ARG | N | B | 111 | 283 | 496 | 1037 | 22 |
| ARG | CA | B | 111 | 274 | 485 | 1035 | 20 |
| ARG | CB | B | 111 | 281 | 472 | 1037 | 20 |
| ARG | CG | B | 111 | 284 | 469 | 1052 | 20 |
| ARG | CD | B | 111 | 292 | 456 | 1053 | 21 |
| ARG | NE | B | 111 | 296 | 453 | 1067 | 20 |
| ARG | CZ | B | 111 | 302 | 442 | 1071 | 20 |
| ARG | NH1 | B | 111 | 305 | 433 | 1062 | 18 |
| ARG | NH2 | B | 111 | 305 | 440 | 1084 | 21 |
| ARG | C | B | 111 | 261 | 486 | 1043 | 19 |
| ARG | O | B | 111 | 262 | 493 | 1054 | 13 |
| TYR | N | B | 112 | 251 | 481 | 1039 | 15 |
| TYR | CA | B | 112 | 238 | 481 | 1046 | 16 |
| TYR | CB | B | 112 | 231 | 495 | 1044 | 18 |
| TYR | CG | B | 112 | 229 | 499 | 1029 | 24 |
| TYR | CD1 | B | 112 | 218 | 494 | 1022 | 25 |
| TYR | CE1 | B | 112 | 215 | 497 | 1009 | 27 |
| TYR | CD2 | B | 112 | 237 | 507 | 1022 | 26 |
| TYR | CE2 | B | 112 | 235 | 510 | 1009 | 29 |
| TYR | CZ | B | 112 | 224 | 506 | 1002 | 30 |
| TYR | OH | B | 112 | 221 | 509 | 989 | 32 |
| TYR | C | B | 112 | 228 | 470 | 1042 | 16 |
| TYR | O | B | 112 | 231 | 463 | 1033 | 15 |
| TYR | N | B | 113 | 218 | 469 | 1050 | 9 |
| TYR | CA | B | 113 | 208 | 459 | 1048 | 9 |
| TYR | CB | B | 113 | 199 | 458 | 1060 | 8 |
| TYR | CG | B | 113 | 187 | 449 | 1060 | 8 |
| TYR | CD1 | B | 113 | 188 | 436 | 1055 | 8 |
| TYR | CE1 | B | 113 | 178 | 427 | 1055 | 9 |
| TYR | CD2 | B | 113 | 175 | 452 | 1067 | 9 |
| TYR | CE2 | B | 113 | 165 | 443 | 1068 | 9 |
| TYR | CZ | B | 113 | 166 | 430 | 1062 | 9 |
| TYR | OH | B | 113 | 156 | 421 | 1064 | 9 |

TABLE 2-continued

Structure Coordinates for BACE complexed to Inhibitor

| | | | | | | | |
|---|---|---|---|---|---|---|---|
| TYR | C | B | 113 | 199 | 462 | 1036 | 9 |
| TYR | O | B | 113 | 193 | 472 | 1035 | 9 |
| GLN | N | B | 114 | 199 | 452 | 1026 | 10 |
| GLN | CA | B | 114 | 192 | 454 | 1014 | 12 |
| GLN | CB | B | 114 | 201 | 451 | 1002 | 15 |
| GLN | CG | B | 114 | 211 | 461 | 999 | 18 |
| GLN | CD | B | 114 | 221 | 458 | 988 | 21 |
| GLN | OE1 | B | 114 | 229 | 449 | 989 | 24 |
| GLN | NE2 | B | 114 | 219 | 465 | 977 | 23 |
| GLN | C | B | 114 | 180 | 444 | 1014 | 12 |
| GLN | O | B | 114 | 182 | 432 | 1011 | 10 |
| ARG | N | B | 115 | 169 | 448 | 1019 | 12 |
| ARG | CA | B | 115 | 157 | 440 | 1020 | 10 |
| ARG | CB | B | 115 | 145 | 449 | 1026 | 9 |
| ARG | CG | B | 115 | 148 | 453 | 1041 | 9 |
| ARG | CD | B | 115 | 138 | 464 | 1045 | 9 |
| ARG | NE | B | 115 | 141 | 476 | 1039 | 11 |
| ARG | CZ | B | 115 | 134 | 487 | 1040 | 11 |
| ARG | NH1 | B | 115 | 123 | 487 | 1047 | 10 |
| ARG | NH2 | B | 115 | 138 | 499 | 1034 | 14 |
| ARG | C | B | 115 | 152 | 433 | 1008 | 11 |
| ARG | O | B | 115 | 148 | 422 | 1008 | 11 |
| GLN | N | B | 116 | 154 | 440 | 996 | 12 |
| GLN | CA | B | 116 | 149 | 434 | 984 | 13 |
| GLN | CB | B | 116 | 150 | 445 | 973 | 17 |
| GLN | CG | B | 116 | 164 | 448 | 967 | 22 |
| GLN | CD | B | 116 | 171 | 458 | 976 | 26 |
| GLN | OE1 | B | 116 | 167 | 461 | 988 | 24 |
| GLN | NE2 | B | 116 | 183 | 462 | 972 | 27 |
| GLN | C | B | 116 | 158 | 422 | 979 | 14 |
| GLN | O | B | 116 | 153 | 414 | 971 | 12 |
| LEU | N | B | 117 | 169 | 420 | 985 | 11 |
| LEU | CA | B | 117 | 178 | 409 | 982 | 12 |
| LEU | CB | B | 117 | 193 | 414 | 982 | 11 |
| LEU | CG | B | 117 | 196 | 425 | 972 | 14 |
| LEU | CD1 | B | 117 | 211 | 428 | 972 | 15 |
| LEU | CD2 | B | 117 | 191 | 422 | 958 | 16 |
| LEU | C | B | 117 | 177 | 397 | 992 | 11 |
| LEU | O | B | 117 | 184 | 387 | 991 | 11 |
| SER | N | B | 118 | 168 | 399 | 1001 | 10 |
| SER | CA | B | 118 | 165 | 388 | 1011 | 10 |
| SER | CB | B | 118 | 165 | 394 | 1025 | 8 |
| SER | OG | B | 118 | 162 | 384 | 1035 | 7 |
| SER | C | B | 118 | 152 | 381 | 1008 | 8 |
| SER | O | B | 118 | 141 | 388 | 1009 | 10 |
| SER | N | B | 119 | 152 | 368 | 1006 | 9 |
| SER | CA | B | 119 | 140 | 361 | 1003 | 10 |
| SER | CB | B | 119 | 144 | 347 | 997 | 12 |
| SER | OG | B | 119 | 152 | 339 | 1006 | 13 |
| SER | C | B | 119 | 132 | 358 | 1015 | 10 |
| SER | O | B | 119 | 120 | 355 | 1014 | 11 |
| THR | N | B | 120 | 138 | 360 | 1027 | 9 |
| THR | CA | B | 120 | 130 | 358 | 1040 | 9 |
| THR | CB | B | 120 | 139 | 349 | 1049 | 11 |
| THR | OG1 | B | 120 | 153 | 355 | 1049 | 10 |
| THR | CG2 | B | 120 | 140 | 335 | 1045 | 11 |
| THR | C | B | 120 | 126 | 371 | 1046 | 10 |
| THR | O | B | 120 | 121 | 370 | 1057 | 10 |
| TYR | N | B | 121 | 128 | 382 | 1040 | 9 |
| TYR | CA | B | 121 | 123 | 395 | 1045 | 9 |
| TYR | CB | B | 121 | 128 | 406 | 1036 | 10 |
| TYR | CG | B | 121 | 121 | 419 | 1038 | 10 |
| TYR | CD1 | B | 121 | 123 | 426 | 1050 | 12 |
| TYR | CE1 | B | 121 | 116 | 438 | 1053 | 10 |
| TYR | CD2 | B | 121 | 113 | 425 | 1029 | 11 |
| TYR | CE2 | B | 121 | 106 | 437 | 1031 | 12 |
| TYR | CZ | B | 121 | 108 | 443 | 1043 | 13 |
| TYR | OH | B | 121 | 101 | 455 | 1046 | 12 |
| TYR | C | B | 121 | 108 | 395 | 1046 | 10 |
| TYR | O | B | 121 | 101 | 391 | 1036 | 9 |
| ARG | N | B | 122 | 103 | 400 | 1057 | 8 |
| ARG | CA | B | 122 | 89 | 402 | 1059 | 9 |
| ARG | CB | B | 122 | 83 | 393 | 1069 | 8 |
| ARG | CG | B | 122 | 84 | 378 | 1065 | 9 |
| ARG | CD | B | 122 | 79 | 369 | 1077 | 10 |
| ARG | NE | B | 122 | 77 | 355 | 1073 | 10 |
| ARG | CZ | B | 122 | 74 | 346 | 1082 | 9 |
| ARG | NH1 | B | 122 | 72 | 349 | 1095 | 11 |
| ARG | NH2 | B | 122 | 73 | 333 | 1078 | 11 |
| ARG | C | B | 122 | 86 | 416 | 1063 | 10 |
| ARG | O | B | 122 | 92 | 421 | 1073 | 10 |
| ASP | N | B | 123 | 77 | 423 | 1055 | 8 |
| ASP | CA | B | 123 | 74 | 437 | 1058 | 9 |
| ASP | CB | B | 123 | 70 | 444 | 1045 | 11 |
| ASP | CG | B | 123 | 68 | 459 | 1047 | 12 |
| ASP | OD1 | B | 123 | 70 | 465 | 1057 | 12 |
| ASP | OD2 | B | 123 | 63 | 465 | 1037 | 14 |
| ASP | C | B | 123 | 63 | 438 | 1069 | 8 |
| ASP | O | B | 123 | 53 | 432 | 1068 | 9 |
| LEU | N | B | 124 | 66 | 446 | 1079 | 9 |
| LEU | CA | B | 124 | 56 | 448 | 1090 | 8 |
| LEU | CB | B | 124 | 63 | 450 | 1103 | 10 |
| LEU | CG | B | 124 | 68 | 437 | 1109 | 12 |
| LEU | CD1 | B | 124 | 75 | 439 | 1122 | 15 |
| LEU | CD2 | B | 124 | 57 | 427 | 1111 | 12 |
| LEU | C | B | 124 | 47 | 461 | 1087 | 10 |
| LEU | O | B | 124 | 38 | 464 | 1094 | 13 |
| ARG | N | B | 125 | 50 | 468 | 1076 | 9 |
| ARG | CA | B | 125 | 42 | 479 | 1071 | 11 |
| ARG | CB | B | 125 | 29 | 475 | 1066 | 11 |
| ARG | CG | B | 125 | 29 | 465 | 1055 | 11 |
| ARG | CD | B | 125 | 15 | 460 | 1052 | 13 |
| ARG | NE | B | 125 | 15 | 450 | 1041 | 17 |
| ARG | CZ | B | 125 | 6 | 441 | 1039 | 19 |
| ARG | NH1 | B | 125 | −5 | 441 | 1047 | 18 |
| ARG | NH2 | B | 125 | 7 | 432 | 1030 | 18 |
| ARG | C | B | 125 | 40 | 489 | 1082 | 14 |
| ARG | O | B | 125 | 29 | 495 | 1084 | 12 |
| LYS | N | B | 126 | 51 | 492 | 1090 | 12 |
| LYS | CA | B | 126 | 50 | 502 | 1101 | 16 |
| LYS | CB | B | 126 | 46 | 494 | 1113 | 21 |
| LYS | CG | B | 126 | 45 | 503 | 1126 | 30 |
| LYS | CD | B | 126 | 39 | 495 | 1137 | 32 |
| LYS | CE | B | 126 | 46 | 482 | 1140 | 35 |
| LYS | NZ | B | 126 | 40 | 474 | 1151 | 37 |
| LYS | C | B | 126 | 63 | 509 | 1103 | 15 |
| LYS | O | B | 126 | 74 | 503 | 1101 | 12 |
| GLY | N | B | 127 | 62 | 522 | 1106 | 14 |
| GLY | CA | B | 127 | 75 | 529 | 1109 | 13 |
| GLY | C | B | 127 | 79 | 529 | 1123 | 12 |
| GLY | O | B | 127 | 71 | 524 | 1132 | 13 |
| VAL | N | B | 128 | 91 | 533 | 1126 | 11 |
| VAL | CA | B | 128 | 96 | 533 | 1140 | 13 |
| VAL | CB | B | 128 | 102 | 519 | 1143 | 14 |
| VAL | CG1 | B | 128 | 113 | 516 | 1133 | 13 |
| VAL | CG2 | B | 128 | 108 | 519 | 1157 | 14 |
| VAL | C | B | 128 | 106 | 544 | 1142 | 12 |
| VAL | O | B | 128 | 114 | 547 | 1133 | 10 |
| TYR | N | B | 129 | 105 | 551 | 1153 | 12 |
| TYR | CA | B | 129 | 114 | 562 | 1156 | 13 |
| TYR | CB | B | 129 | 106 | 575 | 1156 | 13 |
| TYR | CG | B | 129 | 113 | 587 | 1162 | 15 |
| TYR | CD1 | B | 129 | 125 | 592 | 1156 | 17 |
| TYR | CE1 | B | 129 | 132 | 603 | 1162 | 17 |
| TYR | CD2 | B | 129 | 109 | 593 | 1174 | 16 |
| TYR | CE2 | B | 129 | 115 | 604 | 1179 | 18 |
| TYR | CZ | B | 129 | 127 | 609 | 1173 | 17 |
| TYR | OH | B | 129 | 133 | 619 | 1179 | 20 |
| TYR | C | B | 129 | 121 | 559 | 1170 | 12 |
| TYR | O | B | 129 | 114 | 557 | 1180 | 11 |
| VAL | N | B | 130 | 134 | 560 | 1170 | 11 |
| VAL | CA | B | 130 | 141 | 557 | 1182 | 9 |
| VAL | CB | B | 130 | 149 | 544 | 1182 | 11 |
| VAL | CG1 | B | 130 | 156 | 542 | 1195 | 12 |
| VAL | CG2 | B | 130 | 139 | 532 | 1181 | 11 |
| VAL | C | B | 130 | 151 | 568 | 1186 | 7 |
| VAL | O | B | 130 | 161 | 570 | 1179 | 8 |
| PRO | N | B | 131 | 148 | 576 | 1196 | 8 |
| PRO | CD | B | 131 | 135 | 579 | 1201 | 10 |
| PRO | CA | B | 131 | 158 | 587 | 1200 | 9 |
| PRO | CB | B | 131 | 148 | 598 | 1204 | 11 |
| PRO | CG | B | 131 | 137 | 591 | 1211 | 10 |
| PRO | C | B | 131 | 166 | 582 | 1212 | 11 |
| PRO | O | B | 131 | 160 | 575 | 1221 | 9 |

TABLE 2-continued

Structure Coordinates for BACE complexed to Inhibitor

| | | | | | | | |
|---|---|---|---|---|---|---|---|
| TYR | N | B | 132 | 179 | 585 | 1213 | 9 |
| TYR | CA | B | 132 | 187 | 581 | 1223 | 9 |
| TYR | CB | B | 132 | 200 | 574 | 1218 | 7 |
| TYR | CG | B | 132 | 197 | 561 | 1210 | 7 |
| TYR | CD1 | B | 132 | 195 | 549 | 1216 | 6 |
| TYR | CE1 | B | 132 | 192 | 537 | 1208 | 8 |
| TYR | CD2 | B | 132 | 195 | 562 | 1196 | 10 |
| TYR | CE2 | B | 132 | 192 | 551 | 1188 | 9 |
| TYR | CZ | B | 132 | 191 | 538 | 1195 | 10 |
| TYR | OH | B | 132 | 188 | 527 | 1187 | 9 |
| TYR | C | B | 132 | 192 | 594 | 1231 | 8 |
| TYR | O | B | 132 | 189 | 605 | 1226 | 10 |
| THR | N | B | 133 | 199 | 592 | 1242 | 7 |
| THR | CA | B | 133 | 205 | 603 | 1249 | 10 |
| THR | CB | B | 133 | 214 | 599 | 1260 | 8 |
| THR | OG1 | B | 133 | 207 | 592 | 1270 | 8 |
| THR | CG2 | B | 133 | 221 | 611 | 1266 | 10 |
| THR | C | B | 133 | 211 | 613 | 1239 | 10 |
| THR | O | B | 133 | 210 | 625 | 1240 | 11 |
| GLN | N | B | 134 | 219 | 607 | 1229 | 10 |
| GLN | CA | B | 134 | 225 | 614 | 1219 | 12 |
| GLN | CB | B | 134 | 240 | 617 | 1222 | 15 |
| GLN | CG | B | 134 | 242 | 627 | 1234 | 24 |
| GLN | CD | B | 134 | 255 | 634 | 1233 | 29 |
| GLN | OE1 | B | 134 | 266 | 627 | 1233 | 33 |
| GLN | NE2 | B | 134 | 255 | 647 | 1234 | 33 |
| GLN | C | B | 134 | 224 | 606 | 1206 | 11 |
| GLN | O | B | 134 | 229 | 595 | 1206 | 11 |
| GLY | N | B | 135 | 218 | 611 | 1196 | 11 |
| GLY | CA | B | 135 | 216 | 604 | 1184 | 11 |
| GLY | C | B | 135 | 202 | 598 | 1183 | 10 |
| GLY | O | B | 135 | 195 | 596 | 1193 | 7 |
| LYS | N | B | 136 | 197 | 597 | 1170 | 10 |
| LYS | CA | B | 136 | 184 | 592 | 1168 | 10 |
| LYS | CB | B | 136 | 173 | 602 | 1172 | 13 |
| LYS | CG | B | 136 | 175 | 615 | 1164 | 17 |
| LYS | CD | B | 136 | 166 | 626 | 1170 | 21 |
| LYS | CE | B | 136 | 168 | 639 | 1163 | 26 |
| LYS | NZ | B | 136 | 162 | 650 | 1170 | 31 |
| LYS | C | B | 136 | 182 | 587 | 1154 | 8 |
| LYS | O | B | 136 | 190 | 591 | 1145 | 8 |
| TRP | N | B | 137 | 172 | 579 | 1151 | 11 |
| TRP | CA | B | 137 | 170 | 574 | 1137 | 10 |
| TRP | CB | B | 137 | 179 | 562 | 1134 | 9 |
| TRP | CG | B | 137 | 178 | 550 | 1143 | 10 |
| TRP | CD2 | B | 137 | 167 | 541 | 1144 | 9 |
| TRP | CE2 | B | 137 | 171 | 532 | 1154 | 9 |
| TRP | CE3 | B | 137 | 155 | 539 | 1137 | 10 |
| TRP | CD1 | B | 137 | 187 | 547 | 1153 | 8 |
| TRP | NE1 | B | 137 | 183 | 536 | 1159 | 8 |
| TRP | CZ2 | B | 137 | 163 | 521 | 1158 | 8 |
| TRP | CZ3 | B | 137 | 147 | 528 | 1141 | 9 |
| TRP | CH2 | B | 137 | 151 | 519 | 1151 | 10 |
| TRP | C | B | 137 | 155 | 571 | 1135 | 10 |
| TRP | O | B | 137 | 148 | 569 | 1144 | 10 |
| GLU | N | B | 138 | 152 | 570 | 1122 | 10 |
| GLU | CA | B | 138 | 138 | 567 | 1118 | 9 |
| GLU | CB | B | 138 | 133 | 579 | 1109 | 15 |
| GLU | CG | B | 138 | 118 | 578 | 1106 | 26 |
| GLU | CD | B | 138 | 109 | 584 | 1117 | 30 |
| GLU | OE1 | B | 138 | 111 | 596 | 1120 | 31 |
| GLU | OE2 | B | 138 | 100 | 577 | 1122 | 36 |
| GLU | C | B | 138 | 139 | 555 | 1109 | 9 |
| GLU | O | B | 138 | 149 | 554 | 1101 | 8 |
| GLY | N | B | 139 | 130 | 546 | 1110 | 8 |
| GLY | CA | B | 139 | 131 | 534 | 1102 | 10 |
| GLY | C | B | 139 | 118 | 527 | 1099 | 11 |
| GLY | O | B | 139 | 107 | 532 | 1102 | 11 |
| GLU | N | B | 140 | 119 | 516 | 1092 | 10 |
| GLU | CA | B | 140 | 107 | 508 | 1087 | 11 |
| GLU | CB | B | 140 | 107 | 508 | 1072 | 11 |
| GLU | CG | B | 140 | 106 | 522 | 1066 | 12 |
| GLU | CD | B | 140 | 107 | 522 | 1050 | 16 |
| GLU | OE1 | B | 140 | 104 | 532 | 1044 | 18 |
| GLU | OE2 | B | 140 | 110 | 511 | 1044 | 14 |
| GLU | C | B | 140 | 109 | 494 | 1093 | 10 |
| GLU | O | B | 140 | 119 | 488 | 1091 | 9 |
| LEU | N | B | 141 | 98 | 490 | 1100 | 9 |
| LEU | CA | B | 141 | 99 | 477 | 1106 | 9 |
| LEU | CB | B | 141 | 89 | 476 | 1118 | 10 |
| LEU | CG | B | 141 | 92 | 485 | 1130 | 11 |
| LEU | CD1 | B | 141 | 81 | 485 | 1140 | 11 |
| LEU | CD2 | B | 141 | 105 | 479 | 1137 | 13 |
| LEU | C | B | 141 | 96 | 465 | 1097 | 10 |
| LEU | O | B | 141 | 89 | 466 | 1087 | 11 |
| GLY | N | B | 142 | 102 | 453 | 1101 | 10 |
| GLY | CA | B | 142 | 100 | 441 | 1094 | 10 |
| GLY | C | B | 142 | 107 | 430 | 1102 | 9 |
| GLY | O | B | 142 | 111 | 432 | 1113 | 9 |
| THR | N | B | 143 | 107 | 418 | 1096 | 8 |
| THR | CA | B | 143 | 114 | 407 | 1103 | 8 |
| THR | CB | B | 143 | 105 | 397 | 1110 | 10 |
| THR | OG1 | B | 143 | 98 | 389 | 1099 | 8 |
| THR | CG2 | B | 143 | 94 | 404 | 1118 | 9 |
| THR | C | B | 143 | 123 | 399 | 1093 | 9 |
| THR | O | B | 143 | 120 | 401 | 1081 | 9 |
| ASP | N | B | 144 | 132 | 392 | 1097 | 8 |
| ASP | CA | B | 144 | 141 | 384 | 1088 | 8 |
| ASP | CB | B | 144 | 151 | 393 | 1081 | 8 |
| ASP | CG | B | 144 | 154 | 388 | 1067 | 7 |
| ASP | OD1 | B | 144 | 154 | 375 | 1065 | 10 |
| ASP | OD2 | B | 144 | 157 | 396 | 1058 | 8 |
| ASP | C | B | 144 | 148 | 374 | 1097 | 10 |
| ASP | O | B | 144 | 147 | 374 | 1109 | 9 |
| LEU | N | B | 145 | 156 | 365 | 1090 | 8 |
| LEU | CA | B | 145 | 164 | 355 | 1097 | 7 |
| LEU | CB | B | 145 | 166 | 343 | 1088 | 9 |
| LEU | CG | B | 145 | 153 | 336 | 1084 | 9 |
| LEU | CD1 | B | 145 | 157 | 323 | 1076 | 12 |
| LEU | CD2 | B | 145 | 144 | 332 | 1095 | 9 |
| LEU | C | B | 145 | 177 | 361 | 1101 | 9 |
| LEU | O | B | 145 | 184 | 368 | 1093 | 10 |
| VAL | N | B | 146 | 180 | 360 | 1114 | 10 |
| VAL | CA | B | 146 | 193 | 366 | 1119 | 10 |
| VAL | CB | B | 146 | 189 | 377 | 1130 | 9 |
| VAL | CG1 | B | 146 | 202 | 383 | 1134 | 9 |
| VAL | CG2 | B | 146 | 180 | 387 | 1124 | 8 |
| VAL | C | B | 146 | 202 | 355 | 1126 | 9 |
| VAL | O | B | 146 | 197 | 346 | 1133 | 9 |
| SER | N | B | 147 | 215 | 357 | 1124 | 11 |
| SER | CA | B | 147 | 224 | 348 | 1130 | 11 |
| SER | CB | B | 147 | 229 | 337 | 1120 | 14 |
| SER | OG | B | 147 | 218 | 330 | 1114 | 21 |
| SER | C | B | 147 | 236 | 356 | 1135 | 12 |
| SER | O | B | 147 | 239 | 367 | 1131 | 11 |
| ILE | N | B | 148 | 244 | 349 | 1144 | 11 |
| ILE | CA | B | 148 | 256 | 355 | 1149 | 10 |
| ILE | CB | B | 148 | 255 | 358 | 1165 | 11 |
| ILE | CG2 | B | 148 | 268 | 365 | 1170 | 11 |
| ILE | CG1 | B | 148 | 243 | 367 | 1167 | 12 |
| ILE | CD1 | B | 148 | 240 | 370 | 1182 | 14 |
| ILE | C | B | 148 | 268 | 345 | 1147 | 11 |
| ILE | O | B | 148 | 269 | 335 | 1154 | 14 |
| PRO | N | B | 149 | 275 | 348 | 1136 | 11 |
| PRO | CD | B | 149 | 275 | 360 | 1128 | 11 |
| PRO | CA | B | 149 | 286 | 339 | 1132 | 14 |
| PRO | CB | B | 149 | 294 | 348 | 1122 | 12 |
| PRO | CG | B | 149 | 284 | 356 | 1116 | 14 |
| PRO | C | B | 149 | 295 | 334 | 1144 | 15 |
| PRO | O | B | 149 | 298 | 322 | 1144 | 16 |
| HIS | N | B | 150 | 299 | 343 | 1152 | 13 |
| HIS | CA | B | 150 | 307 | 339 | 1164 | 14 |
| HIS | CB | B | 150 | 319 | 349 | 1165 | 16 |
| HIS | CG | B | 150 | 328 | 348 | 1153 | 18 |
| HIS | CD2 | B | 150 | 329 | 357 | 1143 | 19 |
| HIS | ND1 | B | 150 | 336 | 338 | 1150 | 21 |
| HIS | CE1 | B | 150 | 342 | 340 | 1138 | 20 |
| HIS | NE2 | B | 150 | 338 | 352 | 1134 | 22 |
| HIS | C | B | 150 | 299 | 339 | 1176 | 16 |
| HIS | O | B | 150 | 301 | 347 | 1186 | 17 |
| GLY | N | B | 151 | 288 | 331 | 1176 | 18 |
| GLY | CA | B | 151 | 279 | 331 | 1187 | 16 |
| GLY | C | B | 151 | 272 | 317 | 1187 | 17 |
| GLY | O | B | 151 | 278 | 308 | 1181 | 19 |

TABLE 2-continued

Structure Coordinates for BACE complexed to Inhibitor

| | | | | | | | |
|---|---|---|---|---|---|---|---|
| PRO | N | B | 152 | 261 | 315 | 1193 | 18 |
| PRO | CD | B | 152 | 252 | 325 | 1199 | 18 |
| PRO | CA | B | 152 | 254 | 302 | 1193 | 19 |
| PRO | CB | B | 152 | 241 | 304 | 1201 | 20 |
| PRO | CG | B | 152 | 238 | 319 | 1198 | 22 |
| PRO | C | B | 152 | 251 | 298 | 1179 | 21 |
| PRO | O | B | 152 | 248 | 306 | 1170 | 19 |
| ASN | N | B | 153 | 252 | 285 | 1176 | 22 |
| ASN | CA | B | 153 | 250 | 279 | 1163 | 23 |
| ASN | CB | B | 153 | 256 | 266 | 1161 | 28 |
| ASN | CG | B | 153 | 255 | 260 | 1147 | 32 |
| ASN | OD1 | B | 153 | 259 | 267 | 1138 | 35 |
| ASN | ND2 | B | 153 | 251 | 248 | 1146 | 35 |
| ASN | C | B | 153 | 235 | 278 | 1160 | 21 |
| ASN | O | B | 153 | 229 | 268 | 1159 | 22 |
| VAL | N | B | 154 | 228 | 290 | 1159 | 19 |
| VAL | CA | B | 154 | 214 | 290 | 1157 | 18 |
| VAL | CB | B | 154 | 206 | 292 | 1170 | 18 |
| VAL | CG1 | B | 154 | 208 | 280 | 1179 | 19 |
| VAL | CG2 | B | 154 | 210 | 305 | 1177 | 19 |
| VAL | C | B | 154 | 210 | 302 | 1148 | 17 |
| VAL | O | B | 154 | 218 | 311 | 1146 | 16 |
| THR | N | B | 155 | 198 | 301 | 1142 | 14 |
| THR | CA | B | 155 | 193 | 312 | 1134 | 15 |
| THR | CB | B | 155 | 192 | 307 | 1119 | 16 |
| THR | OG1 | B | 155 | 205 | 306 | 1114 | 19 |
| THR | CG2 | B | 155 | 185 | 318 | 1111 | 17 |
| THR | C | B | 155 | 179 | 314 | 1139 | 14 |
| THR | O | B | 155 | 171 | 305 | 1141 | 16 |
| VAL | N | B | 156 | 175 | 327 | 1140 | 12 |
| VAL | CA | B | 156 | 162 | 330 | 1145 | 15 |
| VAL | CB | B | 156 | 162 | 334 | 1160 | 17 |
| VAL | CG1 | B | 156 | 167 | 323 | 1169 | 18 |
| VAL | CG2 | B | 156 | 170 | 347 | 1162 | 16 |
| VAL | C | B | 156 | 155 | 341 | 1137 | 12 |
| VAL | O | B | 156 | 162 | 349 | 1131 | 12 |
| ARG | N | B | 157 | 142 | 341 | 1137 | 10 |
| ARG | CA | B | 157 | 135 | 352 | 1130 | 11 |
| ARG | CB | B | 157 | 121 | 347 | 1124 | 14 |
| ARG | CG | B | 157 | 114 | 359 | 1117 | 15 |
| ARG | CD | B | 157 | 102 | 354 | 1109 | 17 |
| ARG | NE | B | 157 | 106 | 346 | 1097 | 14 |
| ARG | CZ | B | 157 | 110 | 352 | 1086 | 13 |
| ARG | NH1 | B | 157 | 111 | 365 | 1085 | 10 |
| ARG | NH2 | B | 157 | 113 | 344 | 1075 | 10 |
| ARG | C | B | 157 | 132 | 363 | 1141 | 9 |
| ARG | O | B | 157 | 126 | 361 | 1151 | 11 |
| ALA | N | B | 158 | 138 | 375 | 1138 | 9 |
| ALA | CA | B | 158 | 137 | 386 | 1147 | 9 |
| ALA | CB | B | 158 | 150 | 388 | 1154 | 13 |
| ALA | C | B | 158 | 132 | 399 | 1140 | 9 |
| ALA | O | B | 158 | 132 | 400 | 1128 | 8 |
| ASN | N | B | 159 | 127 | 408 | 1149 | 7 |
| ASN | CA | B | 159 | 123 | 421 | 1144 | 7 |
| ASN | CB | B | 159 | 115 | 428 | 1154 | 9 |
| ASN | CG | B | 159 | 102 | 422 | 1157 | 11 |
| ASN | OD1 | B | 159 | 94 | 419 | 1148 | 12 |
| ASN | ND2 | B | 159 | 99 | 419 | 1170 | 9 |
| ASN | C | B | 159 | 135 | 429 | 1140 | 7 |
| ASN | O | B | 159 | 145 | 428 | 1147 | 9 |
| ILE | N | B | 160 | 134 | 436 | 1129 | 6 |
| ILE | CA | B | 160 | 145 | 444 | 1124 | 7 |
| ILE | CB | B | 160 | 153 | 438 | 1112 | 7 |
| ILE | CG2 | B | 160 | 164 | 446 | 1108 | 9 |
| ILE | CG1 | B | 160 | 158 | 424 | 1116 | 9 |
| ILE | CD1 | B | 160 | 165 | 416 | 1105 | 11 |
| ILE | C | B | 160 | 140 | 458 | 1119 | 8 |
| ILE | O | B | 160 | 131 | 458 | 1111 | 8 |
| ALA | N | B | 161 | 146 | 468 | 1124 | 6 |
| ALA | CA | B | 161 | 142 | 482 | 1120 | 8 |
| ALA | CB | B | 161 | 143 | 491 | 1132 | 7 |
| ALA | C | B | 161 | 152 | 486 | 1110 | 9 |
| ALA | O | B | 161 | 164 | 487 | 1112 | 10 |
| ALA | N | B | 162 | 147 | 488 | 1097 | 7 |
| ALA | CA | B | 162 | 155 | 492 | 1086 | 9 |
| ALA | CB | B | 162 | 149 | 488 | 1073 | 10 |
| ALA | C | B | 162 | 156 | 507 | 1087 | 10 |
| ALA | O | B | 162 | 147 | 514 | 1084 | 8 |
| ILE | N | B | 163 | 168 | 512 | 1091 | 10 |
| ILE | CA | B | 163 | 170 | 526 | 1093 | 8 |
| ILE | CB | B | 163 | 183 | 529 | 1100 | 8 |
| ILE | CG2 | B | 163 | 186 | 544 | 1101 | 10 |
| ILE | CG1 | B | 163 | 182 | 523 | 1114 | 7 |
| ILE | CD1 | B | 163 | 195 | 523 | 1122 | 9 |
| ILE | C | B | 163 | 171 | 534 | 1079 | 10 |
| ILE | O | B | 163 | 179 | 530 | 1071 | 10 |
| THR | N | B | 164 | 162 | 543 | 1077 | 9 |
| THR | CA | B | 164 | 161 | 551 | 1065 | 12 |
| THR | CB | B | 164 | 147 | 551 | 1059 | 14 |
| THR | OG1 | B | 164 | 138 | 556 | 1069 | 15 |
| THR | CG2 | B | 164 | 143 | 537 | 1055 | 15 |
| THR | C | B | 164 | 166 | 565 | 1067 | 12 |
| THR | O | B | 164 | 170 | 572 | 1057 | 12 |
| GLU | N | B | 165 | 165 | 570 | 1079 | 12 |
| GLU | CA | B | 165 | 170 | 584 | 1082 | 13 |
| GLU | CB | B | 165 | 157 | 593 | 1082 | 16 |
| GLU | CG | B | 165 | 151 | 596 | 1069 | 19 |
| GLU | CD | B | 165 | 138 | 603 | 1069 | 24 |
| GLU | OE1 | B | 165 | 136 | 611 | 1078 | 23 |
| GLU | OE2 | B | 165 | 129 | 600 | 1061 | 27 |
| GLU | C | B | 165 | 176 | 584 | 1096 | 12 |
| GLU | O | B | 165 | 172 | 577 | 1105 | 11 |
| SER | N | B | 166 | 187 | 592 | 1098 | 11 |
| SER | CA | B | 166 | 193 | 592 | 1110 | 11 |
| SER | CB | B | 166 | 204 | 581 | 1111 | 9 |
| SER | OG | B | 166 | 213 | 582 | 1100 | 14 |
| SER | C | B | 166 | 200 | 606 | 1113 | 10 |
| SER | O | B | 166 | 203 | 614 | 1104 | 13 |
| ASP | N | B | 167 | 202 | 609 | 1126 | 10 |
| ASP | CA | B | 167 | 208 | 621 | 1130 | 9 |
| ASP | CB | B | 167 | 196 | 630 | 1136 | 10 |
| ASP | CG | B | 167 | 201 | 645 | 1139 | 13 |
| ASP | OD1 | B | 167 | 213 | 647 | 1139 | 12 |
| ASP | OD2 | B | 167 | 192 | 653 | 1140 | 14 |
| ASP | C | B | 167 | 218 | 619 | 1141 | 9 |
| ASP | O | B | 167 | 214 | 615 | 1152 | 10 |
| LYS | N | B | 168 | 231 | 621 | 1138 | 9 |
| LYS | CA | B | 168 | 242 | 619 | 1147 | 13 |
| LYS | CB | B | 168 | 241 | 630 | 1158 | 16 |
| LYS | CG | B | 168 | 244 | 644 | 1153 | 20 |
| LYS | CD | B | 168 | 245 | 654 | 1164 | 24 |
| LYS | CE | B | 168 | 232 | 656 | 1171 | 25 |
| LYS | NZ | B | 168 | 222 | 662 | 1162 | 26 |
| LYS | C | B | 168 | 241 | 605 | 1154 | 13 |
| LYS | O | B | 168 | 245 | 603 | 1166 | 10 |
| PHE | N | B | 169 | 237 | 595 | 1146 | 9 |
| PHE | CA | B | 169 | 237 | 581 | 1151 | 10 |
| PHE | CB | B | 169 | 224 | 574 | 1146 | 8 |
| PHE | CG | B | 169 | 223 | 560 | 1150 | 9 |
| PHE | CD1 | B | 169 | 222 | 556 | 1164 | 8 |
| PHE | CD2 | B | 169 | 223 | 550 | 1141 | 9 |
| PHE | CE1 | B | 169 | 220 | 543 | 1167 | 9 |
| PHE | CE2 | B | 169 | 222 | 536 | 1144 | 10 |
| PHE | CZ | B | 169 | 221 | 533 | 1158 | 9 |
| PHE | C | B | 169 | 249 | 574 | 1147 | 11 |
| PHE | O | B | 169 | 257 | 569 | 1155 | 11 |
| PHE | N | B | 170 | 251 | 572 | 1134 | 10 |
| PHE | CA | B | 170 | 262 | 565 | 1128 | 13 |
| PHE | CB | B | 170 | 261 | 563 | 1113 | 11 |
| PHE | CG | B | 170 | 249 | 553 | 1110 | 10 |
| PHE | CD1 | B | 170 | 238 | 558 | 1103 | 11 |
| PHE | CD2 | B | 170 | 249 | 540 | 1115 | 10 |
| PHE | CE1 | B | 170 | 228 | 549 | 1100 | 11 |
| PHE | CE2 | B | 170 | 239 | 531 | 1112 | 11 |
| PHE | CZ | B | 170 | 228 | 536 | 1104 | 11 |
| PHE | C | B | 170 | 275 | 574 | 1131 | 16 |
| PHE | O | B | 170 | 274 | 586 | 1131 | 14 |
| ILE | N | B | 171 | 286 | 567 | 1133 | 14 |
| ILE | CA | B | 171 | 299 | 574 | 1135 | 18 |
| ILE | CB | B | 171 | 305 | 569 | 1149 | 16 |
| ILE | CG2 | B | 171 | 319 | 575 | 1151 | 17 |
| ILE | CG1 | B | 171 | 295 | 574 | 1160 | 17 |
| ILE | CD1 | B | 171 | 300 | 569 | 1174 | 17 |
| ILE | C | B | 171 | 308 | 570 | 1124 | 18 |

TABLE 2-continued

Structure Coordinates for BACE complexed to Inhibitor

| ILE | O | B | 171 | 310 | 559 | 1121 | 18 |
|---|---|---|---|---|---|---|---|
| ASN | N | B | 172 | 315 | 581 | 1119 | 20 |
| ASN | CA | B | 172 | 324 | 579 | 1108 | 23 |
| ASN | CB | B | 172 | 329 | 592 | 1102 | 26 |
| ASN | CG | B | 172 | 335 | 591 | 1089 | 30 |
| ASN | OD1 | B | 172 | 341 | 601 | 1084 | 34 |
| ASN | ND2 | B | 172 | 334 | 580 | 1082 | 31 |
| ASN | C | B | 172 | 336 | 571 | 1112 | 21 |
| ASN | O | B | 172 | 343 | 574 | 1122 | 21 |
| GLY | N | B | 173 | 339 | 559 | 1106 | 20 |
| GLY | CA | B | 173 | 350 | 551 | 1109 | 20 |
| GLY | C | B | 173 | 348 | 541 | 1121 | 20 |
| GLY | O | B | 173 | 358 | 534 | 1125 | 20 |
| SER | N | B | 174 | 336 | 540 | 1126 | 19 |
| SER | CA | B | 174 | 333 | 531 | 1137 | 16 |
| SER | CB | B | 174 | 320 | 534 | 1143 | 16 |
| SER | OG | B | 174 | 309 | 531 | 1134 | 17 |
| SER | C | B | 174 | 333 | 516 | 1133 | 15 |
| SER | O | B | 174 | 335 | 507 | 1141 | 14 |
| ASN | N | B | 175 | 331 | 514 | 1120 | 12 |
| ASN | CA | B | 175 | 330 | 501 | 1114 | 12 |
| ASN | CB | B | 175 | 342 | 493 | 1117 | 14 |
| ASN | CG | B | 175 | 345 | 482 | 1107 | 17 |
| ASN | OD1 | B | 175 | 344 | 484 | 1095 | 19 |
| ASN | ND2 | B | 175 | 348 | 470 | 1112 | 16 |
| ASN | C | B | 175 | 317 | 493 | 1117 | 12 |
| ASN | O | B | 175 | 317 | 481 | 1114 | 14 |
| TRP | N | B | 176 | 307 | 499 | 1123 | 11 |
| TRP | CA | B | 176 | 295 | 492 | 1126 | 9 |
| TRP | CB | B | 176 | 291 | 491 | 1141 | 10 |
| TRP | CG | B | 176 | 291 | 504 | 1149 | 10 |
| TRP | CD2 | B | 176 | 280 | 513 | 1150 | 9 |
| TRP | CE2 | B | 176 | 285 | 523 | 1159 | 11 |
| TRP | CE3 | B | 176 | 268 | 514 | 1145 | 11 |
| TRP | CD1 | B | 176 | 301 | 508 | 1157 | 10 |
| TRP | NE1 | B | 176 | 298 | 520 | 1163 | 11 |
| TRP | CZ2 | B | 176 | 277 | 534 | 1163 | 10 |
| TRP | CZ3 | B | 176 | 260 | 525 | 1149 | 9 |
| TRP | CH2 | B | 176 | 264 | 534 | 1158 | 10 |
| TRP | C | B | 176 | 283 | 499 | 1118 | 10 |
| TRP | O | B | 176 | 284 | 511 | 1115 | 10 |
| GLU | N | B | 177 | 274 | 491 | 1114 | 9 |
| GLU | CA | B | 177 | 263 | 495 | 1106 | 10 |
| GLU | CB | B | 177 | 263 | 488 | 1092 | 11 |
| GLU | CG | B | 177 | 275 | 490 | 1084 | 15 |
| GLU | CD | B | 177 | 286 | 480 | 1087 | 17 |
| GLU | OE1 | B | 177 | 298 | 484 | 1087 | 22 |
| GLU | OE2 | B | 177 | 283 | 468 | 1090 | 12 |
| GLU | C | B | 177 | 249 | 493 | 1112 | 10 |
| GLU | O | B | 177 | 239 | 496 | 1106 | 10 |
| GLY | N | B | 178 | 249 | 489 | 1124 | 8 |
| GLY | CA | B | 178 | 236 | 486 | 1131 | 7 |
| GLY | C | B | 178 | 238 | 486 | 1146 | 8 |
| GLY | O | B | 178 | 249 | 487 | 1151 | 6 |
| ILE | N | B | 179 | 226 | 484 | 1153 | 6 |
| ILE | CA | B | 179 | 227 | 484 | 1168 | 7 |
| ILE | CB | B | 179 | 221 | 497 | 1173 | 5 |
| ILE | CG2 | B | 179 | 207 | 499 | 1169 | 7 |
| ILE | CG1 | B | 179 | 223 | 498 | 1188 | 9 |
| ILE | CD1 | B | 179 | 221 | 512 | 1194 | 7 |
| ILE | C | B | 179 | 218 | 472 | 1173 | 8 |
| ILE | O | B | 179 | 208 | 469 | 1168 | 6 |
| LEU | N | B | 180 | 223 | 466 | 1184 | 6 |
| LEU | CA | B | 180 | 216 | 455 | 1190 | 8 |
| LEU | CB | B | 180 | 225 | 443 | 1191 | 9 |
| LEU | CG | B | 180 | 219 | 430 | 1197 | 7 |
| LEU | CD1 | B | 180 | 207 | 426 | 1188 | 11 |
| LEU | CD2 | B | 180 | 229 | 419 | 1197 | 8 |
| LEU | C | B | 180 | 212 | 459 | 1204 | 8 |
| LEU | O | B | 180 | 220 | 459 | 1213 | 9 |
| GLY | N | B | 181 | 199 | 463 | 1206 | 7 |
| GLY | CA | B | 181 | 194 | 467 | 1219 | 8 |
| GLY | C | B | 181 | 191 | 454 | 1227 | 9 |
| GLY | O | B | 181 | 182 | 446 | 1223 | 9 |
| LEU | N | B | 182 | 199 | 452 | 1237 | 6 |
| LEU | CA | B | 182 | 198 | 440 | 1246 | 6 |
| LEU | CB | B | 182 | 212 | 435 | 1250 | 10 |
| LEU | CG | B | 182 | 220 | 430 | 1238 | 10 |
| LEU | CD1 | B | 182 | 235 | 428 | 1242 | 10 |
| LEU | CD2 | B | 182 | 214 | 417 | 1233 | 11 |
| LEU | C | B | 182 | 189 | 442 | 1258 | 6 |
| LEU | O | B | 182 | 188 | 432 | 1266 | 10 |
| ALA | N | B | 183 | 183 | 454 | 1260 | 8 |
| ALA | CA | B | 183 | 175 | 456 | 1272 | 8 |
| ALA | CB | B | 183 | 174 | 471 | 1275 | 10 |
| ALA | C | B | 183 | 161 | 450 | 1269 | 9 |
| ALA | O | B | 183 | 158 | 444 | 1259 | 9 |
| TYR | N | B | 184 | 152 | 453 | 1279 | 9 |
| TYR | CA | B | 184 | 138 | 447 | 1278 | 10 |
| TYR | CB | B | 184 | 133 | 445 | 1292 | 10 |
| TYR | CG | B | 184 | 142 | 437 | 1301 | 10 |
| TYR | CD1 | B | 184 | 152 | 443 | 1309 | 9 |
| TYR | CE1 | B | 184 | 161 | 435 | 1317 | 9 |
| TYR | CD2 | B | 184 | 141 | 423 | 1302 | 11 |
| TYR | CE2 | B | 184 | 149 | 415 | 1310 | 12 |
| TYR | CZ | B | 184 | 159 | 421 | 1318 | 12 |
| TYR | OH | B | 184 | 167 | 413 | 1326 | 12 |
| TYR | C | B | 184 | 128 | 454 | 1270 | 10 |
| TYR | O | B | 184 | 129 | 466 | 1267 | 10 |
| ALA | N | B | 185 | 118 | 447 | 1266 | 11 |
| ALA | CA | B | 185 | 107 | 452 | 1258 | 11 |
| ALA | CB | B | 185 | 96 | 441 | 1255 | 11 |
| ALA | C | B | 185 | 100 | 464 | 1263 | 11 |
| ALA | O | B | 185 | 95 | 472 | 1255 | 10 |
| GLU | N | B | 186 | 100 | 466 | 1276 | 13 |
| GLU | CA | B | 186 | 93 | 478 | 1282 | 14 |
| GLU | CB | B | 186 | 96 | 479 | 1297 | 18 |
| GLU | CG | B | 186 | 87 | 489 | 1304 | 26 |
| GLU | CD | B | 186 | 90 | 490 | 1319 | 31 |
| GLU | OE1 | B | 186 | 89 | 480 | 1326 | 35 |
| GLU | OE2 | B | 186 | 94 | 501 | 1323 | 36 |
| GLU | C | B | 186 | 98 | 491 | 1275 | 13 |
| GLU | O | B | 186 | 90 | 500 | 1274 | 15 |
| ILE | N | B | 187 | 110 | 492 | 1271 | 11 |
| ILE | CA | B | 187 | 115 | 504 | 1265 | 11 |
| ILE | CB | B | 187 | 128 | 509 | 1272 | 11 |
| ILE | CG2 | B | 187 | 126 | 513 | 1286 | 11 |
| ILE | CG1 | B | 187 | 139 | 499 | 1271 | 11 |
| ILE | CD1 | B | 187 | 153 | 503 | 1276 | 12 |
| ILE | C | B | 187 | 118 | 503 | 1250 | 11 |
| ILE | O | B | 187 | 124 | 512 | 1244 | 13 |
| ALA | N | B | 188 | 112 | 493 | 1244 | 11 |
| ALA | CA | B | 188 | 113 | 491 | 1229 | 11 |
| ALA | CB | B | 188 | 110 | 477 | 1225 | 11 |
| ALA | C | B | 188 | 103 | 501 | 1222 | 13 |
| ALA | O | B | 188 | 93 | 504 | 1227 | 12 |
| ARG | N | B | 189 | 107 | 505 | 1210 | 11 |
| ARG | CA | B | 189 | 99 | 514 | 1202 | 11 |
| ARG | CB | B | 189 | 107 | 526 | 1197 | 13 |
| ARG | CG | B | 189 | 112 | 535 | 1207 | 16 |
| ARG | CD | B | 189 | 100 | 541 | 1215 | 21 |
| ARG | NE | B | 189 | 105 | 552 | 1225 | 25 |
| ARG | CZ | B | 189 | 106 | 564 | 1222 | 27 |
| ARG | NH1 | B | 189 | 103 | 569 | 1210 | 31 |
| ARG | NH2 | B | 189 | 111 | 573 | 1231 | 26 |
| ARG | C | B | 189 | 94 | 505 | 1190 | 12 |
| ARG | O | B | 189 | 101 | 497 | 1186 | 10 |
| PRO | N | B | 190 | 81 | 508 | 1185 | 13 |
| PRO | CD | B | 190 | 76 | 501 | 1174 | 15 |
| PRO | CA | B | 190 | 72 | 519 | 1190 | 14 |
| PRO | CB | B | 190 | 62 | 519 | 1179 | 15 |
| PRO | CG | B | 190 | 61 | 505 | 1174 | 17 |
| PRO | C | B | 190 | 66 | 516 | 1204 | 16 |
| PRO | O | B | 190 | 62 | 526 | 1211 | 17 |
| ASP | N | B | 191 | 65 | 504 | 1208 | 15 |
| ASP | CA | B | 191 | 60 | 500 | 1221 | 17 |
| ASP | CB | B | 191 | 44 | 500 | 1220 | 19 |
| ASP | CG | B | 191 | 39 | 491 | 1209 | 23 |
| ASP | OD1 | B | 191 | 37 | 497 | 1198 | 26 |
| ASP | OD2 | B | 191 | 37 | 479 | 1211 | 22 |
| ASP | C | B | 191 | 65 | 486 | 1225 | 16 |
| ASP | O | B | 191 | 72 | 480 | 1217 | 16 |
| ASP | N | B | 192 | 61 | 481 | 1237 | 16 |
| ASP | CA | B | 192 | 66 | 469 | 1242 | 16 |

TABLE 2-continued

Structure Coordinates for BACE complexed to Inhibitor

| | | | | | | | |
|---|---|---|---|---|---|---|---|
| ASP | CB | B | 192 | 63 | 467 | 1257 | 18 |
| ASP | CG | B | 192 | 48 | 467 | 1260 | 22 |
| ASP | OD1 | B | 192 | 40 | 465 | 1251 | 19 |
| ASP | OD2 | B | 192 | 44 | 469 | 1272 | 22 |
| ASP | C | B | 192 | 60 | 456 | 1234 | 15 |
| ASP | O | B | 192 | 63 | 445 | 1239 | 16 |
| SER | N | B | 193 | 53 | 458 | 1224 | 14 |
| SER | CA | B | 193 | 48 | 447 | 1216 | 14 |
| SER | CB | B | 193 | 35 | 450 | 1209 | 15 |
| SER | OG | B | 193 | 37 | 459 | 1198 | 18 |
| SER | C | B | 193 | 59 | 442 | 1206 | 14 |
| SER | O | B | 193 | 58 | 431 | 1201 | 14 |
| LEU | N | B | 194 | 69 | 450 | 1204 | 13 |
| LEU | CA | B | 194 | 80 | 446 | 1195 | 10 |
| LEU | CB | B | 194 | 86 | 459 | 1188 | 11 |
| LEU | CG | B | 194 | 95 | 456 | 1176 | 10 |
| LEU | CD1 | B | 194 | 86 | 451 | 1164 | 11 |
| LEU | CD2 | B | 194 | 103 | 468 | 1172 | 11 |
| LEU | C | B | 194 | 90 | 439 | 1202 | 11 |
| LEU | O | B | 194 | 99 | 445 | 1209 | 10 |
| GLU | N | B | 195 | 89 | 426 | 1202 | 11 |
| GLU | CA | B | 195 | 98 | 417 | 1209 | 10 |
| GLU | CB | B | 195 | 95 | 402 | 1205 | 12 |
| GLU | CG | B | 195 | 104 | 392 | 1211 | 12 |
| GLU | CD | B | 195 | 99 | 378 | 1209 | 15 |
| GLU | OE1 | B | 195 | 90 | 373 | 1217 | 18 |
| GLU | OE2 | B | 195 | 103 | 371 | 1199 | 15 |
| GLU | C | B | 195 | 113 | 419 | 1205 | 11 |
| GLU | O | B | 195 | 117 | 419 | 1194 | 9 |
| PRO | N | B | 196 | 121 | 422 | 1216 | 9 |
| PRO | CD | B | 196 | 117 | 426 | 1229 | 10 |
| PRO | CA | B | 196 | 136 | 425 | 1214 | 9 |
| PRO | CB | B | 196 | 140 | 429 | 1228 | 10 |
| PRO | CG | B | 196 | 128 | 436 | 1234 | 9 |
| PRO | C | B | 196 | 143 | 412 | 1209 | 11 |
| PRO | O | B | 196 | 138 | 401 | 1210 | 8 |
| PHE | N | B | 197 | 154 | 414 | 1203 | 8 |
| PHE | CA | B | 197 | 162 | 403 | 1197 | 8 |
| PHE | CB | B | 197 | 175 | 408 | 1191 | 8 |
| PHE | CG | B | 197 | 184 | 396 | 1186 | 8 |
| PHE | CD1 | B | 197 | 181 | 390 | 1174 | 9 |
| PHE | CD2 | B | 197 | 194 | 391 | 1194 | 10 |
| PHE | CE1 | B | 197 | 189 | 379 | 1170 | 10 |
| PHE | CE2 | B | 197 | 202 | 380 | 1190 | 11 |
| PHE | CZ | B | 197 | 199 | 375 | 1178 | 10 |
| PHE | C | B | 197 | 165 | 392 | 1207 | 10 |
| PHE | O | B | 197 | 162 | 380 | 1204 | 9 |
| PHE | N | B | 198 | 170 | 395 | 1219 | 8 |
| PHE | CA | B | 198 | 174 | 384 | 1228 | 7 |
| PHE | CB | B | 198 | 181 | 390 | 1240 | 8 |
| PHE | CG | B | 198 | 190 | 380 | 1247 | 11 |
| PHE | CD1 | B | 198 | 203 | 378 | 1242 | 11 |
| PHE | CD2 | B | 198 | 186 | 373 | 1258 | 11 |
| PHE | CE1 | B | 198 | 211 | 368 | 1247 | 11 |
| PHE | CE2 | B | 198 | 195 | 364 | 1264 | 10 |
| PHE | CZ | B | 198 | 207 | 361 | 1259 | 11 |
| PHE | C | B | 198 | 162 | 376 | 1232 | 9 |
| PHE | O | B | 198 | 163 | 364 | 1235 | 9 |
| ASP | N | B | 199 | 150 | 383 | 1233 | 11 |
| ASP | CA | B | 199 | 138 | 376 | 1237 | 10 |
| ASP | CB | B | 199 | 127 | 386 | 1239 | 11 |
| ASP | CG | B | 199 | 128 | 394 | 1252 | 16 |
| ASP | OD1 | B | 199 | 123 | 390 | 1262 | 21 |
| ASP | OD2 | B | 199 | 135 | 405 | 1251 | 19 |
| ASP | C | B | 199 | 134 | 366 | 1227 | 10 |
| ASP | O | B | 199 | 130 | 355 | 1230 | 10 |
| SER | N | B | 200 | 136 | 370 | 1214 | 11 |
| SER | CA | B | 200 | 133 | 360 | 1203 | 12 |
| SER | CB | B | 200 | 134 | 368 | 1189 | 10 |
| SER | OG | B | 200 | 125 | 378 | 1188 | 13 |
| SER | C | B | 200 | 143 | 349 | 1203 | 13 |
| SER | O | B | 200 | 139 | 337 | 1201 | 14 |
| LEU | N | B | 201 | 155 | 352 | 1206 | 12 |
| LEU | CA | B | 201 | 166 | 342 | 1206 | 11 |
| LEU | CB | B | 201 | 179 | 348 | 1210 | 12 |
| LEU | CG | B | 201 | 191 | 339 | 1212 | 13 |
| LEU | CD1 | B | 201 | 194 | 331 | 1199 | 15 |
| LEU | CD2 | B | 201 | 203 | 347 | 1216 | 14 |
| LEU | C | B | 201 | 163 | 331 | 1217 | 12 |
| LEU | O | B | 201 | 163 | 319 | 1214 | 13 |
| VAL | N | B | 202 | 160 | 335 | 1229 | 10 |
| VAL | CA | B | 202 | 157 | 326 | 1240 | 11 |
| VAL | CB | B | 202 | 156 | 334 | 1253 | 13 |
| VAL | CG1 | B | 202 | 150 | 324 | 1264 | 17 |
| VAL | CG2 | B | 202 | 169 | 339 | 1257 | 12 |
| VAL | C | B | 202 | 144 | 318 | 1237 | 14 |
| VAL | O | B | 202 | 143 | 306 | 1240 | 16 |
| LYS | N | B | 203 | 134 | 325 | 1232 | 13 |
| LYS | CA | B | 203 | 121 | 318 | 1229 | 16 |
| LYS | CB | B | 203 | 110 | 328 | 1226 | 17 |
| LYS | CG | B | 203 | 96 | 322 | 1224 | 25 |
| LYS | CD | B | 203 | 86 | 333 | 1222 | 28 |
| LYS | CE | B | 203 | 72 | 326 | 1221 | 32 |
| LYS | NZ | B | 203 | 61 | 337 | 1220 | 36 |
| LYS | C | B | 203 | 122 | 308 | 1218 | 16 |
| LYS | O | B | 203 | 116 | 297 | 1219 | 16 |
| GLN | N | B | 204 | 130 | 311 | 1208 | 15 |
| GLN | CA | B | 204 | 131 | 302 | 1196 | 14 |
| GLN | CB | B | 204 | 133 | 310 | 1184 | 13 |
| GLN | CG | B | 204 | 121 | 319 | 1180 | 14 |
| GLN | CD | B | 204 | 124 | 328 | 1169 | 13 |
| GLN | OE1 | B | 204 | 130 | 324 | 1159 | 13 |
| GLN | NE2 | B | 204 | 120 | 341 | 1170 | 13 |
| GLN | C | B | 204 | 142 | 291 | 1197 | 16 |
| GLN | O | B | 204 | 142 | 282 | 1189 | 17 |
| THR | N | B | 205 | 151 | 292 | 1207 | 15 |
| THR | CA | B | 205 | 162 | 282 | 1208 | 16 |
| THR | CB | B | 205 | 175 | 288 | 1204 | 17 |
| THR | OG1 | B | 205 | 179 | 298 | 1214 | 15 |
| THR | CG2 | B | 205 | 173 | 296 | 1190 | 15 |
| THR | C | B | 205 | 163 | 277 | 1223 | 17 |
| THR | O | B | 205 | 155 | 281 | 1231 | 20 |
| HIS | N | B | 206 | 174 | 270 | 1225 | 18 |
| HIS | CA | B | 206 | 176 | 264 | 1238 | 21 |
| HIS | CB | B | 206 | 181 | 250 | 1238 | 27 |
| HIS | CG | B | 206 | 170 | 240 | 1233 | 30 |
| HIS | CD2 | B | 206 | 159 | 236 | 1239 | 32 |
| HIS | ND1 | B | 206 | 170 | 235 | 1220 | 32 |
| HIS | CE1 | B | 206 | 159 | 228 | 1219 | 33 |
| HIS | NE2 | B | 206 | 153 | 228 | 1230 | 33 |
| HIS | C | B | 206 | 187 | 273 | 1245 | 20 |
| HIS | O | B | 206 | 192 | 269 | 1256 | 21 |
| VAL | N | B | 207 | 191 | 284 | 1239 | 17 |
| VAL | CA | B | 207 | 201 | 293 | 1245 | 14 |
| VAL | CB | B | 207 | 204 | 305 | 1236 | 14 |
| VAL | CG1 | B | 207 | 214 | 314 | 1242 | 15 |
| VAL | CG2 | B | 207 | 210 | 300 | 1222 | 13 |
| VAL | C | B | 207 | 196 | 298 | 1258 | 15 |
| VAL | O | B | 207 | 185 | 303 | 1259 | 15 |
| PRO | N | B | 208 | 204 | 296 | 1269 | 13 |
| PRO | CD | B | 208 | 216 | 288 | 1269 | 15 |
| PRO | CA | B | 208 | 200 | 301 | 1282 | 14 |
| PRO | CB | B | 208 | 213 | 297 | 1291 | 14 |
| PRO | CG | B | 208 | 217 | 285 | 1284 | 16 |
| PRO | C | B | 208 | 198 | 316 | 1282 | 13 |
| PRO | O | B | 208 | 204 | 323 | 1275 | 12 |
| ASN | N | B | 209 | 188 | 320 | 1291 | 12 |
| ASN | CA | B | 209 | 184 | 334 | 1292 | 12 |
| ASN | CB | B | 209 | 171 | 335 | 1298 | 12 |
| ASN | CG | B | 209 | 165 | 349 | 1297 | 13 |
| ASN | OD1 | B | 209 | 169 | 357 | 1289 | 12 |
| ASN | ND2 | B | 209 | 156 | 353 | 1307 | 11 |
| ASN | C | B | 209 | 195 | 342 | 1299 | 12 |
| ASN | O | B | 209 | 192 | 347 | 1310 | 11 |
| LEU | N | B | 210 | 206 | 344 | 1293 | 10 |
| LEU | CA | B | 210 | 217 | 351 | 1300 | 10 |
| LEU | CB | B | 210 | 223 | 343 | 1311 | 14 |
| LEU | CG | B | 210 | 236 | 347 | 1318 | 16 |
| LEU | CD1 | B | 210 | 236 | 339 | 1332 | 15 |
| LEU | CD2 | B | 210 | 248 | 343 | 1310 | 14 |
| LEU | C | B | 210 | 228 | 354 | 1289 | 10 |
| LEU | O | B | 210 | 230 | 346 | 1280 | 10 |
| PHE | N | B | 211 | 235 | 365 | 1291 | 10 |
| PHE | CA | B | 211 | 247 | 368 | 1283 | 8 |

TABLE 2-continued

Structure Coordinates for BACE complexed to Inhibitor

| | | | | | | | |
|---|---|---|---|---|---|---|---|
| PHE | CB  | B | 211 | 243 | 376 | 1270 | 10 |
| PHE | CG  | B | 211 | 238 | 390 | 1273 | 10 |
| PHE | CD1 | B | 211 | 224 | 393 | 1275 | 7 |
| PHE | CD2 | B | 211 | 246 | 401 | 1274 | 9 |
| PHE | CE1 | B | 211 | 219 | 406 | 1278 | 9 |
| PHE | CE2 | B | 211 | 242 | 414 | 1277 | 8 |
| PHE | CZ  | B | 211 | 228 | 416 | 1278 | 7 |
| PHE | C   | B | 211 | 256 | 376 | 1292 | 8 |
| PHE | O   | B | 211 | 253 | 382 | 1302 | 8 |
| SER | N   | B | 212 | 269 | 376 | 1288 | 7 |
| SER | CA  | B | 212 | 279 | 383 | 1296 | 7 |
| SER | CB  | B | 212 | 288 | 373 | 1304 | 8 |
| SER | OG  | B | 212 | 292 | 362 | 1296 | 9 |
| SER | C   | B | 212 | 288 | 391 | 1286 | 10 |
| SER | O   | B | 212 | 290 | 387 | 1275 | 11 |
| LEU | N   | B | 213 | 293 | 402 | 1291 | 8 |
| LEU | CA  | B | 213 | 301 | 411 | 1283 | 7 |
| LEU | CB  | B | 213 | 294 | 424 | 1280 | 8 |
| LEU | CG  | B | 213 | 282 | 424 | 1271 | 10 |
| LEU | CD1 | B | 213 | 275 | 438 | 1271 | 9 |
| LEU | CD2 | B | 213 | 286 | 420 | 1257 | 11 |
| LEU | C   | B | 213 | 315 | 414 | 1289 | 8 |
| LEU | O   | B | 213 | 315 | 418 | 1301 | 9 |
| GLN | N   | B | 214 | 325 | 413 | 1281 | 7 |
| GLN | CA  | B | 214 | 339 | 417 | 1286 | 8 |
| GLN | CB  | B | 214 | 348 | 405 | 1285 | 8 |
| GLN | CG  | B | 214 | 362 | 408 | 1288 | 9 |
| GLN | CD  | B | 214 | 372 | 398 | 1283 | 13 |
| GLN | OE1 | B | 214 | 372 | 394 | 1271 | 16 |
| GLN | NE2 | B | 214 | 382 | 394 | 1292 | 15 |
| GLN | C   | B | 214 | 343 | 427 | 1276 | 8 |
| GLN | O   | B | 214 | 347 | 424 | 1264 | 9 |
| LEU | N   | B | 215 | 342 | 440 | 1279 | 7 |
| LEU | CA  | B | 215 | 347 | 450 | 1270 | 9 |
| LEU | CB  | B | 215 | 338 | 463 | 1272 | 7 |
| LEU | CG  | B | 215 | 323 | 461 | 1270 | 8 |
| LEU | CD1 | B | 215 | 316 | 475 | 1271 | 8 |
| LEU | CD2 | B | 215 | 320 | 454 | 1257 | 8 |
| LEU | C   | B | 215 | 361 | 453 | 1274 | 9 |
| LEU | O   | B | 215 | 365 | 456 | 1285 | 9 |
| CYS | N   | B | 216 | 370 | 453 | 1264 | 8 |
| CYS | CA  | B | 216 | 384 | 455 | 1266 | 8 |
| CYS | C   | B | 216 | 390 | 468 | 1260 | 10 |
| CYS | O   | B | 216 | 392 | 469 | 1248 | 9 |
| CYS | CB  | B | 216 | 392 | 443 | 1261 | 9 |
| CYS | SG  | B | 216 | 387 | 427 | 1268 | 10 |
| GLY | N   | B | 217 | 393 | 477 | 1269 | 7 |
| GLY | CA  | B | 217 | 399 | 490 | 1265 | 8 |
| GLY | C   | B | 217 | 414 | 486 | 1263 | 8 |
| GLY | O   | B | 217 | 419 | 478 | 1270 | 10 |
| ALA | N   | B | 218 | 420 | 493 | 1253 | 8 |
| ALA | CA  | B | 218 | 434 | 490 | 1250 | 9 |
| ALA | CB  | B | 218 | 438 | 493 | 1236 | 11 |
| ALA | C   | B | 218 | 444 | 497 | 1260 | 11 |
| ALA | O   | B | 218 | 455 | 493 | 1262 | 14 |
| GLY | N   | B | 219 | 439 | 509 | 1265 | 11 |
| GLY | CA  | B | 219 | 448 | 516 | 1274 | 11 |
| GLY | C   | B | 219 | 456 | 527 | 1267 | 12 |
| GLY | O   | B | 219 | 463 | 535 | 1273 | 12 |
| PHE | N   | B | 220 | 454 | 527 | 1254 | 9 |
| PHE | CA  | B | 220 | 461 | 536 | 1245 | 10 |
| PHE | CB  | B | 220 | 475 | 532 | 1241 | 12 |
| PHE | CG  | B | 220 | 476 | 517 | 1237 | 12 |
| PHE | CD1 | B | 220 | 478 | 507 | 1246 | 13 |
| PHE | CD2 | B | 220 | 474 | 514 | 1223 | 15 |
| PHE | CE1 | B | 220 | 478 | 494 | 1242 | 14 |
| PHE | CE2 | B | 220 | 475 | 501 | 1219 | 14 |
| PHE | CZ  | B | 220 | 477 | 491 | 1227 | 12 |
| PHE | C   | B | 220 | 452 | 538 | 1233 | 11 |
| PHE | O   | B | 220 | 443 | 531 | 1230 | 10 |
| PRO | N   | B | 221 | 455 | 549 | 1225 | 13 |
| PRO | CD  | B | 221 | 465 | 560 | 1227 | 12 |
| PRO | CA  | B | 221 | 447 | 552 | 1213 | 15 |
| PRO | CB  | B | 221 | 453 | 565 | 1208 | 14 |
| PRO | CG  | B | 221 | 458 | 572 | 1221 | 15 |
| PRO | C   | B | 221 | 449 | 541 | 1202 | 17 |
| PRO | O   | B | 221 | 460 | 535 | 1201 | 18 |
| LEU | N   | B | 222 | 439 | 539 | 1195 | 15 |
| LEU | CA  | B | 222 | 439 | 529 | 1184 | 16 |
| LEU | CB  | B | 222 | 429 | 518 | 1187 | 17 |
| LEU | CG  | B | 222 | 431 | 509 | 1199 | 15 |
| LEU | CD1 | B | 222 | 419 | 500 | 1200 | 15 |
| LEU | CD2 | B | 222 | 444 | 501 | 1198 | 17 |
| LEU | C   | B | 222 | 435 | 536 | 1171 | 18 |
| LEU | O   | B | 222 | 424 | 542 | 1171 | 18 |
| ASN | N   | B | 223 | 444 | 537 | 1161 | 21 |
| ASN | CA  | B | 223 | 441 | 543 | 1149 | 22 |
| ASN | CB  | B | 223 | 453 | 547 | 1141 | 23 |
| ASN | CG  | B | 223 | 461 | 534 | 1137 | 24 |
| ASN | OD1 | B | 223 | 456 | 524 | 1133 | 25 |
| ASN | ND2 | B | 223 | 474 | 535 | 1139 | 27 |
| ASN | C   | B | 223 | 431 | 535 | 1141 | 23 |
| ASN | O   | B | 223 | 427 | 524 | 1145 | 20 |
| GLN | N   | B | 224 | 427 | 539 | 1129 | 25 |
| GLN | CA  | B | 224 | 418 | 532 | 1121 | 29 |
| GLN | CB  | B | 224 | 416 | 539 | 1107 | 35 |
| GLN | CG  | B | 224 | 404 | 534 | 1099 | 41 |
| GLN | CD  | B | 224 | 402 | 540 | 1086 | 46 |
| GLN | OE1 | B | 224 | 401 | 553 | 1085 | 48 |
| GLN | NE2 | B | 224 | 402 | 532 | 1075 | 48 |
| GLN | C   | B | 224 | 422 | 517 | 1118 | 27 |
| GLN | O   | B | 224 | 414 | 508 | 1121 | 27 |
| SER | N   | B | 225 | 434 | 515 | 1114 | 25 |
| SER | CA  | B | 225 | 438 | 502 | 1111 | 24 |
| SER | CB  | B | 225 | 452 | 502 | 1103 | 26 |
| SER | OG  | B | 225 | 461 | 510 | 1111 | 33 |
| SER | C   | B | 225 | 440 | 493 | 1123 | 22 |
| SER | O   | B | 225 | 436 | 481 | 1123 | 22 |
| GLU | N   | B | 226 | 445 | 499 | 1134 | 20 |
| GLU | CA  | B | 226 | 447 | 492 | 1147 | 19 |
| GLU | CB  | B | 226 | 454 | 501 | 1157 | 20 |
| GLU | CG  | B | 226 | 469 | 502 | 1154 | 22 |
| GLU | CD  | B | 226 | 476 | 513 | 1162 | 24 |
| GLU | OE1 | B | 226 | 488 | 512 | 1164 | 26 |
| GLU | OE2 | B | 226 | 469 | 522 | 1167 | 23 |
| GLU | C   | B | 226 | 434 | 487 | 1153 | 17 |
| GLU | O   | B | 226 | 433 | 476 | 1157 | 16 |
| VAL | N   | B | 227 | 424 | 496 | 1153 | 15 |
| VAL | CA  | B | 227 | 411 | 492 | 1159 | 16 |
| VAL | CB  | B | 227 | 401 | 504 | 1160 | 17 |
| VAL | CG1 | B | 227 | 397 | 509 | 1146 | 18 |
| VAL | CG2 | B | 227 | 389 | 501 | 1169 | 20 |
| VAL | C   | B | 227 | 404 | 481 | 1151 | 19 |
| VAL | O   | B | 227 | 396 | 473 | 1157 | 18 |
| LEU | N   | B | 228 | 407 | 480 | 1139 | 17 |
| LEU | CA  | B | 228 | 401 | 469 | 1130 | 18 |
| LEU | CB  | B | 228 | 403 | 473 | 1115 | 20 |
| LEU | CG  | B | 228 | 396 | 485 | 1110 | 22 |
| LEU | CD1 | B | 228 | 400 | 488 | 1096 | 23 |
| LEU | CD2 | B | 228 | 381 | 483 | 1111 | 21 |
| LEU | C   | B | 228 | 408 | 455 | 1133 | 18 |
| LEU | O   | B | 228 | 401 | 445 | 1132 | 19 |
| ALA | N   | B | 229 | 420 | 456 | 1137 | 17 |
| ALA | CA  | B | 229 | 428 | 443 | 1140 | 17 |
| ALA | CB  | B | 229 | 442 | 445 | 1135 | 18 |
| ALA | C   | B | 229 | 427 | 439 | 1155 | 18 |
| ALA | O   | B | 229 | 429 | 427 | 1158 | 21 |
| SER | N   | B | 230 | 425 | 449 | 1163 | 15 |
| SER | CA  | B | 230 | 425 | 446 | 1178 | 13 |
| SER | CB  | B | 230 | 426 | 459 | 1185 | 14 |
| SER | OG  | B | 230 | 426 | 457 | 1199 | 14 |
| SER | C   | B | 230 | 412 | 439 | 1183 | 14 |
| SER | O   | B | 230 | 401 | 440 | 1177 | 12 |
| VAL | N   | B | 231 | 414 | 431 | 1193 | 14 |
| VAL | CA  | B | 231 | 403 | 423 | 1199 | 12 |
| VAL | CB  | B | 231 | 407 | 410 | 1206 | 13 |
| VAL | CG1 | B | 231 | 396 | 405 | 1214 | 12 |
| VAL | CG2 | B | 231 | 411 | 400 | 1196 | 13 |
| VAL | C   | B | 231 | 397 | 433 | 1210 | 13 |
| VAL | O   | B | 231 | 403 | 437 | 1219 | 13 |
| GLY | N   | B | 232 | 384 | 437 | 1208 | 10 |
| GLY | CA  | B | 232 | 378 | 446 | 1217 | 9 |
| GLY | C   | B | 232 | 371 | 439 | 1229 | 9 |
| GLY | O   | B | 232 | 366 | 446 | 1237 | 13 |

TABLE 2-continued

Structure Coordinates for BACE complexed to Inhibitor

| | | | | | | | |
|---|---|---|---|---|---|---|---|
| GLY | N | B | 233 | 370 | 426 | 1229 | 8 |
| GLY | CA | B | 233 | 363 | 419 | 1240 | 10 |
| GLY | C | B | 233 | 355 | 407 | 1236 | 9 |
| GLY | O | B | 233 | 357 | 401 | 1225 | 9 |
| SER | N | B | 234 | 346 | 403 | 1245 | 8 |
| SER | CA | B | 234 | 338 | 391 | 1242 | 8 |
| SER | CB | B | 234 | 344 | 379 | 1250 | 10 |
| SER | OG | B | 234 | 358 | 377 | 1247 | 10 |
| SER | C | B | 234 | 324 | 393 | 1247 | 8 |
| SER | O | B | 234 | 321 | 399 | 1257 | 8 |
| MET | N | B | 235 | 315 | 387 | 1239 | 7 |
| MET | CA | B | 235 | 301 | 387 | 1243 | 7 |
| MET | CB | B | 235 | 292 | 394 | 1233 | 7 |
| MET | CG | B | 235 | 277 | 392 | 1236 | 10 |
| MET | SD | B | 235 | 265 | 403 | 1227 | 12 |
| MET | CE | B | 235 | 267 | 396 | 1210 | 17 |
| MET | C | B | 235 | 297 | 372 | 1242 | 8 |
| MET | O | B | 235 | 296 | 366 | 1232 | 9 |
| ILE | N | B | 236 | 296 | 367 | 1254 | 9 |
| ILE | CA | B | 236 | 293 | 352 | 1256 | 10 |
| ILE | CB | B | 236 | 299 | 346 | 1268 | 9 |
| ILE | CG2 | B | 236 | 296 | 331 | 1268 | 10 |
| ILE | CG1 | B | 236 | 314 | 349 | 1269 | 8 |
| ILE | CD1 | B | 236 | 322 | 344 | 1256 | 12 |
| ILE | C | B | 236 | 277 | 351 | 1256 | 12 |
| ILE | O | B | 236 | 271 | 356 | 1266 | 11 |
| ILE | N | B | 237 | 271 | 346 | 1246 | 11 |
| ILE | CA | B | 237 | 257 | 344 | 1246 | 12 |
| ILE | CB | B | 237 | 252 | 345 | 1231 | 13 |
| ILE | CG2 | B | 237 | 237 | 342 | 1230 | 13 |
| ILE | CG1 | B | 237 | 255 | 358 | 1225 | 18 |
| ILE | CD1 | B | 237 | 248 | 370 | 1231 | 21 |
| ILE | C | B | 237 | 252 | 331 | 1252 | 12 |
| ILE | O | B | 237 | 256 | 320 | 1247 | 14 |
| GLY | N | B | 238 | 245 | 332 | 1262 | 11 |
| GLY | CA | B | 238 | 240 | 320 | 1269 | 12 |
| GLY | C | B | 238 | 249 | 314 | 1280 | 14 |
| GLY | O | B | 238 | 246 | 303 | 1285 | 14 |
| GLY | N | B | 239 | 259 | 321 | 1284 | 12 |
| GLY | CA | B | 239 | 267 | 316 | 1295 | 13 |
| GLY | C | B | 239 | 278 | 325 | 1300 | 15 |
| GLY | O | B | 239 | 279 | 337 | 1296 | 15 |
| ILE | N | B | 240 | 287 | 320 | 1308 | 13 |
| ILE | CA | B | 240 | 298 | 327 | 1315 | 16 |
| ILE | CB | B | 240 | 296 | 327 | 1330 | 16 |
| ILE | CG2 | B | 240 | 308 | 334 | 1337 | 17 |
| ILE | CG1 | B | 240 | 283 | 334 | 1333 | 16 |
| ILE | CD1 | B | 240 | 279 | 333 | 1348 | 18 |
| ILE | C | B | 240 | 311 | 319 | 1312 | 17 |
| ILE | O | B | 240 | 312 | 307 | 1314 | 19 |
| ASP | N | B | 241 | 321 | 326 | 1307 | 14 |
| ASP | CA | B | 241 | 334 | 320 | 1304 | 15 |
| ASP | CB | B | 241 | 339 | 324 | 1290 | 15 |
| ASP | CG | B | 241 | 351 | 317 | 1286 | 16 |
| ASP | OD1 | B | 241 | 351 | 310 | 1275 | 15 |
| ASP | OD2 | B | 241 | 362 | 318 | 1293 | 15 |
| ASP | C | B | 241 | 343 | 324 | 1315 | 17 |
| ASP | O | B | 241 | 346 | 336 | 1317 | 15 |
| HIS | N | B | 242 | 348 | 314 | 1322 | 17 |
| HIS | CA | B | 242 | 357 | 317 | 1333 | 19 |
| HIS | CB | B | 242 | 359 | 304 | 1342 | 25 |
| HIS | CG | B | 242 | 346 | 300 | 1348 | 29 |
| HIS | CD2 | B | 242 | 335 | 294 | 1342 | 32 |
| HIS | ND1 | B | 242 | 343 | 301 | 1361 | 33 |
| HIS | CE1 | B | 242 | 331 | 297 | 1364 | 33 |
| HIS | NE2 | B | 242 | 326 | 293 | 1353 | 34 |
| HIS | C | B | 242 | 371 | 323 | 1330 | 16 |
| HIS | O | B | 242 | 378 | 328 | 1339 | 16 |
| SER | N | B | 243 | 375 | 322 | 1318 | 13 |
| SER | CA | B | 243 | 388 | 328 | 1314 | 14 |
| SER | CB | B | 243 | 393 | 322 | 1301 | 15 |
| SER | OG | B | 243 | 385 | 327 | 1290 | 17 |
| SER | C | B | 243 | 388 | 343 | 1313 | 12 |
| SER | O | B | 243 | 399 | 349 | 1312 | 15 |
| LEU | N | B | 244 | 376 | 349 | 1313 | 11 |
| LEU | CA | B | 244 | 375 | 363 | 1311 | 9 |
| LEU | CB | B | 244 | 362 | 366 | 1304 | 11 |
| LEU | CG | B | 244 | 360 | 358 | 1291 | 10 |
| LEU | CD1 | B | 244 | 347 | 362 | 1284 | 11 |
| LEU | CD2 | B | 244 | 372 | 361 | 1282 | 12 |
| LEU | C | B | 244 | 376 | 371 | 1324 | 10 |
| LEU | O | B | 244 | 375 | 384 | 1324 | 12 |
| TYR | N | B | 245 | 377 | 365 | 1336 | 8 |
| TYR | CA | B | 245 | 378 | 372 | 1348 | 10 |
| TYR | CB | B | 245 | 364 | 375 | 1354 | 10 |
| TYR | CG | B | 245 | 356 | 362 | 1359 | 10 |
| TYR | CD1 | B | 245 | 350 | 354 | 1350 | 11 |
| TYR | CE1 | B | 245 | 343 | 342 | 1354 | 14 |
| TYR | CD2 | B | 245 | 356 | 359 | 1372 | 10 |
| TYR | CE2 | B | 245 | 349 | 348 | 1377 | 14 |
| TYR | CZ | B | 245 | 343 | 340 | 1368 | 15 |
| TYR | OH | B | 245 | 336 | 329 | 1373 | 18 |
| TYR | C | B | 245 | 386 | 365 | 1359 | 13 |
| TYR | O | B | 245 | 390 | 343 | 1357 | 11 |
| THR | N | B | 246 | 389 | 372 | 1369 | 14 |
| THR | CA | B | 246 | 397 | 367 | 1380 | 14 |
| THR | CB | B | 246 | 411 | 373 | 1381 | 15 |
| THR | OG1 | B | 246 | 409 | 387 | 1383 | 13 |
| THR | CG2 | B | 246 | 419 | 370 | 1369 | 17 |
| THR | C | B | 246 | 389 | 370 | 1393 | 15 |
| THR | O | B | 246 | 380 | 379 | 1393 | 13 |
| GLY | N | B | 247 | 391 | 362 | 1404 | 16 |
| GLY | CA | B | 247 | 384 | 364 | 1416 | 14 |
| GLY | C | B | 247 | 369 | 360 | 1415 | 15 |
| GLY | O | B | 247 | 366 | 352 | 1406 | 17 |
| SER | N | B | 248 | 361 | 364 | 1424 | 13 |
| SER | CA | B | 248 | 347 | 360 | 1425 | 16 |
| SER | CB | B | 248 | 343 | 358 | 1439 | 19 |
| SER | OG | B | 248 | 351 | 348 | 1446 | 23 |
| SER | C | B | 248 | 337 | 369 | 1418 | 15 |
| SER | O | B | 248 | 340 | 381 | 1416 | 14 |
| LEU | N | B | 249 | 326 | 364 | 1414 | 14 |
| LEU | CA | B | 249 | 315 | 372 | 1408 | 12 |
| LEU | CB | B | 249 | 308 | 364 | 1397 | 13 |
| LEU | CG | B | 249 | 313 | 363 | 1383 | 13 |
| LEU | CD1 | B | 249 | 307 | 351 | 1376 | 14 |
| LEU | CD2 | B | 249 | 310 | 376 | 1376 | 13 |
| LEU | C | B | 249 | 306 | 376 | 1419 | 13 |
| LEU | O | B | 249 | 302 | 368 | 1427 | 17 |
| TRP | N | B | 250 | 302 | 389 | 1419 | 11 |
| TRP | CA | B | 250 | 293 | 394 | 1429 | 11 |
| TRP | CB | B | 250 | 299 | 406 | 1437 | 10 |
| TRP | CG | B | 250 | 308 | 401 | 1448 | 11 |
| TRP | CD2 | B | 250 | 305 | 398 | 1462 | 13 |
| TRP | CE2 | B | 250 | 317 | 393 | 1468 | 13 |
| TRP | CE3 | B | 250 | 293 | 400 | 1469 | 14 |
| TRP | CD1 | B | 250 | 321 | 397 | 1446 | 13 |
| TRP | NE1 | B | 250 | 327 | 393 | 1458 | 13 |
| TRP | CZ2 | B | 250 | 317 | 390 | 1481 | 15 |
| TRP | CZ3 | B | 250 | 294 | 396 | 1483 | 16 |
| TRP | CH2 | B | 250 | 305 | 391 | 1489 | 15 |
| TRP | C | B | 250 | 281 | 400 | 1421 | 11 |
| TRP | O | B | 250 | 282 | 407 | 1411 | 11 |
| TYR | N | B | 251 | 269 | 396 | 1426 | 10 |
| TYR | CA | B | 251 | 257 | 400 | 1419 | 10 |
| TYR | CB | B | 251 | 248 | 388 | 1416 | 11 |
| TYR | CG | B | 251 | 254 | 378 | 1407 | 12 |
| TYR | CD1 | B | 251 | 263 | 368 | 1411 | 12 |
| TYR | CE1 | B | 251 | 268 | 359 | 1402 | 11 |
| TYR | CD2 | B | 251 | 250 | 378 | 1393 | 12 |
| TYR | CE2 | B | 251 | 256 | 369 | 1385 | 13 |
| TYR | CZ | B | 251 | 265 | 359 | 1389 | 12 |
| TYR | OH | B | 251 | 270 | 350 | 1380 | 14 |
| TYR | C | B | 251 | 248 | 411 | 1426 | 11 |
| TYR | O | B | 251 | 247 | 411 | 1438 | 11 |
| THR | N | B | 252 | 243 | 420 | 1418 | 10 |
| THR | CA | B | 252 | 234 | 430 | 1423 | 11 |
| THR | CB | B | 252 | 239 | 444 | 1420 | 10 |
| THR | OG1 | B | 252 | 231 | 454 | 1427 | 12 |
| THR | CG2 | B | 252 | 238 | 447 | 1405 | 11 |
| THR | C | B | 252 | 221 | 428 | 1416 | 11 |
| THR | O | B | 252 | 220 | 423 | 1405 | 12 |
| PRO | N | B | 253 | 209 | 430 | 1423 | 11 |
| PRO | CD | B | 253 | 207 | 433 | 1437 | 11 |

TABLE 2-continued

Structure Coordinates for BACE complexed to Inhibitor

| | | | | | | | |
|---|---|---|---|---|---|---|---|
| PRO | CA | B | 253 | 196 | 427 | 1417 | 12 |
| PRO | CB | B | 253 | 186 | 428 | 1428 | 13 |
| PRO | CG | B | 253 | 195 | 426 | 1440 | 12 |
| PRO | C | B | 253 | 193 | 437 | 1405 | 13 |
| PRO | O | B | 253 | 196 | 449 | 1406 | 12 |
| ILE | N | B | 254 | 186 | 432 | 1395 | 10 |
| ILE | CA | B | 254 | 181 | 441 | 1385 | 11 |
| ILE | CB | B | 254 | 178 | 433 | 1372 | 13 |
| ILE | CG2 | B | 254 | 169 | 441 | 1362 | 11 |
| ILE | CG1 | B | 254 | 191 | 428 | 1365 | 11 |
| ILE | CD1 | B | 254 | 189 | 420 | 1353 | 11 |
| ILE | C | B | 254 | 168 | 446 | 1391 | 12 |
| ILE | O | B | 254 | 158 | 438 | 1393 | 13 |
| ARG | N | B | 255 | 167 | 458 | 1394 | 12 |
| ARG | CA | B | 255 | 156 | 464 | 1401 | 14 |
| ARG | CB | B | 255 | 158 | 479 | 1404 | 15 |
| ARG | CG | B | 255 | 148 | 485 | 1414 | 17 |
| ARG | CD | B | 255 | 149 | 500 | 1414 | 16 |
| ARG | NE | B | 255 | 140 | 506 | 1423 | 18 |
| ARG | CZ | B | 255 | 136 | 519 | 1423 | 19 |
| ARG | NH1 | B | 255 | 141 | 527 | 1414 | 17 |
| ARG | NH2 | B | 255 | 128 | 523 | 1433 | 20 |
| ARG | C | B | 255 | 143 | 463 | 1393 | 16 |
| ARG | O | B | 255 | 132 | 460 | 1399 | 17 |
| ARG | N | B | 256 | 143 | 466 | 1380 | 14 |
| ARG | CA | B | 256 | 132 | 465 | 1372 | 14 |
| ARG | CB | B | 256 | 125 | 479 | 1372 | 13 |
| ARG | CG | B | 256 | 114 | 481 | 1362 | 16 |
| ARG | CD | B | 256 | 109 | 496 | 1362 | 20 |
| ARG | NE | B | 256 | 100 | 500 | 1352 | 23 |
| ARG | CZ | B | 256 | 96 | 513 | 1350 | 25 |
| ARG | NH1 | B | 256 | 102 | 522 | 1357 | 25 |
| ARG | NH2 | B | 256 | 87 | 516 | 1341 | 29 |
| ARG | C | B | 256 | 136 | 462 | 1358 | 13 |
| ARG | O | B | 256 | 147 | 466 | 1354 | 11 |
| GLU | N | B | 257 | 128 | 454 | 1351 | 13 |
| GLU | CA | B | 257 | 132 | 449 | 1338 | 12 |
| GLU | CB | B | 257 | 127 | 435 | 1335 | 15 |
| GLU | CG | B | 257 | 133 | 425 | 1344 | 17 |
| GLU | CD | B | 257 | 125 | 412 | 1346 | 21 |
| GLU | OE1 | B | 257 | 113 | 413 | 1350 | 26 |
| GLU | OE2 | B | 257 | 130 | 401 | 1343 | 18 |
| GLU | C | B | 257 | 128 | 459 | 1326 | 13 |
| GLU | O | B | 257 | 117 | 456 | 1320 | 15 |
| TRP | N | B | 258 | 136 | 469 | 1324 | 10 |
| TRP | CA | B | 258 | 133 | 479 | 1313 | 11 |
| TRP | CB | B | 258 | 126 | 491 | 1318 | 11 |
| TRP | CG | B | 258 | 131 | 499 | 1330 | 12 |
| TRP | CD2 | B | 258 | 129 | 513 | 1332 | 13 |
| TRP | CE2 | B | 258 | 136 | 516 | 1344 | 13 |
| TRP | CE3 | B | 258 | 123 | 523 | 1325 | 12 |
| TRP | CD1 | B | 258 | 138 | 494 | 1341 | 13 |
| TRP | NE1 | B | 258 | 141 | 505 | 1349 | 12 |
| TRP | CZ2 | B | 258 | 136 | 529 | 1350 | 14 |
| TRP | CZ3 | B | 258 | 123 | 536 | 1330 | 15 |
| TRP | CH2 | B | 258 | 129 | 539 | 1343 | 13 |
| TRP | C | B | 258 | 147 | 481 | 1309 | 11 |
| TRP | O | B | 258 | 152 | 475 | 1299 | 10 |
| TYR | N | B | 259 | 155 | 490 | 1316 | 13 |
| TYR | CA | B | 259 | 169 | 492 | 1312 | 10 |
| TYR | CB | B | 259 | 174 | 506 | 1317 | 10 |
| TYR | CG | B | 259 | 168 | 518 | 1310 | 8 |
| TYR | CD1 | B | 259 | 175 | 522 | 1298 | 9 |
| TYR | CE1 | B | 259 | 170 | 533 | 1291 | 9 |
| TYR | CD2 | B | 259 | 157 | 525 | 1314 | 10 |
| TYR | CE2 | B | 259 | 152 | 536 | 1308 | 9 |
| TYR | CZ | B | 259 | 159 | 540 | 1296 | 11 |
| TYR | OH | B | 259 | 154 | 551 | 1289 | 12 |
| TYR | C | B | 259 | 174 | 482 | 1322 | 9 |
| TYR | O | B | 259 | 167 | 475 | 1329 | 9 |
| TYR | N | B | 260 | 188 | 480 | 1322 | 8 |
| TYR | CA | B | 260 | 193 | 471 | 1332 | 9 |
| TYR | CB | B | 260 | 206 | 464 | 1327 | 7 |
| TYR | CG | B | 260 | 203 | 453 | 1317 | 9 |
| TYR | CD1 | B | 260 | 205 | 455 | 1303 | 9 |
| TYR | CE1 | B | 260 | 201 | 445 | 1294 | 10 |
| TYR | CD2 | B | 260 | 199 | 441 | 1321 | 8 |
| TYR | CE2 | B | 260 | 195 | 431 | 1312 | 9 |
| TYR | CZ | B | 260 | 197 | 433 | 1298 | 8 |
| TYR | OH | B | 260 | 193 | 423 | 1289 | 10 |
| TYR | C | B | 260 | 196 | 480 | 1344 | 11 |
| TYR | O | B | 260 | 207 | 485 | 1346 | 10 |
| GLU | N | B | 261 | 186 | 482 | 1352 | 9 |
| GLU | CA | B | 261 | 186 | 491 | 1363 | 9 |
| GLU | CB | B | 261 | 173 | 497 | 1366 | 12 |
| GLU | CG | B | 261 | 172 | 506 | 1378 | 9 |
| GLU | CD | B | 261 | 158 | 512 | 1381 | 11 |
| GLU | OE1 | B | 261 | 148 | 506 | 1377 | 11 |
| GLU | OE2 | B | 261 | 158 | 523 | 1388 | 12 |
| GLU | C | B | 261 | 192 | 484 | 1376 | 10 |
| GLU | O | B | 261 | 188 | 473 | 1380 | 10 |
| VAL | N | B | 262 | 200 | 492 | 1383 | 9 |
| VAL | CA | B | 262 | 206 | 487 | 1395 | 10 |
| VAL | CB | B | 262 | 221 | 482 | 1394 | 12 |
| VAL | CG1 | B | 262 | 222 | 471 | 1383 | 10 |
| VAL | CG2 | B | 262 | 229 | 494 | 1389 | 11 |
| VAL | C | B | 262 | 206 | 498 | 1406 | 11 |
| VAL | O | B | 262 | 202 | 509 | 1403 | 11 |
| ILE | N | B | 263 | 209 | 495 | 1418 | 9 |
| ILE | CA | B | 263 | 209 | 505 | 1429 | 8 |
| ILE | CB | B | 263 | 199 | 501 | 1440 | 13 |
| ILE | CG2 | B | 263 | 199 | 511 | 1451 | 12 |
| ILE | CG1 | B | 263 | 185 | 500 | 1434 | 14 |
| ILE | CD1 | B | 263 | 174 | 497 | 1444 | 16 |
| ILE | C | B | 263 | 223 | 507 | 1435 | 8 |
| ILE | O | B | 263 | 229 | 497 | 1441 | 10 |
| ILE | N | B | 264 | 228 | 519 | 1435 | 8 |
| ILE | CA | B | 264 | 241 | 522 | 1441 | 8 |
| ILE | CB | B | 264 | 248 | 534 | 1433 | 9 |
| ILE | CG2 | B | 264 | 261 | 538 | 1440 | 8 |
| ILE | CG1 | B | 264 | 251 | 529 | 1419 | 9 |
| ILE | CD1 | B | 264 | 255 | 540 | 1409 | 12 |
| ILE | C | B | 264 | 238 | 527 | 1455 | 9 |
| ILE | O | B | 264 | 229 | 536 | 1456 | 10 |
| VAL | N | B | 265 | 245 | 522 | 1465 | 9 |
| VAL | CA | B | 265 | 242 | 526 | 1479 | 10 |
| VAL | CB | B | 265 | 239 | 514 | 1487 | 9 |
| VAL | CG1 | B | 265 | 227 | 506 | 1482 | 13 |
| VAL | CG2 | B | 265 | 252 | 505 | 1488 | 11 |
| VAL | C | B | 265 | 253 | 535 | 1485 | 12 |
| VAL | O | B | 265 | 250 | 540 | 1496 | 12 |
| ARG | N | B | 266 | 265 | 535 | 1479 | 10 |
| ARG | CA | B | 266 | 276 | 543 | 1485 | 10 |
| ARG | CB | B | 266 | 282 | 535 | 1497 | 8 |
| ARG | CG | B | 266 | 294 | 542 | 1503 | 9 |
| ARG | CD | B | 266 | 300 | 533 | 1513 | 8 |
| ARG | NE | B | 266 | 314 | 537 | 1518 | 9 |
| ARG | CZ | B | 266 | 316 | 545 | 1529 | 11 |
| ARG | NH1 | B | 266 | 306 | 550 | 1536 | 11 |
| ARG | NH2 | B | 266 | 328 | 548 | 1532 | 12 |
| ARG | C | B | 266 | 286 | 546 | 1474 | 9 |
| ARG | O | B | 266 | 288 | 538 | 1465 | 9 |
| VAL | N | B | 267 | 292 | 558 | 1475 | 7 |
| VAL | CA | B | 267 | 302 | 561 | 1465 | 7 |
| VAL | CB | B | 267 | 297 | 573 | 1456 | 8 |
| VAL | CG1 | B | 267 | 309 | 577 | 1447 | 9 |
| VAL | CG2 | B | 267 | 286 | 567 | 1447 | 8 |
| VAL | C | B | 267 | 315 | 567 | 1473 | 9 |
| VAL | O | B | 267 | 314 | 575 | 1482 | 10 |
| GLU | N | B | 268 | 326 | 562 | 1469 | 8 |
| GLU | CA | B | 268 | 339 | 566 | 1475 | 7 |
| GLU | CB | B | 268 | 346 | 554 | 1482 | 10 |
| GLU | CG | B | 268 | 339 | 550 | 1495 | 10 |
| GLU | CD | B | 268 | 346 | 538 | 1501 | 9 |
| GLU | OE1 | B | 268 | 356 | 534 | 1496 | 10 |
| GLU | OE2 | B | 268 | 340 | 532 | 1511 | 12 |
| GLU | C | B | 268 | 349 | 571 | 1464 | 8 |
| GLU | O | B | 268 | 349 | 566 | 1453 | 9 |
| ILE | N | B | 269 | 357 | 580 | 1468 | 6 |
| ILE | CA | B | 269 | 368 | 586 | 1460 | 7 |
| ILE | CB | B | 269 | 366 | 601 | 1457 | 9 |
| ILE | CG2 | B | 269 | 377 | 606 | 1448 | 8 |
| ILE | CG1 | B | 269 | 353 | 603 | 1450 | 11 |
| ILE | CD1 | B | 269 | 351 | 596 | 1437 | 12 |

TABLE 2-continued

Structure Coordinates for BACE complexed to Inhibitor

| | | | | | | | |
|---|---|---|---|---|---|---|---|
| ILE | C | B | 269 | 380 | 584 | 1468 | 7 |
| ILE | O | B | 269 | 382 | 591 | 1478 | 7 |
| ASN | N | B | 270 | 388 | 574 | 1465 | 7 |
| ASN | CA | B | 270 | 400 | 570 | 1472 | 6 |
| ASN | CB | B | 270 | 411 | 582 | 1472 | 8 |
| ASN | CG | B | 270 | 423 | 578 | 1463 | 7 |
| ASN | OD1 | B | 270 | 423 | 568 | 1457 | 8 |
| ASN | ND2 | B | 270 | 433 | 587 | 1464 | 8 |
| ASN | C | B | 270 | 397 | 568 | 1487 | 9 |
| ASN | O | B | 270 | 403 | 573 | 1496 | 9 |
| GLY | N | B | 271 | 386 | 560 | 1489 | 8 |
| GLY | CA | B | 271 | 382 | 556 | 1502 | 7 |
| GLY | C | B | 271 | 374 | 567 | 1509 | 7 |
| GLY | O | B | 271 | 367 | 563 | 1520 | 8 |
| GLN | N | B | 272 | 373 | 579 | 1504 | 5 |
| GLN | CA | B | 272 | 365 | 589 | 1511 | 6 |
| GLN | CB | B | 272 | 372 | 603 | 1508 | 7 |
| GLN | CG | B | 272 | 364 | 614 | 1515 | 11 |
| GLN | CD | B | 272 | 372 | 627 | 1515 | 16 |
| GLN | OE1 | B | 272 | 379 | 631 | 1506 | 23 |
| GLN | NE2 | B | 272 | 370 | 635 | 1526 | 17 |
| GLN | C | B | 272 | 351 | 589 | 1506 | 8 |
| GLN | O | B | 272 | 348 | 590 | 1494 | 9 |
| ASP | N | B | 273 | 342 | 588 | 1516 | 7 |
| ASP | CA | B | 273 | 327 | 587 | 1513 | 7 |
| ASP | CB | B | 273 | 320 | 584 | 1526 | 9 |
| ASP | CG | B | 273 | 305 | 584 | 1524 | 12 |
| ASP | OD1 | B | 273 | 300 | 582 | 1513 | 10 |
| ASP | OD2 | B | 273 | 298 | 584 | 1535 | 13 |
| ASP | C | B | 273 | 323 | 601 | 1507 | 9 |
| ASP | O | B | 273 | 325 | 611 | 1513 | 9 |
| LEU | N | B | 274 | 316 | 600 | 1496 | 8 |
| LEU | CA | B | 274 | 311 | 612 | 1489 | 11 |
| LEU | CB | B | 274 | 304 | 608 | 1476 | 12 |
| LEU | CG | B | 274 | 304 | 620 | 1465 | 15 |
| LEU | CD1 | B | 274 | 318 | 625 | 1463 | 15 |
| LEU | CD2 | B | 274 | 298 | 614 | 1452 | 13 |
| LEU | C | B | 274 | 300 | 618 | 1499 | 13 |
| LEU | O | B | 274 | 296 | 630 | 1498 | 14 |
| LYS | N | B | 275 | 295 | 609 | 1508 | 12 |
| LYS | CA | B | 275 | 285 | 613 | 1518 | 16 |
| LYS | CB | B | 275 | 292 | 621 | 1529 | 21 |
| LYS | CG | B | 275 | 285 | 621 | 1542 | 27 |
| LYS | CD | B | 275 | 293 | 628 | 1553 | 32 |
| LYS | CE | B | 275 | 286 | 628 | 1566 | 35 |
| LYS | NZ | B | 275 | 293 | 635 | 1577 | 37 |
| LYS | C | B | 275 | 273 | 620 | 1513 | 18 |
| LYS | O | B | 275 | 268 | 630 | 1520 | 18 |
| MET | N | B | 276 | 266 | 615 | 1503 | 17 |
| MET | CA | B | 276 | 254 | 621 | 1498 | 16 |
| MET | CB | B | 276 | 255 | 623 | 1483 | 16 |
| MET | CG | B | 276 | 265 | 633 | 1478 | 18 |
| MET | SD | B | 276 | 264 | 634 | 1460 | 16 |
| MET | CE | B | 276 | 250 | 645 | 1458 | 18 |
| MET | C | B | 276 | 243 | 612 | 1501 | 16 |
| MET | O | B | 276 | 245 | 600 | 1504 | 16 |
| ASP | N | B | 277 | 230 | 617 | 1501 | 16 |
| ASP | CA | B | 277 | 219 | 608 | 1503 | 15 |
| ASP | CB | B | 277 | 206 | 617 | 1502 | 18 |
| ASP | CG | B | 277 | 193 | 609 | 1506 | 23 |
| ASP | OD1 | B | 277 | 192 | 598 | 1500 | 21 |
| ASP | OD2 | B | 277 | 185 | 614 | 1514 | 26 |
| ASP | C | B | 277 | 220 | 598 | 1492 | 15 |
| ASP | O | B | 277 | 220 | 602 | 1480 | 16 |
| CYS | N | B | 278 | 220 | 585 | 1495 | 14 |
| CYS | CA | B | 278 | 221 | 575 | 1485 | 15 |
| CYS | C | B | 278 | 211 | 576 | 1474 | 16 |
| CYS | O | B | 278 | 212 | 570 | 1463 | 15 |
| CYS | CB | B | 278 | 222 | 561 | 1491 | 17 |
| CYS | SG | B | 278 | 207 | 555 | 1499 | 18 |
| LYS | N | B | 279 | 200 | 583 | 1476 | 14 |
| LYS | CA | B | 279 | 189 | 583 | 1466 | 15 |
| LYS | CB | B | 279 | 176 | 589 | 1472 | 17 |
| LYS | CG | B | 279 | 164 | 588 | 1463 | 23 |
| LYS | CD | B | 279 | 151 | 593 | 1469 | 23 |
| LYS | CE | B | 279 | 147 | 585 | 1481 | 25 |
| LYS | NZ | B | 279 | 143 | 572 | 1478 | 27 |
| LYS | C | B | 279 | 194 | 592 | 1455 | 13 |
| LYS | O | B | 279 | 190 | 591 | 1443 | 12 |
| GLU | N | B | 280 | 203 | 601 | 1458 | 12 |
| GLU | CA | B | 280 | 209 | 610 | 1448 | 12 |
| GLU | CB | B | 280 | 218 | 621 | 1454 | 13 |
| GLU | CG | B | 280 | 212 | 630 | 1464 | 15 |
| GLU | CD | B | 280 | 203 | 641 | 1458 | 18 |
| GLU | OE1 | B | 280 | 202 | 641 | 1445 | 16 |
| GLU | OE2 | B | 280 | 198 | 649 | 1465 | 20 |
| GLU | C | B | 280 | 217 | 602 | 1437 | 10 |
| GLU | O | B | 280 | 217 | 606 | 1425 | 11 |
| TYR | N | B | 281 | 223 | 592 | 1441 | 11 |
| TYR | CA | B | 281 | 231 | 583 | 1433 | 9 |
| TYR | CB | B | 281 | 238 | 572 | 1441 | 8 |
| TYR | CG | B | 281 | 248 | 578 | 1451 | 8 |
| TYR | CD1 | B | 281 | 250 | 571 | 1463 | 9 |
| TYR | CE1 | B | 281 | 258 | 576 | 1473 | 10 |
| TYR | CD2 | B | 281 | 255 | 590 | 1450 | 11 |
| TYR | CE2 | B | 281 | 263 | 595 | 1459 | 12 |
| TYR | CZ | B | 281 | 265 | 588 | 1471 | 11 |
| TYR | OH | B | 281 | 274 | 592 | 1481 | 13 |
| TYR | C | B | 281 | 223 | 576 | 1422 | 11 |
| TYR | O | B | 281 | 228 | 572 | 1412 | 13 |
| ASN | N | B | 282 | 210 | 574 | 1425 | 10 |
| ASN | CA | B | 282 | 201 | 567 | 1416 | 11 |
| ASN | CB | B | 282 | 196 | 555 | 1423 | 11 |
| ASN | CG | B | 282 | 207 | 546 | 1429 | 12 |
| ASN | OD1 | B | 282 | 215 | 541 | 1421 | 11 |
| ASN | ND2 | B | 282 | 207 | 546 | 1442 | 10 |
| ASN | C | B | 282 | 189 | 576 | 1411 | 11 |
| ASN | O | B | 282 | 179 | 571 | 1407 | 12 |
| TYR | N | B | 283 | 191 | 589 | 1410 | 11 |
| TYR | CA | B | 283 | 181 | 598 | 1406 | 11 |
| TYR | CB | B | 283 | 181 | 611 | 1414 | 13 |
| TYR | CG | B | 283 | 173 | 622 | 1409 | 14 |
| TYR | CD1 | B | 283 | 159 | 621 | 1407 | 17 |
| TYR | CE1 | B | 283 | 152 | 631 | 1401 | 18 |
| TYR | CD2 | B | 283 | 179 | 634 | 1405 | 16 |
| TYR | CE2 | B | 283 | 172 | 645 | 1399 | 18 |
| TYR | CZ | B | 283 | 158 | 643 | 1397 | 19 |
| TYR | OH | B | 283 | 151 | 653 | 1392 | 23 |
| TYR | C | B | 283 | 184 | 602 | 1391 | 9 |
| TYR | O | B | 283 | 193 | 608 | 1388 | 11 |
| ASP | N | B | 284 | 175 | 598 | 1382 | 11 |
| ASP | CA | B | 284 | 162 | 591 | 1385 | 10 |
| ASP | CB | B | 284 | 150 | 597 | 1377 | 13 |
| ASP | CG | B | 284 | 153 | 598 | 1362 | 18 |
| ASP | OD1 | B | 284 | 145 | 603 | 1355 | 20 |
| ASP | OD2 | B | 284 | 164 | 593 | 1358 | 13 |
| ASP | C | B | 284 | 163 | 576 | 1383 | 12 |
| ASP | O | B | 284 | 153 | 569 | 1384 | 12 |
| LYS | N | B | 285 | 175 | 571 | 1381 | 10 |
| LYS | CA | B | 285 | 178 | 557 | 1378 | 10 |
| LYS | CB | B | 285 | 170 | 552 | 1366 | 10 |
| LYS | CG | B | 285 | 174 | 558 | 1353 | 11 |
| LYS | CD | B | 285 | 167 | 552 | 1341 | 14 |
| LYS | CE | B | 285 | 168 | 560 | 1329 | 20 |
| LYS | NZ | B | 285 | 162 | 574 | 1331 | 19 |
| LYS | C | B | 285 | 192 | 555 | 1376 | 9 |
| LYS | O | B | 285 | 200 | 564 | 1374 | 10 |
| SER | N | B | 286 | 197 | 543 | 1378 | 9 |
| SER | CA | B | 286 | 211 | 539 | 1375 | 9 |
| SER | CB | B | 286 | 218 | 535 | 1388 | 10 |
| SER | OG | B | 286 | 220 | 547 | 1396 | 9 |
| SER | C | B | 286 | 210 | 527 | 1366 | 10 |
| SER | O | B | 286 | 204 | 517 | 1369 | 9 |
| ILE | N | B | 287 | 217 | 528 | 1355 | 9 |
| ILE | CA | B | 287 | 217 | 517 | 1346 | 7 |
| ILE | CB | B | 287 | 209 | 520 | 1333 | 7 |
| ILE | CG2 | B | 287 | 195 | 525 | 1337 | 9 |
| ILE | CG1 | B | 287 | 216 | 531 | 1325 | 8 |
| ILE | CD1 | B | 287 | 209 | 533 | 1311 | 9 |
| ILE | C | B | 287 | 231 | 513 | 1341 | 9 |
| ILE | O | B | 287 | 241 | 520 | 1342 | 8 |
| VAL | N | B | 288 | 232 | 501 | 1335 | 8 |
| VAL | CA | B | 288 | 245 | 495 | 1330 | 9 |
| VAL | CB | B | 288 | 247 | 481 | 1334 | 7 |

TABLE 2-continued

Structure Coordinates for BACE complexed to Inhibitor

| | | | | | | | |
|---|---|---|---|---|---|---|---|
| VAL | CG1 | B | 288 | 260 | 476 | 1329 | 7 |
| VAL | CG2 | B | 288 | 247 | 480 | 1350 | 8 |
| VAL | C | B | 288 | 243 | 496 | 1315 | 9 |
| VAL | O | B | 288 | 234 | 489 | 1309 | 10 |
| ASP | N | B | 289 | 251 | 504 | 1308 | 7 |
| ASP | CA | B | 289 | 250 | 506 | 1294 | 5 |
| ASP | CB | B | 289 | 243 | 519 | 1291 | 8 |
| ASP | CG | B | 289 | 241 | 522 | 1276 | 8 |
| ASP | OD1 | B | 289 | 241 | 512 | 1268 | 9 |
| ASP | OD2 | B | 289 | 238 | 533 | 1273 | 8 |
| ASP | C | B | 289 | 263 | 505 | 1286 | 7 |
| ASP | O | B | 289 | 271 | 514 | 1286 | 6 |
| SER | N | B | 290 | 264 | 494 | 1278 | 6 |
| SER | CA | B | 290 | 276 | 492 | 1270 | 6 |
| SER | CB | B | 290 | 276 | 477 | 1264 | 8 |
| SER | OG | B | 290 | 264 | 475 | 1257 | 9 |
| SER | C | B | 290 | 277 | 502 | 1259 | 7 |
| SER | O | B | 290 | 287 | 504 | 1252 | 6 |
| GLY | N | B | 291 | 266 | 508 | 1256 | 6 |
| GLY | CA | B | 291 | 265 | 518 | 1245 | 7 |
| GLY | C | B | 291 | 268 | 532 | 1249 | 6 |
| GLY | O | B | 291 | 266 | 541 | 1241 | 6 |
| THR | N | B | 292 | 272 | 534 | 1261 | 6 |
| THR | CA | B | 292 | 276 | 548 | 1266 | 7 |
| THR | CB | B | 292 | 268 | 551 | 1279 | 7 |
| THR | OG1 | B | 292 | 254 | 554 | 1275 | 6 |
| THR | CG2 | B | 292 | 274 | 564 | 1285 | 5 |
| THR | C | B | 292 | 291 | 548 | 1269 | 7 |
| THR | O | B | 292 | 296 | 539 | 1276 | 8 |
| THR | N | B | 293 | 298 | 558 | 1264 | 7 |
| THR | CA | B | 293 | 312 | 558 | 1267 | 8 |
| THR | CB | B | 293 | 319 | 570 | 1258 | 7 |
| THR | OG1 | B | 293 | 316 | 568 | 1244 | 7 |
| THR | CG2 | B | 293 | 334 | 570 | 1261 | 8 |
| THR | C | B | 293 | 316 | 561 | 1281 | 9 |
| THR | O | B | 293 | 324 | 553 | 1287 | 8 |
| ASN | N | B | 294 | 311 | 571 | 1287 | 8 |
| ASN | CA | B | 294 | 314 | 575 | 1300 | 9 |
| ASN | CB | B | 294 | 312 | 591 | 1302 | 9 |
| ASN | CG | B | 294 | 320 | 599 | 1292 | 10 |
| ASN | OD1 | B | 294 | 328 | 594 | 1285 | 9 |
| ASN | ND2 | B | 294 | 317 | 612 | 1292 | 10 |
| ASN | C | B | 294 | 307 | 569 | 1312 | 11 |
| ASN | O | B | 294 | 298 | 561 | 1310 | 9 |
| LEU | N | B | 295 | 311 | 573 | 1324 | 9 |
| LEU | CA | B | 295 | 304 | 570 | 1336 | 7 |
| LEU | CB | B | 295 | 314 | 569 | 1348 | 8 |
| LEU | CG | B | 295 | 307 | 570 | 1362 | 8 |
| LEU | CD1 | B | 295 | 296 | 559 | 1363 | 10 |
| LEU | CD2 | B | 295 | 318 | 569 | 1373 | 10 |
| LEU | C | B | 295 | 297 | 583 | 1337 | 9 |
| LEU | O | B | 295 | 303 | 593 | 1339 | 9 |
| ARG | N | B | 296 | 283 | 583 | 1336 | 8 |
| ARG | CA | B | 296 | 276 | 595 | 1337 | 9 |
| ARG | CB | B | 296 | 266 | 596 | 1325 | 11 |
| ARG | CG | B | 296 | 273 | 595 | 1312 | 13 |
| ARG | CD | B | 296 | 264 | 600 | 1300 | 17 |
| ARG | NE | B | 296 | 261 | 615 | 1302 | 18 |
| ARG | CZ | B | 296 | 256 | 622 | 1292 | 19 |
| ARG | NH1 | B | 296 | 254 | 635 | 1294 | 23 |
| ARG | NH2 | B | 296 | 253 | 617 | 1280 | 24 |
| ARG | C | B | 296 | 269 | 595 | 1350 | 7 |
| ARG | O | B | 296 | 264 | 585 | 1355 | 6 |
| LEU | N | B | 297 | 270 | 607 | 1357 | 8 |
| LEU | CA | B | 297 | 264 | 609 | 1370 | 9 |
| LEU | CB | B | 297 | 275 | 611 | 1380 | 9 |
| LEU | CG | B | 297 | 286 | 601 | 1381 | 8 |
| LEU | CD1 | B | 297 | 298 | 607 | 1389 | 6 |
| LEU | CD2 | B | 297 | 281 | 588 | 1387 | 9 |
| LEU | C | B | 297 | 254 | 620 | 1371 | 8 |
| LEU | O | B | 297 | 255 | 630 | 1364 | 9 |
| PRO | N | B | 298 | 244 | 619 | 1379 | 8 |
| PRO | CD | B | 298 | 241 | 607 | 1388 | 9 |
| PRO | CA | B | 298 | 233 | 629 | 1381 | 9 |
| PRO | CB | B | 298 | 225 | 624 | 1393 | 8 |
| PRO | CG | B | 298 | 226 | 609 | 1391 | 10 |
| PRO | C | B | 298 | 240 | 642 | 1384 | 9 |
| PRO | O | B | 298 | 251 | 642 | 1391 | 8 |
| LYS | N | B | 299 | 235 | 653 | 1379 | 10 |
| LYS | CA | B | 299 | 241 | 666 | 1382 | 13 |
| LYS | CB | B | 299 | 230 | 677 | 1379 | 14 |
| LYS | CG | B | 299 | 236 | 692 | 1380 | 18 |
| LYS | CD | B | 299 | 225 | 702 | 1376 | 22 |
| LYS | CE | B | 299 | 230 | 716 | 1375 | 26 |
| LYS | NZ | B | 299 | 235 | 721 | 1388 | 27 |
| LYS | C | B | 299 | 247 | 669 | 1395 | 11 |
| LYS | O | B | 299 | 259 | 672 | 1396 | 12 |
| LYS | N | B | 300 | 239 | 667 | 1406 | 13 |
| LYS | CA | B | 300 | 244 | 669 | 1419 | 13 |
| LYS | CB | B | 300 | 233 | 668 | 1429 | 15 |
| LYS | CG | B | 300 | 236 | 673 | 1443 | 20 |
| LYS | CD | B | 300 | 224 | 671 | 1453 | 25 |
| LYS | CE | B | 300 | 212 | 679 | 1448 | 27 |
| LYS | NZ | B | 300 | 201 | 678 | 1457 | 28 |
| LYS | C | B | 300 | 256 | 660 | 1423 | 12 |
| LYS | O | B | 300 | 265 | 664 | 1430 | 12 |
| VAL | N | B | 301 | 255 | 647 | 1419 | 10 |
| VAL | CA | B | 301 | 265 | 638 | 1422 | 9 |
| VAL | CB | B | 301 | 260 | 623 | 1419 | 9 |
| VAL | CGA | B | 301 | 271 | 613 | 1422 | 8 |
| VAL | CG2 | B | 301 | 247 | 620 | 1426 | 8 |
| VAL | C | B | 301 | 278 | 641 | 1414 | 11 |
| VAL | O | B | 301 | 289 | 640 | 1419 | 9 |
| PHE | N | B | 302 | 276 | 645 | 1402 | 9 |
| PHE | CA | B | 302 | 287 | 648 | 1393 | 9 |
| PHE | CB | B | 302 | 282 | 652 | 1379 | 10 |
| PHE | CG | B | 302 | 293 | 657 | 1370 | 11 |
| PHE | CD1 | B | 302 | 302 | 648 | 1365 | 12 |
| PHE | CD2 | B | 302 | 294 | 671 | 1368 | 12 |
| PHE | CE1 | B | 302 | 313 | 653 | 1357 | 12 |
| PHE | CE2 | B | 302 | 305 | 675 | 1360 | 14 |
| PHE | CZ | B | 302 | 314 | 666 | 1354 | 15 |
| PHE | C | B | 302 | 295 | 660 | 1399 | 10 |
| PHE | O | B | 302 | 307 | 659 | 1400 | 8 |
| GLU | N | B | 303 | 288 | 670 | 1403 | 10 |
| GLU | CA | B | 303 | 294 | 682 | 1409 | 11 |
| GLU | CB | B | 303 | 284 | 692 | 1412 | 13 |
| GLU | CG | B | 303 | 276 | 697 | 1400 | 18 |
| GLU | CD | B | 303 | 265 | 706 | 1403 | 23 |
| GLU | OE1 | B | 303 | 257 | 704 | 1412 | 26 |
| GLU | OE2 | B | 303 | 263 | 716 | 1395 | 26 |
| GLU | C | B | 303 | 302 | 678 | 1422 | 10 |
| GLU | O | B | 303 | 314 | 683 | 1424 | 11 |
| ALA | N | B | 304 | 297 | 669 | 1430 | 9 |
| ALA | CA | B | 304 | 304 | 665 | 1442 | 9 |
| ALA | CB | B | 304 | 294 | 658 | 1451 | 11 |
| ALA | C | B | 304 | 316 | 656 | 1439 | 10 |
| ALA | O | B | 304 | 326 | 657 | 1445 | 10 |
| ALA | N | B | 305 | 314 | 648 | 1429 | 9 |
| ALA | CA | B | 305 | 325 | 639 | 1425 | 10 |
| ALA | CB | B | 305 | 320 | 628 | 1415 | 10 |
| ALA | C | B | 305 | 337 | 646 | 1419 | 9 |
| ALA | O | B | 305 | 348 | 643 | 1422 | 10 |
| VAL | N | B | 306 | 334 | 656 | 1410 | 8 |
| VAL | CA | B | 306 | 345 | 663 | 1404 | 11 |
| VAL | CB | B | 306 | 339 | 673 | 1393 | 13 |
| VAL | CG1 | B | 306 | 350 | 682 | 1389 | 16 |
| VAL | CG2 | B | 306 | 334 | 665 | 1382 | 16 |
| VAL | C | B | 306 | 352 | 671 | 1415 | 9 |
| VAL | O | B | 306 | 364 | 673 | 1414 | 10 |
| LYS | N | B | 307 | 345 | 677 | 1424 | 10 |
| LYS | CA | B | 307 | 352 | 684 | 1435 | 10 |
| LYS | CB | B | 307 | 342 | 690 | 1445 | 13 |
| LYS | CG | B | 307 | 333 | 702 | 1439 | 18 |
| LYS | CD | B | 307 | 323 | 707 | 1449 | 21 |
| LYS | CE | B | 307 | 314 | 718 | 1443 | 22 |
| LYS | NZ | B | 307 | 303 | 722 | 1453 | 24 |
| LYS | C | B | 307 | 361 | 675 | 1442 | 9 |
| LYS | O | B | 307 | 373 | 679 | 1445 | 9 |
| SER | N | B | 308 | 357 | 663 | 1445 | 9 |
| SER | CA | B | 308 | 366 | 653 | 1452 | 8 |
| SER | CB | B | 308 | 357 | 641 | 1457 | 10 |
| SER | OG | B | 308 | 365 | 633 | 1465 | 12 |
| SER | C | B | 308 | 377 | 649 | 1444 | 7 |

TABLE 2-continued

Structure Coordinates for BACE complexed to Inhibitor

| | | | | | | | |
|---|---|---|---|---|---|---|---|
| SER | O | B | 308 | 388 | 647 | 1449 | 7 |
| ILE | N | B | 309 | 375 | 646 | 1431 | 8 |
| ILE | CA | B | 309 | 385 | 641 | 1422 | 7 |
| ILE | CB | B | 309 | 380 | 636 | 1409 | 6 |
| ILE | CG2 | B | 309 | 391 | 632 | 1399 | 6 |
| ILE | CG1 | B | 309 | 371 | 624 | 1412 | 7 |
| ILE | CD1 | B | 309 | 363 | 619 | 1400 | 7 |
| ILE | C | B | 309 | 396 | 652 | 1420 | 9 |
| ILE | O | B | 309 | 408 | 650 | 1419 | 8 |
| LYS | N | B | 310 | 391 | 665 | 1420 | 8 |
| LYS | CA | B | 310 | 400 | 676 | 1418 | 10 |
| LYS | CB | B | 310 | 392 | 689 | 1416 | 10 |
| LYS | CG | B | 310 | 386 | 692 | 1403 | 13 |
| LYS | CD | B | 310 | 379 | 705 | 1403 | 14 |
| LYS | CE | B | 310 | 374 | 709 | 1389 | 16 |
| LYS | NZ | B | 310 | 365 | 721 | 1390 | 17 |
| LYS | C | B | 310 | 409 | 677 | 1430 | 10 |
| LYS | O | B | 310 | 421 | 679 | 1429 | 11 |
| ALA | N | B | 311 | 403 | 676 | 1442 | 8 |
| ALA | CA | B | 311 | 410 | 677 | 1455 | 9 |
| ALA | CB | B | 311 | 400 | 676 | 1466 | 8 |
| ALA | C | B | 311 | 421 | 666 | 1456 | 11 |
| ALA | O | B | 311 | 432 | 669 | 1460 | 10 |
| ALA | N | B | 312 | 417 | 654 | 1452 | 9 |
| ALA | CA | B | 312 | 427 | 643 | 1452 | 8 |
| ALA | CB | B | 312 | 419 | 630 | 1450 | 9 |
| ALA | C | B | 312 | 438 | 644 | 1443 | 8 |
| ALA | O | B | 312 | 449 | 640 | 1446 | 10 |
| SER | N | B | 313 | 436 | 650 | 1431 | 9 |
| SER | CA | B | 313 | 446 | 652 | 1421 | 8 |
| SER | CB | B | 313 | 440 | 649 | 1407 | 10 |
| SER | OG | B | 313 | 430 | 658 | 1404 | 10 |
| SER | C | B | 313 | 452 | 666 | 1421 | 10 |
| SER | O | B | 313 | 459 | 670 | 1411 | 10 |
| SER | N | B | 314 | 450 | 674 | 1431 | 12 |
| SER | CA | B | 314 | 454 | 688 | 1432 | 14 |
| SER | CB | B | 314 | 450 | 694 | 1446 | 12 |
| SER | OG | B | 314 | 458 | 689 | 1456 | 16 |
| SER | C | B | 314 | 469 | 691 | 1430 | 14 |
| SER | O | B | 314 | 473 | 702 | 1428 | 14 |
| THR | N | B | 315 | 478 | 681 | 1430 | 11 |
| THR | CA | B | 315 | 492 | 684 | 1428 | 14 |
| THR | CB | B | 315 | 501 | 671 | 1431 | 17 |
| THR | OG1 | B | 315 | 497 | 660 | 1423 | 20 |
| THR | CG2 | B | 315 | 500 | 668 | 1446 | 17 |
| THR | C | B | 315 | 494 | 688 | 1414 | 16 |
| THR | O | B | 315 | 505 | 694 | 1411 | 15 |
| GLU | N | B | 316 | 485 | 686 | 1405 | 15 |
| GLU | CA | B | 316 | 485 | 691 | 1391 | 16 |
| GLU | CB | B | 316 | 488 | 679 | 1382 | 18 |
| GLU | CG | B | 316 | 503 | 676 | 1381 | 23 |
| GLU | CD | B | 316 | 506 | 665 | 1371 | 24 |
| GLU | OE1 | B | 316 | 501 | 665 | 1359 | 20 |
| GLU | OE2 | B | 316 | 514 | 656 | 1374 | 26 |
| GLU | C | B | 316 | 472 | 697 | 1388 | 15 |
| GLU | O | B | 316 | 461 | 692 | 1391 | 18 |
| LYS | N | B | 317 | 472 | 709 | 1382 | 16 |
| LYS | CA | B | 317 | 460 | 716 | 1378 | 16 |
| LYS | CB | B | 317 | 461 | 731 | 1382 | 18 |
| LYS | CG | B | 317 | 462 | 733 | 1397 | 22 |
| LYS | CD | B | 317 | 450 | 728 | 1404 | 27 |
| LYS | CE | B | 317 | 450 | 732 | 1419 | 28 |
| LYS | NZ | B | 317 | 463 | 727 | 1426 | 31 |
| LYS | C | B | 317 | 457 | 715 | 1364 | 15 |
| LYS | O | B | 317 | 465 | 716 | 1355 | 16 |
| PHE | N | B | 318 | 444 | 712 | 1361 | 15 |
| PHE | CA | B | 318 | 439 | 711 | 1347 | 15 |
| PHE | CB | B | 318 | 434 | 697 | 1345 | 15 |
| PHE | CG | B | 318 | 443 | 686 | 1350 | 13 |
| PHE | CD1 | B | 318 | 441 | 680 | 1363 | 15 |
| PHE | CD2 | B | 318 | 453 | 681 | 1342 | 15 |
| PHE | CE1 | B | 318 | 450 | 671 | 1367 | 14 |
| PHE | CE2 | B | 318 | 462 | 672 | 1347 | 15 |
| PHE | CZ | B | 318 | 460 | 666 | 1359 | 13 |
| PHE | C | B | 318 | 428 | 721 | 1344 | 16 |
| PHE | O | B | 318 | 421 | 725 | 1353 | 17 |
| PRO | N | B | 319 | 428 | 726 | 1331 | 18 |
| PRO | CD | B | 319 | 436 | 721 | 1320 | 20 |
| PRO | CA | B | 319 | 419 | 736 | 1327 | 18 |
| PRO | CB | B | 319 | 422 | 738 | 1313 | 19 |
| PRO | CG | B | 319 | 427 | 725 | 1308 | 21 |
| PRO | C | B | 319 | 404 | 731 | 1329 | 16 |
| PRO | O | B | 319 | 401 | 719 | 1329 | 15 |
| ASP | N | B | 320 | 394 | 740 | 1330 | 16 |
| ASP | CA | B | 320 | 380 | 736 | 1332 | 17 |
| ASP | CB | B | 320 | 371 | 748 | 1332 | 22 |
| ASP | CG | B | 320 | 375 | 757 | 1344 | 27 |
| ASP | OD1 | B | 320 | 377 | 752 | 1355 | 27 |
| ASP | OD2 | B | 320 | 375 | 770 | 1342 | 30 |
| ASP | C | B | 320 | 375 | 727 | 1320 | 14 |
| ASP | O | B | 320 | 367 | 718 | 1323 | 15 |
| GLY | N | B | 321 | 381 | 729 | 1308 | 14 |
| GLY | CA | B | 321 | 377 | 721 | 1297 | 14 |
| GLY | C | B | 321 | 380 | 707 | 1299 | 14 |
| GLY | O | B | 321 | 372 | 698 | 1294 | 14 |
| PHE | N | B | 322 | 390 | 703 | 1306 | 11 |
| PHE | CA | B | 322 | 393 | 690 | 1309 | 11 |
| PHE | CB | B | 322 | 407 | 688 | 1316 | 10 |
| PHE | CG | B | 322 | 410 | 675 | 1321 | 10 |
| PHE | CD1 | B | 322 | 413 | 664 | 1313 | 11 |
| PHE | CD2 | B | 322 | 409 | 672 | 1335 | 8 |
| PHE | CE1 | B | 322 | 415 | 651 | 1317 | 12 |
| PHE | CE2 | B | 322 | 412 | 659 | 1340 | 11 |
| PHE | CZ | B | 322 | 415 | 649 | 1331 | 9 |
| PHE | C | B | 322 | 382 | 683 | 1318 | 11 |
| PHE | O | B | 322 | 377 | 672 | 1314 | 10 |
| TRP | N | B | 323 | 379 | 690 | 1329 | 10 |
| TRP | CA | B | 323 | 369 | 685 | 1338 | 10 |
| TRP | CB | B | 323 | 369 | 693 | 1351 | 10 |
| TRP | CG | B | 323 | 382 | 692 | 1358 | 12 |
| TRP | CD2 | B | 323 | 387 | 680 | 1365 | 11 |
| TRP | CE2 | B | 323 | 399 | 683 | 1370 | 13 |
| TRP | CE3 | B | 323 | 382 | 667 | 1367 | 11 |
| TRP | CD1 | B | 323 | 391 | 701 | 1359 | 12 |
| TRP | NE1 | B | 323 | 402 | 696 | 1366 | 11 |
| TRP | CZ2 | B | 323 | 407 | 674 | 1377 | 12 |
| TRP | CZ3 | B | 323 | 389 | 658 | 1374 | 12 |
| TRP | CH2 | B | 323 | 402 | 662 | 1379 | 14 |
| TRP | C | B | 323 | 355 | 684 | 1331 | 10 |
| TRP | O | B | 323 | 346 | 677 | 1337 | 9 |
| LEU | N | B | 324 | 353 | 691 | 1320 | 12 |
| LEU | CA | B | 324 | 340 | 691 | 1313 | 13 |
| LEU | CB | B | 324 | 338 | 704 | 1306 | 17 |
| LEU | CG | B | 324 | 336 | 716 | 1316 | 21 |
| LEU | CD1 | B | 324 | 334 | 729 | 1308 | 22 |
| LEU | CD2 | B | 324 | 324 | 714 | 1325 | 22 |
| LEU | C | B | 324 | 340 | 680 | 1303 | 13 |
| LEU | O | B | 324 | 330 | 678 | 1296 | 12 |
| GLY | N | B | 325 | 351 | 672 | 1303 | 11 |
| GLY | CA | B | 325 | 352 | 661 | 1293 | 11 |
| GLY | C | B | 325 | 354 | 665 | 1279 | 12 |
| GLY | O | B | 325 | 353 | 657 | 1270 | 12 |
| GLU | N | B | 326 | 356 | 678 | 1277 | 13 |
| GLU | CA | B | 326 | 358 | 684 | 1263 | 14 |
| GLU | CB | B | 326 | 352 | 698 | 1263 | 16 |
| GLU | CG | B | 326 | 337 | 698 | 1266 | 21 |
| GLU | CD | B | 326 | 331 | 712 | 1268 | 24 |
| GLU | OE1 | B | 326 | 319 | 714 | 1269 | 25 |
| GLU | OE2 | B | 326 | 340 | 722 | 1269 | 25 |
| GLU | C | B | 326 | 372 | 685 | 1258 | 15 |
| GLU | O | B | 326 | 374 | 683 | 1246 | 18 |
| GLN | N | B | 327 | 382 | 687 | 1266 | 14 |
| GLN | CA | B | 327 | 395 | 688 | 1261 | 15 |
| GLN | CB | B | 327 | 401 | 702 | 1262 | 20 |
| GLN | CG | B | 327 | 404 | 706 | 1277 | 26 |
| GLN | CD | B | 327 | 408 | 721 | 1278 | 30 |
| GLN | OE1 | B | 327 | 400 | 730 | 1276 | 33 |
| GLN | NE2 | B | 327 | 421 | 723 | 1280 | 32 |
| GLN | C | B | 327 | 405 | 678 | 1266 | 13 |
| GLN | O | B | 327 | 403 | 673 | 1278 | 11 |
| LEU | N | B | 328 | 415 | 674 | 1259 | 13 |
| LEU | CA | B | 328 | 424 | 664 | 1263 | 15 |
| LEU | CB | B | 328 | 429 | 655 | 1251 | 19 |
| LEU | CG | B | 328 | 436 | 662 | 1240 | 24 |

TABLE 2-continued

Structure Coordinates for BACE complexed to Inhibitor

| | | | | | | | |
|---|---|---|---|---|---|---|---|
| LEU | CD1 | B | 328 | 449 | 669 | 1244 | 26 |
| LEU | CD2 | B | 328 | 439 | 652 | 1229 | 25 |
| LEU | C | B | 328 | 436 | 670 | 1271 | 13 |
| LEU | O | B | 328 | 438 | 682 | 1270 | 13 |
| VAL | N | B | 329 | 442 | 661 | 1278 | 13 |
| VAL | CA | B | 329 | 454 | 665 | 1286 | 14 |
| VAL | CB | B | 329 | 452 | 665 | 1301 | 17 |
| VAL | CG1 | B | 329 | 465 | 666 | 1308 | 18 |
| VAL | CG2 | B | 329 | 443 | 676 | 1306 | 19 |
| VAL | C | B | 329 | 465 | 655 | 1282 | 14 |
| VAL | O | B | 329 | 461 | 643 | 1280 | 12 |
| CYS | N | B | 330 | 477 | 660 | 1280 | 12 |
| CYS | CA | B | 330 | 488 | 651 | 1275 | 12 |
| CYS | C | B | 330 | 500 | 651 | 1285 | 13 |
| CYS | O | B | 330 | 502 | 661 | 1292 | 13 |
| CYS | CB | B | 330 | 493 | 655 | 1262 | 14 |
| CYS | SG | B | 330 | 481 | 655 | 1248 | 15 |
| TRP | N | B | 331 | 507 | 640 | 1284 | 12 |
| TRP | CA | B | 331 | 519 | 639 | 1292 | 11 |
| TRP | CB | B | 331 | 517 | 630 | 1304 | 11 |
| TRP | CG | B | 331 | 510 | 636 | 1315 | 11 |
| TRP | CD2 | B | 331 | 496 | 635 | 1319 | 11 |
| TRP | CE2 | B | 331 | 493 | 643 | 1330 | 13 |
| TRP | CE3 | B | 331 | 485 | 627 | 1313 | 11 |
| TRP | CD1 | B | 331 | 515 | 645 | 1325 | 13 |
| TRP | NE1 | B | 331 | 505 | 649 | 1333 | 13 |
| TRP | CZ2 | B | 331 | 480 | 644 | 1336 | 12 |
| TRP | CZ3 | B | 331 | 473 | 628 | 1319 | 13 |
| TRP | CH2 | B | 331 | 470 | 636 | 1330 | 14 |
| TRP | C | B | 331 | 530 | 632 | 1283 | 10 |
| TRP | O | B | 331 | 526 | 625 | 1274 | 12 |
| GLN | N | B | 332 | 543 | 635 | 1286 | 10 |
| GLN | CA | B | 332 | 553 | 629 | 1278 | 12 |
| GLN | CB | B | 332 | 567 | 632 | 1284 | 17 |
| GLN | CG | B | 332 | 579 | 627 | 1276 | 26 |
| GLN | CD | B | 332 | 592 | 630 | 1282 | 31 |
| GLN | OE1 | B | 332 | 596 | 626 | 1293 | 36 |
| GLN | NE2 | B | 332 | 600 | 638 | 1275 | 36 |
| GLN | C | B | 332 | 551 | 614 | 1279 | 13 |
| GLN | O | B | 332 | 547 | 608 | 1289 | 9 |
| ALA | N | B | 333 | 554 | 607 | 1268 | 10 |
| ALA | CA | B | 333 | 553 | 593 | 1266 | 11 |
| ALA | CB | B | 333 | 561 | 588 | 1254 | 13 |
| ALA | C | B | 333 | 557 | 585 | 1279 | 10 |
| ALA | O | B | 333 | 568 | 586 | 1284 | 11 |
| GLY | N | B | 334 | 547 | 577 | 1284 | 10 |
| GLY | CA | B | 334 | 549 | 569 | 1296 | 9 |
| GLY | C | B | 334 | 549 | 575 | 1309 | 11 |
| GLY | O | B | 334 | 550 | 568 | 1319 | 11 |
| THR | N | B | 335 | 548 | 588 | 1310 | 8 |
| THR | CA | B | 335 | 548 | 596 | 1322 | 9 |
| THR | CB | B | 335 | 556 | 608 | 1321 | 9 |
| THR | OG1 | B | 335 | 550 | 618 | 1314 | 10 |
| THR | CG2 | B | 335 | 570 | 605 | 1315 | 11 |
| THR | C | B | 335 | 534 | 599 | 1329 | 11 |
| THR | O | B | 335 | 534 | 607 | 1338 | 11 |
| THR | N | B | 336 | 523 | 594 | 1323 | 8 |
| THR | CA | B | 336 | 510 | 597 | 1329 | 8 |
| THR | CB | B | 336 | 499 | 588 | 1323 | 9 |
| THR | OG1 | B | 336 | 499 | 589 | 1309 | 8 |
| THR | CG2 | B | 336 | 486 | 592 | 1328 | 8 |
| THR | C | B | 336 | 511 | 595 | 1344 | 7 |
| THR | O | B | 336 | 515 | 584 | 1348 | 8 |
| PRO | N | B | 337 | 508 | 605 | 1352 | 7 |
| PRO | CD | B | 337 | 504 | 618 | 1348 | 9 |
| PRO | CA | B | 337 | 508 | 604 | 1367 | 9 |
| PRO | CB | B | 337 | 509 | 618 | 1371 | 8 |
| PRO | CG | B | 337 | 500 | 625 | 1361 | 10 |
| PRO | C | B | 337 | 496 | 597 | 1373 | 8 |
| PRO | O | B | 337 | 489 | 603 | 1381 | 7 |
| TRP | N | B | 338 | 494 | 584 | 1369 | 6 |
| TRP | CA | B | 338 | 482 | 576 | 1374 | 6 |
| TRP | CB | B | 338 | 484 | 562 | 1371 | 7 |
| TRP | CG | B | 338 | 485 | 559 | 1356 | 7 |
| TRP | CD2 | B | 338 | 475 | 561 | 1346 | 6 |
| TRP | CE2 | B | 338 | 481 | 557 | 1334 | 8 |
| TRP | CE3 | B | 338 | 462 | 565 | 1347 | 8 |
| TRP | CD1 | B | 338 | 496 | 554 | 1350 | 8 |
| TRP | NE1 | B | 338 | 494 | 553 | 1336 | 9 |
| TRP | CZ2 | B | 338 | 474 | 558 | 1322 | 8 |
| TRP | CZ3 | B | 338 | 455 | 566 | 1335 | 9 |
| TRP | CH2 | B | 338 | 461 | 562 | 1323 | 8 |
| TRP | C | B | 338 | 481 | 578 | 1389 | 7 |
| TRP | O | B | 338 | 469 | 579 | 1394 | 5 |
| ASN | N | B | 339 | 492 | 577 | 1396 | 7 |
| ASN | CA | B | 339 | 491 | 578 | 1411 | 7 |
| ASN | CB | B | 339 | 506 | 576 | 1417 | 8 |
| ASN | CG | B | 339 | 514 | 588 | 1416 | 8 |
| ASN | OD1 | B | 339 | 515 | 596 | 1426 | 8 |
| ASN | ND2 | B | 339 | 521 | 590 | 1405 | 8 |
| ASN | C | B | 339 | 485 | 590 | 1417 | 6 |
| ASN | O | B | 339 | 481 | 590 | 1429 | 7 |
| ILE | N | B | 340 | 485 | 601 | 1410 | 7 |
| ILE | CA | B | 340 | 479 | 614 | 1416 | 7 |
| ILE | CB | B | 340 | 484 | 627 | 1410 | 7 |
| ILE | CG2 | B | 340 | 500 | 626 | 1409 | 10 |
| ILE | CG1 | B | 340 | 479 | 629 | 1396 | 6 |
| ILE | CD1 | B | 340 | 482 | 643 | 1390 | 10 |
| ILE | C | B | 340 | 464 | 613 | 1415 | 7 |
| ILE | O | B | 340 | 457 | 621 | 1422 | 7 |
| PHE | N | B | 341 | 458 | 605 | 1406 | 7 |
| PHE | CA | B | 341 | 444 | 604 | 1404 | 7 |
| PHE | CB | B | 341 | 441 | 600 | 1390 | 7 |
| PHE | CG | B | 341 | 442 | 612 | 1380 | 10 |
| PHE | CD1 | B | 341 | 432 | 621 | 1378 | 11 |
| PHE | CD2 | B | 341 | 454 | 614 | 1374 | 10 |
| PHE | CE1 | B | 341 | 434 | 632 | 1370 | 11 |
| PHE | CE2 | B | 341 | 456 | 624 | 1365 | 10 |
| PHE | CZ | B | 341 | 446 | 633 | 1363 | 9 |
| PHE | C | B | 341 | 439 | 593 | 1414 | 5 |
| PHE | O | B | 341 | 445 | 583 | 1416 | 7 |
| PRO | N | B | 342 | 427 | 595 | 1419 | 5 |
| PRO | CD | B | 342 | 419 | 608 | 1419 | 7 |
| PRO | CA | B | 342 | 421 | 586 | 1429 | 5 |
| PRO | CB | B | 342 | 411 | 595 | 1437 | 6 |
| PRO | CG | B | 342 | 406 | 604 | 1426 | 8 |
| PRO | C | B | 342 | 413 | 574 | 1422 | 8 |
| PRO | O | B | 342 | 409 | 575 | 1410 | 8 |
| VAL | N | B | 343 | 411 | 564 | 1430 | 8 |
| VAL | CA | B | 343 | 403 | 552 | 1425 | 6 |
| VAL | CB | B | 343 | 407 | 539 | 1432 | 8 |
| VAL | CG1 | B | 343 | 422 | 536 | 1429 | 8 |
| VAL | CG2 | B | 343 | 405 | 540 | 1447 | 10 |
| VAL | C | B | 343 | 389 | 556 | 1429 | 7 |
| VAL | O | B | 343 | 387 | 564 | 1437 | 9 |
| ILE | N | B | 344 | 379 | 550 | 1422 | 6 |
| ILE | CA | B | 344 | 365 | 553 | 1424 | 6 |
| ILE | CB | B | 344 | 358 | 560 | 1412 | 6 |
| ILE | CG2 | B | 344 | 343 | 562 | 1415 | 8 |
| ILE | CG1 | B | 344 | 365 | 574 | 1409 | 6 |
| ILE | CD1 | B | 344 | 360 | 580 | 1397 | 9 |
| ILE | C | B | 344 | 358 | 540 | 1428 | 6 |
| ILE | O | B | 344 | 359 | 530 | 1420 | 7 |
| SER | N | B | 345 | 350 | 540 | 1439 | 7 |
| SER | CA | B | 345 | 343 | 528 | 1443 | 7 |
| SER | CB | B | 345 | 348 | 524 | 1457 | 9 |
| SER | OG | B | 345 | 362 | 520 | 1457 | 8 |
| SER | C | B | 345 | 328 | 531 | 1443 | 7 |
| SER | O | B | 345 | 323 | 540 | 1449 | 9 |
| LEU | N | B | 346 | 321 | 522 | 1437 | 6 |
| LEU | CA | B | 346 | 306 | 522 | 1437 | 8 |
| LEU | CB | B | 346 | 301 | 522 | 1422 | 7 |
| LEU | CG | B | 346 | 306 | 533 | 1413 | 10 |
| LEU | CD1 | B | 346 | 299 | 530 | 1399 | 11 |
| LEU | CD2 | B | 346 | 302 | 546 | 1418 | 9 |
| LEU | C | B | 346 | 301 | 510 | 1444 | 7 |
| LEU | O | B | 346 | 305 | 499 | 1441 | 7 |
| TYR | N | B | 347 | 294 | 512 | 1455 | 7 |
| TYR | CA | B | 347 | 288 | 501 | 1463 | 8 |
| TYR | CB | B | 347 | 287 | 504 | 1477 | 8 |
| TYR | CG | B | 347 | 300 | 505 | 1485 | 8 |
| TYR | CD1 | B | 347 | 310 | 515 | 1482 | 8 |
| TYR | CE1 | B | 347 | 322 | 515 | 1489 | 10 |
| TYR | CD2 | B | 347 | 303 | 496 | 1495 | 9 |

TABLE 2-continued

Structure Coordinates for BACE complexed to Inhibitor

| | | | | | | | |
|---|---|---|---|---|---|---|---|
| TYR | CE2 | B | 347 | 315 | 496 | 1502 | 10 |
| TYR | CZ | B | 347 | 324 | 506 | 1499 | 11 |
| TYR | OH | B | 347 | 336 | 506 | 1506 | 10 |
| TYR | C | B | 347 | 275 | 498 | 1457 | 7 |
| TYR | O | B | 347 | 267 | 507 | 1455 | 9 |
| LEU | N | B | 348 | 272 | 485 | 1454 | 9 |
| LEU | CA | B | 348 | 259 | 481 | 1448 | 8 |
| LEU | CB | B | 348 | 262 | 473 | 1435 | 9 |
| LEU | CG | B | 348 | 269 | 481 | 1424 | 10 |
| LEU | CD1 | B | 348 | 273 | 471 | 1413 | 10 |
| LEU | CD2 | B | 348 | 261 | 492 | 1419 | 15 |
| LEU | C | B | 348 | 252 | 472 | 1458 | 9 |
| LEU | O | B | 348 | 258 | 465 | 1466 | 10 |
| MET | N | B | 349 | 239 | 472 | 1457 | 11 |
| MET | CA | B | 349 | 230 | 464 | 1466 | 14 |
| MET | CB | B | 349 | 216 | 466 | 1462 | 16 |
| MET | CG | B | 349 | 206 | 458 | 1470 | 20 |
| MET | SD | B | 349 | 189 | 462 | 1466 | 27 |
| MET | CE | B | 349 | 188 | 479 | 1472 | 18 |
| MET | C | B | 349 | 234 | 449 | 1463 | 14 |
| MET | O | B | 349 | 235 | 445 | 1451 | 13 |
| GLY | N | B | 350 | 235 | 441 | 1474 | 13 |
| GLY | CA | B | 350 | 238 | 427 | 1472 | 13 |
| GLY | C | B | 350 | 225 | 419 | 1471 | 13 |
| GLY | O | B | 350 | 214 | 424 | 1472 | 14 |
| GLU | N | B | 351 | 226 | 406 | 1469 | 15 |
| GLU | CA | B | 351 | 214 | 397 | 1468 | 17 |
| GLU | CB | B | 351 | 217 | 385 | 1459 | 18 |
| GLU | CG | B | 351 | 218 | 387 | 1444 | 19 |
| GLU | CD | B | 351 | 215 | 375 | 1436 | 19 |
| GLU | OE1 | B | 351 | 223 | 366 | 1436 | 18 |
| GLU | OE2 | B | 351 | 204 | 375 | 1429 | 21 |
| GLU | C | B | 351 | 209 | 393 | 1481 | 20 |
| GLU | O | B | 351 | 198 | 389 | 1483 | 20 |
| VAL | N | B | 352 | 218 | 394 | 1491 | 19 |
| VAL | CA | B | 352 | 215 | 390 | 1505 | 21 |
| VAL | CB | B | 352 | 227 | 385 | 1512 | 22 |
| VAL | CG1 | B | 352 | 223 | 382 | 1527 | 24 |
| VAL | CG2 | B | 352 | 231 | 372 | 1506 | 23 |
| VAL | C | B | 352 | 210 | 403 | 1512 | 21 |
| VAL | O | B | 352 | 215 | 414 | 1510 | 19 |
| THR | N | B | 353 | 200 | 401 | 1521 | 22 |
| THR | CA | B | 353 | 194 | 412 | 1528 | 22 |
| THR | CB | B | 353 | 183 | 407 | 1538 | 23 |
| THR | OG1 | B | 353 | 173 | 400 | 1531 | 27 |
| THR | CG2 | B | 353 | 176 | 419 | 1544 | 24 |
| THR | C | B | 353 | 205 | 420 | 1536 | 19 |
| THR | O | B | 353 | 213 | 414 | 1543 | 20 |
| ASN | N | B | 354 | 204 | 433 | 1535 | 21 |
| ASN | CA | B | 354 | 213 | 442 | 1542 | 20 |
| ASN | CB | B | 354 | 212 | 441 | 1558 | 23 |
| ASN | CG | B | 354 | 198 | 445 | 1562 | 24 |
| ASN | OD1 | B | 354 | 193 | 456 | 1558 | 26 |
| ASN | ND2 | B | 354 | 191 | 437 | 1570 | 26 |
| ASN | C | B | 354 | 228 | 440 | 1539 | 20 |
| ASN | O | B | 354 | 237 | 443 | 1547 | 20 |
| GLN | N | B | 355 | 231 | 435 | 1527 | 17 |
| GLN | CA | B | 355 | 244 | 432 | 1522 | 17 |
| GLN | CB | B | 355 | 246 | 417 | 1521 | 21 |
| GLN | CG | B | 355 | 261 | 413 | 1524 | 28 |
| GLN | CD | B | 355 | 262 | 398 | 1523 | 29 |
| GLN | OE1 | B | 355 | 261 | 392 | 1512 | 32 |
| GLN | NE2 | B | 355 | 264 | 392 | 1535 | 33 |
| GLN | C | B | 355 | 247 | 440 | 1509 | 15 |
| GLN | O | B | 355 | 238 | 441 | 1501 | 14 |
| SER | N | B | 356 | 259 | 445 | 1508 | 14 |
| SER | CA | B | 356 | 263 | 452 | 1496 | 12 |
| SER | CB | B | 356 | 262 | 467 | 1498 | 13 |
| SER | OG | B | 356 | 272 | 471 | 1507 | 15 |
| SER | C | B | 356 | 278 | 448 | 1492 | 13 |
| SER | O | B | 356 | 284 | 441 | 1501 | 14 |
| PHE | N | B | 357 | 282 | 451 | 1481 | 11 |
| PHE | CA | B | 357 | 296 | 449 | 1476 | 9 |
| PHE | CB | B | 357 | 296 | 436 | 1468 | 9 |
| PHE | CG | B | 357 | 290 | 437 | 1455 | 10 |
| PHE | CD1 | B | 357 | 297 | 441 | 1443 | 11 |
| PHE | CD2 | B | 357 | 276 | 433 | 1453 | 11 |
| PHE | CE1 | B | 357 | 290 | 441 | 1431 | 11 |
| PHE | CE2 | B | 357 | 270 | 434 | 1441 | 13 |
| PHE | CZ | B | 357 | 277 | 438 | 1430 | 10 |
| PHE | C | B | 357 | 300 | 461 | 1469 | 8 |
| PHE | O | B | 357 | 292 | 469 | 1465 | 8 |
| ARG | N | B | 358 | 313 | 462 | 1466 | 9 |
| ARG | CA | B | 358 | 318 | 474 | 1458 | 8 |
| ARG | CB | B | 358 | 326 | 483 | 1468 | 8 |
| ARG | CG | B | 358 | 340 | 477 | 1472 | 9 |
| ARG | CD | B | 358 | 346 | 485 | 1483 | 9 |
| ARG | NE | B | 358 | 359 | 480 | 1486 | 11 |
| ARG | CZ | B | 358 | 366 | 483 | 1498 | 12 |
| ARG | NH1 | B | 358 | 360 | 492 | 1506 | 10 |
| ARG | NH2 | B | 358 | 378 | 478 | 1500 | 13 |
| ARG | C | B | 358 | 326 | 470 | 1446 | 8 |
| ARG | O | B | 358 | 333 | 459 | 1446 | 7 |
| ILE | N | B | 359 | 326 | 478 | 1436 | 8 |
| ILE | CA | B | 359 | 334 | 476 | 1424 | 7 |
| ILE | CB | B | 359 | 326 | 475 | 1411 | 8 |
| ILE | CG2 | B | 359 | 317 | 463 | 1412 | 10 |
| ILE | CG1 | B | 359 | 318 | 488 | 1409 | 8 |
| ILE | CD1 | B | 359 | 310 | 488 | 1395 | 10 |
| ILE | C | B | 359 | 343 | 489 | 1424 | 6 |
| ILE | O | B | 359 | 338 | 500 | 1426 | 9 |
| THR | N | B | 360 | 356 | 487 | 1422 | 6 |
| THR | CA | B | 360 | 365 | 499 | 1422 | 6 |
| THR | CB | B | 360 | 375 | 497 | 1433 | 8 |
| THR | OG1 | B | 360 | 368 | 495 | 1445 | 9 |
| THR | CG2 | B | 360 | 384 | 509 | 1434 | 7 |
| THR | C | B | 360 | 372 | 500 | 1409 | 6 |
| THR | O | B | 360 | 378 | 490 | 1404 | 6 |
| ILE | N | B | 361 | 372 | 512 | 1403 | 7 |
| ILE | CA | B | 361 | 379 | 514 | 1390 | 9 |
| ILE | CB | B | 361 | 370 | 520 | 1379 | 9 |
| ILE | CG2 | B | 361 | 359 | 510 | 1376 | 13 |
| ILE | CG1 | B | 361 | 364 | 533 | 1384 | 9 |
| ILE | CD1 | B | 361 | 357 | 541 | 1373 | 13 |
| ILE | C | B | 361 | 390 | 524 | 1392 | 7 |
| ILE | O | B | 361 | 391 | 531 | 1402 | 6 |
| LEU | N | B | 362 | 400 | 524 | 1383 | 6 |
| LEU | CA | B | 362 | 412 | 532 | 1384 | 6 |
| LEU | CB | B | 362 | 424 | 523 | 1381 | 7 |
| LEU | CG | B | 362 | 426 | 510 | 1387 | 7 |
| LEU | CD1 | B | 362 | 438 | 503 | 1381 | 7 |
| LEU | CD2 | B | 362 | 428 | 512 | 1402 | 9 |
| LEU | C | B | 362 | 411 | 543 | 1373 | 6 |
| LEU | O | B | 362 | 402 | 543 | 1365 | 7 |
| PRO | N | B | 363 | 420 | 553 | 1374 | 6 |
| PRO | CD | B | 363 | 430 | 555 | 1385 | 8 |
| PRO | CA | B | 363 | 420 | 563 | 1364 | 6 |
| PRO | CB | B | 363 | 431 | 573 | 1369 | 7 |
| PRO | CG | B | 363 | 440 | 564 | 1377 | 5 |
| PRO | C | B | 363 | 423 | 557 | 1350 | 8 |
| PRO | O | B | 363 | 419 | 563 | 1340 | 7 |
| GLN | N | B | 364 | 429 | 545 | 1350 | 6 |
| GLN | CA | B | 364 | 431 | 539 | 1337 | 6 |
| GLN | CB | B | 364 | 440 | 526 | 1339 | 7 |
| GLN | CG | B | 364 | 454 | 529 | 1341 | 6 |
| GLN | CD | B | 364 | 459 | 530 | 1355 | 8 |
| GLN | OE1 | B | 364 | 452 | 534 | 1364 | 7 |
| GLN | NE2 | B | 364 | 472 | 528 | 1357 | 8 |
| GLN | C | B | 364 | 418 | 535 | 1331 | 7 |
| GLN | O | B | 364 | 417 | 532 | 1319 | 9 |
| GLN | N | B | 365 | 407 | 536 | 1339 | 7 |
| GLN | CA | B | 365 | 394 | 533 | 1333 | 8 |
| GLN | CB | B | 365 | 385 | 525 | 1343 | 8 |
| GLN | CG | B | 365 | 386 | 510 | 1342 | 8 |
| GLN | CD | B | 365 | 399 | 505 | 1347 | 10 |
| GLN | OE1 | B | 365 | 407 | 499 | 1340 | 12 |
| GLN | NE2 | B | 365 | 402 | 507 | 1360 | 6 |
| GLN | C | B | 365 | 387 | 546 | 1330 | 8 |
| GLN | O | B | 365 | 381 | 548 | 1319 | 7 |
| TYR | N | B | 366 | 387 | 556 | 1339 | 7 |
| TYR | CA | B | 366 | 380 | 568 | 1337 | 6 |
| TYR | CB | B | 366 | 374 | 574 | 1350 | 7 |
| TYR | CG | B | 366 | 383 | 579 | 1360 | 8 |
| TYR | CD1 | B | 366 | 390 | 591 | 1359 | 8 |

TABLE 2-continued

Structure Coordinates for BACE complexed to Inhibitor

| | | | | | | | |
|---|---|---|---|---|---|---|---|
| TYR | CE1 | B | 366 | 398 | 596 | 1369 | 7 |
| TYR | CD2 | B | 366 | 385 | 571 | 1372 | 7 |
| TYR | CE2 | B | 366 | 393 | 576 | 1382 | 7 |
| TYR | CZ | B | 366 | 400 | 588 | 1381 | 6 |
| TYR | OH | B | 366 | 408 | 593 | 1391 | 7 |
| TYR | C | B | 366 | 387 | 579 | 1329 | 8 |
| TYR | O | B | 366 | 381 | 590 | 1326 | 8 |
| LEU | N | B | 367 | 400 | 577 | 1326 | 7 |
| LEU | CA | B | 367 | 407 | 586 | 1317 | 7 |
| LEU | CB | B | 367 | 421 | 589 | 1323 | 8 |
| LEU | CG | B | 367 | 421 | 597 | 1336 | 5 |
| LEU | CD1 | B | 367 | 436 | 601 | 1339 | 6 |
| LEU | CD2 | B | 367 | 413 | 609 | 1335 | 6 |
| LEU | C | B | 367 | 408 | 579 | 1304 | 9 |
| LEU | O | B | 367 | 415 | 569 | 1303 | 9 |
| ARG | N | B | 368 | 400 | 583 | 1294 | 7 |
| ARG | CA | B | 368 | 399 | 577 | 1281 | 8 |
| ARG | CB | B | 368 | 386 | 580 | 1274 | 7 |
| ARG | CG | B | 368 | 383 | 573 | 1261 | 9 |
| ARG | CD | B | 368 | 368 | 574 | 1257 | 8 |
| ARG | NE | B | 368 | 364 | 587 | 1255 | 10 |
| ARG | CZ | B | 368 | 367 | 594 | 1243 | 10 |
| ARG | NH1 | B | 368 | 373 | 588 | 1233 | 12 |
| ARG | NH2 | B | 368 | 362 | 606 | 1242 | 12 |
| ARG | C | B | 368 | 410 | 581 | 1271 | 8 |
| ARG | O | B | 368 | 412 | 593 | 1268 | 7 |
| PRO | N | B | 369 | 418 | 571 | 1267 | 9 |
| PRO | CD | B | 369 | 418 | 557 | 1270 | 9 |
| PRO | CA | B | 369 | 429 | 574 | 1257 | 10 |
| PRO | CB | B | 369 | 436 | 561 | 1255 | 10 |
| PRO | CG | B | 369 | 433 | 553 | 1268 | 12 |
| PRO | C | B | 369 | 424 | 580 | 1244 | 10 |
| PRO | O | B | 369 | 415 | 575 | 1238 | 10 |
| VAL | N | B | 370 | 431 | 591 | 1240 | 11 |
| VAL | CA | B | 370 | 427 | 598 | 1228 | 12 |
| VAL | CB | B | 370 | 418 | 610 | 1230 | 11 |
| VAL | CG1 | B | 370 | 405 | 606 | 1237 | 11 |
| VAL | CG2 | B | 370 | 425 | 621 | 1238 | 16 |
| VAL | C | B | 370 | 439 | 602 | 1220 | 15 |
| VAL | O | B | 370 | 450 | 605 | 1227 | 17 |
| GLU | N | B | 371 | 439 | 604 | 1207 | 17 |
| GLU | CA | B | 371 | 450 | 608 | 1199 | 24 |
| GLU | CB | B | 371 | 449 | 603 | 1185 | 27 |
| GLU | CG | B | 371 | 461 | 605 | 1176 | 30 |
| GLU | CD | B | 371 | 474 | 600 | 1183 | 33 |
| GLU | OE1 | B | 371 | 479 | 607 | 1192 | 31 |
| GLU | OE2 | B | 371 | 478 | 589 | 1180 | 33 |
| GLU | C | B | 371 | 452 | 623 | 1200 | 27 |
| GLU | O | B | 371 | 443 | 630 | 1201 | 27 |
| ASP | N | B | 372 | 465 | 627 | 1199 | 31 |
| ASP | CA | B | 372 | 469 | 641 | 1199 | 37 |
| ASP | CB | B | 372 | 484 | 642 | 1202 | 39 |
| ASP | CG | B | 372 | 488 | 655 | 1208 | 43 |
| ASP | OD1 | B | 372 | 484 | 666 | 1203 | 46 |
| ASP | OD2 | B | 372 | 495 | 655 | 1218 | 45 |
| ASP | C | B | 372 | 466 | 646 | 1185 | 38 |
| ASP | O | B | 372 | 465 | 639 | 1176 | 37 |
| VAL | N | B | 373 | 464 | 660 | 1185 | 41 |
| VAL | CA | B | 373 | 461 | 666 | 1172 | 42 |
| VAL | CB | B | 373 | 458 | 681 | 1174 | 44 |
| VAL | CG1 | B | 373 | 454 | 687 | 1160 | 44 |
| VAL | CG2 | B | 373 | 446 | 683 | 1184 | 45 |
| VAL | C | B | 373 | 473 | 665 | 1162 | 42 |
| VAL | O | B | 373 | 472 | 665 | 1150 | 42 |
| ALA | N | B | 374 | 485 | 664 | 1168 | 40 |
| ALA | CA | B | 374 | 497 | 662 | 1161 | 39 |
| ALA | CB | B | 374 | 508 | 670 | 1167 | 38 |
| ALA | C | B | 374 | 502 | 648 | 1160 | 39 |
| ALA | O | B | 374 | 512 | 644 | 1154 | 38 |
| THR | N | B | 375 | 494 | 639 | 1166 | 38 |
| THR | CA | B | 375 | 497 | 625 | 1167 | 38 |
| THR | CB | B | 375 | 496 | 619 | 1152 | 40 |
| THR | OG1 | B | 375 | 484 | 623 | 1146 | 42 |
| THR | CG2 | B | 375 | 496 | 603 | 1153 | 40 |
| THR | C | B | 375 | 511 | 622 | 1172 | 37 |
| THR | O | B | 375 | 518 | 613 | 1168 | 37 |
| SER | N | B | 376 | 515 | 631 | 1182 | 33 |
| SER | CA | B | 376 | 528 | 630 | 1188 | 29 |
| SER | CB | B | 376 | 530 | 642 | 1197 | 28 |
| SER | OG | B | 376 | 521 | 641 | 1208 | 26 |
| SER | C | B | 376 | 529 | 617 | 1196 | 25 |
| SER | O | B | 376 | 520 | 609 | 1196 | 26 |
| GLN | N | B | 377 | 540 | 615 | 1203 | 20 |
| GLN | CA | B | 377 | 542 | 603 | 1211 | 19 |
| GLN | CB | B | 377 | 557 | 599 | 1211 | 22 |
| GLN | CG | B | 377 | 563 | 599 | 1197 | 25 |
| GLN | CD | B | 377 | 577 | 593 | 1198 | 25 |
| GLN | OE1 | B | 377 | 585 | 595 | 1207 | 26 |
| GLN | NE2 | B | 377 | 580 | 584 | 1188 | 27 |
| GLN | C | B | 377 | 537 | 605 | 1225 | 17 |
| GLN | O | B | 377 | 539 | 596 | 1234 | 14 |
| ASP | N | B | 378 | 531 | 617 | 1227 | 13 |
| ASP | CA | B | 378 | 526 | 620 | 1241 | 14 |
| ASP | CB | B | 378 | 520 | 634 | 1241 | 13 |
| ASP | CG | B | 378 | 531 | 644 | 1243 | 16 |
| ASP | OD1 | B | 378 | 543 | 641 | 1242 | 16 |
| ASP | OD2 | B | 378 | 527 | 656 | 1244 | 18 |
| ASP | C | B | 378 | 514 | 610 | 1243 | 10 |
| ASP | O | B | 378 | 508 | 605 | 1234 | 11 |
| ASP | N | B | 379 | 512 | 607 | 1256 | 10 |
| ASP | CA | B | 379 | 501 | 599 | 1260 | 10 |
| ASP | CB | B | 379 | 505 | 590 | 1272 | 10 |
| ASP | CG | B | 379 | 513 | 578 | 1267 | 12 |
| ASP | OD1 | B | 379 | 521 | 572 | 1275 | 10 |
| ASP | OD2 | B | 379 | 512 | 574 | 1255 | 12 |
| ASP | C | B | 379 | 490 | 609 | 1265 | 9 |
| ASP | O | B | 379 | 492 | 616 | 1275 | 10 |
| CYS | N | B | 380 | 479 | 609 | 1257 | 9 |
| CYS | CA | B | 380 | 468 | 619 | 1261 | 9 |
| CYS | C | B | 380 | 455 | 612 | 1264 | 9 |
| CYS | O | B | 380 | 452 | 601 | 1260 | 9 |
| CYS | CB | B | 380 | 466 | 628 | 1249 | 10 |
| CYS | SG | B | 380 | 481 | 635 | 1241 | 12 |
| TYR | N | B | 381 | 447 | 619 | 1272 | 7 |
| TYR | CA | B | 381 | 434 | 614 | 1276 | 9 |
| TYR | CB | B | 381 | 435 | 606 | 1289 | 11 |
| TYR | CG | B | 381 | 447 | 597 | 1290 | 11 |
| TYR | CD1 | B | 381 | 459 | 603 | 1293 | 12 |
| TYR | CE1 | B | 381 | 471 | 595 | 1295 | 12 |
| TYR | CD2 | B | 381 | 446 | 584 | 1289 | 9 |
| TYR | CE2 | B | 381 | 457 | 576 | 1290 | 11 |
| TYR | CZ | B | 381 | 470 | 581 | 1293 | 11 |
| TYR | OH | B | 381 | 481 | 573 | 1295 | 12 |
| TYR | C | B | 381 | 423 | 625 | 1278 | 9 |
| TYR | O | B | 381 | 426 | 636 | 1279 | 10 |
| LYS | N | B | 382 | 411 | 620 | 1279 | 9 |
| LYS | CA | B | 382 | 400 | 629 | 1281 | 9 |
| LYS | CB | B | 382 | 389 | 629 | 1270 | 10 |
| LYS | CG | B | 382 | 393 | 638 | 1258 | 12 |
| LYS | CD | B | 382 | 381 | 639 | 1249 | 13 |
| LYS | CE | B | 382 | 385 | 649 | 1237 | 15 |
| LYS | NZ | B | 382 | 374 | 650 | 1227 | 17 |
| LYS | C | B | 382 | 393 | 623 | 1294 | 9 |
| LYS | O | B | 382 | 394 | 611 | 1297 | 9 |
| PHE | N | B | 383 | 387 | 632 | 1302 | 7 |
| PHE | CA | B | 383 | 381 | 628 | 1315 | 7 |
| PHE | CB | B | 383 | 378 | 641 | 1323 | 8 |
| PHE | CG | B | 383 | 372 | 638 | 1337 | 8 |
| PHE | CD1 | B | 383 | 379 | 630 | 1346 | 8 |
| PHE | CD2 | B | 383 | 361 | 645 | 1340 | 8 |
| PHE | CE1 | B | 383 | 373 | 628 | 1359 | 9 |
| PHE | CE2 | B | 383 | 355 | 643 | 1353 | 8 |
| PHE | CZ | B | 383 | 362 | 635 | 1362 | 7 |
| PHE | C | B | 383 | 368 | 622 | 1310 | 8 |
| PHE | O | B | 383 | 359 | 629 | 1304 | 10 |
| ALA | N | B | 384 | 366 | 609 | 1313 | 7 |
| ALA | CA | B | 384 | 354 | 602 | 1308 | 6 |
| ALA | CB | B | 384 | 358 | 588 | 1303 | 8 |
| ALA | C | B | 384 | 343 | 600 | 1318 | 7 |
| ALA | O | B | 384 | 336 | 590 | 1319 | 9 |
| ILE | N | B | 385 | 341 | 611 | 1326 | 7 |
| ILE | CA | B | 385 | 330 | 611 | 1336 | 7 |
| ILE | CB | B | 385 | 336 | 612 | 1351 | 6 |
| ILE | CG2 | B | 385 | 324 | 613 | 1361 | 8 |

TABLE 2-continued

Structure Coordinates for BACE complexed to Inhibitor

| | | | | | | | |
|---|---|---|---|---|---|---|---|
| ILE | CG1 | B | 385 | 344 | 600 | 1354 | 6 |
| ILE | CD1 | B | 385 | 349 | 599 | 1368 | 7 |
| ILE | C | B | 385 | 323 | 624 | 1333 | 7 |
| ILE | O | B | 385 | 329 | 635 | 1332 | 7 |
| SER | N | B | 386 | 310 | 624 | 1331 | 7 |
| SER | CA | B | 386 | 302 | 635 | 1327 | 8 |
| SER | CB | B | 386 | 300 | 636 | 1312 | 10 |
| SER | OG | B | 386 | 294 | 625 | 1307 | 11 |
| SER | C | B | 386 | 289 | 636 | 1334 | 8 |
| SER | O | B | 386 | 284 | 626 | 1340 | 9 |
| GLN | N | B | 387 | 283 | 648 | 1334 | 10 |
| GLN | CA | B | 387 | 270 | 651 | 1340 | 11 |
| GLN | CB | B | 387 | 268 | 666 | 1341 | 14 |
| GLN | CG | B | 387 | 256 | 670 | 1349 | 20 |
| GLN | CD | B | 387 | 255 | 685 | 1349 | 21 |
| GLN | OE1 | B | 387 | 265 | 693 | 1350 | 24 |
| GLN | NE2 | B | 387 | 243 | 690 | 1347 | 23 |
| GLN | C | B | 387 | 258 | 644 | 1332 | 11 |
| GLN | O | B | 387 | 259 | 643 | 1320 | 14 |
| SER | N | B | 388 | 248 | 640 | 1339 | 9 |
| SER | CA | B | 388 | 236 | 634 | 1334 | 12 |
| SER | CB | B | 388 | 236 | 619 | 1336 | 10 |
| SER | OG | B | 388 | 224 | 613 | 1333 | 9 |
| SER | C | B | 388 | 223 | 640 | 1339 | 13 |
| SER | O | B | 388 | 223 | 645 | 1351 | 10 |
| SER | N | B | 389 | 213 | 640 | 1332 | 13 |
| SER | CA | B | 389 | 200 | 645 | 1336 | 14 |
| SER | CB | B | 389 | 195 | 656 | 1327 | 16 |
| SER | OG | B | 389 | 193 | 652 | 1314 | 16 |
| SER | C | B | 389 | 190 | 634 | 1336 | 13 |
| SER | O | B | 389 | 178 | 636 | 1339 | 12 |
| THR | N | B | 390 | 194 | 622 | 1333 | 11 |
| THR | CA | B | 390 | 186 | 610 | 1333 | 11 |
| THR | CB | B | 390 | 184 | 605 | 1318 | 14 |
| THR | OG1 | B | 390 | 196 | 603 | 1312 | 12 |
| THR | CG2 | B | 390 | 196 | 615 | 1310 | 16 |
| THR | C | B | 390 | 191 | 598 | 1341 | 10 |
| THR | O | B | 390 | 190 | 587 | 1338 | 11 |
| GLY | N | B | 391 | 198 | 602 | 1352 | 8 |
| GLY | CA | B | 391 | 204 | 592 | 1361 | 9 |
| GLY | C | B | 391 | 218 | 588 | 1358 | 8 |
| GLY | O | B | 391 | 225 | 593 | 1350 | 10 |
| THR | N | B | 392 | 223 | 578 | 1366 | 7 |
| THR | CA | B | 392 | 236 | 573 | 1365 | 6 |
| THR | CB | B | 392 | 241 | 566 | 1378 | 9 |
| THR | OG1 | B | 392 | 242 | 575 | 1389 | 9 |
| THR | CG2 | B | 392 | 254 | 559 | 1376 | 8 |
| THR | C | B | 392 | 237 | 563 | 1354 | 6 |
| THR | O | B | 392 | 228 | 555 | 1351 | 8 |
| VAL | N | B | 393 | 248 | 564 | 1346 | 7 |
| VAL | CA | B | 393 | 250 | 555 | 1335 | 7 |
| VAL | CB | B | 393 | 249 | 561 | 1321 | 9 |
| VAL | CG1 | B | 393 | 251 | 551 | 1310 | 9 |
| VAL | CG2 | B | 393 | 236 | 569 | 1320 | 9 |
| VAL | C | B | 393 | 264 | 548 | 1337 | 8 |
| VAL | O | B | 393 | 274 | 555 | 1336 | 8 |
| MET | N | B | 394 | 264 | 535 | 1340 | 8 |
| MET | CA | B | 394 | 277 | 528 | 1341 | 8 |
| MET | CB | B | 394 | 275 | 517 | 1351 | 10 |
| MET | CG | B | 394 | 272 | 521 | 1365 | 13 |
| MET | SD | B | 394 | 267 | 508 | 1376 | 19 |
| MET | CE | B | 394 | 282 | 499 | 1377 | 17 |
| MET | C | B | 394 | 280 | 524 | 1327 | 8 |
| MET | O | B | 394 | 276 | 513 | 1323 | 10 |
| GLY | N | B | 395 | 287 | 532 | 1320 | 7 |
| GLY | CA | B | 395 | 291 | 529 | 1306 | 9 |
| GLY | C | B | 395 | 303 | 522 | 1304 | 9 |
| GLY | O | B | 395 | 308 | 515 | 1313 | 9 |
| ALA | N | B | 396 | 309 | 522 | 1292 | 9 |
| ALA | CA | B | 396 | 321 | 515 | 1289 | 15 |
| ALA | CB | B | 396 | 326 | 519 | 1275 | 16 |
| ALA | C | B | 396 | 332 | 518 | 1299 | 17 |
| ALA | O | B | 396 | 340 | 509 | 1302 | 18 |
| VAL | N | B | 397 | 333 | 530 | 1304 | 19 |
| VAL | CA | B | 397 | 343 | 534 | 1314 | 22 |
| VAL | CB | B | 397 | 341 | 548 | 1320 | 23 |
| VAL | CG1 | B | 397 | 349 | 550 | 1333 | 22 |
| VAL | CG2 | B | 397 | 344 | 558 | 1310 | 22 |
| VAL | C | B | 397 | 343 | 524 | 1325 | 20 |
| VAL | O | B | 397 | 354 | 518 | 1329 | 24 |
| ILE | N | B | 398 | 331 | 521 | 1330 | 16 |
| ILE | CA | B | 398 | 330 | 512 | 1341 | 15 |
| ILE | CB | B | 398 | 316 | 513 | 1348 | 18 |
| ILE | CG2 | B | 398 | 313 | 501 | 1357 | 18 |
| ILE | CG1 | B | 398 | 314 | 526 | 1355 | 22 |
| ILE | CD1 | B | 398 | 323 | 528 | 1367 | 25 |
| ILE | C | B | 398 | 331 | 497 | 1337 | 12 |
| ILE | O | B | 398 | 339 | 490 | 1342 | 11 |
| MET | N | B | 399 | 324 | 494 | 1326 | 9 |
| MET | CA | B | 399 | 325 | 480 | 1321 | 8 |
| MET | CB | B | 399 | 315 | 479 | 1309 | 8 |
| MET | CG | B | 399 | 300 | 481 | 1314 | 8 |
| MET | SD | B | 399 | 288 | 478 | 1301 | 9 |
| MET | CE | B | 399 | 289 | 460 | 1300 | 10 |
| MET | C | B | 399 | 339 | 475 | 1316 | 9 |
| MET | O | B | 399 | 341 | 463 | 1317 | 9 |
| GLU | N | B | 400 | 348 | 484 | 1312 | 8 |
| GLU | CA | B | 400 | 361 | 480 | 1308 | 7 |
| GLU | CB | B | 400 | 368 | 491 | 1301 | 8 |
| GLU | CG | B | 400 | 364 | 493 | 1286 | 7 |
| GLU | CD | B | 400 | 371 | 505 | 1278 | 11 |
| GLU | OE1 | B | 400 | 368 | 507 | 1267 | 10 |
| GLU | OE2 | B | 400 | 379 | 512 | 1286 | 8 |
| GLU | C | B | 400 | 369 | 474 | 1319 | 7 |
| GLU | O | B | 400 | 379 | 467 | 1317 | 8 |
| GLY | N | B | 401 | 365 | 477 | 1332 | 8 |
| GLY | CA | B | 401 | 372 | 472 | 1343 | 9 |
| GLY | C | B | 401 | 367 | 458 | 1348 | 9 |
| GLY | O | B | 401 | 374 | 452 | 1356 | 9 |
| PHE | N | B | 402 | 355 | 454 | 1343 | 8 |
| PHE | CA | B | 402 | 349 | 442 | 1348 | 8 |
| PHE | CB | B | 402 | 339 | 444 | 1358 | 10 |
| PHE | CG | B | 402 | 343 | 455 | 1368 | 10 |
| PHE | CD1 | B | 402 | 340 | 468 | 1366 | 10 |
| PHE | CD2 | B | 402 | 350 | 452 | 1379 | 9 |
| PHE | CE1 | B | 402 | 344 | 478 | 1374 | 9 |
| PHE | CE2 | B | 402 | 355 | 462 | 1388 | 8 |
| PHE | CZ | B | 402 | 351 | 475 | 1386 | 10 |
| PHE | C | B | 402 | 343 | 433 | 1337 | 10 |
| PHE | O | B | 402 | 340 | 437 | 1326 | 9 |
| TYR | N | B | 403 | 341 | 420 | 1341 | 9 |
| TYR | CA | B | 403 | 334 | 410 | 1333 | 9 |
| TYR | CB | B | 403 | 339 | 396 | 1335 | 9 |
| TYR | CG | B | 403 | 332 | 386 | 1327 | 9 |
| TYR | CD1 | B | 403 | 329 | 388 | 1314 | 9 |
| TYR | CE1 | B | 403 | 323 | 378 | 1306 | 9 |
| TYR | CD2 | B | 403 | 330 | 373 | 1333 | 11 |
| TYR | CE2 | B | 403 | 324 | 363 | 1325 | 11 |
| TYR | CZ | B | 403 | 321 | 365 | 1312 | 10 |
| TYR | OH | B | 403 | 316 | 355 | 1304 | 10 |
| TYR | C | B | 403 | 320 | 412 | 1339 | 10 |
| TYR | O | B | 403 | 318 | 410 | 1351 | 10 |
| VAL | N | B | 404 | 310 | 416 | 1330 | 6 |
| VAL | CA | B | 404 | 297 | 418 | 1335 | 9 |
| VAL | CB | B | 404 | 292 | 432 | 1330 | 7 |
| VAL | CG1 | B | 404 | 279 | 435 | 1337 | 8 |
| VAL | CG2 | B | 404 | 303 | 442 | 1335 | 8 |
| VAL | C | B | 404 | 287 | 407 | 1330 | 9 |
| VAL | O | B | 404 | 286 | 405 | 1318 | 9 |
| VAL | N | B | 405 | 280 | 401 | 1339 | 8 |
| VAL | CA | B | 405 | 271 | 391 | 1336 | 9 |
| VAL | CB | B | 405 | 272 | 379 | 1345 | 9 |
| VAL | CG1 | B | 405 | 262 | 368 | 1341 | 8 |
| VAL | CG2 | B | 405 | 287 | 374 | 1345 | 8 |
| VAL | C | B | 405 | 256 | 396 | 1337 | 9 |
| VAL | O | B | 405 | 252 | 399 | 1348 | 10 |
| PHE | N | B | 406 | 249 | 396 | 1326 | 7 |
| PHE | CA | B | 406 | 235 | 400 | 1325 | 10 |
| PHE | CB | B | 406 | 233 | 407 | 1312 | 7 |
| PHE | CG | B | 406 | 240 | 420 | 1311 | 8 |
| PHE | CD1 | B | 406 | 234 | 432 | 1314 | 9 |
| PHE | CD2 | B | 406 | 254 | 420 | 1307 | 8 |
| PHE | CE1 | B | 406 | 241 | 444 | 1313 | 7 |
| PHE | CE2 | B | 406 | 261 | 432 | 1306 | 8 |

TABLE 2-continued

Structure Coordinates for BACE complexed to Inhibitor

| | | | | | | | |
|---|---|---|---|---|---|---|---|
| PHE | CZ | B | 406 | 254 | 445 | 1309 | 8 |
| PHE | C | B | 406 | 227 | 387 | 1327 | 9 |
| PHE | O | B | 406 | 223 | 381 | 1317 | 8 |
| ASP | N | B | 407 | 225 | 383 | 1339 | 11 |
| ASP | CA | B | 407 | 217 | 371 | 1342 | 11 |
| ASP | CB | B | 407 | 222 | 366 | 1356 | 11 |
| ASP | CG | B | 407 | 216 | 352 | 1359 | 14 |
| ASP | OD1 | B | 407 | 207 | 348 | 1353 | 14 |
| ASP | OD2 | B | 407 | 222 | 346 | 1369 | 12 |
| ASP | C | B | 407 | 202 | 375 | 1343 | 10 |
| ASP | O | B | 407 | 196 | 377 | 1353 | 10 |
| ARG | N | B | 408 | 196 | 375 | 1331 | 10 |
| ARG | CA | B | 408 | 182 | 378 | 1330 | 10 |
| ARG | CB | B | 408 | 178 | 379 | 1315 | 9 |
| ARG | CG | B | 408 | 185 | 390 | 1307 | 12 |
| ARG | CD | B | 408 | 186 | 387 | 1292 | 10 |
| ARG | NE | B | 408 | 173 | 385 | 1286 | 11 |
| ARG | CZ | B | 408 | 166 | 394 | 1280 | 11 |
| ARG | NH1 | B | 408 | 171 | 406 | 1278 | 9 |
| ARG | NH2 | B | 408 | 154 | 391 | 1274 | 12 |
| ARG | C | B | 408 | 174 | 367 | 1336 | 12 |
| ARG | O | B | 408 | 164 | 370 | 1343 | 12 |
| ALA | N | B | 409 | 178 | 355 | 1335 | 13 |
| ALA | CA | B | 409 | 171 | 344 | 1341 | 13 |
| ALA | CB | B | 409 | 178 | 330 | 1338 | 13 |
| ALA | C | B | 409 | 169 | 345 | 1356 | 15 |
| ALA | O | B | 409 | 158 | 342 | 1362 | 16 |
| ARG | N | B | 410 | 179 | 351 | 1363 | 15 |
| ARG | CA | B | 410 | 178 | 352 | 1377 | 15 |
| ARG | CB | B | 410 | 190 | 346 | 1384 | 16 |
| ARG | CG | B | 410 | 191 | 331 | 1381 | 20 |
| ARG | CD | B | 410 | 203 | 324 | 1387 | 22 |
| ARG | NE | B | 410 | 203 | 324 | 1401 | 26 |
| ARG | CZ | B | 410 | 212 | 316 | 1408 | 28 |
| ARG | NH1 | B | 410 | 221 | 308 | 1402 | 28 |
| ARG | NH2 | B | 410 | 211 | 317 | 1422 | 29 |
| ARG | C | B | 410 | 177 | 367 | 1381 | 15 |
| ARG | O | B | 410 | 179 | 371 | 1393 | 15 |
| LYS | N | B | 411 | 173 | 376 | 1372 | 13 |
| LYS | CA | B | 411 | 171 | 390 | 1374 | 11 |
| LYS | CB | B | 411 | 158 | 392 | 1381 | 14 |
| LYS | CG | B | 411 | 152 | 406 | 1381 | 18 |
| LYS | CD | B | 411 | 138 | 406 | 1386 | 22 |
| LYS | CE | B | 411 | 132 | 420 | 1386 | 22 |
| LYS | NZ | B | 411 | 118 | 420 | 1391 | 25 |
| LYS | C | B | 411 | 182 | 396 | 1383 | 11 |
| LYS | O | B | 411 | 180 | 403 | 1393 | 11 |
| ARG | N | B | 412 | 195 | 395 | 1378 | 10 |
| ARG | CA | B | 412 | 206 | 400 | 1385 | 10 |
| ARG | CB | B | 412 | 211 | 390 | 1396 | 10 |
| ARG | CG | B | 412 | 216 | 377 | 1390 | 9 |
| ARG | CD | B | 412 | 219 | 367 | 1401 | 12 |
| ARG | NE | B | 412 | 225 | 355 | 1396 | 13 |
| ARG | CZ | B | 412 | 231 | 345 | 1403 | 15 |
| ARG | NH1 | B | 412 | 231 | 346 | 1416 | 15 |
| ARG | NH2 | B | 412 | 236 | 335 | 1397 | 17 |
| ARG | C | B | 412 | 218 | 403 | 1376 | 10 |
| ARG | O | B | 412 | 218 | 398 | 1365 | 10 |
| ILE | N | B | 413 | 227 | 412 | 1380 | 10 |
| ILE | CA | B | 413 | 238 | 415 | 1372 | 10 |
| ILE | CB | B | 413 | 238 | 430 | 1368 | 11 |
| ILE | CG2 | B | 413 | 251 | 433 | 1360 | 10 |
| ILE | CG1 | B | 413 | 226 | 433 | 1359 | 14 |
| ILE | CD1 | B | 413 | 225 | 447 | 1355 | 17 |
| ILE | C | B | 413 | 251 | 412 | 1380 | 10 |
| ILE | O | B | 413 | 252 | 417 | 1392 | 11 |
| GLY | N | B | 414 | 260 | 404 | 1375 | 9 |
| GLY | CA | B | 414 | 272 | 401 | 1382 | 10 |
| GLY | C | B | 414 | 284 | 409 | 1377 | 9 |
| GLY | O | B | 414 | 285 | 412 | 1365 | 8 |
| PHE | N | B | 415 | 293 | 411 | 1386 | 7 |
| PHE | CA | B | 415 | 306 | 418 | 1383 | 7 |
| PHE | CB | B | 415 | 306 | 432 | 1390 | 7 |
| PHE | CG | B | 415 | 296 | 442 | 1384 | 6 |
| PHE | CD1 | B | 415 | 283 | 441 | 1388 | 8 |
| PHE | CD2 | B | 415 | 300 | 452 | 1375 | 10 |
| PHE | CE1 | B | 415 | 273 | 450 | 1383 | 9 |
| PHE | CE2 | B | 415 | 291 | 461 | 1370 | 10 |
| PHE | CZ | B | 415 | 277 | 460 | 1374 | 9 |
| PHE | C | B | 415 | 318 | 411 | 1389 | 9 |
| PHE | O | B | 415 | 317 | 405 | 1400 | 10 |
| ALA | N | B | 416 | 328 | 410 | 1381 | 9 |
| ALA | CA | B | 416 | 341 | 404 | 1385 | 11 |
| ALA | CB | B | 416 | 341 | 389 | 1380 | 9 |
| ALA | C | B | 416 | 352 | 411 | 1378 | 10 |
| ALA | O | B | 416 | 350 | 417 | 1367 | 8 |
| VAL | N | B | 417 | 364 | 412 | 1384 | 9 |
| VAL | CA | B | 417 | 375 | 419 | 1379 | 9 |
| VAL | CB | B | 417 | 387 | 417 | 1388 | 9 |
| VAL | CG1 | B | 417 | 399 | 425 | 1381 | 12 |
| VAL | CG2 | B | 417 | 385 | 423 | 1402 | 10 |
| VAL | C | B | 417 | 378 | 413 | 1365 | 9 |
| VAL | O | B | 417 | 380 | 401 | 1363 | 9 |
| SER | N | B | 418 | 379 | 422 | 1355 | 7 |
| SER | CA | B | 418 | 381 | 418 | 1341 | 9 |
| SER | CB | B | 418 | 378 | 428 | 1331 | 9 |
| SER | OG | B | 418 | 381 | 424 | 1318 | 10 |
| SER | C | B | 418 | 396 | 413 | 1339 | 11 |
| SER | O | B | 418 | 405 | 420 | 1343 | 9 |
| ALA | N | B | 419 | 397 | 403 | 1331 | 8 |
| ALA | CA | B | 419 | 411 | 398 | 1328 | 9 |
| ALA | CB | B | 419 | 410 | 384 | 1322 | 11 |
| ALA | C | B | 419 | 418 | 407 | 1318 | 10 |
| ALA | O | B | 419 | 429 | 406 | 1316 | 11 |
| CYS | N | B | 420 | 410 | 417 | 1312 | 10 |
| CYS | CA | B | 420 | 416 | 426 | 1303 | 11 |
| CYS | C | B | 420 | 415 | 441 | 1307 | 11 |
| CYS | O | B | 420 | 416 | 450 | 1299 | 11 |
| CYS | CB | B | 420 | 410 | 424 | 1289 | 11 |
| CYS | SG | B | 420 | 392 | 430 | 1288 | 10 |
| HIS | N | B | 421 | 413 | 443 | 1320 | 10 |
| HIS | CA | B | 421 | 413 | 457 | 1325 | 9 |
| HIS | CB | B | 421 | 405 | 459 | 1338 | 10 |
| HIS | CG | B | 421 | 414 | 456 | 1350 | 10 |
| HIS | CD2 | B | 421 | 420 | 465 | 1359 | 10 |
| HIS | ND1 | B | 421 | 417 | 444 | 1355 | 10 |
| HIS | CE1 | B | 421 | 424 | 445 | 1366 | 12 |
| HIS | NE2 | B | 421 | 426 | 458 | 1368 | 10 |
| HIS | C | B | 421 | 427 | 463 | 1326 | 8 |
| HIS | O | B | 421 | 436 | 456 | 1329 | 10 |
| VAL | N | B | 422 | 428 | 475 | 1322 | 8 |
| VAL | CA | B | 422 | 441 | 482 | 1323 | 8 |
| VAL | CB | B | 422 | 441 | 494 | 1313 | 8 |
| VAL | CG1 | B | 422 | 455 | 501 | 1313 | 7 |
| VAL | CG2 | B | 422 | 438 | 490 | 1299 | 8 |
| VAL | C | B | 422 | 444 | 487 | 1337 | 9 |
| VAL | O | B | 422 | 436 | 492 | 1344 | 8 |
| HIS | N | B | 423 | 457 | 485 | 1341 | 8 |
| HIS | CA | B | 423 | 461 | 489 | 1354 | 9 |
| HIS | CB | B | 423 | 457 | 479 | 1365 | 9 |
| HIS | CG | B | 423 | 464 | 466 | 1363 | 12 |
| HIS | CD2 | B | 423 | 475 | 460 | 1368 | 12 |
| HIS | ND1 | B | 423 | 459 | 456 | 1355 | 14 |
| HIS | CE1 | B | 423 | 467 | 445 | 1355 | 16 |
| HIS | NE2 | B | 423 | 477 | 448 | 1363 | 19 |
| HIS | C | B | 423 | 476 | 491 | 1354 | 9 |
| HIS | O | B | 423 | 482 | 491 | 1344 | 12 |
| ASP | N | B | 424 | 482 | 493 | 1366 | 8 |
| ASP | CA | B | 424 | 496 | 495 | 1367 | 10 |
| ASP | CB | B | 424 | 500 | 510 | 1371 | 9 |
| ASP | CG | B | 424 | 492 | 515 | 1383 | 10 |
| ASP | OD1 | B | 424 | 491 | 508 | 1393 | 10 |
| ASP | OD2 | B | 424 | 488 | 527 | 1382 | 10 |
| ASP | C | B | 424 | 501 | 485 | 1378 | 9 |
| ASP | O | B | 424 | 494 | 477 | 1383 | 8 |
| GLU | N | B | 425 | 514 | 486 | 1381 | 10 |
| GLU | CA | B | 425 | 520 | 477 | 1391 | 13 |
| GLU | CB | B | 425 | 535 | 477 | 1390 | 18 |
| GLU | CG | B | 425 | 541 | 491 | 1394 | 22 |
| GLU | CD | B | 425 | 544 | 500 | 1382 | 28 |
| GLU | OE1 | B | 425 | 534 | 502 | 1375 | 25 |
| GLU | OE2 | B | 425 | 555 | 504 | 1381 | 29 |
| GLU | C | B | 425 | 515 | 480 | 1406 | 13 |
| GLU | O | B | 425 | 517 | 471 | 1414 | 11 |

TABLE 2-continued

Structure Coordinates for BACE complexed to Inhibitor

| | | | | | | | |
|---|---|---|---|---|---|---|---|
| PHE | N | B | 426 | 509 | 491 | 1408 | 9 |
| PHE | CA | B | 426 | 505 | 495 | 1421 | 9 |
| PHE | CB | B | 426 | 509 | 510 | 1424 | 9 |
| PHE | CG | B | 426 | 524 | 512 | 1422 | 12 |
| PHE | CD1 | B | 426 | 528 | 520 | 1411 | 12 |
| PHE | CD2 | B | 426 | 534 | 507 | 1431 | 11 |
| PHE | CE1 | B | 426 | 542 | 522 | 1409 | 12 |
| PHE | CE2 | B | 426 | 547 | 509 | 1429 | 10 |
| PHE | CZ | B | 426 | 551 | 517 | 1418 | 12 |
| PHE | C | B | 426 | 491 | 493 | 1425 | 9 |
| PHE | O | B | 426 | 488 | 491 | 1437 | 9 |
| ARG | N | B | 427 | 482 | 494 | 1415 | 7 |
| ARG | CA | B | 427 | 468 | 493 | 1418 | 9 |
| ARG | CB | B | 427 | 461 | 507 | 1419 | 8 |
| ARG | CG | B | 427 | 466 | 516 | 1430 | 10 |
| ARG | CD | B | 427 | 458 | 529 | 1431 | 9 |
| ARG | NE | B | 427 | 459 | 537 | 1419 | 8 |
| ARG | CZ | B | 427 | 456 | 550 | 1419 | 7 |
| ARG | NH1 | B | 427 | 453 | 557 | 1430 | 6 |
| ARG | NH2 | B | 427 | 457 | 557 | 1407 | 8 |
| ARG | C | B | 427 | 460 | 485 | 1407 | 8 |
| ARG | O | B | 427 | 465 | 484 | 1396 | 9 |
| THR | N | B | 428 | 449 | 479 | 1411 | 10 |
| THR | CA | B | 428 | 441 | 471 | 1402 | 9 |
| THR | CB | B | 428 | 444 | 456 | 1404 | 14 |
| THR | OG1 | B | 428 | 435 | 448 | 1396 | 18 |
| THR | CG2 | B | 428 | 441 | 452 | 1419 | 13 |
| THR | C | B | 428 | 426 | 473 | 1405 | 10 |
| THR | O | B | 428 | 423 | 478 | 1416 | 9 |
| ALA | N | B | 429 | 418 | 471 | 1395 | 8 |
| ALA | CA | B | 429 | 404 | 472 | 1397 | 7 |
| ALA | CB | B | 429 | 396 | 470 | 1384 | 8 |
| ALA | C | B | 429 | 400 | 461 | 1407 | 10 |
| ALA | O | B | 429 | 408 | 452 | 1409 | 9 |
| ALA | N | B | 430 | 388 | 462 | 1413 | 7 |
| ALA | CA | B | 430 | 384 | 452 | 1423 | 9 |
| ALA | CB | B | 430 | 391 | 455 | 1436 | 11 |
| ALA | C | B | 430 | 369 | 451 | 1424 | 8 |
| ALA | O | B | 430 | 362 | 460 | 1421 | 8 |
| VAL | N | B | 431 | 365 | 439 | 1429 | 9 |
| VAL | CA | B | 431 | 351 | 436 | 1432 | 8 |
| VAL | CB | B | 431 | 345 | 426 | 1422 | 9 |
| VAL | CG1 | B | 431 | 331 | 424 | 1425 | 9 |
| VAL | CG2 | B | 431 | 346 | 432 | 1408 | 9 |
| VAL | C | B | 431 | 353 | 430 | 1446 | 9 |
| VAL | O | B | 431 | 358 | 419 | 1447 | 10 |
| GLU | N | B | 432 | 348 | 436 | 1456 | 10 |
| GLU | CA | B | 432 | 349 | 431 | 1470 | 11 |
| GLU | CB | B | 432 | 360 | 439 | 1477 | 13 |
| GLU | CG | B | 432 | 373 | 439 | 1470 | 15 |
| GLU | CD | B | 432 | 383 | 449 | 1475 | 15 |
| GLU | OE1 | B | 432 | 395 | 446 | 1476 | 19 |
| GLU | OE2 | B | 432 | 379 | 461 | 1477 | 14 |
| GLU | C | B | 432 | 337 | 432 | 1478 | 10 |
| GLU | O | B | 432 | 328 | 440 | 1476 | 9 |
| GLY | N | B | 433 | 335 | 423 | 1488 | 11 |
| GLY | CA | B | 433 | 324 | 422 | 1496 | 12 |
| GLY | C | B | 433 | 324 | 411 | 1506 | 14 |
| GLY | O | B | 433 | 335 | 404 | 1506 | 13 |
| PRO | N | B | 434 | 315 | 410 | 1515 | 15 |
| PRO | CD | B | 434 | 313 | 397 | 1523 | 16 |
| PRO | CA | B | 434 | 303 | 418 | 1516 | 14 |
| PRO | CB | B | 434 | 293 | 408 | 1520 | 16 |
| PRO | CG | B | 434 | 300 | 400 | 1530 | 16 |
| PRO | C | B | 434 | 305 | 429 | 1527 | 16 |
| PRO | O | B | 434 | 314 | 429 | 1535 | 17 |
| PHE | N | B | 435 | 296 | 439 | 1526 | 12 |
| PHE | CA | B | 435 | 295 | 450 | 1536 | 14 |
| PHE | CB | B | 435 | 299 | 463 | 1529 | 12 |
| PHE | CG | B | 435 | 312 | 464 | 1523 | 11 |
| PHE | CD1 | B | 435 | 313 | 460 | 1510 | 12 |
| PHE | CD2 | B | 435 | 323 | 468 | 1530 | 14 |
| PHE | CE1 | B | 435 | 326 | 460 | 1503 | 13 |
| PHE | CE2 | B | 435 | 336 | 468 | 1523 | 13 |
| PHE | CZ | B | 435 | 337 | 464 | 1510 | 14 |
| PHE | C | B | 435 | 281 | 450 | 1541 | 14 |
| PHE | O | B | 435 | 272 | 447 | 1534 | 16 |
| VAL | N | B | 436 | 280 | 454 | 1554 | 18 |
| VAL | CA | B | 436 | 267 | 454 | 1560 | 21 |
| VAL | CB | B | 436 | 268 | 453 | 1576 | 24 |
| VAL | CG1 | B | 436 | 254 | 455 | 1582 | 22 |
| VAL | CG2 | B | 436 | 273 | 439 | 1579 | 21 |
| VAL | C | B | 436 | 261 | 468 | 1557 | 26 |
| VAL | O | B | 436 | 266 | 478 | 1563 | 27 |
| THR | N | B | 437 | 251 | 469 | 1549 | 27 |
| THR | CA | B | 437 | 244 | 481 | 1545 | 28 |
| THR | CB | B | 437 | 247 | 484 | 1530 | 29 |
| THR | OG1 | B | 437 | 261 | 483 | 1527 | 29 |
| THR | CG2 | B | 437 | 243 | 499 | 1527 | 30 |
| THR | C | B | 437 | 230 | 481 | 1548 | 28 |
| THR | O | B | 437 | 223 | 471 | 1543 | 27 |
| LEU | N | B | 438 | 224 | 490 | 1555 | 29 |
| LEU | CA | B | 438 | 210 | 490 | 1559 | 29 |
| LEU | CB | B | 438 | 209 | 495 | 1573 | 30 |
| LEU | CG | B | 438 | 216 | 487 | 1584 | 29 |
| LEU | CD1 | B | 438 | 214 | 494 | 1598 | 30 |
| LEU | CD2 | B | 438 | 212 | 473 | 1584 | 28 |
| LEU | C | B | 438 | 202 | 500 | 1550 | 29 |
| LEU | O | B | 438 | 207 | 509 | 1543 | 25 |
| ASP | N | B | 439 | 189 | 497 | 1550 | 29 |
| ASP | CA | B | 439 | 179 | 505 | 1542 | 32 |
| ASP | CB | B | 439 | 176 | 518 | 1550 | 34 |
| ASP | CG | B | 439 | 171 | 515 | 1564 | 36 |
| ASP | OD1 | B | 439 | 175 | 521 | 1574 | 38 |
| ASP | OD2 | B | 439 | 161 | 506 | 1565 | 39 |
| ASP | C | B | 439 | 184 | 509 | 1528 | 31 |
| ASP | O | B | 439 | 183 | 520 | 1524 | 31 |
| MET | N | B | 440 | 189 | 499 | 1521 | 31 |
| MET | CA | B | 440 | 193 | 501 | 1507 | 31 |
| MET | CB | B | 440 | 202 | 489 | 1502 | 29 |
| MET | CG | B | 440 | 214 | 487 | 1511 | 28 |
| MET | SD | B | 440 | 225 | 474 | 1504 | 25 |
| MET | CE | B | 440 | 217 | 459 | 1511 | 26 |
| MET | C | B | 440 | 182 | 504 | 1497 | 32 |
| MET | O | B | 440 | 184 | 510 | 1487 | 31 |
| GLU | N | B | 441 | 170 | 499 | 1501 | 34 |
| GLU | CA | B | 441 | 159 | 501 | 1492 | 35 |
| GLU | CB | B | 441 | 146 | 494 | 1497 | 39 |
| GLU | CG | B | 441 | 148 | 478 | 1497 | 45 |
| GLU | CD | B | 441 | 137 | 471 | 1503 | 49 |
| GLU | OE1 | B | 441 | 125 | 472 | 1498 | 51 |
| GLU | OE2 | B | 441 | 139 | 464 | 1513 | 51 |
| GLU | C | B | 441 | 155 | 516 | 1491 | 34 |
| GLU | O | B | 441 | 150 | 521 | 1481 | 33 |
| ASP | N | B | 442 | 159 | 523 | 1502 | 30 |
| ASP | CA | B | 442 | 156 | 538 | 1503 | 28 |
| ASP | CB | B | 442 | 159 | 543 | 1517 | 33 |
| ASP | CG | B | 442 | 149 | 538 | 1527 | 38 |
| ASP | OD1 | B | 442 | 137 | 541 | 1525 | 40 |
| ASP | OD2 | B | 442 | 153 | 531 | 1536 | 41 |
| ASP | C | B | 442 | 165 | 545 | 1493 | 24 |
| ASP | O | B | 442 | 163 | 557 | 1490 | 22 |
| CYS | N | B | 443 | 175 | 539 | 1487 | 18 |
| CYS | CA | B | 443 | 184 | 545 | 1478 | 17 |
| CYS | C | B | 443 | 178 | 545 | 1464 | 16 |
| CYS | O | B | 443 | 182 | 553 | 1455 | 17 |
| CYS | CB | B | 443 | 197 | 537 | 1477 | 16 |
| CYS | SG | B | 443 | 206 | 536 | 1493 | 19 |
| GLY | N | B | 444 | 167 | 537 | 1462 | 16 |
| GLY | CA | B | 444 | 160 | 536 | 1449 | 16 |
| GLY | C | B | 444 | 151 | 548 | 1448 | 18 |
| GLY | O | B | 444 | 145 | 553 | 1457 | 20 |
| TYR | N | B | 445 | 150 | 553 | 1436 | 19 |
| TYR | CA | B | 445 | 141 | 565 | 1433 | 20 |
| TYR | CB | B | 445 | 148 | 574 | 1423 | 21 |
| TYR | CG | B | 445 | 140 | 587 | 1420 | 24 |
| TYR | CD1 | B | 445 | 139 | 597 | 1429 | 25 |
| TYR | CE1 | B | 445 | 131 | 608 | 1427 | 25 |
| TYR | CD2 | B | 445 | 134 | 588 | 1407 | 22 |
| TYR | CE2 | B | 445 | 127 | 600 | 1404 | 24 |
| TYR | CZ | B | 445 | 125 | 610 | 1414 | 24 |
| TYR | OH | B | 445 | 118 | 621 | 1411 | 25 |
| TYR | C | B | 445 | 128 | 560 | 1427 | 20 |
| TYR | O | B | 445 | 128 | 551 | 1419 | 19 |

TABLE 2-continued

Structure Coordinates for BACE complexed to Inhibitor

| | | | | | | | |
|---|---|---|---|---|---|---|---|
| ASN | N | B | 446 | 117 | 567 | 1430 | 21 |
| ASN | CA | B | 446 | 104 | 563 | 1425 | 23 |
| ASN | CB | B | 446 | 95 | 559 | 1436 | 25 |
| ASN | CG | B | 446 | 100 | 547 | 1444 | 27 |
| ASN | OD1 | B | 446 | 103 | 536 | 1438 | 29 |
| ASN | ND2 | B | 446 | 102 | 548 | 1457 | 28 |
| ASN | C | B | 446 | 98 | 575 | 1418 | 25 |
| ASN | O | B | 446 | 96 | 585 | 1423 | 27 |
| SCH | N1 | S | 1 | 325 | 598 | 1209 | 12 |
| SCH | C1 | S | 1 | 317 | 594 | 1221 | 10 |
| SCH | C2 | S | 1 | 304 | 588 | 1218 | 9 |
| SCH | O1 | S | 1 | 298 | 593 | 1208 | 13 |
| SCH | C3 | S | 1 | 316 | 606 | 1231 | 14 |
| SCH | C4 | S | 1 | 309 | 602 | 1244 | 10 |
| SCH | C5 | S | 1 | 308 | 614 | 1254 | 11 |
| SCH | O2 | S | 1 | 316 | 624 | 1252 | 13 |
| SCH | O3 | S | 1 | 299 | 614 | 1262 | 10 |
| SCH | N2 | S | 1 | 299 | 579 | 1225 | 8 |
| SCH | C6 | S | 1 | 286 | 573 | 1222 | 8 |
| SCH | C7 | S | 1 | 277 | 574 | 1235 | 10 |
| SCH | O4 | S | 1 | 282 | 573 | 1246 | 9 |
| SCH | C8 | S | 1 | 286 | 558 | 1218 | 11 |
| SCH | C9 | S | 1 | 291 | 557 | 1204 | 12 |
| SCH | C10 | S | 1 | 295 | 550 | 1227 | 9 |
| SCH | N3 | S | 1 | 264 | 577 | 1233 | 9 |
| SCH | C11 | S | 1 | 255 | 578 | 1244 | 7 |
| SCH | C12 | S | 1 | 242 | 572 | 1239 | 8 |
| SCH | O5 | S | 1 | 232 | 579 | 1237 | 8 |
| SCH | C13 | S | 1 | 253 | 593 | 1248 | 10 |
| SCH | C14 | S | 1 | 265 | 598 | 1255 | 9 |
| SCH | O6 | S | 1 | 273 | 606 | 1250 | 12 |
| SCH | N4 | S | 1 | 266 | 594 | 1268 | 6 |
| SCH | C15 | S | 1 | 250 | 540 | 1201 | 11 |
| SCH | C16 | S | 1 | 233 | 558 | 1201 | 9 |
| SCH | C17 | S | 1 | 242 | 550 | 1209 | 8 |
| SCH | C18 | S | 1 | 235 | 542 | 1220 | 8 |
| SCH | N5 | S | 1 | 242 | 559 | 1237 | 7 |
| SCH | C19 | S | 1 | 230 | 552 | 1232 | 8 |
| SCH | C20 | S | 1 | 223 | 543 | 1243 | 7 |
| SCH | O7 | S | 1 | 232 | 533 | 1248 | 9 |
| SCH | C21 | S | 1 | 219 | 553 | 1254 | 8 |
| SCH | C22 | S | 1 | 206 | 548 | 1262 | 8 |
| SCH | C23 | S | 1 | 206 | 554 | 1276 | 9 |
| SCH | C24 | S | 1 | 194 | 553 | 1254 | 9 |
| SCH | O8 | S | 1 | 193 | 565 | 1250 | 7 |
| SCH | N6 | S | 1 | 184 | 544 | 1253 | 10 |
| SCH | C25 | S | 1 | 171 | 548 | 1246 | 11 |
| SCH | C26 | S | 1 | 164 | 558 | 1255 | 14 |
| SCH | O9 | S | 1 | 164 | 557 | 1268 | 15 |
| SCH | C27 | S | 1 | 163 | 536 | 1244 | 12 |
| SCH | N7 | S | 1 | 158 | 568 | 1249 | 14 |
| SCH | C28 | S | 1 | 151 | 578 | 1257 | 18 |
| SCH | C29 | S | 1 | 137 | 572 | 1261 | 21 |
| SCH | O10 | S | 1 | 132 | 564 | 1252 | 19 |
| SCH | C30 | S | 1 | 149 | 591 | 1250 | 20 |
| SCH | C31 | S | 1 | 161 | 599 | 1247 | 22 |
| SCH | C32 | S | 1 | 159 | 613 | 1245 | 25 |
| SCH | O11 | S | 1 | 168 | 621 | 1250 | 24 |
| SCH | O12 | S | 1 | 149 | 617 | 1239 | 24 |
| SCH | N8 | S | 1 | 132 | 574 | 1272 | 23 |
| SCH | C33 | S | 1 | 119 | 569 | 1276 | 28 |
| SCH | C34 | S | 1 | 111 | 578 | 1285 | 31 |
| SCH | O13 | S | 1 | 100 | 581 | 1282 | 34 |
| SCH | C35 | S | 1 | 121 | 555 | 1284 | 30 |
| SCH | C36 | S | 1 | 109 | 548 | 1288 | 33 |
| SCH | C37 | S | 1 | 101 | 541 | 1278 | 33 |
| SCH | C38 | S | 1 | 104 | 548 | 1301 | 34 |
| SCH | C39 | S | 1 | 90 | 534 | 1281 | 34 |
| SCH | C40 | S | 1 | 92 | 542 | 1304 | 35 |
| SCH | C41 | S | 1 | 85 | 535 | 1295 | 34 |
| SCH | O14 | S | 1 | 117 | 583 | 1295 | 34 |
| SCH | N1 | S | 2 | 325 | 155 | 209 | 10 |
| SCH | C1 | S | 2 | 318 | 151 | 221 | 9 |
| SCH | C2 | S | 2 | 304 | 146 | 217 | 9 |
| SCH | O1 | S | 2 | 298 | 150 | 207 | 13 |
| SCH | C3 | S | 2 | 316 | 163 | 231 | 12 |
| SCH | C4 | S | 2 | 310 | 159 | 245 | 11 |
| SCH | C5 | S | 2 | 309 | 171 | 254 | 10 |
| SCH | O2 | S | 2 | 316 | 181 | 252 | 13 |
| SCH | O3 | S | 2 | 300 | 171 | 262 | 9 |
| SCH | N2 | S | 2 | 299 | 136 | 225 | 10 |
| SCH | C6 | S | 2 | 286 | 131 | 222 | 10 |
| SCH | C7 | S | 2 | 277 | 132 | 235 | 8 |
| SCH | O4 | S | 2 | 282 | 130 | 246 | 8 |
| SCH | C8 | S | 2 | 286 | 116 | 218 | 11 |
| SCH | C9 | S | 2 | 291 | 114 | 204 | 12 |
| SCH | C10 | S | 2 | 295 | 108 | 227 | 9 |
| SCH | N3 | S | 2 | 264 | 134 | 233 | 9 |
| SCH | C11 | S | 2 | 255 | 135 | 244 | 9 |
| SCH | C12 | S | 2 | 242 | 129 | 238 | 6 |
| SCH | O5 | S | 2 | 232 | 136 | 236 | 7 |
| SCH | C13 | S | 2 | 253 | 150 | 247 | 8 |
| SCH | C14 | S | 2 | 265 | 156 | 255 | 7 |
| SCH | O6 | S | 2 | 273 | 163 | 250 | 10 |
| SCH | N4 | S | 2 | 266 | 152 | 268 | 5 |
| SCH | C15 | S | 2 | 250 | 97 | 201 | 11 |
| SCH | C16 | S | 2 | 233 | 115 | 201 | 7 |
| SCH | C17 | S | 2 | 243 | 107 | 209 | 7 |
| SCH | C18 | S | 2 | 235 | 100 | 220 | 7 |
| SCH | N5 | S | 2 | 242 | 116 | 237 | 8 |
| SCH | C19 | S | 2 | 230 | 109 | 231 | 7 |
| SCH | C20 | S | 2 | 223 | 101 | 242 | 7 |
| SCH | O7 | S | 2 | 232 | 91 | 248 | 8 |
| SCH | C21 | S | 2 | 219 | 110 | 254 | 8 |
| SCH | C22 | S | 2 | 206 | 106 | 261 | 9 |
| SCH | C23 | S | 2 | 207 | 112 | 275 | 9 |
| SCH | C24 | S | 2 | 194 | 111 | 254 | 10 |
| SCH | O8 | S | 2 | 193 | 122 | 250 | 8 |
| SCH | N6 | S | 2 | 184 | 102 | 253 | 10 |
| SCH | C25 | S | 2 | 172 | 106 | 246 | 12 |
| SCH | C26 | S | 2 | 165 | 116 | 255 | 14 |
| SCH | O9 | S | 2 | 165 | 115 | 267 | 14 |
| SCH | C27 | S | 2 | 163 | 94 | 244 | 13 |
| SCH | N7 | S | 2 | 158 | 126 | 249 | 14 |
| SCH | C28 | S | 2 | 151 | 136 | 257 | 20 |
| SCH | C29 | S | 2 | 137 | 129 | 259 | 23 |
| SCH | O10 | S | 2 | 132 | 122 | 251 | 24 |
| SCH | C30 | S | 2 | 149 | 149 | 249 | 22 |
| SCH | C31 | S | 2 | 162 | 156 | 247 | 24 |
| SCH | C32 | S | 2 | 160 | 171 | 244 | 27 |
| SCH | O11 | S | 2 | 168 | 179 | 250 | 27 |
| SCH | O12 | S | 2 | 150 | 175 | 238 | 27 |
| SCH | N8 | S | 2 | 132 | 132 | 271 | 27 |
| SCH | C33 | S | 2 | 119 | 126 | 275 | 31 |
| SCH | C34 | S | 2 | 110 | 137 | 281 | 35 |
| SCH | O13 | S | 2 | 113 | 142 | 292 | 37 |
| SCH | C35 | S | 2 | 120 | 115 | 284 | 33 |
| SCH | C36 | S | 2 | 108 | 107 | 286 | 33 |
| SCH | C37 | S | 2 | 101 | 101 | 275 | 33 |
| SCH | C38 | S | 2 | 103 | 104 | 299 | 34 |
| SCH | C39 | S | 2 | 90 | 93 | 277 | 35 |
| SCH | C40 | S | 2 | 91 | 97 | 301 | 34 |
| SCH | C41 | S | 2 | 85 | 91 | 290 | 34 |
| SCH | O14 | S | 2 | 99 | 140 | 274 | 38 |
| WAT | OH2 | W | 1 | 205 | 51 | 305 | 6 |
| WAT | OH2 | W | 2 | 403 | 65 | 236 | 7 |
| WAT | OH2 | W | 3 | 324 | 3 | 303 | 7 |
| WAT | OH2 | W | 4 | 182 | 60 | 198 | 7 |
| WAT | OH2 | W | 5 | 320 | −54 | 159 | 7 |
| WAT | OH2 | W | 6 | 149 | −20 | 173 | 7 |
| WAT | OH2 | W | 7 | 405 | 46 | 313 | 7 |
| WAT | OH2 | W | 8 | 221 | 143 | 290 | 7 |
| WAT | OH2 | W | 9 | 165 | −2 | 201 | 7 |
| WAT | OH2 | W | 10 | 327 | 217 | 325 | 8 |
| WAT | OH2 | W | 11 | 394 | 26 | 297 | 8 |
| WAT | OH2 | W | 12 | 174 | −22 | 230 | 8 |
| WAT | OH2 | W | 13 | 462 | 90 | 391 | 8 |
| WAT | OH2 | W | 14 | 433 | 103 | 302 | 8 |
| WAT | OH2 | W | 15 | 140 | 6 | 179 | 8 |
| WAT | OH2 | W | 16 | 244 | 137 | 278 | 8 |
| WAT | OH2 | W | 17 | 205 | 122 | 334 | 8 |
| WAT | OH2 | W | 18 | 382 | 77 | 250 | 9 |
| WAT | OH2 | W | 19 | 360 | −6 | 306 | 9 |
| WAT | OH2 | W | 20 | 298 | −72 | 154 | 9 |

TABLE 2-continued

Structure Coordinates for BACE complexed to Inhibitor

| | | | | | | | |
|---|---|---|---|---|---|---|---|
| WAT | OH2 | W | 21 | 293 | 147 | 275 | 9 |
| WAT | OH2 | W | 22 | 488 | 74 | 336 | 9 |
| WAT | OH2 | W | 23 | 348 | 162 | 271 | 9 |
| WAT | OH2 | W | 24 | 496 | 98 | 405 | 9 |
| WAT | OH2 | W | 25 | 435 | 242 | 402 | 9 |
| WAT | OH2 | W | 26 | 389 | 20 | 182 | 9 |
| WAT | OH2 | W | 27 | 392 | 42 | 226 | 9 |
| WAT | OH2 | W | 28 | 474 | 27 | 322 | 9 |
| WAT | OH2 | W | 29 | 491 | 77 | 452 | 10 |
| WAT | OH2 | W | 30 | 129 | −40 | 177 | 10 |
| WAT | OH2 | W | 31 | 362 | −48 | 410 | 10 |
| WAT | OH2 | W | 32 | 373 | 77 | 517 | 10 |
| WAT | OH2 | W | 33 | 402 | 23 | 206 | 10 |
| WAT | OH2 | W | 34 | 137 | 29 | 161 | 10 |
| WAT | OH2 | W | 35 | 168 | 32 | 24 | 10 |
| WAT | OH2 | W | 36 | 134 | −15 | 81 | 10 |
| WAT | OH2 | W | 37 | 385 | 215 | 292 | 10 |
| WAT | OH2 | W | 38 | 181 | 87 | 399 | 10 |
| WAT | OH2 | W | 39 | 132 | 13 | 82 | 10 |
| WAT | OH2 | W | 40 | 351 | 188 | 280 | 10 |
| WAT | OH2 | W | 41 | 213 | 192 | 423 | 10 |
| WAT | OH2 | W | 42 | 415 | 16 | 235 | 10 |
| WAT | OH2 | W | 43 | 424 | 261 | 385 | 10 |
| WAT | OH2 | W | 44 | 446 | 203 | 482 | 10 |
| WAT | OH2 | W | 45 | 255 | 142 | 206 | 10 |
| WAT | OH2 | W | 46 | 428 | 261 | 421 | 10 |
| WAT | OH2 | W | 47 | 124 | 12 | 199 | 10 |
| WAT | OH2 | W | 48 | 417 | 203 | 488 | 10 |
| WAT | OH2 | W | 49 | 299 | 226 | 325 | 10 |
| WAT | OH2 | W | 50 | 148 | 64 | 224 | 11 |
| WAT | OH2 | W | 51 | 279 | 130 | 499 | 11 |
| WAT | OH2 | W | 52 | 459 | 93 | 300 | 11 |
| WAT | OH2 | W | 53 | 519 | 129 | 302 | 11 |
| WAT | OH2 | W | 54 | 290 | 51 | 227 | 11 |
| WAT | OH2 | W | 55 | 118 | −23 | 272 | 11 |
| WAT | OH2 | W | 56 | 404 | 71 | 299 | 11 |
| WAT | OH2 | W | 57 | 207 | 24 | 422 | 11 |
| WAT | OH2 | W | 58 | 284 | 96 | 128 | 11 |
| WAT | OH2 | W | 59 | 213 | 212 | 405 | 11 |
| WAT | OH2 | W | 60 | 396 | 102 | 296 | 11 |
| WAT | OH2 | W | 61 | 421 | 103 | 512 | 11 |
| WAT | OH2 | W | 62 | 393 | 195 | 476 | 11 |
| WAT | OH2 | W | 63 | 442 | 103 | 457 | 11 |
| WAT | OH2 | W | 64 | 416 | 87 | 227 | 12 |
| WAT | OH2 | W | 65 | 333 | −21 | 160 | 12 |
| WAT | OH2 | W | 66 | 372 | 96 | 536 | 12 |
| WAT | OH2 | W | 67 | 383 | 259 | 450 | 12 |
| WAT | OH2 | W | 68 | 377 | 114 | 227 | 12 |
| WAT | OH2 | W | 69 | 481 | 83 | 310 | 12 |
| WAT | OH2 | W | 70 | 206 | 209 | 378 | 12 |
| WAT | OH2 | W | 71 | 158 | −25 | 254 | 12 |
| WAT | OH2 | W | 72 | 289 | 188 | 282 | 12 |
| WAT | OH2 | W | 73 | 350 | 211 | 244 | 12 |
| WAT | OH2 | W | 74 | 383 | −45 | 427 | 12 |
| WAT | OH2 | W | 75 | 324 | 192 | 277 | 12 |
| WAT | OH2 | W | 76 | 518 | 125 | 384 | 12 |
| WAT | OH2 | W | 77 | 388 | −21 | 439 | 12 |
| WAT | OH2 | W | 78 | 473 | 207 | 441 | 13 |
| WAT | OH2 | W | 79 | 530 | 172 | 431 | 13 |
| WAT | OH2 | W | 80 | 506 | 69 | 203 | 13 |
| WAT | OH2 | W | 81 | 326 | 221 | 472 | 13 |
| WAT | OH2 | W | 82 | 164 | 106 | 412 | 13 |
| WAT | OH2 | W | 83 | 404 | −65 | 284 | 13 |
| WAT | OH2 | W | 84 | 113 | 24 | 67 | 13 |
| WAT | OH2 | W | 85 | 413 | 76 | 272 | 13 |
| WAT | OH2 | W | 86 | 448 | 163 | 445 | 14 |
| WAT | OH2 | W | 87 | 274 | −147 | 319 | 14 |
| WAT | OH2 | W | 88 | 102 | −96 | 191 | 14 |
| WAT | OH2 | W | 89 | 390 | 207 | 531 | 14 |
| WAT | OH2 | W | 90 | 235 | 149 | 118 | 14 |
| WAT | OH2 | W | 91 | 501 | 34 | 162 | 14 |
| WAT | OH2 | W | 92 | 373 | 91 | 475 | 14 |
| WAT | OH2 | W | 93 | 254 | −43 | 463 | 14 |
| WAT | OH2 | W | 94 | 431 | 239 | 486 | 14 |
| WAT | OH2 | W | 95 | 104 | −126 | 74 | 14 |
| WAT | OH2 | W | 96 | 468 | 131 | 258 | 14 |
| WAT | OH2 | W | 97 | 207 | −122 | 352 | 14 |
| WAT | OH2 | W | 98 | 458 | −4 | 200 | 14 |
| WAT | OH2 | W | 99 | 198 | 184 | 367 | 14 |
| WAT | OH2 | W | 100 | 230 | 165 | 306 | 14 |
| WAT | OH2 | W | 101 | 337 | 68 | 169 | 14 |
| WAT | OH2 | W | 102 | 203 | −57 | 12 | 15 |
| WAT | OH2 | W | 103 | 332 | −23 | 134 | 15 |
| WAT | OH2 | W | 104 | 268 | 241 | 450 | 15 |
| WAT | OH2 | W | 105 | 393 | 170 | 484 | 15 |
| WAT | OH2 | W | 106 | 374 | −38 | 179 | 15 |
| WAT | OH2 | W | 107 | 71 | −31 | 179 | 15 |
| WAT | OH2 | W | 108 | 402 | −80 | 260 | 15 |
| WAT | OH2 | W | 109 | 84 | 101 | 170 | 15 |
| WAT | OH2 | W | 110 | 535 | 128 | 239 | 15 |
| WAT | OH2 | W | 111 | 534 | 124 | 209 | 15 |
| WAT | OH2 | W | 112 | 204 | 133 | 308 | 16 |
| WAT | OH2 | W | 113 | 349 | 174 | 484 | 16 |
| WAT | OH2 | W | 114 | 77 | 44 | 72 | 16 |
| WAT | OH2 | W | 115 | 414 | −39 | 250 | 16 |
| WAT | OH2 | W | 116 | 67 | −33 | 33 | 16 |
| WAT | OH2 | W | 117 | 402 | 107 | 239 | 16 |
| WAT | OH2 | W | 118 | 383 | 41 | 465 | 16 |
| WAT | OH2 | W | 119 | 206 | 126 | 78 | 16 |
| WAT | OH2 | W | 120 | 265 | −65 | 449 | 16 |
| WAT | OH2 | W | 121 | 387 | −47 | 250 | 16 |
| WAT | OH2 | W | 122 | 242 | −79 | 449 | 16 |
| WAT | OH2 | W | 123 | 412 | −13 | 428 | 16 |
| WAT | OH2 | W | 124 | 320 | 262 | 414 | 16 |
| WAT | OH2 | W | 125 | 465 | 217 | 465 | 16 |
| WAT | OH2 | W | 126 | 410 | 265 | 445 | 16 |
| WAT | OH2 | W | 127 | 311 | 77 | 242 | 16 |
| WAT | OH2 | W | 128 | 292 | 251 | 335 | 16 |
| WAT | OH2 | W | 129 | 348 | −97 | 188 | 16 |
| WAT | OH2 | W | 130 | 27 | 6 | 113 | 16 |
| WAT | OH2 | W | 131 | 296 | 252 | 453 | 16 |
| WAT | OH2 | W | 132 | −44 | 49 | 63 | 16 |
| WAT | OH2 | W | 133 | 457 | 21 | 167 | 17 |
| WAT | OH2 | W | 134 | 347 | 271 | 415 | 17 |
| WAT | OH2 | W | 135 | 361 | 138 | 179 | 17 |
| WAT | OH2 | W | 136 | 372 | 180 | 219 | 17 |
| WAT | OH2 | W | 137 | 400 | 218 | 505 | 17 |
| WAT | OH2 | W | 138 | 342 | 185 | 243 | 17 |
| WAT | OH2 | W | 139 | 140 | 102 | 386 | 17 |
| WAT | OH2 | W | 140 | 512 | 104 | 313 | 17 |
| WAT | OH2 | W | 141 | 473 | 43 | 283 | 17 |
| WAT | OH2 | W | 142 | 245 | −105 | 366 | 17 |
| WAT | OH2 | W | 143 | 540 | 130 | 368 | 17 |
| WAT | OH2 | W | 144 | 210 | −86 | 83 | 17 |
| WAT | OH2 | W | 145 | 515 | 76 | 339 | 17 |
| WAT | OH2 | W | 146 | 436 | −16 | 335 | 17 |
| WAT | OH2 | W | 147 | 394 | 68 | 505 | 17 |
| WAT | OH2 | W | 148 | 387 | 92 | 273 | 18 |
| WAT | OH2 | W | 149 | 467 | 69 | 465 | 18 |
| WAT | OH2 | W | 150 | 562 | 178 | 247 | 18 |
| WAT | OH2 | W | 151 | 555 | 140 | 408 | 18 |
| WAT | OH2 | W | 152 | 309 | 140 | 561 | 18 |
| WAT | OH2 | W | 153 | 452 | 20 | 209 | 18 |
| WAT | OH2 | W | 154 | 400 | −107 | 272 | 18 |
| WAT | OH2 | W | 155 | 138 | 114 | 227 | 18 |
| WAT | OH2 | W | 156 | 140 | −65 | 308 | 18 |
| WAT | OH2 | W | 157 | 559 | 11 | 401 | 18 |
| WAT | OH2 | W | 158 | 225 | −58 | 28 | 18 |
| WAT | OH2 | W | 159 | 483 | 110 | 274 | 18 |
| WAT | OH2 | W | 160 | 320 | 28 | 86 | 18 |
| WAT | OH2 | W | 161 | 206 | 99 | 66 | 18 |
| WAT | OH2 | W | 162 | 226 | −49 | −2 | 19 |
| WAT | OH2 | W | 163 | 468 | 20 | 298 | 19 |
| WAT | OH2 | W | 164 | 265 | −13 | 40 | 19 |
| WAT | OH2 | W | 165 | 352 | 280 | 346 | 19 |
| WAT | OH2 | W | 166 | 316 | 217 | 280 | 19 |
| WAT | OH2 | W | 167 | 486 | 212 | 479 | 19 |
| WAT | OH2 | W | 168 | 164 | −44 | 416 | 19 |
| WAT | OH2 | W | 169 | 338 | −156 | 313 | 19 |
| WAT | OH2 | W | 170 | 339 | 192 | 502 | 19 |
| WAT | OH2 | W | 171 | 259 | 160 | 114 | 19 |
| WAT | OH2 | W | 172 | 407 | −50 | 411 | 19 |
| WAT | OH2 | W | 173 | 529 | 95 | 351 | 19 |
| WAT | OH2 | W | 174 | −8 | 17 | 74 | 19 |

TABLE 2-continued

Structure Coordinates for BACE complexed to Inhibitor

| | | | | | | | |
|---|---|---|---|---|---|---|---|
| WAT | OH2 | W | 175 | 75 | −23 | 231 | 19 |
| WAT | OH2 | W | 176 | 278 | −114 | 391 | 19 |
| WAT | OH2 | W | 177 | 379 | −118 | 210 | 19 |
| WAT | OH2 | W | 178 | 195 | 231 | 412 | 19 |
| WAT | OH2 | W | 179 | 384 | 264 | 478 | 19 |
| WAT | OH2 | W | 180 | 180 | 177 | 204 | 20 |
| WAT | OH2 | W | 181 | 447 | 32 | 441 | 20 |
| WAT | OH2 | W | 182 | 275 | −42 | 33 | 20 |
| WAT | OH2 | W | 183 | 244 | −42 | 491 | 20 |
| WAT | OH2 | W | 184 | 183 | −49 | 435 | 20 |
| WAT | OH2 | W | 185 | 306 | 241 | 475 | 20 |
| WAT | OH2 | W | 186 | 208 | −134 | 326 | 20 |
| WAT | OH2 | W | 187 | 415 | −84 | 297 | 20 |
| WAT | OH2 | W | 188 | 122 | 71 | 386 | 20 |
| WAT | OH2 | W | 189 | 531 | 119 | 341 | 20 |
| WAT | OH2 | W | 190 | 141 | −113 | 321 | 20 |
| WAT | OH2 | W | 191 | 370 | −142 | 266 | 20 |
| WAT | OH2 | W | 192 | 124 | −35 | −3 | 20 |
| WAT | OH2 | W | 193 | 391 | −129 | 255 | 20 |
| WAT | OH2 | W | 194 | 104 | −50 | 9 | 20 |
| WAT | OH2 | W | 195 | 275 | 104 | 537 | 20 |
| WAT | OH2 | W | 196 | 216 | 133 | 524 | 20 |
| WAT | OH2 | W | 197 | 488 | 49 | 185 | 20 |
| WAT | OH2 | W | 198 | 344 | 176 | 217 | 20 |
| WAT | OH2 | W | 199 | 463 | 21 | 257 | 20 |
| WAT | OH2 | W | 200 | 322 | 116 | 560 | 20 |
| WAT | OH2 | W | 201 | 104 | −2 | 362 | 20 |
| WAT | OH2 | W | 202 | 331 | 82 | 93 | 20 |
| WAT | OH2 | W | 203 | 539 | 115 | 411 | 20 |
| WAT | OH2 | W | 204 | 145 | −79 | 272 | 21 |
| WAT | OH2 | W | 205 | 81 | 69 | 249 | 21 |
| WAT | OH2 | W | 206 | 484 | 242 | 283 | 21 |
| WAT | OH2 | W | 207 | 273 | 165 | 219 | 21 |
| WAT | OH2 | W | 208 | 416 | 101 | 485 | 21 |
| WAT | OH2 | W | 209 | 216 | 190 | 303 | 21 |
| WAT | OH2 | W | 210 | 358 | −42 | 487 | 21 |
| WAT | OH2 | W | 211 | −17 | 40 | 63 | 21 |
| WAT | OH2 | W | 212 | 461 | −5 | 173 | 21 |
| WAT | OH2 | W | 213 | 236 | −116 | 161 | 21 |
| WAT | OH2 | W | 214 | 488 | 61 | 296 | 21 |
| WAT | OH2 | W | 215 | 495 | 47 | 318 | 21 |
| WAT | OH2 | W | 216 | 158 | −151 | 258 | 21 |
| WAT | OH2 | W | 217 | 415 | −84 | 199 | 21 |
| WAT | OH2 | W | 218 | 246 | −130 | 360 | 21 |
| WAT | OH2 | W | 219 | 170 | 17 | −13 | 21 |
| WAT | OH2 | W | 220 | 266 | 238 | 475 | 21 |
| WAT | OH2 | W | 221 | 273 | 270 | 370 | 21 |
| WAT | OH2 | W | 222 | 180 | −82 | 419 | 21 |
| WAT | OH2 | W | 223 | 416 | −103 | 233 | 21 |
| WAT | OH2 | W | 224 | 72 | −93 | 46 | 21 |
| WAT | OH2 | W | 225 | 425 | −47 | 274 | 21 |
| WAT | OH2 | W | 226 | 412 | −170 | 236 | 21 |
| WAT | OH2 | W | 227 | 72 | 71 | 69 | 22 |
| WAT | OH2 | W | 228 | 92 | −37 | 247 | 22 |
| WAT | OH2 | W | 229 | 318 | 205 | 494 | 22 |
| WAT | OH2 | W | 230 | 371 | 38 | 150 | 22 |
| WAT | OH2 | W | 231 | 150 | −131 | 7 | 22 |
| WAT | OH2 | W | 232 | 96 | 1 | 293 | 22 |
| WAT | OH2 | W | 233 | 54 | −38 | 222 | 22 |
| WAT | OH2 | W | 234 | 398 | −124 | 228 | 22 |
| WAT | OH2 | W | 235 | 326 | 108 | 82 | 22 |
| WAT | OH2 | W | 236 | 396 | 305 | 297 | 22 |
| WAT | OH2 | W | 237 | 77 | 18 | 13 | 22 |
| WAT | OH2 | W | 238 | 29 | 7 | 139 | 22 |
| WAT | OH2 | W | 239 | 366 | 289 | 368 | 22 |
| WAT | OH2 | W | 240 | 272 | 135 | 537 | 22 |
| WAT | OH2 | W | 241 | 158 | 17 | 437 | 22 |
| WAT | OH2 | W | 242 | 356 | 108 | 285 | 22 |
| WAT | OH2 | W | 243 | 476 | 151 | 233 | 22 |
| WAT | OH2 | W | 244 | 522 | 103 | 395 | 23 |
| WAT | OH2 | W | 245 | 321 | −23 | 92 | 23 |
| WAT | OH2 | W | 246 | 532 | 58 | 370 | 23 |
| WAT | OH2 | W | 247 | 233 | 65 | 623 | 23 |
| WAT | OH2 | W | 248 | 558 | 5 | 372 | 23 |
| WAT | OH2 | W | 249 | 174 | −86 | −20 | 23 |
| WAT | OH2 | W | 250 | 187 | −140 | 359 | 23 |
| WAT | OH2 | W | 251 | 42 | 12 | 20 | 23 |
| WAT | OH2 | W | 252 | 101 | 28 | 22 | 23 |
| WAT | OH2 | W | 253 | 56 | 47 | 37 | 23 |
| WAT | OH2 | W | 254 | 124 | −54 | 290 | 23 |
| WAT | OH2 | W | 255 | 312 | 178 | 195 | 23 |
| WAT | OH2 | W | 256 | 231 | 172 | 94 | 23 |
| WAT | OH2 | W | 257 | 439 | −70 | 194 | 23 |
| WAT | OH2 | W | 258 | 307 | 267 | 350 | 23 |
| WAT | OH2 | W | 259 | 129 | −12 | −88 | 23 |
| WAT | OH2 | W | 260 | 414 | 280 | 401 | 23 |
| WAT | OH2 | W | 261 | 242 | −4 | 27 | 24 |
| WAT | OH2 | W | 262 | 334 | 260 | 355 | 24 |
| WAT | OH2 | W | 263 | 97 | −83 | 30 | 24 |
| WAT | OH2 | W | 264 | 240 | 188 | 113 | 24 |
| WAT | OH2 | W | 265 | 327 | −33 | 61 | 24 |
| WAT | OH2 | W | 266 | 512 | 33 | 303 | 24 |
| WAT | OH2 | W | 267 | 481 | −7 | 140 | 24 |
| WAT | OH2 | W | 268 | 145 | 128 | 306 | 24 |
| WAT | OH2 | W | 269 | 185 | 218 | 436 | 24 |
| WAT | OH2 | W | 270 | 510 | 70 | 284 | 24 |
| WAT | OH2 | W | 271 | 120 | −92 | 254 | 24 |
| WAT | OH2 | W | 272 | 117 | 97 | 249 | 24 |
| WAT | OH2 | W | 273 | 47 | 86 | 141 | 24 |
| WAT | OH2 | W | 274 | 548 | 212 | 306 | 24 |
| WAT | OH2 | W | 275 | 192 | 262 | 456 | 24 |
| WAT | OH2 | W | 276 | 195 | 163 | 72 | 24 |
| WAT | OH2 | W | 277 | 535 | 85 | 376 | 24 |
| WAT | OH2 | W | 278 | 295 | −77 | 82 | 24 |
| WAT | OH2 | W | 279 | 321 | −107 | 417 | 25 |
| WAT | OH2 | W | 280 | 49 | 58 | 254 | 25 |
| WAT | OH2 | W | 281 | 151 | −49 | 335 | 25 |
| WAT | OH2 | W | 282 | 271 | −136 | 153 | 25 |
| WAT | OH2 | W | 283 | 423 | −107 | 285 | 25 |
| WAT | OH2 | W | 284 | 368 | 279 | 435 | 25 |
| WAT | OH2 | W | 285 | 345 | −4 | 94 | 25 |
| WAT | OH2 | W | 286 | 296 | 98 | 103 | 25 |
| WAT | OH2 | W | 287 | 193 | 230 | 367 | 25 |
| WAT | OH2 | W | 288 | 436 | 75 | 458 | 25 |
| WAT | OH2 | W | 289 | 41 | 16 | −15 | 25 |
| WAT | OH2 | W | 290 | 543 | 185 | 349 | 25 |
| WAT | OH2 | W | 291 | 521 | 197 | 436 | 25 |
| WAT | OH2 | W | 292 | 258 | −182 | 124 | 25 |
| WAT | OH2 | W | 293 | 30 | 69 | 159 | 25 |
| WAT | OH2 | W | 294 | 223 | 232 | 344 | 26 |
| WAT | OH2 | W | 295 | 144 | −61 | 418 | 26 |
| WAT | OH2 | W | 296 | 83 | −7 | 0 | 26 |
| WAT | OH2 | W | 297 | 547 | 155 | 367 | 26 |
| WAT | OH2 | W | 298 | 539 | 167 | 405 | 26 |
| WAT | OH2 | W | 299 | 441 | 20 | 104 | 26 |
| WAT | OH2 | W | 300 | 403 | 129 | 213 | 26 |
| WAT | OH2 | W | 301 | 354 | 149 | 200 | 26 |
| WAT | OH2 | W | 302 | 77 | −67 | 30 | 26 |
| WAT | OH2 | W | 303 | 157 | −66 | −32 | 26 |
| WAT | OH2 | W | 304 | 410 | −95 | 341 | 26 |
| WAT | OH2 | W | 305 | 474 | −16 | 328 | 26 |
| WAT | OH2 | W | 306 | 312 | 163 | 130 | 26 |
| WAT | OH2 | W | 307 | 373 | −64 | 444 | 26 |
| WAT | OH2 | W | 308 | 178 | −133 | 48 | 26 |
| WAT | OH2 | W | 309 | 302 | 62 | 70 | 26 |
| WAT | OH2 | W | 310 | 37 | −17 | 16 | 27 |
| WAT | OH2 | W | 311 | 305 | 74 | 94 | 27 |
| WAT | OH2 | W | 312 | 424 | 76 | 509 | 27 |
| WAT | OH2 | W | 313 | 289 | −155 | 206 | 27 |
| WAT | OH2 | W | 314 | 464 | 81 | 488 | 27 |
| WAT | OH2 | W | 315 | 341 | −57 | 143 | 27 |
| WAT | OH2 | W | 316 | 79 | −74 | 134 | 27 |
| WAT | OH2 | W | 317 | 255 | 133 | 515 | 27 |
| WAT | OH2 | W | 318 | 338 | −127 | 166 | 27 |
| WAT | OH2 | W | 319 | 334 | −83 | 105 | 27 |
| WAT | OH2 | W | 320 | 414 | 108 | 205 | 27 |
| WAT | OH2 | W | 321 | 262 | 98 | 20 | 27 |
| WAT | OH2 | W | 322 | 593 | 152 | 280 | 27 |
| WAT | OH2 | W | 323 | 406 | 322 | 333 | 27 |
| WAT | OH2 | W | 324 | 199 | −10 | 493 | 27 |
| WAT | OH2 | W | 325 | 583 | 132 | 306 | 27 |
| WAT | OH2 | W | 326 | 121 | 21 | 7 | 27 |
| WAT | OH2 | W | 327 | 118 | −61 | 361 | 27 |
| WAT | OH2 | W | 328 | 127 | −6 | −59 | 27 |

TABLE 2-continued

Structure Coordinates for BACE complexed to Inhibitor

| | | | | | | | |
|---|---|---|---|---|---|---|---|
| WAT | OH2 | W | 329 | 440 | −24 | 198 | 27 |
| WAT | OH2 | W | 330 | 439 | −44 | 216 | 27 |
| WAT | OH2 | W | 331 | 285 | 228 | 494 | 27 |
| WAT | OH2 | W | 332 | 198 | 193 | 284 | 27 |
| WAT | OH2 | W | 333 | 175 | 34 | 565 | 27 |
| WAT | OH2 | W | 334 | 249 | −109 | 88 | 27 |
| WAT | OH2 | W | 335 | 272 | −74 | 46 | 27 |
| WAT | OH2 | W | 336 | 202 | 191 | 194 | 28 |
| WAT | OH2 | W | 337 | 401 | 42 | 510 | 28 |
| WAT | OH2 | W | 338 | 408 | 40 | 457 | 28 |
| WAT | OH2 | W | 339 | 62 | 60 | 276 | 28 |
| WAT | OH2 | W | 340 | 260 | −212 | 161 | 28 |
| WAT | OH2 | W | 341 | 341 | 271 | 377 | 28 |
| WAT | OH2 | W | 342 | 283 | 155 | 187 | 28 |
| WAT | OH2 | W | 343 | 406 | −103 | 400 | 28 |
| WAT | OH2 | W | 344 | 400 | 293 | 366 | 28 |
| WAT | OH2 | W | 345 | 39 | 94 | 106 | 28 |
| WAT | OH2 | W | 346 | 51 | 9 | 171 | 28 |
| WAT | OH2 | W | 347 | 106 | 56 | 403 | 28 |
| WAT | OH2 | W | 348 | 169 | 261 | 443 | 28 |
| WAT | OH2 | W | 349 | 418 | 40 | 484 | 28 |
| WAT | OH2 | W | 350 | 6 | −21 | 211 | 28 |
| WAT | OH2 | W | 351 | 252 | −148 | 240 | 28 |
| WAT | OH2 | W | 352 | 247 | −63 | 9 | 28 |
| WAT | OH2 | W | 353 | 275 | 60 | 524 | 28 |
| WAT | OH2 | W | 354 | 100 | −58 | 143 | 29 |
| WAT | OH2 | W | 355 | 65 | −135 | 90 | 29 |
| WAT | OH2 | W | 356 | 451 | −7 | 303 | 29 |
| WAT | OH2 | W | 357 | 262 | −119 | 111 | 29 |
| WAT | OH2 | W | 358 | 386 | 133 | 177 | 29 |
| WAT | OH2 | W | 359 | 174 | 134 | 509 | 29 |
| WAT | OH2 | W | 360 | 47 | −16 | 161 | 29 |
| WAT | OH2 | W | 361 | 282 | 166 | 142 | 29 |
| WAT | OH2 | W | 362 | 95 | 112 | 88 | 29 |
| WAT | OH2 | W | 363 | 493 | 9 | 332 | 29 |
| WAT | OH2 | W | 364 | 198 | 130 | 18 | 29 |
| WAT | OH2 | W | 365 | 277 | 46 | 584 | 29 |
| WAT | OH2 | W | 366 | 184 | 197 | 512 | 29 |
| WAT | OH2 | W | 367 | 260 | 173 | 185 | 29 |
| WAT | OH2 | W | 368 | 412 | −145 | 225 | 29 |
| WAT | OH2 | W | 369 | 414 | 248 | 236 | 29 |
| WAT | OH2 | W | 370 | 259 | −90 | 18 | 29 |
| WAT | OH2 | W | 371 | 179 | 129 | 297 | 29 |
| WAT | OH2 | W | 372 | 103 | −70 | 262 | 29 |
| WAT | OH2 | W | 373 | 252 | −139 | 333 | 29 |
| WAT | OH2 | W | 374 | 149 | −20 | 415 | 30 |
| WAT | OH2 | W | 375 | 402 | 99 | 154 | 30 |
| WAT | OH2 | W | 376 | 257 | 23 | 12 | 30 |
| WAT | OH2 | W | 377 | 200 | 207 | 493 | 30 |
| WAT | OH2 | W | 378 | 126 | 15 | 425 | 30 |
| WAT | OH2 | W | 379 | 337 | −65 | 513 | 30 |
| WAT | OH2 | W | 380 | 434 | −85 | 340 | 30 |
| WAT | OH2 | W | 381 | 117 | 140 | 453 | 30 |
| WAT | OH2 | W | 382 | 373 | 129 | 202 | 30 |
| WAT | OH2 | W | 383 | 164 | 209 | 309 | 30 |
| WAT | OH2 | W | 384 | 408 | −148 | 315 | 30 |
| WAT | OH2 | W | 385 | 384 | 228 | 211 | 30 |
| WAT | OH2 | W | 386 | 362 | 80 | 166 | 30 |
| WAT | OH2 | W | 387 | 237 | 92 | 520 | 30 |
| WAT | OH2 | W | 388 | 359 | −39 | 156 | 30 |
| WAT | OH2 | W | 389 | 397 | −24 | 465 | 30 |
| WAT | OH2 | W | 390 | 516 | 217 | 407 | 30 |
| WAT | OH2 | W | 391 | 147 | 150 | 289 | 30 |
| WAT | OH2 | W | 392 | 336 | 301 | 341 | 30 |
| WAT | OH2 | W | 393 | 298 | 262 | 373 | 31 |
| WAT | OH2 | W | 394 | 191 | 29 | 532 | 31 |
| WAT | OH2 | W | 395 | 180 | −140 | 313 | 31 |
| WAT | OH2 | W | 396 | 486 | 13 | 407 | 31 |
| WAT | OH2 | W | 397 | 46 | −99 | 133 | 31 |
| WAT | OH2 | W | 398 | 288 | 214 | 281 | 31 |
| WAT | OH2 | W | 399 | 122 | −27 | 418 | 31 |
| WAT | OH2 | W | 400 | 268 | −163 | 227 | 31 |
| WAT | OH2 | W | 401 | 9 | 36 | 144 | 31 |
| WAT | OH2 | W | 402 | 271 | 221 | 302 | 31 |
| WAT | OH2 | W | 403 | 85 | −64 | 242 | 31 |
| WAT | OH2 | W | 404 | 494 | 170 | 215 | 31 |
| WAT | OH2 | W | 405 | 445 | −34 | 170 | 32 |
| WAT | OH2 | W | 406 | 426 | 54 | 439 | 32 |
| WAT | OH2 | W | 407 | 156 | 194 | 284 | 32 |
| WAT | OH2 | W | 408 | 88 | 120 | 188 | 32 |
| WAT | OH2 | W | 409 | 538 | 94 | 323 | 32 |
| WAT | OH2 | W | 410 | 307 | 203 | 240 | 32 |
| WAT | OH2 | W | 411 | 354 | −51 | 457 | 32 |
| WAT | OH2 | W | 412 | 507 | 21 | 352 | 32 |
| WAT | OH2 | W | 413 | 204 | −129 | 29 | 33 |
| WAT | OH2 | W | 414 | 428 | −5 | 102 | 33 |
| WAT | OH2 | W | 415 | 402 | −30 | 132 | 33 |
| WAT | OH2 | W | 416 | 253 | −135 | 132 | 33 |
| WAT | OH2 | W | 417 | 398 | −34 | 164 | 33 |
| WAT | OH2 | W | 418 | 67 | 12 | 290 | 33 |
| WAT | OH2 | W | 419 | 237 | 117 | 526 | 33 |
| WAT | OH2 | W | 420 | 160 | 164 | 123 | 33 |
| WAT | OH2 | W | 421 | 279 | −99 | 54 | 33 |
| WAT | OH2 | W | 422 | 211 | 271 | 346 | 33 |
| WAT | OH2 | W | 423 | 61 | 106 | 155 | 34 |
| WAT | OH2 | W | 424 | 208 | 139 | 53 | 34 |
| WAT | OH2 | W | 425 | 118 | 164 | 362 | 34 |
| WAT | OH2 | W | 426 | 121 | 131 | 318 | 34 |
| WAT | OH2 | W | 427 | 421 | 142 | 195 | 34 |
| WAT | OH2 | W | 428 | 252 | 58 | 606 | 34 |
| WAT | OH2 | W | 429 | 254 | −125 | 409 | 34 |
| WAT | OH2 | W | 430 | 251 | −108 | 436 | 34 |
| WAT | OH2 | W | 431 | 293 | 103 | 616 | 34 |
| WAT | OH2 | W | 432 | 310 | −163 | 320 | 34 |
| WAT | OH2 | W | 433 | 479 | 100 | 180 | 34 |
| WAT | OH2 | W | 434 | 509 | 230 | 237 | 34 |
| WAT | OH2 | W | 435 | 438 | −84 | 312 | 34 |
| WAT | OH2 | W | 436 | 462 | 124 | 173 | 34 |
| WAT | OH2 | W | 437 | 175 | 68 | 599 | 35 |
| WAT | OH2 | W | 438 | 221 | −136 | 371 | 35 |
| WAT | OH2 | W | 439 | 387 | −74 | 176 | 35 |
| WAT | OH2 | W | 440 | 360 | 232 | 481 | 35 |
| WAT | OH2 | W | 441 | 427 | −128 | 312 | 35 |
| WAT | OH2 | W | 442 | 195 | −127 | 4 | 35 |
| WAT | OH2 | W | 443 | 169 | 220 | 354 | 35 |
| WAT | OH2 | W | 444 | 166 | 185 | 474 | 35 |
| WAT | OH2 | W | 445 | 449 | −60 | 386 | 35 |
| WAT | OH2 | W | 446 | 232 | −141 | 58 | 35 |
| WAT | OH2 | W | 447 | 419 | 70 | 478 | 35 |
| WAT | OH2 | W | 448 | 431 | −33 | 356 | 35 |
| WAT | OH2 | W | 449 | 625 | 125 | 309 | 35 |
| WAT | OH2 | W | 450 | 178 | 180 | 273 | 35 |
| WAT | OH2 | W | 451 | 91 | −29 | 277 | 35 |
| WAT | OH2 | W | 452 | 341 | −45 | 120 | 35 |
| WAT | OH2 | W | 453 | 247 | 196 | 263 | 35 |
| WAT | OH2 | W | 454 | 334 | 297 | 380 | 35 |
| WAT | OH2 | W | 455 | 414 | 324 | 307 | 36 |
| WAT | OH2 | W | 456 | 64 | 109 | 200 | 36 |
| WAT | OH2 | W | 457 | 183 | −67 | 521 | 36 |
| WAT | OH2 | W | 458 | 181 | −108 | 420 | 36 |
| WAT | OH2 | W | 459 | 333 | −55 | 80 | 36 |
| WAT | OH2 | W | 460 | 99 | 55 | 21 | 36 |
| WAT | OH2 | W | 461 | 153 | −178 | 262 | 36 |
| WAT | OH2 | W | 462 | 55 | −50 | 194 | 36 |
| WAT | OH2 | W | 463 | 196 | −180 | 209 | 36 |
| WAT | OH2 | W | 464 | 189 | 125 | 529 | 36 |
| WAT | OH2 | W | 465 | 290 | 105 | 570 | 36 |
| WAT | OH2 | W | 466 | 173 | −146 | 7 | 36 |
| WAT | OH2 | W | 467 | 184 | 4 | 520 | 36 |
| WAT | OH2 | W | 468 | 97 | 156 | 210 | 37 |
| WAT | OH2 | W | 469 | 38 | 64 | 49 | 37 |
| WAT | OH2 | W | 470 | 69 | −85 | 206 | 37 |
| WAT | OH2 | W | 471 | 362 | −38 | 103 | 37 |
| WAT | OH2 | W | 472 | 231 | −166 | 239 | 37 |
| WAT | OH2 | W | 473 | 384 | 191 | 199 | 37 |
| WAT | OH2 | W | 474 | 177 | −47 | 461 | 37 |
| WAT | OH2 | W | 475 | 168 | 124 | 29 | 37 |
| WAT | OH2 | W | 476 | 265 | 124 | 11 | 37 |
| WAT | OH2 | W | 477 | 366 | 286 | 267 | 37 |
| WAT | OH2 | W | 478 | 229 | −126 | 82 | 37 |
| WAT | OH2 | W | 479 | 379 | −43 | 131 | 37 |
| WAT | OH2 | W | 480 | 20 | 8 | 6 | 37 |
| WAT | OH2 | W | 481 | 48 | 1258 | 464 | 37 |
| WAT | OH2 | W | 482 | 605 | 148 | 307 | 37 |

TABLE 2-continued

Structure Coordinates for BACE complexed to Inhibitor

| | | | | | | | |
|---|---|---|---|---|---|---|---|
| WAT | OH2 | W | 483 | 211 | −100 | 447 | 37 |
| WAT | OH2 | W | 484 | 139 | 39 | −4 | 37 |
| WAT | OH2 | W | 485 | 197 | 40 | −20 | 37 |
| WAT | OH2 | W | 486 | 297 | 37 | 563 | 37 |
| WAT | OH2 | W | 487 | 127 | 97 | 474 | 37 |
| WAT | OH2 | W | 488 | 575 | 194 | 340 | 37 |
| WAT | OH2 | W | 489 | 298 | 235 | 300 | 37 |
| WAT | OH2 | W | 490 | 74 | 143 | 179 | 37 |
| WAT | OH2 | W | 491 | 185 | 193 | 236 | 37 |
| WAT | OH2 | W | 492 | 191 | −169 | 140 | 38 |
| WAT | OH2 | W | 493 | 306 | 293 | 350 | 38 |
| WAT | OH2 | W | 494 | 362 | −89 | 167 | 38 |
| WAT | OH2 | W | 495 | 295 | 81 | 586 | 38 |
| WAT | OH2 | W | 496 | 372 | 6 | 533 | 38 |
| WAT | OH2 | W | 497 | 202 | 245 | 348 | 38 |
| WAT | OH2 | W | 498 | 422 | 22 | 446 | 38 |
| WAT | OH2 | W | 499 | 66 | −109 | 118 | 38 |
| WAT | OH2 | W | 500 | 106 | −34 | 307 | 38 |
| WAT | OH2 | W | 501 | 335 | −180 | 328 | 38 |
| WAT | OH2 | W | 502 | 449 | −54 | 322 | 38 |
| WAT | OH2 | W | 503 | 360 | 3 | 65 | 38 |
| WAT | OH2 | W | 504 | 36 | 29 | −37 | 38 |
| WAT | OH2 | W | 505 | 114 | 102 | 392 | 38 |
| WAT | OH2 | W | 506 | 183 | 17 | −35 | 39 |
| WAT | OH2 | W | 507 | 204 | −110 | 76 | 39 |
| WAT | OH2 | W | 508 | 106 | −94 | −10 | 39 |
| WAT | OH2 | W | 509 | 284 | −79 | 464 | 39 |
| WAT | OH2 | W | 510 | 519 | 44 | 340 | 39 |
| WAT | OH2 | W | 511 | 393 | 151 | 199 | 39 |
| WAT | OH2 | W | 512 | 426 | 273 | 465 | 39 |
| WAT | OH2 | W | 513 | 104 | 4 | 389 | 39 |
| WAT | OH2 | W | 514 | 200 | 198 | 168 | 39 |
| WAT | OH2 | W | 515 | 247 | −166 | 266 | 39 |
| WAT | OH2 | W | 516 | 127 | −162 | 244 | 39 |
| WAT | OH2 | W | 517 | 430 | 127 | 175 | 39 |
| WAT | OH2 | W | 518 | 337 | −5 | 48 | 39 |
| WAT | OH2 | W | 519 | 425 | −3 | 449 | 39 |
| WAT | OH2 | W | 520 | 82 | −116 | 189 | 39 |
| WAT | OH2 | W | 521 | 236 | −132 | 16 | 39 |
| WAT | OH2 | W | 522 | 309 | −84 | 458 | 39 |
| WAT | OH2 | W | 523 | 304 | −165 | 99 | 39 |
| WAT | OH2 | W | 524 | 291 | 171 | 167 | 39 |
| WAT | OH2 | W | 525 | 364 | 63 | 145 | 39 |
| WAT | OH2 | W | 526 | 188 | 34 | 619 | 39 |
| WAT | OH2 | W | 527 | 131 | −117 | 296 | 39 |
| WAT | OH2 | W | 528 | 317 | 268 | 387 | 39 |
| WAT | OH2 | W | 529 | 228 | −199 | 175 | 39 |
| WAT | OH2 | W | 530 | 555 | 85 | 342 | 39 |
| WAT | OH2 | W | 531 | 309 | 105 | 588 | 39 |
| WAT | OH2 | W | 532 | 254 | −175 | 201 | 39 |
| WAT | OH2 | W | 533 | 269 | −174 | 312 | 40 |
| WAT | OH2 | W | 534 | 76 | 64 | 41 | 40 |
| WAT | OH2 | W | 535 | 184 | 23 | 436 | 40 |
| WAT | OH2 | W | 536 | 385 | 319 | 383 | 40 |
| WAT | OH2 | W | 537 | 160 | 236 | 392 | 40 |
| WAT | OH2 | W | 538 | 437 | −14 | 220 | 40 |
| WAT | OH2 | W | 539 | 440 | −58 | 347 | 40 |
| WAT | OH2 | W | 540 | 97 | 170 | 144 | 40 |
| WAT | OH2 | W | 541 | 99 | 124 | 332 | 40 |
| WAT | OH2 | W | 542 | 74 | 125 | 135 | 40 |
| WAT | OH2 | W | 543 | 44 | 78 | 70 | 40 |
| WAT | OH2 | W | 544 | 266 | 189 | 111 | 40 |
| WAT | OH2 | W | 545 | 216 | −95 | 476 | 40 |
| WAT | OH2 | W | 546 | 385 | 298 | 400 | 40 |
| WAT | OH2 | W | 547 | 345 | 154 | 174 | 40 |
| WAT | OH2 | W | 548 | 256 | −82 | −10 | 41 |
| WAT | OH2 | W | 549 | 149 | 163 | 327 | 41 |
| WAT | OH2 | W | 550 | 134 | −80 | 345 | 41 |
| WAT | OH2 | W | 551 | 363 | −77 | 144 | 41 |
| WAT | OH2 | W | 552 | 564 | 215 | 260 | 41 |
| WAT | OH2 | W | 553 | 118 | −144 | 266 | 41 |
| WAT | OH2 | W | 554 | 249 | 146 | 14 | 41 |
| WAT | OH2 | W | 555 | 525 | 71 | 315 | 41 |
| WAT | OH2 | W | 556 | 267 | 136 | 565 | 41 |
| WAT | OH2 | W | 557 | 414 | −70 | 428 | 41 |
| WAT | OH2 | W | 558 | 294 | −132 | 377 | 42 |
| WAT | OH2 | W | 559 | 129 | 187 | 200 | 42 |
| WAT | OH2 | W | 560 | 235 | 72 | 554 | 42 |
| WAT | OH2 | W | 561 | 159 | 193 | 212 | 42 |
| WAT | OH2 | W | 562 | 287 | −100 | 430 | 42 |
| WAT | OH2 | W | 563 | 436 | −112 | 215 | 42 |
| WAT | OH2 | W | 564 | 98 | −72 | 166 | 42 |
| WAT | OH2 | W | 565 | 492 | 58 | 123 | 42 |
| WAT | OH2 | W | 566 | 360 | 181 | 192 | 42 |
| WAT | OH2 | W | 567 | 392 | 70 | 478 | 42 |
| WAT | OH2 | W | 568 | 236 | 221 | 310 | 42 |
| WAT | OH2 | W | 569 | 358 | −17 | 522 | 43 |
| WAT | OH2 | W | 570 | 322 | 185 | 117 | 43 |
| WAT | OH2 | W | 571 | 520 | 0 | 407 | 43 |
| WAT | OH2 | W | 572 | 359 | −182 | 355 | 44 |
| WAT | OH2 | W | 573 | 179 | −188 | 192 | 44 |
| WAT | OH2 | W | 574 | 355 | 243 | 225 | 44 |
| WAT | OH2 | W | 575 | 372 | 156 | 160 | 44 |
| WAT | OH2 | W | 576 | 325 | 202 | 214 | 44 |
| WAT | OH2 | W | 577 | 329 | 228 | 241 | 44 |
| WAT | OH2 | W | 578 | 323 | 38 | 10 | 45 |
| WAT | OH2 | W | 579 | 555 | 53 | 361 | 45 |
| WAT | OH2 | W | 580 | 555 | 106 | 382 | 45 |
| WAT | OH2 | W | 581 | 315 | −157 | 224 | 45 |
| WAT | OH2 | W | 582 | 343 | −154 | 157 | 46 |
| WAT | OH2 | W | 583 | 251 | −167 | 293 | 46 |
| WAT | OH2 | W | 584 | 162 | 62 | 12 | 46 |
| WAT | OH2 | W | 585 | 559 | 27 | 354 | 47 |
| WAT | OH2 | W | 586 | 583 | 84 | 397 | 47 |
| WAT | OH2 | W | 587 | 488 | 119 | 150 | 47 |
| WAT | OH2 | W | 588 | 151 | 215 | 429 | 48 |
| WAT | OH2 | W | 589 | 143 | −86 | 396 | 48 |
| WAT | OH2 | W | 590 | 130 | 125 | 363 | 48 |
| WAT | OH2 | W | 591 | 258 | −92 | 492 | 48 |
| WAT | OH2 | W | 592 | 173 | 229 | 476 | 48 |
| WAT | OH2 | W | 593 | 110 | 165 | 266 | 49 |
| WAT | OH2 | W | 594 | 236 | 301 | 370 | 49 |
| WAT | OH2 | W | 595 | 257 | 66 | 581 | 49 |
| WAT | OH2 | W | 596 | 234 | 55 | −46 | 49 |
| WAT | OH2 | W | 597 | 305 | 251 | 262 | 49 |
| WAT | OH2 | W | 598 | 177 | −177 | 281 | 49 |
| WAT | OH2 | W | 599 | 241 | 121 | 553 | 49 |
| WAT | OH2 | W | 600 | 288 | −151 | 357 | 50 |
| WAT | OH2 | W | 601 | 152 | 94 | 15 | 50 |
| WAT | OH2 | W | 602 | 436 | −28 | 389 | 50 |
| WAT | OH2 | W | 603 | 204 | 17 | −61 | 51 |
| WAT | OH2 | W | 604 | 257 | 32 | −14 | 51 |
| WAT | OH2 | W | 605 | 405 | −125 | 417 | 52 |
| WAT | OH2 | W | 606 | 173 | −60 | −100 | 52 |
| WAT | OH2 | W | 607 | 125 | 197 | 102 | 52 |
| WAT | OH2 | W | 608 | 219 | 154 | 542 | 53 |
| WAT | OH2 | W | 609 | 70 | −90 | 19 | 54 |
| WAT | OH2 | W | 610 | 386 | 331 | 271 | 55 |
| WAT | OH2 | W | 611 | 374 | 196 | 174 | 55 |
| WAT | OH2 | W | 612 | 343 | 279 | 235 | 55 |
| WAT | OH2 | W | 613 | 564 | 81 | 378 | 55 |
| WAT | OH2 | W | 614 | 463 | 139 | 145 | 56 |
| WAT | OH2 | W | 615 | 221 | 585 | 1291 | 8 |
| WAT | OH2 | W | 616 | 148 | 422 | 1173 | 8 |
| WAT | OH2 | W | 617 | 326 | 445 | 1302 | 8 |
| WAT | OH2 | W | 618 | 206 | 493 | 1305 | 8 |
| WAT | OH2 | W | 619 | 319 | 389 | 1158 | 8 |
| WAT | OH2 | W | 620 | 137 | 471 | 1161 | 8 |
| WAT | OH2 | W | 621 | 175 | 421 | 1231 | 8 |
| WAT | OH2 | W | 622 | 404 | 584 | 1522 | 8 |
| WAT | OH2 | W | 623 | 182 | 503 | 1198 | 8 |
| WAT | OH2 | W | 624 | 385 | 659 | 1291 | 9 |
| WAT | OH2 | W | 625 | 165 | 441 | 1202 | 9 |
| WAT | OH2 | W | 626 | 293 | 590 | 1275 | 9 |
| WAT | OH2 | W | 627 | 130 | 402 | 1177 | 9 |
| WAT | OH2 | W | 628 | 326 | 661 | 1325 | 9 |
| WAT | OH2 | W | 629 | 140 | 448 | 1179 | 9 |
| WAT | OH2 | W | 630 | 395 | 469 | 1296 | 9 |
| WAT | OH2 | W | 631 | 383 | 519 | 1249 | 9 |
| WAT | OH2 | W | 632 | 463 | 534 | 1389 | 9 |
| WAT | OH2 | W | 633 | 244 | 580 | 1278 | 9 |
| WAT | OH2 | W | 634 | 347 | 605 | 1270 | 9 |
| WAT | OH2 | W | 635 | 460 | 584 | 1446 | 10 |
| WAT | OH2 | W | 636 | 298 | 372 | 1153 | 10 |

TABLE 2-continued

Structure Coordinates for BACE complexed to Inhibitor

| | | | | | | | |
|---|---|---|---|---|---|---|---|
| WAT | OH2 | W | 637 | 148 | 507 | 1224 | 10 |
| WAT | OH2 | W | 638 | 519 | 570 | 1384 | 10 |
| WAT | OH2 | W | 639 | 182 | 529 | 1400 | 10 |
| WAT | OH2 | W | 640 | 124 | 455 | 1200 | 10 |
| WAT | OH2 | W | 641 | 167 | 477 | 1025 | 10 |
| WAT | OH2 | W | 642 | 402 | 467 | 1206 | 10 |
| WAT | OH2 | W | 643 | 404 | 508 | 1235 | 10 |
| WAT | OH2 | W | 644 | 435 | 547 | 1302 | 10 |
| WAT | OH2 | W | 645 | 291 | 493 | 1227 | 10 |
| WAT | OH2 | W | 646 | 489 | 519 | 1335 | 10 |
| WAT | OH2 | W | 647 | 406 | 490 | 1313 | 10 |
| WAT | OH2 | W | 648 | 205 | 563 | 1335 | 10 |
| WAT | OH2 | W | 649 | 497 | 543 | 1404 | 10 |
| WAT | OH2 | W | 650 | 392 | 484 | 1225 | 10 |
| WAT | OH2 | W | 651 | 397 | 546 | 1295 | 10 |
| WAT | OH2 | W | 652 | 255 | 585 | 1207 | 10 |
| WAT | OH2 | W | 653 | 134 | 428 | 1082 | 10 |
| WAT | OH2 | W | 654 | 206 | 651 | 1378 | 11 |
| WAT | OH2 | W | 655 | 165 | 547 | 1413 | 11 |
| WAT | OH2 | W | 656 | 284 | 538 | 1128 | 11 |
| WAT | OH2 | W | 657 | 361 | 437 | 1305 | 11 |
| WAT | OH2 | W | 658 | 351 | 631 | 1279 | 11 |
| WAT | OH2 | W | 659 | 415 | 460 | 1234 | 11 |
| WAT | OH2 | W | 660 | 389 | 464 | 1180 | 11 |
| WAT | OH2 | W | 661 | 518 | 573 | 1302 | 11 |
| WAT | OH2 | W | 662 | 131 | 456 | 1083 | 11 |
| WAT | OH2 | W | 663 | 435 | 687 | 1399 | 11 |
| WAT | OH2 | W | 664 | 159 | 418 | 1254 | 11 |
| WAT | OH2 | W | 665 | 324 | 635 | 1276 | 11 |
| WAT | OH2 | W | 666 | 415 | 530 | 1226 | 11 |
| WAT | OH2 | W | 667 | 234 | 592 | 1118 | 11 |
| WAT | OH2 | W | 668 | 213 | 634 | 1422 | 12 |
| WAT | OH2 | W | 669 | 459 | 537 | 1300 | 12 |
| WAT | OH2 | W | 670 | 475 | 470 | 1322 | 12 |
| WAT | OH2 | W | 671 | 112 | 468 | 1067 | 12 |
| WAT | OH2 | W | 672 | 530 | 618 | 1430 | 12 |
| WAT | OH2 | W | 673 | 279 | 573 | 1499 | 12 |
| WAT | OH2 | W | 674 | 364 | 395 | 1409 | 12 |
| WAT | OH2 | W | 675 | 299 | 670 | 1324 | 12 |
| WAT | OH2 | W | 676 | 433 | 607 | 1484 | 12 |
| WAT | OH2 | W | 677 | 118 | 420 | 1273 | 12 |
| WAT | OH2 | W | 678 | 506 | 512 | 1203 | 12 |
| WAT | OH2 | W | 679 | 393 | 640 | 1475 | 12 |
| WAT | OH2 | W | 680 | 404 | 514 | 1299 | 13 |
| WAT | OH2 | W | 681 | 377 | 558 | 1226 | 13 |
| WAT | OH2 | W | 682 | 201 | 387 | 1011 | 13 |
| WAT | OH2 | W | 683 | 333 | 422 | 1160 | 13 |
| WAT | OH2 | W | 684 | 212 | 655 | 1404 | 13 |
| WAT | OH2 | W | 685 | 331 | 420 | 1133 | 13 |
| WAT | OH2 | W | 686 | 209 | 466 | 1422 | 13 |
| WAT | OH2 | W | 687 | 482 | 527 | 1309 | 13 |
| WAT | OH2 | W | 688 | 372 | 541 | 1536 | 13 |
| WAT | OH2 | W | 689 | 230 | 607 | 1307 | 13 |
| WAT | OH2 | W | 690 | 349 | 618 | 1484 | 13 |
| WAT | OH2 | W | 691 | 312 | 519 | 1241 | 13 |
| WAT | OH2 | W | 692 | 77 | 486 | 1072 | 14 |
| WAT | OH2 | W | 693 | 413 | 432 | 1427 | 14 |
| WAT | OH2 | W | 694 | 385 | 398 | 1426 | 14 |
| WAT | OH2 | W | 695 | 67 | 410 | 1033 | 14 |
| WAT | OH2 | W | 696 | 326 | 666 | 1471 | 14 |
| WAT | OH2 | W | 697 | 289 | 630 | 1282 | 14 |
| WAT | OH2 | W | 698 | 414 | 521 | 1272 | 14 |
| WAT | OH2 | W | 699 | 512 | 548 | 1312 | 14 |
| WAT | OH2 | W | 700 | 389 | 422 | 1437 | 14 |
| WAT | OH2 | W | 701 | 424 | 707 | 1382 | 14 |
| WAT | OH2 | W | 702 | 257 | 400 | 1463 | 15 |
| WAT | OH2 | W | 703 | 197 | 625 | 1367 | 15 |
| WAT | OH2 | W | 704 | 267 | 685 | 1448 | 15 |
| WAT | OH2 | W | 705 | 395 | 615 | 1481 | 15 |
| WAT | OH2 | W | 706 | 336 | 511 | 1169 | 15 |
| WAT | OH2 | W | 707 | 449 | 609 | 1444 | 15 |
| WAT | OH2 | W | 708 | 292 | 696 | 1453 | 15 |
| WAT | OH2 | W | 709 | 428 | 706 | 1418 | 15 |
| WAT | OH2 | W | 710 | 350 | 654 | 1243 | 15 |
| WAT | OH2 | W | 711 | 414 | 621 | 1498 | 16 |
| WAT | OH2 | W | 712 | 290 | 694 | 1336 | 16 |
| WAT | OH2 | W | 713 | 192 | 609 | 1073 | 16 |
| WAT | OH2 | W | 714 | -10 | 460 | 1073 | 16 |
| WAT | OH2 | W | 715 | 374 | 535 | 1474 | 16 |
| WAT | OH2 | W | 716 | 468 | 575 | 1257 | 16 |
| WAT | OH2 | W | 717 | 341 | 627 | 1242 | 16 |
| WAT | OH2 | W | 718 | 268 | 377 | 1448 | 16 |
| WAT | OH2 | W | 719 | 452 | 465 | 1208 | 16 |
| WAT | OH2 | W | 720 | 486 | 658 | 1478 | 17 |
| WAT | OH2 | W | 721 | 72 | 412 | 1180 | 17 |
| WAT | OH2 | W | 722 | 373 | 404 | 1178 | 17 |
| WAT | OH2 | W | 723 | 406 | 379 | 1282 | 17 |
| WAT | OH2 | W | 724 | 142 | 377 | 1308 | 17 |
| WAT | OH2 | W | 725 | 224 | 395 | 998 | 17 |
| WAT | OH2 | W | 726 | 204 | 575 | 1309 | 17 |
| WAT | OH2 | W | 727 | 409 | 392 | 1410 | 17 |
| WAT | OH2 | W | 728 | -9 | 504 | 1079 | 17 |
| WAT | OH2 | W | 729 | 102 | 346 | 1192 | 17 |
| WAT | OH2 | W | 730 | 359 | 402 | 1485 | 17 |
| WAT | OH2 | W | 731 | 531 | 564 | 1341 | 17 |
| WAT | OH2 | W | 732 | 205 | 570 | 1078 | 17 |
| WAT | OH2 | W | 733 | 386 | 535 | 1272 | 17 |
| WAT | OH2 | W | 734 | 138 | 556 | 1227 | 17 |
| WAT | OH2 | W | 735 | 259 | 583 | 1180 | 17 |
| WAT | OH2 | W | 736 | 381 | 705 | 1447 | 17 |
| WAT | OH2 | W | 737 | 418 | 546 | 1484 | 17 |
| WAT | OH2 | W | 738 | 104 | 396 | 1009 | 18 |
| WAT | OH2 | W | 739 | 533 | 567 | 1208 | 18 |
| WAT | OH2 | W | 740 | 248 | 339 | 1366 | 18 |
| WAT | OH2 | W | 741 | 501 | 478 | 1163 | 18 |
| WAT | OH2 | W | 742 | 318 | 470 | 1085 | 18 |
| WAT | OH2 | W | 743 | 322 | 705 | 1409 | 18 |
| WAT | OH2 | W | 744 | 349 | 346 | 1186 | 18 |
| WAT | OH2 | W | 745 | 124 | 409 | 997 | 18 |
| WAT | OH2 | W | 746 | 450 | 622 | 1470 | 18 |
| WAT | OH2 | W | 747 | 75 | 421 | 1231 | 18 |
| WAT | OH2 | W | 748 | 217 | 579 | 1524 | 18 |
| WAT | OH2 | W | 749 | 84 | 544 | 1171 | 18 |
| WAT | OH2 | W | 750 | 214 | 630 | 1303 | 18 |
| WAT | OH2 | W | 751 | 340 | 638 | 1500 | 18 |
| WAT | OH2 | W | 752 | 516 | 520 | 1338 | 18 |
| WAT | OH2 | W | 753 | 82 | 513 | 1249 | 19 |
| WAT | OH2 | W | 754 | 175 | 626 | 1097 | 19 |
| WAT | OH2 | W | 755 | 209 | 321 | 1352 | 19 |
| WAT | OH2 | W | 756 | 141 | 544 | 1387 | 19 |
| WAT | OH2 | W | 757 | 71 | 513 | 1068 | 19 |
| WAT | OH2 | W | 758 | 372 | 623 | 1218 | 19 |
| WAT | OH2 | W | 759 | 124 | 512 | 1386 | 19 |
| WAT | OH2 | W | 760 | 101 | 340 | 1047 | 19 |
| WAT | OH2 | W | 761 | 561 | 622 | 1244 | 19 |
| WAT | OH2 | W | 762 | 166 | 398 | 1417 | 19 |
| WAT | OH2 | W | 763 | 404 | 365 | 1259 | 19 |
| WAT | OH2 | W | 764 | 532 | 548 | 1264 | 19 |
| WAT | OH2 | W | 765 | 245 | 364 | 1448 | 19 |
| WAT | OH2 | W | 766 | 179 | 621 | 1207 | 20 |
| WAT | OH2 | W | 767 | 343 | 619 | 1217 | 20 |
| WAT | OH2 | W | 768 | 481 | 687 | 1278 | 20 |
| WAT | OH2 | W | 769 | 209 | 503 | 1629 | 20 |
| WAT | OH2 | W | 770 | 277 | 549 | 1535 | 20 |
| WAT | OH2 | W | 771 | 74 | 350 | 1045 | 20 |
| WAT | OH2 | W | 772 | 92 | 407 | 1248 | 20 |
| WAT | OH2 | W | 773 | 483 | 555 | 1273 | 20 |
| WAT | OH2 | W | 774 | 440 | 373 | 1193 | 20 |
| WAT | OH2 | W | 775 | 78 | 461 | 1014 | 20 |
| WAT | OH2 | W | 776 | 489 | 492 | 1185 | 20 |
| WAT | OH2 | W | 777 | 209 | 357 | 1081 | 20 |
| WAT | OH2 | W | 778 | 375 | 378 | 1445 | 20 |
| WAT | OH2 | W | 779 | 370 | 481 | 1149 | 20 |
| WAT | OH2 | W | 780 | 446 | 481 | 1441 | 21 |
| WAT | OH2 | W | 781 | 401 | 549 | 1239 | 21 |
| WAT | OH2 | W | 782 | 529 | 539 | 1351 | 21 |
| WAT | OH2 | W | 783 | 457 | 464 | 1165 | 21 |
| WAT | OH2 | W | 784 | 265 | 431 | 1040 | 21 |
| WAT | OH2 | W | 785 | 473 | 486 | 1283 | 21 |
| WAT | OH2 | W | 786 | 241 | 440 | 1024 | 21 |
| WAT | OH2 | W | 787 | 204 | 544 | 1067 | 21 |
| WAT | OH2 | W | 788 | 416 | 360 | 1198 | 21 |
| WAT | OH2 | W | 789 | 387 | 485 | 1462 | 21 |
| WAT | OH2 | W | 790 | 228 | 645 | 1496 | 21 |

TABLE 2-continued

Structure Coordinates for BACE complexed to Inhibitor

| | | | | | | | |
|---|---|---|---|---|---|---|---|
| WAT | OH2 | W | 791 | 160 | 292 | 1259 | 21 |
| WAT | OH2 | W | 792 | 257 | 607 | 1120 | 21 |
| WAT | OH2 | W | 793 | 274 | 608 | 1220 | 21 |
| WAT | OH2 | W | 794 | 248 | 400 | 1491 | 21 |
| WAT | OH2 | W | 795 | 437 | 428 | 1334 | 21 |
| WAT | OH2 | W | 796 | 234 | 511 | 1623 | 22 |
| WAT | OH2 | W | 797 | 101 | 472 | 1024 | 22 |
| WAT | OH2 | W | 798 | 343 | 439 | 1094 | 22 |
| WAT | OH2 | W | 799 | 278 | 294 | 1317 | 22 |
| WAT | OH2 | W | 800 | 313 | 621 | 1195 | 22 |
| WAT | OH2 | W | 801 | 440 | 420 | 1198 | 22 |
| WAT | OH2 | W | 802 | 82 | 438 | 1000 | 22 |
| WAT | OH2 | W | 803 | 144 | 329 | 1322 | 22 |
| WAT | OH2 | W | 804 | 184 | 360 | 1418 | 22 |
| WAT | OH2 | W | 805 | 547 | 656 | 1304 | 22 |
| WAT | OH2 | W | 806 | 346 | 716 | 1412 | 22 |
| WAT | OH2 | W | 807 | 306 | 687 | 1474 | 22 |
| WAT | OH2 | W | 808 | 195 | 674 | 1413 | 22 |
| WAT | OH2 | W | 809 | 121 | 350 | 1256 | 22 |
| WAT | OH2 | W | 810 | 186 | 394 | 1435 | 22 |
| WAT | OH2 | W | 811 | 276 | 403 | 1033 | 22 |
| WAT | OH2 | W | 812 | 234 | 327 | 1160 | 22 |
| WAT | OH2 | W | 813 | 56 | 490 | 1038 | 22 |
| WAT | OH2 | W | 814 | 48 | 426 | 1160 | 22 |
| WAT | OH2 | W | 815 | 99 | 447 | 1296 | 22 |
| WAT | OH2 | W | 816 | 142 | 319 | 973 | 23 |
| WAT | OH2 | W | 817 | 189 | 302 | 1360 | 23 |
| WAT | OH2 | W | 818 | 316 | 660 | 1279 | 23 |
| WAT | OH2 | W | 819 | 299 | 505 | 1070 | 23 |
| WAT | OH2 | W | 820 | 425 | 386 | 1233 | 23 |
| WAT | OH2 | W | 821 | 323 | 336 | 1417 | 23 |
| WAT | OH2 | W | 822 | 330 | 527 | 1095 | 23 |
| WAT | OH2 | W | 823 | 43 | 457 | 1019 | 23 |
| WAT | OH2 | W | 824 | 540 | 576 | 1368 | 23 |
| WAT | OH2 | W | 825 | 105 | 439 | 1363 | 23 |
| WAT | OH2 | W | 826 | 117 | 540 | 1248 | 23 |
| WAT | OH2 | W | 827 | 540 | 610 | 1402 | 23 |
| WAT | OH2 | W | 828 | 12 | 432 | 1076 | 23 |
| WAT | OH2 | W | 829 | 362 | 523 | 1166 | 23 |
| WAT | OH2 | W | 830 | 282 | 596 | 1186 | 23 |
| WAT | OH2 | W | 831 | 321 | 420 | 1090 | 23 |
| WAT | OH2 | W | 832 | 119 | 580 | 1457 | 23 |
| WAT | OH2 | W | 833 | 33 | 410 | 1125 | 23 |
| WAT | OH2 | W | 834 | 417 | 360 | 1295 | 23 |
| WAT | OH2 | W | 835 | 280 | 329 | 1390 | 24 |
| WAT | OH2 | W | 836 | 79 | 370 | 1135 | 24 |
| WAT | OH2 | W | 837 | 205 | 692 | 1157 | 24 |
| WAT | OH2 | W | 838 | 475 | 597 | 1232 | 24 |
| WAT | OH2 | W | 839 | 222 | 673 | 1345 | 24 |
| WAT | OH2 | W | 840 | 241 | 536 | 1520 | 24 |
| WAT | OH2 | W | 841 | 357 | 393 | 1457 | 24 |
| WAT | OH2 | W | 842 | 304 | 519 | 1095 | 24 |
| WAT | OH2 | W | 843 | 488 | 504 | 1297 | 24 |
| WAT | OH2 | W | 844 | 277 | 504 | 1524 | 24 |
| WAT | OH2 | W | 845 | 273 | 578 | 1537 | 24 |
| WAT | OH2 | W | 846 | 185 | 661 | 1435 | 24 |
| WAT | OH2 | W | 847 | 319 | 652 | 1492 | 24 |
| WAT | OH2 | W | 848 | 98 | 360 | 1030 | 24 |
| WAT | OH2 | W | 849 | 12 | 481 | 1022 | 24 |
| WAT | OH2 | W | 850 | 50 | 501 | 1256 | 24 |
| WAT | OH2 | W | 851 | 427 | 411 | 1416 | 24 |
| WAT | OH2 | W | 852 | 327 | 551 | 1083 | 24 |
| WAT | OH2 | W | 853 | 173 | 360 | 981 | 24 |
| WAT | OH2 | W | 854 | 261 | 326 | 1110 | 24 |
| WAT | OH2 | W | 855 | 146 | 362 | 1272 | 24 |
| WAT | OH2 | W | 856 | 269 | 663 | 1299 | 25 |
| WAT | OH2 | W | 857 | 66 | 309 | 1088 | 25 |
| WAT | OH2 | W | 858 | 534 | 531 | 1375 | 25 |
| WAT | OH2 | W | 859 | 247 | 383 | 1008 | 25 |
| WAT | OH2 | W | 860 | 159 | 460 | 1437 | 25 |
| WAT | OH2 | W | 861 | 272 | 713 | 1367 | 25 |
| WAT | OH2 | W | 862 | 39 | 538 | 1107 | 25 |
| WAT | OH2 | W | 863 | 178 | 572 | 1300 | 25 |
| WAT | OH2 | W | 864 | 201 | 636 | 1197 | 25 |
| WAT | OH2 | W | 865 | 153 | 394 | 1337 | 25 |
| WAT | OH2 | W | 866 | 134 | 612 | 1104 | 25 |
| WAT | OH2 | W | 867 | 202 | 653 | 1491 | 25 |
| WAT | OH2 | W | 868 | 198 | 638 | 1283 | 25 |
| WAT | OH2 | W | 869 | 56 | 405 | 1220 | 25 |
| WAT | OH2 | W | 870 | 463 | 467 | 1257 | 25 |
| WAT | OH2 | W | 871 | 592 | 597 | 1277 | 26 |
| WAT | OH2 | W | 872 | 353 | 592 | 1198 | 26 |
| WAT | OH2 | W | 873 | 253 | 296 | 1237 | 26 |
| WAT | OH2 | W | 874 | 438 | 402 | 1217 | 26 |
| WAT | OH2 | W | 875 | 151 | 422 | 1416 | 26 |
| WAT | OH2 | W | 876 | 494 | 615 | 1213 | 26 |
| WAT | OH2 | W | 877 | 341 | 386 | 1142 | 26 |
| WAT | OH2 | W | 878 | 295 | 541 | 1105 | 26 |
| WAT | OH2 | W | 879 | 394 | 751 | 1295 | 26 |
| WAT | OH2 | W | 880 | 499 | 677 | 1317 | 26 |
| WAT | OH2 | W | 881 | 401 | 337 | 1269 | 26 |
| WAT | OH2 | W | 882 | 255 | 465 | 1011 | 26 |
| WAT | OH2 | W | 883 | 521 | 548 | 1394 | 26 |
| WAT | OH2 | W | 884 | 146 | 570 | 1306 | 26 |
| WAT | OH2 | W | 885 | 210 | 308 | 1328 | 26 |
| WAT | OH2 | W | 886 | 427 | 396 | 1274 | 26 |
| WAT | OH2 | W | 887 | 398 | 410 | 1164 | 26 |
| WAT | OH2 | W | 888 | 465 | 479 | 1186 | 27 |
| WAT | OH2 | W | 889 | 365 | 722 | 1433 | 27 |
| WAT | OH2 | W | 890 | 414 | 552 | 1202 | 27 |
| WAT | OH2 | W | 891 | 30 | 514 | 1159 | 27 |
| WAT | OH2 | W | 892 | 494 | 681 | 1342 | 27 |
| WAT | OH2 | W | 893 | 155 | 624 | 1138 | 27 |
| WAT | OH2 | W | 894 | 405 | 767 | 1328 | 27 |
| WAT | OH2 | W | 895 | 126 | 388 | 1290 | 27 |
| WAT | OH2 | W | 896 | 495 | 491 | 1319 | 27 |
| WAT | OH2 | W | 897 | 272 | 305 | 1148 | 27 |
| WAT | OH2 | W | 898 | 312 | 606 | 1130 | 27 |
| WAT | OH2 | W | 899 | 72 | 584 | 1176 | 27 |
| WAT | OH2 | W | 900 | 86 | 379 | 1242 | 27 |
| WAT | OH2 | W | 901 | 48 | 527 | 1142 | 27 |
| WAT | OH2 | W | 902 | 417 | 342 | 1232 | 27 |
| WAT | OH2 | W | 903 | 175 | 579 | 1509 | 27 |
| WAT | OH2 | W | 904 | 498 | 720 | 1376 | 27 |
| WAT | OH2 | W | 905 | 410 | 711 | 1443 | 27 |
| WAT | OH2 | W | 906 | 187 | 670 | 1369 | 27 |
| WAT | OH2 | W | 907 | 350 | 723 | 1345 | 27 |
| WAT | OH2 | W | 908 | 402 | 489 | 1510 | 27 |
| WAT | OH2 | W | 909 | 398 | 736 | 1363 | 27 |
| WAT | OH2 | W | 910 | 356 | 674 | 1480 | 27 |
| WAT | OH2 | W | 911 | 121 | 465 | 1006 | 27 |
| WAT | OH2 | W | 912 | 162 | 610 | 1117 | 27 |
| WAT | OH2 | W | 913 | 403 | 572 | 1213 | 28 |
| WAT | OH2 | W | 914 | 545 | 603 | 1364 | 28 |
| WAT | OH2 | W | 915 | 286 | 365 | 1466 | 28 |
| WAT | OH2 | W | 916 | 308 | 646 | 1238 | 28 |
| WAT | OH2 | W | 917 | 96 | 554 | 1088 | 28 |
| WAT | OH2 | W | 918 | 376 | 331 | 1394 | 28 |
| WAT | OH2 | W | 919 | 575 | 572 | 1339 | 28 |
| WAT | OH2 | W | 920 | 522 | 643 | 1437 | 28 |
| WAT | OH2 | W | 921 | 335 | 362 | 1105 | 28 |
| WAT | OH2 | W | 922 | 379 | 326 | 1205 | 28 |
| WAT | OH2 | W | 923 | 74 | 539 | 1074 | 28 |
| WAT | OH2 | W | 924 | 356 | 549 | 1285 | 28 |
| WAT | OH2 | W | 925 | 295 | 367 | 1081 | 28 |
| WAT | OH2 | W | 926 | 238 | 561 | 1527 | 28 |
| WAT | OH2 | W | 927 | 413 | 727 | 1396 | 28 |
| WAT | OH2 | W | 928 | 256 | 617 | 1189 | 28 |
| WAT | OH2 | W | 929 | 513 | 477 | 1302 | 28 |
| WAT | OH2 | W | 930 | 220 | 612 | 1080 | 29 |
| WAT | OH2 | W | 931 | 179 | 311 | 1047 | 29 |
| WAT | OH2 | W | 932 | 343 | 379 | 1515 | 29 |
| WAT | OH2 | W | 933 | 100 | 384 | 1143 | 29 |
| WAT | OH2 | W | 934 | 256 | 577 | 1516 | 29 |
| WAT | OH2 | W | 935 | 111 | 558 | 1062 | 29 |
| WAT | OH2 | W | 936 | 395 | 415 | 1462 | 29 |
| WAT | OH2 | W | 937 | 181 | 302 | 1312 | 29 |
| WAT | OH2 | W | 938 | 419 | 586 | 1195 | 29 |
| WAT | OH2 | W | 939 | 155 | 633 | 1215 | 29 |
| WAT | OH2 | W | 940 | 374 | 571 | 1202 | 30 |
| WAT | OH2 | W | 941 | 282 | 609 | 1144 | 30 |
| WAT | OH2 | W | 942 | 104 | 370 | 1262 | 30 |
| WAT | OH2 | W | 943 | 419 | 486 | 1484 | 30 |
| WAT | OH2 | W | 944 | 182 | 594 | 1049 | 30 |

TABLE 2-continued

Structure Coordinates for BACE complexed to Inhibitor

| | | | | | | | |
|---|---|---|---|---|---|---|---|
| WAT | OH2 | W | 945 | 377 | 327 | 1366 | 30 |
| WAT | OH2 | W | 946 | 97 | 499 | 1023 | 30 |
| WAT | OH2 | W | 947 | 374 | 297 | 1267 | 30 |
| WAT | OH2 | W | 948 | 165 | 652 | 1307 | 30 |
| WAT | OH2 | W | 949 | 335 | 315 | 1164 | 30 |
| WAT | OH2 | W | 950 | 333 | 702 | 1355 | 30 |
| WAT | OH2 | W | 951 | 381 | 671 | 1211 | 30 |
| WAT | OH2 | W | 952 | 177 | 475 | 1563 | 30 |
| WAT | OH2 | W | 953 | 410 | 340 | 1401 | 30 |
| WAT | OH2 | W | 954 | 272 | 371 | 1045 | 31 |
| WAT | OH2 | W | 955 | 414 | 690 | 1235 | 31 |
| WAT | OH2 | W | 956 | 364 | 730 | 1365 | 31 |
| WAT | OH2 | W | 957 | 306 | 710 | 1351 | 31 |
| WAT | OH2 | W | 958 | 360 | 476 | 1074 | 31 |
| WAT | OH2 | W | 959 | 198 | 687 | 1350 | 31 |
| WAT | OH2 | W | 960 | 191 | 568 | 1529 | 31 |
| WAT | OH2 | W | 961 | 341 | 597 | 1175 | 31 |
| WAT | OH2 | W | 962 | 209 | 584 | 1054 | 31 |
| WAT | OH2 | W | 963 | 296 | 674 | 1299 | 31 |
| WAT | OH2 | W | 964 | 204 | 436 | 1494 | 31 |
| WAT | OH2 | W | 965 | 25 | 473 | 997 | 31 |
| WAT | OH2 | W | 966 | 31 | 489 | 1173 | 32 |
| WAT | OH2 | W | 967 | 446 | 408 | 1288 | 32 |
| WAT | OH2 | W | 968 | 139 | 342 | 959 | 32 |
| WAT | OH2 | W | 969 | 470 | 475 | 1125 | 32 |
| WAT | OH2 | W | 970 | 328 | 411 | 1061 | 32 |
| WAT | OH2 | W | 971 | 415 | 346 | 1338 | 32 |
| WAT | OH2 | W | 972 | 333 | 387 | 1078 | 32 |
| WAT | OH2 | W | 973 | 494 | 454 | 1332 | 32 |
| WAT | OH2 | W | 974 | 169 | 630 | 1367 | 32 |
| WAT | OH2 | W | 975 | 225 | 308 | 1368 | 32 |
| WAT | OH2 | W | 976 | 360 | 446 | 1065 | 32 |
| WAT | OH2 | W | 977 | 62 | 502 | 1278 | 32 |
| WAT | OH2 | W | 978 | 426 | 438 | 1449 | 33 |
| WAT | OH2 | W | 979 | 179 | 623 | 1273 | 33 |
| WAT | OH2 | W | 980 | 454 | 706 | 1481 | 33 |
| WAT | OH2 | W | 981 | 340 | 422 | 1541 | 33 |
| WAT | OH2 | W | 982 | 336 | 738 | 1379 | 33 |
| WAT | OH2 | W | 983 | 205 | 637 | 1171 | 33 |
| WAT | OH2 | W | 984 | 526 | 674 | 1312 | 33 |
| WAT | OH2 | W | 985 | 297 | 328 | 1412 | 33 |
| WAT | OH2 | W | 986 | 581 | 497 | 1422 | 33 |
| WAT | OH2 | W | 987 | 205 | 317 | 1027 | 33 |
| WAT | OH2 | W | 988 | 148 | 376 | 1416 | 33 |
| WAT | OH2 | W | 989 | 154 | 656 | 1432 | 33 |
| WAT | OH2 | W | 990 | 186 | 464 | 1437 | 33 |
| WAT | OH2 | W | 991 | 278 | 488 | 1584 | 33 |
| WAT | OH2 | W | 992 | 40 | 416 | 1185 | 33 |
| WAT | OH2 | W | 993 | 62 | 547 | 1154 | 33 |
| WAT | OH2 | W | 994 | 154 | 379 | 968 | 33 |
| WAT | OH2 | W | 995 | 108 | 444 | 1390 | 34 |
| WAT | OH2 | W | 996 | 398 | 318 | 1224 | 34 |
| WAT | OH2 | W | 997 | 290 | 656 | 1280 | 34 |
| WAT | OH2 | W | 998 | 584 | 609 | 1231 | 34 |
| WAT | OH2 | W | 999 | 75 | 509 | 1042 | 34 |
| WAT | OH2 | W | 1000 | 352 | 508 | 1084 | 34 |
| WAT | OH2 | W | 1001 | 356 | 406 | 1157 | 34 |
| WAT | OH2 | W | 1002 | 403 | 543 | 1154 | 34 |
| WAT | OH2 | W | 1003 | 162 | 571 | 1031 | 34 |
| WAT | OH2 | W | 1004 | 243 | 640 | 1264 | 34 |
| WAT | OH2 | W | 1005 | 364 | 729 | 1265 | 34 |
| WAT | OH2 | W | 1006 | 251 | 313 | 1359 | 35 |
| WAT | OH2 | W | 1007 | 186 | 276 | 1145 | 35 |
| WAT | OH2 | W | 1008 | 250 | 321 | 1422 | 35 |
| WAT | OH2 | W | 1009 | 463 | 568 | 1172 | 35 |
| WAT | OH2 | W | 1010 | 336 | 746 | 1338 | 35 |
| WAT | OH2 | W | 1011 | 506 | 465 | 1352 | 35 |
| WAT | OH2 | W | 1012 | 121 | 383 | 1365 | 35 |
| WAT | OH2 | W | 1013 | 107 | 497 | 1402 | 35 |
| WAT | OH2 | W | 1014 | 362 | 506 | 1145 | 35 |
| WAT | OH2 | W | 1015 | 310 | 361 | 1456 | 35 |
| WAT | OH2 | W | 1016 | 111 | 620 | 1385 | 35 |
| WAT | OH2 | W | 1017 | 340 | 399 | 1119 | 35 |
| WAT | OH2 | W | 1018 | 517 | 661 | 1406 | 35 |
| WAT | OH2 | W | 1019 | 129 | 540 | 1474 | 35 |
| WAT | OH2 | W | 1020 | 90 | 639 | 1387 | 36 |
| WAT | OH2 | W | 1021 | 186 | 637 | 1238 | 36 |
| WAT | OH2 | W | 1022 | 71 | 358 | 1209 | 36 |
| WAT | OH2 | W | 1023 | 98 | 603 | 1214 | 36 |
| WAT | OH2 | W | 1024 | 417 | 371 | 1424 | 36 |
| WAT | OH2 | W | 1025 | 387 | 577 | 1177 | 36 |
| WAT | OH2 | W | 1026 | 560 | 649 | 1220 | 36 |
| WAT | OH2 | W | 1027 | 487 | 735 | 1485 | 36 |
| WAT | OH2 | W | 1028 | 116 | 541 | 1383 | 36 |
| WAT | OH2 | W | 1029 | 484 | 704 | 1337 | 36 |
| WAT | OH2 | W | 1030 | 66 | 552 | 1203 | 36 |
| WAT | OH2 | W | 1031 | 100 | 372 | 1168 | 36 |
| WAT | OH2 | W | 1032 | 307 | 736 | 1344 | 37 |
| WAT | OH2 | W | 1033 | 216 | 646 | 1257 | 37 |
| WAT | OH2 | W | 1034 | 148 | 593 | 1290 | 37 |
| WAT | OH2 | W | 1035 | 175 | 512 | 1599 | 37 |
| WAT | OH2 | W | 1036 | 287 | 344 | 1431 | 37 |
| WAT | OH2 | W | 1037 | 263 | 542 | 1019 | 37 |
| WAT | OH2 | W | 1038 | 379 | 402 | 1132 | 37 |
| WAT | OH2 | W | 1039 | 315 | 670 | 1254 | 37 |
| WAT | OH2 | W | 1040 | 87 | 566 | 1189 | 37 |
| WAT | OH2 | W | 1041 | 162 | 627 | 1479 | 37 |
| WAT | OH2 | W | 1042 | 439 | 360 | 1338 | 37 |
| WAT | OH2 | W | 1043 | 148 | 604 | 1326 | 37 |
| WAT | OH2 | W | 1044 | 336 | 625 | 1176 | 37 |
| WAT | OH2 | W | 1045 | 83 | 327 | 1192 | 37 |
| WAT | OH2 | W | 1046 | 34 | 505 | 1049 | 37 |
| WAT | OH2 | W | 1047 | 459 | 743 | 1338 | 37 |
| WAT | OH2 | W | 1048 | 163 | 483 | 1524 | 37 |
| WAT | OH2 | W | 1049 | 178 | 387 | 950 | 37 |
| WAT | OH2 | W | 1050 | 140 | 485 | 1445 | 38 |
| WAT | OH2 | W | 1051 | 129 | 456 | 1427 | 38 |
| WAT | OH2 | W | 1052 | 427 | 463 | 1450 | 38 |
| WAT | OH2 | W | 1053 | 375 | 288 | 1301 | 38 |
| WAT | OH2 | W | 1054 | 79 | 602 | 1155 | 38 |
| WAT | OH2 | W | 1055 | 555 | 529 | 1343 | 38 |
| WAT | OH2 | W | 1056 | 183 | 674 | 1157 | 38 |
| WAT | OH2 | W | 1057 | 450 | 393 | 1325 | 38 |
| WAT | OH2 | W | 1058 | 289 | 628 | 1207 | 38 |
| WAT | OH2 | W | 1059 | 546 | 437 | 1409 | 38 |
| WAT | OH2 | W | 1060 | 231 | 318 | 1080 | 38 |
| WAT | OH2 | W | 1061 | 75 | 514 | 1457 | 38 |
| WAT | OH2 | W | 1062 | 272 | 280 | 1225 | 38 |
| WAT | OH2 | W | 1063 | 437 | 420 | 1392 | 38 |
| WAT | OH2 | W | 1064 | 508 | 671 | 1230 | 38 |
| WAT | OH2 | W | 1065 | 402 | 415 | 1133 | 38 |
| WAT | OH2 | W | 1066 | 275 | 634 | 1182 | 39 |
| WAT | OH2 | W | 1067 | 498 | 584 | 1196 | 39 |
| WAT | OH2 | W | 1068 | 0 | 529 | 1051 | 39 |
| WAT | OH2 | W | 1069 | 335 | 441 | 1052 | 39 |
| WAT | OH2 | W | 1070 | 320 | 437 | 1560 | 39 |
| WAT | OH2 | W | 1071 | 429 | 747 | 1371 | 39 |
| WAT | OH2 | W | 1072 | 190 | 259 | 1204 | 39 |
| WAT | OH2 | W | 1073 | 223 | 648 | 1525 | 39 |
| WAT | OH2 | W | 1074 | 173 | 405 | 1491 | 39 |
| WAT | OH2 | W | 1075 | 123 | 572 | 1322 | 39 |
| WAT | OH2 | W | 1076 | 98 | 568 | 1331 | 39 |
| WAT | OH2 | W | 1077 | 241 | 370 | 962 | 39 |
| WAT | OH2 | W | 1078 | 186 | 447 | 1521 | 39 |
| WAT | OH2 | W | 1079 | 166 | 631 | 1454 | 39 |
| WAT | OH2 | W | 1080 | 198 | 489 | 980 | 39 |
| WAT | OH2 | W | 1081 | 237 | 422 | 1000 | 39 |
| WAT | OH2 | W | 1082 | 253 | 267 | 1202 | 39 |
| WAT | OH2 | W | 1083 | 394 | 310 | 1251 | 39 |
| WAT | OH2 | W | 1084 | 270 | 679 | 1173 | 39 |
| WAT | OH2 | W | 1085 | 203 | 332 | 1072 | 39 |
| WAT | OH2 | W | 1086 | 254 | 284 | 1302 | 39 |
| WAT | OH2 | W | 1087 | 276 | 344 | 1056 | 40 |
| WAT | OH2 | W | 1088 | 428 | 440 | 1100 | 40 |
| WAT | OH2 | W | 1089 | 264 | 527 | 1532 | 40 |
| WAT | OH2 | W | 1090 | 533 | 573 | 1180 | 40 |
| WAT | OH2 | W | 1091 | 176 | 398 | 1464 | 40 |
| WAT | OH2 | W | 1092 | 256 | 351 | 1019 | 40 |
| WAT | OH2 | W | 1093 | 456 | 463 | 1475 | 40 |
| WAT | OH2 | W | 1094 | 302 | 289 | 1337 | 40 |
| WAT | OH2 | W | 1095 | 152 | 543 | 1020 | 40 |
| WAT | OH2 | W | 1096 | 130 | 337 | 1344 | 40 |
| WAT | OH2 | W | 1097 | 128 | 631 | 1202 | 40 |
| WAT | OH2 | W | 1098 | 158 | 636 | 1284 | 40 |

TABLE 2-continued

Structure Coordinates for BACE complexed to Inhibitor

| WAT | OH2 | W | 1099 | 544 | 629 | 1350 | 40 |
|---|---|---|---|---|---|---|---|
| WAT | OH2 | W | 1100 | 120 | 612 | 1360 | 41 |
| WAT | OH2 | W | 1101 | 484 | 701 | 1461 | 41 |
| WAT | OH2 | W | 1102 | 385 | 408 | 1488 | 41 |
| WAT | OH2 | W | 1103 | 487 | 565 | 1151 | 41 |
| WAT | OH2 | W | 1104 | 48 | 372 | 1120 | 41 |
| WAT | OH2 | W | 1105 | 568 | 655 | 1263 | 41 |
| WAT | OH2 | W | 1106 | 124 | 568 | 1367 | 41 |
| WAT | OH2 | W | 1107 | 215 | 248 | 1263 | 41 |
| WAT | OH2 | W | 1108 | 124 | 277 | 1169 | 41 |
| WAT | OH2 | W | 1109 | 255 | 364 | 987 | 41 |
| WAT | OH2 | W | 1110 | 361 | 359 | 1162 | 42 |
| WAT | OH2 | W | 1111 | 524 | 446 | 1408 | 42 |
| WAT | OH2 | W | 1112 | 237 | 515 | 1555 | 42 |
| WAT | OH2 | W | 1113 | 285 | 673 | 1488 | 42 |
| WAT | OH2 | W | 1114 | 410 | 463 | 1491 | 42 |
| WAT | OH2 | W | 1115 | 430 | 572 | 1175 | 42 |
| WAT | OH2 | W | 1116 | 436 | 702 | 1290 | 42 |
| WAT | OH2 | W | 1117 | 557 | 470 | 1354 | 42 |
| WAT | OH2 | W | 1118 | 235 | 296 | 1430 | 42 |
| WAT | OH2 | W | 1119 | 260 | 340 | 1436 | 42 |
| WAT | OH2 | W | 1120 | 332 | 321 | 1398 | 42 |
| WAT | OH2 | W | 1121 | 388 | 368 | 1176 | 42 |
| WAT | OH2 | W | 1122 | 127 | 279 | 1243 | 42 |
| WAT | OH2 | W | 1123 | 364 | 401 | 1105 | 43 |
| WAT | OH2 | W | 1124 | 102 | 467 | 1399 | 43 |
| WAT | OH2 | W | 1125 | 561 | 633 | 1198 | 43 |
| WAT | OH2 | W | 1126 | 125 | 386 | 979 | 43 |
| WAT | OH2 | W | 1127 | 273 | 508 | 1003 | 43 |
| WAT | OH2 | W | 1128 | 361 | 574 | 1076 | 43 |
| WAT | OH2 | W | 1129 | 258 | 304 | 1331 | 43 |
| WAT | OH2 | W | 1130 | 432 | 414 | 1356 | 43 |
| WAT | OH2 | W | 1131 | 436 | 383 | 1168 | 43 |
| WAT | OH2 | W | 1132 | 178 | 268 | 1281 | 43 |
| WAT | OH2 | W | 1133 | 251 | 644 | 1198 | 43 |
| WAT | OH2 | W | 1134 | 124 | 617 | 1234 | 44 |
| WAT | OH2 | W | 1135 | 268 | 490 | 969 | 44 |
| WAT | OH2 | W | 1136 | 183 | 686 | 1391 | 44 |
| WAT | OH2 | W | 1137 | 52 | 538 | 1236 | 44 |
| WAT | OH2 | W | 1138 | 427 | 339 | 1281 | 44 |
| WAT | OH2 | W | 1139 | 88 | 542 | 1246 | 44 |
| WAT | OH2 | W | 1140 | 507 | 713 | 1454 | 44 |
| WAT | OH2 | W | 1141 | 264 | 620 | 1075 | 44 |
| WAT | OH2 | W | 1142 | 380 | 542 | 1141 | 45 |
| WAT | OH2 | W | 1143 | 322 | 364 | 1063 | 45 |
| WAT | OH2 | W | 1144 | 116 | 458 | 1466 | 45 |
| WAT | OH2 | W | 1145 | 555 | 496 | 1356 | 45 |
| WAT | OH2 | W | 1146 | 321 | 629 | 1115 | 45 |
| WAT | OH2 | W | 1147 | 104 | 589 | 1062 | 45 |
| WAT | OH2 | W | 1148 | 571 | 640 | 1336 | 46 |
| WAT | OH2 | W | 1149 | 234 | 665 | 1314 | 46 |
| WAT | OH2 | W | 1150 | 161 | 687 | 1433 | 46 |
| WAT | OH2 | W | 1151 | 209 | 315 | 982 | 46 |
| WAT | OH2 | W | 1152 | 246 | 462 | 959 | 46 |
| WAT | OH2 | W | 1153 | 411 | 505 | 1468 | 46 |
| WAT | OH2 | W | 1154 | 62 | 308 | 1114 | 46 |
| WAT | OH2 | W | 1155 | 126 | 685 | 1250 | 46 |
| WAT | OH2 | W | 1156 | 523 | 452 | 1367 | 46 |
| WAT | OH2 | W | 1157 | 556 | 505 | 1331 | 46 |
| WAT | OH2 | W | 1158 | 319 | 312 | 1125 | 47 |
| WAT | OH2 | W | 1159 | 242 | 569 | 1552 | 47 |
| WAT | OH2 | W | 1160 | 54 | 560 | 1114 | 47 |
| WAT | OH2 | W | 1161 | 258 | 503 | 1575 | 47 |
| WAT | OH2 | W | 1162 | 218 | 526 | 1528 | 47 |
| WAT | OH2 | W | 1163 | 72 | 338 | 1124 | 47 |
| WAT | OH2 | W | 1164 | 324 | 336 | 1103 | 47 |
| WAT | OH2 | W | 1165 | 202 | 569 | 1015 | 48 |
| WAT | OH2 | W | 1166 | 480 | 519 | 1191 | 48 |
| WAT | OH2 | W | 1167 | 90 | 588 | 1250 | 48 |
| WAT | OH2 | W | 1168 | 90 | 544 | 1344 | 48 |
| WAT | OH2 | W | 1169 | 312 | 393 | 1046 | 49 |
| WAT | OH2 | W | 1170 | 128 | 525 | 1503 | 49 |
| WAT | OH2 | W | 1171 | 167 | 658 | 1357 | 49 |
| WAT | OH2 | W | 1172 | 74 | 498 | 1375 | 49 |
| WAT | OH2 | W | 1173 | 53 | 378 | 1254 | 49 |
| WAT | OH2 | W | 1174 | 533 | 640 | 1395 | 50 |
| WAT | OH2 | W | 1175 | 120 | 601 | 1316 | 51 |
| WAT | OH2 | W | 1176 | 296 | 305 | 1375 | 51 |
| WAT | OH2 | W | 1177 | 82 | 576 | 1047 | 52 |
| WAT | OH2 | W | 1178 | 253 | 651 | 1108 | 52 |
| WAT | OH2 | W | 1179 | 519 | 545 | 1170 | 52 |
| WAT | OH2 | W | 1180 | 266 | 572 | 1008 | 53 |
| WAT | OH2 | W | 1181 | 234 | 296 | 1126 | 54 |
| WAT | OH2 | W | 1182 | 222 | 602 | 1542 | 54 |
| WAT | OH2 | W | 1183 | 130 | 257 | 1220 | 55 |
| WAT | OH2 | W | 1184 | 66 | 349 | 1019 | 55 |
| WAT | OH2 | W | 1185 | 225 | 249 | 1299 | 57 |
| WAT | OH2 | W | 1186 | 164 | 686 | 1239 | 59 |

What is claimed is:

1. An isolated or recombinant nucleic acid comprising the nucleotide sequence set forth in SEQ ID NO: 17.

2. An expression vector comprising the nucleic acid of claim 1.

3. A host cell comprising the vector of claim 2.

4. The host cell of claim 3 which is *E. coli*.

5. A method for making a β-secretase polypeptide comprising transforming a host cell with the vector of claim 2 and culturing said cell under conditions in which said polypeptide is expressed.

6. The method of claim 5 wherein said host cell is *E. coli*.

7. An isolated polynucleotide consisting of the nucleotide sequence of SEQ ID NO: 17.

8. A method for refolding a polypeptide comprising the amino acid sequence of SEQ ID NO: 18 comprising incubating said polypeptide in the presence of 0.5 mM reduced glutathione and 0.5 mM oxidized glutathione.

9. The method of claim 8 wherein the polypeptide is incubated in the presence of 1 mM cysteine.

10. The method of claim 8 wherein said polypeptide comprising the amino acid sequence of SEQ ID NO: 18 is produced by a process comprising expressing said polypeptide in a host cell comprising a vector comprising a nucleic acid encoding said polypeptide.

11. The method of claim 10 wherein said host cell is *E. coli*.

12. A method for producing a processed β-secretase polypeptide comprising the amino acid sequence of SEQ ID NO: 18 comprising exchanging the polypeptide into 20 mM Hepes at pH 7.5 and 150 mM NaCl; concentrating the polypeptide to 5 mg/ml and incubating the polypeptide for two weeks at 4° C.

13. The method of claim 12 wherein said processed polypeptide comprises the amino acid sequence set forth in SEQ ID NO: 20 or 22; or wherein an equimolar mixture of polypeptides comprising the amino acid sequence set forth in SEQ ID NOs: 20 and 22 is produced.

14. The method of claim 13 wherein said processed polypeptide comprises said equimolar mixture.

15. The method of claim 12 wherein said polypeptide comprising the amino acid sequence of SEQ ID NO: 18 is produced by a process comprising expressing said polypeptide in a host cell comprising a vector comprising a nucleic acid encoding said polypeptide.

16. The method of claim 15 wherein said host cell is *E. coli*.

17. A method for making a β-secretase polypeptide comprising:

(a) expressing a polypeptide comprising the amino acid sequence of SEQ ID NO: 18 in a host cell comprising a vector comprising a nucleic acid encoding said polypeptide;

(b) isolating said polypeptide from said cell;

(c) refolding said polypeptide by incubating in the presence of 0.5 mM reduced glutathione and 0.5 mM oxidized glutathione; and (d) processing said polypeptide by exchanging said polypeptide into 20 mM Hepes at pH 7.5 and 150 mM NaCl, concentrating said polypeptide to 5 mg/ml and incubating at 4° C. for two weeks.

18. The method of claim 17 wherein said nucleic acid in said vector comprises the nucleotide sequence of SEQ ID NO: 17.

19. The method of claim 17 wherein said processed polypeptide comprises the amino acid sequence set forth in SEQ ID NO: 20 or 22; or wherein an equimolar mixture of polypeptides comprising the amino acid sequence set forth in SEQ ID NOs: 20 and 22 is produced.

20. The method of claim 19 wherein said processed polypeptide comprises said equimolar mixture.

* * * * *

SEQUENCE LISTING

<160> NUMBER OF SEQ ID NOS: 22

<210> SEQ ID NO 1
<211> LENGTH: 420
<212> TYPE: DNA
<213> ORGANISM: Artificial Sequence
<220> FEATURE:
<223> OTHER INFORMATION: artificial sequence for first approximately 1/3
      of BACE gene

<400> SEQUENCE: 1

```
atggctcaag ctttgccatg gttattgttg tggatgggtg ctggtgtttt acctgcacat      60
ggtactcagc acgtatccg tttacccttta cgttctggtt taggtggtgc accattaggt    120
ttacgtttac ctcgtgagac tgacgaagag ccagaagagc caggtcgtcg tggttcttt    180 gttgagatgg ttgacaactt acgtggtaag tctggtcagg gttactacgt tgagatgact   240
```

-continued

```
gttggttctc caccacagac tttaaacatc ttagttgata ctggttcttc taactttgca      300
gttggtgcag caccacaccc attcttacat cgttactacc agcgtcagtt atcttctact      360
taccgtgact tacgtaaggg tgtttatgtt ccatacaccc agggcaagtg ggaaggggag      420
```

<210> SEQ ID NO 2
<211> LENGTH: 140
<212> TYPE: PRT
<213> ORGANISM: Artificial Sequence
<220> FEATURE:
<223> OTHER INFORMATION: artificial sequence for first approximately 1/3
      of BACE gene

<400> SEQUENCE: 2

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu
    130                 135                 140
```

<210> SEQ ID NO 3
<211> LENGTH: 80
<212> TYPE: DNA
<213> ORGANISM: Artificial Sequence
<220> FEATURE:
<223> OTHER INFORMATION: primer

<400> SEQUENCE: 3

```
atggctcaag cttgccatg gttattgttg tggatgggtg ctggtgtttt acctgcacat      60
ggtactcagc acggtatccg                                                  80
```

<210> SEQ ID NO 4
<211> LENGTH: 75
<212> TYPE: DNA
<213> ORGANISM: Artificial Sequence
<220> FEATURE:
<223> OTHER INFORMATION: primer

<400> SEQUENCE: 4

```
tttaccttta cgttctggtt taggtggtgc accattaggt ttacgtttac ctcgtgagac      60
tgacgaagag ccaga                                                       75
```

<210> SEQ ID NO 5
<211> LENGTH: 80
<212> TYPE: DNA
<213> ORGANISM: Artificial Sequence
<220> FEATURE:
<223> OTHER INFORMATION: primer

```
<400> SEQUENCE: 5
caggtcgtcg tggttctttt gttgagatgg ttgacaactt acgtggtaag tctggtcagg    60
gttactacgt tgagatgact                                                80

<210> SEQ ID NO 6
<211> LENGTH: 80
<212> TYPE: DNA
<213> ORGANISM: Artificial Sequence
<220> FEATURE:
<223> OTHER INFORMATION: primer

<400> SEQUENCE: 6
gttggttctc caccacagac tttaaacatc ttagttgata ctggttcttc taactttgca    60
gttggtgcag caccacaccc                                                80

<210> SEQ ID NO 7
<211> LENGTH: 74
<212> TYPE: DNA
<213> ORGANISM: Artificial Sequence
<220> FEATURE:
<223> OTHER INFORMATION: primer

<400> SEQUENCE: 7
attcttacat cgttactacc agcgtcagtt atcttctact taccgtgact tacgtaaggg    60
tgtttatgtt ccat                                                      74

<210> SEQ ID NO 8
<211> LENGTH: 81
<212> TYPE: DNA
<213> ORGANISM: Artificial Sequence
<220> FEATURE:
<223> OTHER INFORMATION: primer

<400> SEQUENCE: 8
acctaatggt gcaccaccta aaccagaacg taaaggtaaa cggataccgt gctgagtacc    60
atgtgcaggt aaaacaccag c                                              81

<210> SEQ ID NO 9
<211> LENGTH: 80
<212> TYPE: DNA
<213> ORGANISM: Artificial Sequence
<220> FEATURE:
<223> OTHER INFORMATION: primer

<400> SEQUENCE: 9
aagttgtcaa ccatctcaac aaaagaacca cgacgacctg gctcctctgg ctcttcgtca    60
gtctcacgag gtaaacgtaa                                                80

<210> SEQ ID NO 10
<211> LENGTH: 80
<212> TYPE: DNA
<213> ORGANISM: Artificial Sequence
<220> FEATURE:
<223> OTHER INFORMATION: primer

<400> SEQUENCE: 10
tatcaactaa gatgtttaaa gtctgtggtg gagaaccaac agtcatctca acgtagtaac    60
cctgaccaga cttaccacgt                                                80
```

```
<210> SEQ ID NO 11
<211> LENGTH: 80
<212> TYPE: DNA
<213> ORGANISM: Artificial Sequence
<220> FEATURE:
<223> OTHER INFORMATION: primer

<400> SEQUENCE: 11
agtagaagat aactgacgct ggtagtaacg atgtaagaat gggtgtggtg ctgcaccaac      60
tgcaaagtta gaagaaccag                                                 80

<210> SEQ ID NO 12
<211> LENGTH: 59
<212> TYPE: DNA
<213> ORGANISM: Artificial Sequence
<220> FEATURE:
<223> OTHER INFORMATION: primer

<400> SEQUENCE: 12
ctcaccttcc cacttaccct gagtgtatgg aacataaaca cccttacgta agtcacgga      59

<210> SEQ ID NO 13
<211> LENGTH: 62
<212> TYPE: DNA
<213> ORGANISM: Artificial Sequence
<220> FEATURE:
<223> OTHER INFORMATION: primer

<400> SEQUENCE: 13
acggatcctt agtggtggtg gtggtggtgg ctccctgact catctgtctg tggaatgttg      60
ta                                                                    62

<210> SEQ ID NO 14
<211> LENGTH: 11
<212> TYPE: PRT
<213> ORGANISM: Artificial Sequence
<220> FEATURE:
<223> OTHER INFORMATION: T7 tag

<400> SEQUENCE: 14

Met Ala Ser Met Thr Gly Gly Gln Gln Met Gly
1               5                   10

<210> SEQ ID NO 15
<211> LENGTH: 8
<212> TYPE: PRT
<213> ORGANISM: Artificial Sequence
<220> FEATURE:
<223> OTHER INFORMATION: OM-99-2

<400> SEQUENCE: 15

Glu Val Asn Leu Ala Ala Glu Phe
1               5

<210> SEQ ID NO 16
<211> LENGTH: 12
<212> TYPE: PRT
<213> ORGANISM: Artificial Sequence
<220> FEATURE:
<223> OTHER INFORMATION: substrate for B-secretase

<400> SEQUENCE: 16

Lys Ser Glu Val Asn Leu Asp Ala Glu Phe Arg Lys
1               5                   10
```

<210> SEQ ID NO 17
<211> LENGTH: 1362
<212> TYPE: DNA
<213> ORGANISM: Artificial Sequence
<220> FEATURE:
<223> OTHER INFORMATION: BACE without C-terminus

<400> SEQUENCE: 17

| | | | | | |
|---|---|---|---|---|---|
| atggctcaag | ctttgccatg | gttattgttg | tggatgggtg | ctggtgtttt | acctgcacat | 60 |
| ggtactcagc | acggtatccg | tttacctta | cgttctggtt | aggtggtgc | accattaggt | 120 |
| ttacgtttac | ctcgtgagac | tgacgaagag | ccagaagagc | caggtcgtcg | tggttctttt | 180 |
| gttgagatgg | ttgacaactt | acgtggtaag | tctggtcagg | gttactacgt | tgagatgact | 240 |
| gttggttctc | caccacagac | tttaaacatc | ttagttgata | ctggttcttc | taactttgca | 300 |
| gttggtgcag | caccacaccc | attcttacat | cgttactacc | agcgtcagtt | atcttctact | 360 |
| taccgtgact | tacgtaaggg | tgttatgtt | ccatacaccc | agggcaagtg | ggaaggggag | 420 |
| ctgggcaccg | acctggtaag | catcccccat | ggccccaacg | tcactgtgcg | tgccaacatt | 480 |
| gctgccatca | ctgaatcaga | caagttcttc | atcaacggct | ccaactggga | aggcatcctg | 540 |
| gggctggcct | atgctgagat | tgccaggcct | gacgactccc | tggagccttt | ctttgactct | 600 |
| ctggtaaagc | agaccacgt | tcccaacctc | ttctccctgc | agctttgtgg | tgctggcttc | 660 |
| cccctcaacc | agtctgaagt | gctggcctct | gtcggaggga | gcatgatcat | tggaggtatc | 720 |
| gaccactcgc | tgtacacagg | cagtctctgg | tatacaccca | tccggcggga | gtggtattat | 780 |
| gaggtgatca | ttgtgcgggt | ggagatcaat | ggacaggatc | tgaaaatgga | ctgcaaggag | 840 |
| tacaactatg | acaagagcat | tgtggacagt | ggcaccacca | accttcgttt | gcccaagaaa | 900 |
| gtgtttgaag | ctgcagtcaa | atccatcaag | gcagcctcct | ccacggagaa | gttccctgat | 960 |
| ggtttctggc | taggagagca | gctggtgtgc | tggcaagcag | gcaccacccc | ttggaacatt | 1020 |
| ttcccagtca | tctcactcta | cctaatgggt | gaggttacca | accagtcctt | ccgcatcacc | 1080 |
| atccttccgc | agcaataccc | gcggccagtg | aagatgtgg | ccacgtccca | agacgactgt | 1140 |
| tacaagtttg | ccatctcaca | gtcatccacg | ggcactgtta | tgggagctgt | tatcatggag | 1200 |
| ggcttctacg | ttgtctttga | tcgggcccga | aaacgaattg | gctttgctgt | cagcgcttgc | 1260 |
| catgtgcacg | atgagttcag | gacggcagcg | gtggaaggcc | cttttgtcac | cttggacatg | 1320 |
| gaagactgtg | gctacaacat | tccacagaca | gatgagtcaa | cc | | 1362 |

<210> SEQ ID NO 18
<211> LENGTH: 454
<212> TYPE: PRT
<213> ORGANISM: Artificial Sequence
<220> FEATURE:
<223> OTHER INFORMATION: BACE without C-terminus

<400> SEQUENCE: 18

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
65                  70                  75                  80

```
Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
            420                 425                 430

Gly Pro Phe Val Thr Leu Asp Met Glu Asp Cys Gly Tyr Asn Ile Pro
        435                 440                 445

Gln Thr Asp Glu Ser Thr
    450

<210> SEQ ID NO 19
<211> LENGTH: 1242
<212> TYPE: DNA
<213> ORGANISM: Artificial Sequence
<220> FEATURE:
<223> OTHER INFORMATION: BACE without C-terminus and without propeptide
```

-continued

```
<400> SEQUENCE: 19
ttacgtttac ctcgtgagac tgacgaagag ccagaagagc caggtcgtcg tggttctttt      60
gttgagatgg ttgacaactt acgtggtaag tctggtcagg ttactacgt tgagatgact     120
gttggttctc caccacagac tttaaacatc ttagttgata ctggttcttc aactttgca     180
gttggtgcag caccacaccc attcttacat cgttactacc agcgtcagtt atcttctact     240
taccgtgact tacgtaaggg tgtttatgtt ccatacaccc agggcaagtg ggaaggggag     300
ctgggcaccg acctggtaag catcccccat ggccccaacg tcactgtgcg tgccaacatt     360
gctgccatca ctgaatcaga caagttcttc atcaacggct ccaactggga aggcatcctg     420
gggctggcct atgctgagat tgccaggcct gacgactccc tggagccttt ctttgactct     480
ctggtaaagc agacccacgt tcccaacctc ttctccctgc agctttgtgg tgctggcttc     540
cccctcaacc agtctgaagt gctggcctct gtcggaggga gcatgatcat tggaggtatc     600
gaccactcgc tgtacacagg cagtctctgg tatacaccca tccggcggga gtggtattat     660
gaggtgatca ttgtgcgggt ggagatcaat ggacaggatc tgaaaatgga ctgcaaggag     720
tacaactatg acaagagcat tgtggacagt ggcaccacca accttcgttt gcccaagaaa     780
gtgtttgaag ctgcagtcaa atccatcaag gcagcctcct ccacggagaa gttccctgat     840
ggtttctggc taggagagca gctggtgtgc tggcaagcag gcaccacccc ttggaacatt     900
ttcccagtca tctcactcta cctaatgggt gaggttacca ccagtcctt ccgcatcacc     960
atccttccgc agcaatacct gcggccagtg gaagatgtgg ccacgtccca agacgactgt    1020
tacaagtttg ccatctcaca gtcatccacg ggcactgtta tgggagctgt tatcatggag    1080
ggcttctacg ttgtctttga tcgggcccga aaacgaattg gctttgctgt cagcgcttgc    1140
catgtgcacg atgagttcag gacggcagcg gtggaaggcc ttttgtcac cttggacatg    1200
gaagactgtg gctacaacat tccacagaca gatgagtcaa cc                       1242
```

<210> SEQ ID NO 20
<211> LENGTH: 414
<212> TYPE: PRT
<213> ORGANISM: Artificial Sequence
<220> FEATURE:
<223> OTHER INFORMATION: BACE without C-terminus and without propeptide

<400> SEQUENCE: 20

```
Leu Arg Leu Pro Arg Glu Thr Asp Glu Glu Pro Glu Glu Pro Gly Arg
1               5                   10                  15

Arg Gly Ser Phe Val Glu Met Val Asp Asn Leu Arg Gly Lys Ser Gly
            20                  25                  30

Gln Gly Tyr Tyr Val Glu Met Thr Val Gly Ser Pro Pro Gln Thr Leu
        35                  40                  45

Asn Ile Leu Val Asp Thr Gly Ser Ser Asn Phe Ala Val Gly Ala Ala
    50                  55                  60

Pro His Pro Phe Leu His Arg Tyr Tyr Gln Arg Gln Leu Ser Ser Thr
65                  70                  75                  80

Tyr Arg Asp Leu Arg Lys Gly Val Tyr Val Pro Tyr Thr Gln Gly Lys
                85                  90                  95

Trp Glu Gly Glu Leu Gly Thr Asp Leu Val Ser Ile Pro His Gly Pro
            100                 105                 110

Asn Val Thr Val Arg Ala Asn Ile Ala Ala Ile Thr Glu Ser Asp Lys
        115                 120                 125
```

```
Phe Phe Ile Asn Gly Ser Asn Trp Glu Gly Ile Leu Gly Leu Ala Tyr
    130                 135                 140

Ala Glu Ile Ala Arg Pro Asp Asp Ser Leu Glu Pro Phe Phe Asp Ser
145                 150                 155                 160

Leu Val Lys Gln Thr His Val Pro Asn Leu Phe Ser Leu Gln Leu Cys
                165                 170                 175

Gly Ala Gly Phe Pro Leu Asn Gln Ser Glu Val Leu Ala Ser Val Gly
            180                 185                 190

Gly Ser Met Ile Ile Gly Gly Ile Asp His Ser Leu Tyr Thr Gly Ser
        195                 200                 205

Leu Trp Tyr Thr Pro Ile Arg Arg Glu Trp Tyr Tyr Glu Val Ile Ile
    210                 215                 220

Val Arg Val Glu Ile Asn Gly Gln Asp Leu Lys Met Asp Cys Lys Glu
225                 230                 235                 240

Tyr Asn Tyr Asp Lys Ser Ile Val Asp Ser Gly Thr Thr Asn Leu Arg
                245                 250                 255

Leu Pro Lys Lys Val Phe Glu Ala Ala Val Lys Ser Ile Lys Ala Ala
            260                 265                 270

Ser Ser Thr Glu Lys Phe Pro Asp Gly Phe Trp Leu Gly Glu Gln Leu
        275                 280                 285

Val Cys Trp Gln Ala Gly Thr Thr Pro Trp Asn Ile Phe Pro Val Ile
    290                 295                 300

Ser Leu Tyr Leu Met Gly Glu Val Thr Asn Gln Ser Phe Arg Ile Thr
305                 310                 315                 320

Ile Leu Pro Gln Gln Tyr Leu Arg Pro Val Glu Asp Val Ala Thr Ser
                325                 330                 335

Gln Asp Asp Cys Tyr Lys Phe Ala Ile Ser Gln Ser Ser Thr Gly Thr
            340                 345                 350

Val Met Gly Ala Val Ile Met Glu Gly Phe Tyr Val Val Phe Asp Arg
        355                 360                 365

Ala Arg Lys Arg Ile Gly Phe Ala Val Ser Ala Cys His Val His Asp
    370                 375                 380

Glu Phe Arg Thr Ala Ala Val Glu Gly Pro Phe Val Thr Leu Asp Met
385                 390                 395                 400

Glu Asp Cys Gly Tyr Asn Ile Pro Gln Thr Asp Glu Ser Thr
                405                 410
```

<210> SEQ ID NO 21
<211> LENGTH: 1236
<212> TYPE: DNA
<213> ORGANISM: Artificial Sequence
<220> FEATURE:
<223> OTHER INFORMATION: BACE without C-terminus and without propeptide

<400> SEQUENCE: 21

```
ttacctcgtg agactgacga agagccagaa gagccaggtc gtcgtggttc ttttgttgag    60
atggttgaca acttacgtgg taagtctggt cagggttact acgttgagat gactgttggt   120
tctccaccac agactttaaa catcttagtt gatactggtt cttctaactt tgcagttggt   180
gcagcaccac acccattctt acatcgttac taccagcgtc agttatcttc tacttaccgt   240
gacttacgta agggtgttta tgttccatac acccagggca gtgggaaggg gagctgggc    300 accgacctgg taagcatccc ccatggcccc aacgtcactg tgcgtgccaa cattgctgcc   360
atcactgaat cagacaagtt cttcatcaac ggctccaact gggaaggcat cctgggctg    420 gcctatgctg agattgccag gcctgacgac tccctggagc cttttctttga ctctctggta   480
```

-continued

```
aagcagaccc acgttcccaa cctcttctcc ctgcagcttt gtggtgctgg cttccccctc      540
aaccagtctg aagtgctggc ctctgtcgga gggagcatga tcattggagg tatcgaccac      600
tcgctgtaca caggcagtct ctggtataca cccatccggc gggagtggta ttatgaggtg      660
atcattgtgc gggtggagat caatggacag gatctgaaaa tggactgcaa ggagtacaac      720
tatgacaaga gcattgtgga cagtggcacc accaaccttc gtttgcccaa gaaagtgttt      780
gaagctgcag tcaaatccat caaggcagcc tcctccacgg agaagttccc tgatggtttc      840
tggctaggag agcagctggt gtgctggcaa gcaggcacca ccccttggaa catttttccca     900 gtcatctcac tctacctaat gggtgaggtt accaaccagt ccttccgcat caccatcctt     960
ccgcagcaat acctgcggcc agtggaagat gtggccacgt cccaagacga ctgttacaag    1020
tttgccatct cacagtcatc cacgggcact gttatgggag ctgttatcat ggagggcttc    1080
tacgttgtct tgatcgggc ccgaaaacga attggctttg ctgtcagcgc ttgccatgtg     1140
cacgatgagt tcaggacggc agcggtggaa ggcccttttg tcaccttgga catggaagac    1200
tgtggctaca acattccaca gacagatgag tcaacc                              1236
```

<210> SEQ ID NO 22
<211> LENGTH: 412
<212> TYPE: PRT
<213> ORGANISM: Artificial Sequence
<220> FEATURE:
<223> OTHER INFORMATION: BACE without C-terminus and without propeptide

<400> SEQUENCE: 22

```
Leu Pro Arg Glu Thr Asp Glu Glu Pro Glu Glu Pro Gly Arg Arg Gly
1               5                  10                  15

Ser Phe Val Glu Met Val Asp Asn Leu Arg Gly Lys Ser Gly Gln Gly
            20                  25                  30

Tyr Tyr Val Glu Met Thr Val Gly Ser Pro Pro Gln Thr Leu Asn Ile
        35                  40                  45

Leu Val Asp Thr Gly Ser Ser Asn Phe Ala Val Gly Ala Ala Pro His
    50                  55                  60

Pro Phe Leu His Arg Tyr Tyr Gln Arg Gln Leu Ser Ser Thr Tyr Arg
65                  70                  75                  80

Asp Leu Arg Lys Gly Val Tyr Val Pro Tyr Thr Gln Gly Lys Trp Glu
                85                  90                  95

Gly Glu Leu Gly Thr Asp Leu Val Ser Ile Pro His Gly Pro Asn Val
            100                 105                 110

Thr Val Arg Ala Asn Ile Ala Ala Ile Thr Glu Ser Asp Lys Phe Phe
        115                 120                 125

Ile Asn Gly Ser Asn Trp Glu Gly Ile Leu Gly Leu Ala Tyr Ala Glu
    130                 135                 140

Ile Ala Arg Pro Asp Asp Ser Leu Glu Pro Phe Phe Asp Ser Leu Val
145                 150                 155                 160

Lys Gln Thr His Val Pro Asn Leu Phe Ser Leu Gln Leu Cys Gly Ala
                165                 170                 175

Gly Phe Pro Leu Asn Gln Ser Glu Val Leu Ala Ser Val Gly Gly Ser
            180                 185                 190

Met Ile Ile Gly Gly Ile Asp His Ser Leu Tyr Thr Gly Ser Leu Trp
        195                 200                 205

Tyr Thr Pro Ile Arg Arg Glu Trp Tyr Tyr Glu Val Ile Ile Val Arg
    210                 215                 220
```

```
-continued

Val Glu Ile Asn Gly Gln Asp Leu Lys Met Asp Cys Lys Glu Tyr Asn
225                 230                 235                 240

Tyr Asp Lys Ser Ile Val Asp Ser Gly Thr Thr Asn Leu Arg Leu Pro
            245                 250                 255

Lys Lys Val Phe Glu Ala Ala Val Lys Ser Ile Lys Ala Ala Ser Ser
            260                 265                 270

Thr Glu Lys Phe Pro Asp Gly Phe Trp Leu Gly Glu Gln Leu Val Cys
        275                 280                 285

Trp Gln Ala Gly Thr Thr Pro Trp Asn Ile Phe Pro Val Ile Ser Leu
    290                 295                 300

Tyr Leu Met Gly Glu Val Thr Asn Gln Ser Phe Arg Ile Thr Ile Leu
305                 310                 315                 320

Pro Gln Gln Tyr Leu Arg Pro Val Glu Asp Val Ala Thr Ser Gln Asp
            325                 330                 335

Asp Cys Tyr Lys Phe Ala Ile Ser Gln Ser Ser Thr Gly Thr Val Met
            340                 345                 350

Gly Ala Val Ile Met Glu Gly Phe Tyr Val Val Phe Asp Arg Ala Arg
        355                 360                 365

Lys Arg Ile Gly Phe Ala Val Ser Ala Cys His Val His Asp Glu Phe
        370                 375                 380

Arg Thr Ala Ala Val Glu Gly Pro Phe Val Thr Leu Asp Met Glu Asp
385                 390                 395                 400

Cys Gly Tyr Asn Ile Pro Gln Thr Asp Glu Ser Thr
                405                 410
```